(12) United States Patent
Gandhi et al.

(10) Patent No.: US 9,283,222 B2
(45) Date of Patent: *Mar. 15, 2016

(54) INHIBITORS OF POLY(ADP-RIBOSE)POLYMERASE

(71) Applicant: Abbvie Inc., North Chicago, IL (US)

(72) Inventors: Virajkumar B. Gandhi, Gurnee, IL (US); Vincent L. Giranda, Gurnee, IL (US); Jianchun Gong, Deerfield, IL (US); Thomas D. Penning, Elmhurst, IL (US); Gui-Dong Zhu, Gurnee, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/902,055

(22) Filed: May 24, 2013

(65) Prior Publication Data

US 2014/0212509 A1    Jul. 31, 2014

Related U.S. Application Data

(63) Continuation of application No. 12/138,168, filed on Jun. 12, 2008, now Pat. No. 8,466,150, which is a continuation-in-part of application No. 11/964,822, filed on Dec. 27, 2007, now abandoned.

(60) Provisional application No. 60/882,317, filed on Dec. 28, 2006.

(51) Int. Cl.
| | |
|---|---|
| *A61K 31/502* | (2006.01) |
| *C07D 237/32* | (2006.01) |
| *C07D 401/12* | (2006.01) |
| *C07D 401/14* | (2006.01) |
| *C07D 403/10* | (2006.01) |
| *C07D 403/12* | (2006.01) |
| *C07D 403/14* | (2006.01) |
| *A61K 31/551* | (2006.01) |
| *A61K 45/06* | (2006.01) |
| *A61N 5/10* | (2006.01) |

(52) U.S. Cl.
CPC ............ *A61K 31/502* (2013.01); *A61K 31/551* (2013.01); *A61K 45/06* (2013.01); *A61N 5/10* (2013.01); *C07D 237/32* (2013.01); *C07D 401/12* (2013.01); *C07D 401/14* (2013.01); *C07D 403/10* (2013.01); *C07D 403/12* (2013.01); *C07D 403/14* (2013.01)

(58) Field of Classification Search
CPC .. C07D 403/10; C07D 237/32; A61K 31/551; A61K 31/502
USPC ....................................................... 544/237
See application file for complete search history.

(56) References Cited

U.S. PATENT DOCUMENTS

| | | | |
|---|---|---|---|
| 6,903,098 B1 | 6/2005 | Lubisch et al. | |
| 7,151,102 B2 | 12/2006 | Martin et al. | |
| 7,196,085 B2 | 3/2007 | Martin et al. | |
| 7,402,580 B2 | 7/2008 | Seko et al. | |
| 7,407,957 B2 | 8/2008 | Javaid et al. | |
| 7,425,563 B2 | 9/2008 | Shiga et al. | |
| 7,470,688 B2 | 12/2008 | Javaid et al. | |
| 7,981,890 B2 | 7/2011 | Javaid et al. | |
| 8,466,150 B2 * | 6/2013 | Gandhi et al. | 514/248 |
| 2002/0183325 A1 | 12/2002 | Martin et al. | |
| 2004/0023968 A1 | 2/2004 | Martin et al. | |
| 2004/0087588 A1 | 5/2004 | Beaton et al. | |
| 2005/0059663 A1 | 3/2005 | Martin et al. | |
| 2005/0080096 A1 | 4/2005 | Ishida et al. | |
| 2005/0085476 A1 | 4/2005 | Seko et al. | |
| 2005/0159427 A1 | 7/2005 | Bruncko et al. | |
| 2006/0063767 A1 | 3/2006 | Javaid et al. | |
| 2006/0142293 A1 | 6/2006 | Martin et al. | |
| 2006/0149059 A1 | 7/2006 | Martin et al. | |
| 2007/0093489 A1 | 4/2007 | Javaid et al. | |
| 2008/0146575 A1 | 6/2008 | Menear et al. | |
| 2008/0161280 A1 * | 7/2008 | Gandhi et al. | 514/210.02 |
| 2009/0069303 A1 | 3/2009 | Javaid et al. | |
| 2010/0179153 A1 | 7/2010 | Mattes et al. | |
| 2010/0184770 A1 | 7/2010 | Gore et al. | |
| 2011/0065684 A1 | 3/2011 | Mevellec et al. | |

FOREIGN PATENT DOCUMENTS

| | | | |
|---|---|---|---|
| CN | 102952118 | * | 3/2013 |
| EP | 1908481 A1 | | 4/2008 |
| WO | 03093261 A1 | | 11/2003 |

OTHER PUBLICATIONS

National Cancer Institute (http://www.cancer.gov/) (Downloaded May 29, 2014).*
H.A. Fine, Neoplasms of the Central Nervous System in, 2 Cancer Principles & Practice of Oncology 1834-1887 (V.T. DeVita, Jr. et al. eds., 5th ed., 2005).*
B.C. Bastian, Genetic Progression, in From Melanocytes to Melanoma the Progression to Malignancy 197, 201 (V. J. Hearing et al., eds., 2006).*
A. Kamb, Nature Reviews Drug Discovery 2, 161-165 (2005).*
N.F. Smith, Molecular Cancer Therapeutics, 6, 428-440, 428 (2007).*
N.E. Sharpless et al., Nature Reviews Drug Discovery 5, 741-754, 742 (2006).*

(Continued)

*Primary Examiner* — Alexander R Pagano

(74) *Attorney, Agent, or Firm* — Glen J. Gesicki

(57) ABSTRACT

Inhibitors of poly(ADP-ribose)polymerase, ways to make them and methods of treating patients using them are disclosed.

3 Claims, No Drawings

(56) References Cited

OTHER PUBLICATIONS

C.J. Lord et al., 8 Current Opinion in Pharmacology, 363-369 (2008).*
G. Srinivas et al., 473 European Journal of Pharmacology, 117-125 (2003).*
S.H. Kaufmann et al., 53 Cancer Research, 3976-3985 (1993).*
C.L. Cheng et al., 4 Molecular Cancer Therapeutics, 1364-1368 (2005).*
L. Tentori et al., 9 Clinical Cancer Research, 5370-5379 (2003).*
C.K. Donawho et al., 13 Clinical Cancer Research, 2728-2737 (2007).*
T.J. Haymes et al., 94 haematologica, 638-646 (2009).*
E. Chu, Drug Development in, 1 Cancer: Principles & Practice of Oncology 307-317, 316 (V.T. DeVita, Jr. et al. eds., 7th ed., 2005) ("Chu").*
J. Luo et al., 136 Cell, 823-837 (2009).*
L.C. Cantley, Signal Transduction Systems in, 1 Cancer: Principles & Practice of Oncology, 73-83 (V.T. DeVita, Jr. et al. eds., 7th ed., 2005).*
A-M Bleau et al., 8 Cell Cycle 2937-2945 (2009).*
Abad-Zapatero C., et al., "Ligand Efficiency Indices for an Effective Mapping of Chemico-Biological Space: The Concept of an Atlas-like Representation," Drug Discovery Today, 2010, pp. 1-8.
Amundson S.A., et al., "An Informatics Approach Identifying Markers of Chemosensitivity in Human Cancer Cell Lines," Cancer Research, 2000, vol. 60 (21), pp. 6101-6110.
Bastian B.C., "Genetic Progression from Melanocyte to Malignant Melanoma" in: From Melanocytes to Melanona, Chapter 11, Hearing V.J., eds., Humana Press Inc., 2006, pp. 197-209.
Burkart V., et al., "Mice Lacking the Poly (ADP-ribose) Polymerase Gene Are Resistant to Pancreatic Beta-Cell Destruction and Diabetes Development Induced by Streptozocin," Nature Medicine, 1999, vol. 5 (3), pp. 314-319.
Cannistra S.A., et al., "Ovarian Cancer, Fallopian Tube Carcinoma, and Peritoneal Carcinoma" in: Cancer, 8th Edition, DeVita V.T., eds., Lippincott Williams and Wilkins, 2008, pp. 1568-1594.
Chabner B.A., et al., "Antineoplastic Agents" in: The Pharmacological Basis of Therapeutics, 11th Edition, Brunton L.L., eds., McGraw-Hill, 2006, pp. 1315-1403.
Chen G., et al., "Potentiation of the Antitumor Activity of Cisplatin in Mice by 3-am inobenzamide and Nicotinamide," Cancer Chemotherapy and Pharmacology, 1988, vol. 22 (4), pp. 303-307.
Chen K.G., et al., "How Melanoma Cells Evade Chemotherapy", in: From Melanocytes to Melanona, Chapter 33, Hearing V.J., eds., Humana Press Inc., 2006, pp. 591-603.
Collins I., et al., "Design and Development of Signal Transduction Inhibitors for Cancer Treatment: Experience and Challenges with Kinase Targets," Current Signal Transduction Therapy, 2006, vol. 1, pp. 13-23.
Csende F., et al., "Copper(II) Chloride as an Efficient Reagent for the Dehydrogenation of Pyridazinone Derivatives," Synthesis, 1995, vol. 10, pp. 1240-1242.
Csende F., et al., "Partial Dehydrogenation of Saturated 4-Phenyl-1(2H)-Phthalazinone Derivatives by Thionyl Chloride," Synthetic Communications, 1993, vol. 23 (21), pp. 2957-2964.
Cuzzocrea S., et al., "Protective Effects of 3-Aminobenzamide, an Inhibitor of Poly (ADP-ribose) Synthase in a Carrageenan-Induced Model of Local Inflammation," European Journal of Pharmacology, 1998, vol. 342, pp. 67-76.
De Arruda F.F., et al., "Intensity-Modulated Radiation Therapy for the Treatment of Oropharyngeal Carcinoma: the Memorial Sloan-Kettering Cancer Center Experience," International Journal of Radiation Oncology, Biology, Physics, 2006, vol. 64 (2), pp. 363-373.
Ehrlich W., et al., "Inhibition of the Induction of Collagenase by Interleukin-1β in Cultured Rabbit Synovial Fibroblasts After Treatment with the poly(ADP-Ribose)-Polymerase Inhibitor 3-Aminobenzamide," Rheumatology International, 1995, vol. 15, pp. 171-172.

Hann B., et al., "Building 'Validated' Mouse Models of Human Cancer," Current Opinion in Cell Biology, 2001, vol. 13 (6), pp. 778-784.
Holzelova, E. et al., "Autoimmune Lymphoproliferative Syndrome with Somatic Fas Mutations," New England Journal of Medicine, 2004, vol. 351 (14), pp. 1409-1418.
International Search Report for Application No. PCT/US2007/088319, mailed on May 16, 2008, 1 page.
International Search Report for Application No. PCT/US2007/87791, mailed on Apr. 18, 2008, 2 pages.
Kamb A., "What's Wrong with our Cancer Models," Nature Reviews Drug Discovery, 2005, vol. 4, pp. 161-165.
Kroger H., et al., "Synergistic Effects of Thalidomide and Poly(ADP-rose) Polymerase Inhibition on Type II Collagen-Induced Arthristis in Mice," Inflammation, 1996, vol. 20(2), pp. 203-215.
Libutti S.K., et al., "Colon Cancer" in: Cancer, 8th Edition, DeVita V.T., eds., Lippincott Williams and Wilkins, 2008, pp. 1232-1285.
Non-Final Office Action mailed Sep. 1, 2011 for U.S. Appl. No. 11/964,822, filed Dec. 27, 2007.
Non-Final Office Action mailed Sep. 29, 2011 for U.S. Appl. No. 12/138,168, filed Jun. 12, 2008.
Odunsi K., et al., "Molucular Biology of Gynecologic Cancers" in: Cancer, 8th Edition, DeVita V.T., eds., Lippincott Williams and Wilkins, 2008, pp. 1487-1496.
Olive K.P., et al., "The Use of Targeted Mouse Models for Preclinical Testing of Novel Cancer Therapeutics," Clinical Cancer Research, 2006, vol. 12 (18), pp. 5277-5287.
Poupaert J.H., "Drug Design: Basic Principles and Applications," Encyclopedia of Pharmaceutical Technology, 3rd Edition, 2007, vol. 1367, pp. 1362-1369.
Puck J.M., et al., "Immune Disorders Caused by Defects in the Caspase Cascade ," Current Allergy and Asthma Reports, 2003, vol. 3, pp. 378-384.
Pusztai L., et al., Histopathologic and Molecular Markets of Prognosis and Response to Therapy, 2nd Edition, Chapter 11, 2008, pp. 324-343.
Rengan R., et al., "Actin Cytoskeletal Function is Spared, but Apoptosis is Increased, in WAS Patient Hematopoietic Cells," Blood, 2000, vol. 95 (4), pp. 1283-1292.
Rustgi A.K., "Cancers of the Gastrointestinal Tract" in: Cancer, 8th Edition, DeVita V.T., eds., Lippincott Williams and Wilkins, 2008, pp. 989-993.
Sharpless N.E., et al., "The Mighty Mouse: Genetically Engineered Mouse Models in Cancer Drug Development," Nature Reviews Drug Discovery, 2006, vol. 5 (9), pp. 741-754.
Shimazaki K., et al., "Evaluation of Apoptosis as a Prognostic Factor in Myelodysplastic Syndromes," British J Haematology, 2000, vol. 110 (3), pp. 584-590.
Smith N. F., et al., "The Application of Cassette Dosing for Pharmacokinetic Screening in Small-Molecule Cancer Drug Discovery," Molecular Cancer Therapeutics, 2007, vol. 6 (2), pp. 428-440.
Song Y., et al., "Cancer: A Conceptual Framework" in: Cancer, 8th Edition, DeVita V.T., eds., Lippincott Williams and Wilkins, 2008, pp. 1-12.
Szabo C., et al., "Protection Against Peroxynitrite-Induced Fibroblast Injury and Arthritis Development by Inhibition of Poly(Adp-Ribose) Synthase," Proceedings of the National Academy of Sciences USA, 1998, vol. 95, pp. 3867-3872.
Thiemermann C., et al., "'Inhibition of the Activity of Poly (ADP ribose) Synthhetase Reduces Ischemia-Reperfusion Injury in the Heart and Skeletal Muscle,'" Proceedings of the National Academy of Sciences of the United States of America, 1997, vol. 94, pp. 679-683.
Traynor A.M., et al., "Systemic Treatment of Advanced Non-Small Cell Lung Cancer," Drugs of Today, 2004, vol. 40 (8), pp. 697-710.
Weltin D., et al., "Immunosuppressive Activities of 6(5h)-Phenanthridinone, a New Polu(Adp-Ribose)Polumerase Inhibitor," International Journal of Immunopharmacology , 1995, vol. 17 (4), pp. 265-271.
European Search Report for Application No. 13191894 dated Jan. 10, 2014 (3 pages).

* cited by examiner

INHIBITORS OF POLY(ADP-RIBOSE)POLYMERASE

This application is a continuation application of U.S. patent application Ser. No. 12/138,168, filed Jun. 12, 2008, now U.S. Pat. No. 8,466,150, which is a continuation-in-part of U.S. patent application Ser. No. 11/964,822, filed Dec. 27, 2007, which claims priority from Provisional U.S. patent application Ser. No. 60/882,317, filed Dec. 28, 2006, all of which are incorporated by reference in their entireties.

FIELD OF THE INVENTION

This invention relates to inhibitors of poly(ADP-ribose) polymerase, ways to make them and methods of treating patients using them.

BACKGROUND OF THE INVENTION

Poly(ADP-ribose)polymerase (PARP) is essential for facilitating DNA repair, controlling RNA transcription, mediating cell death and regulating immune response. This activity makes PARP inhibitors targets for a number of disorders. PARP inhibitors have shown utility for treating diseases such as ischemia reperfusion injury, inflammatory disease, retroviral infections, ischemia reperfusion injury, myocardial infarction, stroke and other neural trauma, organ transplantation, reperfusion of the eye, kidney, gut and skeletal muscle, arthritis, gout, inflammatory bowel disease, CNS inflammation such as MS and allergic encephalitis, sepsis, septic shock, hemmorhagic shock, pulmonary fibrosis, and uveitis, diabetes and Parkinsons disease, liver toxicity following acetominophen overdose, cardiac and kidney toxicities from doxorubicin and platinum-based antineoplastic agents and skin damage secondary to sulfur mustards. PARP inhibitors have also been shown to potentiate radiation and chemotherapy by increasing cell death of cancer cells, limiting tumor growth, decreasing metastasis, and prolonging the survival of tumor-bearing animals.

US 2002/0183325 A1 describes phthalazinone derivatives as PARP inhibitors. US 2004/0023968 A1 describes phthalazinone derivatives as PARP inhibitors. US 2005/0085476 A1 describes fused pyridazine derivatives as PARP inhibitors. US 2005/0059663 A1 describes phthalazinone derivatives as PARP inhibitors. US 2006/0063767 A1 describes phthalazinone derivatives as PARP inhibitors. US 2006/0142293 A1 describes phthalazinone derivatives as PARP inhibitors. US 2006/0149059 A1 describes phthalazinone derivatives as PARP inhibitors. US 2007/0093489 A1 describes phthalazinone derivatives as PARP inhibitors.

There is therefore a need in the therapeutic arts for PARP inhibitors. Such compounds can be used to treat subjects suffering from cancer, and can further expand the range of treatment options available for such subjects.

SUMMARY OF THE INVENTION

One embodiment of this invention, therefore, pertains to compounds that inhibit the activity of poly(ADP-ribose) polymerase and have formula I

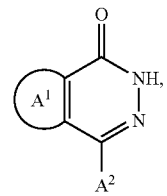

(I)

and pharmaceutically acceptable salts thereof, wherein $A^1$ is $R^1$ or $R^2$, wherein $A^1$ is unsubstituted or substituted with one or two OH, CN, $C_1$-alkyl, $C_2$-alkyl, $C_3$-alkyl, $C_4$-alkyl, $C_5$-alkyl, cycloalkane, $OR^A$ or $NR^A R^A$;

$R^A$ is H or alkyl;

$R^1$ is cycloalkane or cycloalkene each of which is unfused or fused with $R^{1A}$;

$R^{1A}$ is benzene, heteroarene, cycloalkane, cycloalkene, heterocycloalkane or heterocycloalkene;

$R^2$ is heterocycloalkane or heterocycloalkene; each of which is unfused or fused with $R^{2A}$;

$R^{2A}$ is benzene, heteroarene, cycloalkane, cycloalkene, heterocycloalkane or heterocycloalkene;

$A^2$ is $OR^4$, $NHR^4$, $N(R^4)_2$, $SR^4$, $S(O)R^4$, $SO_2R^4$ or $R^5$;

wherein each $R^4$ is $C_1$-alkyl, $C_2$-alkyl or $C_3$-alkyl; each of which is substituted with $R^{10}$;

$R^5$ is $C_1$-alkyl, $C_2$-alkyl, $C_3$-alkyl, $C_4$-alkyl or $C_5$-alkyl; each of which is substituted with $R^{10}$, and further unsubstituted or substituted with one or two or three of independently selected $OR^{10}$, $NHR^{10}$, $N(R^{10})_2$, $SR^{10}$, $S(O)R^{10}$, $SO_2R^{10}$ or $CF_3$;

wherein each $R^{10}$ is $R^{10A}$, $R^{10B}$ or $R^{10C}$; each of which must be attached at a carbon atom;

$R^{10A}$ is phenyl which is unfused or fused with benzene, heteroarene, cycloalkane, cycloalkene, heterocycloalkane or heterocycloalkene; each of which are unfused or fused with benzene, heteroarene, cycloalkane, cycloalkene, heterocycloalkane or heterocycloalkene;

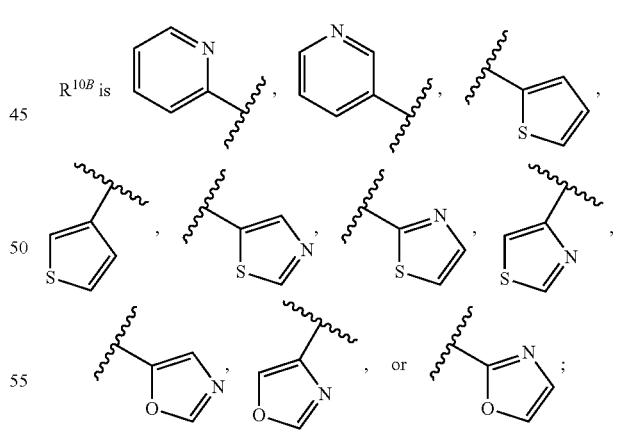

each of which is unfused or fused with benzene, heteroarene, cycloalkane, cycloalkene, heterocycloalkane or heterocycloalkene; each of which are unfused or fused with benzene, heteroarene, cycloalkane, cycloalkene, heterocycloalkane or heterocycloalkene;

$R^{10C}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene;

wherein each $R^{10}$ is independently unsubstituted or substituted with one or two or three of independently selected, $R^{11}$, $OR^{11}$, $SR^{11}$, $S(O)R^{11}$, $SO_2R^{11}$, $NH_2$, $NHR^{11}$, $N(R^{11})_2$, $C(O)R^{11}$, $C(O)OR^{11}$, $C(O)NH_2$, $C(O)NHR^{11}$, $C(O)N(R^{11})_2$, $NHC(O)R^{11}$, $NR^{11}C(O)R^{11}$, $NHSO_2R^{11}$, $NR^{11}SO_2R^{11}$, $NHC(O)OR^{11}$, $NR^{11}C(O)OR^{11}$, $NHSO_2NH_2$, $NHSO_2NHR^{11}$, $NHSO_2N(R^{11})_2$, $SO_2NH_2$, $SO_2NHR^{11}$, $SO_2N(R^{11})_2$, $NHC(O)NH_2$, $NHC(O)NHR^{11}$, $NHC(O)N(R^{11})_2$, $NR^{11}C(O)N(R^{11})_2$, $NO_2$, $OH$, $(O)$, $C(O)H$, $C(O)OH$, $CN$, $CF_3$, $OCF_3$, $CF_2CF_3$, F, Cl, Br or I;

wherein each $R^{11}$ is $R^{12}$, $R^{13}$, $R^{14}$ or $R^{15}$;

$R^{12}$ is phenyl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{13}$ is heteroaryl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{14}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{15}$ is alkyl, alkenyl or alkynyl; each of which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NH_2$, $C(O)NHR^{16}$, $C(O)N(R^{16})_2$, $NHC(O)R^{16}$, $NR^{16}C(O)R^{16}$, $NHC(O)OR^{16}$, $NR^{16}C(O)OR^{16}$, OH, F, Cl, Br or I;

wherein each $R^{16}$ is $R^{17}$ or $R^{17A}$;

$R^{17}$ is alkyl, alkenyl or alkynyl; each of which is unsubstituted or substituted with one or two of independently selected $R^{18}$, $C(O)OH$, $NH_2$, $NHR^{18}$ or $N(R^{18})_2$, $C(O)R^{18}$, $C(O)NH_2$, $C(O)NHR^{18}$, $C(O)N(R^{18})_2$, $NHC(O)R^{18}$, $NR^{18}C(O)R^{18}$, F, Cl, Br or I;

$R^{17A}$ is phenyl, heteroaryl, cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

wherein each $R^{18}$ is phenyl, heteroaryl, cycloalkyl, cycloalkenyl, heterocycloalkyl or heterocycloalkenyl;

wherein each of the moieties represented by $R^{12}$, $R^{13}$, $R^{14}$, $R^{17A}$, and $R^{18}$ are independently unsubstituted or substituted with one or two or three or four of independently selected $R^{19}$, $OR^{19}$, $SR^{19}$, $S(O)R^{19}$, $SO_2R^{19}$, $C(O)R^{19}$, $CO(O)R^{19}$, $OC(O)R^{19}$, $OC(O)OR^{19}$, $NH_2$, $NHR^{19}$, $N(R^{19})_2$, $NHC(O)R^{19}$, $NR^{19}C(O)R^{19}$, $NHS(O)_2R^{19}$, $NR^{19}S(O)_2R^{19}$, $NHC(O)OR^{19}$, $NR^{19}C(O)OR^{19}$, $NHC(O)NH_2$, $NHC(O)NHR^{19}$, $NHC(O)N(R^{19})_2$, $NR^{19}(O)NHR^{19}$, $NR^{19}C(O)N(R^{19})_2$, $C(O)NH_2$, $C(O)NHR^{19}$, $C(O)N(R^{19})_2$, $C(O)NHOH$, $C(O)NHOR^{19}$, $C(O)NHSO_2R^{19}$, $C(O)NR^{19}SO_2R^{19}$, $SO_2NH_2$, $SO_2NHR^{19}$, $SO_2N(R^{19})_2$, $C(O)H$, $C(O)OH$, $C(N)NH_2$, $C(N)NHR^{19}$, $C(N)N(R^{19})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

wherein each $R^{19}$ is $R^{20}$, $R^{21}$, $R^{22}$ or $R^{23}$;

$R^{20}$ is phenyl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{21}$ is heteroaryl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{22}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{23}$ is alkyl, alkenyl or alkynyl; each of which is unsubstituted or substituted with one or two of independently selected $R^{24}$, $OR^{24}$, $SR^{24}$, $S(O)_2R^{24}$, $C(O)OH$, $NH_2$, $NHR^{24}N(R^{24})_2$, $C(O)R^{24}$, $C(O)NH_2$, $C(O)NHR^{24}$, $C(O)N(R^{24})_2$, $NHC(O)R^{24}$, $NR^{24}C(O)R^{24}$, $NHC(O)OR^{24}$, $NR^{24}C(O)OR^{24}$, $NHS(O)_2R^{24}$, $NR^{24}S(O)_2R^{24}$, OH, F, Cl, Br or I;

wherein each $R^{24}$ is $R^{24A}$ or $R^{24B}$;

$R^{24A}$ is phenyl, heteroaryl, cycloalkyl, cycloalkenyl, heterocycloalkyl or heterocycloalkenyl each of which is unfused or fused with benzene, heteroarene, cycloalkane, cycloalkene, heterocycloalkane or heterocycloalkene;

$R^{24B}$ is alkyl, alkenyl or alkynyl each of which is unsubstituted or substituted with one or two of independently selected $R^{25}$, $OR^{25}$, $SR^{25}$, $S(O)_2R^{25}$, $C(O)OH$, $NH_2$, $NHR^{25}N(R^{25})_2$, $C(O)R^{25}$, $C(O)NH_2$, $C(O)NHR^{25}$, $C(O)N(R^{25})_2$, $NHC(O)R^{25}$, $NR^{25}C(O)R^{25}$, $NHC(O)OR^{25}$, $NR^{25}C(O)OR^{25}$, OH, F, Cl, Br or I;

wherein each $R^{25}$ is alkyl, phenyl, heteroaryl, cycloalkyl, cycloalkenyl, heterocycloalkyl or heterocycloalkenyl; each of which is unsubstituted or substituted with $NH_2$, $NH(CH_3)$, $N(CH_3)_2$, OH or $OCH_3$;

wherein each of the moieties represented by $R^{20}$, $R^{21}$, $R^{22}$, and $R^{24A}$ are independently unsubstituted or substituted with one or two of independently selected $R^{26}$, $OR^{26}$, alkenyl, alkynyl, phenyl, OH, (O), $C(O)OH$, CN, $CF_3$, $OCF_3$, $CF_2CF_3$, F, Cl, Br or I; and $R^{26}$ is alkyl.

Still another embodiment comprises pharmaceutical compositions comprising a compound having formula I and an excipient.

Still another embodiment comprises methods of inhibiting PARP in a mammal comprising administering thereto a therapeutically acceptable amount of a compound having formula I.

Still another embodiment comprises methods of treating cancer in a mammal comprising administering thereto a therapeutically acceptable amount of a compound having formula I

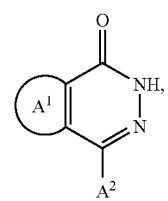

(I)

or a salt thereof, wherein $A^1$ is $R^1$ or $R^2$, wherein $A^1$ is unsubstituted or substituted with one or two OH, CN, $C_1$-alkyl, $C_2$-alkyl, $C_3$-alkyl, $C_4$-alkyl, $C_5$-alkyl, cycloalkane, $OR^A$ or $NR^AR^A$;

$R^A$ is H or alkyl;

$R^1$ is cycloalkane or cycloalkene each of which is unfused or fused with $R^{1A}$;

$R^{1A}$ is benzene, heteroarene, cycloalkane, cycloalkene, heterocycloalkane or heterocycloalkene;

$R^2$ is heterocycloalkane or heterocycloalkene; each of which is unfused or fused with $R^{2A}$;

$R^{2A}$ is benzene, heteroarene, cycloalkane, cycloalkene, heterocycloalkane or heterocycloalkene;

$A^2$ is $OR^4$, $NHR^4$, $N(R^4)_2$, $SR^4$, $S(O)R^4$, $SO_2R^4$ or $R^5$;

wherein each $R^4$ is $C_1$-alkyl, $C_2$-alkyl or $C_3$-alkyl; each of which is substituted with $R^{10}$;

$R^5$ is $C_1$-alkyl, $C_2$-alkyl, $C_3$-alkyl, $C_4$-alkyl or $C_5$-alkyl; each of which is substituted with $R^{10}$, and further unsubstituted or substituted with one or two or three of independently selected $OR^{10}$, $NHR^{10}$, $N(R^{10})_2$, $SR^{10}$, $S(O)R^{10}$, $SO_2R^{10}$ or $CF_3$;

wherein each $R^{10}$ is $R^{10A}$, $R^{10B}$ or $R^{10C}$; each of which must be attached at a carbon atom;

$R^{10A}$ is phenyl which is unfused or fused with benzene, heteroarene, cycloalkane, cycloalkene, heterocycloalkane or heterocycloalkene; each of which are unfused or fused with benzene, heteroarene, cycloalkane, cycloalkene, heterocycloalkane or heterocycloalkene;

$R^{10B}$ is

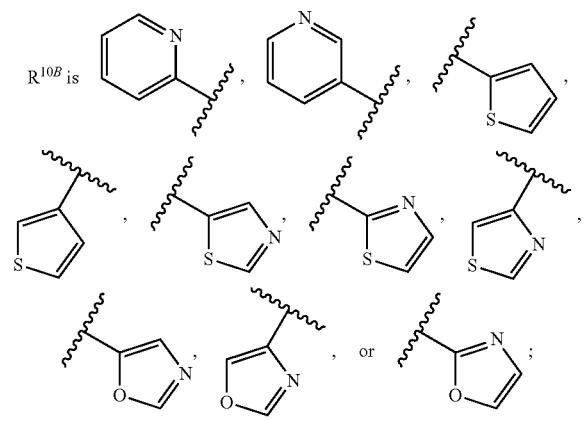

each of which is unfused or fused with benzene, heteroarene, cycloalkane, cycloalkene, heterocycloalkane or heterocycloalkene; each of which are unfused or fused with benzene, heteroarene, cycloalkane, cycloalkene, heterocycloalkane or heterocycloalkene;

$R^{10C}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene;

wherein each $R^{10}$ is independently unsubstituted or substituted with one or two or three of independently selected, $R^{11}$, $OR^{11}$, $SR^{11}$, $S(O)R^{11}$, $SO_2R^{11}$, $NH_2$, $NHR^{11}$, $N(R^{11})_2$, $C(O)R^{11}$, $C(O)OR^{11}$, $C(O)NH_2$, $C(O)NHR^{11}$, $C(O)N(R^{11})_2$, $NHC(O)R^{11}$, $NR^{11}C(O)R^{11}$, $NHSO_2R^{11}$), $NR^{11}SO_2R^{11}$, $NHC^{11}(O)OR^{11}$, $NR^{11}C(O)OR^{11}$, $NHSO_2NH_2$, $NHSO_2NHR^{11}$, $NHSO_2N(R^{11})_2$, $SO_2NH_2$, $SO_2NHR^{11}$, $SO_2N(R^{11})_2$, $NHC(O)NH_2$, $NHC(O)NHR^{11}$, $NHC(O)N(R^{11})_2$, $NR^{11}C(O)N(R^{11})_2$, $NO_2$, $OH$, $(O)$, $C(O)H$, $C(O)OH$, $CN$, $CF_3$, $OCF_3$, $CF_2CF_3$, $F$, $Cl$, $Br$ or $I$;

wherein each $R^{11}$ is $R^{12}$, $R^{13}$, $R^{14}$ or $R^{15}$;

$R^{12}$ is phenyl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{13}$ is heteroaryl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{14}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{15}$ is alkyl, alkenyl or alkynyl; each of which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NH_2$, $C(O)NHR^{16}$, $C(O)N(R^{16})_2$, $NHC(O)R^{16}$, $NR^{16}C(O)R^{16}$, $NHC(O)OR^{16}$, $NR^{16}C(O)OR^{16}$, $OH$, $F$, $Cl$, $Br$ or $I$;

wherein each $R^{16}$ is $R^{17}$ or $R^{17A}$;

$R^{17}$ is alkyl, alkenyl or alkynyl; each of which is unsubstituted or substituted with one or two of independently selected $R^{18}$, $C(O)OH$, $NH_2$, $NHR^{IS}$ or $N(R^{18})_2$, $C(O)R^{18}$, $C(O)NH_2$, $C(O)NHR^{18}$, $C(O)N(R^{18})_2$, $NHC(O)R^{18}$, $NR^{18}C(O)R^{18}$, $F$, $Cl$, $Br$ or $I$;

$R^{17A}$ is phenyl, heteroaryl, cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

wherein each $R^{18}$ is phenyl, heteroaryl, cycloalkyl, cycloalkenyl, heterocycloalkyl or heterocycloalkenyl;

wherein each of the moieties represented by $R^{12}$, $R^{13}$, $R^{14}$, $R^{17A}$, and $R^{18}$ are independently unsubstituted or substituted with one or two or three or four of independently selected $R^{19}$, $OR^{19}$, $SR^{19}$, $S(O)R^{19}$, $SO_2R^{19}$, $C(O)R^{19}$, $CO(O)R^{19}$, $OC(O)R^{19}$, $OC(O)OR^{19}$, $NH_2$, $NHR^{19}$, $N(R^{19})_2$, $NHC(O)R^{19}$, $NR^{19}C(O)R^{19}$, $NHS(O)_2R^{19}$, $NR^{19}S(O)_2R^{19}$, $NHC(O)OR^{19}$, $NR^{19}C(O)OR^{19}$, $NHC(O)NH_2$, $NHC(O)NHR^{19}$, $NHC(O)N(R^{19})_2$, $NR^{19}C(O)NHR^{19}$, $NR^{19}C(O)N(R^{19})_2$, $C(O)NH_2$, $C(O)NHR^{19}$, $C(O)N(R^{19})_2$, $C(O)NHOH$, $C(O)NHOR^{19}$, $C(O)NHSO_2R^{19}$, $C(O)NR^{19}SO_2R^{19}$, $SO_2NH_2$, $SO_2NHR^{19}$, $SO_2N(R^{19})_2$, $C(O)H$, $C(O)OH$, $C(N)NH_2$, $C(N)NHR^{19}$, $C(N)N(R^{19})_2$, $CNOH$, $CNOCH_3$, $OH$, $(O)$, $CN$, $N_3$, $NO_2$, $CF_3$, $CF_2CF_3$, $OCF_3$, $OCF_2CF_3$, $F$, $Cl$, $Br$ or $I$;

wherein each $R^{19}$ is $R^{20}$, $R^{21}$, $R^{22}$ or $R^{23}$;

$R^{20}$ is phenyl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{21}$ is heteroaryl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{22}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{23}$ is alkyl, alkenyl or alkynyl; each of which is unsubstituted or substituted with one or two of independently selected $R^{24}$, $OR^{24}$, $SR^{24}$, $S(O)_2R^{24}$, $C(O)OH$, $NH_2$, $NHR^{24}N(R^{24})_2$, $C(O)R^{24}$, $C(O)NH_2$, $C(O)NHR^{24}$, $C(O)N(R^{24})_2$, $NHC(O)R^{24}$, $NR^{24}C(O)R^{24}$, $NHC(O)OR^{24}$, $NR^{24}C(O)OR^{24}$, $NHS(O)_2R^{24}$, $NR^{24}S(O)_2R^{24}$, $OH$, $F$, $Cl$, $Br$ or $I$;

wherein each $R^{24}$ is $R^{24A}$ or $R^{24B}$;

$R^{24A}$ is phenyl, heteroaryl, cycloalkyl, cycloalkenyl, heterocycloalkyl or heterocycloalkenyl each of which is unfused or fused with benzene, heteroarene, cycloalkane, cycloalkene, heterocycloalkane or heterocycloalkene;

R²⁴ᴮ is alkyl, alkenyl or alkynyl each of which is unsubstituted or substituted with one or two of independently selected R²⁵, OR²⁵, SR²⁵, S(O)₂R²⁵, C(O)OH, NH₂, NHR²⁵N(R²⁵)₂, C(O)R²⁵, C(O)NH₂, C(O)NHR²⁵, C(O)N(R²⁵)₂, NHC(O)R²⁵, NR²⁵C(O)R²⁵, NHC(O)OR²⁵NR²⁵C(O)OR²⁵, OH, F, Cl, Br or I;

wherein each R²⁵ is alkyl, phenyl, heteroaryl, cycloalkyl, cycloalkenyl, heterocycloalkyl or heterocycloalkenyl; each of which is unsubstituted or substituted with NH₂, NH(CH₃), N(CH₃)₂, OH or OCH₃;

wherein each of the moieties represented by R²⁰, R²¹, R²², and R²⁴ᴬ are independently unsubstituted or substituted with one or two of independently selected R²⁶, OR²⁶, alkenyl, alkynyl, phenyl, OH, (O), C(O)OH, CN, CF₃, OCF₃, CF₂CF₃, F, Cl, Br or I; and R²⁶ is alkyl.

Still another embodiment comprises methods for decreasing tumor volume in a mammal comprising administering thereto a therapeutically acceptable amount of a compound having formula I Still another embodiment comprises the use of a compound of Formula I for the preparation of a medicament for the treatment of cancer.

Still another embodiment comprises a method of treating leukemia, colon cancer, glioblastomas, lymphomas, melanomas, carcinomas of the breast or cervical carcinomas in a mammal comprising administering thereto a therapeutically acceptable amount of a compound having formula I.

Still another embodiment comprises the use of a compound of Formula I for the preparation of a medicament for the treatment of leukemia, colon cancer, glioblastomas, lymphomas, melanomas, carcinomas of the breast or cervical carcinomas.

Still another embodiment comprises methods for potentiation of cytotoxic cancer therapy in a mammal comprising administering thereto a therapeutically acceptable amount of a compound having formula I.

Still another embodiment comprises methods for potentiation of radiation therapy in a mammal comprising administering thereto a therapeutically acceptable amount of a compound having formula I.

Still another embodiment comprises methods of treating ischemia reperfusion injury associated with myocardial infarction, stroke, neural trauma or organ transplantation in a mammal comprising administering thereto a therapeutically acceptable amount of a compound having formula I.

Still another embodiment comprises methods of treating reperfusion of the eye, kidney, gut or skeletal muscle in a mammal comprising administering thereto a therapeutically acceptable amount of a compound having formula I.

Still another embodiment comprises methods of treating arthritis, gout, inflammatory bowel disease, CNS inflammation, multiple sclerosis, allergic encephalitis, sepsis, septic shock, hemmorhagic shock, pulmonary fibrosis or uveitis in a mammal comprising administering thereto a therapeutically acceptable amount of a compound having formula I.

Still another embodiment comprises a method of treating rheumatoid arthritis or septic shock in a mammal comprising administering thereto a therapeutically acceptable amount of a compound having formula I.

Still another embodiment comprises methods of treating diabetes or Parkinsons disease in a mammal comprising administering thereto a therapeutically acceptable amount of a compound having formula I.

Still another embodiment comprises methods of treating hypoglycemia in a mammal comprising administering thereto a therapeutically acceptable amount of a compound having formula I.

Still another embodiment comprises methods of treating retroviral infection in a mammal comprising administering thereto a therapeutically acceptable amount of a compound having formula I.

Still another embodiment comprises methods of treating liver toxicity following acetaminophen overdose in a mammal comprising administering thereto a therapeutically acceptable amount of a compound having formula I.

Still another embodiment comprises a method of treating cardiac or kidney toxicities from doxorubicin or platinum based antineoplastic agents in a mammal comprising administering thereto a therapeutically acceptable amount of a compound having formula I.

Still another embodiment comprises methods of treating skin damage secondary to sulfur mustards in a mammal comprising administering thereto a therapeutically acceptable amount of a compound having formula I.

Still another embodiment comprises the compounds 2-fluoro-5-((4-oxo-3,4,5,6,7,8-hexahydrophthalazin-1-yl)methyl)benzoic acid;

4-(3-amino-4-fluorobenzyl)-5,6,7,8-tetrahydrophthalazin-1(2H)-one;

4-((2-fluoro-5-((4-oxo-3,4,5,6,7,8-hexahydrophthalazin-1-yl)methyl)phenyl)amino)-4-oxobutanoic acid;

1-(2-fluoro-5-((4-oxo-3,4,5,6,7,8-hexahydrophthalazin-1-yl)methyl)phenyl)pyrrolidine-2,5-dione;

4-(3-(1,4-diazepan-1-ylcarbonyl)-4-fluorobenzyl)-5,6,7,8-tetrahydrophthalazin-1(2H)-one;

4-(3-(aminomethyl)-4-fluorobenzyl)-5,6,7,8-tetrahydrophthalazin-1(2H)-one;

4-(3-((dimethylamino)methyl)-4-fluorobenzyl)-5,6,7,8-tetrahydrophthalazin-1(2H)-one;

4-(4-fluoro-3-((isopropylamino)methyl)benzyl)-5,6,7,8-tetrahydrophthalazin-1(2H)-one;

4-(3-((cyclohexylamino)methyl)-4-fluorobenzyl)-5,6,7,8-tetrahydrophthalazin-1(2H)-one;

4-(4-fluoro-3-((tetrahydro-2H-pyran-4-ylamino)methyl)benzyl)-5,6,7,8-tetrahydrophthalazin-1(2H)-one;

4-(4-fluoro-3-((methyl((1-methylpyrrolidin-3-yl)methyl)amino)methyl)benzyl)-5,6,7,8-tetrahydrophthalazin-1(2H)-one;

4-(4-fluoro-3-((methyl(((2R)-1-methylpyrrolidin-2-yl)methyl)amino)methyl)benzyl)-5,6,7,8-tetrahydrophthalazin-1(2H)-one;

4-(3-((cyclopropylamino)methyl)benzyl)-5,6,7,8-tetrahydrophthalazin-1(2H)-one;

4-(3-((ispropyamino)methy)benzyl)-5,6,7,8-tetrahydrophthalazin-1(2H)-one;

4-(3-(morpholin-4-ylmethyl)benzyl)-5,6,7,8-tetrahydrophthalazin-1(2H)-one;

4-(3-(pyrrolidin-1-ylmethyl)benzyl)-5,6,7,8-tetrahydrophthalazin-1(2H)-one;

4-(3-((cyclohexylamino)methyl)benzyl)-5,6,7,8-tetrahydrophthalazin-1(2H)-one;

4-(3-((methylamino)methyl)benzyl)-5,6,7,8-tetrahydrophthalazin-1(2H)-one;

4-(3-((ethylamino)methyl)benzyl)-5,6,7,8-tetrahydrophthalazin-1(2H)-one;

4-(3-((4-methylpiperidin-1-yl)methyl)benzyl)-5,6,7,8-tetrahydrophthalazin-1(2H)-one;

4-(3-(((2-(4-(trifluoromethyl)phenyl)ethyl)amino)methyl)benzyl)-5,6,7,8-tetrahydrophthalazin-1(2H)-one;

4-(3-((cyclohexyl(methyl)amino)methyl)benzyl)-5,6,7,8-tetrahydrophthalazin-1(2H)-one;
4-(3-((2-ethylpyrrolidin-1-yl)methyl)benzyl)-5,6,7,8-tetrahydrophthalazin-1(2H)-one;
4-(4-((cyclopropylamino)methyl)benzyl)-5,6,7,8-tetrahydrophthalazin-1(2H)-one;
4-(4-((isopropylamino)methyl)benzyl)-5,6,7,8-tetrahydrophthalazin-1(2H)-one;
4-(4-(morpholin-4-ylmethyl)benzyl)-5,6,7,8-tetrahydrophthalazin-1(2H)-one;
4-(4-(pyrrolidin-1-ylmethyl)benzyl)-5,6,7,8-tetrahydrophthalazin-1(2H)-one;
4-(4-((cyclohexylamino)methyl)benzyl)-5,6,7,8-tetrahydrophthalazin-1(2H)-one;
4-(4-((4-phenylpiperidin-1-yl)methyl)benzyl)-5,6,7,8-tetrahydrophthalazin-1(2H)-one;
4-(4-((methylamino)methyl)benzyl)-5,6,7,8-tetrahydrophthalazin-1(2H)-one;
4-(4-((ethylamino)methyl)benzyl)-5,6,7,8-tetrahydrophthalazin-1(2H)-one;
4-(4-((4-methylpiperidin-1-yl)methyl)benzyl)-5,6,7,8-tetrahydrophthalazin-1(2H)-one;
4-(4-(((2-(3-(trifluoromethyl)phenyl)ethyl)amino)methyl)benzyl)-5,6,7,8-tetrahydrophthalazin-1(2H)-one;
4-(4-((cyclohexyl(methyl)amino)methyl)benzyl)-5,6,7,8-tetrahydrophthalazin-1(2H)-one;
4-(4-((2-methylpyrrolidin-1-yl)methyl)benzyl)-5,6,7,8-tetrahydrophthalazin-1(2H)-one;
4-(4-((4-methyl-1,4-diazepan-1-yl)methyl)benzyl)-5,6,7,8-tetrahydrophthalazin-1(2H)-one;
4-(3-((4-methyl-1,4-diazepan-1-yl)methyl)benzyl)-5,6,7,8-tetrahydrophthalazin-1(2H)-one;
4-(4-fluoro-3-pyrimidin-2-ylbenzyl)-5,6,7,8-tetrahydrophthalazin-1(2H)-one;
4-(4-fluoro-3-pyridin-3-ylbenzyl)-5,6,7,8-tetrahydrophthalazin-1(2H)-one;
4-(4-fluoro-3-pyridin-4-ylbenzyl)-5,6,7,8-tetrahydrophthalazin-1(2H)-one;
N,N-diethyl-2'-fluoro-5'-((4-oxo-3,4,5,6,7,8-hexahydrophthalazin-1-yl)methyl)-1,1'-biphenyl-2-carboxamide;
N-(2-fluoro-5-((4-oxo-3,4,5,6,7,8-hexahydrophthalazin-1-yl)methyl)phenyl)-3-piperidin-1-ylpropanamide;
N-(2-fluoro-5-((4-oxo-3,4,5,6,7,8-hexahydrophthalazin-1-yl)methyl)phenyl)-3-(4-methylpiperazin-1-yl)propanamide;
2-amino-N-(2-fluoro-5-((4-oxo-3,4,5,6,7,8-hexahydrophthalazin-1-yl)methyl)phenyl)acetamide.
3-cyclohexyl-N-(2-fluoro-5-((4-oxo-3,4,5,6,7,8-hexahydrophthalazin-1-yl)methyl)phenyl)propanamide;
N-(2-fluoro-5-((4-oxo-3,4,5,6,7,8-hexahydrophthalazin-1-yl)methyl)phenyl)piperidine-3-carboxamide;
4-(4-fluoro-3-(2-oxopyrrolidin-1-yl)benzyl)-5,6,7,8-tetrahydrophthalazin-1(2H)-one;
N-(2-fluoro-5-((4-oxo-3,4,5,6,7,8-hexahydrophthalazin-1-yl)methyl)phenyl)azetidine-3-carboxamide;
N-(2-(isopropylamino)ethyl)-3-((4-oxo-3,4,5,6,7,8-hexahydrophthalazin-1-yl)methyl)benzamide;
N-(2-fluoro-5-((4-oxo-3,4,5,6,7,8-hexahydrophthalazin-1-yl)methyl)phenyl)-2-morpholin-4-ylacetamide;
N-(2-morpholin-4-ylethyl)-3-((4-oxo-3,4,5,6,7,8-hexahydrophthalazin-1-yl)methyl)benzamide;
3-((4-oxo-3,4,5,6,7,8-hexahydrophthialazin-1-yl)methyl)-N-(2-pyrrolidin-1-ylethyl)benzamide;
4-(3-((2-methylpyrrolidin-1-yl)carbonyl)benzyl)-5,6,7,8-tetrahydrophthalazin-1(2H)-one;
N-azepan-1-yl-3-((4-oxo-3,4,5,6,7,8-hexahydrophthalazin-1-yl)methyl)benzamide;
4-(3-(piperazin-1-ylcarbonyl)benzyl)-5,6,7,8-tetrahydrophthalazin-1(2H)-one;
N-azetidin-3-yl-3-((4-oxo-3,4,5,6,7,8-hexahydrophthalazin-1-yl)methyl)benzamide;
3-((4-oxo-3,4,5,6,7,8-hexahydrophthialazin-1-yl)methyl)N-piperidin-3-ylbenzamide;
N-(4-(dimethylamino)phenyl)-3-((4-oxo-3,4,5,6,7,8-hexahydrophthalazin-1-yl)methyl)benzamide;
N-(2-(4-methylpiperazin-1-yl)ethyl)-3-((4-oxo-3,4,5,6,7,8-hexahydrophthalazin-1-yl)methyl)benzamide;
4-(3-((4-(isoxazol-5-ylcarbonyl)piperazin-1-yl)carbonyl)benzyl)-5,6,7,8-tetrahydrophthalazin-1(2H)-one;
4-(3-((4-phenylpiperidin-1-yl)carbonyl)benzyl)-5,6,7,8-tetrahydrophthalazin-1(2H)-one;
3-((4-oxo-3,4,5,6,7,8-hexahydrophthalazin-1-yl)methyl)-N-(piperidin-2-ylmethyl)benzamide;
3-((4-oxo-3,4,5,6,7,8-hexahydrophthalazin-1-yl)methyl)-N-(piperidin-4-ylmethyl)benzamide;
3-((4-oxo-3,4,5,6,7,8-hexahydrophthalazin-1-yl)methyl)-N-(2-piperidin-1-ylethyl)benzamide;
N-(1-methylazetidin-3-yl)-3-((4-oxo-3,4,5,6,7,8-hexahydrophthalazin-1-yl)methyl)benzamide;
methyl 4-((4-oxo-3,4,5,6,7,8-hexahydrophthalazin-1-yl)methyl)pyridine-2-carboxylate;
N-methyl-4-((4-oxo-3,4,5,6,7,8-hexahydrophthalazin-1-yl)methyl)pyridine-2-carboxamide;
4-((2-(methylthio)pyrimidin-4-yl)methyl)-5,6,7,8-tetrahydrophthalazin-1(2H)-one;
4-((2-(methylsulfonyl)pyrimidin-4-yl)methyl)-5,6,7,8-tetrahydrophthalazin-1(2H)-one;
4-((2-(methylsulfinyl)pyrimidin-4-yl)methyl)-5,6,7,8-tetrahydrophthalazin-1(2H)-one;
4-((3-bromopyridin-4-yl)methyl)-5,6,7,8-tetrahydrophthalazin-1(2H)-one;
4-((6-bromopyridin-3-yl)methyl)-5,6,7,8-tetrahydrophthalazin-1(2H)-one;
4-((2-bromopyridin-3-yl)methyl)-5,6,7,8-tetrahydrophthalazin-1(2H)-one;
methyl 6-((4-oxo-3,4,5,6,7,8-hexahydrophthalazin-1-yl)methyl)pyridine-2-carboxylate;
N-ethyl-4-((4-oxo-3,4,5,6,7,8-hexahydrophthalazin-1-yl)methyl)pyridine-2-carboxamide;
N-isopropyl-4-((4-oxo-3,4,5,6,7,8-hexahydrophthalazin-1-yl)methyl)pyridine-2-carboxamide;
N-cyclohexyl-4-((4-oxo-3,4,5,6,7,8-hexahydrophthalazin-1-yl)methyl)pyridine-2-carboxamide;
N-((1-methylpiperidin-2-yl)methyl)-3-((4-oxo-3,4,5,6,7,8-hexahydrophthalazin-1-yl)methyl)benzamide;
N-((1-methylpiperidin-4-yl)methyl)-3-((4-oxo-3,4,5,6,7,8-hexahydrophthalazin-1-yl)methyl)benzamide;
N-methyl-6-((4-oxo-3,4,5,6,7,8-hexahydrophthalazin-1-yl)methyl)pyridine-2-carboxamide;
N-ethyl-6-((4-oxo-3,4,5,6,7,8-hexahydrophthalazin-1-yl)methyl)pyridine-2-carboxamide;
N-isopropyl-6-((4-oxo-3,4,5,6,7,8-hexahydrophthalazin-1-yl)methyl)pyridine-2-carboxamide;
N-cyclopropyl-6-((4-oxo-3,4,5,6,7,8-hexahydrophthalazin-1-yl)methyl)pyridine-2-carboxamide;
N-cyclohexyl-6-((4-oxo-3,4,5,6,7,8-hexahydrophthalazin-1-yl)methyl)pyridine-2-carboxamide;
methyl 3-((4-oxo-3,4,5,6,7,8-hexahydrophthalazin-1-yl)methyl)pyridine-2-carboxylate;
methyl 5-((4-oxo-3,4,5,6,7,8-hexahydrophthalazin-1-yl)methyl)pyridine-2-carboxylate;
4-((5-bromothien-2-yl)methyl)-5,6,7,8-tetrahydrophthalazin-1(2H)-one;

4-((3-bromothien-2-yl)methyl)-5,6,7,8-tetrahydrophthalazin-1(2H)-one;
4-(3-aminobenzyl)-5,6,7,8-tetrahydrophthalazin-1(2H)-one;
4-(3-bromobenzyl)-5,6,7,8-tetrahydrophthalazin-1(2H)-one;
4-(thien-2-ylmethyl)-5,6,7,8-tetrahydrophthalazin-1(2H)-one;
methyl 5-((4-oxo-3,4,5,6,7,8-hexahydrophthalazin-1-yl)methyl)thiophene-2-carboxylate;
N-methyl-5-((4-oxo-3,4,5,6,7,8-hexahydrophthalazin-1-yl)methyl)pyridine-2-carboxamide;
N-ethyl-5-((4-oxo-3,4,5,6,7,8-hexahydrophthalazin-1-yl)methyl)pyridine-2-carboxamide;
N-methyl-3-((4-oxo-3,4,5,6,7,8-hexahydrophthalazin-1-yl)methyl)pyridine-2-carboxamide;
N-ethyl-3-((4-oxo-3,4,5,6,7,8-hexahydrophthalazin-1-yl)methyl)pyridine-2-carboxamide;
N,N-dimethyl-N'-(3-((4-oxo-3,4,5,6,7,8-hexahydrophthalazin-1-yl)methyl)phenyl)sulfamide;
N-(3-((4-oxo-3,4,5,6,7,8-hexahydrophthalazin-1-yl)methyl)phenyl)-3-piperidin-1-ylpropanamide;
4-chloro-N-(3-((4-oxo-3,4,5,6,7,8-hexahydrophthalazin-1-yl)methyl)phenyl)butanamide;
4-(2-oxopyrrolidin-1-yl)benzyl)-5,6,7,8-tetrahydrophthalazin-1(2H)-one;
4-((2-(2-oxoazetidin-1-yl)pyridin-4-yl)methyl)-5,6,7,8-tetrahydrophthalazin-1(2H)-one;
4-((2-(2-oxopyrrolidin-1-yl)pyridin-4-yl)methyl)-5,6,7,8-tetrahydrophthalazin-1(2H)-one;
4-((2-bromopyridin-4-yl)methyl)-5,6,7,8-tetrahydrophthalazin-1(2H)-one;
4-((6-(2-oxopyrrolidin-1-yl)pyridin-3-yl)methyl)-5,6,7,8-tetrahydrophthalazin-1(2H)-one;
4-((6-(2-oxoazetidin-1-yl)pyridin-3-yl)methyl)-5,6,7,8-tetrahydrophthalazin-1(2H)-one;
N-(5-((4-oxo-3,4,5,6,7,8-hexahydrophthalazin-1-yl)methyl)pyridin-2-yl)benzamide;
N-(5-((4-oxo-3,4,5,6,7,8-hexahydrophthalazin-1-yl)methyl)pyridin-2-yl)isonicotinamide;
N-(5-((4-oxo-3,4,5,6,7,8-hexahydrophthalazin-1-yl)methyl)pyridin-2-yl)nicotinamide;
4-((5'-((4-oxo-3,4,5,6,7,8-hexahydrophthalazin-1-yl)methyl)-2,2'-bipyridin-5-yl)methyl)-5,6,7,8-tetrahydrophthalazin-1(2H)-one;
N-methyl-5-((4-oxo-3,4,5,6,7,8-hexahydrophthalazin-1-yl)methyl)thiophene-2-carboxamide;
$N^1$-(3-((4-oxo-3,4,5,6,7,8-hexahydrophthalazin-1-yl)methyl)phenyl)glycinamide.
N-(3-((4-oxo-3,4,5,6,7,8-hexahydrophthalazin-1-yl)methyl)phenyl)azetidine-2-carboxamide;
N-(3-((4-oxo-3,4,5,6,7,8-hexahydrophthalazin-1-yl)methyl)phenyl)azetidine-3-carboxamide;
N-(3-((4-oxo-3,4,5,6,7,8-hexahydrophthalazin-1-yl)methyl)phenyl)methanesulfonamide;
N-(3-((4-oxo-3,4,5,6,7,8-hexahydrophthalazin-1-yl)methyl)phenyl)propane-2-sulfonamide;
N-(3-((4-oxo-3,4,5,6,7,8-hexahydrophthalazin-1-yl)methyl)phenyl)benzenesulfonamide;
N-(3-((4-oxo-3,4,5,6,7,8-hexahydrophthalazin-1-yl)methyl)phenyl)pyridine-3-sulfonamide;
N-(3-((4-oxo-3,4,5,6,7,8-hexahydrophthalazin-1-yl)methyl)phenyl)furan-2-sulfonamide;
1-methyl-N-(3-((4-oxo-3,4,5,6,7,8-hexahydrophthalazin-1-yl)methyl)phenyl)-1H-imidazole-4-sulfonamide;
N-(3-((4-oxo-3,4,5,6,7,8-hexahydrophthalazin-1-yl)methyl)phenyl)thiophene-2-sulfonamide;
4-cyano-N-(3-((4-oxo-3,4,5,6,7,8-hexahydrophthalazin-1-yl)methyl)phenyl)benzenesulfonamide;
N-(3-((4-oxo-3,4,5,6,7,8-hexahydrophthalazin-1-yl)methyl)phenyl)naphthalene-1-sulfonamide;
4-((6-bromopyridin-2-yl)methyl)-5,6,7,8-tetrahydrophthalazin-1(2H)-one;
4-((6-(2-oxopyrrolidin-1-yl)pyridin-2-yl)methyl)-5,6,7,8-tetrahydrophthalazin-1(2H)-one;
N-(6-((4-oxo-3,4,5,6,7,8-hexahydrophthalazin-1-yl)methyl)pyridin-2-yl)benzamide;
4-((3'-((isopropylamino)methyl)-1,1'-biphenyl-3-yl)methyl)-5,6,7,8-tetrahydrophthalazin-1(2H)-one;
4-((3'-((cyclopentylamino)methyl)-1,1'-biphenyl-3-yl)methyl)-5,6,7,8-tetrahydrophthalazin-1(2H)-one;
4-((3'-((2-methylpyrrolidin-1-yl)methyl)-1,1'-biphenyl-3-yl)methyl)-5,6,7,8-tetrahydrophthalazin-1(2H)-one;
4-((3'-((cyclopropylamino)methyl)-1,1'-biphenyl-3-yl)methyl)-5,6,7,8-tetrahydrophthalazin-1(2H)-one;
4-((3'-((cyclobutylamino)methyl)-1,1'-biphenyl-3-yl)methyl)-5,6,7,8-tetrahydrophthalazin-1(2H)-one;
4-((2-bromo-1-oxidopyridin-4-yl)methyl)-5,6,7,8-tetrahydrophthalazin-1(2H)-one;
4-((1-oxido-2-(2-oxopyrrolidin-1-yl)pyridin-4-yl)methyl)-5,6,7,8-tetrahydrophthalazin-1(2H)-one;
methyl 5-((4-oxo-3,4,5,6,7,8-hexahydrophthalazin-1-yl)methyl)thiophene-3-carboxylate;
4-(3-((4-(24(2-(2-aminoethoxy)ethoxy)ethyl)-1,4-diazepan-1-yl)carbonyl)-4-fluorobenzyl)phthalazin-1(2H)-one;
1-methyl-N-(3-((4-oxo-3,4,5,6,7,8-hexahydrophthalazin-1-yl)methyl)phenyl)cyclopropanecarboxamide;
2-methyl-N-(3-((4-oxo-3,4,5,6,7,8-hexahydrophthalazin-1-yl)methyl)phenyl)cyclopropanecarboxamide;
3-ethoxy-N-(3-((4-oxo-3,4,5,6,7,8-hexahydrophthalazin-1-yl)methyl)phenyl)propanamide;
5-oxo-N-(3-((4-oxo-3,4,5,6,7,8-hexahydrophthalazin-1-yl)methyl)phenyl)-L-prolinamide;
5-oxo-N-(3-((4-oxo-3,4,5,6,7,8-hexahydrophthalazin-1-yl)methyl)phenyl)-D-prolinamide;
$N^1$-(3-((4-oxo-3,4,5,6,7,8-hexahydrophthalazin-1-yl)methyl)phenyl)cyclopropane-1,1-dicarboxamide;
2-(benzyloxy)-N-(3-((4-oxo-3,4,5,6,7,8-hexahydrophthalazin-1-yl)methyl)phenyl)acetamide;
N-(3-((4-oxo-3,4,5,6,7,8-hexahydrophthalazin-1-yl)methyl)phenyl)-3-phenylpropanamide;
3-(2,5-dimethoxyphenyl)-N-(3-((4-oxo-3,4,5,6,7,8-hexahydrophthalazin-1-yl)methyl)phenyl)propanamide;
N-(3-((4-oxo-3,4,5,6,7,8-hexahydrophthalazin-1-yl)methyl)phenyl)-1-phenylcyclopropanecarboxamide;
(2S)—N-(3-((4-oxo-3,4,5,6,7,8-hexahydrophthalazin-1-yl)methyl)phenyl)-2-phenylbutanamide;
N-(3-((4-oxo-3,4,5,6,7,8-hexahydrophthalazin-1-yl)methyl)phenyl)-4-phenylbutanamide;
2-(3-methylphenoxy)-N-(3-((4-oxo-3,4,5,6,7,8-hexahydrophthalazin-1-yl)methyl)phenyl)acetamide;
2-(2-methylphenoxy)-N-(3-((4-oxo-3,4,5,6,7,8-hexahydrophthalazin-1-yl)methyl)phenyl)acetamide;
2-(4-methylphenoxy)-N-(3-((4-oxo-3,4,5,6,7,8-hexahydrophthalazin-1-yl)methyl)phenyl)acetamide;
(2R)-2-methoxy-N-(3-((4-oxo-3,4,5,6,7,8-hexahydrophthalazin-1-yl)methyl)phenyl)-2-phenylacetamide;
(2S)-2-methoxy-N-(3-((4-oxo-3,4,5,6,7,8-hexahydrophthalazin-1-yl)methyl)phenyl)-2-phenylacetamide;
N-(3-((4-oxo-3,4,5,6,7,8-hexahydrophthalazin-1-yl)methyl)phenyl)-3-phenoxypropanamide;
N-(3-((4-oxo-3,4,5,6,7,8-hexahydrophthalazin-1-yl)methyl)phenyl)-4-thien-2-ylbutanamide;

1-acetyl-N-(3-((4-oxo-3,4,5,6,7,8-hexahydrophthalazin-1-yl)methyl)phenyl)piperidine-4-carboxamide;
2-(3,5-difluorophenyl)-N-(3-((4-oxo-3,4,5,6,7,8-hexahydrophthalazin-1-yl)methyl)phenyl)acetamide;
$N^2$-acetyl-$N^1$-(3-((4-oxo-3,4,5,6,7,8-hexahydrophthalazin-1-yl)methyl)phenyl)-L-leucinamide;
$N^1$-(3-((4-oxo-3,4,5,6,7,8-hexahydrophthalazin-1-yl)methyl)phenyl)-$N^2$,$N^2$-dipropyl-1-alaninamide;
4-oxo-N-(3-((4-oxo-3,4,5,6,7,8-hexahydrophthalazin-1-yl)methyl)phenyl)-4-phenylbutanamide;
N-(2-oxo-2-(3-((4-oxo-3,4,5,6,7,8-hexahydrophthalazin-1-yl)methyl)phenylamino)ethyl)benzamide;
3-(3-methoxyphenyl)-N-(3-((4-oxo-3,4,5,6,7,8-hexahydrophthalazin-1-yl)methyl)phenyl)propanamide;
3-(4-methoxyphenyl)-N-(34((4-oxo-3,4,5,6,7,8-hexahydrophthalazin-1-yl)methyl)phenyl)propanamide;
2-(3,4-dimethylphenoxy)-N-(3-((4-oxo-3,4,5,6,7,8-hexahydrophthalazin-1-yl)methyl)phenyl)acetamide;
(2R)-2-hydroxy-N-(3-((4-oxo-3,4,5,6,7,8-hexahydrophthalazin-1-yl)methyl)phenyl)-4-phenylbutanamide;
N-(3-((4-oxo-3,4,5,6,7,8-hexahydrophthalazin-1-yl)methyl)phenyl)-4-phenoxybutanamide;
4-oxo-N-(3-((4-oxo-3,4,5,6,7,8-hexahydrophthalazin-1-yl)methyl)phenyl)-4-thien-2-ylbutanamide;
2-((4-methylpyrimidin-2-yl)thio)-N-(3-((4-oxo-3,4,5,6,7,8-hexahydrophthalazin-1-yl)methyl)phenyl)acetamide;
3-(2-chlorophenyl)-N-(3-((4-oxo-3,4,5,6,7,8-hexahydrophthalazin-1-yl)methyl)phenyl)propanamide;
3-(4-chlorophenyl)-N-(3-((4-oxo-3,4,5,6,7,8-hexahydrophthalazin-1-yl)methyl)phenyl)propanamide;
3-methyl-N-(3-((4-oxo-3,4,5,6,7,8-hexahydrophthalazin-1-yl)methyl)phenyl)-2-phenylpentanamide;
2-(4-chloro-2-methylphenoxy)-N-(3-((4-oxo-3,4,5,6,7,8-hexahydrophthalazin-1-yl)methyl)phenyl)acetamide;
N-(3-((4-oxo-3,4,5,6,7,8-hexahydrophthalazin-1-yl)methyl)phenyl)-N'-phenylpentanediamide;
4-(4-methoxyphenyl)-4-oxo-N-(3-((4-oxo-3,4,5,6,7,8-hexahydrophthalazin-1-yl)methyl)phenyl)butanamide;
N-(3-((4-oxo-3,4,5,6,7,8-hexahydrophthalazin-1-yl)methyl)phenyl)-2,2-diphenylacetamide;
N-(3-((4-oxo-3,4,5,6,7,8-hexahydrophthalazin-1-yl)methyl)phenyl)-3-(phenylsulfonyl)propanamide;
N-(3-((4-oxo-3,4,5,6,7,8-hexahydrophthalazin-1-yl)methyl)phenyl)-2-(3-phenoxyphenyl)acetamide;
4-ethyl-N-(3-((4-oxo-3,4,5,6,7,8-hexahydrophthalazin-1-yl)methyl)phenyl)benzamide;
3-fluoro-2-methyl-N-(3-((4-oxo-3,4,5,6,7,8-hexahydrophthalazin-1-yl)methyl)phenyl)benzamide;
5-fluoro-2-methyl-N-(3-((4-oxo-3,4,5,6,7,8-hexahydrophthalazin-1-yl)methyl)phenyl)benzamide;
3-fluoro-4-methyl-N-(3-((4-oxo-3,4,5,6,7,8-hexahydrophthalazin-1-yl)methyl)phenyl)benzamide;
2,3-difluoro-N-(3-((4-oxo-3,4,5,6,7,8-hexahydrophthalazin-1-yl)methyl)phenyl)benzamide;
2,4-difluoro-N-(3-((4-oxo-3,4,5,6,7,8-hexahydrophthalazin-1-yl)methyl)phenyl)benzamide;
2,5-difluoro-N-(3-((4-oxo-3,4,5,6,7,8-hexahydrophthalazin-1-yl)methyl)phenyl)benzamide;
3,5-difluoro-N-(3-((4-oxo-3,4,5,6,7,8-hexahydrophthalazin-1-yl)methyl)phenyl)benzamide;
N-(3-((4-oxo-3,4,5,6,7,8-hexahydrophthalazin-1-yl)methyl)phenyl)-4-propylbenzamide;
4-isopropyl-N-(3-((4-oxo-3,4,5,6,7,8-hexahydrophthalazin-1-yl)methyl)phenyl)benzamide;
2-ethoxy-N-(3-((4-oxo-3,4,5,6,7,8-hexahydrophthalazin-1-yl)methyl)phenyl)benzamide;
4-isopropoxy-N-(3-((4-oxo-3,4,5,6,7,8-hexahydrophthalazin-1-yl)methyl)phenyl)benzamide;
4-(diethylamino)-N-(3-((4-oxo-3,4,5,6,7,8-hexahydrophthalazin-1-yl)methyl)phenyl)benzamide;
4-butoxy-N-(3-((4-oxo-3,4,5,6,7,8-hexahydrophthalazin-1-yl)methyl)phenyl)benzamide;
2-fluoro-N-(3-((4-oxo-3,4,5,6,7,8-hexahydrophthalazin-1-yl)methyl)phenyl)-5-(trifluoromethyl)benzamide;
2-chloro-N-(3-((4-oxo-3,4,5,6,7,8-hexahydrophthalazin-1-yl)methyl)phenyl)-5-(trifluoromethyl)benzamide;
N-(3-((4-oxo-3,4,5,6,7,8-hexahydrophthalazin-1-yl)methyl)phenyl)-2-furamide;
N-(3-((4-oxo-3,4,5,6,7,8-hexahydrophthalazin-1-yl)methyl)phenyl)-3-furamide;
2,5-dimethyl-N-(3-((4-oxo-3,4,5,6,7,8-hexahydrophthalazin-1-yl)methyl)phenyl)-3-furamide;
N-(3-((4-oxo-3,4,5,6,7,8-hexahydrophthalazin-1-yl)methyl)phenyl)thiophene-2-carboxamide;
N-(3-((4-oxo-3,4,5,6,7,8-hexahydrophthalazin-1-yl)methyl)phenyl)thiophene-3-carboxamide;
3-methyl-N-(3-((4-oxo-3,4,5,6,7,8-hexahydrophthalazin-1-yl)methyl)phenyl)thiophene-2-carboxamide;
5-methyl-N-(3-((4-oxo-3,4,5,6,7,8-hexahydrophthalazin-1-yl)methyl)phenyl)thiophene-2-carboxamide;
N-(3-((4-oxo-3,4,5,6,7,8-hexahydrophthalazin-1-yl)methyl)phenyl)-1H-pyrrole-2-carboxamide;
1-methyl-N-(3-((4-oxo-3,4,5,6,7,8-hexahydrophthalazin-1-yl)methyl)phenyl)-1H-pyrrole-2-carboxamide;
2,5-dimethyl-N-(3-((4-oxo-3,4,5,6,7,8-hexahydrophthalazin-1-yl)methyl)phenyl)-1H-pyrrole-3-carboxamide;
1,2,5-trimethyl-N-(3-((4-oxo-3,4,5,6,7,8-hexahydrophthalazin-1-yl)methyl)phenyl)-1H-pyrrole-3-carboxamide;
N-(3-((4-oxo-3,4,5,6,7,8-hexahydrophthalazin-1-yl)methyl)phenyl)-1,3-thiazole-2-carboxamide;
N-(3-((4-oxo-3,4,5,6,7,8-hexahydrophthalazin-1-yl)methyl)phenyl)-1,3-thiazole-4-carboxamide;
N-(3-((4-oxo-3,4,5,6,7,8-hexahydrophthalazin-1-yl)methyl)phenyl)-1,3-thiazole-5-carboxamide;
N-(3-((4-oxo-3,4,5,6,7,8-hexahydrophthalazin-1-yl)methyl)phenyl)isoxazole-5-carboxamide;
3,5-dimethyl-N-(3-((4-oxo-3,4,5,6,7,8-hexahydrophthalazin-1-yl)methyl)phenyl)isoxazole-4-carboxamide;
N-(3-((4-oxo-3,4,5,6,7,8-hexahydrophthalazin-1-yl)methyl)phenyl)nicotinamide;
N-(3-((4-oxo-3,4,5,6,7,8-hexahydrophthalazin-1-yl)methyl)phenyl)isonicotinamide;
3-hydroxy-N-(3-((4-oxo-3,4,5,6,7,8-hexahydrophthalazin-1-yl)methyl)phenyl)pyridine-2-carboxamide;
2-hydroxy-N-(3-((4-oxo-3,4,5,6,7,8-hexahydrophthalazin-1-yl)methyl)phenyl)nicotinamide;
6-hydroxy-N-(3-((4 oxo-3,4,5,6,7,8-hexahydrophthalazin-1-yl)methyl)phenyl)nicotinamide;
N-(3-((4-oxo-3,4,5,6,7,8-hexahydrophthalazin-1-yl)methyl)phenyl)-2-pyridin-2-ylacetamide;
N-(3-((4-oxo-3,4,5,6,7,8-hexahydrophthalazin-1-yl)methyl)phenyl)-2-pyridin-3-ylacetamide;
5-methyl-N-(3-((4-oxo-3,4,5,6,7,8-hexahydrophthalazin-1-yl)methyl)phenyl)pyrazine-2-carboxamide;
N-(3-((4-oxo-3,4,5,6,7,8-hexahydrophthalazin-1-yl)methyl)phenyl)-1H-indole-3-carboxamide;
5-methyl-N-(3-((4-oxo-3,4,5,6,7,8-hexahydrophthalazin-1-yl)methyl)phenyl)-1-phenyl-1H-pyrazole-4-carboxamide;
6-chloro-N-(3-((4-oxo-3,4,5,6,7,8-hexahydrophthalazin-1-yl)methyl)phenyl)-2H-chromene-3-carboxamide;

N³,N³-dimethyl-N¹-(3-((4-oxo-3,4,5,6,7,8-hexahydrophthalazin-1-yl)methyl)phenyl)-beta-alaninamide;
4-(2-(3-bromophenyl)ethyl)-5,6,7,8-tetrahydrophthalazin-1(2H)-one;
4-(2-(3-bromo-4-fluorophenyl)ethyl)-5,6,7,8-tetrahydrophthalazin-1(2H)-one;
4-(2,2,2-trifluoro-1-phenylethyl)-5,6,7,8-tetrahydrophthalazin-1(2H)-one;
2-hydroxy-4-methyl-N-(3-((4-oxo-3,4,5,6,7,8-hexahydrophthalazin-1-yl)methyl)phenyl)benzamide;
4-acetyl-N-(3-((4-oxo-3,4,5,6,7,8-hexahydrophthalazin-1-yl)methyl)phenyl)benzamide;
3-methoxy-4-methyl-N-(3-((4-oxo-3,4,5,6,7,8-hexahydrophthalazin-1-yl)methyl)phenyl)benzamide;
4-ethoxy-N-(3-((4-oxo-3,4,5,6,7,8-hexahydrophthalazin-1-yl)methyl)phenyl)benzamide;
3-fluoro-4-methoxy-N-(3-((4-oxo-3,4,5,6,7,8-hexahydrophthalazin-1-yl)methyl)phenyl)benzamide;
N-(3-((4-oxo-3,4,5,6,7,8-hexahydrophthalazin-1-yl)methyl)phenyl)-1-naphthamide;
N-(3-((4-oxo-3,4,5,6,7,8-hexahydrophthalazin-1-yl)methyl)phenyl)-2-naphthamide;
5-chloro-2-hydroxy-N-(3-((4-oxo-3,4,5,6,7,8-hexahydrophthalazin-1-yl)methyl)phenyl)benzamide;
4-tert-butyl-N-(3-((4-oxo-3,4,5,6,7,8-hexahydrophthalazin-1-yl)methyl)phenyl)benzamide;
4-(acetylamino)-N-(3-((4-oxo-3,4,5,6,7,8-hexahydrophthalazin-1-yl)methyl)phenyl)benzamide;
N-(3-((4-oxo-3,4,5,6,7,8-hexahydrophthalazin-1-yl)methyl)phenyl)-4-propoxybenzamide;
1-hydroxy-N-(3-((4-oxo-3,4,5,6,7,8-hexahydrophthalazin-1-yl)methyl)phenyl)-2-naphthamide;
2-chloro-5-(methylthio)-N-(3-((4-oxo-3,4,5,6,7,8-hexahydrophthalazin-1-yl)methyl)phenyl)benzamide;
3,4-diethoxy-N-(3-((4-oxo-3,4,5,6,7,8-hexahydrophthialazin-1-yl)methyl)phenyl)benzamide;
2-benzyl-N-(3-((4-oxo-3,4,5,6,7,8-hexahydrophthalazin-1-yl)methyl)phenyl)benzamide;
2-anilino-N-(3-((4-oxo-3,4,5,6,7,8-hexahydrophthalazin-1-yl)methyl)phenyl)benzamide;
2-benzoyl-N-(3-((4-oxo-3,4,5,6,7,8-hexahydrophthalazin-1-yl)methyl)phenyl)benzamide;
N-(3-((4-oxo-3,4,5,6,7,8-hexahydrophthalazin-1-yl)methyl)phenyl)-2-(2-phenylethyl)benzamide;
5-bromo-2-chloro-N-(3-((4-oxo-3,4,5,6,7,8-hexahydrophthalazin-1-yl)methyl)phenyl)benzamide;
2-(4-methylbenzoyl)-N-(3-((4-oxo-3,4,5,6,7,8-hexahydrophthalazin-1-yl)methyl)phenyl)benzamide;
2-iodo-N-(3-((4-oxo-3,4,5,6,7,8-hexahydrophthalazin-1-yl)methyl)phenyl)benzamide;
3-iodo-N-(3-((4-oxo-3,4,5,6,7,8-hexahydrophthalazin-1-yl)methyl)phenyl)benzamide;
4-iodo-N-(3-((4-oxo-3,4,5,6,7,8-hexahydrophthalazin-1-yl)methyl)phenyl)benzamide;
N-(2'-fluoro-5'-((4-oxo-3,4,5,6,7,8-hexahydrophthalazin-1-yl)methyl)-1,1'-biphenyl-3-yl)acetamide;
4-((6-fluoro-3'-(methylsulfonyl)-1,1'-biphenyl-3-yl)methyl)-5,6,7,8-tetrahydrophthalazin-1(2H)-one;
4-((6-fluoro-3'-(pyrrolidin-1-ylcarbonyl)-1,1'-biphenyl-3-yl)methyl)-5,6,7,8-tetrahydrophthalazin-1(2H)-one;
4-((6-fluoro-4'-(pyrrolidin-1-ylcarbonyl)-1,1'-biphenyl-3-yl)methyl)-5,6,7,8-tetrahydrophthalazin-1(2H)-one;
2'-fluoro-5'-((4-oxo-3,4,5,6,7,8-hexahydrophthalazin-1-yl)methyl)-1,1'-biphenyl-3-carboxamide;
2'-fluoro-N,N-dimethyl-5'-((4-oxo-3,4,5,6,7,8-hexahydrophthalazin-1-yl)methyl)-1,1'-biphenyl-4-carboxamide;
4-(3,3,3-trifluoro-2-phenylpropyl)-5,6,7,8-tetrahydrophthalazin-1(2H)-one;
4-(2-phenylethyl)-5,6,7,8-tetrahydrophthalazin-1(2H)-one;
4-(2-(3-bromophenyl)propyl)-5,6,7,8-tetrahydrophthalazin-1(2H)-one;
tert-butyl 2-((4-oxo-3,4,5,6,7,8-hexahydrophthalazin-1-yl)methyl)piperazine-1-carboxylate;
4-benzyl 1-tert-butyl 2-((4-oxo-3,4,5,6,7,8-hexahydrophthalazin-1-yl)methyl)piperazine-1,4-dicarboxylate;
4-(2-(3-nitrophenyl)ethyl)-5,6,7,8-tetrahydrophthalazin-1(2H)-one;
4-(2-(3-aminophenyl)ethyl)-5,6,7,8-tetrahydrophthalazin-1(2H)-one;
4-(piperazin-2-ylmethyl)-5,6,7,8-tetrahydrophthalazin-1(2H)-one;
4-(2-(3-(2-oxopyrrolidin-1-yl)phenyl)ethyl)-5,6,7,8-tetrahydrophthalazin-1(2H)-one;
N-(3-(2-(4-oxo-3,4,5,6,7,8-hexahydrophthalazin-1-yl)ethyl)phenyl)-2-phenoxyacetamide;
4-(2-(6-fluoro-3'-(morpholin-4-ylcarbonyl)-1,1'-biphenyl-3-yl)ethyl)-5,6,7,8-tetrahydrophthalazin-1(2H)-one;
methyl 3-(2-(4-oxo-3,4,5,6,7,8-hexahydrophthalazin-1-yl)ethyl)benzoate;
methyl 3-(1-methyl-2-(4-oxo-3,4,5,6,7,8-hexahydrophthalazin-1-yl)ethyl)benzoate;
4-(2-(6-fluoro-4'-(morpholin-4-ylcarbonyl)-1,1'-biphenyl-3-yl)ethyl)-5,6,7,8-tetrahydrophthalazin-1(2H)-one;
4-(2-(6-fluoro-2'-(pyrrolidin-1-ylcarbonyl)-1,1'-biphenyl-3-yl)ethyl)-5,6,7,8-tetrahydrophthalazin-1(2H)-one;
4-(2-(6-fluoro-3'-(pyrrolidin-1-ylcarbonyl)-1,1'-biphenyl-3-yl)ethyl)-5,6,7,8-tetrahydrophthalazin-1(2H)-one;
N-cyclopropyl-2'-fluoro-5'-(2-(4-oxo-3,4,5,6,7,8-hexahydrophthalazin-1-yl)ethyl)-1,1'-biphenyl-3-carboxamide;
N-(2-(dimethylamino)ethyl)-2'-fluoro-5'-(2-(4-oxo-3,4,5,6,7,8-hexahydrophthalazin-1-yl)ethyl)-1,1'-biphenyl-3-carboxamide;
2'-fluoro-5'-(2-(4-oxo-3,4,5,6,7,8-hexahydrophthalazin-1-yl)ethyl)-1,1'-biphenyl-3-carboxamide;
N-(2'-fluoro-5'-(2-(4-oxo-3,4,5,6,7,8-hexahydrophthalazin-1-yl)ethyl)-1,1'-biphenyl-3-yl)methanesulfonamide;
N-(2'-fluoro-5'-(2-(4-oxo-3,4,5,6,7,8-hexahydrophthalazin-1-yl)ethyl)-1,1'-biphenyl-3-yl)acetamide;
4-(2-(6-fluoro-3'-(morpholin-4-ylcarbonyl)-1,1'-biphenyl-3-yl)propyl)-5,6,7,8-tetrahydrophthalazin-1(2H)-one;
4-(2-(6-fluoro-3'-(pyrrolidin-1-ylcarbonyl)-1,1'-biphenyl-3-yl)propyl)-5,6,7,8-tetrahydrophthalazin-1(2H)-one;
N-cyclopropyl-2'-fluoro-5'-(1-methyl-2-(4-oxo-3,4,5,6,7,8-hexahydrophthalazin-1-yl)ethyl)-1,1'-biphenyl-3-carboxamide;
4-(3-amino-4-chlorobenzyl)-5,6,7,8-tetrahydrophthalazin-1(2H)-one;
4-(3-amino-4-methoxybenzyl)-5,6,7,8-tetrahydrophthalazin-1(2H)-one;
4-(3-amino-4-hydroxybenzyl)-5,6,7,8-tetrahydrophthalazin-1(2H)-one;
4-(3-amino-4-methylbenzyl)-5,6,7,8-tetrahydrophthalazin-1(2H)-one;
N-(2-(dimethylamino)ethyl)-3'-(1-methyl-2-(4-oxo-3,4,5,6,7,8-hexahydrophthalazin-1-yl)ethyl)-1,1'-biphenyl-3-carboxamide;
3'-(1-methyl-2-(4-oxo-3,4,5,6,7,8-hexahydrophthalazin-1-yl)ethyl)-1,1'-biphenyl-3-carboxamide;
N-(3'-(1-methyl-2-(4-oxo-3,4,5,6,7,8-hexahydrophthalazin-1-yl)ethyl)-1,1'-biphenyl-3-yl)acetamide;
3'-(1-(4-oxo-3,4,5,6,7,8-hexahydrophthalazin-1-yl)ethyl)-1,1'-biphenyl-3-carboxamide;

N-(3'-(1-(4-oxo-3,4,5,6,7,8-hexahydrophthalazin-1-yl)ethyl)-1,1'-biphenyl-3-yl)acetamide;
N-(2-(dimethylamino)ethyl)-3'-(1-(4-oxo-3,4,5,6,7,8-hexahydrophthalazin-1-yl)ethyl)-1,1'-biphenyl-3-carboxamide;
3-(1-methyl-2-(4-oxo-3,4,5,6,7,8-hexahydrophthalazin-1-yl)ethyl)benzoic acid;
N-(2-fluoro-5-((4-oxo-3,4,5,6,7,8-hexahydrophthalazin-1-yl)methyl)phenyl)-4-(4-methoxyphenyl)-4-oxobutanamide;
1-(2-fluoro-5-((4-oxo-3,4,5,6,7,8-hexahydrophthalazin-1-yl)methyl)phenyl)-3,4-dimethyl-1H-pyrrole-2,5-dione;
3-(2-fluoro-5-((4-oxo-3,4,5,6,7,8-hexahydrophthalazin-1-yl)methyl)phenyl)-3-azabicyclo(3.1.0)hexane-2,4-dione;
4-((4-(phenoxyacetyl)piperazin-2-yl)methyl)-5,6,7,8-tetrahydrophthalazin-1(2H)-one;
4-(2-(3-bromo-4-fluorophenyl)propyl)-5,6,7,8-tetrahydrophthalazin-1(2H)-one;
4-oxo-N-(3-(2-(4-oxo-3,4,5,6,7,8-hexahydrophthalazin-1-yl)ethyl)phenyl)-4-phenylbutanamide;
2'-fluoro-5'-(1-methyl-2-(4-oxo-3,4,5,6,7,8-hexahydrophthalazin-1-yl)ethyl)-1,1'-biphenyl-3-carboxamide;
N-(2'-fluoro-5'-(1-methyl-2-(4-oxo-3,4,5,6,7,8-hexahydrophthalazin-1-yl)ethyl)-1,1'-biphenyl-3-yl)acetamide;
N-((2'-fluoro-5'-(1-methyl-2-(4-oxo-3,4,5,6,7,8-hexahydrophthalazin-1-yl)ethyl)-1,1'-biphenyl-3-yl)methyl)methanesulfonamide;
2-(2-fluoro-5-((4-oxo-3,4,5,6,7,8-hexahydrophthalazin-1-yl)methyl)phenyl)hexahydro-1H-isoindole-1,3(2H)-dione;
1-(2-fluoro-5-((4-oxo-3,4,5,6,7,8-hexahydrophthalazin-1-yl)methyl)phenyl)-3,3-dimethylpyrrolidine-2,5-dione;
4-(4-fluoro-3-(2-methyl-5-oxopyrrolidin-1-yl)benzyl)-5,6,7,8-tetrahydrophthalazin-1(2H)-one;
4-(4-fluoro-3-(2-oxo-1,3-oxazolidin-3-yl)benzyl)-5,6,7,8-tetrahydrophthalazin-1(2H)-one;
4-(4-fluoro-3-(2-oxoazepan-1-yl)benzyl)-5,6,7,8-tetrahydrophthalazin-1(2H)-one;
1-(2-fluoro-5-((4-oxo-3,4,5,6,7,8-hexahydrophthalazin-1-yl)methyl)phenyl)piperidine-2,6-dione;
4-(4-fluoro-3-(2-oxoimidazolidin-1-yl)benzyl)-5,6,7,8-tetrahydrophthalazin-1(2H)-one.
4-(3-(1,1-dioxidoisothiazolidin-2-yl)-4-fluorobenzyl)-5,6,7,8-tetrahydrophthalazin-1(2H)-one;
4-(4-fluoro-3-(2-oxoazetidin-1-yl)benzyl)-5,6,7,8-tetrahydrophthalazin-1(2H)-one;
4-(4-fluoro-3-(2-oxopiperidin-1-yl)benzyl)-5,6,7,8-tetrahydrophthalazin-1(2H)-one;
N-(3-furylmethyl)-3-((4-oxo-3,4,5,6,7,8-hexahydrophthalazin-1-yl)methyl)benzamide;
3-((4-oxo-3,4,5,6,7,8-hexahydrophthalazin-1-yl)methyl)-N-(thien-2-ylmethyl)benzamide;
3-((4-oxo-3,4,5,6,7,8-hexahydrophthalazin-1-yl)methyl)-N-(thien-3-ylmethyl)benzamide;
3-((4-oxo-3,4,5,6,7,8-hexahydrophthalazin-1-yl)methyl)-N-(pyridin-3-ylmethyl)benzamide;
3-((4-oxo-3,4,5,6,7,8-hexahydrophthalazin-1-yl)methyl)-N-(pyridin-4-ylmethyl)benzamide;
N-(2-(dimethylamino)ethyl)-3-((4-oxo-3,4,5,6,7,8-hexahydrophthalazin-1-yl)methyl)benzamide;
N-(34(dimethylamino)propyl)-3-((4-oxo-3,4,5,6,7,8-hexahydrophthalazin-1-yl)methyl)benzamide;
3-((4-oxo-3,4,5,6,7,8-hexahydrophthialazin-1-yl)methyl)-N-(3-pyrrolidin-1-ylpropyl)benzamide;
3-((4-oxo-3,4,5,6,7,8-hexahydrophthalazin-1-yl)methyl)-N-(3-piperidin-1-ylpropyl)benzamide;
N-(3-morpholin-4-ylpropyl)-3-((4-oxo-3,4,5,6,7,8-hexahydrophthalazin-1-yl)methyl)benzamide;
N-(2-(1H-indol-3-yl)ethyl)-3-((4-oxo-3,4,5,6,7,8-hexahydrophthalazin-1-yl)methyl)benzamide;
3-((4-oxo-3,4,5,6,7,8-hexahydrophthalazin-1-yl)methyl)-N-1,3-thiazol-2-ylbenzamide;
benzyl 2-oxo-2-(3-(2-(4-oxo-3,4,5,6,7,8-hexahydrophthalazin-1-yl)ethyl)phenylamino)ethylcarbamate;
4-oxo-N-(3-(2-(4-oxo-3,4,5,6,7,8-hexahydrophthalazin-1-yl)ethyl)phenyl)-4-(4-phenoxyphenyl)butanamide;
benzyl 3-(((3-(2-(4-oxo-3,4,5,6,7,8-hexahydrophthalazin-1-yl)ethyl)phenyl)amino)carbonyl)piperidine-1-carboxylate;
2-(4-methylphenoxy)-N-(3-(2-(4-oxo-3,4,5,6,7,8-hexahydrophthalazin-1-yl)ethyl)phenyl)acetamide;
2-(4-methoxyphenoxy)-N-(3-(2-(4-oxo-3,4,5,6,7,8-hexahydrophthalazin-1-yl)ethyl)phenyl)acetamide;
4-(4-fluoro-3-(3-methyl-2-oxoimidazolidin-1-yl)benzyl)-5,6,7,8-tetrahydrophthalazin-1(2H)-one;
4-(4-fluoro-3-(2-oxotetrahydropyrimidin-1(2H)-yl)benzyl)-5,6,7,8-tetrahydrophthalazin-1(2H)-one;
4-(3-(3-tert-butyl-2-oxoimidazolidin-1-yl)-4-fluorobenzyl)-5,6,7,8-tetrahydrophthalazin-1(2H)-one;
4-(4-fluoro-3-((1S,4R)-3-oxo-2-azabicyclo(2.2.1)hept-2-yl)benzyl)-5,6,7,8-tetrahydrophthalazin-1(2H)-one;
N-(2-ethylphenyl)-3-((4-oxo-3,4,5,6,7,8-hexahydrophthalazin-1-yl)methyl)benzamide;
N-(3-ethylphenyl)-3-((4-oxo-3,4,5,6,7,8-hexahydrophthalazin-1-yl)methyl)benzamide;
N-(4-ethylphenyl)-3-((4-oxo-3,4,5,6,7,8-hexahydrophthalazin-1-yl)methyl)benzamide;
3-((4-oxo-3,4,5,6,7,8-hexahydrophthalazin-1-yl)methyl)-N-(2-propylphenyl)benzamide;
N-(2-isopropylphenyl)-3-((4-oxo-3,4,5,6,7,8-hexahydrophthalazin-1-yl)methyl)benzamide;
N-(4-isopropylphenyl)-3-((4-oxo-3,4,5,6,7,8-hexahydrophthalazin-1-yl)methyl)benzamide;
N-(3-tert-butylphenyl)-3-((4-oxo-3,4,5,6,7,8-hexahydrophthalazin-1-yl)methyl)benzamide;
N-(4-tert-butylphenyl)-3-((4-oxo-3,4,5,6,7,8-hexahydrophthalazin-1-yl)methyl)benzamide;
N-1,1'-biphenyl-4-yl-3-((4-oxo-3,4,5,6,7,8-hexahydrophthalazin-1-yl)methyl)benzamide;
N-(2-fluoro-4-methylphenyl)-3-((4-oxo-3,4,5,6,7,8-hexahydrophthalazin-1-yl)methyl)benzamide;
N-(3-fluoro-4-methylphenyl)-3-((4-oxo-3,4,5,6,7,8-hexahydrophthialazin-1-yl)methyl)benzamide;
N-(4-fluoro-2-methylphenyl)-3-((4-oxo-3,4,5,6,7,8-hexahydrophthalazin-1-yl)methyl)benzamide;
N-(4-fluoro-3-methylphenyl)-3-((4-oxo-3,4,5,6,7,8-hexahydrophthalazin-1-yl)methyl)benzamide;
N-(3-chloro-4-methylphenyl)-3-((4-oxo-3,4,5,6,7,8-hexahydrophthalazin-1-yl)methyl)benzamide;
N-(4-chloro-3-methylphenyl)-3-((4-oxo-3,4,5,6,7,8-hexahydrophthalazin-1-yl)methyl)benzamide;
N-(3-bromo-4-methylphenyl)-3-((4-oxo-3,4,5,6,7,8-hexahydrophthalazin-1-yl)methyl)benzamide;
N-(4-bromo-3-methylphenyl)-3-((4-oxo-3,4,5,6,7,8-hexahydrophthalazin-1-yl)methyl)benzamide;
N-(3-fluoro-4-methoxyphenyl)-3-((4-oxo-3,4,5,6,7,8-hexahydrophthalazin-1-yl)methyl)benzamide;
N-(3-methoxy-5-(trifluoromethyl)phenyl)-3-((4-oxo-3,4,5,6,7,8-hexahydrophthalazin-1-yl)methyl)benzamide;
N-(2-hydroxy-6-methylphenyl)-3-((4-oxo-3,4,5,6,7,8-hexahydrophthalazin-1-yl)methyl)benzamide;
N-(3-hydroxy-2-methylphenyl)-3-((4-oxo-3,4,5,6,7,8-hexahydrophthalazin-1-yl)methyl)benzamide;

N-(3-hydroxy-4-methylphenyl)-3-((4-oxo-3,4,5,6,7,8-hexahydrophthialazin-1-yl)methyl)benzamide;
N-(2-methoxy-5-methylphenyl)-3-((4-oxo-3,4,5,6,7,8-hexahydrophthalazin-1-yl)methyl)benzamide;
N-(3-methoxy-4-methylphenyl)-3-((4-oxo-3,4,5,6,7,8-hexahydrophthalazin-1-yl)methyl)benzamide;
N-(3-hydroxy-4-methoxyphenyl)-3-((4-oxo-3,4,5,6,7,8-hexahydrophthalazin-1-yl)methyl)benzamide;
N-(2-ethoxyphenyl)-((3-((4-oxo-3,4,5,6,7,8-hexahydrophthalazin-1-yl)methyl)benzamide;
3-((4-oxo-3,4,5,6,7,8-hexahydrophthalazin-1-yl)methyl)-N-(4-propoxyphenyl)benzamide;
N-(5-tert-butyl-2-methoxyphenyl)-3-((4-oxo-3,4,5,6,7,8-hexahydrophthalazin-1-yl)methyl)benzamide;
N-(5-(acetylamino)-2-methoxyphenyl)-3-((4-oxo-3,4,5,6,7,8-hexahydrophthalazin-1-yl)methyl)benzamide;
N-2,3-dihydro-1,4-benzodioxin-6-yl-3-((4-oxo-3,4,5,6,7,8-hexahydrophthialazin-1-yl)methyl)benzamide;
N-(5-chloro-2,4-dimethoxyphenyl)-3-((4-oxo-3,4,5,6,7,8-hexahydrophthalazin-1-yl)methyl)benzamide;
N-(3-(methylthio)phenyl)-3-((4-oxo-3,4,5,6,7,8-hexahydrophthalazin-1-yl)methyl)benzamide;
N-(4-(methylthio)phenyl)-3-((4-oxo-3,4,5,6,7,8-hexahydrophthalazin-1-yl)methyl)benzamide;
3-((4-oxo-3,4,5,6,7,8-hexahydrophthalazin-1-yl)methyl)-N-(4-piperidin-1-ylphenyl)benzamide;
N-(4-morpholin-4-ylphenyl)-3-((4-oxo-3,4,5,6,7,8-hexahydrophthalazin-1-yl)methyl)benzamide;
N-(2-anilinophenyl)-3-((4-oxo-3,4,5,6,7,8-hexahydrophthalazin-1-yl)methyl)benzamide;
N-(4-((4-methoxyphenyl)amino)phenyl)-3-((4-oxo-3,4,5,6,7,8-hexahydrophthalazin-1-yl)methyl)benzamide;
3-((4-oxo-3,4,5,6,7,8-hexahydrophthalazin-1-yl)methyl)-N-quinolin-6-ylbenzamide;
N-(5-hydroxy-1-naphthyl)-3-((4-oxo-3,4,5,6,7,8-hexahydrophthalazin-1-yl)methyl)benzamide;
N-1H-indazol-6-yl-3-((4-oxo-3,4,5,6,7,8-hexahydrophthalazin-1-yl)methyl)benzamide;
8-(4-fluorobenzyl)pyrido(2,3-d)pyridazin-5(6H)-one;
8-(3-chloro-4-fluorobenzyl)pyrido(2,3-d)pyridazin-5(6H)-one;
(3aR)-8-((4-oxo-3,4,5,6,7,8-hexahydrophthalazin-1-yl)methyl)-2,3,3a,4-tetrahydro-1H-pyrrolo(2,1-c)(1,4)benzoxazin-1-one;
N-(2-fluoro-5-((4-oxo-3,4,5,6,7,8-hexahydrophthalazin-1-yl)methyl)phenyl)-N-methylmethanesulfonamide;
N-(2-fluoro-5-((4-oxo-3,4,5,6,7,8-hexahydrophthalazin-1-yl)methyl)phenyl)-2-hydroxy-2
methylpropanamide;
(3aS)-8-((4-oxo-3,4,5,6,7,8-hexahydrophthalazin-1-yl)methyl)-2,3,3a,4-tetrahydro-1H-pyrrolo(2,1-c)(1,4)benzoxazin-1-one;
3-((4-oxo-3,4,5,6,7,8-hexahydrophthalazin-1-yl)methyl)-N-(2-phenylethyl)benzamide;
N-(2-(2-methylphenyl)ethyl)-3-((4-oxo-3,4,5,6,7,8-hexahydrophthalazin-1-yl)methyl)benzamide;
N-(2-(3-methylphenyl)ethyl)-3-((4-oxo-3,4,5,6,7,8-hexahydrophthalazin-1-yl)methyl)benzamide;
N-(2-(4-methylphenyl)ethyl)-3-((4-oxo-3,4,5,6,7,8-hexahydrophthalazin-1-yl)methyl)benzamide;
3-((4-oxo-3,4,5,6,7,8-hexahydrophthalazin-1-yl)methyl)-N-(2-pyridin-2-ylethyl)benzamide;
3-((4-oxo-3,4,5,6,7,8-hexahydrophthalazin-1-yl)methyl)-N-(2-pyridin-3-ylethyl)benzamide;
3-((4-oxo-3,4,5,6,7,8-hexahydrophthalazin-1-yl)methyl)-N-(2-pyridin-4-ylethyl)benzamide;
N-(2-(2-methoxyphenyl)ethyl)-3-((4-oxo-3,4,5,6,7,8-hexahydrophthalazin-1-yl)methyl)benzamide;
N-(2-(3-methoxyphenyl)ethyl)-3-((4-oxo-3,4,5,6,7,8-hexahydrophthalazin-1-yl)methyl)benzamide;
N-(2-(4-methoxyphenyl)ethyl)-3-((4-oxo-3,4,5,6,7,8-hexahydrophthalazin-1-yl)methyl)benzamide;
N-(2-(2-fluorophenyl)ethyl)-3-((4-oxo-3,4,5,6,7,8-hexahydrophthalazin-1-yl)methyl)benzamide;
N-(2-(3-fluorophenyl)ethyl)-3-((4-oxo-3,4,5,6,7,8-hexahydrophthalazin-1-yl)methyl)benzamide;
N-(2-(4-fluorophenyl)ethyl)-3-((4-oxo-3,4,5,6,7,8-hexahydrophthalazin-1-yl)methyl)benzamide;
N-(2-(2-chlorophenyl)ethyl)-3-((4-oxo-3,4,5,6,7,8-hexahydrophthalazin-1-yl)methyl)benzamide;
N-(2-(3-chlorophenyl)ethyl)-3-((4-oxo-3,4,5,6,7,8-hexahydrophthalazin-1-yl)methyl)benzamide;
N-(2-(4-chlorophenyl)ethyl)-3-((4-oxo-3,4,5,6,7,8-hexahydrophthalazin-1-yl)methyl)benzamide;
N-(2-(3-bromophenyl)ethyl)-3-((4-oxo-3,4,5,6,7,8-hexahydrophthalazin-1-yl)methyl)benzamide;
N-(2-(4-bromophenyl)ethyl)-3-((4-oxo-3,4,5,6,7,8-hexahydrophthalazin-1-yl)methyl)benzamide;
N-(2-(1,1'-biphenyl-4-yl)ethyl)-3-((4-oxo-3,4,5,6,7,8-hexahydrophthalazin-1-yl)methyl)benzamide;
3-((4-oxo-3,4,5,6,7,8-hexahydrophthalazin-1-yl)methyl)-N-(2-(3-(trifluoromethyl)phenyl)ethyl)benzamide;
3-((4-oxo-3,4,5,6,7,8-hexahydrophthialazin-1-yl)methyl)-N4(2-(4-(trifluoromethyl)phenyl)ethyl)benzamide;
3-((4-oxo-3,4,5,6,7,8-hexahydrophthalazin-1-yl)methyl)-N-(2-(4-phenoxyphenyl)ethyl)benzamide;
N-(2-(3,4-dimethylphenyl)ethyl)-3-((4-oxo-3,4,5,6,7,8-hexahydrophthalazin-1-yl)methyl)benzamide;
N-(2-(2,4-dimethylphenyl)ethyl)-3-((4-oxo-3,4,5,6,7,8-hexahydrophthalazin-1-yl)methyl)benzamide;
N-(2-(2,5-dimethylphenyl)ethyl)-3-((4-oxo-3,4,5,6,7,8-hexahydrophthalazin-1-yl)methyl)benzamide;
N-(2-(3-ethoxy-4-methoxyphenyl)ethyl)-3-((4-oxo-3,4,5,6,7,8-hexahydrophthalazin-1-yl)methyl)benzamide;
N-(2-(4-ethoxy-3-methoxyphenyl)ethyl)-3-((4-oxo-3,4,5,6,7,8-hexahydrophthalazin-1-yl)methyl)benzamide;
N-(2-(2,3-dimethoxyphenyl)ethyl)-3-((4-oxo-3,4,5,6,7,8-hexahydrophthalazin-1-yl)methyl)benzamide;
N-(2-(2,4-dimethoxyphenyl)ethyl)-3-((4-oxo-3,4,5,6,7,8-hexahydrophthalazin-1-yl)methyl)benzamide;
N-(2-(2,5-dimethoxyphenyl)ethyl)-3-((4-oxo-3,4,5,6,7,8-hexahydrophthalazin-1-yl)methyl)benzamide;
N-(2-(3,4-dimethoxyphenyl)ethyl)-3-((4-oxo-3,4,5,6,7,8-hexahydrophthalazin-1-yl)methyl)benzamide;
N-(2-(3,5-dimethoxyphenyl)ethyl)-3-((4-oxo-3,4,5,6,7,8-hexahydrophthalazin-1-yl)methyl)benzamide;
N-(2-(1,3-benzodioxol-5-yl)ethyl)-3-((4-oxo-3,4,5,6,7,8-hexahydrophthalazin-1-yl)methyl)benzamide;
N-(2-(2,3-dichlorophenyl)ethyl)-3-((4-oxo-3,4,5,6,7,8-hexahydrophthalazin-1-yl)methyl)benzamide;
N-(2-(3,4-dichlorophenyl)ethyl)-3-((4-oxo-3,4,5,6,7,8-hexahydrophthalazin-1-yl)methyl)benzamide;
N-(2-(2,6-dichlorophenyl)ethyl)-3-((4-oxo-3,4,5,6,78-hexahydrophthalazin-1-yl)methyl)benzamide;
(3aS4R,7S,7aR)-5-(2-fluoro-5-((4-oxo-3,4,5,6,7,8-hexahydrophthalazin-1-yl)methyl)phenyl)-2,2-dimethyltetrahydro-4,7-methano(1,3)dioxolo(4,5-c)pyridin-6(3aH)-one;
4-(1-(3-bromo-4-fluorophenyl)ethyl)-5,6,7,8-tetrahydrophthalazin-1(2H)-one;
4-(1-(4-fluoro-3-(2-oxopyrrolidin-1-yl)phenyl)ethyl)-5,6,7,8-tetrahydrophthalazin-1(2H)-one;
8-(4-fluorobenzyl)-2,3,4,6-tetrahydropyrido(2,3-d)pyridazin-5(1H)-one;

8-(3-bromo-4-fluorobenzyl)pyrido(2,3-d)pyridazin-5(6H)-one;
N-(2-(dimethylamino)ethyl)-N-ethyl-3-((4-oxo-3,4,5,6,7,8-hexahydrophthalazin-1-yl)methyl)benzamide;
N-(2-(diethylamino)ethyl)-N-methyl-3-((4-oxo-3,4,5,6,7,8-hexahydrophthalazin-1-yl)methyl)benzamide;
N-benzyl-N-ethyl-3-((4-oxo-3,4,5,6,7,8-hexahydro-phthalazin-1-yl)methyl)benzamide;
N-benzyl-N-isopropyl-3-((4-oxo-3,4,5,6,7,8-hexahydro-phthalazin-1-yl)methyl)benzamide;
N-benzyl-N-butyl-3-((4-oxo-3,4,5,6,7,8-hexahydro-phthalazin-1-yl)methyl)benzamide;
N,N-dibenzyl-3-((4-oxo-3,4,5,6,7,8-hexahydrophthalazin-1-yl)methyl)benzamide;
N-benzyl-N-(2-hydroxyethyl)-3-((4-oxo-3,4,5,6,7,8-hexahydrophthalazin-1-yl)methyl)benzamide;
N-methyl-3-((4-oxo-3,4,5,6,7,8-hexahydrophthalazin-1-yl)methyl)-N-(2-pyridin-2-ylethyl)benzamide;
N-(2-(3,4-dimethoxyphenyl)ethyl)-N-methyl-3-((4-oxo-3,4,5,6,7,8-hexahydrophthalazin-1-yl)methyl)benzamide;
4-(3-((4-hydroxypiperidin-1-yl)carbonyl)benzyl)-5,6,7,8-tetrahydrophthalazin-1(2H)-one;
1-(3-((4-oxo-3,4,5,6,7,8-hexahydrophthalazin-1-yl)methyl)benzoyl)piperidine-3-carboxamide;
1-(3-((4-oxo-3,4,5,6,7,8-hexahydrophthalazin-1-yl)methyl)benzoyl)piperidine-4-carboxamide;
4-(3-((4-(2-oxo-2,3-dihydro-1H-benzimidazol-1-yl)piperidin-1-yl)carbonyl)benzyl)-5,6,7,8-tetrahydrophthalazin-1(2H)-one;
4-(3-((4-methylpiperazin-1-yl)carbonyl)benzyl)-5,6,7,8-tetrahydrophthalazin-1(2H)-one;
4-(3-((4-ethylpiperazin-1-yl)carbonyl)benzyl)-5,6,7,8-tetrahydrophthalazin-1(2H)-one;
4-(3-((4-oxo-3,4,5,6,7,8-hexahydrophthalazin-1-yl)methyl)benzoyl)piperazine-1-carbaldehyde;
4-(3-((4-acetylpiperazin-1-yl)carbonyl)benzyl)-5,6,7,8-tetrahydrophthalazin-1(2H)-one;
4-(3-((4-(2-hydroxyethyl)piperazin-1-yl)carbonyl)benzyl)-5,6,7,8-tetrahydrophthalazin-1(2H)-one;
4-(3-((4-phenylpiperazin-1-yl)carbonyl)benzyl)-5,6,7,8-tetrahydrophthalazin-1(2H)-one;
4-(3-((4-pyridin-2-ylpiperazin-1-yl)carbonyl)benzyl)-5,6,7,8-tetrahydrophthalazin-1(2H)-one;
4-(3-((4-pyrimidin-2-ylpiperazin-1-yl)carbonyl)benzyl)-5,6,7,8-tetrahydrophthalazin-1(2H)-one;
4-(3-((4-(2-(2-hydroxyethoxy)ethyl)piperazin-1-yl)carbonyl)benzyl)-5,6,7,8-tetrahydrophthalazin-1(2H)-one;
4-(3-((4-(2-fluorophenyl)piperazin-1-yl)carbonyl)benzyl)-5,6,7,8-tetrahydrophthalazin-1(2H)-one;
4-(3-((4-(4-fluorophenyl)piperazin-1-yl)carbonyl)benzyl)-5,6,7,8-tetrahydrophthalazin-1(2H)-one;
4-(3-((4-(2-chlorophenyl)piperazin-1-yl)carbonyl)benzyl)-5,6,7,8-tetrahydrophthalazin-1(2H)-one;
4-(3-((4-methyl-1,4-diazepan-1-yl)carbonyl)benzyl)-5,6,7,8-tetrahydrophthalazin-1(2H)-one;
4-(3-(1,1-dioxido-1,2-thiazinan-2-yl)-4-fluorobenzyl)-5,6,7,8-tetrahydrophthalazin-1(2H)-one;
8-(4-fluoro-3-(2-oxoazetidin-1-yl)benzyl)pyrido(2,3-d)pyridazin-5(6H)-one;
8-(3-chloro-4-fluorobenzyl)-2,3,4,6-tetrahydropyrido(2,3-d)pyridazin-5(1H)-one;
4-(1-(4-fluoro-3-(2-oxoazetidin-1-yl)phenyl)ethyl)-5,6,7,8-tetrahydrophthalazin-1(2H)-one;
1-(3-((4-oxo-3,4,5,6,7,8-hexahydrophthalazin-1-yl)methyl)phenyl)pyrrolidine-2,5-dione;
N-(2-fluoro-5-((4-oxo-3,4,5,6,7,8-hexahydrophthalazin-1-yl)methyl)phenyl)-2-(2-oxopyrrolidin-1-yl)acetamide;
N-(2-fluoro-5-((4-oxo-3,4,5,6,7,8-hexahydrophthalazin-1-yl)methyl)phenyl)-5-methyl-1-phenyl-1H-pyrazole-4-carboxamide;
N-(2-fluoro-5-((4-oxo-3,4,5,6,7,8-hexahydrophthalazin-1-yl)methyl)phenyl)-5-oxohexanamide;
N-(2-fluoro-5-((4-oxo-3,4,5,6,7,8-hexahydrophthalazin-1-yl)methyl)phenyl)-3-methoxypropanamide;
N-(2-fluoro-5-((4-oxo-3,4,5,6,7,8-hexahydrophthalazin-1-yl)methyl)phenyl)-N'-phenylpentanediamide;
benzyl 2-(dimethylamino)-5-((4-oxo-3,4,5,6,7,8-hexahydro-phthalazin-1-yl)methyl)phenylcarbamate;
8-(4-fluoro-3-(2-oxoazetidin-1-yl)benzyl)-2,3,4,6-tetrahydropyrido(2,3-d)pyridazin-5(1H)-one;
4-(3-bromo-4-fluorophenyl)-5,6,7,8-tetrahydrophthalazin-1(2H)-one;
4-(4-fluoro-3-(2-oxoazetidin-1-yl)phenyl)-5,6,7,8-tetrahydrophthalazin-1(2H)-one;
2-fluoro-5-((5-oxo-5,6-dihydropyrido(2,3-d)pyridazin-8-yl)methyl)benzamide;
8-(3-amino-4-fluorobenzyl)pyrido(2,3-d)pyridazin-5(6H)-one;
8-(4-fluoro-3-(2-oxopyrrolidin-1-yl)benzyl)-2,3,4,6-tetrahydropyrido(2,3-d)pyridazin-5(1H)-one;
methyl 2-fluoro-5-((5-oxo-1,2,3,4,5,6-hexahydropyrido(2,3-d)pyridazin-8-yl)methyl)benzoate;
8-(3-amino-4-fluorobenzyl)-2,3,4,6-tetrahydropyrido(2,3-d)pyridazin-5(1H)-one;
2-fluoro-5-((5-oxo-1,2,3,4,5,6-hexahydropyrido(2,3-d)pyridazin-8-yl)methyl)benzoic acid;
N-ethyl-2-fluoro-5-((5-oxo-1,2,3,4,5,6-hexahydropyrido(2,3-d)pyridazin-8-yl)methyl)benzamide;
N-cyclobutyl-2-fluoro-5-((5-oxo-1,2,3,4,5,6-hexahydropyrido(2,3-d)pyridazin-8-yl)methyl)benzamide;
2-fluoro-5-((5-oxo-1,2,3,4,5,6-hexahydropyrido(2,3-d)pyridazin-8-yl)methyl)-N-(2-pyrrolidin-1-ylethyl)benzamide;
8-(4-fluoro-3-((4-(morpholin-4-ylcarbonyl)piperazin-1-yl)carbonyl)benzyl)-2,3,4,6-tetrahydropyrido(2,3-d)pyridazin-5(1H)-one;
N-(2-fluoro-5-((5-oxo-1,2,3,4,5,6-hexahydropyrido(2,3-d)pyridazin-8-yl)methyl)phenyl)-N'-phenylpentanediamide;
1-(2-fluoro-5-((5-oxo-1,2,3,4,5,6-hexahydropyrido(2,3-d)pyridazin-8-yl)methyl)phenyl)pyrrolidine-2,5-dione;
N-(2-fluoro-5-((5-oxo-1,2,3,4,5,6-hexahydropyrido(2,3-d)pyridazin-8-yl)methyl)phenyl)-3-methoxypropanamide;
N-(2-fluoro-5-((5-oxo-1,2,3,4,5,6-hexahydropyrido(2,3-d)pyridazin-8-yl)methyl)phenyl)-5-oxohexanamide;
N-(2-fluoro-5-((5-oxo-1,2,3,4,5,6-hexahydropyrido(2,3-d)pyridazin-8-yl)methyl)phenyl)-3-phenoxypropanamide;
N-(2-fluoro-5-((5-oxo-1,2,3,4,5,6-hexahydropyrido(2,3-d)pyridazin-8-yl)methyl)phenyl)-4-oxo-4-phenylbutanamide;
2-(4-(benzyloxy)phenoxy)-N-(2-fluoro-5-((5-oxo-1,2,3,4,5,6-hexahydropyrido(2,3-d)pyridazin-8-yl)methyl)phenyl)acetamide;
N-(2-fluoro-5-((5-oxo-1,2,3,4,5,6-hexahydropyrido(2,3-d)pyridazin-8-yl)methyl)phenyl)-2-(4-methoxyphenoxy)acetamide.
N-cyclopropyl-2-fluoro-5-((5-oxo-1,2,3,4,5,6-hexahydropyrido(2,3-d)pyridazin-8-yl)methyl)benzamide;
8-(3-((4-(2-ethoxyethyl)piperazin-1-yl)carbonyl)-4-fluorobenzyl)-2,3,4,6-tetrahydropyrido(2,3-d)pyridazin-5(1H)-one;
2-fluoro-5-((5-oxo-1,2,3,4,5,6-hexahydropyrido(2,3-d)pyridazin-8-yl)methyl)-N-(2-piperidin-1-ylethyl)benzamide;

2-fluoro-5-((5-oxo-1,2,3,4,5,6-hexahydropyrido(3,2-d)pyridazin-8-yl)methyl)-N-(2-oxo-2-(piperidin-1-yl)ethyl)benzamide;
4-(4-fluoro-3-((4-pyrimidin-2-ylpiperazin-1-yl)carbonyl)benzyl)-5,6,7,8-tetrahydrophthalazin-1(2H)-one; and
4-(4-fluoro-3-(2-oxopyrrolidin-1-yl)phenyl)-5,6,7,8-tetrahydrophthalazin-1(2H)-one;
4-(3-{[4-(cyclopropylcarbonyl)piperazin-1-yl]carbonyl}-4-fluorobenzyl)-5,6,7,8-tetrahydrophthalazin-1(2H)-one;
4-{2-fluoro-5-[(4-oxo-3,4,5,6,7,8-hexahydrophthalazin-1-yl)methyl]benzoyl}-N,N-dimethylpiperazine-1-carboxamide;
4-(4-fluoro-3-{[4-(piperidin-1-ylcarbonyl)piperazin-1-yl]carbonyl}benzyl)-5,6,7,8-tetrahydrophthalazin-1(2H)-one;
4-{4-fluoro-3-[(4-pyrazin-2-ylpiperazin-1-yl)carbonyl]benzyl}-5,6,7,8-tetrahydrophthalazin-1(2H)-one;
4-{4-fluoro-3-[(4-pyridin-4-ylpiperazin-1-yl)carbonyl]benzyl}-5,6,7,8-tetrahydrophthalazin-1(2H)-one;
1-{2-fluoro-5-[(4-oxo-3,4,5,6,7,8-hexahydrophthalazin-1-yl)methyl]benzoyl}piperidine-4-carboxamide;
4-(4-fluoro-3-{[4-(6-methylpyrazin-2-yl)piperazin-1-yl]carbonyl}benzyl)-5,6,7,8-tetrahydrophthalazin-1(2H)-one;
1-{2-fluoro-5-[(4-oxo-3,4,5,6,7,8-hexahydrophthalazin-1-yl)methyl]benzoyl}piperidine-3-carboxamide;
4-[3-({4-[2-(dimethylamino)ethyl]piperazin-1-yl}carbonyl)-4-fluorobenzyl]-5,6,7,8-tetrahydrophthalazin-1(2H)-one;
4-{4-fluoro-3-[(4-methyl-1,4-diazepan-1-yl)carbonyl]benzyl}-5,6,7,8-tetrahydrophthalazin-1(2H)-one;
4-{4-fluoro-3-[(4-hydroxypiperidin-1-yl)carbonyl]benzyl}-5,6,7,8-tetrahydrophthalazin-1(2H)-one;
N-[2-(dimethylamino)ethyl]-2-fluoro-N-methyl-5-[(4-oxo-3,4,5,6,7,8-hexahydrophthalazin-1-yl)methyl]benzamide;
N,N-diethyl-1-{2-fluoro-5-[(4-oxo-3,4,5,6,7,8-hexahydrophthalazin-1-yl)methyl]benzoyl}piperidine-3-carboxamide;
8-(3-{[4(cyclopropylcarbonyl)piperazin-1-yl]carbonyl}-4-fluorobenzyl)-2,3,4,6-tetrahydropyrido[2,3-d]pyridazin-5(1H)-one;
1-{2-fluoro-5-[(5-oxo-1,2,3,4,5,6-hexahydropyrido[2,3-d]pyridazin-8-yl)methyl]phenyl}piperidine-2,6-dione;
8-[3-({4-[2-(dimethylamino)ethyl]piperazin-1-yl}carbonyl)-4-fluorobenzyl]-2,3,4,6-tetrahydropyrido[2,3-d]pyridazin-5(1H)-one;
8-{4-fluoro-3-[(4-methyl-1,4-diazepan-1-yl)carbonyl]benzyl}-2,3,4,6-tetrahydropyrido[2,3-d]pyridazin-5(1H)-one;
8-{4-fluoro-3-[(4-pyridin-4-ylpiperazin-1-yl)carbonyl]benzyl}-2,3,4,6-tetrahydropyrido[2,3-d]pyridazin-5(1H)-one;
8-{4-fluoro-3-[(4-pyrazin-2-ylpiperazin-1-yl)carbonyl]benzyl}-2,3,4,6-tetrahydropyrido[2,3-d]pyridazin-5(1H)-one;
4-{2-fluoro-5-[(5-oxo-1,2,3,4,5,6-hexahydropyrido[2,3-d]pyridazin-8-yl)methyl]benzoyl}-N,N-dimethylpiperazine-1-carboxamide;
N-[2-(dimethylamino)ethyl]-2-fluoro-N-methyl-5-[(5-oxo-1,2,3,4,5,6-hexahydropyrido[2,3-d]pyridazin-8-yl)methyl]benzamide;
4-(3-{[4-(3-chlorobenzyl)piperazin-1-yl]carbonyl}-4-fluorobenzyl)-5,6,7,8-tetrahydrophthalazin-1(2H)-one;
4-{4-fluoro-3-[(4-phenylpiperazin-1-yl)carbonyl]benzyl}-5,6,7,8-tetrahydrophthalazin-1(2H)-one;
8-{4-fluoro-3-[(4-methylpiperazin-1-yl)carbonyl]benzyl}-2,3,4,6-tetrahydropyrido[2,3-d]pyridazin-5(1H)-one;
4-(3-{[4-(2-chlorophenyl)piperazin-1-yl]carbonyl}-4-fluorobenzyl)-5,6,7,8-tetrahydrophthalazin-1(2H)-one;
4-(3-{[4-(2-chlorobenzyl)piperazin-1-yl]carbonyl}-4-fluorobenzyl)-5,6,7,8-tetrahydrophthalazin-1(2H)-one;
1-{2-fluoro-5-[(5-oxo-1,2,3,4,5,6-hexahydropyrido[2,3-d]pyridazin-8-yl)methyl]benzoyl}piperidine-3-carboxamide;
4-{3-[(4-acetylpiperazin-1-yl)carbonyl]-4-fluorobenzyl}-5,6,7,8-tetrahydrophthalazin-1(2H)-one;
4-(4-fluoro-3-{[4-(2-furoyl)piperazin-1-yl]carbonyl}benzyl)-5,6,7,8-tetrahydrophthalazin-1(2H)-one;
4-(4-fluoro-3-{[4-(2-fluorophenyl)piperazin-1-yl]carbonyl}benzyl)-5,6,7,8-tetrahydrophthalazin-1(2H)-one;
4-(3-{[44(2,4-difluorophenyl)piperazin-1-yl]carbonyl}-4-fluorobenzyl)-5,6,7,8-tetrahydrophthalazin-1(2H)-one;
4-{3-[(4-benzoylpiperazin-1-yl)carbonyl]-4-fluorobenzyl}-5,6,7,8-tetrahydrophthalazin-1(2H)-one;
8-(4-fluoro-3-{[4-(piperidin-1-ylcarbonyl)piperazin-1-yl]carbonyl}benzyl)-2,3,4,6-tetrahydropyrido[2,3-d]pyridazin-5(1H)-one;
4-(4-fluoro-3-{[4-(3-fluorophenyl)piperazin-1-yl]carbonyl}benzyl)-5,6,7,8-tetrahydrophthalazin-1(2H)-one;
4-(4-fluoro-3-{[4-(4-fluorophenyl)piperazin-1-yl]carbonyl}benzyl)-5,6,7,8-tetrahydrophthalazin-1(2H)-one;
4-{4-fluoro-3-[(4-pyridin-2-ylpiperazin-1-yl)carbonyl]benzyl}-5,6,7,8-tetrahydrophthalazin-1(2H)-one;
N,N-diethyl-4-{2-fluoro-5-[(4-oxo-3,4,5,6,7,8-hexahydrophthalazin-1-yl)methyl]benzoyl}piperazine-1-carboxamide;
4-{4-fluoro-3-[(4-isopropylpiperazin-1-yl)carbonyl]benzyl}-5,6,7,8-tetrahydrophthalazin-1(2H)-one;
8-(4-fluoro-3-{[4-(2-oxo-2-pyrrolidin-1-ylethyl)piperazin-1-yl]carbonyl}benzyl)-2,3,4,6-tetrahydropyrido[2,3-d]pyridazin-5(1H)-one;
4-(4-fluoro-3-{[4-(morpholin-4-ylcarbonyl)piperazin-1-yl]carbonyl}benzyl)-5,6,7,8-tetrahydrophthalazin-1(2H)-one;
1-{2-fluoro-5-[(5-oxo-1,2,3,4,5,6-hexahydropyrido[2,3-d]pyridazin-8-yl)methyl]benzoyl}piperidine-4-carboxamide;
8-(4-fluoro-3-{[4-(2-hydroxyethyl)piperazin-1-yl]carbonyl}benzyl)-2,3,4,6-tetrahydropyrido[2,3-d]pyridazin-5(1H)-one;
8-{4-fluoro-3-[(4-pyrimidin-2-ylpiperazin-1-yl)carbonyl]benzyl}-2,3,4,6-tetrahydropyrido[2,3-d]pyridazin-5(1H)-one;
4-(4-fluoro-3-{[4-(2-oxo-2-pyrrolidin-1-ylethyl)piperazin-1-yl]carbonyl}benzyl)-5,6,7,8-tetrahydrophthalazin-1(2H)-one;
N-{2-fluoro-5-[(4-oxo-3,4,5,6,7,8-hexahydrophthalazin-1-yl)methyl]phenyl}-N'-isopropylurea;
N-{2-fluoro-5-[(4-oxo-3,4,5,6,7,8-hexahydrophthalazin-1-yl)methyl]phenyl}-N'-propylurea;
N-cyclopentyl-N'-{2-fluoro-5-[(4-oxo-3,4,5,6,7,8-hexahydrophthalazin-1-yl)methyl]phenyl}urea;
N-(2,4-difluorophenyl)-N'-{2-fluoro-5-[(4-oxo-3,4,5,6,7,8-hexahydrophthalazin-1-yl)methyl]phenyl}urea;
N-(tert-butyl)-N'-{2-fluoro-5-[(4-oxo-3,4,5,6,7,8-hexahydrophthalazin-1-yl)methyl]phenyl}urea;
benzyl 4-{2-fluoro-5-[(4-oxo-3,4,5,6,7,8-hexahydrophthalazin-1-yl)methyl]benzoyl}piperazine-1-carboxylate;

benzyl 4-{2-fluoro-5-[(4-oxo-3,4,5,6,7,8-hexahydrophthalazin-1-yl)methyl]benzoyl}-1,4-diazepane-1-carboxylate;

8-{4-fluoro-3-[(4-pyridin-2-ylpiperazin-1-yl)carbonyl]benzyl}-2,3,4,6-tetrahydropyrido[2,3-d]pyridazin-5(1H)-one;

8-{4-fluoro-3-[(4-phenylpiperazin-1-yl)carbonyl]benzyl}-2,3,4,6-tetrahydropyrido[2,3-d]pyridazin-5(1H)-one;

8-(4-fluoro-3-{[4-(3-fluorophenyl)piperazin-1-yl]carbonyl}benzyl)-2,3,4,6-tetrahydropyrido[2,3-d]pyridazin-5(1H)-one;

8-(4-fluoro-3-{[4-(4-fluorophenyl)piperazin-1-yl]carbonyl}benzyl)-2,3,4,6-tetrahydropyrido[2,3-d]pyridazin-5(1H)-one;

8-(4-fluoro-3-{[4-(2-fluorophenyl)piperazin-1-yl]carbonyl}benzyl)-2,3,4,6-tetrahydropyrido[2,3-d]pyridazin-5(1H)-one;

8-(3-{[4-(2,4-difluorophenyl)piperazin-1-yl]carbonyl}-4-fluorobenzyl)-2,3,4,6-tetrahydropyrido[2,3-d]pyridazin-5(1H)-one;

8-{3-[(4-benzoylpiperazin-1-yl)carbonyl]-4-fluorobenzyl}-2,3,4,6-tetrahydropyrido[2,3-d]pyridazin-5(1H)-one;

8-(4-fluoro-3-{[4-(2-furoyl)piperazin-1-yl]carbonyl}benzyl)-2,3,4,6-tetrahydropyrido[2,3-d]pyridazin-5(1H)-one;

8-(3-{[4(2-chlorophenyl)piperazin-1-yl]carbonyl}-4-fluorobenzyl)-2,3,4,6-tetrahydropyrido[2,3-d]pyridazin-5(1H)-one;

4-(2-fluoro-5-[(5-oxo-1,2,3,4,5,6-hexahydropyrido[2,3-d]pyridazin-8-yl)methyl]benzoyl)-2-morpholin-4-ylpiperazine-1-carbaldehyde;

8-(4-fluoro-3-{[4-(methylsulfonyl)piperazin-1-yl]carbonyl}benzyl)-2,3,4,6-tetrahydropyrido[2,3-d]pyridazin-5(1H)-one;

N,N-diethyl-4-{2-fluoro-5-[(5-oxo-1,2,3,4,5,6-hexahydropyrido[2,3-d]pyridazin-8-yl)methyl]benzoyl}piperazine-1-carboxamide;

8-{3-[(4-acetylpiperazin-1-yl)carbonyl]-4-fluorobenzyl}-2,3,4,6-tetrahydropyrido[2,3-d]pyridazin-5(1H)-one;

2-(4-{2-fluoro-5-[(5-oxo-1,2,3,4,5,6-hexahydropyrido[2,3-d]pyridazin-8-yl)methyl]benzoyl}piperazin-1-yl)-N,N-dimethylacetamide;

8-(4-fluoro-3-{[4-(2-phenoxyethyl)piperazin-1-yl]carbonyl}benzyl)-2,3,4,6-tetrahydropyrido[2,3-d]pyridazin-5(1H)-one;

8-(4-fluoro-3-{[4-(phenylsulfonyl)piperazin-1-yl]carbonyl}benzyl)-2,3,4,6-tetrahydropyrido[2,3-d]pyridazin-5(1H)-one;

2-fluoro-N-[2-(4-methylpiperazin-1-yl)ethyl]-5-[(5-oxo-1,2,3,4,5,6-hexahydropyrido[2,3-d]pyridazin-8-yl)methyl]benzamide;

8-{3-[(4-cyclopentylpiperazin-1-yl)carbonyl]-4-fluorobenzyl}-2,3,4,6-tetrahydropyrido[2,3-d]pyridazin-5(1H)-one;

8-{4-fluoro-3-[(4-isobutyrylpiperazin-1-yl)carbonyl]benzyl}-2,3,4,6-tetrahydropyrido[2,3-d]pyridazin-5(1H)-one;

8-(4-fluoro-3-{[4-(2-morpholin-4-ylethyl)piperazin-1-yl]carbonyl}benzyl)-2,3,4,6-tetrahydropyrido[2,3-d]pyridazin-5(1H)-one;

8-(4-fluoro-3-{[4-(pyrrolidin-1-ylcarbonyl)piperazin-1-yl]carbonyl}benzyl)-2,3,4,6-tetrahydropyrido[2,3-d]pyridazin-5(1H)-one;

8-(3-{[4-(cyclohexylcarbonyl)piperazin-1-yl]carbonyl}-4-fluorobenzyl)-2,3,4,6-tetrahydropyrido[2,3-d]pyridazin-5(1H)-one;

8-(4-fluoro-3-{[4-(tetrahydrofuran-2-ylcarbonyl)piperazin-1-yl]carbonyl}benzyl)-2,3,4,6-tetrahydropyrido[2,3-d]pyridazin-5(1H)-one;

8-(4-fluoro-3-{[4-(2-piperidin-1-ylethyl)piperazin-1-yl]carbonyl}benzyl)-2,3,4,6-tetrahydropyrido[2,3-d]pyridazin-5(1H)-one;

4-(4-fluoro-3-{[4-(2-morpholin-4-ylethyl)piperazin-1-yl]carbonyl}benzyl)-5,6,7,8-tetrahydrophthalazin-1(2H)-one;

8-{4-fluoro-3-[(4-hydroxypiperidin-1-yl)carbonyl]benzyl}-2,3,4,6-tetrahydropyrido[2,3-d]pyridazin-5(1H)-one;

8-(4-fluoro-3-{[4-(6-methylpyrazin-2-yl)piperazin-1-yl]carbonyl}benzyl)-2,3,4,6-tetrahydropyrido[2,3-d]pyridazin-5(1H)-one;

4-(4-fluoro-3-{[4-(phenylsulfonyl)piperazin-1-yl]carbonyl}benzyl)-5,6,7,8-tetrahydrophthalazin-1(2H)-one;

4-{3-[(4-cyclopentylpiperazin-1-yl)carbonyl]-4-fluorobenzyl}-5,6,7,8-tetrahydrophthalazin-1(2H)-one;

4-(4-fluoro-3-{[4-(pyrrolidin-1-ylcarbonyl)piperazin-1-yl]carbonyl}benzyl)-5,6,7,8-tetrahydrophthalazin-1(2H)-one;

4-(4-fluoro-3-{[4-(2-phenoxyethyl)piperazin-1-yl]carbonyl}benzyl)-5,6,7,8-tetrahydrophthalazin-1(2H)-one;

2-fluoro-N-[2-(4-methylpiperazin-1-yl)ethyl]-5-[(4-oxo-3,4,5,6,7,8-hexahydrophthalazin-1-yl)methyl]benzamide;

4-{4-fluoro-3-[(4-isobutyrylpiperazin-1-yl)carbonyl]benzyl}-5,6,7,8-tetrahydrophthalazin-1(2H)-one;

4-{3-[(4-ethylpiperazin-1-yl)carbonyl]-4-fluorobenzyl}-5,6,7,8-tetrahydrophthalazin-1(2H)-one;

benzyl (3S)-1-{2-fluoro-5-[(4-oxo-3,4,5,6,7,8-hexahydrophthalazin-1-yl)methyl]phenyl}-2,5-dioxopyrrolidin-3-ylcarbamate;

3-{2-fluoro-5-[(5-oxo-1,2,3,4,5,6-hexahydropyrido[2,3-d]pyridazin-8-yl)methyl]phenyl}-5-isopropylimidazolidine-2,4-dione;

(3S)-3-amino-1-{2-fluoro-5-[(4-oxo-3,4,5,6,7,8-hexahydrophthalazin-1-yl)methyl]phenyl}pyrrolidine-2,5-dione;

N-{2-fluoro-5-[(4-oxo-3,4,5,6,7,8-hexahydrophthalazin-1-yl)methyl]phenyl}-4-methylpiperazine-1-carboxamide;

4-{4-fluoro-3-[(4-propionylpiperazin-1-yl)carbonyl]benzyl}-5,6,7,8-tetrahydrophthalazin-1(2H)-one;

4-(3-{[4-(ethylsulfonyl)piperazin-1-yl]carbonyl}-4-fluorobenzyl)-5,6,7,8-tetrahydrophthalazin-1(2H)-one;

4-(3-{[4-(2,2-dimethylpropanoyl)piperazin-1-yl]carbonyl}-4-fluorobenzyl)-5,6,7,8-tetrahydrophthalazin-1(2H)-one;

4-(4-fluoro-3-{[4-(phenoxyacetyl)piperazin-1-yl]carbonyl}benzyl)-5,6,7,8-tetrahydrophthalazin-1(2H)-one;

8-(4-fluoro-3-{[4-(phenoxyacetyl)piperazin-1-yl]carbonyl}benzyl)-2,3,4,6-tetrahydropyrido[2,3-d]pyridazin-5(1H)-one;

8-(3-{[4(2,2-dimethylpropanoyl)piperazin-1-yl]carbonyl}-4-fluorobenzyl)-2,3,4,6-tetrahydropyrido[2,3-d]pyridazin-5(1H)-one;

8-(3-{[4-(ethylsulfonyl)piperazin-1-yl]carbonyl}-4-fluorobenzyl)-2,3,4,6-tetrahydropyrido[2,3-d]pyridazin-5(1H)-one;

N-(1-{2-fluoro-5-[(5-oxo-1,2,3,4,5,6-hexahydropyrido[2,3-d]pyridazin-8-yl)methyl]benzoyl}pyrrolidin-3-yl)-N-methylacetamide;

N-ethyl-N-(1-{2-fluoro-5-[(5-oxo-1,2,3,4,5,6-hexahydropyrido[2,3-d]pyridazin-8-yl)methyl]benzoyl}pyrrolidin-3-yl)acetamide;

8-{4-fluoro-3-[(4-propionylpiperazin-1-yl)carbonyl]benzyl}-2,3,4,6-tetrahydropyrido[2,3-d]pyridazin-5(1H)-one;

3-{2-fluoro-5-[(5-oxo-1,2,3,4,5,6-hexahydropyrido[2,3-d]pyridazin-8-yl)methyl]phenyl}-5-methylimidazolidine-2,4-dione;

8-(4-fluoro-3-{[4-(4-methoxyphenyl)piperazin-1-yl]carbonyl}benzyl)-2,3,4,6-tetrahydropyrido[2,3-d]pyridazin-5(1H)-one;

8-[4-fluoro-3-({4-[(4-methoxyphenyl)sulfonyl]piperazin-1-yl}carbonyl)benzyl]-2,3,4,6-tetrahydropyrido[2,3-d]pyridazin-5(1H)-one;

8-(4-fluoro-3-{[4-(4-methoxybenzoyl)piperazin-1-yl]carbonyl}benzyl)-2,3,4,6-tetrahydropyrido[2,3-d]pyridazin-5(1H)-one;

8-[4-fluoro-3-({4-[3-(trifluoromethyl)phenyl]piperazin-1-yl}carbonyl)benzyl]-2,3,4,6-tetrahydropyrido[2,3-d]pyridazin-5(1H)-one;

tert-butyl 3-{2-fluoro-5-[(5-oxo-1,2,3,4,5,6-hexahydropyrido[2,3-d]pyridazin-8-yl)methyl]benzoyl}tetrahydropyrimidine-1(2H)-carboxylate;

8-(3-{[3-[3-(dimethylamino)propyl]tetrahydropyrimidin-1(2H)-yl]carbonyl}-4-fluorobenzyl)-2,3,4,6-tetrahydropyrido[2,3-d]pyridazin-5(1H)-one;

5-benzyl-3-{2-fluoro-5-[(5-oxo-1,2,3,4,5,6-hexahydropyrido[2,3-d]pyridazin-8-yl)methyl]phenyl}imidazolidine-2,4-dione;

3-{2-fluoro-5-[(5-oxo-1,2,3,4,5,6-hexahydropyrido[2,3-d]pyridazin-8-yl)methyl]phenyl}dihydropyrimidine-2,4(1H,3H)-dione;

8-{4-fluoro-3-[(3-oxopiperazin-1-yl)carbonyl]benzyl}-2,3,4,6-tetrahydropyrido[2,3-d]pyridazin-5(1H)-one;

8-{3-[(4-benzoylpiperidin-1-yl)carbonyl]-4-fluorobenzyl}-2,3,4,6-tetrahydropyrido[2,3-d]pyridazin-5(1H)-one;

8-(4-fluoro-3-{[4-(4-methoxybenzoyl)piperidin-1-yl]carbonyl}benzyl)-2,3,4,6-tetrahydropyrido[2,3-d]pyridazin-5(1H)-one;

8-(4-fluoro-3-{[4-(1H-indol-6-ylcarbonyl)piperazin-1-yl]carbonyl}benzyl)-2,3,4,6-tetrahydropyrido[2,3-d]pyridazin-5(1H)-one;

8-(3-{[4-(3-chlorobenzoyl)piperidin-1-yl]carbonyl}-4-fluorobenzyl)-2,3,4,6-tetrahydropyrido[2,3-d]pyridazin-5(1H)-one;

benzyl 4-{2-fluoro-5-[(5-oxo-1,2,3,4,5,6-hexahydropyrido[2,3-d]pyridazin-8-yl)methyl]benzoyl}piperazine-1-carboxylate;

tert-butyl (3R)-4-{2-fluoro-5-[(5-oxo-1,2,3,4,5,6-hexahydropyrido[2,3-d]pyridazin-8-yl)methyl]benzoyl}-3-phenylpiperazine-1-carboxylate;

8-(3-{[(2R)-4-benzoyl-2-methylpiperazin-1-yl]carbonyl}-4-fluorobenzyl)-2,3,4,6-tetrahydropyrido[2,3-d]pyridazin-5(1H)-one;

8-[4-fluoro-3-(piperazin-1-ylcarbonyl)benzyl]-2,3,4,6-tetrahydropyrido[2,3-d]pyridazin-5(1H)-one;

N'-{2-fluoro-5-[(4-oxo-3,4,5,6,7,8-hexahydrophthalazin-1-yl)methyl]phenyl}-N-methyl-N-phenylurea;

N-ethyl-N-(1-{2-fluoro-5-[(4-oxo-3,4,5,6,7,8-hexahydrophthalazin-1-yl)methyl]benzoyl}pyrrolidin-3-yl)acetamide;

4-[4-fluoro-3-({4-[(4-methoxyphenyl)sulfonyl]piperazin-1-yl}carbonyl)benzyl]-5,6,7,8-tetrahydrophthalazin-1(2H)-one;

4-[4-fluoro-3-({4-[3-(trifluoromethyl)phenyl]piperazin-1-yl}carbonyl)benzyl]-5,6,7,8-tetrahydrophthalazin-1(2H)-one;

4-(4-fluoro-3-{[4-(4-methoxybenzoyl)piperazin-1-yl]carbonyl}benzyl)-5,6,7,8-tetrahydrophthalazin-1(2H)-one;

4-(4-fluoro-3-{[4-(4-methoxyphenyl)piperazin-1-yl]carbonyl}benzyl)-5,6,7,8-tetrahydrophthalazin-1(2H)-one;

4-(3-{[4-(cyclohexylcarbonyl)piperazin-1-yl]carbonyl}-4-fluorobenzyl)-5,6,7,8-tetrahydrophthalazin-1(2H)-one;

N-[({2-fluoro-5-[(4-oxo-3,4,5,6,7,8-hexahydrophthalazin-1-yl)methyl]phenyl}amino)carbonyl]glycine;

N-[({2-fluoro-5-[(4-oxo-3,4,5,6,7,8-hexahydrophthalazin-1-yl)methyl]phenyl}amino)carbonyl]leucine;

N-[({2-fluoro-5-[(4-oxo-3,4,5,6,7,8-hexahydrophthalazin-1-yl)methyl]phenyl}amino)carbonyl]alanine;

N-[({2-fluoro-5-[(4-oxo-3,4,5,6,7,8-hexahydrophthalazin-1-yl)methyl]phenyl}amino)carbonyl]phenylalanine;

3-{2-fluoro-5-[(4-oxo-3,4,5,6,7,8-hexahydrophthalazin-1-yl)methyl]phenyl}imidazolidine-2,4-dione;

8-(4-fluoro-3-{[4-(2-methoxyphenyl)piperazin-1-yl]carbonyl}benzyl)-2,3,4,6-tetrahydropyrido[2,3-d]pyridazin-5(1H)-one;

8-(4-fluoro-3-{[4-(1,3,5-triazin-2-yl)piperazin-1-yl]carbonyl}benzyl)-2,3,4,6-tetrahydropyrido[2,3-d]pyridazin-5(1H)-one;

8-(3-{[4-(2,3-dihydro-1,4-benzodioxin-2-ylcarbonyl)piperazin-1-yl]carbonyl}-4-fluorobenzyl)-2,3,4,6-tetrahydropyrido[2,3-d]pyridazin-5(1H)-one;

4-(3-{[4-(cyclopropylcarbonyl)-1,4-diazepan-1-yl]carbonyl}-4-fluorobenzyl)-5,6,7,8-tetrahydrophthalazin-1(2H)-one;

4-[4-fluoro-3-({4-[(1-methylcyclopropyl)carbonyl]-1,4-diazepan-1-yl}carbonyl)benzyl]-5,6,7,8-tetrahydrophthalazin-1(2H)-one;

4-[4-fluoro-3-({4-[(1-methyl-1H-imidazol-4-yl)carbonyl]-1,4-diazepan-1-yl}carbonyl)benzyl]-5,6,7,8-tetrahydrophthalazin-1(2H)-one;

4-[4-fluoro-3-({4-[(1-methyl-1H-imidazol-5-yl)carbonyl]-1,4-diazepan-1-yl}carbonyl)benzyl]-5,6,7,8-tetrahydrophthalazin-1(2H)-one;

8-(4-fluoro-3-{[(2R)-2-phenylpiperazin-1-yl]carbonyl}benzyl)-2,3,4,6-tetrahydropyrido[2,3-d]pyridazin-5(1H)-one;

8-[4-fluoro-3-({4-[(4R)-1,3-thiazolidin-4-ylcarbonyl]piperazin-1-yl}carbonyl)benzyl]-2,3,4,6-tetrahydropyrido[2,3-d]pyridazin-5(1H)-one;

8-(3-{[4-(cyclopentylcarbonyl)piperazin-1-yl]carbonyl}-4-fluorobenzyl)-2,3,4,6-tetrahydropyrido[2,3-d]pyridazin-5(1H)-one;

8-(3-({4-[(5-chloropyridin-2-yl)carbonyl]piperazin-1-yl}carbonyl)-4-fluorobenzyl]-2,3,4,6-tetrahydropyrido[2,3-d]pyridazin-5(1H)-one;

8-[4-fluoro-3-({4-[(1-isopropyl-1H-1,2,3-benzotriazol-5-yl)carbonyl]piperazin-1-yl}carbonyl)benzyl]-2,3,4,6-tetrahydropyrido[2,3-d]pyridazin-5(1H)-one;

8-(4-fluoro-3-{[4-(4-methylpiperazin-1-yl)piperidin-1-yl]carbonyl}benzyl)-2,3,4,6-tetrahydropyrido[2,3-d]pyridazin-5(1H)-one;

8-(4-fluoro-3-{[4-(quinolin-2-ylcarbonyl)piperazin-1-yl]carbonyl}benzyl)-2,3,4,6-tetrahydropyrido[2,3-d]pyridazin-5(1H)-one;

8-[3-({4-[(6-chloropyridin-3-yl)carbonyl]piperazin-1-yl}carbonyl)-4-fluorobenzyl]-2,3,4,6-tetrahydropyrido[2,3-d]pyridazin-5(1H)-one;

8-{4-fluoro-3-[(4-{[1-isopropyl-2-(trifluoromethyl)-1H-benzimidazol-5-yl]carbonyl}piperazin-1-yl)carbonyl]benzyl}-2,3,4,6-tetrahydropyrido[2,3-d]pyridazin-5(1H)-one;

8-[4-fluoro-3-({4-[(6-hydroxypyridin-3-yl)carbonyl]piperazin-1-yl}carbonyl)benzyl]-2,3,4,6-tetrahydropyrido[2,3-d]pyridazin-5(1H)-one;

8-[3-({4-[(6-chloro-5-hydroxypyridin-3-yl)carbonyl]piperazin-1-yl}carbonyl)-4-fluorobenzyl]-2,3,4,6-tetrahydropyrido[2,3-d]pyridazin-5(1H)-one;

8-[4-fluoro-3-({4-[(2-methyl-1H-benzimidazol-5-yl)carbonyl]piperazin-1-yl}carbonyl)benzyl]-2,3,4,6-tetrahydropyrido[2,3-d]pyridazin-5(1H)-one;

8-(3-{[4-(1H-benzimidazol-6-ylcarbonyl)piperazin-1-yl]carbonyl}-4-fluorobenzyl)-2,3,4,6-tetrahydropyrido[2,3-d]pyridazin-5(1H)-one;

8-(4-fluoro-3-{[4-(quinolin-3-ylcarbonyl)piperazin-1-yl]carbonyl}benzyl)-2,3,4,6-tetrahydropyrido[2,3-d]pyridazin-5(1H)-one;

8-[3-({4-[(2-chloropyridin-3-yl)carbonyl]piperazin-1-yl}carbonyl)-4-fluorobenzyl]-2,3,4,6-tetrahydropyrido[2,3-d]pyridazin-5(1H)-one;

benzyl 4-{2-fluoro-5-[(5-oxo-1,2,3,4,5,6-hexahydropyrido[2,3-d]pyridazin-8-yl)methyl]benzoyl}-1,4-diazepane-1-carboxylate;

8-{4-fluoro-3-[(4-isonicotinoylpiperazin-1-yl)carbonyl]benzyl}-2,3,4,6-tetrahydropyrido[2,3-d]pyridazin-5(1H)-one;

8-(4-fluoro-3-{[4-(pyridin-3-ylcarbonyl)piperazin-1-yl]carbonyl}benzyl)-2,3,4,6-tetrahydropyrido[2,3-d]pyridazin-5(1H)-one;

8-(4-fluoro-3-{[4-(pyrazin-2-ylcarbonyl)piperazin-1-yl]carbonyl}benzyl)-2,3,4,6-tetrahydropyrido[2,3-d]pyridazin-5(1H)-one;

8-(3-{[4-(1H-benzimidazol-5-ylcarbonyl)piperazin-1-yl]carbonyl}-4-fluorobenzyl)-2,3,4,6-tetrahydropyrido[2,3-d]pyridazin-5(1H)-one;

8-(4-fluoro-3-{[4-(pyrimidin-5-ylcarbonyl)piperazin-1-yl]carbonyl}benzyl)-2,3,4,6-tetrahydropyrido[2,3-d]pyridazin-5(1H)-one;

8-(4-fluoro-3-{[4-(pyridin-2-ylcarbonyl)piperazin-1-yl]carbonyl}benzyl)-2,3,4,6-tetrahydropyrido[2,3-d]pyridazin-5(1H)-one;

ethyl 4-{2-fluoro-5-[(5-oxo-1,2,3,4,5,6-hexahydropyrido[2,3-d]pyridazin-8-yl)methyl]benzoyl}piperazine-1-carboxylate;

8-{3-[(2,2-dimethyl-3-oxopiperazin-1-yl)carbonyl]-4-fluorobenzyl}-2,3,4,6-tetrahydropyrido[2,3-d]pyridazin-5(1H)-one;

4-(3-{[(2R)-4-benzoyl-2-methylpiperazin-1-yl]carbonyl}-4-fluorobenzyl)-5,6,7,8-tetrahydrophthalazin-1(2H)-one;

4-(4-fluoro-3-{[4-(1,3,5-triazin-2-yl)piperazin-1-yl]carbonyl}benzyl)-5,6,7,8-tetrahydrophthalazin-1(2H)-one;

5-benzyl-3-{2-fluoro-5-[(4-oxo-3,4,5,6,7,8-hexahydrophthalazin-1-yl)methyl]phenyl}imidazolidine-2,4-dione;

4-[3-({4-[(6-chloropyridin-3-yl)carbonyl]piperazin-1-yl}carbonyl)-4-fluorobenzyl]-5,6,7,8-tetrahydrophthalazin-1(2H)-one;

4-(4-fluoro-3-{[4-(1,3-thiazol-4-ylcarbonyl)piperazin-1-yl]carbonyl}benzyl)-5,6,7,8-tetrahydrophthalazin-1(2H)-one;

4-[4-fluoro-3-({4-[(5-oxopyrrolidin-2-yl)carbonyl]piperazin-1-yl}carbonyl)benzyl]-5,6,7,8-tetrahydrophthalazin-1(2H)-one;

4-{3-[(4-{[(4R)-5,5-dimethyl-1,3-thiazolidin-4-yl]carbonyl}piperazin-1-yl)carbonyl]-4-fluorobenzyl}-5,6,7,8-tetrahydrophthalazin-1(2H)-one;

4-(4-fluoro-3-{[4-(1H-pyrazol-3-ylcarbonyl)piperazin-1-yl]carbonyl}benzyl)-5,6,7,8-tetrahydrophthalazin-1(2H)-one;

4-(4-fluoro-3-{[4-(pyrazin-2-ylcarbonyl)piperazin-1-yl]carbonyl}benzyl)-5,6,7,8-tetrahydrophthalazin-1(2H)-one;

4-(3-{[4-(1H-benzimidazol-5-ylcarbonyl)piperazin-1-yl]carbonyl}-4-fluorobenzyl)-5,6,7,8-tetrahydrophthalazin-1(2H)-one;

4-[4-fluoro-3-(methylamino)benzyl]-5,6,7,8-tetrahydrophthalazin-1(2H)-one;

8-{4-fluoro-3-[(4-isonicotinoyl-1,4-diazepan-1-yl)carbonyl]benzyl}-2,3,4,6-tetrahydropyrido[2,3-d]pyridazin-5(1H)-one;

8-(4-fluoro-3-{[4-(pyridin-3-ylcarbonyl)-1,4-diazepan-1-yl]carbonyl}benzyl)-2,3,4,6-tetrahydropyrido[2,3-d]pyridazin-5(1H)-one;

8-(4-fluoro-3-{[4-(pyridin-2-ylcarbonyl)-1,4-diazepan-1-yl]carbonyl}benzyl)-2,3,4,6-tetrahydropyrido[2,3-d]pyridazin-5(1H)-one;

8-(4-fluoro-3-{[4-(pyrimidin-5-ylcarbonyl)-1,4-diazepan-1-yl]carbonyl}benzyl)-2,3,4,6-tetrahydropyrido[2,3-d]pyridazin-5(1H)-one;

8-(3-{[4-(1H-benzimidazol-6-ylcarbonyl)-1,4-diazepan-1-yl]carbonyl}-4-fluorobenzyl)-2,3,4,6-tetrahydropyrido[2,3-d]pyridazin-5(1H)-one;

8-(4-fluoro-3-{[4-(quinolin-2-ylcarbonyl)-1,4-diazepan-1-yl]carbonyl}benzyl)-2,3,4,6-tetrahydropyrido[2,3-d]pyridazin-5(1H)-one;

8-(4-fluoro-3-{[4-(quinolin-3-ylcarbonyl)-1,4-diazepan-1-yl]carbonyl}benzyl)-2,3,4,6-tetrahydropyrido[2,3-d]pyridazin-5(1H)-one;

8-[4-fluoro-3-({4-[(2-methyl-1H-benzimidazol-5-yl)carbonyl]-1,4-diazepan-1-yl}carbonyl)benzyl]-2,3,4,6-tetrahydropyrido[2,3-d]pyridazin-5(1H)-one;

8-[4-fluoro-3-({4-[(1-isopropyl-1H-1,2,3-benzotriazol-5-yl)carbonyl]-1,4-diazepan-1-yl}carbonyl)benzyl]-2,3,4,6-tetrahydropyrido[2,3-d]pyridazin-5(1H)-one;

8-(4-fluoro-3-{[4-(4-fluorobenzoyl)piperidin-1-yl]carbonyl}benzyl)-2,3,4,6-tetrahydropyrido[2,3-d]pyridazin-5(1H)-one;

8-[3-({4-[(5,5-dimethyl-1,3-thiazolidin-4-yl)carbonyl]piperazin-1-yl}carbonyl)-4-fluorobenzyl-2,3,4,6-tetrahydropyrido[2,3-d]pyridazin-5(1H)-one;

8-(4-fluoro-3-{[4-(pyrazin-2-ylcarbonyl)-1,4-diazepan-1-yl]carbonyl}benzyl)-2,3,4,6-tetrahydropyrido[2,3-d]pyridazin-5(1H)-one;

8-(4-fluoro-3-{[4-(2-furoyl)-1,4-diazepan-1-yl]carbonyl}benzyl)-2,3,4,6-tetrahydropyrido[2,3-d]pyridazin-5(1H)-one;

8-{4-fluoro-3-[(4-pyridin-3-ylpiperazin-1-yl)carbonyl]benzyl}-2,3,4,6-tetrahydropyrido[2,3-d]pyridazin-5(1H)-one;

8-{4-fluoro-3-[(4-pyrimidin-5-ylpiperazin-1-yl)carbonyl]benzyl}-2,3,4,6-tetrahydropyrido[2,3-d]pyridazin-5(1H)-one;

8-{4-fluoro-3-[(4-methyl-3-oxopiperazin-1-yl)carbonyl]benzyl}-2,3,4,6-tetrahydropyrido[2,3-d]pyridazin-5(1H)-one;

tert-butyl 4-[{2-fluoro-5-[(5-oxo-1,2,3,4,5,6-hexahydropyrido[2,3-d]pyridazin-8-yl)methyl]benzoyl}(methyl)amino]piperidine-1-carboxylate;

tert-butyl 4-({2-fluoro-5-[(5-oxo-1,2,3,4,5,6-hexahydropyrido[2,3-d]pyridazin-8-yl)methyl]benzoyl}amino)piperidine-1-carboxylate;

tert-butyl 1-{2-fluoro-5-[(5-oxo-1,2,3,4,5,6-hexahydropyrido[2,3-d]pyridazin-8-yl)methyl]benzoyl}piperidin-4-ylcarbamate;

8-[4-fluoro-3-({4-[(4R)-1,3-thiazolidin-4-ylcarbonyl]-1,4-diazepan-1-yl}carbonyl)benzyl]-2,3,4,6-tetrahydropyrido[2,3-d]pyridazin-5(1H)-one;

8-(4-fluoro-3-{[4-(1H-pyrazol-3-ylcarbonyl)-1,4-diazepan-1-yl]carbonyl}benzyl)-2,3,4,6-tetrahydropyrido[2,3-d]pyridazin-5(1H)-one;

8-(4-fluoro-3-{[4-(1,3-thiazol-4-ylcarbonyl)-1,4-diazepan-1-yl]carbonyl}benzyl)-2,3,4,6-tetrahydropyrido[2,3-d]pyridazin-5(1H)-one;

8-(4-fluoro-3-{[4-(1H-pyrazol-3-ylcarbonyl)piperazin-1-yl]carbonyl}benzyl)-2,3,4,6-tetrahydropyrido[2,3-d]pyridazin-5(1H)-one;

8-(4-fluoro-3-{[4-(1,3-thiazol-4-ylcarbonyl)piperazin-1-yl]carbonyl}benzyl)-2,3,4,6-tetrahydropyrido[2,3-d]pyridazin-5(1H)-one;

2-fluoro-N-methyl-5-[(5-oxo-1,2,3,4,5,6-hexahydropyrido[2,3-d]pyridazin-8-yl)methyl]-N-piperidin-4-ylbenzamide;

2-fluoro-5-[(5-oxo-1,2,3,4,5,6-hexahydropyrido[2,3-d]pyridazin-8-yl)methyl]-N-piperidin-4-ylbenzamide;

8-{3-[(4-aminopiperidin-1-yl)carbonyl]-4-fluorobenzyl}-2,3,4,6-tetrahydropyrido[2,3-d]pyridazin-5(1H)-one;

2-fluoro-N-(4-hydroxycyclohexyl)-5-[(5-oxo-1,2,3,4,5,6-hexahydropyrido[2,3-d]pyridazin-8-yl)methyl]benzamide;

2-fluoro-N-methyl-5-[(5-oxo-1,2,3,4,5,6-hexahydropyrido[2,3-d]pyridazin-8-yl)methyl]-N-[1-(pyridin-3-ylcarbonyl)piperidin-4-yl]benzamide;

tert-butyl 2-(ethyl {2-fluoro-5-[(4-oxo-3,4,5,6,7,8-hexahydrophthalazin-1-yl)methyl]benzoyl}amino)ethylcarbamate;

2-fluoro-N-(1-isonicotinoylpiperidin-4-yl)-N-methyl-5-[(5-oxo-1,2,3,4,5,6-hexahydropyrido[2,3-d]pyridazin-8-yl)methyl]benzamide;

N-[1-(1H-benzimidazol-5-ylcarbonyl)piperidin-4-yl]-2-fluoro-5-[(5-oxo-1,2,3,4,5,6-hexahydropyrido[2,3-d]pyridazin-8-yl)methyl]benzamide;

2-fluoro-5-[(4-oxo-3,4,5,6,7,8-hexahydrophthalazin-1-yl)methyl]-N-[2-(2-oxopyrrolidin-1-yl)ethyl]benzamide;

2-fluoro-N-[1-(2-furoyl)piperidin-4-yl]-N-methyl-5-[(5-oxo-1,2,3,4,5,6-hexahydropyrido[2,3-d]pyridazin-8-yl)methyl]benzamide;

2-fluoro-N-methyl-5-[(5-oxo-1,2,3,4,5,6-hexahydropyrido[2,3-d]pyridazin-8-yl)methyl]-N-{1-[(4R)-1,3-thiazolidin-4-ylcarbonyl]piperidin-4-yl}benzamide;

2-fluoro-N-methyl-5-[(5-oxo-1,2,3,4,5,6-hexahydropyrido[2,3-d]pyridazin-8-yl)methyl]-N-[1-(1,3-thiazol-4-ylcarbonyl)piperidin-4-yl]benzamide;

2-fluoro-N-methyl-5-[(5-oxo-1,2,3,4,5,6-hexahydropyrido[2,3-d]pyridazin-8-yl)methyl]-N-[1-(1H-pyrazol-4-ylcarbonyl)piperidin-4-yl]benzamide;

N-(2-aminoethyl)-N-ethyl-2-fluoro-5-[(4-oxo-3,4,5,6,7,8-hexahydrophthalazin-1-yl)methyl]benzamide;

4-{4-fluoro-3-[(4-isonicotinoylpiperazin-1-yl)carbonyl]benzyl}-5,6,7,8-tetrahydrophthalazin-1(2H)-one;

2-fluoro-N-methyl-5-[(5-oxo-1,2,3,4,5,6-hexahydropyrido[2,3-d]pyridazin-8-yl)methyl]-N-[1-(pyridin-2-ylcarbonyl)piperidin-4-yl]benzamide;

4-(4-fluoro-3-{[4-(pyridin-3-ylcarbonyl)piperazin-1-yl]carbonyl}benzyl)-5,6,7,8-tetrahydrophthalazin-1(2H)-one;

4-[3-({4-[(5-chloro-6-hydroxypyridin-3-yl)carbonyl]piperazin-1-yl}carbonyl)-4-fluorobenzyl]-5,6,7,8-tetrahydrophthalazin-1(2H)-one;

2-fluoro-5-[(5-oxo-1,2,3,4,5,6-hexahydropyrido[2,3-d]pyridazin-8-yl)methyl]-N-[1-(pyridin-3-ylcarbonyl)piperidin-4-yl]benzamide;

4-{4-fluoro-3-[(4-{[1-isopropyl-2-(trifluoromethyl)-1H-benzimidazol-5-yl]carbonyl}piperazin-1-yl)carbonyl]benzyl}-5,6,7,8-tetrahydrophthalazin-1(2H)-one;

2-fluoro-N-[1-(2-furoyl)piperidin-4-yl]-5-[(5-oxo-1,2,3,4,5,6-hexahydropyrido[2,3-d]pyridazin-8-yl)methyl]benzamide;

4-[4-fluoro-3-({4-[(4R)-1,3-thiazolidin-4-ylcarbonyl]piperazin-1-yl}carbonyl)benzyl]-5,6,7,8-tetrahydrophthalazin-1(2H)-one;

4-[4-fluoro-3-({4-[(1-isopropyl-1H-1,2,3-benzotriazol-5-yl)carbonyl]piperazin-1-yl}carbonyl)benzyl]-5,6,7,8-tetrahydrophthalazin-1(2H)-one;

2-fluoro-5-[(5-oxo-1,2,3,4,5,6-hexahydropyrido[2,3-d]pyridazin-8-yl)methyl]-N-{1-[(4R)-1,3-thiazolidin-4-ylcarbonyl]piperidin-4-yl}benzamide;

4-(4-fluoro-3-{[4-(pyridin-2-ylcarbonyl)piperazin-1-yl]carbonyl}benzyl)-5,6,7,8-tetrahydrophthalazin-1(2H)-one;

2-fluoro-5-[(5-oxo-1,2,3,4,5,6-hexahydropyrido[2,3-d]pyridazin-8-yl)methyl]-N-[1-(1,3-thiazol-4-ylcarbonyl)piperidin-4-yl]benzamide;

4-(4-fluoro-3-{[4-(pyrimidin-5-ylcarbonyl)piperazin-1-yl]carbonyl}benzyl)-5,6,7,8-tetrahydrophthalazin-1(2H)-one;

2-fluoro-5-[(5-oxo-1,2,3,4,5,6-hexahydropyrido[2,3-d]pyridazin-8-yl)methyl]-N-[1-(1H-pyrazol-4-ylcarbonyl)piperidin-4-yl]benzamide;

4-[4-fluoro-3-({4-[(6-hydroxypyridin-3-yl)carbonyl]piperazin-1-yl}carbonyl)benzyl]-5,6,7,8-tetrahydrophthalazin-1(2H)-one;

2-fluoro-5-[(5-oxo-1,2,3,4,5,6-hexahydropyrido[2,3-d]pyridazin-8-yl)methyl]-N-[1-(pyridin-2-ylcarbonyl)piperidin-4-yl]benzamide;

2-fluoro-N-(1-isonicotinoylpiperidin-4-yl)-5-[(5-oxo-1,2,3,4,5,6-hexahydropyrido[2,3-d]pyridazin-8-yl)methyl]benzamide;

4-(4-fluoro-3-{[4-(quinolin-2-ylcarbonyl)piperazin-1-yl]carbonyl}benzyl)-5,6,7,8-tetrahydrophthalazin-1(2H)-one;

N-[(1S,2S)-2-aminocyclohexyl]-2-fluoro-5-[(5-oxo-1,2,3,4,5,6-hexahydropyrido[2,3-d]pyridazin-8-yl)methyl]benzamide;

N-[2-(benzoylamino)ethyl]-N-ethyl-2-fluoro-5-[(4-oxo-3,4,5,6,7,8-hexahydrophthialazin-1-yl)methyl]benzamide;

N-[2-(ethyl {2-fluoro-5-[(4-oxo-3,4,5,6,7,8-hexahydrophthialazin-1-yl)methyl]benzoyl}amino)ethyl]pyrrolidine-1-carboxamide;

2-fluoro-5-[(5-oxo-1,2,3,4,5,6-hexahydropyrido[2,3-d]pyridazin-8-yl)methyl]-N-(1-pyridin-2-ylpiperidin-4-yl)benzamide;

N-(1-{2-fluoro-5-[(5-oxo-1,2,3,4,5,6-hexahydropyrido[2,3-d]pyridazin-8-yl)methyl]benzoyl}piperidin-4-yl)pyridine-2-carboxamide;

N-(1-{2-fluoro-5-[(5-oxo-1,2,3,4,5,6-hexahydropyrido[2,3-d]pyridazin-8-yl)methyl]benzoyl}piperidin-4-yl)nicotinamide;

N-(1-{2-fluoro-5-[(5-oxo-1,2,3,4,5,6-hexahydropyrido[2,3-d]pyridazin-8-yl)methyl]benzoyl}piperidin-4-yl)isonicotinamide;

N-(1-{2-fluoro-5-[(5-oxo-1,2,3,4,5,6-hexahydropyrido[2,3-d]pyridazin-8-yl)methyl]benzoyl}piperidin-4-yl)-1H-indazole-6-carboxamide;

N-(1-{2-fluoro-5-[(5-oxo-1,2,3,4,5,6-hexahydropyrido[2,3-d]pyridazin-8-yl)methyl]benzoyl}piperidin-4-yl)-2-furamide;

N-(1-{2-fluoro-5-[(5-oxo-1,2,3,4,5,6-hexahydropyrido[2,3-d]pyridazin-8-yl)methyl]benzoyl}piperidin-4-yl)-1,3-thiazole-4-carboxamide;
N-{2-fluoro-5-[(4-oxo-3,4,5,6,7,8-hexahydrophthalazin-1-yl)methyl]phenyl}-N-methylcyclobutanecarboxamide;
4-[4-fluoro-3-({4-[(2-methyl-1H-benzimidazol-5-yl)carbonyl]piperazin-1-yl}carbonyl)benzyl]-5,6,7,8-tetrahydrophthalazin-1(2H)-one;
4-[3-({4-[(2-chloropyridin-3-yl)carbonyl]piperazin-1-yl}carbonyl)-4-fluorobenzyl]-5,6,7,8-tetrahydrophthalazin-1(2H)-one;
4-{4-fluoro-3-[(4-pyridin-3-ylpiperazin-1-yl)carbonyl]benzyl}-5,6,7,8-tetrahydrophthalazin-1(2H)-one;
4-{4-fluoro-3-[(4-pyrimidin-5-ylpiperazin-1-yl)carbonyl]benzyl}-5,6,7,8-tetrahydrophthalazin-1(2H)-one;
N-(1-{2-fluoro-5-[(5-oxo-1,2,3,4,5,6-hexahydropyrido[2,3-d]pyridazin-8-yl)methyl]benzoyl}piperidin-4-yl)-1H-pyrazole-4-carboxamide;
4-{4-fluoro-3-[(4-methyl-3-oxopiperazin-1-yl)carbonyl]benzyl}-5,6,7,8-tetrahydrophthalazin-1(2H)-one;
N-{2-[(cyclopropylcarbonyl)amino]ethyl}-N-ethyl-2-fluoro-5-[(4-oxo-3,4,5,6,7,8-hexahydrophthalazin-1-yl)methyl]benzamide;
N-{2-[(2,6-difluorobenzoyl)amino]ethyl}-N-ethyl-2-fluoro-5-[(4-oxo-3,4,5,6,7,8-hexahydrophthalazin-1-yl)methyl]benzamide;
N-[2-(ethyl {2-fluoro-5-[(4-oxo-3,4,5,6,7,8-hexahydrophthalazin-1-yl)methyl]benzoyl}amino)ethyl]nicotinamide; and therapeutically acceptable salts, prodrugs, esters, amides, salts of prodrugs, salts of esters and salts of amides thereof.

DETAILED DESCRIPTION OF THE INVENTION

Variable moieties of compounds herein are represented by identifiers (capital letters with numerical and/or alphabetical superscripts) and may be specifically embodied.

It is meant to be understood that proper valences are maintained for all combinations herein, that monovalent moieties having more than one atom are attached through their left ends.

It is also meant to be understood that a specific embodiment of a variable moiety may be the same or different as another specific embodiment having the same identifier.

Abbreviations which have been used in the descriptions of the schemes and the examples that follow are:
BOC is Di-tert-butyl dicarbonate
C-18 is dimethyl-octadecylsilane
DCI for chemical ionization for direct introduction,
DME for 1,2-dimethoxyethane,
DMSO for dimethylsulfoxide,
ESI for electrospray ionization,
HATU for O-(7-azabenzotriazol-1-yl)-N,N,N',N'-tetramethyluronium hexafluorophosphate,
HPLC for high performance liquid chromatography,
MS for mass spectrometry,
TFA for trifluoroacetic acid,
As used in reference to $^1$H NMR, the symbol "δ" refers to a $^1$H NMR chemical shift.
As used in reference to $^1$H NMR, the abbreviation "br" refers to a broad $^1$H NMR signal.
As used in reference to $^1$H NMR, the abbreviation "d" refers to a doublet $^1$H NMR peak.
As used in reference to $^1$H NMR, the abbreviation "dd" refers to a doublet of doublets $^1$H NMR peak.
As used in reference to $^1$H NMR, the abbreviation "m" refers to a multiplet $^1$H NMR peak.
As used in reference to $^1$H NMR, the abbreviation "q" refers to a quartet $^1$H NMR peak.
As used in reference to $^1$H NMR, the abbreviation "s" refers to a singlet $^1$H NMR peak.
As used in reference to $^1$H NMR, the abbreviation "t" refers to a triplet $^1$H NMR peak.

The term "alkenyl," as used herein, means monovalent, straight or branched chain hydrocarbon moieties having one or more than one carbon-carbon double bonds, such as $C_2$-alkenyl, $C_3$-alkenyl, $C_4$-alkenyl, $C_5$-alkenyl, $C_6$-alkenyl and the like.

The term "alkyl," as used herein, means monovalent, saturated, straight or branched chain hydrocarbon moieties, such as $C_1$-alkyl, $C_2$-alkyl, $C_3$-alkyl, $C_4$-alkyl, $C_5$-alkyl, $C_6$-alkyl and the like.

The term "alkynyl," as used herein, means monovalent, straight or branched chain hydrocarbon moieties having one or more than one carbon-carbon triple bonds, such as $C_2$-alkynyl, $C_3$-alkynyl, $C_4$-alkynyl, $C_5$-alkynyl, $C_6$-alkynyl and the like.

The term "cycloalkane," as used herein, means saturated cyclic or bicyclic hydrocarbon moieties, such as $C_4$-cycloalkane, $C_5$-cycloalkane, $C_6$-cycloalkane, $C_7$-cycloalkane, $C_8$-cycloalkane, $C_9$-cycloalkane, $C_{10}$-cycloalkane, $C_{11}$-cycloalkane, $C_{12}$-cycloalkane and the like.

The term "cycloalkyl," as used herein, means monovalent, saturated cyclic and bicyclic hydrocarbon moieties, such as $C_3$-cycloalkyl, $C_4$-cycloalkyl, $C_5$-cycloalkyl, $C_6$-cycloalkyl, $C_7$-cycloalkyl, $C_8$-cycloalkyl, $C_9$-cycloalkyl, $C_{10}$-cycloalkyl, $C_{11}$-cycloalkyl, $C_{12}$-cycloalkyl and the like.

The term "cycloalkene," as used herein, means cyclic and bicyclic hydrocarbon moieties having one or more than one carbon-carbon double bonds, such as $C_5$-cycloalkene, $C_6$-cycloalkene, $C_7$-cycloalkene, $C_8$-cycloalkene, $C_9$-cycloalkene, $C_{10}$-cycloalkene, $C_{11}$-cycloalkene, $C_{12}$-cycloalkene and the like.

The term "cycloalkenyl," as used herein, means monovalent, cyclic hydrocarbon moieties having one or more than one carbon-carbon double bonds, such as $C_4$-cycloalkenyl, $C_5$-cycloalkenyl, $C_6$-cycloalkenyl, $C_7$-cycloalkenyl, $C_8$-cycloalkenyl, $C_9$-cycloalkenyl, $C_{10}$-cycloalkenyl, $C_{11}$-cycloalkenyl, $C_{12}$-cycloalkenyl and the like.

The term "heteroarene," as used herein, means furan, imidazole, isothiazole, isoxazole, 1,2,3-oxadiazole, 1,2,5-oxadiazole, 1,3,4-oxadiazole, oxazole, pyrazine, pyrazole, pyridazine, pyridine, pyrimidine, pyrrole, thiazole, 1,3,4-thiadiazole, thiophene, triazine and 1,2,3-triazole.

The term "heteroaryl," as used herein, means furanyl, imidazolyl, isothiazolyl, isoxazolyl, 1,2,3-oxadiazoyl, 1,2,5-oxadiazolyl, 1,3,4-oxadiazolyl, oxazolyl, pyrazinyl, pyrazolyl, pyridazinyl, pyridinyl, pyrimidinyl, pyrrolyl, tetrazolyl, thiazolyl, 1,2,3-thiadiazoyl, 1,2,5-thiadiazolyl, 1,3,4-thiadiazolyl, thiophenyl, triazinyl and 1,2,3-triazolyl.

The term "heterocycloalkane," as used herein, means cycloalkane having one or two or three $CH_2$ moieties replaced with independently selected O, S, S(O), $SO_2$ or NH and one or two CH moieties unreplaced or replaced with N and also means cycloalkane having one or two or three $CH_2$ moieties unreplaced or replaced with independently selected O, S, S(O), $SO_2$ or NH and one or two CH moieties replaced with N.

The term "heterocycloalkene," as used herein, means cycloalkene having one or two or three $CH_2$ moieties replaced with independently selected O, S, S(O), $SO_2$ or NH and one or two CH moieties unreplaced or replaced with N and also means cycloalkene having one or two or three $CH_2$ moieties unreplaced or replaced with independently selected O, S, S(O), SO$_2$ or NH and one or two CH moieties replaced with N.

The term "heterocycloalkyl," as used herein, means cycloalkyl having one or two or three CH$_2$ moieties replaced with independently selected O, S, S(O), SO$_2$ or NH and one or two CH moieties unreplaced or replaced with N and also means cycloalkyl having one or two or three CH$_2$ moieties unreplaced or replaced with independently selected O, S, S(O), SO$_2$ or NH and one or two CH moieties replaced with N.

The term "heterocycloalkenyl," as used herein, means cycloalkenyl having one or two or three CH$_2$ moieties replaced with independently selected O, S, S(O), SO$_2$ or NH and one or two CH moieties unreplaced or replaced with N and also means cycloalkenyl having one or two or three CH$_2$ moieties unreplaced or replaced with independently selected O, S, S(O), SO$_2$ or NH and one or two CH moieties replaced with N.

The term "cyclic moiety," as used herein, means benzene, cycloalkane, cycloalkyl, cycloalkene, cycloalkenyl, heteroarene, heteroaryl, heterocycloalkane, heterocycloalkyl, heterocycloalkene, heterocycloalkenyl and phenyl.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures, relative and absolute diastereoisomers and the compounds thereof.

Compounds of this invention may also contain carbon-carbon double bonds or carbon-nitrogen double bonds in the Z or E configuration, in which the term "Z" represents the larger two substituents on the same side of a carbon-carbon or carbon-nitrogen double bond and the term "E" represents the larger two substituents on opposite sides of a carbon-carbon or carbon-nitrogen double bond. The compounds of this invention may also exist as a mixture of "Z" and "E" isomers.

Compounds of this invention containing NH, C(O)H, C(O)OH, C(O)NH$_2$, OH or SH moieties may have attached thereto prodrug-forming moieties. The prodrug-forming moieties are removed by metabolic processes and release the compounds having the freed NH, C(O)H, C(O)OH, C(O)NH$_2$, OH or SH in vivo. Prodrugs are useful for adjusting such pharmacokinetic properties of the compounds as solubility and/or hydrophobicity, absorption in the gastrointestinal tract, bioavailability, tissue penetration, and rate of clearance.

Metabolites of compounds having Formula I, produced by in vitro or in vivo metabolic processes, may also have utility for treating diseases caused or exacerbated by unregulated or overexpressed poly(ADP-ribose)polymerase.

Certain precursor compounds of compounds having Formula I may be metabolized in vitro or in vivo to form compounds having Formula I and may thereby also have utility for treating diseases caused or exacerbated by unregulared or overexpressed poly(ADP-ribose)polymerase.

Compounds having Formula I may exist as acid addition salts, basic addition salts or zwitterions. Salts of compounds having Formula I are prepared during their isolation or following their purification. Acid addition salts are those derived from the reaction of a compound having Formula I with acid. Accordingly, salts including the acetate, adipate, alginate, bicarbonate, citrate, aspartate, benzoate, benzenesulfonate (besylate), bisulfate, butyrate, camphorate, camphorsulfonate, digluconate, formate, fumarate, glycerophosphate, glutamate, hemisulfate, heptanoate, hexanoate, hydrochloride, hydrobromide, hydroiodide, lactobionate, lactate, maleate, mesitylenesulfonate, methanesulfonate, naphthylenesulfonate, nicotinate, oxalate, pamoate, pectinate, persulfate, phosphate, picrate, propionate, succinate, tartrate, thiocyanate, trichloroacetic, trifluoroacetic, para-toluenesulfonate and undecanoate salts of the compounds having Formula I are meant to be embraced by this invention. Basic addition salts of compounds are those derived from the reaction of the compounds having Formula I with the bicarbonate, carbonate, hydroxide, or phosphate of cations such as lithium, sodium, potassium, calcium and magnesium.

Compounds having Formula I may be administered, for example, bucally, ophthalmically, orally, osmotically, parenterally (intramuscularly, intraperintoneally intrasternally, intravenously, subcutaneously), rectally, topically, transdermally and vaginally.

Therapeutically effective amounts of a compound having Formula I depend on recipient of treatment, disease treated and severity thereof, composition comprising it, time of administration, route of administration, duration of treatment, potency, rate of clearance and whether or not another drug is co-administered. The amount of a compound having Formula I used to make a composition to be administered daily to a patient in a single dose or in divided doses is from about 0.001 to about 200 mg/kg body weight. Single dose compositions contain these amounts or a combination of submultiples thereof.

Compounds having Formula I may be administered with or without an excipient.

Excipients include, for example, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents and mixtures thereof.

Compounds having Formula I may be radiolabeled with a radioactive isotope such as carbon (i.e. $^{13}$C), hydrogen (i.e. $^3$H), nitrogen (i.e. $^{15}$N), phosphorus (i.e. $^{32}$P), sulfur (i.e. $^{35}$S), iodide (i.e. $^{125}$I) and the like. Radioactive isotopes may be incorporated into the compounds having Formula I by reacting the same and a radioactive derivitizing agent or by incorporating a radiolabeled intermediate into their syntheses. The radiolabeled compounds of Formula I are useful for both prognostic and diagnostic applications and for in vivo and in vitro imaging.

Compounds having Formula I may be incorporated into devices such as, but not limited to, arterio-venous grafts, billiary stents, by-pass grafts, catheters, central nervous system shunts, coronary stents, drug delivery balloons, peripheral stents and ureteural stents, each of which may be used in areas such as, but not limited to, the vasculature for introduction of a compound having Formula I into selected tissues or organs in the body. One measure of the effectiveness of compounds having Formula I is reduction or elimination of device-associated thrombi and complications associated therewith.

Compounds having Formula I can used as a radiosensitizers which enhance the efficacy of radiotherapy. Examples of radiotherapy include, but are not limited to, external beam radiotherapy, teletherapy, brachtherapy and sealed and unsealed source radiotherapy.

Excipients for preparation of compositions comprising a compound having Formula I to be administered orally include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water and mixtures thereof. Excipients for preparation of compositions comprising a compound having Formula I to be administered ophthalmically or orally include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water and mixtures thereof. Excipients for preparation of compositions comprising a compound having Formula I to be administered osmotically include, for example, chlorofluoro-hydrocarbons, ethanol, water and mixtures thereof. Excipients for preparation of compositions comprising a compound having Formula I to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water and mixtures thereof. Excipients for preparation of compositions comprising a compound having Formula I to be administered rectally or vaginally include, for example, cocoa butter, polyethylene glycol, wax and mixtures thereof.

Compounds having formula I are also expected to be useful when used with alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcr-Abl kinase inhibitors include DASATINIBx (BMS-354825). GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin® (trastuzumab), TYKERB® (lapatinib), OMNITARG® (2C4, petuzumab), TAK-165, GW-572016 (ionafamib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FCl, PU-3, radicicol, SNX-2112, STA-9090 VER49009 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW- 786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB1089, CB1093), lexacalcitrol (KH 1060), fenretinide, PANRETIN® (aliretinoin), ATRAGEN® (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG 132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n 1, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having formula I may be combined with other chemptherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafamib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY® (atrasentan), XYOTAX™ (paclitaxel poliglumex), YONDELIS™ (trabectedin), ZD-6126, ZINECARD® (dexrazoxane), zometa (zolendronic acid), zorubicin and the like.

In one embodiment, compounds having Formula I are used in a method of treating cancer in a mammal comprising administering thereto a therapeutically acceptable amount of a compound of claim 1 in combination with a chemotherapeutic agent selected from temozolomide, dacarbazine, cyclophosphamide, carmustine, melphalan, lomustine, carboplatin, cisplatin, 5-FU+/−leucovorin, gemcitabine, methotrexate, bleomycin, irinotecan, camptothecin, or topotecan.

It is expected that compounds having formula I would also inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous system, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like (commonly-owned U.S. application Ser. No. 10/988,338), Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Br. J. Haematol. 2000 September; 110(3): 584-90; Blood 2000 Feb. 15; 95(4):1283-92; and New England Journal of Medicine 2004 September; 351(14): 1409-1418).

PARP Enzyme Inhibition Assay

Nicotinamide[2,5',8-3H]adenine dinucleotide and streptavidin SPA beads were purchased from Amersham Biosciences. Recombinant Human Poly(ADP-Ribose) Polymerase (PARP), purified from *E. coli* and 6-Biotin-17-NAD$^+$, were purchase from Trevigen. NAD$^+$, histone, aminobenzamide, 3-amino benzamide and Calf Thymus DNA (dcDNA) were purchased from Sigma. Stem loop oligonucleotide containing MCAT sequence was obtained from Qiagen. The oligos were dissolved to 1 mM in annealing buffer containing 10 mM Tris HCl pH 7.5, 1 mM EDTA, and 50 mM NaCl, incubated for 5 minutes at 95° C., and annealed at 45° C. for 45 minutes. Histone H1 (95% electrophoretically pure) was purchased from Roche. Biotinylated histone H1 was prepared by treating the protein with Sulfo-NHS-LC-Biotin from Pierce. The biotinylation reaction was conducted by slowly and intermittently adding 3 equivalents of 10 mM Sulfo-NHS-LC-Biotin to 100 μM Histone H1 in phosphate-buffered saline, pH 7.5, at 4° C. with gentle vortexing over 1 minute followed by subsequent 4° C. incubation for 1 hour. Streptavidin coated (FlashPlate Plus) microplates were purchased from Perkin Elmer.

PARP1 assay was conducted in PARP assay buffer containing 50 mM Tris pH 8.0, 1 mM DTT, 4 mM MgCl$_2$. PARP reactions contained 1.5 μM [$^3$H]-NAD$^+$ (1.6 uCi/mmol), 200 nM biotinylated histone H1, 200 nM sIDNA, and 1 nM PARP enzyme. Auto reactions utilizing SPA bead-based detection were carried out in 100 μL volumes in white 96 well plates. Reactions were initiated by adding 50 μl of 2×NAD$^+$ substrate mixture to 50 μL of 2× enzyme mixture containing PARP and DNA. These reactions were terminated by the addition of 150 μL of 1.5 mM benzamide (~1000-fold over its IC$_{50}$). 170 μL of the stopped reaction mixtures were transferred to streptavidin Flash Plates, incubated for 1 hour, and counted using a TopCount microplate scintillation counter. The EC$_{50s}$ for exemplified compounds of this invention are provided in Table 1.

Cellular PARP Assay:

C41 cells were treated with a compound of this invention for 30 minutes in 96 well plate. PARP was then activated by damaging DNA with 1 mM H$_2$O$_2$ for 10 minutes. The cells were then washed with ice-cold PBS once and fixed with pre-chilled methanol:acetone (7:3) at −20° C. for 10 minutes. After air-drying, the plates were rehydrated with PBS and blocked 5% non-fat dry milk in PBS-TWEEN20® (Sigma, St. Louis, Mo.) (0.05%) (blocking solution) for 30 minutes at room temperature. The cells were incubated with anti-PAR antibody 10H (1:50) in Blocking solution at 37° C. for 60 minutes followed by washing with PBS— TWEEN20® 5 times, and incubation with goat anti-mouse fluorescein 5(6)-isothiocyanate-coupled antibody (1:50) and 1 μg/ml 4',6-diamidino-2-phenylindole (DAPI) in blocking solution at 37° C. for 60 minutes. After washing with PBS-TWEEN20® 5 times, the analysis was performed using an FMAX FLUORESCENCE MICROPLATE READER® (Molecular Devices, Sunnyvale, Calif.), set at the excitation wavelength of 490 nm and emission wavelength of 528 nm fluorescein 5(6)-isothiocyanate (FITC) or the excitation wavelength of 355 nm and emission wavelength of 460 nm (DAPI). The PARP activity (FITC signal) was normalized with cell numbers (DAPI).

The cellular assay measures the formation of poly ADP-ribose by PARP within cells and demonstrates that compounds of this invention penetrate cell membranes and inhibit PARP in intact cells. Due to variability in the cellular assay, 2-(1-propylpiperidin-4-yl)-1H-benzimidazole-4-carboxamide was run as a comparator in each assay and data reported as the ratio of test compound EC$_{50}$ relative to the EC$_{50}$ of 2-(1-propylpiperidin-4-yl)-1H-benzimidazole-4-carboxamide obtained in that particular assay. The mean EC$_{50}$ of 2-(1-propylpiperidin-4-yl)-1H-benzimidazole-4-carboxamide for all assays carried out was 0.0032 μM (n=270) and generally ranged from 0.001 to 0.013 μM. (ratio $EC_{50}=EC_{50}$ test compound/EC50 comparator compound). The $EC_{50}$ data (nM) are shown in TABLE 1.

TABLE 1

Inhibition of PARP by Compounds Having Formula I

| Example | PARP-1 ($K_i$, nM) | Cell, Ratio $EC_{50}$, nM |
|---|---|---|
| 1 | 91 | |
| 2 | 44 | |
| 3 | 3 | >300 |
| 4 | 1.5 | 0.5 |
| 5 | 1.1 | 17 |
| 6 | 108 | |
| 7 | 534 | |
| 8 | 862 | |
| 9 | 319 | |
| 10 | 411 | |
| 11 | 1489 | |
| 12 | 963 | |
| 13 | 225 | |
| 14 | 173 | |
| 15 | 390 | |
| 16 | 307 | |
| 17 | 283 | |
| 18 | 83 | |
| 19 | 75 | 278 |
| 20 | 480 | |
| 21 | 148 | |
| 22 | 372 | |
| 23 | 562 | |
| 24 | 794 | |
| 25 | 1610 | |
| 26 | 1720 | |
| 27 | 2110 | |
| 28 | 682 | |
| 29 | 516 | |
| 30 | 766 | |
| 31 | 700 | |
| 32 | 1960 | |
| 33 | 347 | |
| 34 | 1030 | |
| 35 | 1820 | |
| 36 | 2130 | |
| 37 | 673 | |
| 38 | 6 | 75 |
| 39 | 48 | >300 |
| 40 | 23 | >300 |
| 41 | 1010 | |
| 42 | 20 | 13 |
| 43 | 8 | 2.3 |
| 44 | 2 | 13 |
| 45 | 14 | >300 |
| 46 | 42 | |
| 47 | 1.2 | 1.2 |
| 48 | 0.7 | 49 |
| 49 | 20 | 59 |
| 50 | 19 | >300 |
| 51 | 47 | |
| 52 | 13 | 15 |
| 53 | 10 | 15 |
| 54 | 205 | |
| 55 | 1 | 15 |
| 56 | 5 | >300 |
| 57 | 60 | |
| 58 | 51 | 373 |
| 59 | 24 | 69 |
| 60 | 3 | 6.9 |
| 61 | 6 | 12 |
| 62 | 42 | |
| 63 | 23 | >1000 |
| 64 | 40 | 11 |
| 65 | 82 | |
| 66 | 87 | >1000 |
| 67 | 50 | 700 |
| 68 | 351 | |
| 69 | 40 | 43 |
| 70 | 101 | |
| 71 | 639 | |
| 72 | 144 | |
| 73 | 86 | |
| 74 | 102 | |
| 75 | 56 | >1000 |
| 76 | 473 | |
| 77 | 195 | |
| 78 | 165 | |
| 79 | 18 | 121 |
| 80 | 47 | 570 |
| 81 | 123 | |
| 82 | 691 | |
| 83 | 126 | |
| 84 | 617 | |
| 85 | 396 | |
| 86 | 390 | |
| 87 | 56 | |
| 88 | 96 | |
| 89 | 111 | |
| 90 | 68 | |
| 91 | 70 | |
| 92 | 167 | |
| 93 | 840 | |
| 94 | 856 | |
| 95 | 1260 | |
| 96 | 2610 | |
| 97 | 390 | |
| 98 | 286 | |
| 99 | 44 | 179 |
| 100 | 39 | 110 |
| 101 | 21 | 162 |
| 102 | 26 | 148 |
| 103 | 1050 | |
| 104 | 1230 | |
| 105 | 725 | |
| 106 | 290 | |
| 107 | 216 | |
| 108 | 576 | |
| 109 | 609 | |
| 110 | 372 | |
| 111 | 12 | 61 |
| 112 | 136 | |
| 113 | 6 | 662 |
| 114 | 65 | 286 |
| 115 | 157 | |
| 116 | 578 | |
| 117 | 477 | |
| 118 | 2030 | |
| 119 | 703 | |
| 120 | 626 | |
| 121 | 776 | |
| 122 | 644 | |
| 123 | 121 | |
| 125 | 47 | 798 |
| 126 | 286 | |
| 127 | 14 | 13 |
| 128 | 43 | |
| 129 | 41 | 53 |
| 130 | 24 | 57 |
| 131 | 32 | |
| 132 | 1040 | |
| 133 | 724 | |
| 134 | 133 | |
| 135 | 16 | |
| 136 | 76 | |
| 137 | 69 | |
| 138 | 22 | 62 |
| 139 | 206 | |
| 140 | 60 | |
| 141 | 77 | |
| 142 | 11 | 41 |
| 143 | 78 | |
| 144 | 125 | |
| 145 | 57 | |
| 146 | 678 | |

TABLE 1-continued

Inhibition of PARP by Compounds Having Formula I

| Example | PARP-1 ($K_i$, nM) | Cell, Ratio $EC_{50}$, nM |
|---|---|---|
| 147 | 41 | |
| 148 | 74 | |
| 149 | 22 | 262 |
| 150 | 16 | 140 |
| 151 | 531 | |
| 152 | 741 | |
| 153 | 6 | 95 |
| 154 | 56 | |
| 155 | 126 | |
| 156 | 25 | |
| 157 | 124 | |
| 158 | 1590 | |
| 159 | 4 | 30 |
| 160 | 11 | 40 |
| 161 | 64 | |
| 162 | 51 | |
| 163 | 35 | |
| 164 | 28 | 98 |
| 165 | 14 | 244 |
| 166 | 5 | 40 |
| 167 | 56 | |
| 168 | 127 | |
| 169 | 99 | |
| 170 | 1700 | |
| 171 | 56 | |
| 172 | 3 | 5 |
| 173 | 2 | 32 |
| 174 | 655 | |
| 175 | 21 | 215 |

| Example | PARP-1 ($K_i$, nM) | Cell, Ratio $EC_{50}$, nM |
|---|---|---|
| 176 | 43 | |
| 177 | 156 | |
| 178 | 462 | |
| 179 | 238 | |
| 180 | 159 | |
| 181 | 212 | |
| 182 | 292 | |
| 183 | 166 | |
| 184 | 154 | |
| 185 | 250 | |
| 186 | 160 | |
| 187 | 1250 | |
| 188 | 185 | |
| 189 | 175 | |
| 190 | 263 | |
| 191 | 31 | 143 |
| 192 | 43 | |
| 193 | 100 | |
| 194 | 61 | |
| 195 | 177 | |
| 196 | 286 | |
| 197 | 146 | |
| 198 | 403 | |
| 199 | 196 | |
| 200 | 158 | |
| 201 | 570 | |
| 202 | 93 | |
| 203 | 103 | |
| 204 | 203 | |
| 205 | 176 | |
| 206 | 18 | 212 |
| 208 | 22 | 423 |
| 209 | 395 | |
| 210 | | |
| 211 | 98 | |
| 212 | 65 | |
| 213 | 82 | |
| 214 | 7 | 238 |

-continued

| Example | PARP-1 ($K_i$, nM) | Cell, Ratio $EC_{50}$, nM |
|---|---|---|
| 215 | 85 | |
| 216 | 82 | |
| 217 | 5 | 44 |
| 218 | 86 | |
| 219 | 9 | 38 |
| 220 | 14 | 137 |
| 221 | 1540 | |
| 222 | 248 | |
| 223 | 206 | |
| 224 | 9220 | |
| 225 | 41 | |
| 226 | 40 | >1000 |
| 227 | 60 | |
| 228 | 98 | |
| 229 | 49 | |
| 230 | 96 | |
| 231 | 110 | |
| 232 | 12 | >1000 |
| 233 | 158 | |
| 234 | 57 | |
| 235 | 198 | |
| 236 | 4 | >1000 |
| 237 | 68 | |
| 238 | 47 | |
| 239 | 554 | |
| 240 | 285 | |
| 241 | 1450 | |
| 242 | 610 | |
| 243 | 92 | |
| 244 | 2340 | |
| 245 | 963 | |
| 246 | 52 | |
| 247 | 48 | |
| 248 | 2 | 43 |
| 249 | 85 | |
| 250 | 210 | |
| 251 | 446 | |
| 252 | 19 | >1000 |
| 253 | 229 | |
| 254 | 4120 | |
| 255 | 335 | |
| 256 | 346 | |
| 257 | 2280 | |
| 258 | 1770 | |
| 259 | 91 | |
| 260 | 243 | |
| 261 | 556 | |
| 262 | 304 | |
| 263 | 144 | |
| 264 | 662 | |
| 265 | 58 | >1000 |
| 266 | 19 | >1000 |
| 267 | 534 | |
| 268 | 638 | |
| 269 | 1050 | |
| 270 | 487 | |
| 271 | 1140 | |
| 272 | 204 | |
| 273 | 257 | |
| 274 | 222 | |
| 275 | 471 | |
| 276 | 943 | |
| 277 | 436 | |
| 278 | 185 | |
| 279 | 467 | |
| 280 | 303 | |
| 281 | 309 | |
| 282 | 1710 | |
| 283 | 442 | |
| 284 | 2210 | |
| 285 | 150 | |
| 286 | 58 | >1000 |
| 287 | 771 | |
| 288 | 431 | |
| 289 | 0.7 | 16 |
| 290 | 1 | 6 |

| Example | PARP-1 (K$_i$, nM) | Cell, Ratio EC$_{50}$, nM |
|---|---|---|
| 291 | 0.7 | 0.2 |
| 292 | 116 | |
| 293 | 338 | |
| 294 | 204 | |
| 295 | 912 | |
| 296 | 683 | |
| 297 | 1440 | |
| 298 | 2 | 2.7 |
| 299 | 4 | 5.5 |
| 300 | 2 | 1.2 |
| 301 | 6 | 26 |
| 302 | 2 | 2.6 |
| 303 | 0.8 | 0.4 |
| 304 | 17 | 26 |
| 305 | 3 | 4 |
| 306 | 6 | 23 |
| 307 | 2 | 4 |
| 308 | 30 | |
| 309 | 29 | |
| 310 | 26 | |
| 311 | 58 | |
| 312 | 131 | |
| 313 | 95 | |
| 314 | 32 | |
| 315 | 23 | 10 |
| 316 | 34 | |
| 317 | 25 | 39 |
| 318 | 28 | |
| 319 | 94 | |
| 320 | 165 | |
| 321 | 223 | |
| 322 | 556 | |
| 323 | 237 | |
| 324 | 131 | |
| 325 | 5 | 36 |
| 326 | 70 | |
| 327 | 1630 | |
| 328 | 7 | 48 |
| 329 | 789 | |
| 330 | 99 | |
| 331 | 140 | |
| 332 | 635 | |
| 333 | 892 | |
| 334 | 191 | |
| 335 | 122 | |
| 336 | 363 | |
| 337 | 124 | |
| 338 | 136 | |
| 339 | 120 | |
| 340 | 279 | |
| 341 | 154 | |
| 342 | 134 | |
| 343 | 87 | |
| 344 | 194 | |
| 345 | 149 | |
| 346 | 33 | 158 |
| 347 | 337 | |
| 348 | 259 | |
| 349 | 55 | |
| 350 | 143 | |
| 351 | 277 | |
| 352 | 154 | |
| 353 | 59 | |
| 354 | 363 | |
| 355 | 92 | |
| 356 | 180 | |
| 357 | 402 | |
| 358 | 66 | |
| 359 | 151 | |
| 360 | 94 | |
| 361 | 76 | |
| 362 | 185 | |
| 363 | 132 | |
| 364 | 316 | |
| 365 | 120 | |
| 366 | 23 | 105 |
| 367 | 45 | |
| 368 | 56 | |
| 369 | 4210 | |
| 370 | 4310 | |
| 371 | 14 | 51 |
| 372 | 1570 | |
| 373 | 22 | 211 |
| 374 | 27 | |
| 375 | 51 | |
| 376 | 173 | |
| 377 | 42 | |
| 378 | 28 | |
| 379 | 20 | 173 |
| 380 | 71 | |
| 381 | 67 | |
| 382 | 79 | |
| 383 | 44 | |
| 384 | 40 | |
| 385 | 42 | |
| 386 | 33 | |
| 387 | 44 | |
| 388 | 88 | |
| 389 | 48 | |
| 390 | 31 | |
| 391 | 44 | |
| 392 | 30 | |
| 393 | 70 | |
| 394 | 22 | |
| 395 | 38 | |
| 396 | 83 | |
| 397 | 50 | |
| 398 | 82 | |
| 399 | 65 | |
| 400 | 22 | |
| 401 | 48 | |
| 402 | 86 | |
| 403 | 56 | |
| 404 | 55 | |
| 405 | 19 | 135 |
| 406 | 42 | |
| 407 | 22 | 659 |
| 408 | 69 | |
| 409 | 33 | |
| 410 | 242 | |
| 411 | 8 | 4.6 |
| 412 | 324 | |
| 413 | 18 | 51 |
| 414 | 119 | |
| 415 | 3200 | |
| 418 | 34 | |
| 419 | 16 | 2.1 |
| 420 | 21 | |
| 421 | 68 | |
| 422 | 105 | |
| 423 | 120 | |
| 424 | 31 | |
| 426 | 14 | 28 |
| 427 | 22 | 132 |
| 428 | 5 | 14 |
| 429 | 19 | |
| 430 | 5 | 226 |
| 434 | 6 | 6.3 |
| 435 | 20 | 13 |
| 436 | 10 | 1.8 |
| 437 | 4 | |
| 438 | 3 | 6.4 |
| 439 | 8 | 9.4 |
| 440 | 3 | 3.4 |
| 441 | 3 | 2 |
| 442 | 0.8 | 0.9 |
| 443 | 16 | 14 |
| 444 | 4 | |
| 445 | 6 | 2.3 |
| 446 | 10 | 16 |
| 447 | 10 | 4 |
| 448 | 694 | |

| Example | PARP-1 ($K_i$, nM) | Cell, Ratio $EC_{50}$, nM |
|---|---|---|
| 449 | 103 | |
| 450 | 122 | |
| 451 | 56 | |
| 452 | 2 | 2.5 |
| 453 | 14 | |
| 454 | 16 | |
| 455 | 1.3 | 0.9 |
| 456 | 5 | 14 |
| 457 | 0.7 | 0.2 |
| 458 | 2490 | |
| 459 | 3 | 7 |
| 460 | 580 | |
| 461 | 404 | |
| 462 | 163 | |
| 463 | 1880 | |
| 464 | 5 | 3.1 |
| 465 | 3.5 | 13 |
| 467 | 116 | |
| 468 | 249 | |
| 470 | 18 | 10 |
| 471 | 51 | |
| 472 | 9 | 25 |
| 473 | 2 | 106 |
| 474 | 1.4 | 4 |
| 475 | 1.4 | 13 |
| 476 | 12 | 30 |
| 477 | 4 | 6 |
| 478 | 2 | 15 |
| 479 | 1.3 | 3.5 |
| 481 | 12 | 33 |
| 483 | 5 | 16 |
| 484 | 14 | 18 |
| 485 | 14 | 53 |
| 486 | 15 | 9.6 |
| 487 | 10 | 41 |
| 490 | 0.7 | 0.7 |
| 491 | 191 | |
| 492 | 1.6 | 0.35 |
| 494 | 0.9 | 0.6 |
| 495 | 1.9 | 0.4 |
| 496 | 0.8 | 0.3 |
| 497 | 1.1 | 0.8 |
| 498 | 2.7 | 25 |
| 499 | 1.6 | 2 |
| 500 | 3 | 28 |
| 501 | 4 | 3 |
| 502 | 1.5 | 0.6 |
| 503 | 1.3 | 2 |
| 504 | 3.6 | 0.7 |
| 505 | 6 | 17 |
| 506 | 1.4 | 4.4 |
| 507 | 0.8 | 1.2 |
| 508 | 7 | |
| 509 | 3 | 27 |
| 510 | 1.2 | 8 |
| 511 | 0.4 | 0.7 |
| 512 | 1.3 | 10 |
| 513 | 6 | 10 |
| 514 | 9 | 18 |
| 515 | 3 | 0.9 |
| 516 | 6 | 6 |
| 517 | 5 | 6 |
| 518 | 10 | |
| 519 | 5 | 166 |
| 520 | 0.1 | 2.3 |
| 522 | 1.9 | 0.4 |
| 523 | 13 | 0.4 |
| 524 | 5 | 2.7 |
| 525 | 1.6 | 0.2 |
| 526 | 4 | 2 |
| 527 | 3 | 1.3 |
| 528 | 4 | 0.8 |
| 529 | 2 | 0.4 |
| 530 | 2 | 0.6 |
| 531 | 2 | 0.5 |
| 532 | 4 | 71 |

| Example | PARP-1 ($K_i$, nM) | Cell, Ratio $EC_{50}$, nM |
|---|---|---|
| 533 | 2 | 1 |
| 534 | 2 | 110 |
| 535 | 4 | |
| 536 | 0.5 | 0.2 |
| 537 | 2.5 | 3.4 |
| 538 | 374 | |
| 539 | 191 | |
| 540 | 204 | |
| 541 | 71 | |
| 542 | 548 | |
| 543 | 5 | 5 |
| 544 | 4 | |
| 545 | 1 | 0.3 |
| 546 | 1.2 | 0.3 |
| 547 | 2.3 | 0.8 |
| 548 | 2 | 0.4 |
| 549 | 1 | 0.2 |
| 550 | 1.1 | 0.7 |
| 551 | 0.9 | 2.3 |
| 553 | 0.8 | 3 |
| 554 | 2.1 | 2.3 |
| 555 | 0.8 | |
| 556 | 0.8 | 29 |
| 557 | 1.1 | 3 |
| 559 | 1.4 | 35 |
| 560 | 2 | 149 |
| 561 | 3 | 1.7 |
| 562 | 0.9 | 3.4 |
| 563 | 3.5 | 58 |
| 564 | 2.5 | 1.5 |
| 565 | 1.4 | 9 |
| 566 | 4 | 6 |
| 567 | 0.9 | 10 |
| 568 | 1.1 | 0.8 |
| 569 | 1.2 | 8 |
| 570 | 8 | 114 |
| 571 | 4 | 5 |
| 572 | 3 | 22 |
| 573 | 0.9 | 3 |
| 574 | 1.3 | 4 |
| 575 | 2 | 0.6 |
| 576 | 0.9 | 0.3 |
| 577 | 3 | 3 |
| 578 | 1.1 | 0.6 |
| 579 | 1 | 0.25 |
| 580 | 1.8 | 0.4 |
| 581 | 0.5 | 5 |
| 582 | 65 | |
| 583 | 2.3 | 7 |
| 584 | 68 | |
| 585 | 1.3 | 0.4 |
| 586 | 1.1 | 0.7 |
| 587 | 1 | 0.3 |
| 590 | 1.9 | 0.7 |
| 591 | 0.5 | 1 |
| 593 | 1.3 | 2.5 |
| 594 | 0.7 | 2 |
| 595 | 6 | 43 |
| 596 | 6 | 35 |
| 597 | 0.8 | 3.6 |
| 598 | 9 | 54 |
| 599 | 1.1 | 0.4 |
| 600 | 0.7 | 2 |
| 601 | 1.1 | 1.7 |
| 602 | 3 | 0.8 |
| 603 | 8 | |
| 604 | 15 | |
| 605 | 32 | |
| 606 | 17 | |
| 607 | 0.9 | 38 |
| 609 | 1.8 | 1.1 |
| 610 | 1.7 | 0.4 |
| 611 | 1.6 | 6 |
| 612 | 3 | 1.6 |
| 613 | 1.8 | 0.5 |
| 614 | 25 | |

-continued

| Example | PARP-1 ($K_i$, nM) | Cell, Ratio $EC_{50}$, nM |
|---|---|---|
| 616 | 2.3 | 10 |
| 617 | 1.9 | |
| 618 | 41 | |
| 619 | 4 | 2.6 |
| 620 | 2.2 | 8 |
| 621 | 8 | 2.4 |
| 622 | 2.4 | 0.7 |
| 623 | 3 | 0.9 |
| 624 | 2.5 | 0.2 |
| 625 | 21 | |
| 626 | 173 | |
| 627 | 85 | |
| 628 | 54 | |
| 630 | 0.7 | 1 |
| 631 | 2.8 | 3.5 |
| 632 | 0.9 | 1.2 |
| 633 | 0.6 | 0.9 |
| 634 | 1.9 | 1.4 |
| 635 | 1.8 | 0.8 |
| 636 | 1.8 | 10 |
| 637 | 4 | 16 |
| 638 | 7 | 6 |
| 639 | 3 | 55 |
| 640 | 0.7 | 2.4 |
| 641 | 1.3 | 45 |
| 643 | 1.2 | 72 |
| 644 | 3 | 114 |
| 645 | 1.5 | 47 |
| 646 | 0.7 | 13 |
| 647 | 1.7 | 18 |
| 649 | 0.6 | |
| 651 | 1.1 | 0.4 |
| 654 | 1.2 | |
| 655 | 0.7 | |
| 657 | 0.8 | 10 |
| 658 | 1 | 17 |
| 659 | 2.5 | 5 |
| 660 | 1.4 | 36 |
| 661 | 1.5 | 37 |
| 662 | 1.5 | 17 |
| 663 | 1 | 100 |
| 664 | 1.3 | |
| 665 | 1.1 | 13 |
| 666 | 1.5 | 0.8 |
| 667 | 20 | |
| 668 | 1.9 | 2.4 |
| 669 | 1.2 | 0.2 |
| 672 | 84 | |
| 673 | 1 | 2 |
| 674 | 1.1 | 0.6 |
| 675 | 1.2 | 34 |
| 677 | 1.5 | 0.8 |
| 678 | 1.1 | 1.1 |
| 679 | 1.4 | 0.6 |
| 680 | 1.1 | |
| 681 | 40 | |
| 682 | 2.4 | 106 |
| 683 | 2.6 | 125 |
| 684 | 2.8 | 22 |
| 685 | 2.2 | |
| 686 | 1.9 | |
| 687 | 4.2 | 6 |
| 688 | 2.4 | 9 |
| 689 | 2.7 | |
| 690 | 2.4 | 18 |
| 691 | 2.1 | 0.7 |
| 692 | 1.6 | 11 |
| 693 | 2 | 34 |
| 694 | 1.7 | 11 |
| 695 | 1 | 1.7 |
| 696 | 2.5 | |
| 697 | 2.2 | 56 |
| 698 | 11 | |
| 699 | 74 | |
| 700 | 2.8 | 3 |
| 701 | 2.3 | |
| 702 | 2.1 | |
| 703 | 2.3 | |
| 704 | 0.6 | 23 |
| 705 | 1.4 | 9 |
| 706 | 5 | |
| 707 | 32 | |
| 708 | 1.7 | |
| 709 | 53 | |
| 710 | 7 | |
| 711 | 3 | 9 |
| 712 | 4 | |
| 713 | 1.8 | |
| 714 | 0.8 | 1 |
| 715 | 4 | |
| 716 | 5 | |
| 717 | 4 | |
| 718 | 2.6 | |
| 719 | 7 | 9 |
| 720 | 1.4 | 1.6 |
| 721 | 3 | 64 |
| 722 | 1.2 | 1 |
| 723 | 1.3 | 19 |
| 724 | 7 | |
| 725 | 5 | 8 |
| 726 | 4 | 15 |
| 727 | 1.4 | 0.7 |
| 728 | 1.8 | 2.1 |
| 729 | 48 | |
| 730 | 1.3 | 0.6 |
| 731 | 11 | 49 |
| 733 | 1.7 | 2.3 |
| 734 | 9 | 58 |
| 735 | 1.5 | 25 |
| 736 | 4 | 76 |
| 738 | 14 | |
| 739 | 1.3 | 2 |
| 740 | 52 | |
| 742 | 1.8 | 3 |
| 743 | 2.7 | 6 |
| 745 | 8 | 10 |
| 746 | 1.5 | 4 |
| 747 | 1.5 | |
| 748 | 1 | |
| 749 | 1.4 | |
| 750 | 1.1 | 13 |
| 751 | 1.5 | 5 |
| 753 | 92 | |
| 754 | 0.6 | 17 |
| 755 | 1.5 | 0.5 |
| 756 | 0.9 | 0.4 |
| 757 | 1.2 | 1.6 |
| 758 | 1.4 | |
| 759 | 0.3 | 1.3 |
| 761 | 0.6 | 1.4 |
| 762 | 1 | 7 |
| 763 | 1 | 2.4 |

Selected compounds of Formula I wherein $A^1$ is $R^1$, wherein $R^1$ is unsubstituted cyclohexane which is unfused, and $A^2$ is $R^5$, $R^5$ is $C_1$-alkyl were run in the PARP Enzyme Inhibition Assay and the PARP Cellular Assay described above. Compounds outside of Formula I wherein at the position of $A^2$ is instead a bond also were run in the PARP Enzyme Inhibition Assay and the PARP Cellular Assay described above. The results of the assays are described in TABLE 2, below:

TABLE 2

| A² is R⁵, wherein R⁵ is C₁-alkyl | PARP-1 (Ki, nM) | Cell Ratio EC₅₀ | No A² | PARP-1 (Ki, nM) | Cell Ratio EC₅₀ |
|---|---|---|---|---|---|
| (structure) | 6 | 16.4 | (structure) | 291 | |
| (structure) | 1.2 | 0.85 | (structure) | 191 | |

Selected compounds of Formula I wherein $A^1$ is $R^1$, wherein $R^1$ is unsubstituted cyclohexane which is unfused, and $A^2$ is $R^5$, $R^5$ is $C_1$-alkyl wherein $R^5$ is substituted with $R^{10}$, wherein $R^{10}$ is phenyl, either with a para-substituted F, as shown in Formula (Is):

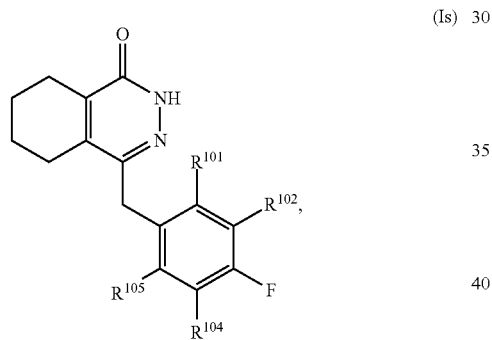

(Is)

or without a para-substituted F were run in the PARP Enzyme Inhibition Assay and the PARP Cellular Assay described above. Results are shown in Table 3.

TABLE 3
| H analogs | PARP-1 (K$_i$, nM) | Cell EC$_{50}$ ratio | F analogs | PARP-1 (K$_i$, nM) | Cell EC$_{50}$ ratio |
|---|---|---|---|---|---|
| 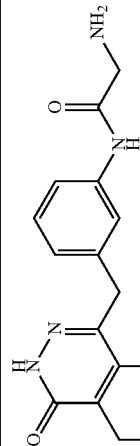 | 12 | 22.5 | 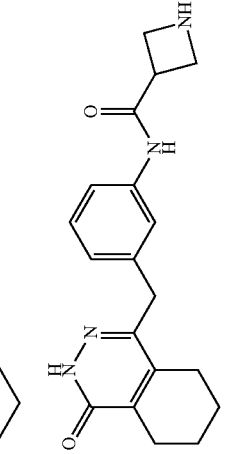 | 2.9 | 5.8 |
| 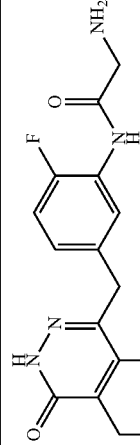 | 6.3 | 246 | 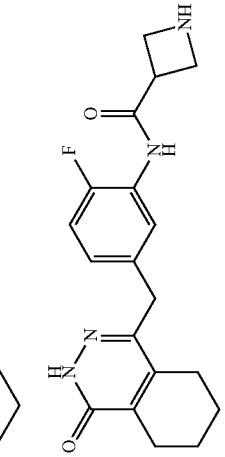 | 0.7 | 34.4 |
| 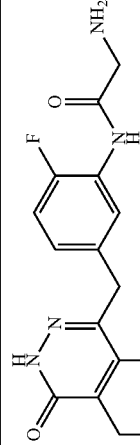 | 1.9 | 20.9 | 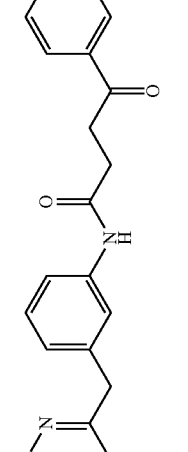 | 0.7 | 2.6 |
| 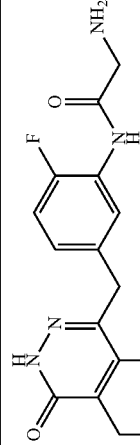 | 39.6 | 40.9 | 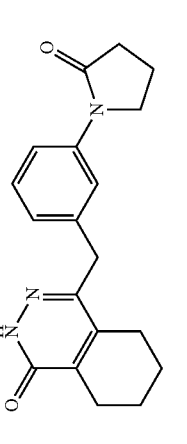 | 1.2 | 0.85 |
| 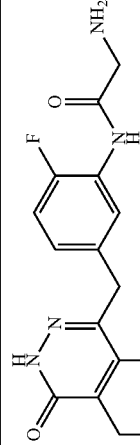 | 2 | 1.7 | 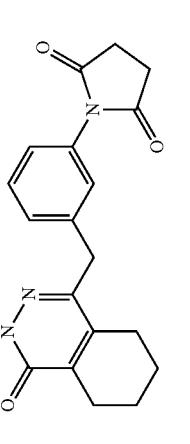 | 1.1 | 0.19 |

TABLE 3-continued

| H analogs | PARP-1 (K$_i$, nM) | Cell EC$_{50}$ ratio | F analogs | PARP-1 (K$_i$, nM) | Cell EC$_{50}$ ratio |
|---|---|---|---|---|---|
| | 3.2 | 3.2 | | 0.6 | 0.34 |
| | 9 | 14.1 | | 15.8 | 17.6 |
| | 280 | — | | 18.4 | 5.6 |
| | 0.8 | 0.93 | | 0.7 | 0.3 |
| | 3 | 6.1 | | 0.1 | 2.3 |

TABLE 3-continued

| H analogs | PARP-1 (K$_i$, nM) | Cell EC$_{50}$ ratio | F analogs | PARP-1 (K$_i$, nM) | Cell EC$_{50}$ ratio |
|---|---|---|---|---|---|
| (H analog, N-ethyl piperazine) | 10 | 1.8 | (F analog, N-ethyl piperazine) | 1.8 | 0.4 |
| (H analog, N-pyridin-2-yl piperazine) | 3 | 1.9 | (F analog, N-pyridin-2-yl piperazine) | 2 | 0.4 |
| (H analog, N-phenyl piperazine) | 3 | 3.2 | (F analog, N-phenyl piperazine) | 3 | 0.9 |
| (H analog, N-(2-chlorophenyl) piperazine) | 10 | 15 | (F analog, N-(2-chlorophenyl) piperazine) | 5 | 6 |

TABLE 3-continued

| H analogs | PARP-1 (K$_i$, nM) | Cell EC$_{50}$ ratio | F analogs | PARP-1 (K$_i$, nM) | Cell EC$_{50}$ ratio |
|---|---|---|---|---|---|
| [2-F phenyl piperazine H analog] | 4 | — | [2-F phenyl piperazine F analog] | 13 | 1.3 |
| [4-F phenyl piperazine H analog] | 6 | 2.2 | [4-F phenyl piperazine F analog] | 4 | 0.8 |
| [N-methyl diazepane H analog] | 10 | 3.8 | [N-methyl diazepane F analog] | 1.5 | 0.6 |
| [CONH$_2$ piperidine H analog] | 19 | — | [CONH$_2$ piperidine F analog] | 3 | 28 |
| [OH piperidine H analog] | 5 | 13 | [OH piperidine F analog] | 1.3 | 2 |

TABLE 3-continued

| H analogs | PARP-1 (K$_i$, nM) | Cell EC$_{50}$ ratio | F analogs | PARP-1 (K$_i$, nM) | Cell EC$_{50}$ ratio |
|---|---|---|---|---|---|
| (piperidine-4-CONH$_2$ H analog) | 5 | 215 | (piperidine-4-CONH$_2$ F analog) | 2.7 | 25 |
| (piperidine-3-CONEt$_2$ H analog) | 27 | — | (piperidine-3-CONEt$_2$ F analog) | 6 | 17 |
| (N,N-dimethylaminoethyl-N-methyl H analog) | 13 | 3 | (N,N-dimethylaminoethyl-N-methyl F analog) | 3.6 | 0.7 |
| (N-methylpiperazinylethyl H analog) | 24 | 31 | (N-methylpiperazinylethyl F analog) | 1.1 | 0.6 |

As PARP inhibitors, the compounds of this invention have numerous therapeutic applications related to ischemia reperfusion injury, inflammatory diseases, degenerative diseases, protection from adverse effects of cytotoxic compounds, and potentiation of cytotoxic cancer therapy. In particular, compounds of this invention potentiate radiation and chemotherapy by increasing cell death of cancer cells, limiting tumor growth, decreasing metastasis, and prolonging the survival of tumor-bearing mammals. Compounds having formula I can treat leukemia, colon cancer, glioblastomas, lymphomas, melanomas, carcinomas of the breast, and cervical carcinomas.

Other therapeutic applications include retroviral infection, arthritis, gout, inflammatory bowel disease, CNS inflammation, multiple sclerosis, allergic encephalitis, sepsis, septic shock, hemmorhagic shock, pulmonary fibrosis, uveitis, diabetes, Parkinsons disease, myocardial infarction, stroke, other neural trauma, organ transplantation, reperfusion of the eye, reperfusion of the kidney, reperfusion of the gut, reperfusion of skeletal muscle, liver toxicity following acetominophen overdose, cardiac and kidney toxicities from doxorubicin and platinum based antineoplastic agents, and skin damage secondary to sulfur mustards. (G. Chen et al. Cancer Chemo. Pharmacol. 22 (1988), 303; C. Thiemermann et al., Proc. Natl. Acad. Sci. USA 94 (1997), 679-683 D. Weltin et al. Int. J. Immunopharmacol. 17 (1995), 265-271; H. Kriger et al. Inflammation 20 (1996), 203-215; W. Ehrlich et al. Rheumatol. Int. 15 (1995), 171-172; C. Szabo et al., Proc. Natl. Acad. Sci. USA 95 (1998), 3867-3872; S. Cuzzocrea et al. Eur. J. Pharmacol. 342 (1998), 67-76; V. Burkhart et al., Nature Medicine (1999), 5314-19).

Compounds of Formula I

In one embodiment of formula I

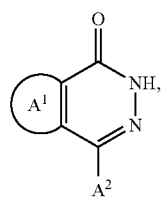

(I)

or a salt thereof, wherein $A^1$ is $R^1$ or $R^2$, wherein $A^1$ is unsubstituted or substituted with one or two OH, CN, $C_1$-alkyl, $C_2$-alkyl, $C_3$-alkyl, $C_4$-alkyl, $C_5$-alkyl, cycloalkane, $OR^A$ or $NR^A R^A$;

$R^A$ is H or alkyl;

$R^1$ is cycloalkane or cycloalkene each of which is unfused or fused with $R^{1A}$;

$R^{1A}$ is benzene, heteroarene, cycloalkane, cycloalkene, heterocycloalkane or heterocycloalkene;

$R^2$ is heterocycloalkane or heterocycloalkene; each of which is unfused or fused with $R^{2A}$;

$R^{2A}$ is benzene, heteroarene, cycloalkane, cycloalkene, heterocycloalkane or heterocycloalkene;

$A^2$ is $OR^4$, $NHR^4$, $N(R^4)_2$, $SR^4$, $S(O)R^4$, $SO_2R^4$ or $R^5$;

wherein each $R^4$ is $C_1$-alkyl, $C_2$-alkyl or $C_3$-alkyl; each of which is substituted with $R^{10}$;

$R^5$ is $C_1$-alkyl, $C_2$-alkyl, $C_3$-alkyl, $C_4$-alkyl or $C_5$-alkyl; each of which is substituted with $R^{10}$, and further unsubstituted or substituted with one or two or three of independently selected $OR^{10}$, $NHR^{10}$, $N(R^{10})_2$, $SR^{10}$, $S(O)R^{10}$, $SO_2R^{10}$ or $CF_3$;

wherein each $R^{10}$ is $R^{10A}$, $R^{10B}$ or $R^{10C}$; each of which must be attached at a carbon atom;

$R^{10A}$ is phenyl which is unfused or fused with benzene, heteroarene, cycloalkane, cycloalkene, heterocycloalkane or heterocycloalkene; each of which are unfused or fused with benzene, heteroarene, cycloalkane, cycloalkene, heterocycloalkane or heterocycloalkene;

$R^{10B}$ is

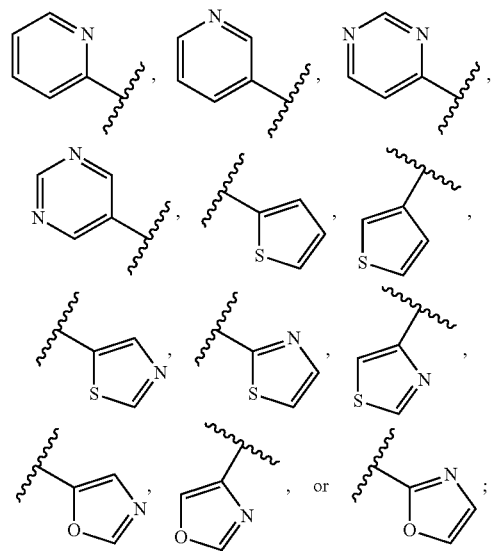

each of which is unfused or fused with benzene, heteroarene, cycloalkane, cycloalkene, heterocycloalkane or heterocycloalkene; each of which are unfused or fused with benzene, heteroarene, cycloalkane, cycloalkene, heterocycloalkane or heterocycloalkene;

$R^{10C}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene;

wherein each $R^{10}$ is independently unsubstituted or substituted with one or two or three of independently selected $R^{11}$, $OR^{11}$, $SR^{11}$, $S(O)R^{11}$, $SO_2R^{11}$, $NH_2$, $NHR^{11}$, $N(R^{11})_2$, $C(O)R^{11}$, $C(O)OR^{11}$, $C(O)NH_2$, $C(O)NHR^{11}$, $C(O)N(R^{11})_2$, $NHC(O)R^{11}$, $NR^{11}C(O)R^{11}$, $NHSO_2R^{11}$, $NR^{11}SO_2R^{11}$, $NHC(O)OR^{11}$, $NR^{11}C(O)OR^{11}$, $NHSO_2NH_2$, $NHSO_2NHR^{11}$, $NHSO_2N(R^{11})_2$, $SO_2NH_2$, $SO_2NHR^{11}$, $SO_2N(R^{11})_2$, $NHC(O)NH_2$, $NHC(O)NHR^{11}$, $NHC(O)N(R^{11})_2$, $NR^{11}C(O)N(R^{11})_2$, $NO_2$, OH, (O), C(O)H, C(O)OH, CN, $CF_3$, $OCF_3$, $CF_2CF_3$, F, Cl, Br or I;

wherein each $R^{11}$ is $R^{12}$, $R^{13}$, $R^{14}$ or $R^{15}$;

$R^{12}$ is phenyl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{13}$ is heteroaryl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{14}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{15}$ is alkyl, alkenyl or alkynyl; each of which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NH_2$, $C(O)NHR^{16}$, $C(O)N(R^{16})_2$, $NHC(O)R^{16}$, $NR^{16}C(O)R^{16}$, $NHC(O)OR^{16}$, $NR^{16}C(O)OR^{16}$, OH, F, Cl, Br or I;

wherein each $R^{16}$ is $R^{17}$ or $R^{17A}$;

$R^{17}$ is alkyl, alkenyl or alkynyl; each of which is unsubstituted or substituted with one or two of independently selected $R^{18}$, $C(O)OH$, $NH_2$, $NHR^{18}$ or $N(R^{18})_2$, $C(O)R^{is}$, $C(O)NH_2$, $C(O)NHR^{18}$, $C(O)N(R^{18})_2$, $NHC(O)R^{18}$, $NR^{18}C(O)R^{18}$, F, Cl, Br or I;

$R^{17A}$ is phenyl, heteroaryl, cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene;

wherein each $R^{18}$ is phenyl, heteroaryl, cycloalkyl, cycloalkenyl, heterocycloalkyl or heterocycloalkenyl;

wherein each of the moieties represented by $R^{12}$, $R^{13}$, $R^{14}$, $R^{17A}$, and $R^{18}$ are independently unsubstituted or substituted with one or two or three or four of independently selected $R^{19}$, $OR^{19}$, $SR^{19}$, $S(O)R^{19}$, $SO_2R^{19}$, $C(O)R^{19}$, $CO(O)R^{19}$, $OC(O)R^{19}$, $OC(O)OR^{19}$, $NH_2$, $NHR^{19}$, $N(R^{19})$, $NHC(O)R^{19}$, $NR^{19}C(O)R^{19}$, $NHS(O)_2R^{19}$, $NR^{19}S(O)_2R^{19}$, $NHC(O)OR^{19}$, $NR^{19}C(O)OR^{19}$, $NHC(O)NH_2$, $NHC(O)NHR^{19}$, $NHC(O)N(R^{19})_2$, $NR^{19}C(O)NHR^{19}$, $NR^{19}C(O)N(R^{19})_2$, $C(O)NH_2$, $C(O)NHR^{19}$, $C(O)N(R^{19})_2$, $C(O)NHOH$, $C(O)NHOR^{19}$, $C(O)NHSO_2R^{19}$, $C(O)NR^{19}SOR^{19}$, $SO_2NH_2$, $SO_2NHR^{19}$, $SO_2N(R^{19})_2$, $C(O)H$, $C(O)OH$, $C(N)NH_2$, $C(N)NHR^{19}$, $C(N)N(R^{19})_2$, CNOH, $CNOCH_3$, OH, (O), CN, $N_3$, $NO_2$, $CF_3$, $CF_2CF_3$, $OCF_3$, $OCF_2CF_3$, F, Cl, Br or I;

wherein each $R^{19}$ is $R^{20}$, $R^{21}$, $R^{22}$ or $R^{23}$;

$R^{20}$ is phenyl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{21}$ is heteroaryl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{22}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene;

$R^{23}$ is alkyl, alkenyl or alkynyl; each of which is unsubstituted or substituted with one or two of independently selected $R^{24}$, $OR^{24}$, $SR^{24}$, $S(O)_2R^{24}$, $C(O)OH$, $NH_2$, $NHR^{24}N(R^{24})_2$, $C(O)R^{24}$, $C(O)NH_2$, $C(O)NHR^{24}$, $C(O)N(R^{24})_2$, $NHC(O)R^{24}$, $NR^{24}C(O)R^{24}$, $NHC(O)OR^{24}$, $NR^{14}C(O)OR^{4}$, $NHS(O)_2R^{24}$, $NR^{24}S(O)_2R^{24}$, OH, F, Cl, Br or I;

wherein each $R^{24}$ is $R^{24A}$ or $R^{24B}$, $R^{24A}$ is phenyl, heteroaryl, cycloalkyl, cycloalkenyl, heterocycloalkyl or heterocycloalkenyl each of which is unfused or fused with benzene, heteroarene, cycloalkane, cycloalkene, heterocycloalkane or heterocycloalkene;

$R^{24B}$ is alkyl, alkenyl or alkynyl each of which is unsubstituted or substituted with one or two of independently selected $R^{25}$, $OR^{25}$, $SR^{25}$, $S(O)_2R^{25}$, $C(O)OH$, $NH_2$, $NHR^{25}N(R^{25})_2$, $C(O)R^{25}$, $C(O)NH_2$, $C(O)NHR^{25}$, $C(O)N(R^{25})_2$, $NHC(O)R^{25}$, $NR^{25}C(O)R^{25}$, $NHC(O)OR^{25}$, $NR^{25}C(O)OR^{25}$, OH, F, Cl, Br or I;

wherein each $R^{25}$ is alkyl, phenyl, heteroaryl, cycloalkyl, cycloalkenyl, heterocycloalkyl or heterocycloalkenyl; each of which is unsubstituted or substituted with $NH_2$, $NH(CH_3)$, $N(CH_3)_2$, OH or $OCH_3$;

wherein each of the moieties represented by $R^{20}$, $R^{21}$, $R^{22}$, and $R^{24A}$ are independently unsubstituted or substituted with one or two of independently selected $R^{26}$, $OR^{26}$, alkenyl, alkynyl, phenyl, OH, (O), C(O)OH, CN, $CF_3$, $OCF_3$, $CF_2CF_3$, F, Cl, Br or I; and $R^{26}$ is alkyl.

Embodiments of Formula I

Selected subclasses of compounds of interest that fall within the scope of the compounds of formula I are shown in the various embodiments described below, wherein $A^1$, $R^1$, $R^A$, $R^{1A}$, $R^2$, $R^{2A}$, $A^2$, $R^4$, $R^5$, $R^{10}$, $R^{10A}$, $R^{10B}$, $R^{10C}$, $R^{11}$, $R^{12}$, $R^{13}$, $R^{14}$, $R^{15}$, $R^{16}$, $R^{17}$, $R^{17A}$, $R^{18}$, $R^{19}$, $R^{20}$, $R^{21}$, $R^{22}$, $R^{23}$, $R^{24}$, $R^{24A}$, $R^{24B}$, $R^{25}$ and $R^{26}$ can be as defined for the compounds of Formula I and as defined in the various embodiments described throughout this specification.

Embodiments of $A^1$

In one embodiment of formula I, $A^1$ is $R^1$ or $R^2$, wherein $R^1$ is an unfused cycloalkane and $R^2$ is an unfused heterocycloalkane, wherein $A^1$ is unsubstituted or is substituted with one or two OH, CN, $C_1$-alkyl, $C_2$-alkyl, $C_3$-alkyl, $C_4$-alkyl, $C_5$-alkyl, cycloalkane, $OR^A$ or $NR^AR^A$; wherein $R^A$ is H or alkyl. In another embodiment of formula I, $A^1$ is $R^1$ or $R^1$, wherein $R^1$ is cyclohexane and $R^2$ is piperidinyl, wherein $A^1$ is unsubstituted or is substituted with one or two $C_L$-alkyl, $C_2$-alkyl or $C_3$-alkyl. In another embodiment of formula I, $A^1$ is $R^1$ or $R^2$, wherein $R^1$ is unsubstituted cyclohexane and $R^2$ is unsubstituted piperidinyl. In another embodiment of formula I, $A^1$ is $R^1$, and $R^1$ is unsubstituted cyclohexane, as shown in formula (Ia):

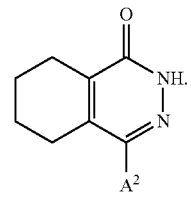

(Ia)

Embodiments of $A^2$

In one embodiment of formula I, $A^2$ is $OR^4$, $NHR^4$, $N(R^4)_2$, $SR^4$, $S(O)R^4$, $SO_2R^4$ or $R^5$; wherein each $R^4$ is $C_1$-alkyl, $C_2$-alkyl or $C_3$-alkyl; each of which is substituted with $R^{10}$ as described in Formula I; and $R^5$ is $C_1$-alkyl, $C_2$-alkyl or $C_3$-alkyl wherein $R^5$ is substituted as described in formula I. In another embodiment of formula I, $A^2$ is $R^5$, and $R^s$ is $C_1$-alkyl, $C_2$-alkyl or $C_3$-alkyl wherein $R^5$ is substituted as described in formula I. In another embodiment of formula I, $A^2$ is $R^5$, wherein $R^5$ is $C_1$-alkyl, which is substituted with $R^{10}$, and further unsubstituted or substituted with one or two or three of independently selected $NHR^{10}$, $N(R^{10})_2$, $SR^{10}$, $S(O)R^{10}$, $SO_2R^{10}$ or $CF_3$, wherein $R^{10}$ is as described in formula I. In another embodiment of formula I, $A^2$ is $R^5$, wherein $R^5$ is $C_1$-alkyl, substituted with $R^{10}$ as described in Formula I and further unsubstituted as shown in formula (Ib):

(Ib)

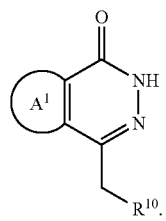

In another embodiment of formula I, A² is R⁵, wherein R⁵ is C₂-alkyl, substituted with R¹⁰ as described in Formula I and further unsubstituted as shown in formulas (Ic) and (Id):

(Ic)

(Id)

In another embodiment of formula I, A² is R⁵, wherein R⁵ is C₃-alkyl, substituted with R¹⁰ as described in Formula I and further unsubstituted. In another embodiment of formula I, A² is R⁵, wherein R⁵ is C₁-alkyl or C₂-alkyl; each of which are substituted with R¹⁰ as described in Formula I and further substituted with CF₃.

Embodiments of R¹⁰

In one embodiment of formula I, R¹⁰ is R¹⁰ᴬ, R¹⁰ᴮ or R¹⁰ᶜ, wherein R¹⁰ᴬ is phenyl which is unfused or fused with heterocycloalkane, which is fused heterocycloalkane, R¹⁰ᴮ is and R¹⁰ᶜ is heterocycloalkyl, which is unfused, wherein R¹⁰ is optionally substituted as described in Formula I. In another embodiment of formula I, R¹⁰ is R¹⁰ᴬ, R¹⁰ᴮ or R¹⁰ᶜ, wherein R¹⁰ᴬ is phenyl which is unfused or fused with heterocycloalkane, which is fused heterocycloalkane, R¹⁰ᴮ is and R¹⁰ᶜ is heterocycloalkyl, which is unfused; wherein R¹⁰ is substituted with F and further unsubstituted or substituted with one or two of independently selected R¹¹, OR¹¹, SR¹¹, S(O)R¹¹, SO₂R¹¹, NH₂, N(R¹¹)₂, C(O)R¹¹, C(O)OR¹¹, C(O)NHR¹¹, C(O)N(R¹¹)₂, NHC(O)R¹¹, NHSO₂R¹¹, NR¹¹SO₂R¹¹, NHC(O)OR¹¹, NHSO₂N(R¹¹)₂, NO₂, OH, (O), C(O)OH, F, Cl or Br, wherein R¹¹ is as described in Formula I. In another embodiment of formula I, R¹⁰ is R¹⁰ᴬ, R¹⁰ᴮ or R¹⁰ᶜ, wherein R¹⁰ᴬ is phenyl which is unfused or fused with heterocycloalkane, which is fused heterocycloalkane, R¹⁰ᴮ is and R¹⁰ᶜ is heterocycloalkyl, which is unfused; wherein R¹⁰ is substituted with F and further unsubstituted or substituted with one or two of independently selected R¹¹, OR¹¹, SR¹¹, S(O)R¹¹, SO₂R¹¹, NH₂, N(R¹¹)₂, C(O)R¹¹, C(O)OR¹¹, C(O)NHR¹¹, C(O)N(R¹¹)₂, NHC(O)R¹¹, NHSO₂R¹¹, NR¹¹SO₂R¹¹, NHC(O)OR¹¹, NHSO₂N(R¹¹)₂, NO₂, OH, (O), C(O)OH, F, Cl or Br; wherein each R¹¹ is R¹², R¹³, R¹⁴ or R¹⁵; wherein R¹² is phenyl which is unfused or fused with benzene, heteroarene, heterocycloalkane or heterocycloalkene; R¹³ is heteroaryl, which is unfused; R¹⁴ is cycloalkyl, heterocycloalkyl or heterocycloalkenyl; each of which is unfused or fused with benzene, cycloalkane, heterocycloalkane or heterocycloalkene; each of which is unfused or fused with benzene; and R¹⁵ is alkyl which is unsubstituted or substituted with one or two of independently selected R¹⁶, OR¹⁶, SR¹⁶, S(O)₂R¹⁶, C(O)OH, NH₂, NHR¹⁶N(R¹⁶)₂, C(O)R¹⁶, C(O)NHR¹⁶, NHC(O)R¹⁶, NHC(O)OR¹⁶, OH, F, Cl, Br or I, wherein R¹⁶ is as described in Formula I. In another embodiment of formula I, R¹⁰ is R¹⁰ᴬ, R¹⁰ᴮ or R¹⁰ᶜ, wherein R¹⁰ᴬ is phenyl which is unfused or fused with heterocycloalkane, which is fused heterocycloalkane, R¹⁰ᴮ is

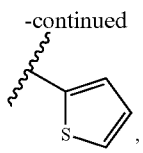

and $R^{10C}$ is heterocycloalkyl, which is unfused; wherein $R^{10}$ is substituted with F and further unsubstituted or substituted with one or two of independently selected $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, OH, (O), C(O)OH, F, Cl or Br; wherein each $R^{11}$ is $R^{12}$, $R^{13}$, $R^{14}$ or $R^{15}$; wherein $R^{12}$ is phenyl which is unfused or fused with benzene, heteroarene, heterocycloalkane or heterocycloalkene; $R^{13}$ is heteroaryl, which is unfused; $R^{14}$ is cycloalkyl, heterocycloalkyl or heterocycloalkenyl; each of which is unfused or fused with benzene, cycloalkane, heterocycloalkane or heterocycloalkene; each of which is unfused or fused with benzene; and $R^{15}$ is alkyl which is unsubstituted or substituted with one or two of independently selected $R^{16}$, $OR^{16}$, $SR^{16}$, $S(O)_2R^{16}$, C(O)OH, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl which is unsubstituted or substituted with $R^{18}$; $R^{17A}$ is phenyl, heteroaryl, cycloalkyl, heterocycloalkyl or heterocycloalkenyl, each of which is unfused or fused with benzene or heterocycloalkane; and $R^{18}$ is phenyl or heterocycloalkyl, which is unfused; wherein the moieties represented by $R^{12}$, $R^{13}$, $R^{14}$, $R^{17A}$, and $R^{18}$ are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, C(O)H, OH, (O), CN, $CF_3$, F, Cl, Br or I, wherein $R^{19}$ is as described in Formula I. In another embodiment of formula I, $R^{10}$ is $R^{10A}$, $R^{10B}$ or $R^{10C}$, wherein $R^{10A}$ is phenyl which is unfused or fused with heterocycloalkane, which is fused heterocycloalkane, $R^{10B}$ is

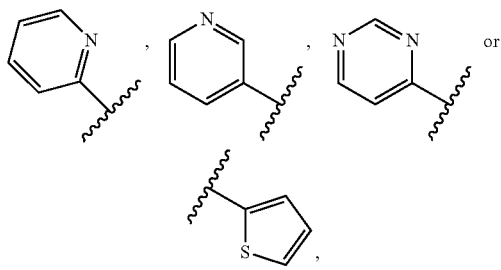

and $R^{10C}$ is heterocycloalkyl, which is unfused; wherein $R^{10}$ is substituted with F and further unsubstituted or substituted with one or two of independently selected $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, OH, (O), C(O)OH, F, Cl or Br; wherein each $R^{11}$ is $R^{11}$, $R^{13}$, $R^{14}$ or $R^{15}$; wherein $R^{12}$ is phenyl which is unfused or fused with benzene, heteroarene, heterocycloalkane or heterocycloalkene; $R^{13}$ is heteroaryl, which is unfused;
$R^{14}$ is cycloalkyl, heterocycloalkyl or heterocycloalkenyl; each of which is unfused or fused with benzene, cycloalkane, heterocycloalkane or heterocycloalkene; each of which is unfused or fused with benzene; and $R^{15}$ is alkyl which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl which is unsubstituted or substituted with $R^{18}$; $R^{17A}$ is phenyl, heteroaryl, cycloalkyl, heterocycloalkyl or heterocycloalkenyl, each of which is unfused or fused with benzene or heterocycloalkane; $R^{18}$ is phenyl or heterocycloalkyl, which is unfused; wherein the moieties represented by $R^{12}$, $R^{13}$, $R^{14}$, $R^{17A}$, and $R^{18}$ are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, C(O)H, OH, (O), CN, $CF_3$, F, Cl, Br or I; wherein each $R^{19}$ is $R^{20}$, $R^{21}$, $R^{22}$ or $R^{23}$; $R^{20}$ is phenyl, which is unfused; $R^{21}$ is heteroaryl, which is unfused; $R^{22}$ is heteroaryl, which is unfused; $R^{23}$ is cycloalkyl or heterocycloalkyl; each of which is unfused or fused with benzene; and $R^{23}$ is alkyl which is unsubstituted or substituted with $R^{24}$, $OR^{24}$, $NHR^{24}N(R^{24})_2$, $NHS(O)R^{24}$ or OH, wherein $R^{24}$ is as described in Formula I. In another embodiment of formula I, $R^{10}R^{10A}$, $R^{10B}$ or $R^{10C}$, wherein $R^{10A}$ is phenyl which is unfused or fused with heterocycloalkane, which is fused heterocycloalkane, $R^{10B}$ is

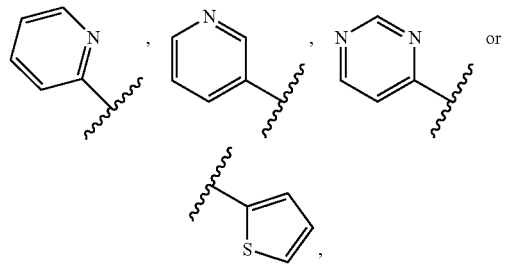

and $R^{10B}$ is heterocycloalkyl, which is unfused; wherein $R^{10}$ is substituted with F and further unsubstituted or substituted with one or two of independently selected $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, OH, (O), C(O)OH, F, Cl or Br; wherein each $R^{11}$ is $R^{12}$, $R^{13}$, $R^{14}$ or $R^{15}$; wherein $R^{12}$ is phenyl which is unfused or fused with benzene, heteroarene, heterocycloalkane or heterocycloalkene; $R^{13}$ is heteroaryl, which is unfused;
$R^{14}$ is cycloalkyl, heterocycloalkyl or heterocycloalkenyl; each of which is unfused or fused with benzene, cycloalkane, heterocycloalkane or heterocycloalkene: each of which is unfused or fused with benzene; and $R^{15}$ is alkyl which is unsubstituted or substituted with one or two of independently selected $R^{16}$, $OR^{16}$, $SR^{16}$, $S(O)_2R^{16}$, C(O)OH, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl which is unsubstituted or substituted with $R^{18}$; $R^{17A}$ is phenyl, heteroaryl, cycloalkyl, heterocycloalkyl or heterocycloalkenyl, each of which is unfused or fused with benzene or heterocycloalkane; $R^{18}$ is phenyl or heterocycloalkyl, which is unfused; wherein the moieties represented by $R^{12}$, $R^{13}$, $R^{14}$, $R^{17A}$, and $R^{18}$ are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, C(O)H, OH, (O), CN, $CF_3$, F, Cl, Br or I; wherein each $R^{19}$ is $R^{20}$, $R^{21}$, $R^{22}$ or $R^{23}$; $R^{20}$ is phenyl, which is unfused; $R^{21}$ is heteroaryl, which is unfused; $R^{22}$ is cycloalkyl or heterocycloalkyl; each of which is unfused or fused with benzene; and $R^{23}$ is alkyl which is unsubstituted or substituted with $R^{24}$, $OR^{24}$, $NHR^{24}N(R^{24})_2$, $NHS(O)_2R^{24}$ or OH; wherein each $R^{24}$ is $R^{24A}$ or $R^{24B}$; $R^{24A}$ is phenyl, cycloalkyl, heterocycloalkyl or heterocycloalkenyl, which is unfused or fused with heterocycloalkane; $R^{24B}$ is alkyl, which is unsubstituted or substituted with $OR^{25}$, OH, F, Cl, Br or I; $R^{25}$ is alkyl, which is unsubstituted or substituted with $NH_2$; wherein the moieties represented by $R^{20}$, $R^{21}$, $R^{22}$, and $R^{24A}$ are independently unsubstituted or substituted with one or two of independently selected $R^{26}$, $OR^{26}$ (O), F, Cl, Br or I; and $R^{26}$ is alkyl. In another embodiment of formula I, $R^{10}$ is $R^{10A}$, $R^{10B}$ or $R^{10C}$, wherein $R^{10A}$ is

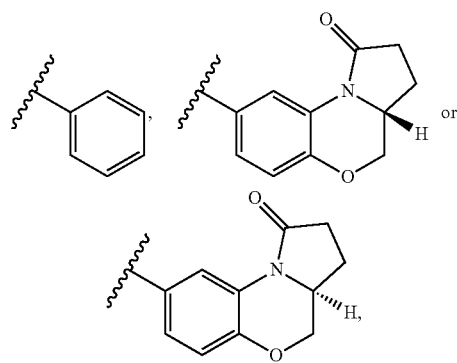

$R^{10B}$ is

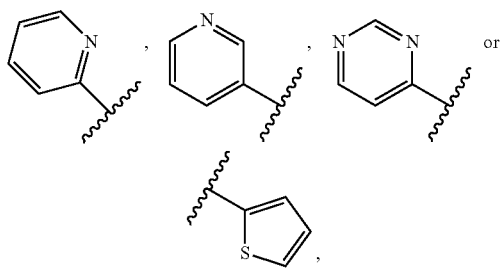

and $R^{10C}$ is

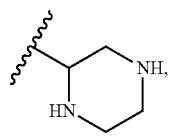

wherein $R^{10}$ is optionally substituted as described in Formula I. In another embodiment of formula I, $R^{10}$ is $R^{10A}$, wherein $R^{10A}$ is phenyl which is unfused, wherein $R^{10}$ is optionally substituted as described in Formula I. In another embodiment of formula I, $R^{10}$ is $R^{10A}$, wherein $R^{10A}$ is phenyl which is unfused, wherein $R^{10}$ is substituted with F and further unsubstituted or substituted with one or two of independently selected $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, OH, (O), $C(O)OH$, F, Cl or Br; wherein each $R^{11}$ is $R^{12}$, $R^{13}$, $R^{14}$ or $R^{15}$; wherein $R^{12}$ is phenyl which is unfused or fused with benzene, heteroarene, heterocycloalkane or heterocycloalkene; $R^{13}$ is heteroaryl, which is unfused;

$R^{14}$ is cycloalkyl, heterocycloalkyl or heterocycloalkenyl; each of which is unfused or fused with benzene, cycloalkane, heterocycloalkane or heterocycloalkene: each of which is unfused or fused with benzene; and $R^{15}$ is alkyl which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl which is unsubstituted or substituted with $R^{18}$; $R^{17A}$ is phenyl, heteroaryl, cycloalkyl, heterocycloalkyl or heterocycloalkenyl, each of which is unfused or fused with benzene or heterocycloalkane; $R^{18}$ is phenyl or heterocycloalkyl, which is unfused; wherein the moieties represented by $R^{12}$, $R^{13}$, $R^{14}$, $R^{17A}$, and $R^{18}$ are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I; wherein each $R^{19}$ is $R^{20}$, $R^{21}$, $R^{22}$ or $R^{23}$; $R^{20}$ is phenyl, which is unfused; $R^{21}$ is heteroaryl, which is unfused; $R^{22}$ is cycloalkyl or heterocycloalkyl: each of which is unfused or fused with benzene; and $R^{23}$ is alkyl which is unsubstituted or substituted with $R^{24}$, $OR^{24}$, $NHR^{24}N(R^{24})_2$, $NHS(O)_2R^{24}$ or OH; wherein each $R^{24}$ is $R^{24A}$ or $R^{24B}$; $R^{24A}$ is phenyl, cycloalkyl, heterocycloalkyl or heterocycloalkenyl, which is unfused or fused with heterocycloalkane; $R^{24B}$ is alkyl, which is unsubstituted or substituted with $OR^{25}$, OH, F, Cl, Br or I; $R^{25}$ is alkyl, which is unsubstituted or substituted with $NH_2$; wherein the moieties represented by $R^{20}$, $R^{21}$, $R^{22}$, and $R^{24A}$ are independently unsubstituted or substituted with one or two of independently selected $R^{26}$, $OR^{26}(O)$, F, Cl, Br or I; and $R^{26}$ is alkyl. In another embodiment of formula I, $R^{10}$ is $R^{10A}$, wherein $R^{10A}$ is phenyl which is unfused, wherein $R^{10}$ is substituted with F and further substituted with $NHC(O)R^{11}$ wherein $R^{11}$ is $R^{15}$, wherein $R^{16}$ is optionally substituted as described in Formula I. In another embodiment of formula I, $R^{10}$ is $R^{10A}$, wherein $R^{10A}$ is phenyl which is unfused, wherein $R^{10}$ is substituted with F and further substituted with $R^{11}$, wherein $R^{11}$ is $R^{12}$ or $R^{14}$, wherein $R^{14}$ is heterocycloalkyl which is unsubstituted or substituted with one or two or three or four of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I, wherein $R^{19}$ is as described in Formula I. In another embodiment of formula I, $R^{10}$ is $R^{10A}$, wherein $R^{10A}$ is phenyl which is unfused, wherein $R^{10}$ is substituted with F and further substituted with $R^{11}$, wherein $R^{11}$ is phenyl, pyrrolidinyl, azabicyclo(3.1.0)hexanyl, hexahydro-1H-isoindolyl, oxazolidinyl, azepanyl, piperidinyl, imidazolidinyl, thiazolidinyl, thiazinyl, azetidinyl, tetrahydropyrimidinyl, or azabicylo(2.2.1)hept-2-yl; each of which are independently unsubstituted or substituted with one or two or three or four of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I wherein $R^{19}$ is as described in Formula I. In another embodiment of formula I, $R^{10}$ is $R^{10A}$, wherein $R^{10A}$ is phenyl which is unfused, wherein $R^{10}$ is substituted with F and further substituted with $R^{11}$, wherein $R^{11}$ is phenyl, pyrrolidinyl, azabicyclo(3.1.0)hexanyl, hexahydro-1H-isoindolyl, oxazolidinyl, azepanyl, piperidinyl, imidazolidinyl, thiazolidinyl, thiazinyl, azetidinyl, tetrahydropyrimidinyl, or azabicylo(2.2.1)hept-2-yl; each of which are independently substituted with one or two (O). In another embodiment of formula I, $R^{10}$ is $R^{10A}$, wherein $R^{10A}$ is phenyl which is unfused, wherein $R^{10}$ is substituted with F and further substituted with $R^{11}$, wherein $R^{11}$ is $R^{14}$, wherein $R^{14}$ is heterocycloalkyl which is unsubstituted or substituted with one or two (O). In another embodiment of formula I, $R^{10}$ is $R^{10A}$, wherein $R^{10A}$ is phenyl which is unfused, wherein $R^{10}$ is substituted with F and further substituted with $R^{11}$, wherein $R^{11}$ is $R^{14}$, wherein $R^{14}$ is pyrrolidinyl which is substituted with one or two or three or four of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, $OH$, (O), $CN$, $CF_3$, F, Cl, Br or I wherein $R^{19}$ is as described in Formula I and wherein $R^{14}$ is substituted with at least one (O). In another embodiment of formula I, $R^{10}$ is $R^{10A}$, wherein $R^{10A}$ is phenyl which is unfused, wherein $R^{10}$ is substituted with F and further substituted with $R^{11}$, wherein $R^{11}$ is $R^{14}$, wherein $R^{14}$ is pyrrolidinyl which is substituted with one or two (O).

Embodiments of Multiple Substituents

The following are additional embodiments of the compounds of Formula I. Unless otherwise specified, substituents are as described in Formula I.

In one embodiment of Formula I, $R^1$ is cycloalkane, which is unfused; $R^2$ is heterocycloalkane, which is unfused, and $A^1$ is $R^5$.

Embodiments where $A^1$ is Cyclohexane, $A^2$ is $R^5$

In one embodiment of Formula I, $A^1$ is $R^1$, wherein $R^1$ is unsubstituted cyclohexane which is unfused, and $A^2$ is $R^5$, which is as described in Formula I. In another embodiment of Formula I, $A^1$ is $R^1$, wherein $R^1$ is unsubstituted cyclohexane which is unfused, and $A^2$ is $R^5$, $R^5$ is $C_1$-alkyl, $C_2$-alkyl or $C_3$-alkyl wherein $R^5$ is substituted as described in Formula I. In another embodiment of Formula I, $A^1$ is $R^1$, wherein $R^1$ is unsubstituted cyclohexane which is unfused, and $A^2$ is $R^5$, $R^5$ is $C_1$-alkyl, $C_2$-alkyl or $C_3$-alkyl wherein $R^{10}$ is $R^{10A}$, wherein is $R^{10A}$ is phenyl which is unfused and substituted with F, and further substituted with $NHC(O)R^{11}$, wherein $R^{11}$ is $R^{15}$. In another embodiment of Formula I, $A^1$ is $R^1$, wherein $R^1$ is unsubstituted cyclohexane which is unfused, and $A^2$ is $R^5$, $R^5$ is $C_1$-alkyl, $C_2$-alkyl or $C_3$-alkyl wherein $R^{10}$ is $R^{10A}$, wherein is $R^{10A}$ is phenyl which is unfused and substituted with F, and further substituted with $NHC(O)R^{11}$, wherein $R^{11}$ is $R^{15}$ wherein $R^{15}$ is alkyl, which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl, which is unsubstituted or substituted with one or two of independently selected $R^{18}$; $R^{17A}$ is phenyl, heteroaryl, cycloalkyl, heterocycloalkyl or heterocycloalkenyl, each of which is unfused or fused with benzene or heterocycloalkane; wherein each $R^{18}$ is phenyl or heterocycloalkyl; wherein each of the moieties represented by $R^{17A}$ and $R^{18}$ are independently unsubstituted or substituted with one or two or three or four of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I; wherein each $R^{19}$ is $R^{20}$, $R^{21}$, $R^{22}$ or $R^{23}$; $R^{20}$ is phenyl which is unfused; $R^{21}$ is heteroaryl which is unfused; $R^{22}$ is cycloalkyl or heterocycloalkyl; each of which are unfused or fused with benzene; $R^{23}$ is alkyl, which is unsubstituted or substituted with one or two of independently selected $R^{24}$, $OR^{24}$, $NHR^{24}N(R^{24})_2$, $NHS(O)_2R^{24}$ or OH; wherein each $R^{24}$ is $R^{24A}$ or $R^{24}$; $R^{24A}$ is unsubstituted phenyl, cycloalkyl, heterocycloalkyl or heterocycloalkenyl each of which is unfused or fused with heterocycloalkane; $R^{24B}$ is alkyl, which is unsubstituted or substituted with one or two of independently selected $OR^{25}$ or OH; wherein each $R^{25}$ is alkyl unsubstituted or substituted with $NH_2$; wherein each $R^{20}$ is unsubstituted or substituted with one or two of independently selected $R^{26}$, $OR^{26}$, (O), F, Cl, Br or I; and $R^{26}$ is alkyl. In another embodiment of Formula I, $A^1$ is $R^1$, wherein $R^1$ is unsubstituted cyclohexane which is unfused, and $A^2$ is $R^5$, $R^5$ is $C_1$-alkyl, $C_2$-alkyl or $C_3$-alkyl wherein $R^{10}$ is substituted with F, and further substituted with $R^{14}$ wherein each $R^{10}$ is independently unsubstituted or substituted with one or two or three of independently selected $R^{11}$, $OR^{11}$, $SR^{11}$, $S(O)R^{11}$, $SO_2R^{11}$, $NH_2$, $NHR^{11}$, $N(R^{11})_2$, $C(O)R^{11}$, $C(O)OR^{11}$, $C(O)NH_2$, $C(O)NHR^{11}$, $C(O)N(R^{11})_2$, $NHC(O)R^{11}$, $NR^{11}C(O)R^{11}$, $NHSO_2R^{11}$, $NR^{11}SO_2R^{11}$, $NHC(O)OR^{11}$, $NR^{11}C(O)OR^{11}$, $NHSO_2NH_2$, $NHSO_2NHR^{11}$, $NHSO_2N(R^{11})_2$, $SO_2NH_2$, $SO_2NHR^{11}$, $SO_2N(R^{11})_2$, $NHC(O)NH_2$, $NHC(O)NHR^{11}$, $NHC(O)N(R^{11})_2$, $NR^{11}C(O)N(R^{11})_2$, $NO_2$, OH, (O), $C(O)H$, $C(O)OH$, CN, $CF_3$, $OCF_3$, $CF_2CF_3$, F, Cl, Br or I; wherein $R^{14}$ is pyrrolidinyl, azetidinyl, pyrrolyl, 1,3-oxazolidinyl, azepanyl, piperidinyl, imidazolidinyl, tetrahydropyrimidin(2H)-yl, azabicyclo(2.2.1)heptyl or 1,6-dihydropyridazyl; each of which unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene; and wherein the moiety represented by $R^{14}$ is substituted with one or two (O) substituents. In another embodiment of Formula I, $A^1$ is $R^1$, wherein $R^1$ is unsubstituted cyclohexane which is unfused, and $A^2$ is $R^5$, $R^5$ is $C_1$-alkyl, $C_2$-alkyl or $C_3$-alkyl wherein $R^5$ is substituted with $R^{10}$, and further unsubstituted or substituted with one or two or three of independently selected $NHR^{10}$, $N(R^{10})_2$, $SR^{10}$, $S(O)R^{10}$, $SO_2R^{10}$ or $CF_3$, wherein $R^{10}$ is as described in formula I. In another embodiment of Formula I, $A^1$ is $R^1$, wherein $R^1$ is unsubstituted cyclohexane which is unfused, and $A^2$ is $R^5$, $R^5$ is $C_1$-alkyl, $C_2$-alkyl or $C_3$-alkyl wherein $R^5$ is substituted with $R^{10}$, and further unsubstituted or substituted with one $CF_3$, wherein $R^{10}$ is as described in formula I. In another embodiment of Formula I, $A^1$ is $R^1$, wherein $R^1$ is unsubstituted cyclohexane which is unfused, and $A^2$ is $R^5$ selected from the following Formulas (Ie), (If), (Ig), (Ih), (Ii) or (Ij):

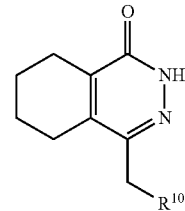

(Ie)

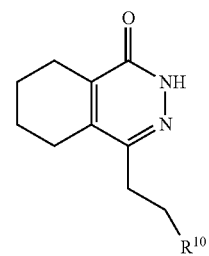

(If)

-continued (Ig)
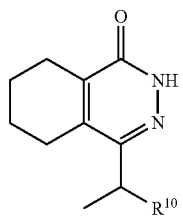

(Ih)
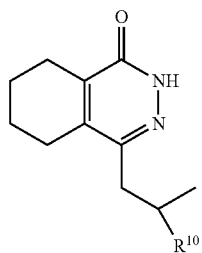

(Ii)
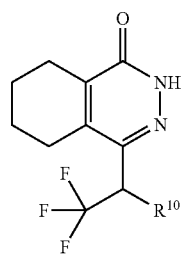

(Ij)
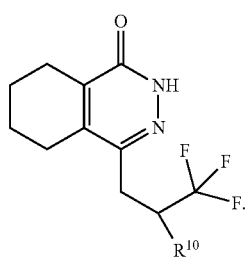

In one embodiment of Formula (Ii), $R^{10}$ is $R^{10A}$, $R^{10B}$ or $R^{10C}$; each of which must be attached at a carbon atom; $R^{10A}$ is phenyl which is unfused or fused with heterocycloalkane, which is fused with heterocycloalkane; $R^{10B}$ is

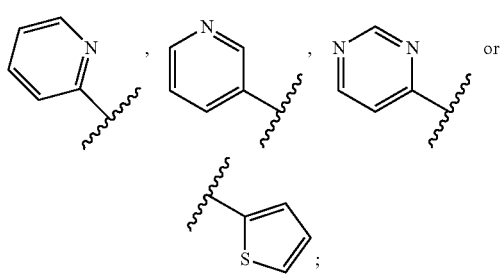

$R^{10C}$ is heterocycloalkyl, which is unfused; wherein $R^{10}$ is substituted with $C(O)R^{11}$, $C(O)NHR^{11}$, $C(O)N(R^{11})_2$ or $NHC(O)R^{11}$, and is further unsubstituted or substituted with one or two or three of independently selected $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, OH, (O), C(O)OH, F, Cl, Br or I; wherein each $R^{11}$ is $R^{12}$, $R^{13}$, $R^{14}$ or $R^{15}$; $R^{12}$ is phenyl which is unfused or fused with benzene, heteroarene, heterocycloalkane or heterocycloalkene; $R^{13}$ is heteroaryl, which is unfused; $R^{14}$ is cycloalkyl, heterocycloalkyl or heterocycloalkenyl; each of which is unfused or fused with benzene, cycloalkane, heterocycloalkane or heterocycloalkene; each of which is unfused or fused with benzene; $R^{15}$ is alkyl, which is unsubstituted or substituted with one or two of independently selected $R^{16}$, $OR^{16}$, $SR^{16}$, $S(O)_2R^{16}$, C(O)OH, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl, which is unsubstituted or substituted with $R^{15}$; $R^{17A}$ is phenyl, heteroaryl, cycloalkyl, heterocycloalkyl or heterocycloalkenyl, each of which is unfused or fused with benzene or heterocycloalkane; $R^{18}$ is phenyl or heterocycloalkyl, which is unfused; wherein the moieties represented by $R^{12}$, $R^{13}$, $R^{14}$, $R^{17A}$, and $R^{18}$ are independently unsubstituted or substituted with one or two independently selected $R^{19}$, $OR^{19}$, $SR^{19}$, $SO_2R^{19}$, $C(O)R^{19}$, $CO(O)R^{19}$, $NHR^{19}$, $N(R^{19})$, $NHC(O)R^{19}$, $NHS(O)_2R^{19}$, $C(O)NH_2$, $C(O)NHR^{19}$, $C(O)N(R^{19})_2$, C(O)H, OH, (O), CN, $CF_3$, F, Cl, Br or I; wherein each $R^{19}$ is $R^{20}$, $R^{21}$, $R^{22}$ or $R^{23}$; $R^{20}$ is phenyl, which is unfused; $R^{21}$ is heteroaryl, which is unfused; $R^{22}$ is cycloalkyl, or heterocycloalkyl each of which is unfused or fused with benzene; $R^{23}$ is alkyl which is unsubstituted or substituted with one or two of independently selected $R^{24}$, $OR^{24}$, $NHR^{24}N(R^{24})_2$, $NHS(O)_2R^{24}$, OH, F, Cl, Br or I; wherein each $R^{24}$ is $R^{24A}$ or $R^{24B}$; $R^{24A}$ is phenyl, cycloalkyl, heterocycloalkyl or heterocycloalkenyl; each of which is unfused or fused with heterocycloalkane; $R^{24B}$ is alkyl which is unsubstituted or substituted with $OR^{25}$, OH, F, Cl, Br or I; $R^{25}$ is alkyl each of which is unsubstituted or substituted with $NH_2$; wherein the moieties represented by $R^{20}$, $R^{21}$, $R^{22}$, and $R^{24A}$ are independently unsubstituted or substituted with one or two of independently selected $R^{26}$, $OR^{26}$, (O), F, Cl, Br or I; and $R^{16}$ is alkyl. In another embodiment of Formula I, $A^1$ is $R^1$, wherein $R^1$ is unsubstituted cyclohexane which is unfused, and $A^2$ is $R^5$, $R^5$ is $C_1$-alkyl wherein $R^5$ is substituted with $R^{10}$, wherein $R^{10}$ is as described in formula I, as described in Formula (Ie)

(Ie)
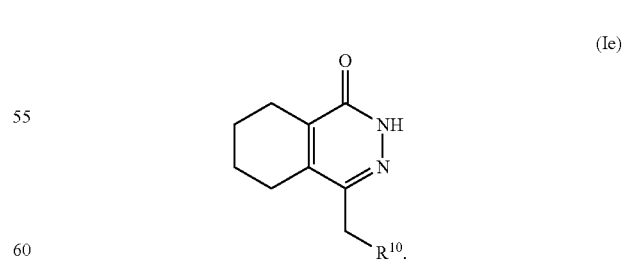

In another embodiment of Formula I, $A^1$ is $R^1$, wherein $R^1$ is unsubstituted cyclohexane which is unfused, and $A^2$ is $R^5$, $R^5$ is unbranched $C_2$-alkyl wherein $R^5$ is substituted with $R^{10}$, wherein $R^{10}$ is as described in formula I, as described in Formula (If)

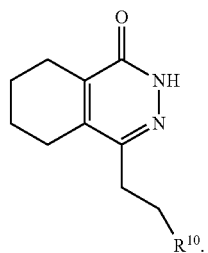

(If)

Embodiments of Formula (Ie)

In one embodiment of Formula (Ie), $R^{10}$ is $R^{10A}$, $R^{10B}$ or $R^{10C}$, wherein $R^{10A}$ is phenyl which is unfused or fused with heterocycloalkane, which is fused heterocycloalkane, $R^{10B}$ is

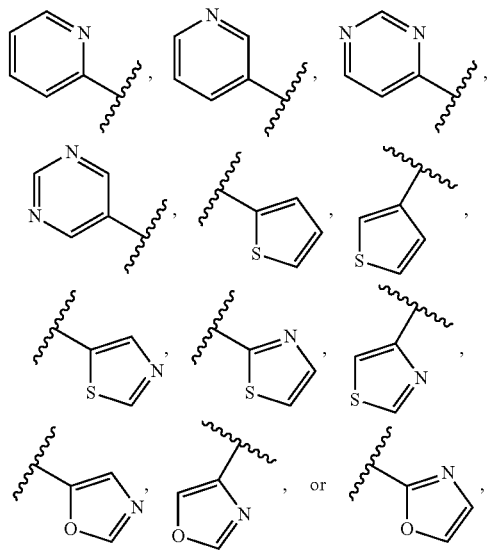

and $R^{10C}$ is heterocycloalkyl, which is unfused; wherein $R^{10}$ is substituted as described in formula I. In another embodiment of Formula (Ie), $R^{10}$ is $R^{10A}$, $R^{10B}$ or $R^{10C}$, wherein $R^{10A}$ is phenyl which is unfused or fused with heterocycloalkane, which is fused heterocycloalkane, $R^{10B}$ is

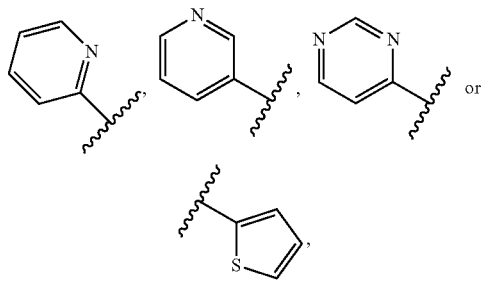

and $R^{10C}$ is heterocycloalkyl, which is unfused; wherein $R^{10}$ is substituted with one or two of independently selected $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, $OH$, $(O)$, $C(O)OH$, $F$, $Cl$ or $Br$; wherein $R^{11}$ is as described in Formula I. In another embodiment of Formula (Ie), $R^{10}$ is $R^{10A}$, $R^{10B}$ or $R^{10C}$, wherein $R^{10A}$ is phenyl which is unfused or fused with heterocycloalkane, which is fused heterocycloalkane, $R^{10B}$ is

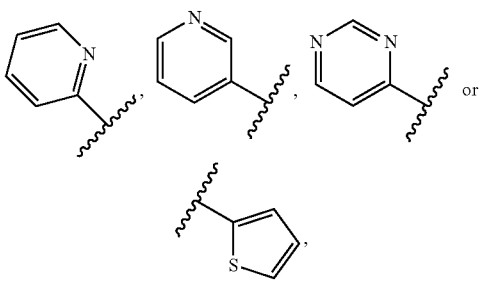

and $R^{10C}$ is heterocycloalkyl, which is unfused; wherein $R^{10}$ is substituted with F and further unsubstituted or substituted with one or two of independently selected $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, $OH$, $(O)$, $C(O)OH$, $F$, $Cl$ or $Br$; wherein $R^{11}$ is as described in Formula I. In another embodiment of Formula (Ie), $R^{10}$ is $R^{10A}$, $R^{10B}$ or $R^{10C}$, wherein $R^{10A}$ is phenyl which is unfused or fused with heterocycloalkane, which is fused heterocycloalkane, $R^{10B}$ is

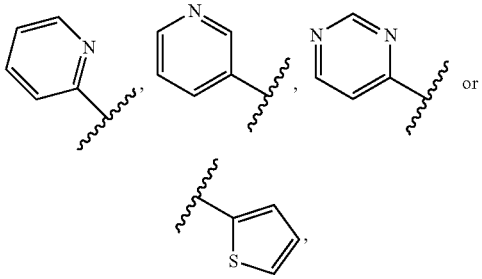

and $R^{10C}$ is heterocycloalkyl, which is unfused; wherein $R^{10}$ is substituted with F and further unsubstituted or substituted with one or two of independently selected $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, $OH$, $(O)$, $C(O)OH$, $F$, $Cl$ or $Br$; wherein $R^{11}$ is $R^{12}$, $R^{13}$, $R^{14}$ or $R^{15}$; $R^{12}$ is phenyl which is unfused or fused with benzene, heteroarene, heterocycloalkane or heterocycloalkene; $R^{13}$ is heteroaryl, which is unfused; $R^{14}$ is cycloalkyl, heterocycloalkyl or heterocycloalkenyl; each of which is unfused or fused with benzene, cycloalkane, heterocycloalkane or heterocycloalkene; each of which is unfused or fused with benzene; $R^{15}$ is alkyl which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NHR^{16}$, $NHC(O)R^{16}$, $NHC(O)OR^{16}$, $OH$, $F$, $Cl$, $Br$ or $I$; wherein each $R^{16}$ is $R^{17}$ or $R^{17A}$; $R^{17}$ is alkyl which is unsubstituted or substituted with $R^{is}$; $R^{17A}$ is phenyl, heteroaryl, cycloalkyl, heterocycloalkyl or heterocycloalkenyl, each of which is unfused or fused with benzene or heterocycloalkane; $R^{18}$ is phenyl or heterocycloalkyl, which is unfused; wherein the moieties represented by $R^{12}$, $R^{13}$, $R^{14}$, $R^{17A}$, and $R^{18}$ are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, $OH$, $(O)$, $CN$, $CF_3$, $F$, $Cl$, $Br$ or $I$; wherein each $R^{19}$ is $R^{20}$, $R^{21}$, $R^{22}$ or $R^{23}$; $R^{20}$ is phenyl, which is unfused; $R^{21}$ is heteroaryl, which is unfused; $R^{22}$ is cycloalkyl or heterocycloalkyl; each of which is unfused or fused with benzene; $R^{23}$ is alkyl which is unsubstituted or substituted with $R^{24}$, $OR^{24}$, $NHR^{24}N(R^{24})_2$, $NHS(O)_2R^{24}$ or $OH$; wherein each $R^{24}$ is $R^{24A}$ or $R^{24B}$; $R^{24A}$ is phenyl, cycloalkyl, heterocycloalkyl or heterocycloalkenyl, which is unfused or fused with heterocycloalkane; $R^{24B}$ is alkyl, which is unsubstituted or substituted with $OR^{25}$, $OH$, $F$, $Cl$, $Br$ or $I$; $R^{25}$ is alkyl, which is unsubstituted or substituted with $NH_2$; wherein the moieties represented by $R^{20}$, $R^{21}$, $R^{22}$, and $R^{24A}$ are independently unsubstituted or substituted with one or two of independently selected $R^{26}$, $OR^{26}$ (O), $F$, $Cl$, $Br$ or $T$; and $R^{26}$ is alkyl. In another embodiment of Formula (Ie), $R^{10}$ is $R^{10A}$, $R^{10B}$ or $R^{10C}$, wherein $R^{10A}$ is phenyl which is unfused.

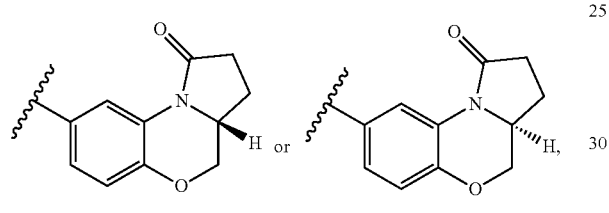

$R^{10B}$ is

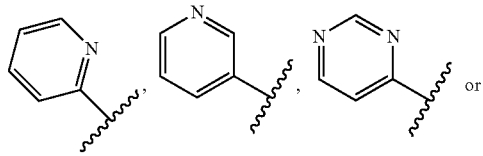

and $R^{10C}$ is

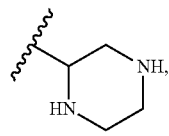

wherein $R^{10}$ is optionally substituted as described in Formula I. In another embodiment of Formula (Ie), $R^{10}$ is $R^{10A}$ $R^{10B}$ or $R^{10C}$ as described in Formulas (Ik), (Il), (Im), (In), (Io) or (Ip)

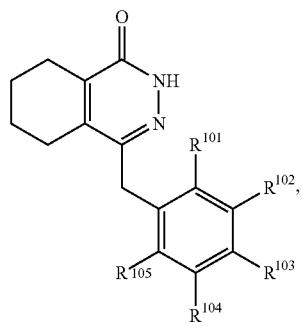
(Ik)

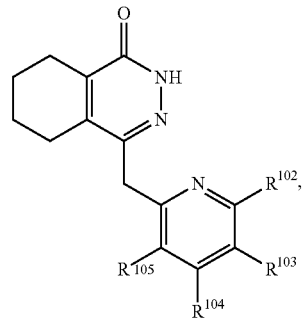
(Il)

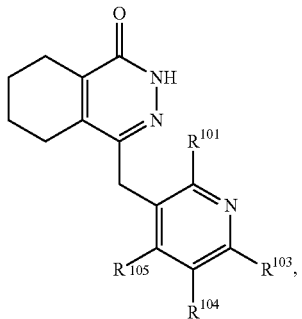
(Im)

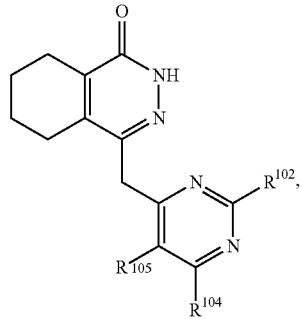
(In)

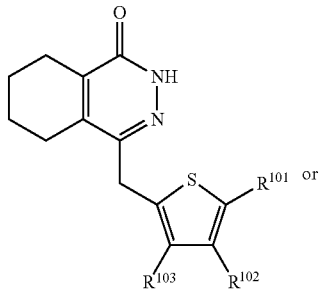
(Io)

-continued

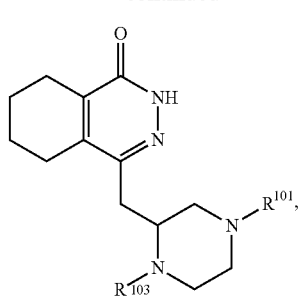
(Ip)

wherein $R^{101}$, $R^{102}$, $R^{103}$, $R^{104}$, and $R^{105}$, are independently selected from $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, OH, (O), C(O)OH, F, Cl or Br; wherein $R^{11}$ is as described in Formula I.

In another embodiment of Formula (Ie), $R^{10}$ is $R^{10A}$ or $R^{10B}$, as described in Formulas (Ik), (Il), (Im), (In), (Io) or (Ip). In another embodiment of Formula (Ie), $R^{10}$ is phenyl, as shown in Formula (Ik):

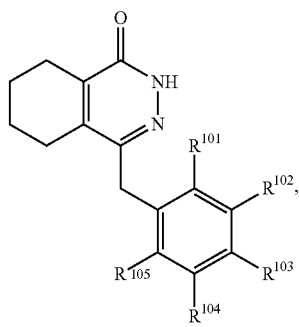
(Ik)

wherein $R^{101}$, $R^{102}$, $R^{103}$, $R^{104}$, and $R^{105}$, are independently selected from H, $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, OH, (O), C(O)OH, F, Cl or Br; wherein $R^{11}$ is as described in Formula I. In another embodiment of Formula (Ik), at least one of $R^{101}$, $R^{102}$, $R^{103}$, $R^{104}$, and $R^{105}$ are F, and at least one is $R^{11}$, wherein $R^{11}$ is phenyl, pyrrolyl, azabicyclo(3.1.0)hexanyl, hexahydro-1H-isoindolyl, 1,3-oxazolidinyl, azepanyl, piperidinyl, imidazolidinyl, thiazolidinyl, thiazinyl, azetidinyl, 1,6-dihydropyridazyl, tetrahydropyrimidin(2H)-yl or azabicylo(2.2.1)hept-2-yl; each of which are independently unsubstituted or substituted with one or two or three of independently selected $R^{19}$, $OR^{19}SR^{19}$, $SO_2R^{19}$, $C(O)R^{19}$, $CO(O)R^{19}$, $NHR^{19}$, $N(R)_2$, $NHC(O)R^{19}$, $NHS(O)_2R^{19}$, $C(O)NH_2$, $C(O)NHR^{19}$, $C(O)N(R^{19})_2$, C(O)H, OH, (O), CN, $CF_3$, F, Cl, Br or I; wherein each $R^{19}$ is $R^{20}$, $R^{21}$, $R^{22}$ or $R^{23}$; $R^{20}$ is phenyl, which is unfused; $R^{21}$ is heteroaryl, which is unfused; $R^{22}$ is cycloalkyl, or heterocycloalkyl each of which is unfused or fused with benzene; $R^{23}$ is alkyl which is unsubstituted or substituted with one or two of independently selected $R^{24}$, $OR^{24}$, $NHR^{24}N(R^{24})_2$, $NHS(O)_2R^{19}$, OH, F, Cl, Br or I; wherein each $R^{24}$ is $R^{24A}$ or $R^{24B}$; $R^{24A}$ is phenyl, cycloalkyl, heterocycloalkyl or heterocycloalkenyl; each of which is unfused or fused with heterocycloalkane; $R^{24B}$ is alkyl which is unsubstituted or substituted with $OR^{25}$, OH, F, Cl, Br or I; $R^{25}$ is alkyl each of which is unsubstituted or substituted with $NH_2$; wherein the moieties represented by $R^{20}$, $R^{21}$, $R^{22}$, and $R^{24A}$ are independently unsubstituted or substituted with one or two of independently selected $R^{26}$, $OR^{26}$, (O), F, Cl, Br or I; and $R^{26}$ is alkyl. In another embodiment of Formula (Ik), $R^{101}$, $R^{104}$ and $R^{105}$ are H, and $R^{102}$ is $R^{11}$, wherein $R^{11}$ is selected from pyrrolidinyl, oxazolyl, imidazolidinyl, isothiazolidinyl, piperidinyl, and azepanyl, wherein $R^{102}$ is substituted with one or two (O) substituents. In another embodiment of Formula (Ik), $R^{101}$, $R^{104}$ and $R^{105}$ are H, and $R^{102}$ is $R^{11}$, wherein $R^{11}$ is pyrrolidinyl.

Further Embodiments of Formula (Ik)

In one embodiment of Formula (Ik), $R^{102}$ is $NHC(O)R^{11}$, as described in Formula (Iq):

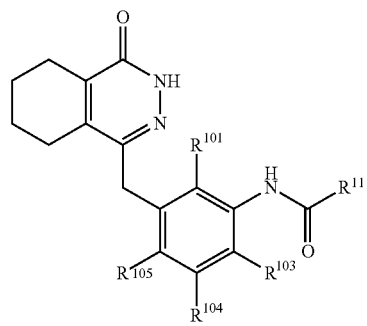
(Iq)

wherein $R^{101}$, $R^{103}$, $R^{104}$ and $R^{105}$ are independently selected from H, $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, OH, (O), C(O)OH, F, Cl or Br; wherein $R^{11}$ is as described in Formula I. In one embodiment of Formula (Iq), $R^{11}$ is $R^{15}$, wherein $R^{16}$ is optionally substituted as described in Formula I and $R^{101}$, $R^{103}$, $R^{104}$ and $R^{105}$ are as described in Formula (Iq). In another embodiment of Formula (Iq), $R^{103}$ is F, and $R^{101}$, $R^{104}$ and $R^{105}$ are independently selected from H, $R^{11}$, $OR^{11}$, $SR^{11}$, $S(O)R^{11}$, $SO_2R^{11}$, $NH_2$, $N(R^{11})_2$, $C(O)R^{11}$, $C(O)OR^{11}$, $C(O)NHR^{11}$, $C(O)N(R^{11})_2$, $NHC(O)R^{11}$, $NHSO_2R^{11}$, $NR^{11}SO_2R^{11}$, $NHC(O)OR^{11}$, $NHSO_2N(R^{11})_2$, $NO_2$, OH, (O), C(O)OH, F, Cl or Br; and $R^{11}$ is $R^{15}$, wherein $R^{16}$ is optionally substituted as described in Formula I. In another embodiment of Formula (Iq), one of $R^{101}$, $R^{103}$, $R^{104}$ and $R^{105}$ is F, $R^{11}$ is $R^{15}$, wherein $R^{16}$ is optionally substituted as described in Formula I. In another embodiment of Formula (Iq), $R^{101}$, $R^{104}$ and $R^{105}$ is F. In another embodiment of Formula (Iq), $R^{103}$ is F. In another embodiment of Formula (Iq), one of $R^{101}$, $R^{103}$, $R^{104}$ and $R^{105}$ is F, $R^{11}$ is $R^{15}$, wherein $R^{16}$ is alkyl, which is unsubstituted or substituted with one or two of independently selected $R^{16}$, $OR^{16}$, $SR^{16}$, $S(O)_2R^{16}$, C(O)OH, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl, which is unsubstituted or substituted with one or two of independently selected $R^{18}$: $R^{17A}$ is phenyl, heteroaryl, cycloalkyl, heterocycloalkyl or heterocycloalkenyl, each of which is unfused or fused with benzene or heterocycloalkane; wherein each $R^{18}$ is phenyl or heterocycloalkyl; wherein each of the moieties represented by $R^{17A}$ and $R^{18}$ are independently unsubstituted or substituted with one or two or three or four of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, C(O)N ($R^{19}$)$_2$, C(O)H, OH, (O), CN, CF$_3$, F, Cl, Br or I; wherein each $R^{19}$ is $R^{20}$, $R^{21}$, $R^{22}$ or $R^{23}$; $R^{20}$ is phenyl which is unfused; $R^{21}$ is heteroaryl which is unfused; $R^{22}$ is cycloalkyl or heterocycloalkyl; each of which are unfused or fused with benzene; $R^{23}$ is alkyl, which is unsubstituted or substituted with one or two of independently selected $R^{24}$, OR$^{24}$, NHR$^{24}$N($R^{24}$)$_2$, NHS(O)$_2$R$^{24}$ or OH; wherein each $R^{24}$ is $R^{24A}$ or $R^{24BA}$; $R^{24A}$ is unsubstituted phenyl, cycloalkyl, heterocycloalkyl or heterocycloalkenyl each of which is unfused or fused with heterocycloalkane; $R^{24B}$ is alkyl, which is unsubstituted or substituted with one or two of independently selected OR$^{25}$ or OH; wherein each $R^{25}$ is alkyl unsubstituted or substituted with NH$_2$; wherein each $R^{20}$ is unsubstituted or substituted with one or two of independently selected $R^{26}$, OR$^{26}$, (O), F, Cl, Br or I; and $R^{26}$ is alkyl. In another embodiment of Formula (Iq), $R^{103}$ is F, and $R^{101}$, $R^{104}$ and $R^{105}$ are each H, $R^{11}$ is $R^{15}$, wherein $R^{16}$ is optionally substituted as described in Formula I. In another embodiment of Formula (Iq), $R^{11}$ is $R^{12}$ or $R^{14}$, wherein $R^{14}$ is heterocycloalkyl which is unsubstituted or substituted with one or two or three or four of independently selected $R^{19}$, OR$^{19}$, SR$^{19}$, SO$_2$R$^{19}$, C(O)R$^{19}$, CO(O)R$^{19}$, NHR$^{19}$, N(R$^{19}$)$_2$, NHC(O)R$^{19}$, NHS(O)$_2$R$^{19}$, C(O)NH$_2$, C(O)NHR$^{19}$, C(O)N(R$^{19}$)$_2$, C(O)H, OH, (O), CN, CF$_3$, F, Cl, Br or I; wherein R$^{19}$ is as described in Formula I. In another embodiment of Formula (Iq), $R^{11}$ is selected from phenyl, pyrrolidinyl, azabicyclo(3.1.0)hexanyl, hexahydro-1H-isoindolyl, oxazolidinyl, azepanyl, piperidinyl, imidazolidinyl, thiazolidinyl, thiazinyl, azetidinyl, tetrahydropyrimidinyl or azabicylo(2.2.1)hept-2-yl; each of which are independently unsubstituted or substituted with one or two or three or four of independently selected $R^{19}$OR$^{19}$, SR$^{19}$, SO$_2$R$^{19}$, C(O)R$^{19}$, CO(O)R$^{19}$, NHR$^{19}$, N(R$^{19}$)$_2$, NHC(O)R$^{19}$, NHS(O)$_2$R$^{19}$, C(O)NH$_2$, C(O)NHR$^{19}$, C(O)N(R$^{19}$)$_2$, C(O)H, OH, (O), CN, CF$_3$, F, Cl, Br or I; wherein R$^{19}$ is as described in Formula I.

In one embodiment of Formula (Ik), $R^{102}$ is $R^{11}$, wherein $R^{11}$ is pyrrolidinyl as described in Formula (Ir):

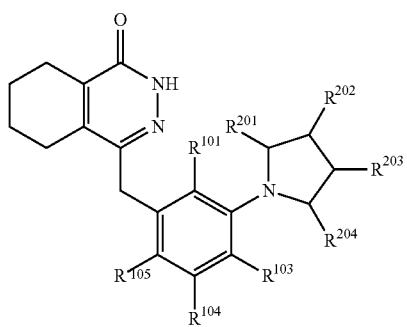

(Ir)

wherein $R^{101}$, $R^{103}$, $R^{104}$, and $R^{105}$, are independently selected from H, $R^{11}$, OR$^{11}$, SR$^{11}$, S(O)R$^{11}$, SO$_2$R$^{11}$, NH$_2$, N(R$^{11}$)$_2$, C(O)R$^{11}$, C(O)OR$^{11}$, C(O)NHR$^{11}$, C(O)N(R$^{11}$)$_2$, NHC(O)R$^{11}$, NHSO$_2$R$^{11}$, NR$^{11}$SO$_2$R$^{11}$, NHC(O)OR$^{11}$, NHSO$_2$N(R$^{11}$)$_2$, NO$_2$, OH, (O), C(O)OH, F, Cl or Br; wherein $R^{11}$ is as described in Formula I, and $R^{201}$, $R^{202}$, $R^{203}$, and $R^{204}$ are independently H, R$^{19}$, OR$^{19}$, SR$^{19}$, SO$_2$R$^{19}$, C(O)R$^{19}$, CO(O)R$^{19}$, NHR$^{19}$, N(R$^{19}$)$_2$, NHC(O)R$^{19}$, NHS(O)$_2$R$^{19}$, C(O)NH$_2$, C(O)NHR$^{19}$, C(O)N(R$^{19}$)$_2$, C(O)H, OH, (O), CN, CF$_3$, F, Cl, Br or I; wherein R$^{19}$ is as described in Formula I. In one embodiment of Formula (Ir), $R^{103}$ is F, and $R^{101}$, $R^{104}$, and $R^{105}$ are H, wherein $R^{201}$, $R^{202}$, $R^{203}$, and $R^{204}$ are independently H, R$^{19}$, OR$^{19}$, SR$^{19}$, SO$_2$R$^{19}$, C(O)R$^{19}$, CO(O)R$^{19}$, NHR$^{19}$, N(R$^{19}$)$_2$, NHC(O)R$^{19}$, NHS(O)$_2$R$^{19}$, C(O)NH$_2$, C(O)NHR$^{19}$, C(O)N(R$^{19}$)$_2$, C(O)H, OH, (O), CN, CF$_3$, F, Cl, Br or I; wherein R$^{19}$ is as described in Formula I. In one embodiment of Formula (Ir), one or two of $R^{201}$, $R^{202}$, $R^{203}$, and $R^{204}$ is (O). In another embodiment of Formula (Ir), two of $R^{201}$, $R^{202}$, $R^{203}$, and $R^{204}$ are (O). In another embodiment of Formula (Ir), $R^{201}$ and $R^{204}$ are (O) and $R^{202}$ and $R^{203}$ are H, as described in Formula (Ir$_1$):

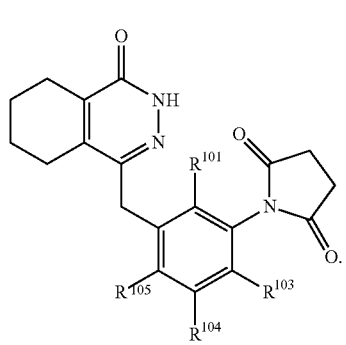

(Ir$_1$)

In one embodiment of Formula (Ir$_1$), $R^{103}$ is F and $R^{101}$, $R^{104}$, and $R^{105}$, are independently selected from H, $R^{11}$, OR$^{11}$, SR$^{11}$, S(O)R$^{11}$, SO$_2$R$^{11}$, NH$_2$, N(R$^{11}$)$_2$, C(O)R$^{11}$, C(O)OR$^{11}$, C(O)NHR$^{11}$, C(O)N(R$^{11}$)$_2$, NHC(O)R$^{11}$, NHSO$_2$R$^{11}$, NR$^{11}$SO$_2$R$^{11}$, NHC(O)OR$^{11}$, NHSO$_2$N(R$^{11}$)$_2$, NO$_2$, OH, (O), C(O)OH, F, Cl or Br; wherein $R^{11}$ is as described in Formula I.

In one embodiment of Formula (Ik), $R^{103}$ is F, as described in Formula (Is):

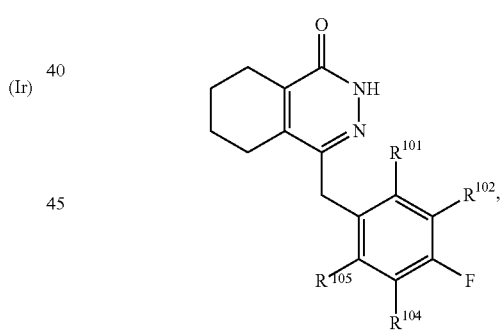

(Is)

wherein $R^{101}$, $R^{102}$, $R^{104}$, and $R^{105}$, are independently selected from H, $R^{11}$, OR$^{11}$, SR$^{11}$, S(O)R$^{11}$, SO$_2$R$^{11}$, NH$_2$, N(R$^{11}$)$_2$, C(O)R$^{11}$, C(O)OR$^{11}$, C(O)NHR$^{11}$, C(O)N(R$^{11}$)$_2$, NHC(O)R$^{11}$, NHSO$_2$R$^{11}$, NR$^{11}$SO$_2$R$^{11}$, NHC(O)OR$^{11}$, NHSO$_2$N(R$^{11}$)$_2$, NO$_2$, OH, (O), C(O)OH, F, Cl or Br; wherein $R^{11}$ is as described in Formula I. In another embodiment of Formula (Is), $R^{101}$, $R^{102}$, $R^{104}$, and $R^{105}$, are independently selected from H, $R^{11}$, OR$^{11}$, SR$^{11}$, S(O)R$^{11}$, SO$_2$R$^{11}$, NH$_2$, N(R$^{11}$)$_2$, C(O)R$^{11}$, C(O)OR$^{11}$, C(O)NHR$^{11}$, C(O)N(R$^{11}$)$_2$, NHC(O)R$^{11}$, NHSO$_2$R$^{11}$, NR$^{11}$SO$_2$R$^{11}$, NHC(O)OR$^{11}$, NHSON(R$^{11}$)$_2$, NO$_2$, OH, (O), C(O)OH, F, Cl or Br; wherein each $R^{11}$ is $R^{12}$, $R^{13}$, $R^{14}$ or $R^{15}$; wherein $R^{12}$ is phenyl which is unfused or fused with benzene, heteroarene, heterocycloalkane or heterocycloalkene; $R^{13}$ heteroaryl, which is unfused; $R^{14}$ is cycloalkyl, heterocycloalkyl or heterocycloalkenyl; each of which is unfused or fused with benzene, cycloalkane, heterocycloalkane or heterocycloalkene; each of which is unfused or fused with benzene; and $R^{15}$ is alkyl which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl which is unsubstituted or substituted with R's; $R^{17A}$ is phenyl, heteroaryl, cycloalkyl, heterocycloalkyl or heterocycloalkenyl, each of which is unfused or fused with benzene or heterocycloalkane: $R^{18}$ is phenyl or heterocycloalkyl, which is unfused; wherein the moieties represented by $R^{12}$, $R^{13}$, $R^{14}$, $R^{17A}$, and $R^{18}$ are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I; wherein each $R^{19}$ is $R^{20}$, $R^{21}$, $R^{22}$ or $R^{23}$; $R^{20}$ is phenyl, which is unfused; $R^{21}$ is heteroaryl, which is unfused; $R^{22}$ is cycloalkyl or heterocycloalkyl; each of which is unfused or fused with benzene; and $R^{23}$ is alkyl which is unsubstituted or substituted with $R^{24}$, $OR^{24}$, $NHR^{24}N(R^{24})_2$, $NHS(O)_2R^{24}$ or OH; wherein each $R^{24}$ is $R^{24A}$ or $R^{24}$; $R^{24A}$ is phenyl, cycloalkyl, heterocycloalkyl or heterocycloalkenyl, which is unfused or fused with heterocycloalkane; $R^{24B}$ is alkyl, which is unsubstituted or substituted with $OR^{25}$, OH, F, Cl, Br or I; $R^{25}$ is alkyl, which is unsubstituted or substituted with $NH_2$; wherein the moieties represented by $R^{20}$, $R^{21}$, $R^{22}$, and $R^{24A}$ are independently unsubstituted or substituted with one or two of independently selected $R^{26}$, $OR^{26}$ (O), F, Cl, Br or I; and $R^{26}$ is alkyl. In another embodiment of Formula (Is), $R^{11}$ is selected from phenyl, pyrrolidinyl, azabicyclo(3.1.0)hexanyl, hexahydro-1H-isoindolyl, oxazolidinyl, azepanyl, piperidinyl, imidazolidinyl, thiazolidinyl, thiazinyl, azetidinyl, tetrahydropyrimidinyl or azabicylo(2.2.1)hept-2-yl; each of which are independently unsubstituted or substituted with one or two or three or four of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I; wherein $R^{19}$ is as described in Formula I. In another embodiment of Formula (Is), $R^{102}$ is $R^{11}$, wherein $R^{11}$ is selected from pyrrolidinyl, oxazolyl, imidazolidinyl, isothiazolidinyl, piperidinyl, piperazinyl and azepanyl, wherein $R^{102}$ is substituted with one or two (O) substituents. In another embodiment of Formula (Is), $R^{102}$ is $R^{11}$, wherein $R^{11}$ is selected from pyrrolidinyl substituted with one or two (O) substituents. In another embodiment of Formula (Is), $R^{101}$, $R^{104}$ and $R^{105}$ are H, and $R^{102}$ is selected from $R^{11}$, $OR^{11}$, $NHC(O)R^{11}$, or $C(O)NHR^{11}$; wherein $R^{11}$ is as described in Formula I. In another embodiment of Formula (Is), wherein $R^{101}$, $R^{104}$ and $R^{105}$ are H, and $R^{102}$ is selected from $R^{11}$, $OR^{11}$, $NHC(O)R^{11}$, or $C(O)NHR^{11}$;

wherein $R^{11}$ is phenyl, pyrrolidinyl, azabicyclo(3.1.0)hexanyl, hexahydro-1H-isoindolyl, oxazolidinyl, azepanyl, piperidinyl, imidazolidinyl, thiazolidinyl, thiazinyl, azetidinyl, tetrahydropyrimidinyl, or azabicylo(2.2.1)hept-2-yl; each of which are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I wherein $R^{19}$ is as described in Formula I. In another embodiment of Formula (Is), wherein $R^{101}$, $R^{104}$ and $R^{105}$ are H, and $R^{102}$ is selected from $R^{11}$, $OR^{11}$, $NHC(O)R^{11}$, or $C(O)NHR^{11}$; wherein $R^{11}$ is $R^{15}$ and $R^{15}$ is alkyl which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl which is unsubstituted or substituted with $R^{18}$; $R^{17A}$ is phenyl, heteroaryl, cycloalkyl, heterocycloalkyl or heterocycloalkenyl each of which is unfused or fused with benzene or heterocycloalkane; $R^{18}$ is phenyl or heterocycloalkyl, which is unfused; wherein the moieties represented by $R^{12}$, $R^{13}$, $R^{14}$, $R^{17A}$, and $R^{18}$ are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I; wherein each $R^{19}$ is $R^{20}$, $R^{21}$, $R^{22}$ or $R^{21}$; $R^{20}$ is phenyl, which is unfused; $R^{21}$ is heteroaryl, which is unfused; $R^{22}$ is cycloalkyl or heterocycloalkyl; each of which is unfused or fused with benzene; and $R^{23}$ is alkyl which is unsubstituted or substituted with $R^{24}$, $OR^{24}$, $NHR^{24}N(R^4)_2$, $NHS(O)_2R^{24}$ or OH; wherein each $R^{24}$ is $R^{24A}$ or $R^{24B}$; $R^{24A}$ is phenyl, cycloalkyl, heterocycloalkyl or heterocycloalkenyl, which is unfused or fused with heterocycloalkane; $R^{24B}$ is alkyl, which is unsubstituted or substituted with $OR^{25}$, OH, F, Cl, Br or I; $R^{25}$ is alkyl, which is unsubstituted or substituted with $NH_2$; wherein the moieties represented by $R^{20}$, $R^{21}$, $R^{22}$, and $R^{24A}$ are independently unsubstituted or substituted with one or two of independently selected $R^{26}$, $OR^{26}$ (O), F, Cl, Br or I; and $R^{26}$ is alkyl.

In one embodiment, the compound of Formula (Is) is selected from:

2-fluoro-5-((4-oxo-3,4,5,6,7,8-hexahydrophthalazin-1-yl)methyl)benzoic acid;

4-(3-amino-4-fluorobenzyl)-5,6,7,8-tetrahydrophthalazin-1(2H)-one;

4-((2-fluoro-5-((4-oxo-3,4,5,6,7,8-hexahydrophthalazin-1-yl)methyl)phenyl)amino)-4-oxobutanoic acid;

1-(2-fluoro-5-((4-oxo-3,4,5,6,7,8-hexahydrophthalazin-1-yl)methyl)phenyl)pyrrolidine-2,5-dione;

4-(3-(1,4-diazepan-1-ylcarbonyl)-4-fluorobenzyl)-5,6,7,8-tetrahydrophthalazin-1(2H)-one;

4-(3-(aminomethyl)-4-fluorobenzyl)-5,6,7,8-tetrahydrophthalazin-1(2H)-one;

4-(3-((dimethylamino)methyl)-4-fluorobenzyl)-5,6,7,8-tetrahydrophthalazin-1(2H)-one;

4-(4-fluoro-3-((isopropylamino)methyl)benzyl)-5,6,7,8-tetrahydrophthalazin-1(2H)-one;

4-(3-((cyclohexylamino)methyl)-4-fluorobenzyl)-5,6,7,8-tetrahydrophthalazin-(2H)-one;

4-(4-fluoro-3-((tetrahydro-2H-pyran-4-ylamino)methyl)benzyl)-5,6,7,8-tetrahydrophthalazin-1(2H)-one;

4-(4-fluoro-3-((methyl((1-methylpyrrolidin-3-yl)methyl)amino)methyl)benzyl)-5,6,7,8-tetrahydrophthalazin-1(2H)-one;

4-(4-fluoro-3-((methyl(((2R)-1-methylpyrrolidin-2-yl)methyl)amino)methyl)benzyl)-5,6,7,8-tetrahydrophthalazin-1(2H)-one;

4-(4-fluoro-3-pyrimidin-2-ylbenzyl)-5,6,7,8-tetrahydrophthalazin-(2H)-one;

4-(4-fluoro-3-pyridin-3-ylbenzyl)-5,6,7,8-tetrahydrophthalazin-1(2H)-one;
4-(4-fluoro-3-pyridin-4-ylbenzyl)-5,6,7,8-tetrahydrophthalazin-1(2H)-one;
N,N-diethyl-2'-fluoro-5'-((4-oxo-3,4,5,6,7,8-hexahydrophthalazin-1-yl)methyl)-1,1'-biphenyl-2-carboxamide;
N-(2-fluoro-5-((4-oxo-3,4,5,6,7,8-hexahydrophthalazin-1-yl)methyl)phenyl)-3-piperidin-1-ylpropanamide;
N-(2-fluoro-5-((4-oxo-3,4,5,6,7,8-hexahydrophthalazin-1-yl)methyl)phenyl)-3-(4-methylpiperazin-1-yl)propanamide;
2-amino-N-(2-fluoro-5-((4-oxo-3,4,5,6,7,8-hexahydrophthalazin-1-yl)methyl)phenyl)acetamide;
3-cyclohexyl-N-(2-fluoro-5-((4-oxo-3,4,5,6,7,8-hexahydrophthalazin-1-yl)methyl)phenyl)propanamide;
N-(2-fluoro-5-((4-oxo-3,4,5,6,7,8-hexahydrophthalazin-1-yl)methyl)phenyl)piperidine-3-carboxamide;
4-(4-fluoro-3-(2-oxopyrrolidin-1-yl)benzyl)-5,6,7,8-tetrahydrophthalazin-1(2H)-one;
N-(2-fluoro-5-((4-oxo-3,4,5,6,7,8-hexahydrophthalazin-1-yl)methyl)phenyl)azetidine-3-carboxamide;
N-(2-fluoro-5-((4-oxo-3,4,5,6,7,8-hexahydrophthalazin-1-yl)methyl)phenyl)-2-morpholin-4-ylacetamide;
N-(2'-fluoro-5'-((4-oxo-3,4,5,6,7,8-hexahydrophthalazin-1-yl)methyl)-1,1'-biphenyl-3-yl)acetamide;
4-((6-fluoro-3'-(methylsulfonyl)-1,1'-biphenyl-3-yl)methyl)-5,6,7,8-tetrahydrophthalazin-1(2H)-one;
4-((6-fluoro-3'-(pyrrolidin-1-ylcarbonyl)-1,1'-biphenyl-3-yl)methyl)-5,6,7,8-tetrahydrophthalazin-1(2H)-one;
4-((6-fluoro-4'-(pyrrolidin-1-ylcarbonyl)-1,1'-biphenyl-3-yl)methyl)-5,6,7,8-tetrahydrophthalazin-1(2H)-one;
N,N-diethyl-2'-fluoro-5'-((4-oxo-3,4,5,6,7,8-hexahydrophthalazin-1-yl)methyl)-1,1'-biphenyl-3-carboxamide;
2'-fluoro-N,N-dimethyl-5'-((4-oxo-3,4,5,6,7,8-hexahydrophthalazin-1-yl)methyl)-1,1'-biphenyl-4-carboxamide;
N-(2-fluoro-5-((4-oxo-3,4,5,6,7,8-hexahydrophthalazin-1-yl)methyl)phenyl)-4-(4-methoxyphenyl)-4-oxobutanamide;
1-(2-fluoro-5-((4-oxo-3,4,5,6,7,8-hexahydrophthalazin-1-yl)methyl)phenyl)-3,4-dimethyl-1H-pyrrole-2,5-dione;
3-(2-fluoro-5-((4-oxo-3,4,5,6,7,8-hexahydrophthalazin-1-yl)methyl)phenyl)-3-azabicyclo(3.1.0)hexane-2,4-dione;
2-(2-fluoro-5-((4-oxo-3,4,5,6,7,8-hexahydrophthalazin-1-yl)methyl)phenyl)hexahydro-1H-isoindole-1,3(2H)-dione;
1-(2-fluoro-5-((4-oxo-3,4,5,6,7,8-hexahydrophthalazin-1-yl)methyl)phenyl)-3,3-dimethylpyrrolidine-2,5-dione;
4-(4-fluoro-3-(2-methyl-5-oxopyrrolidin-1-yl)benzyl)-5,6,7,8-tetrahydrophthalazin-1(2H)-one;
4-(4-fluoro-3-(2-oxo-1,3-oxazolidin-3-yl)benzyl)-5,6,7,8-tetrahydrophthalazin-1(2H)-one;
4-(4-fluoro-3-(2-oxoazepan-1-yl)benzyl)-5,6,7,8-tetrahydrophthalazin-1(2H)-one;
1-(2-fluoro-5-((4-oxo-3,4,5,6,7,8-hexahydrophthalazin-1-yl)methyl)phenyl)piperidine-2,6-dione;
4-(4-fluoro-3-(2-oxoimidazolidin-1-yl)benzyl)-5,6,7,8-tetrahydrophthalazin-1(2H)-one;
4-(3-(1,1-dioxidoisothiazolidin-2-yl)-4-fluorobenzyl)-5,6,7,8-tetrahydrophthalazin-1(2H)-one;
4-(4-fluoro-3-(2-oxoazetidin-1-yl)benzyl)-5,6,7,8-tetrahydrophthalazin-1(2H)-one;
4-(4-fluoro-3-(2-oxopiperidin-1-yl)benzyl)-5,6,7,8-tetrahydrophthalazin-1(2H)-one;
4-(4-fluoro-3-(3-methyl-2-oxoimidazolidin-1-yl)benzyl)-5,6,7,8-tetrahydrophthalazin-1(2H)-one;
4-(4-fluoro-3-(2-oxotetrahydropyrimidin-1(2H)-yl)benzyl)-5,6,7,8-tetrahydrophthalazin-1(2H)-one;
4-(3-(3-tert-butyl-2-oxoimidazolidin-1-yl)-4-fluorobenzyl)-5,6,7,8-tetrahydrophthalazin-1(2H)-one;
4-(4-fluoro-3-((1S,4R)-3-oxo-2-azabicyclo(2.2.1)hept-2-yl)benzyl)-5,6,7,8-tetrahydrophthalazin-1(2H)-one;
N-(2-fluoro-5-((4-oxo-3,4,5,6,7,8-hexahydrophthalazin-1-yl)methyl)phenyl)-N-methylmethanesulfonamide;
N-(2-fluoro-5-((4-oxo-3,4,5,6,7,8-hexahydrophthalazin-1-yl)methyl)phenyl)-2-hydroxy-2-methylpropanamide;
(3aS,4R,7S,7aR)-5-(2-fluoro-5-((4-oxo-3,4,5,6,7,8-hexahydrophthalazin-1-yl)methyl)phenyl)-2,2-dimethyltetrahydro-4,7-methano(1,3)dioxolo(4,5-c)pyridin-6(3aH)-one;
4-(3-(1,1-dioxido-1,2-thiazinan-2-yl)-4-fluorobenzyl)-5,6,7,8-tetrahydrophthalazin-1(2H)-one;
N-(2-fluoro-5-((4-oxo-3,4,5,6,7,8-hexahydrophthalazin-1-yl)methyl)phenyl)-2-(2-oxopyrrolidin-1-yl)acetamide;
N-(2-fluoro-5-((4-oxo-3,4,5,6,7,8-hexahydrophthalazin-1-yl)methyl)phenyl)-5-methyl-1-phenyl-1H-pyrazole-4-carb oxamide;
N-(2-fluoro-5-((4-oxo-3,4,5,6,7,8-hexahydrophthalazin-1-yl)methyl)phenyl)-5-oxohexanamide;
N-(2-fluoro-5-((4-oxo-3,4,5,6,7,8-hexahydrophthalazin-1-yl)methyl)phenyl)-3-methoxypropanamide;
N-(2-fluoro-5-((4-oxo-3,4,5,6,7,8-hexahydrophthalazin-1-yl)methyl)phenyl)-N'-phenylpentanediamide;
4-(4-fluoro-3-((4-pyrimidin-2-ylpiperazin-1-yl)carbonyl)benzyl)-5,6,7,8-tetrahydrophthalazin-1(2H)-one;
4-(4-fluoro-3-(2-oxopyrrolidin-1-yl)phenyl)-5,6,7,8-tetrahydrophthalazin-1(2H)-one;
4-(3-{[4-(cyclopropylcarbonyl)piperazin-1-yl]carbonyl}-4-fluorobenzyl)-5,6,7,8-tetrahydrophthalazin-1(2H)-one;
4-{2-fluoro-5-[(4-oxo-3,4,5,6,7,8-hexahydrophthalazin-1-yl)methyl]benzoyl}-N-dimethylpiperazine-11-carboxamide;
4-(4-fluoro-3-{[4-(piperazin-1-ylcarbonyl)piperazin-1-yl]carbonyl}benzyl)-5,6,7,8-tetrahydrophthalazin-1(2H)-one;
4-{4-fluoro-3-[(4-pyrazin-2-ylpiperazin-1-yl)carbonyl]benzyl}-5,6,7,8-tetrahydrophthalazin-1(2H)-one;
4-{4-fluoro-3-[(4-pyridin-4-ylpiperazin-1-yl)carbonyl]benzyl}-5,6,7,8-tetrahydrophthalazin-1(2H)-one;
1-{2-fluoro-5-[(4-oxo-3,4,5,6,7,8-hexahydrophthalazin-1-yl)methyl]benzoyl}piperidine-4-carboxamide;
4-(4-fluoro-3-{[4-(6-methylpyrazin-2-yl)piperazin-1-yl]carbonyl}benzyl)-5,6,7,8-tetrahydrophthalazin-1(2H)-one;
1-{2-fluoro-5-[(4-oxo-3,4,5,6,7,8-hexahydrophthalazin-1-yl)methyl]benzoyl}piperidine-3-carboxamide;
4-[3-({4-[2-(dimethylamino)ethyl]piperazin-1-yl}carbonyl)-4-fluorobenzyl]-5,6,7,8-tetrahydrophthalazin-1(2H)-one;
4-{4-fluoro-3-[(4-methyl-1,4-diazepan-1-yl)carbonyl]benzyl}-5,6,7,8-tetrahydrophthalazin-1(2H)-one;
4-{4-fluoro-3-[(4-hydroxypiperidin-1-yl)carbonyl]benzyl}-5,6,7,8-tetrahydrophthalazin-1(2H)-one;
N-[2-(dimethylamino)ethyl]-2-fluoro-N-methyl-5-[(4-oxo-3,4,5,6,7,8-hexahydrophthalazin-1-yl)methyl]benzamide;
N,N-diethyl-1-{2-fluoro-5-[(4-oxo-3,4,5,6,7,8-hexahydrophthalazin-1-yl)methyl]benzoyl}piperidine-3-carboxamide;
4-(3-{[4-(3-chlorobenzyl)piperazin-1-yl]carbonyl}-4-fluorobenzyl)-5,6,7,8-tetrahydrophthalazin-1(2H)-one;
4-{4-fluoro-3-[(4-phenylpiperazin-1-yl)carbonyl]benzyl}-5,6,7,8-tetrahydrophthalazin-1(2H)-one;
4({[4-(2-chlorophenyl)piperazin-1-yl]carbonyl}-4-fluorobenzyl)-5,6,7,8-tetrahydrophthalazin-1(2H)-one;
4-(3-{[4-(2-chlorophenyl)piperazin-1-yl]carbonyl}-4-fluorobenzyl)-5,6,7,8-tetrahydrophthalazin-1(2H)-one;

4-{3-[(4-acetylpiperazin-1-yl)carbonyl]-4-fluorobenzyl}-5,6,7,8-tetrahydrophthalazin-1(2H)-one;
4-(4-fluoro-3-{[4-(2-furoyl)piperazin-1-yl]carbonyl}benzyl)-5,6,7,8-tetrahydrophthalazin-1(2H)-one;
4-(4-fluoro-3-{[4-(2-fluorophenyl)piperazin-1-yl]carbonyl}benzyl)-5,6,7,8-tetrahydrophthalazin-1(2H)-one;
4-(3-{[4-(2,4-difluorophenyl)piperazin-1-yl]carbonyl}-4-fluorobenzyl)-5,6,7,8-tetrahydrophthalazin-1(2H)-one;
4-{3-[(4-benzoylpiperazin-1-yl)carbonyl]-4-fluorobenzyl}-5,6,7,8-tetrahydrophthalazin-1(2H)-one;
4-(4-fluoro-3-{[4-(3-fluorophenyl)piperazin-1-yl]carbonyl}benzyl)-5,6,7,8-tetrahydrophthalazin-1(2H)-one;
4-(4-fluoro-3-{[4-(4-fluorophenyl)piperazin-1-yl]carbonyl}benzyl)-5,6,7,8-tetrahydrophthalazin-1(2H)-one;
4-{4-fluoro-3-[(4-pyridin-2-ylpiperazin-1-yl)carbonyl]benzyl}-5,6,7,8-tetrahydrophthalazin-1(2H)-one;
N,N-diethyl-4-{2-fluoro-5-[(4-oxo-3,4,5,6,7,8-hexahydrophthalazin-1-yl)methyl]benzoyl}piperazine-1-carboxamide;
4-{4-fluoro-3-[(4-isopropylpiperazin-1-yl)carbonyl]benzyl}-5,6,7,8-tetrahydrophthalazin-1(2H)-one;
4-(4-fluoro-3-{[4-(morpholin-4-ylcarbonyl)piperazin-1-yl]carbonyl}benzyl)-5,6,7,8-tetrahydrophthalazin-1(2H)-one;
4-(4-fluoro-3-{[4-(2-oxo-2-pyrrolidin-1-ylethyl)piperazin-1-yl]carbonyl}benzyl)-5,6,7,8-tetrahydrophthalazin-1(2H)-one;
N-{2-fluoro-5-[(4-oxo-3,4,5,6,7,8-hexahydrophthalazin-1-yl)methyl]phenyl}-N'-isopropylurea;
N-{2-fluoro-5-[(4-oxo-3,4,5,6,7,8-hexahydrophthalazin-1-yl)methyl]phenyl}-N'-propylurea;
N-cyclopentyl-N'-{2-fluoro-5-[(4-oxo-3,4,5,6,7,8-hexahydrophthalazin-1-yl)methyl]phenyl}urea;
N-(2,4-difluorophenyl)-N'-{2-fluoro-5-[(4-oxo-3,4,5,6,7,8-hexahydrophthalazin-1-yl)methyl]phenyl}urea;
N-(tert-butyl)-N'-{2-fluoro-5-[(4-oxo-3,4,5,6,7,8-hexahydrophthalazin-1-yl)methyl]phenyl}urea;
benzyl 4-{2-fluoro-5-[(4-oxo-3,4,5,6,7,8-hexahydrophthalazin-1-yl)methyl]benzoyl}piperazine-1-carboxylate;
benzyl 4-{2-fluoro-5-[(4-oxo-3,4,5,6,7,8-hexahydrophthalazin-1-yl)methyl]benzoyl}-1,4-diazepane-1-carboxylate;
4-(4-fluoro-3-{[4-(2-morpholin-4-ylethyl)piperazin-1-yl]carbonyl}benzyl)-5,6,7,8-tetrahydrophthalazin-1(2H)-one;
4-(4-fluoro-3-{[4-(2-phenylsulfonyl)piperazin-1-yl]carbonyl}benzyl)-5,6,7,8-tetrahydrophthalazin-1(2H)-one;
4-{3-[(4-cyclopentylpiperazin-1-yl)carbonyl]-4-fluorobenzyl}-5,6,7,8-tetrahydrophthalazin-1(2H)-one;
4-(4-fluoro-3-{[4-(pyrrolidin-1-ylcarbonyl)piperazin-1-yl]carbonyl}benzyl)-5,6,7,8-tetrahydrophthalazin-1(2H)-one;
4-(4-fluoro-3-{[4-(2-phenoxyethyl)piperazin-1-yl]carbonyl}benzyl)-5,6,7,8-tetrahydrophthalazin-1(2H)-one;
2-fluoro-N-[2-(4-methylpiperazin-1-yl)ethyl]-5-[(4-oxo-3,4,5,6,7,8-hexahydrophthalazin-1-yl)methyl]benzamide;
4-{4-fluoro-3-[(4-isobutyrylpiperazin-1-yl)carbonyl]benzyl}-5,6,7,8-tetrahydrophthalazin-1(2H)-one;
4-{3-[(4-ethylpiperazin-1-yl)carbonyl]-4-fluorobenzyl}-5,6,7,8-tetrahydrophthalazin-1(2H)-one;
benzyl (3S)-1-{2-fluoro-5-[(4-oxo-3,4,5,6,7,8-hexahydrophthalazin-1-yl)methyl]phenyl}-2,5-dioxopyrrolidin-3-ylcarbamate;
(3S)-3-amino-1-{2-fluoro-5-[(4-oxo-3,4,5,6,7,8-hexahydrophthalazin-1-yl)methyl]phenyl}pyrrolidine-2,5-dione;
N-{2-fluoro-5-[(4-oxo-3,4,5,6,7,8-hexahydrophthalazin-1-yl)methyl]phenyl}-4-methylpiperazine-1-carboxamide;
4-{4-fluoro-3-[(4-propionylpiperazin-1-yl)carbonyl]benzyl}-5,6,7,8-tetrahydrophthalazin-1(2H)-one;
4-(3-{[4-(ethylsulfonyl)piperazin-1-yl]carbonyl}-4-fluorobenzyl)-5,6,7,8-tetrahydrophthalazin-1(2H)-one;
4-(3-{[4-(2,2-dimethylpropanoyl)piperazin-1-yl]carbonyl}-4-fluorobenzyl)-5,6,7,8-tetrahydrophthalazin-1(2H)-one;
4-(4-fluoro-3-{[4-(phenoxyacetyl)piperazin-1-yl]carbonyl}benzyl)-5,6,7,8-tetrahydrophthalazin-1(2H)-one;
N'-{2-fluoro-5-[(4-oxo-3,4,5,6,7,8-hexahydrophthalazin-1-yl)methyl]phenyl})—N-methyl-N-phenylurea;
N-ethyl-N-(1-{2-fluoro-5-[(4-oxo-3,4,5,6,7,8-hexahydrophthalazin-1-yl)methyl]benzoyl}pyrrolidin-3-yl)acetamide;
4-[4-fluoro-3-({4-[(4-methoxyphenyl)sulfonyl]piperazin-1-yl}carbonyl)benzyl]-5,6,7,8-tetrahydrophthalazin-1(2H)-one;
4-[4-fluoro-3-({4-[3-(trifluoromethyl)phenyl]piperazin-1-yl}carbonyl)benzyl]-5,6,7,8-tetrahydrophthalazin-1(2H)-one;
4-(4-fluoro-3-{[4-(4-methoxybenzoyl)piperazin-1-yl]carbonyl}benzyl)-5,6,7,8-tetrahydrophthalazin-1(2H)-one;
4-(4-fluoro-3-{[4-(4-methoxyphenyl)piperazin-1-yl]carbonyl}benzyl)-5,6,7,8-tetrahydrophthalazin-1(2H)-one;
4-(3-{[4-(cyclohexylcarbonyl)piperazin-1-yl]carbonyl}-4-fluorobenzyl)-5,6,7,8-tetrahydrophthalazin-1(2H)-one;
N-[({2-fluoro-5-[(4-oxo-3,4,5,6,7,8-hexahydrophthalazin-1-yl)methyl]phenyl}amino)carbonyl]glycine;
N-[({2-fluoro-5-[(4-oxo-3,4,5,6,7,8-hexahydrophthalazin-1-yl)methyl]phenyl}amino)carbonyl]leucine;
N-[({2-fluoro-5-[(4-oxo-3,4,5,6,7,8-hexahydrophthalazin-1-yl)methyl]phenyl}amino)carbonyl]alanine;
N-[({2-fluoro-5-[(4-oxo-3,4,5,6,7,8-hexahydrophthalazin-1-yl)methyl]phenyl}amino)carbonyl]phenylalanine;
3-{2-fluoro-5-[(4-oxo-3,4,5,6,7,8-hexahydrophthalazin-1-yl)methyl]phenyl}imidazolidine-2,4-dione;
4(3-{[4-(cyclopropylcarbonyl)-1,4-diazepan-1-yl]carbonyl}-4-fluorobenzyl)-5,6,7,8-tetrahydrophthalazin-1(2H)-one;
4-[4-fluoro-3-({4-[(1-methylcyclopropyl)carbonyl]-1,4-diazepan-1-yl}carbonyl)benzyl]-5,6,7,8-tetrahydrophthalazin-1(2H)-one;
4-[4-fluoro-3-({4-[(1-methyl-1H-imidazol-4-yl)carbonyl]-1,4-diazepan-1-yl}carbonyl)benzyl]-5,6,7,8-tetrahydrophthalazin-1(2H)-one;
4-[4-fluoro-3-({4-[(1-methyl-1H-imidazol-5-yl)carbonyl]-1,4-diazepan-1-yl}carbonyl)benzyl]-5,6,7,8-tetrahydrophthalazin-1(2H)-one;
4-(3-{[(2R)-4-benzoyl-2-methylpiperazin-1-yl]carbonyl}-4-fluorobenzyl)-5,6,7,8-tetrahydrophthalazin-1(2H)-one;
4-(4-fluoro-3-{[4-(1,3,5-triazin-2-yl)piperazin-1-yl]carbonyl}benzyl)-5,6,7,8-tetrahydrophthalazin-1(2H)-one;
5-benzyl-3-{2-fluoro-5-[(4-oxo-3,4,5,6,7,8-hexahydrophthalazin-1-yl)methyl]phenyl}imidazolidine-2,4-dione;
4-[3-({4-[(6-chloropyridin-3-yl)carbonyl]piperazin-1-yl}carbonyl)-4-fluorobenzyl]-5,6,7,8-tetrahydrophthalazin-1(2H)-one;

4-(4-fluoro-3-{[4-(1,3-thiazol-4-ylcarbonyl)piperazin-1-yl]carbonyl}benzyl)-5,6,7,8-tetrahydrophthalazin-1(2H)-one;

4-[4-fluoro-3-({4-[(5-oxopyrrolidin-2-yl)carbonyl]piperazin-1-yl}carbonyl)benzyl]-5,6,7,8-tetrahydrophthalazin-1(2H)-one;

4-{3-[(4-{[(4R)-5,5-dimethyl-1,3-thiazolidin-4-yl]carbonyl}piperazin-1-yl)carbonyl]-4-fluorobenzyl}-5,6,7,8-tetrahydrophthalazin-1(2H)-one;

4-(4-fluoro-3-{[4-(1H-pyrazol-3-ylcarbonyl)piperazin-1-yl]carbonyl}benzyl)-5,6,7,8-tetrahydrophthalazin-1(2H)-one;

4-(4-fluoro-3-{[4-(pyrazin-2-ylcarbonyl)piperazin-1-yl]carbonyl}benzyl)-5,6,7,8-tetrahydrophthalazin-1(2H)-one;

4-(3-{[4(1H-benzimidazol-5-ylcarbonyl)piperazin-1-yl]carbonyl}-4-fluorobenzyl)-5,6,7,8-tetrahydrophthalazin-1(2H)-one;

4-[4-fluoro-3-(methylamino)benzyl]-5,6,7,8-tetrahydrophthalazin-1(2H)-one;

tert-butyl 2-(ethyl {2-fluoro-5-[(4-oxo-3,4,5,6,7,8-hexahydrophthalazin-1-yl)methyl]benzoyl}amino)ethylcarbamate;

2-fluoro-5-[(4-oxo-3,4,5,6,7,8-hexahydrophthalazin-1-yl)methyl]-N-[2-(2-oxopyrrolidin-1-yl)ethyl]benzamide;

N-(2-aminoethyl)-N-ethyl-2-fluoro-5-[(4-oxo-3,4,5,6,7,8-hexahydrophthalazin-1-yl)methyl]benzamide;

4-{4-fluoro-3-[(4-isonicotinoylpiperazin-1-yl)carbonyl]benzyl}-5,6,7,8-tetrahydrophthalazin-1(2H)-one;

2-fluoro-N-methyl-5-[(5-oxo-1,2,3,4,5,6-hexahydropyrido[2,3-d]pyridazin-8-yl)methyl]-N-[1-(pyridin-2-ylcarbonyl)piperidin-4-yl]benzamide;

4-(4-fluoro-3-{[4-(pyridin-3-ylcarbonyl)piperazin-1-yl]carbonyl}benzyl)-5,6,7,8-tetrahydrophthalazin-1(2H)-one;

4-[3-({4-[(5-chloro-6-hydroxypyridin-3-yl)carbonyl]piperazin-1-yl}carbonyl)-4-fluorobenzyl]-5,6,7,8-tetrahydrophthalazin-1(2H)-one;

4-{4-fluoro-3-[(4-([1-isopropyl-2-(trifluoromethyl)-1H-benzimidazol-5-yl]carbonyl)piperazin-1-yl)carbonyl]benzyl}-5,6,7,8-tetrahydrophthalazin-1(2H)-one;

4-[4-fluoro-3-({4-[(4R)-1,3-thiazolidin-4-ylcarbonyl]piperazin-1-yl}carbonyl)benzyl]-5,6,7,8-tetrahydrophthalazin-1(2H)-one;

4-[4-fluoro-3-({4-[(1-isopropyl-1H-1,2,3-benzotriazol-5-yl)carbonyl]piperazin-1-yl}carbonyl)benzyl]-5,6,7,8-tetrahydrophthalazin-1(2H)-one;

4-(4-fluoro-3-{[4-(pyridin-2-ylcarbonyl)piperazin-1-yl]carbonyl}benzyl)-5,6,7,8-tetrahydrophthalazin-1(2H)-one;

4-(4-fluoro-3-{[4-(pyrimidin-5-ylcarbonyl)piperazin-1-yl]carbonyl}benzyl)-5,6,7,8-tetrahydrophthalazin-1(2H)-one;

4-[4-fluoro-3-({4-[(6-hydroxypyridin-3-yl)carbonyl]piperazin-1-yl}carbonyl)benzyl]-5,6,7,8-tetrahydrophthalazin-1(2H)-one;

4-(4-fluoro-3-{[4-(quinolin-2-ylcarbonyl)piperazin-1-yl]carbonyl}benzyl)-5,6,7,8-tetrahydrophthalazin-1(2H)-one;

N-[2-(benzoylamino)ethyl]-N-ethyl-2-fluoro-5-[(4-oxo-3,4,5,6,7,8-hexahydrophthalazin-1-yl)methyl]benzamide;

N-[2-(ethyl {2-fluoro-5-[(4-oxo-3,4,5,6,7,8-hexahydrophthalazin-1-yl)benzoyl}amino)ethyl]pyrrolidine-1-carboxamide;

N-{2-fluoro-5-[(4-oxo-3,4,5,6,7,8-hexahydrophthalazin-1-yl)methyl]phenyl}-N-methylcyclobutanecarboxamide;

4-[4-fluoro-3-({4-[(2-methyl-1H-benzimidazol-5-yl)carbonyl]piperazin-1-yl}carbonyl)benzyl]-5,6,7,8-tetrahydrophthalazin-1(2H)-one;

4-[3-({4-[(2-chloropyridin-3-yl)carbonyl]piperazin-1-yl}carbonyl)-4-fluorobenzyl]-5,6,7,8-tetrahydrophthalazin-1(2H)-one;

4-{4-fluoro-3-[(4-pyridin-3-ylpiperazin-1-yl)carbonyl]benzyl}-5,6,7,8-tetrahydrophthalazin-1(2H)-one;

4-{4-fluoro-3-[(4-pyrimidin-5-ylpiperazin-1-yl)carbonyl]benzyl}-5,6,7,8-tetrahydrophthalazin-1(2H)-one;

4-{4-fluoro-3-[(4-methyl-3-oxopiperazin-1-yl)carbonyl]benzyl}-5,6,7,8-tetrahydrophthalazin-1(2H)-one;

N-{2-[(cyclopropylcarbonyl)amino]ethyl}-N-ethyl-2-fluoro-5-[(4-oxo-3,4,5,6,7,8-hexahydrophthalazin-1-yl)methyl]benzamide;

N-{2-[(2,6-difluorobenzoyl)amino]ethyl}-N-ethyl-2-fluoro-5-[(4-oxo-3,4,5,6,7,8-hexahydrophthalazin-1-yl)methyl]benzamide; or N-[2-(ethyl{2-fluoro-5-[(4-oxo-3,4,5,6,7,8-hexahydrophthalazin-1-yl)methyl]benzoyl}amino)ethyl]nicotinamide.

In another embodiment, the compound of Formula (Is) is selected from 4-((2-fluoro-5-((4-oxo-3,4,5,6,7,8-hexahydrophthalazin-1-yl)methyl)phenyl)amino)-4-oxobutanoic acid;

1-(2-fluoro-5-((4-oxo-3,4,5,6,7,8-hexahydrophthalazin-1-yl)methyl)phenyl)pyrrolidine-2,5-dione;

4-(4-fluoro-3-(2-oxopyrrolidin-1-yl)benzyl)-5,6,7,8-tetrahydrophthalazin-1(2H)-one;

N-(2-fluoro-5-((4-oxo-3,4,5,6,7,8-hexahydrophthalazin-1-yl)methyl)phenyl)-3-(4-methylpiperazin-1-yl)propanamide;

3-(2-fluoro-5-((4-oxo-3,4,5,6,7,8-hexahydrophthalazin-1-yl)methyl)phenyl)-3-azabicyclo(3.1.0)hexane-2,4-dione;

1-(2-fluoro-5-((4-oxo-3,4,5,6,7,8-hexahydrophthalazin-1-yl)methyl)phenyl)-3,3-dimethylpyrrolidine-2,5-dione;

4-(4-fluoro-3-(2-oxo-1,3-oxazolidin-3-yl)benzyl)-5,6,7,8-tetrahydrophthalazin-1(2H)-one;

4-(4-fluoro-3-(3-methyl-2-oxoimidazolidin-1-yl)benzyl)-5,6,7,8-tetrahydrophthalazin-1(2H)-one;

4-(4-fluoro-3-(2-oxoazepan-1-yl)benzyl)-5,6,7,8-tetrahydrophthalazin-1(2H)-one;

1-(2-fluoro-5-((4-oxo-3,4,5,6,7,8-hexahydrophthalazin-1-yl)methyl)phenyl)piperidine-2,6-dione;

4-(3-(1,1-dioxidoisothiazolidin-2-yl)-4-fluorobenzyl)-5,6,7,8-tetrahydrophthalazin-1(2H)-one;

4-(4-fluoro-3-(2-oxopiperidin-1-yl)benzyl)-5,6,7,8-tetrahydrophthalazin-1(2H)-one;

4-(4-fluoro-3-((4-pyrimidin-2-ylpiperazin-1-yl)carbonyl)benzyl)-5,6,7,8-tetrahydrophthalazin-1(2H)-one;

benzyl (3S)-1-{2-fluoro-5-[(4-oxo-3,4,5,6,7,8-hexahydrophthalazin-1-yl)methyl]phenyl}-2,5-dioxopyrrolidin-3-ylcarbamate;

(3S)-3-amino-1-{2-fluoro-5-[(4-oxo-3,4,5,6,7,8-hexahydrophthalazin-1-yl)methyl]phenyl}pyrrolidine-2,5-dione;

N-{2-fluoro-5-[(4-oxo-3,4,5,6,7,8-hexahydrophthalazin-1-yl)methyl]phenyl}-4-methylpiperazine-1-carboxamide;

3-{2-fluoro-5-[(4-oxo-3,4,5,6,7,8-hexahydrophthalazin-1-yl)methyl]phenyl}imidazolidine-2,4-dione;

5-benzyl-3-{2-fluoro-5-[(4-oxo-3,4,5,6,7,8-hexahydrophthalazin-1-yl)methyl]phenyl}imidazolidine-2,4-dione; or N-{2-fluoro-5-[(4-oxo-3,4,5,6,7,8-hexahydrophthalazin-1-yl)methyl]phenyl}-N-methylcyclobutanecarboxamide.

In one embodiment of Formula (Ik), $R^{102}$ is $C(O)R^{11}$, as described in Formula (It):

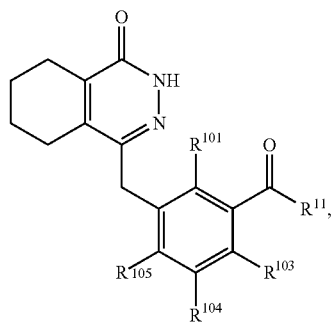

(It)

wherein $R^{11}$ is as described in Formula I. In one embodiment of Formula (It), $R^{101}$, $R^{103}$, $R^{104}$ and $R^{105}$ are H. In another embodiment of Formula (It), $R^{103}$ is F and $R^{101}$, $R^{104}$ and $R^{105}$ are H. In another embodiment of Formula (It), $R^{11}$ is $R^{15}$ and $R^{15}$ is alkyl which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl which is unsubstituted or substituted with $R^{18}$; $R^{17A}$ is phenyl, heteroaryl, cycloalkyl, heterocycloalkyl or heterocycloalkenyl, each of which is unfused or fused with benzene or heterocycloalkane; $R^{18}$ is phenyl or heterocycloalkyl, which is unfused; wherein the moieties represented by $R^{12}$, $R^{13}$, $R^{14}$, $R^{17A}$, and $R^{18}$ are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I; wherein each $R^{19}$ is $R^{20}$, $R^{21}$, $R^{22}$ or $R^{23}$; $R^{20}$ is phenyl, which is unfused; $R^{21}$ is heteroaryl, which is unfused; $R^{22}$ is cycloalkyl or heterocycloalkyl; each of which is unfused or fused with benzene; and $R^{23}$ is alkyl which is unsubstituted or substituted with $R^{24}$, $OR^{24}$, $NHR^{24}N(R^{24})_2$, $NHS(O)_2R^{24}$ or OH; wherein each $R^{24}$ is $R^{24A}$ or $R^{24B}$; $R^{24A}$ is phenyl, cycloalkyl, heterocycloalkyl or heterocycloalkenyl, which is unfused or fused with heterocycloalkane; $R^{24B}$ is alkyl, which is unsubstituted or substituted with $OR^{25}$, OH, F, Cl, Br or I; $R^{15}$ is alkyl, which is unsubstituted or substituted with $NH_2$; wherein the moieties represented by $R^{20}$, $R^{21}$, $R^{22}$, and $R^{24A}$ are independently unsubstituted or substituted with one or two of independently selected $R^{26}$, $OR^{26}$ (O), F, Cl, Br or I; and $R^{26}$ is alkyl. In another embodiment of Formula (It), $R^{11}$ is phenyl, pyrrolidinyl, azabicyclo(3.1.0)hexanyl, hexahydro-1H-isoindolyl, oxazolidinyl, azepanyl, piperidinyl, imidazolidinyl, thiazolidinyl, thiazinyl, azetidinyl, tetrahydropyrimidinyl, or azabicylo(2.2.1)hept-2-yl; each of which are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I wherein $R^{19}$ is as described in Formula I.

In one embodiment of Formula (Ik), $R^{102}$ is $C(O)NHR^{11}$, as described in Formula (Iu):

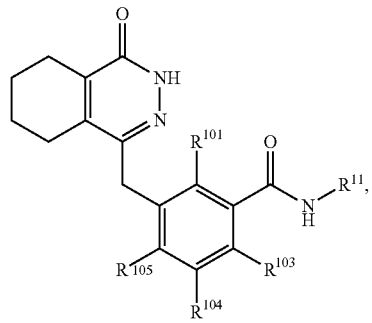

(Iu)

wherein $R^{11}$ is as described in Formula I. In one embodiment of Formula (Iu), $R^{101}$, $R^{103}$, $R^{104}$ and $R^{105}$ are H. In another embodiment of Formula (Iu), $R^{103}$ is F and $R^{101}$, $R^{104}$ and $R^{105}$ are H. In another embodiment of Formula (Iu), $R^{11}$ is $R^{15}$ and $R^{15}$ is alkyl which is unsubstituted or substituted with one or two of independently selected $R^{16}$, $OR^{16}$, $SR^{16}$, $S(O)_2R^{16}$, $C(O)OH$, $NH_2$, $NHR^{16}N(R^{16})_2$, $C(O)R^{16}$, $C(O)NHR^{16}$, $NHC(O)R^{16}$, $NHC(O)OR^{16}$, OH, F, Cl, Br or I; wherein each $R^{16}$ is $R^{17}$ or $R^{17A}$; $R^{17}$ is alkyl which is unsubstituted or substituted with $R^{18}$; $R^{17A}$ is phenyl, heteroaryl, cycloalkyl, heterocycloalkyl or heterocycloalkenyl, each of which is unfused or fused with benzene or heterocycloalkane; $R^{18}$ is phenyl or heterocycloalkyl, which is unfused; wherein the moieties represented by $R^{12}$, $R^{13}$, $R^{14}$, $R^{17A}$, and $R^{18}$ are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I; wherein each $R^{19}$ is $R^{20}$, $R^{21}$, $R^{22}$ or $R^{23}$; $R^{20}$ is phenyl, which is unfused; $R^{21}$ is heteroaryl, which is unfused; $R^{22}$ is cycloalkyl or heterocycloalkyl; each of which is unfused or fused with benzene; and $R^{23}$ is alkyl which is unsubstituted or substituted with $R^{24}$, $OR^{24}$, $NHR^{24}N(R^{24})_2$, $NHS(O)_2R^{24}$ or OH; wherein each $R^{24}$ is $R^{24A}$ or $R^{24B}$; $R^{24A}$ is phenyl, cycloalkyl, heterocycloalkyl or heterocycloalkenyl, which is unfused or fused with heterocycloalkane; $R^{24B}$ is alkyl, which is unsubstituted or substituted with $OR^{25}$, OH, F, Cl, Br or I; $R^{25}$ is alkyl, which is unsubstituted or substituted with $NH_2$; wherein the moieties represented by $R^{20}$, $R^{21}$, $R^{22}$, and $R^{24A}$ are independently unsubstituted or substituted with one or two of independently selected $R^{26}$, $OR^{26}$ (O), F, Cl, Br or I; and $R^{26}$ is alkyl. In another embodiment of Formula (Iu), $R^{11}$ is phenyl, pyrrolidinyl, azabicyclo(3.1.0)hexanyl, hexahydro-1H-isoindolyl, oxazolidinyl, azepanyl, piperidinyl, imidazolidinyl, thiazolidinyl, thiazinyl, azetidinyl, tetrahydropyrimidinyl, or azabicylo(2.2.1)hept-2-yl; each of which are independently unsubstituted or substituted with one or two of independently selected $R^{19}$, $OR^{19}$, $SR^{19}$, $SO_2R^{19}$, $C(O)R^{19}$, $CO(O)R^{19}$, $NHR^{19}$, $N(R^{19})_2$, $NHC(O)R^{19}$, $NHS(O)_2R^{19}$, $C(O)NH_2$, $C(O)NHR^{19}$, $C(O)N(R^{19})_2$, $C(O)H$, OH, (O), CN, $CF_3$, F, Cl, Br or I wherein $R^{19}$ is as described in Formula I.

In one embodiment of Formula (Ik), $R^{102}$ is phenyl which is unsubstituted or substituted with one or two or three or four of independently selected $R^{19}$, $OR^{19}$, $SR^{19}$, $S(O)R^{19}$, $SO_2R^{19}$, $C(O)R^{19}$, $CO(O)R^{19}$, $OC(O)R^{19}$, $OC(O)OR^{19}$, $NH_2$, $NHR^{19}$, $N(R^{19})_2$, $NHC(O)R^{19}$, $NR^{19}C(O)R^{19}$, $NHS(O)_2R^{19}$, $NR^{19}S(O)_2R^{19}$, $NHC(O)OR^{19}$, $NR^{19}C(O)$ OR$^{19}$, NHC(O)NH$_2$, NHC(O)NHR$^{19}$, NHC(O)N(R$^{19}$)$_2$, NR$^{19}$C(O)NHR$^{19}$, NR$^{19}$C(O)N(R$^{19}$)$_2$, C(O)NH$_2$, C(O)NHR$^{19}$, C(O)N(R$^{19}$)$_2$, C(O)NHOH, C(O)NHOR$^{19}$, C(O)NHSO$_2$R$^{19}$, C(O)NR$^{19}$SO$_2$R$^{19}$, SO$_2$NH$_2$, SO$_2$NHR$^{19}$, SO$_2$N(R$^{19}$)$_2$, C(O)H, C(O)OH, C(N)NH$_2$, C(N)NHR$^{19}$, C(N)N(R$^{19}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I; wherein R$^{19}$ is as described in Formula I.

In one embodiment of Formula (Ik), R$^{102}$ is heterocycloalkyl which is unsubstituted or substituted with one or two or three or four of independently selected R$^{19}$, OR$^{19}$, SR$^{19}$, S(O)R$^{19}$, SO$_2$R$^{19}$, C(O)R$^{19}$, CO(O)R$^{19}$, OC(O)R$^{19}$, OC(O)OR$^{19}$, NH$_2$, NHR$^{19}$, N(R$^{19}$)$_2$, NHC(O)R$^{19}$, NR$^{19}$C(O)R$^{19}$, NHS(O)$_2$R$^{19}$, NR$^{19}$S(O)$_2$R$^{19}$, NHC(O)OR$^{19}$, NR$^{19}$C(O)OR$^{19}$, NHC(O)NH$_2$, NHC(O)NHR$^{19}$, NHC(O)N(R$^{19}$)$_2$, NR$^{19}$C(O)NHR$^{19}$, NR$^{19}$C(O)N(R$^{19}$)$_2$, C(O)NH$_2$, C(O)NHR$^{19}$, C(O)N(R$^{19}$)$_2$, C(O)NHOH, C(O)NHOR$^{19}$, C(O)NHSO$_2$R$^{19}$, C(O)NR$^{19}$SOR$^{19}$, SO$_2$NH$_2$, SO$_2$NHR$^{19}$, SO$_2$N(R$^{19}$)$_2$, C(O)H, C(O)OH, C(N)NH$_2$, C(N)NHR$^{19}$, C(N)N(R$^{19}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I; wherein R$^{19}$ is as described in Formula I.

Embodiments where A$^{102}$ is Piperidine, A$^2$ is R$^5$

In one embodiment of Formula (I) A$^1$ is R$^2$, wherein R$^2$ is unsubstituted piperidine which is unfused, and A$^2$ is R$^5$, which is as described in Formula I. In another embodiment of Formula I, A$^1$ is R$^2$, wherein R$^2$ is unsubstituted piperidine which is unfused, and A$^2$ is R$^5$, R$^5$ is C$_1$-alkyl, C$_2$-alkyl or C$_3$-alkyl wherein R$^5$ is substituted with R$^{10}$, and further unsubstituted or substituted with one or two or three of independently selected NHR$^{10}$, N(R$^{10}$)$_2$, SR$^{10}$, S(O)R$^{10}$, SO$_2$R$^{10}$ or CF$_3$, wherein R$^{10}$ is as described in formula I. In another embodiment of Formula I, A$^1$ is R$^2$, wherein R$^1$ is unsubstituted piperidine which is unfused, and A$^2$ is R$^5$, R$^5$ is C$_1$-alkyl, C$_2$-alkyl or C$_3$-alkyl wherein R$^5$ is substituted with R$^{10}$, and further unsubstituted or substituted with one CF$_3$, wherein R$^{10}$ is as described in formula I. In another embodiment of Formula I, A$^1$ is R$^2$, wherein R$^2$ is unsubstituted piperidine which is unfused, A$^2$ is C$_1$-alkyl, and R$^{10}$ is phenyl, as shown in Formula (Iv):

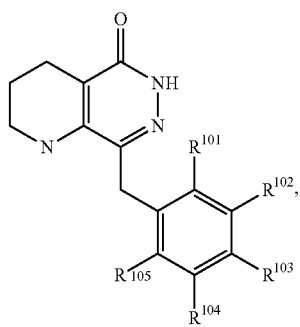

(Iv)

wherein R$^{101}$, R$^{102}$, R$^{103}$, R$^{104}$, and R$^{105}$, are independently selected from H, R$^{11}$, OR$^{11}$, SR$^{11}$, S(O)R$^{11}$, SO$_2$R$^{11}$, NH$_2$, N(R$^{11}$)$_2$, C(O)R$^{11}$, C(O)OR$^{11}$, C(O)NHR$^{11}$, C(O)N(R$^{11}$)$_2$, NHC(O)R$^{11}$, NHSO$_2$R$^{11}$, NR$^{11}$SO$_2$R$^{11}$, NHC(O)OR$^{11}$, NHSO$_2$N(R$^{11}$)$_2$, NO$_2$, OH, (O), C(O)OH, F, Cl or Br; wherein each R$^{11}$ is R$^{12}$, R$^{13}$, R$^{14}$ or R$^{15}$; R$^{12}$ is phenyl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene; R$^{13}$ is heteroaryl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene; R$^{14}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene; R$^{15}$ is alkyl, alkenyl or alkynyl; each of which is unsubstituted or substituted with one or two of independently selected R$^{16}$, OR$^{16}$, SR$^{16}$, S(O)$_2$R$^{16}$, C(O)OH, NH$_2$, NHR$^{16}$N(R$^{16}$)$_2$, C(O)R$^{16}$, C(O)NH$_2$, C(O)NHR$^{16}$, C(O)N(R$^{16}$)$_2$, NHC(O)R$^{16}$, NR$^{16}$C(O)R$^{16}$, NHC(O)OR$^{16}$, NR$^{16}$C(O)OR$^{16}$, OH, F, Cl, Br or I; wherein each R$^{16}$ is R$^{17}$ or R$^{17A}$; R$^{17}$ is alkyl, alkenyl or alkynyl: each of which is unsubstituted or substituted with one or two of independently selected R$^{18}$, C(O)OH, NH$_2$, NHR$^{18}$ or N(R$^{18}$)$_2$, C(O)R$^{18}$, C(O)NH$_2$, C(O)NHR$^{18}$, C(O)N(R$^{18}$)$_2$, NHC(O)R$^{18}$, NR$^{18}$C(O)R$^{18}$, F, Cl, Br or I; R$^{17A}$ is phenyl, heteroaryl, cycloalkyl, cycloalkenyl, heterocycloalkyl or heterocycloalkenyl, each of which is unfused or fused with benzene, heteroarene, cycloalkane, cycloalkene, heterocycloalkane or heterocycloalkene; wherein each R$^{18}$ is phenyl, heteroaryl, cycloalkyl, cycloalkenyl, heterocycloalkyl or heterocycloalkenyl; wherein each of the moieties represented by R$^{12}$, R$^{13}$, R$^{14}$, R$^{17A}$, and R$^{18}$ are independently unsubstituted or substituted with one or two or three or four of independently selected R$^{19}$, OR$^{19}$, SR$^{19}$, S(O)R$^{19}$, SO$_2$R$^{19}$, C(O)R$^{19}$, CO(O)R$^{19}$, OC(O)R$^{19}$, OC(O)OR$^{19}$, NH$_2$, NHR$^{19}$, N(R$^{19}$)$_2$, NHC(O)R$^{19}$, NR$^{19}$C(O)R$^{19}$, NHS(O)$_2$R$^{19}$, NR$^{19}$S(O)$_2$R$^{19}$, NHC(O)OR$^{19}$, NR$^{19}$C(O)OR$^{19}$, NHC(O)NH$_2$, NHC(O)NHR$^{19}$, NHC(O)N(R$^{19}$)$_2$, NR$^{19}$C(O)NHR$^{19}$, NR$^{19}$C(O)N(R$^{19}$)$_2$, C(O)NH$_2$, C(O)NHR$^{19}$, C(O)N(R$^{19}$)$_2$, C(O)NHOH, C(O)NHOR$^{19}$, C(O)NHSO$_2$R$^{19}$, C(O)NR$^{19}$SO$_2$R$^{19}$, SO$_2$NH$_2$, SO$_2$NHR$^{19}$, SO$_2$N(R$^{19}$)$_2$, C(O)H, C(O)OH, C(N)NH$_2$, C(N)NHR$^{19}$, C(N)N(R$^{19}$)$_2$, CNOH, CNOCH$_3$, OH, (O), CN, N$_3$, NO$_2$, CF$_3$, CF$_2$CF$_3$, OCF$_3$, OCF$_2$CF$_3$, F, Cl, Br or I; wherein each R$^{19}$ is R$^{20}$, R$^{21}$, R$^{22}$ or R$^{23}$; R$^{20}$ is phenyl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene; R$^{21}$ is heteroaryl which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene; R$^{22}$ is cycloalkyl, cycloalkenyl, heterocycloalkyl or heterocycloalkenyl; each of which is unfused or fused with benzene, heteroarene, cycloalkane, cycloalkene, heterocycloalkane or heterocycloalkene; each of which is unfused or fused with benzene, heteroarene, cycloalkane, cycloalkene, heterocycloalkane or heterocycloalkene; R$^{23}$ is alkyl, alkenyl or alkynyl, each of which is unsubstituted or substituted with one or two of independently selected R$^{24}$, OR$^{24}$, SR$^{24}$, S(O)$_2$R$^{24}$, C(O)OH, NH$_2$, NHR$^{24}$N(R$^{24}$)$_2$, C(O)R$^{24}$, C(O)NH$_2$, C(O)NHR$^4$, C(O)N(R$^{14}$)$_2$, NHC(O)R$^{14}$, NR$^2$C(O)R$^{24}$, NHC(O)OR$^4$, NR$^{14}$C(O)OR$^{14}$, NHS(O)$_2$R$^{24}$, NR$^4$S(O)$_2$R$^{24}$, OH, F, Cl, Br or I; wherein each R$^{24}$ is R$^{24A}$ or R$^{24B}$; R$^{24A}$ is phenyl, heteroaryl, cycloalkyl, cycloalkenyl, heterocycloalkyl or heterocycloalkenyl each of which is unfused or fused with benzene, heteroarene, cycloalkane, cycloalkene, heterocycloalkane or heterocycloalkene; R$^{24B}$ is alkyl, alkenyl or alkynyl each of which is unsubstituted or substituted with one or two of independently selected R$^{25}$, OR$^{25}$, SR$^{25}$, S(O)$_2$R$^{25}$, C(O)OH, NH$_2$, NHR$^{25}$N(R$^{25}$)$_2$, C(O)R$^{25}$, C(O)NH$_2$, C(O)NHR$^{25}$, C(O)N(R$^{25}$)$_2$, NHC(O)R$^{25}$, NR$^{25}$C(O)R$^5$, NHC(O)OR$^{25}$, NR$^{25}$C(O)OR$^2$, OH, F, Cl, Br or I; wherein each R$^{25}$ is alkyl, phenyl, heteroaryl, cycloalkyl, cycloalkenyl, heterocycloalkyl or heterocycloalkenyl; each of which is unsubstituted or substituted with NH$_2$, NH(CH$_3$), N(CH$_3$)$_2$, OH or OCH$_3$; wherein each of the moieties represented by R$^{20}$, R$^{21}$, R$^{22}$, and R$^{24,4}$ are independently unsubstituted or substituted with one or two of independently selected R$^{26}$, OR$^{26}$, alkenyl, alkynyl, phenyl, OH, (O), C(O)OH, CN, CF$_3$, OCF$_3$, CF$_2$CF$_3$, F, Cl, Br or I; and R$^{26}$ is alkyl. In another embodiment, the compound of Formula (Iv) is selected from 8-(4-fluorobenzyl)-2,3,4,6-tetrahydropyrido(2,3-d)pyridazin-5(1H)-one;

8-(4-fluoro-3-(2-oxoazetidin-1-yl)benzyl)-2,3,4,6-tetrahydropyrido(2,3-d)pyridazin-5(1H)-one;

8-(3-chloro-4-fluorobenzyl)-2,3,4,6-tetrahydropyrido(2,3-d)pyridazin-5(1H)-one 8-(4-fluoro-3-(2-oxopyrrolidin-1-yl)benzyl)-2,3,4,6-tetrahydropyrido(2,3-d)pyridazin-5(1H)-one;

methyl 2-fluoro-5-((5-oxo-1,2,3,4,5,6-hexahydropyrido(2,3-d)pyridazin-8-yl)methyl)benzoate;

8-(3-amino-4-fluorobenzyl)-2,3,4,6-tetrahydropyrido(2,3-d)pyridazin-5(1H)-one;

2-fluoro-5-((5-oxo-1,2,3,4,5,6-hexahydropyrido(2,3-d)pyridazin-8-yl)methyl)benzoic acid;

N-ethyl-2-fluoro-5-((5-oxo-1,2,3,4,5,6-hexahydropyrido(2,3-d)pyridazin-8-yl)methyl)benzamide;

N-cyclobutyl-2-fluoro-5-((5-oxo-1,2,3,4,5,6-hexahydropyrido(2,3-d)pyridazin-8-yl)methyl)benzamide;

2-fluoro-5-((5-oxo-1,2,3,4,5,6-hexahydropyrido(2,3-d)pyridazin-8-yl)methyl)-N-(2-pyrrolidin-1-ylethyl)benzamide;

8-(4-fluoro-3-((4-(morpholin-4-ylcarbonyl)piperazin-1-yl)carbonyl)benzyl)-2,3,4,6-tetrahydropyrido(2,3-d)pyridazin-5(1H)-one;

N-(2-fluoro-5-((5-oxo-1,2,3,4,5,6-hexahydropyrido(2,3-d)pyridazin-8-yl)methyl)phenyl)-N'-phenylpentanediamide;

1-(2-fluoro-5-((5-oxo-1,2,3,4,5,6-hexahydropyrido(2,3-d)pyridazin-8-yl)methyl)phenyl)pyrrolidine-2,5-dione;

N-(2-fluoro-5-((5-oxo-1,2,3,4,5,6-hexahydropyrido(2,3-d)pyridazin-8-yl)methy)phenyl)-3-methoxypropanamide;

N-(2-fluoro-5-((5-oxo-1,2,3,4,5,6-hexahydropyrido(2,3-d)pyridazin-8-yl)methyl)phenyl)-5-oxohexanamide;

N-(2-fluoro-5-((5-oxo-1,2,3,4,5,6-hexahydropyrido(2,3-d)pyridazin-8-yl)methyl)phenyl)-3-phenoxypropanamide;

N-(2-fluoro-5-((5-oxo-1,2,3,4,5,6-hexahydropyrido(2,3-d)pyridazin-8-yl)methy)phenyl)-4-oxo-4-phenylbutanamide;

2-(4-(benzyloxy)phenoxy)-N-(2-fluoro-5-((5-oxo-1,2,3,4,5,6-hexahydropyrido(2,3-d)pyridazin-8-yl)methyl)phenyl)acetamide;

N-(2-fluoro-5-((5-oxo-1,2,3,4,5,6-hexahydropyrido(2,3-d)pyridazin-8-yl)methyl)phenyl)-2-(4-methoxyphenoxy)acetamide;

N-cyclopropyl-2-fluoro-5-((5-oxo-1,2,3,4,5,6-hexahydropyrido(2,3-d)pyridazin-8-yl)methyl)benzamide;

8-(3-((4-(2-ethoxyethyl)piperazin-1-yl)carbonyl)-4-fluorobenzyl)-2,3,4,6-tetrahydropyrido(2,3-d)pyridazin-5(1H)-one;

2-fluoro-5-((5-oxo-1,2,3,4,5,6-hexahydropyrido(2,3-d)pyridazin-8-yl)methyl)-N-(2-piperidin-1-ylethyl)benzamide;

8-(3-{[4-(cyclopropylcarbonyl)piperazin-1-yl]carbonyl}-4-fluorobenzyl)-2,3,4,6-tetrahydropyrido[2,3-d]pyridazin-5(1H)-one;

1-{2-fluoro-5-[(5-oxo-1,2,3,4,5,6-hexahydropyrido[2,3-d]pyridazin-8-yl)methyl]phenyl}piperidine-2,6-dione;

8-[3-({4-[2-(dimethylamino)ethyl]piperazin-1-yl}carbonyl)-4-fluorobenzyl]-2,3,4,6-tetrahydropyrido[2,3-d]pyridazin-5(1H)-one;

8-{4-fluoro-3-[(4-methyl-1,4-diazepan-1-yl)carbonyl]benzyl}-2,3,4,6-tetrahydropyrido[2,3-d]pyridazin-5(1H)-one;

8-{4-fluoro-3-[(4-pyridin-4-ylpiperazin-1-yl)carbonyl]benzyl}-2,3,4,6-tetrahydropyrido[2,3-d]pyridazin-5(1H)-one;

8-{4-fluoro-3-[(4-pyrazin-2-ylpiperazin-1-yl)carbonyl]benzyl}-2,3,4,6-tetrahydropyrido[2,3-d]pyridazin-5(1H)-one;

4-{2-fluoro-5-[(5-oxo-1,2,3,4,5,6-hexahydropyrido[2,3-d]pyridazin-8-yl)methyl]benzoyl}-N,N-dimethylpiperazine-1-carboxamide;

N-[2-(dimethylamino)ethyl]-2-fluoro-N-methyl-5-[(5-oxo-1,2,3,4,5,6-hexahydropyrido[2,3-d]pyridazin-8-yl)methyl]benzamide;

8-{4-fluoro-3-[(4-methylpiperazin-1-yl)carbonyl]benzyl}-2,3,4,6-tetrahydropyrido[2,3-d]pyridazin-5(1H)-one;

1-{2-fluoro-5-[(5-oxo-1,2,3,4,5,6-hexahydropyrido[2,3-d]pyridazin-8-yl)methyl]benzoyl}piperidine-3-carboxamide;

8-(4-fluoro-3-{[4-(piperidin-1-ylcarbonyl)piperazin-1-yl]carbonyl}benzyl)-2,3,4,6-tetrahydropyrido[2,3-d]pyridazin-5(1H)-one;

8-(4-fluoro-3-{[4-(2-oxo-2-pyrrolidin-1-ylethyl)piperazin-1-yl]carbonyl}benzyl)-2,3,4,6-tetrahydropyrido[2,3-d]pyridazin-5(1H)-one;

1-{2-fluoro-5-[(5-oxo-1,2,3,4,5,6-hexahydropyrido[2,3-d]pyridazin-8-yl)methyl]benzoyl}piperidine-4 carboxamide;

8-(4-fluoro-3-{[4-(2-hydroxyethyl)piperazin-1-yl]carbonyl}benzyl)-2,3,4,6-tetrahydropyrido[2,3-d]pyridazin-5(1H)-one;

8-{4-fluoro-3-[(4-pyrimidin-2-ylpiperazin-1-yl)carbonyl]benzyl}-2,3,4,6-tetrahydropyrido[2,3-d]pyridazin-5(1H)-one;

8-{4-fluoro-3-[(4-pyridin-2-ylpiperazin-1-yl)carbonyl]benzyl}-2,3,4,6-tetrahydropyrido[2,3-d]pyridazin-5(1H)-one;

8-{4-fluoro-3-[(4-phenylpiperazin-1-yl)carbonyl]benzyl}-2,3,4,6-tetrahydropyrido[2,3-d]pyridazin-5(1H)-one;

8-(4-fluoro-3-{[4-(3-fluorophenyl)piperazin-1-yl]carbonyl}benzyl)-2,3,4,6-tetrahydropyrido[2,3-d]pyridazin-5(1H)-one;

8-(4-fluoro-3-{[4-(4-fluorophenyl)piperazin-1-yl]carbonyl}benzyl)-2,3,4,6-tetrahydropyrido[2,3-d]pyridazin-5(1H)-one;

8-(4-fluoro-3-{[4-(2-fluorophenyl)piperazin-1-yl]carbonyl}benzyl)-2,3,4,6-tetrahydropyrido[2,3-d]pyridazin-5(1H)-one;

8-(3-{[4-(2,4-difluorophenyl)piperazin-1-yl]carbonyl}-4-fluorobenzyl)-2,3,4,6-tetrahydropyrido[2,3-d]pyridazin-5(1H)-one;

8-{3-[(4-benzoylpiperazin-1-yl)carbonyl]-4-fluorobenzyl}-2,3,4,6-tetrahydropyrido[2,3-d]pyridazin-5(1H)-one;

8-(4-fluoro-3-{[4-(2-furoyl)piperazin-1-yl]carbonyl}benzyl)-2,3,4,6-tetrahydropyrido[2,3-d]pyridazin-5(1H)-one;

8-(3-{[4-(2-chlorophenyl)piperazin-1-yl]carbonyl}-4-fluorobenzyl)-2,3,4,6-tetrahydropyrido[2,3-d]pyridazin-5(1H)-one;

4-{2-fluoro-5-[(5-oxo-1,2,3,4,5,6-hexahydropyrido[2,3-d]pyridazin-8-yl)methyl]benzoyl}-2-morpholin-4-ylpiperazine-1-carbaldehyde;

8-(4-fluoro-3-{[4-(methylsulfonyl)piperazin-1-yl]carbonyl}benzyl)-2,3,4,6-tetrahydropyrido[2,3-d]pyridazin-5(1H)-one;

N,N-diethyl-4-{2-fluoro-5-[(5-oxo-1,2,3,4,5,6-hexahydropyrido[2,3-d]pyridazin-8-yl)methyl]benzoyl}piperazine-1-carboxamide;

8-{3-[(4-acetylpiperazin-1-yl)carbonyl]-4-fluorobenzyl}-2,3,4,6-tetrahydropyrido[2,3-d]pyridazin-5(1H)-one;

2-(4-{2-fluoro-5-[(5-oxo-1,2,3,4,5,6-hexahydropyrido[2,3-d]pyridazin-8-yl)methyl]benzoyl}piperazin-1-yl)-N,N-dimethylacetamide;

8-(4-fluoro-3-{[4-(2-phenoxyethyl)piperazin-1-yl]carbonyl}benzyl)-2,3,4,6-tetrahydropyrido[2,3-d]pyridazin-5(1H)-one;

8-(4-fluoro-3-{[4-(phenylsulfonyl)piperazin-1-yl]carbonyl}benzyl)-2,3,4,6-tetrahydropyrido[2,3-d]pyridazin-5(1H)-one;

2-fluoro-N-[2-(4-methylpiperazin-1-yl)ethyl]-5-[(5-oxo-1,2,3,4,5,6-hexahydropyrido[2,3-d]pyridazin-8-yl)methyl]benzamide;

8-{3-[(4-cyclopentylpiperazin-1-yl)carbonyl]-4-fluorobenzyl}-2,3,4,6-tetrahydropyrido[2,3-d]pyridazin-5(1H)-one;

8-{4-fluoro-3-[(4-isobutyrylpiperazin-1-yl)carbonyl]benzyl}-2,3,4,6-tetrahydropyrido[2,3-d]pyridazin-5(1H)-one;

8-(4-fluoro-3-{[4-(2-morpholin-4-ylethyl)piperazin-1-yl]carbonyl}benzyl)-2,3,4,6-tetrahydropyrido[2,3-d]pyridazin-5(1H)-one;

8-(4-fluoro-3-{[4-(pyrrolidin-1-ylcarbonyl)piperazin-1-yl]carbonyl}benzyl)-2,3,4,6-tetrahydropyrido[2,3-d]pyridazin-5(1H)-one;

8-(3-{[4-(cyclohexylcarbonyl)piperazin-1-yl]carbonyl}-4-fluorobenzyl)-2,3,4,6-tetrahydropyrido[2,3-d]pyridazin-5(1H)-one;

8-(4-fluoro-3-{[4-(tetrahydrofuran-2-ylcarbonyl)piperazin-1-yl]carbonyl}benzyl)-2,3,4,6-tetrahydropyrido[2,3-d]pyridazin-5(1H)-one;

8-(4-fluoro-3-{[4-(2-piperidin-1-ylethyl)piperazin-1-yl]carbonyl}benzyl)-2,3,4,6-tetrahydropyrido[2,3-d]pyridazin-5(1H)-one;

8-{4-fluoro-3-[(4-hydroxypiperidin-1-yl)carbonyl]benzyl}-2,3,4,6-tetrahydropyrido[2,3-d]pyridazin-5(1H)-one;

8-(4-fluoro-3-{[4-(6-methylpyrazin-2-yl)piperazin-1-yl]carbonyl}benzyl)-2,3,4,6-tetrahydropyrido[2,3-d]pyridazin-5(1H)-one;

3-{2-fluoro-5-[(5-oxo-1,2,3,4,5,6-hexahydropyrido[2,3-d]pyridazin-8-yl)methyl]phenyl}-5-isopropylimidazolidine-2,4-dione;

8-(4-fluoro-3-{[4-(phenoxyacetyl)piperazin-1-yl]carbonyl}benzyl)-2,3,4,6-tetrahydropyrido[2,3-d]pyridazin-5(1H)-one;

8-(3-{[4-(2,2-dimethylpropanoyl)piperazin-1-yl]carbonyl}-4-fluorobenzyl)-2,3,4,6-tetrahydropyrido[2,3-d]pyridazin-5(1H)-one;

8-(3-{[44(ethylsulfonyl)piperazin-1-yl]carbonyl}-4-fluorobenzyl)-2,3,4,6-tetrahydropyrido[2,3-d]pyridazin-5(1H)-one;

N-(1-{2-fluoro-5-[(5-oxo-1,2,3,4,5,6-hexahydropyrido[2,3-d]pyridazin-8-yl)methyl]benzoyl}pyrrolidin-3-yl)-N-methylacetamide;

N-ethyl-N-(1-{2-fluoro-5-[(5-oxo-1,2,3,4,5,6-hexahydropyrido[2,3-d]pyridazin-8-yl)methyl]benzoyl}pyrrolidin-3-yl)acetamide;

8-{4-fluoro-3-[(4-propionylpiperazin-1-yl)carbonyl]benzyl}-2,3,4,6-tetrahydropyrido[2,3-d]pyridazin-5(1H)-one;

3-{2-fluoro-5-[(5-oxo-1,2,3,4,5,6-hexahydropyrido[2,3-d]pyridazin-8-yl)methyl]phenyl}-5-methylimidazolidine-2,4-dione;

8-(4-fluoro-3-{[4-(4-methoxyphenyl)piperazin-1-yl]carbonyl}benzyl)-2,3,4,6-tetrahydropyrido[2,3-d]pyridazin-5(1H)-one;

8-[4-fluoro-3-({4-[(4-methoxyphenyl)sulfonyl]piperazin-1-yl}carbonyl)benzyl]-2,3,4,6-tetrahydropyrido[2,3-d]pyridazin-5(1H)-one;

8-(4-fluoro-3-{[4-(4-methoxybenzoyl)piperazin-1-yl]carbonyl}benzyl)-2,3,4,6-tetrahydropyrido[2,3-d]pyridazin-5(1H)-one;

8-[4-fluoro-3-(4-[3-(trifluoromethyl)phenyl]piperazin-1-yl)carbonyl)benzyl]-2,3,4,6-tetrahydropyrido[2,3-d]pyridazin-5(1H)-one;

tert-butyl 3-{2-fluoro-5-[(5-oxo-1,2,3,4,5,6-hexahydropyrido[2,3-d]pyridazin-8-yl)methyl]benzoyl}tetrahydropyrimidine-1(2H)-carboxylate;

8-{4-([3-[3-(dimethylamino)propyl]tetrahydropyrimidin-1(2H)-yl]carbonyl}-4-fluorobenzyl)-2,3,4,6-tetrahydropyrido[2,3-d]pyridazin-5(1H)-one;

5-benzyl-3-{2-fluoro-5-[(5-oxo-1,2,3,4,5,6-hexahydropyrido[2,3-d]pyridazin-8-yl)methyl]phenyl}imidazolidine-2,4-dione;

3-{2-fluoro-5-[(5-oxo-1,2,3,4,5,6-hexahydropyrido[2,3-d]pyridazin-8-yl)methyl]phenyl}dihydropyrimidine-2,4(1H,3H)-dione;

8-{4-fluoro-3-[(3-oxopiperazin-1-yl)carbonyl]benzyl}-2,3,4,6-tetrahydropyrido[2,3-d]pyridazin-5(1H)-one;

8-{3-[(4-benzoylpiperidin-1-yl)carbonyl]-4-fluorobenzyl}-2,3,4,6-tetrahydropyrido[2,3-d]pyridazin-5(1H)-one;

8-(4-fluoro-3-{[4-(4-methoxybenzoyl)piperidin-1-yl]carbonyl}benzyl)-2,3,4,6-tetrahydropyrido[2,3-d]pyridazin-5(1H)-one;

8-(4-fluoro-3-{[4-(1H-indol-6-ylcarbonyl)piperazin-1-yl]carbonyl}benzyl)-2,3,4,6-tetrahydropyrido[2,3-d]pyridazin-5(1H)-one;

8-(3-{[4-(3-chlorobenzoyl)piperidin-1-yl]carbonyl}-4-fluorobenzyl)-2,3,4,6-tetrahydropyrido[2,3-d]pyridazin-5(1H)-one;

benzyl 4-{2-fluoro-5-[(5-oxo-1,2,3,4,5,6-hexahydropyrido[2,3-d]pyridazin-8-yl)methyl]benzoyl}piperazine-1-carboxylate;

tert-butyl (3R)-4-{2-fluoro-5-[(5-oxo-1,2,3,4,5,6-hexahydropyrido[2,3-d]pyridazin-8-yl)methyl]benzoyl}-3-phenylpiperazine-1-carboxylate;

8-(3-{[(2R)-4-benzoyl-2-methylpiperazin-1-yl]carbonyl}-4-fluorobenzyl)-2,3,4,6-tetrahydropyrido[2,3-d]pyridazin-5(1H)-one;

8-[4-fluoro-3-(piperazin-1-ylcarbonyl)benzyl]-2,3,4,6-tetrahydropyrido[2,3-d]pyridazin-5(1H)-one;

8-(4-fluoro-3-{[4-(2-methoxyphenyl)piperazin-1-yl]carbonyl}benzyl)-2,3,4,6-tetrahydropyrido[2,3-d]pyridazin-5(1H)-one;

8-(4-fluoro-3-{[4-(1,3,5-triazin-2-yl)piperazin-1-yl]carbonyl}benzyl)-2,3,4,6-tetrahydropyrido[2,3-d]pyridazin-5(1H)-one;

8-(3-{[4-(2,3-dihydro-1,4-benzodioxin-2-ylcarbonyl)piperazin-1-yl]carbonyl}-4-fluorobenzyl)-2,3,4,6-tetrahydropyrido[2,3-d]pyridazin-5(1H)-one;

8-(4-fluoro-3-{[(2R)-2-phenylpiperazin-1-yl]carbonyl}benzyl)-2,3,4,6-tetrahydropyrido[2,3-d]pyridazin-5(1H)-one;

8-[4-fluoro-3-({4-[(4R)-1,3-thiazolidin-4-ylcarbonyl]piperazin-1-yl}carbonyl)benzyl]-2,3,4,6-tetrahydropyrido[2,3-d]pyridazin-5(1H)-one;
8-(3-{[4-(cyclopentylcarbonyl)piperazin-1-yl]carbonyl}-4-fluorobenzyl)-2,3,4,6-tetrahydropyrido[2,3-d]pyridazin-5(1H)-one;
8-[3-({4-[(5-chloropyridin-2-yl)carbonyl]piperazin-1-yl}carbonyl)-4-fluorobenzyl]-2,3,4,6-tetrahydropyrido[2,3-d]pyridazin-5(1H)-one;
8-[4-fluoro-3-({4-[(1-isopropyl-1H-1,2,3-benzotriazol-5-yl)carbonyl]piperazin-1-yl}carbonyl)benzyl]-2,3,4,6-tetrahydropyrido[2,3-d]pyridazin-5(1H)-one;
8-(4-fluoro-3-{[4-(4-methylpiperazin-1-yl)piperidin-1-yl]carbonyl}benzyl)-2,3,4,6-tetrahydropyrido[2,3-d]pyridazin-5(1H)-one;
8-(4-fluoro-3-{[4-(quinolin-2-ylcarbonyl)piperazin-1-yl]carbonyl}benzyl)-2,3,4,6-tetrahydropyrido[2,3-d]pyridazin-5(1H)-one;
8-[3-({4-[(6-chloropyridin-3-yl)carbonyl]piperazin-1-yl}carbonyl)-4-fluorobenzyl]-2,3,4,6-tetrahydropyrido[2,3-d]pyridazin-5(1H)-one;
8-{4-fluoro-3-[(4-{[1-isopropyl-2-(trifluoromethyl)-1H-benzimidazol-5-yl]carbonyl}piperazin-1-yl)carbonyl]benzyl}-2,3,4,6-tetrahydropyrido[2,3-d]pyridazin-5(1H)-one;
8-[4-fluoro-3-({4-[(6-hydroxypyridin-3-yl)carbonyl]piperazin-1-yl}carbonyl)benzyl]-2,3,4,6-tetrahydropyrido[2,3-d]pyridazin-5(1H)-one;
8-[3-({4-[(6-chloro-5-hydroxypyridin-3-yl)carbonyl]piperazin-1-yl}carbonyl)-4-fluorobenzyl]-2,3,4,6-tetrahydropyrido[2,3-d]pyridazin-5(1H)-one;
8-[4-fluoro-3-({4-[(2-methyl-1H-benzimidazol-5-yl)carbonyl]piperazin-1-yl}carbonyl)benzyl]-2,3,4,6-tetrahydropyrido[2,3-d]pyridazin-5(1H)-one;
8-(3-{[4-(1H-benzimidazol-6-ylcarbonyl)piperazin-1-yl]carbonyl}-4-fluorobenzyl)-2,3,4,6-tetrahydropyrido[2,3-d]pyridazin-5(1H)-one;
8-(4-fluoro-3-{[4-(quinolin-3-ylcarbonyl)piperazin-1-yl]carbonyl}benzyl)-2,3,4,6-tetrahydropyrido[2,3-d]pyridazin-5(1H)-one;
8-[3-({4-[(2-chloropyridin-3-yl)carbonyl]piperazin-1-yl}carbonyl)-4-fluorobenzyl]-2,3,4,6-tetrahydropyrido[2,3-d]pyridazin-5(1H)-one;
benzyl 4-{2-fluoro-5-[(5-oxo-1,2,3,4,5,6-hexahydropyrido[2,3-d]pyridazin-8-yl)methyl]benzoyl}-1,4-diazepane-1-carboxylate;
8-{4-fluoro-3-[(4-isonicotinoylpiperazin-1-yl)carbonyl]benzyl}-2,3,4,6-tetrahydropyrido[2,3-d]pyridazin-5(1H)-one;
8-(4-fluoro-3-{[4-(pyridin-3-ylcarbonyl)piperazin-1-yl]carbonyl}benzyl)-2,3,4,6-tetrahydropyrido[2,3-d]pyridazin-5(1H)-one;
8-(4-fluoro-3-{[4-(pyrazin-2-ylcarbonyl)piperazin-1-yl]carbonyl}benzyl)-2,3,4,6-tetrahydropyrido[2,3-d]pyridazin-5(1H)-one;
8-(3-{[4-(1H-benzimidazol-5-ylcarbonyl)piperazin-1-yl]carbonyl}-4-fluorobenzyl)-2,3,4,6-tetrahydropyrido[2,3-d]pyridazin-5(1H)-one;
8-(4-fluoro-3-{[4-(pyrimidin-5-ylcarbonyl)piperazin-1-yl]carbonyl}benzyl)-2,3,4,6-tetrahydropyrido[2,3-d]pyridazin-5(1H)-one;
8-(4-fluoro-3-{[4-(pyridin-2-ylcarbonyl)piperazin-1-yl]carbonyl}benzyl)-2,3,4,6-tetrahydropyrido[2,3-d]pyridazin-5(1H)-one;
ethyl 4-{2-fluoro-5-[(5-oxo-1,2,3,4,5,6-hexahydropyrido[2,3-d]pyridazin-8-yl)methyl]benzoyl}piperazine-1-carboxylate;
8-{3-[(2,2-dimethyl-3-oxopiperazin-1-yl)carbonyl]-4-fluorobenzyl}-2,3,4,6-tetrahydropyrido[2,3-d]pyridazin-5(1H)-one;
8-{4-fluoro-3-[(4-isonicotinoyl-1,4-diazepan-1-yl)carbonyl]benzyl}-2,3,4,6-tetrahydropyrido[2,3-d]pyridazin-5(1H)-one;
8-{4-fluoro-3-[(4-isonicotinoyl-1,4-diazepan-1-yl)carbonyl]benzyl}-2,3,4,6-tetrahydropyrido[2,3-d]pyridazin-5(1H)-one;
8-(4-fluoro-3-{[4-(pyridin-3-ylcarbonyl)-1,4-diazepan-1-yl]carbonyl}benzyl)-2,3,4,6-tetrahydropyrido[2,3-d]pyridazin-5(1H)-one;
8-(4-fluoro-3-{[4-(pyridin-2-ylcarbonyl)-1,4-diazepan-1-yl]carbonyl}benzyl)-2,3,4,6-tetrahydropyrido[2,3-d]pyridazin-5(1H)-one;
8-(4-fluoro-3-{[4-(pyrimidin-5-ylcarbonyl)-1,4-diazepan-1-yl]carbonyl}benzyl)-2,3,4,6-tetrahydropyrido[2,3-d]pyridazin-5(1H)-one;
8-(3-{[4-(1H-benzimidazol-6-ylcarbonyl)-1,4-diazepan-1-yl]carbonyl}-4-fluorobenzyl)-2,3,4,6-tetrahydropyrido[2,3-d]pyridazin-5(1H)-one;
8-(4-fluoro-3-{[4-(quinolin-2-ylcarbonyl)-1,4-diazepan-1-yl]carbonyl}benzyl)-2,3,4,6-tetrahydropyrido[2,3-d]pyridazin-5(1H)-one;
8-(4-fluoro-3-{[4-(quinolin-3-ylcarbonyl)-1,4-diazepan-1-yl]carbonyl}benzyl)-2,3,4,6-tetrahydropyrido[2,3-d]pyridazin-5(1H)-one;
8-[4-fluoro-3-({4-[(2-methyl-1H-benzimidazol-5-yl)carbonyl]-1,4-diazepan-1-yl}carbonyl)benzyl]-2,3,4,6-tetrahydropyrido[2,3-d]pyridazin-5(1H)-one;
8-[4-fluoro-3-({4-[(1-isopropyl-1H-1,2,3-benzotriazol-5-yl)carbonyl]-1,4-diazepan-1-yl}carbonyl)benzyl]-2,3,4,6-tetrahydropyrido[2,3-d]pyridazin-5(1H)-one;
8-(4-fluoro-3-{[4-(4-fluorobenzoyl)piperidin-1-yl]carbonyl}benzyl)-2,3,4,6-tetrahydropyrido[2,3-d]pyridazin-5(1H)-one;
8-[3-({4-[(5,5-dimethyl-1,3-thiazolidin-4-yl)carbonyl]piperazin-1-yl}carbonyl-4-fluorobenzyl]-2,3,4,6-tetrahydropyrido[2,3-d]pyridazin-5(1H)-one;
8-(4-fluoro-3-{[4-(pyrazin-2-ylcarbonyl)-1,4-diazepan-1-yl]carbonyl}benzyl)-2,3,4,6-tetrahydropyrido[2,3-d]pyridazin-5(1H)-one;
8-(4-fluoro-3-{[4-(2-furoyl)-1,4-diazepan-1-yl]carbonyl}benzyl)-2,3,4,6-tetrahydropyrido[2,3-d]pyridazin-5(1H)-one;
8-{4-fluoro-3-[(4-pyridin-3-ylpiperazin-1-yl)carbonyl]benzyl}-2,3,4,6-tetrahydropyrido[2,3-d]pyridazin-5(1H)-one;
8-{4-fluoro-3-[(4-pyrimidin-5-ylpiperazin-1-yl)carbonyl]benzyl}-2,3,4,6-tetrahydropyrido[2,3-d]pyridazin-5(1H)-one;
8-{4-fluoro-3-[(4-methyl-3-oxopiperazin-1-yl)carbonyl]benzyl}-2,3,4,6-tetrahydropyrido[2,3-d]pyridazin-5(1H)-one;
tert-butyl 4-[{2-fluoro-5-[(5-oxo-1,2,3,4,5,6-hexahydropyrido[2,3-d]pyridazin-8-yl)methyl]benzoyl}(methyl)amino]piperidine-1-carboxylate;
tert-butyl 4-({2-fluoro-5-[(5-oxo-1,2,3,4,5,6-hexahydropyrido[2,3-d]pyridazin-8-yl)methyl]benzoyl}amino)piperidine-1-carboxylate;
tert-butyl 1-{2-fluoro-5-[(5-oxo-1,2,3,4,5,6-hexahydropyrido[2,3-d]pyridazin-8-yl)methyl]benzoyl}piperidin-4-ylcarbamate;
8-[4-fluoro-3-({4-[(4R)-1,3-thiazolidin-4-ylcarbonyl]-1,4-diazepan-1-yl}carbonyl)benzyl]-2,3,4,6-tetrahydropyrido[2,3-d]pyridazin-5(1H)-one;

8-(4-fluoro-3-{[4-(1H-pyrazol-3-ylcarbonyl)-1,4-diazepan-1-yl]carbonyl}benzyl)-2,3,4,6-tetrahydropyrido[2,3-d]pyridazin-5(1H)-one;

8-(4-fluoro-3-{[4-(1,3-thiazol-4-ylcarbonyl)-1,4-diazepan-1-yl]carbonyl}benzyl)-2,3,4,6-tetrahydropyrido[2,3-d]pyridazin-5(1H)-one;

8-(4-fluoro-3-{[4-(1H-pyrazol-3-ylcarbonyl)piperazin-1-yl]carbonyl}benzyl)-2,3,4,6-tetrahydropyrido[2,3-d]pyridazin-5(1H)-one;

8-(4-fluoro-3-{[4-(1,3-thiazol-4-ylcarbonyl)piperazin-1-yl]carbonyl}benzyl)-2,3,4,6-tetrahydropyrido[2,3-d]pyridazin-5(1H)-one;

2-fluoro-N-methyl-5-[(5-oxo-1,2,3,4,5,6-hexahydropyrido[2,3-d]pyridazin-8-yl)methyl]-N-piperidin-4-ylbenzamide;

2-fluoro-5-[(5-oxo-1,2,3,4,5,6-hexahydropyrido[2,3-d]pyridazin-8-yl)methyl]-N-piperidin-4-ylbenzamide;

8-{3-[(4-aminopiperidin-1-yl)carbonyl]-4-fluorobenzyl}-2,3,4,6-tetrahydropyrido[2,3-d]pyridazin-5(1H)-one;

2-fluoro-N-(4-hydroxycyclohexyl)-5-[(5-oxo-1,2,3,4,5,6-hexahydropyrido[2,3-d]pyridazin-8-yl)methyl]benzamide;

2-fluoro-N-methyl-5-[(5-oxo-1,2,3,4,5,6-hexahydropyrido[2,3-d]pyridazin-8-yl)methyl]-N-[1-(pyridin-3-ylcarbonyl)piperidin-4-yl]benzamide;

2-fluoro-N-(1-isonicotinoylpiperidin-4-yl)-N-methyl-5-[(5-oxo-1,2,3,4,5,6-hexahydropyrido[2,3-d]pyridazin-8-yl)methyl]benzamide, N-[1-(1H-benzimidazol-5-ylcarbonyl)piperidin-4-yl]-2-fluoro-5-[(5-oxo-1,2,3,4,5,6-hexahydropyrido[2,3-d]pyridazin-8-yl)methyl]benzamide;

2-fluoro-N-[1-(2-furoyl)piperidin-4-yl]-N-methyl-5-[(5-oxo-1,2,3,4,5,6-hexahydropyrido[2,3-d]pyridazin-8-yl)methyl]benzamide;

2-fluoro-N-methyl-5-[(5-oxo-1,2,3,4,5,6-hexahydropyrido[2,3-d]pyridazin-8-yl)methyl]-N-{1-[(4R)-1,3-thiazolidin-4-ylcarbonyl]piperidin-4-yl}benzamide;

2-fluoro-N-methyl-5-[(5-oxo-1,2,3,4,5,6-hexahydropyrido[2,3-d]pyridazin-8-yl)methyl]-N-[1-(1,3-thiazol-4-ylcarbonyl)piperidin-4-yl]benzamide;

2-fluoro-N-methyl-5-[(5-oxo-1,2,3,4,5,6-hexahydropyrido[2,3-d]pyridazin-8-yl)methyl]-N-[1-(1H-pyrazol-4-ylcarbonyl)piperidin-4-yl]benzamide;

2-fluoro-5-[(5-oxo-1,2,3,4,5,6-hexahydropyrido[2,3-d]pyridazin-8-yl)methyl]-N-[1-(pyridin-3-ylcarbonyl)piperidin-4-yl]benzamide;

2-fluoro-N-[1-(2-furoyl)piperidin-4-yl]-5-[(5-oxo-1,2,3,4,5,6-hexahydropyrido[2,3-d]pyridazin-8-yl)methyl]benzamide;

2-fluoro-5-[(5-oxo-1,2,3,4,5,6-hexahydropyrido[2,3-d]pyridazin-8-yl)methyl]-N-{1-[(4R)-1,3-thiazolidin-4-ylcarbonyl]piperidin-4-yl}benzamide;

2-fluoro-5-[(5-oxo-1,2,3,4,5,6-hexahydropyrido[2,3-d]pyridazin-8-yl)methyl]-N-[1-(1,3-thiazol-4-ylcarbonyl)piperidin-4-yl]benzamide;

2-fluoro-5-[(5-oxo-1,2,3,4,5,6-hexahydropyrido[2,3-d]pyridazin-8-yl)methyl]-N-[1-(1H-pyrazol-4-ylcarbonyl)piperidin-4-yl]benzamide;

2-fluoro-5-[(5-oxo-1,2,3,4,5,6-hexahydropyrido[2,3-d]pyridazin-8-yl)methyl]-N-[1-(pyridin-2-ylcarbonyl)piperidin-4-yl]benzamide;

2-fluoro-N-(1-isonicotinoylpiperidin-4-yl)-5-[(5-oxo-1,2,3,4,5,6-hexahydropyrido[2,3-d]pyridazin-8-yl)methyl]benzamide;

N-[(1S,2S)-2-aminocyclohexyl]-2-fluoro-5-[(5-oxo-1,2,3,4,5,6-hexahydropyrido[2,3-d]pyridazin-8-yl)methyl]benzamide;

2-fluoro-5-[(5-oxo-1,2,3,4,5,6-hexahydropyrido[2,3-d]pyridazin-8-yl)methyl]-N-(1-pyridin-2-ylpiperidin-4-yl)benzamide;

N-(1-{2-fluoro-5-[(5-oxo-1,2,3,4,5,6-hexahydropyrido[2,3-d]pyridazin-8-yl)methyl]benzoyl}piperidin-4-yl)pyridine-2-carboxamide;

N-(1-{2-fluoro-5-[(5-oxo-1,2,3,4,5,6-hexahydropyrido[2,3-d]pyridazin-8-yl)methyl]benzoyl}piperidin-4-yl)nicotinamide, N-(1-{2-fluoro-5-[(5-oxo-1,2,3,4,5,6-hexahydropyrido[2,3-d]pyridazin-8-yl)methyl]benzoyl}piperidin-4-yl)isonicotinamide;

N-(1-{2-fluoro-5-[(5-oxo-1,2,3,4,5,6-hexahydropyrido[2,3-d]pyridazin-8-yl)methyl]benzoyl}piperidin-4-yl)-1H-indazole-6-carboxamide;

N-(1-{2-fluoro-5-[(5-oxo-1,2,3,4,5,6-hexahydropyrido[2,3-d]pyridazin-8-yl)methyl]benzoyl}piperidin-4-yl)-2-furamide;

N-(1-({2-fluoro-5-[(5-oxo-1,2,3,4,5,6-hexahydropyrido[2,3-d]pyridazin-8-yl)methyl]benzoyl}piperidin-4-yl)-1,3-thiazole-4-carboxamide; or N-(1-{2-fluoro-5-[(5-oxo-1,2,3,4,5,6-hexahydropyrido[2,3-d]pyridazin-8-yl)methyl]benzoyl}piperidin-4-yl)-1H-pyrazole-4-carboxamide.

SCHEMES

The starting materials used herein are commercially available or may be prepared by routine methods well known to those of ordinary skill in the art. The compounds of the present invention may be prepared using the methods illustrated in the general synthetic schemes and experimental procedures detailed below. The general synthetic schemes are presented for purposes of illustration and are not intended to be limiting.

Scheme 1

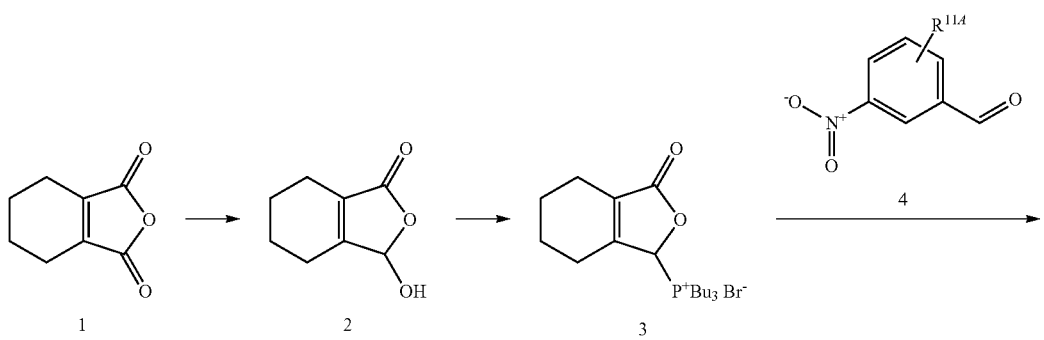

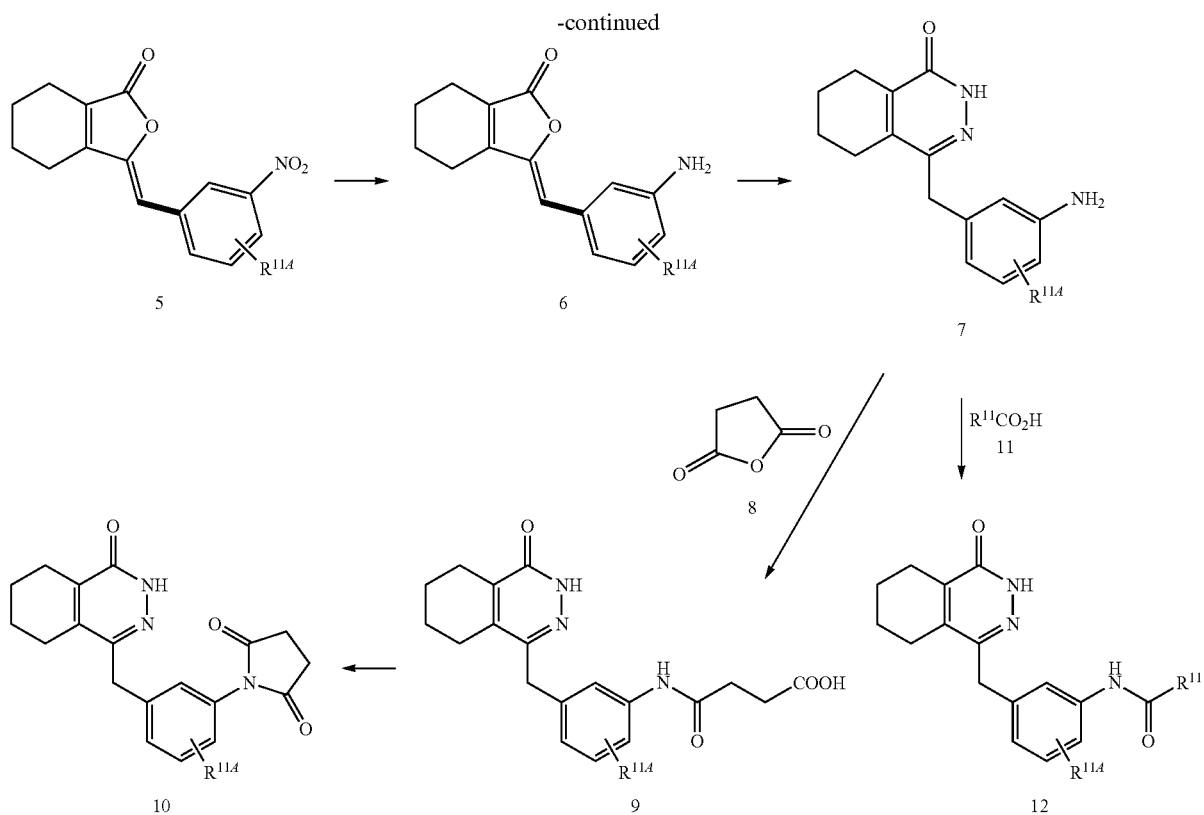

As shown in Scheme 1, the bicyclic anhydride (1) can be reduced to the alcohol (2) using a reducing agent such as but not limited to sodium borohydride. The reaction is typically conducted in a solvent such as but not limited to tetrahydrofuran at below room temperature to reflux. Conversion of (2) to the phosphonium salt (3) may be carried out by reacting the former with a trialkyl phosphine such as but not limited to tri-n-butyl phosphine in the presence of hydrobromic acid. The reaction is typically conducted in a solvent such as but not limited to acetic acid at reflux. Reaction of (3) with a nitrobenzaldehyde of Formula (4), wherein $R^{11A}$ is a substituent on $R^{10}$ as described herein, in the presence of a base such as but not limited to triethylamine will provide a lactone of Formula (5). The reaction is typically conducted in a solvent such as but not limited to dichloromethane at room temperature. Reduction of the nitro group of a compound of Formula (5) with a reducing agent such as but not limited to iron powder and $NH_4Cl$ will provide the corresponding aniline of Formula (6). The reaction is typically conducted in a solvent such as but not limited to ethanol at reflux. Reaction of the aniline of Formula (6) with hydrazine will provide a tetrahydrophthalazinone of Formula (7). The reaction is typically conducted in a solvent such as but not limited to ethanol at an elevated temperature. Reaction of a compound of Formula (7) with either an anhydride of Formula (8) or with an acid of Formula (11) under standard peptide coupling conditions known to those skilled in the art and widely available in the literature will provide compounds of Formula (9) and (12), respectively. An acid of Formula (9) may be further modified to an imide of Formula (10) using standard peptide coupling conditions including the use of 1,1'-carbonyldiimidazole (CDI) as the coupling agent.

Scheme 2

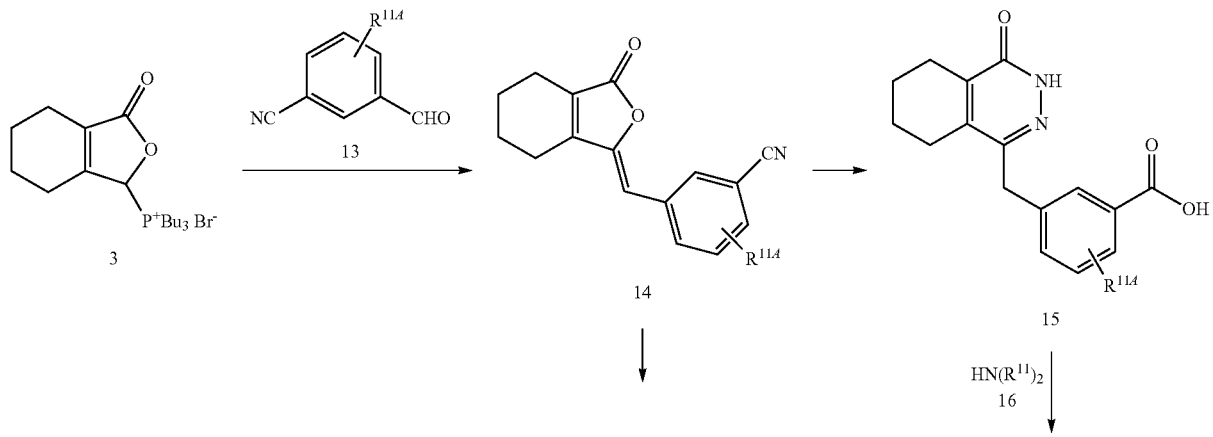

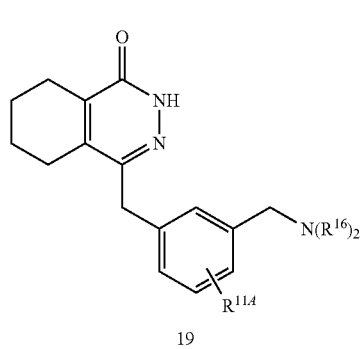

19

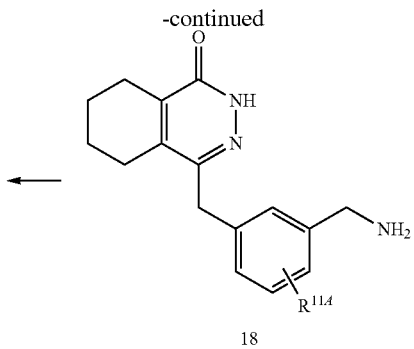

18

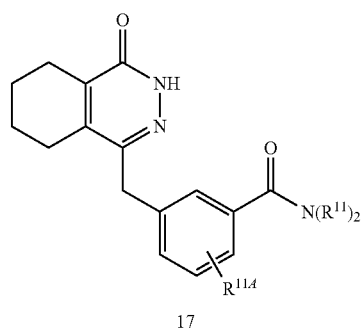

17

Alternatively, as shown in Scheme 2, the phosphonium salt (3) can be reacted with a cyanobenzaldehyde of Formula (13) to provide a lactone of Formula (14). The reaction is typically conducted under basic conditions in a solvent such as but not limited to dichloromethane at room temperature. Hydrolysis of the nitrile of Formula (14) to the corresponding acid, followed by addition of hydrazine will provide the tetrahydrophthalazinone of Formula (15). The hydrolysis step is typically conducted with an aqueous base such as but not limited to sodium hydroxide at elevated temperatures. The second step is also conducted under aqueous conditions at elevated temperatures. Coupling the acid of Formula (15) with an amine of Formula (16), wherein each $R^{11}$ is as described in Formula I herein or is H or is a heterocyclic amine $R^{14}$, under standard peptide coupling conditions known to those skilled in the art and widely available in the literature, will provide an amide of Formula (17). Alternatively, a compound of Formula (14) can be converted to a tetrahydrophthalazinone using hydrazine as previously described, followed by reduction to the primary amine of Formula (18) under standard Raney-nickel reduction conditions. Treatment of compounds of Formula (18) under standard reductive amination conditions with an aldehyde $R^{16}$CHO or ketone $R^{16}$C(O)$R^{16}$ and then optionally with a second aldehyde $R^{16}$CHO or ketone $R^{16}$C(O)$R^{16}$, will provide secondary or tertiary amines of Formula (19) (wherein each $R^{16}$ can be H or as defined in Formula (I)).

Scheme 3

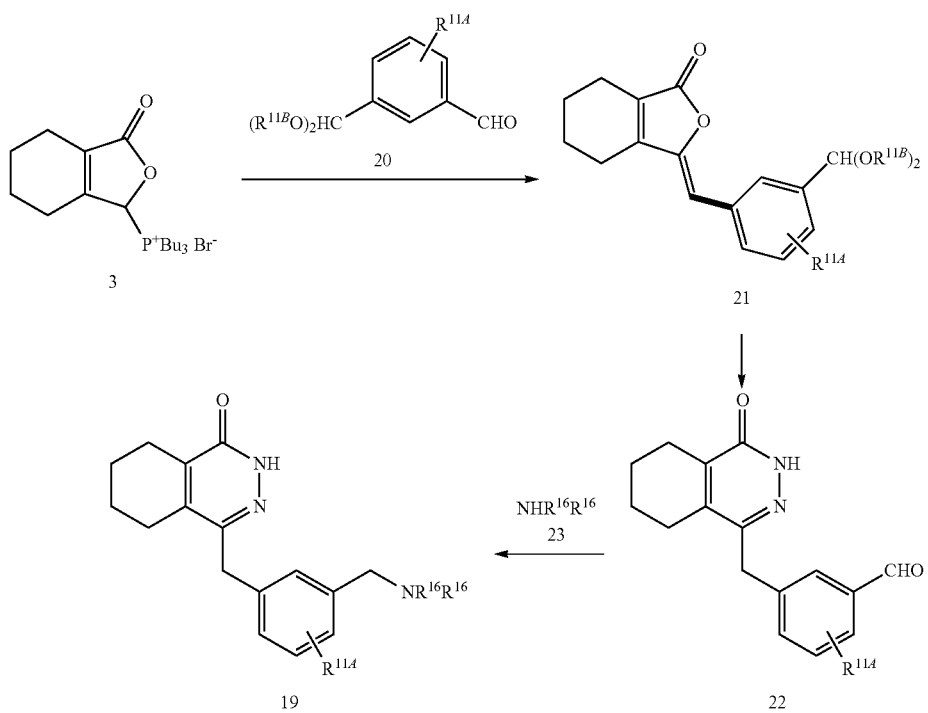

In a manner similar to the procedure described in Scheme I, the phosphonium salt (3) can be reacted with a benzaldehyde of Formula (20), wherein $R^{11B}$ is alkyl such as but not limited to ethyl and $R^{11A}$ is as previously defined in Scheme 1. Reaction of a compound of Formula (21) with hydrazine as described in Scheme 1, followed by hydrolysis using an aqueous acid such as but not limited to sulfuric acid will provide a compound of Formula (22). The reaction is typically performed at elevated temperatures in a solvent such as but not limited tot ethanol. Reaction of a compound of Formula (22) with an amine of Formula (23) under reductive amination conditions known to those skilled in the art and widely available in the literature will provide a tetrahydrophthalazinone of Formula (19).

Scheme 4

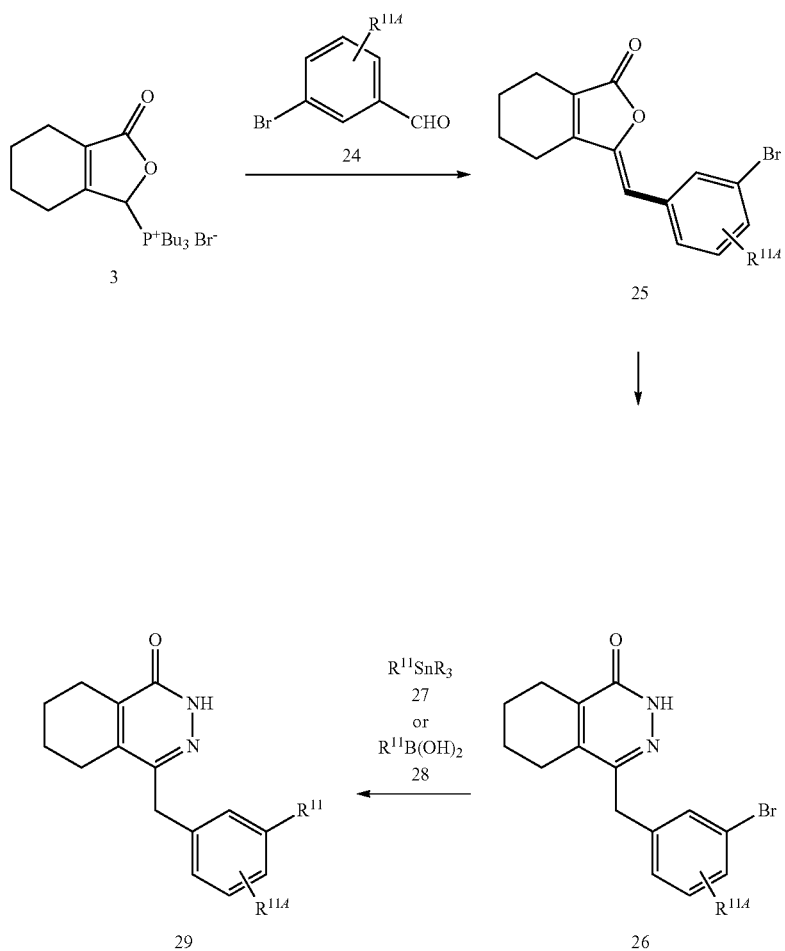

As shown in Scheme 4, the phosphonium salt (3) can be reacted with a bromobenzaldehyde of Formula (24) to provide a compound of Formula (25) using the conditions described in Scheme 1. Reaction of a compound of Formula (25) with hydrazine as described in Scheme 1 will provide a tetrahydrophthalazinone of Formula (26), which can be coupled with stannane of Formula (27) or a borate of Formula (28) to provide a compound of Formula (29) wherein $R^{11}$ is a substituted or unsubstituted phenyl or heteroaryl. Coupling conditions include those known by those skilled in the art and widely available in the literature for Suzuki and Stille type couplings.

Scheme 5

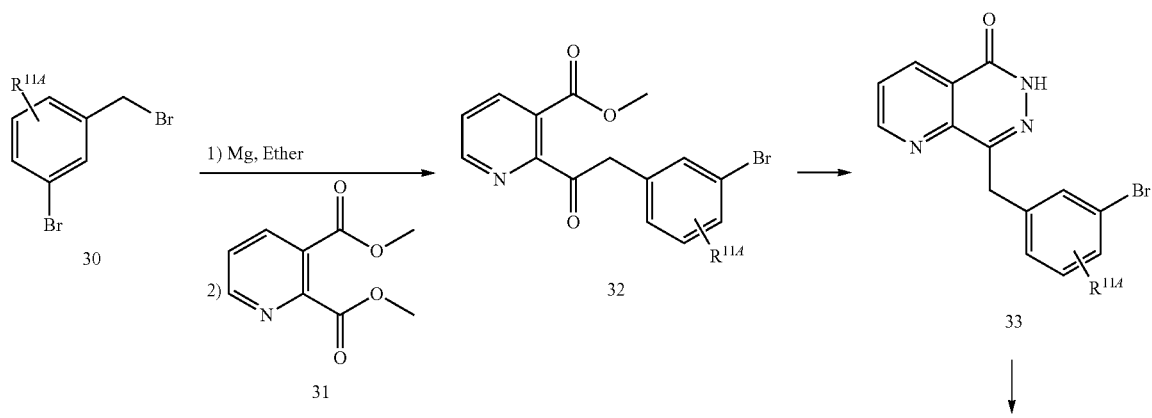

-continued

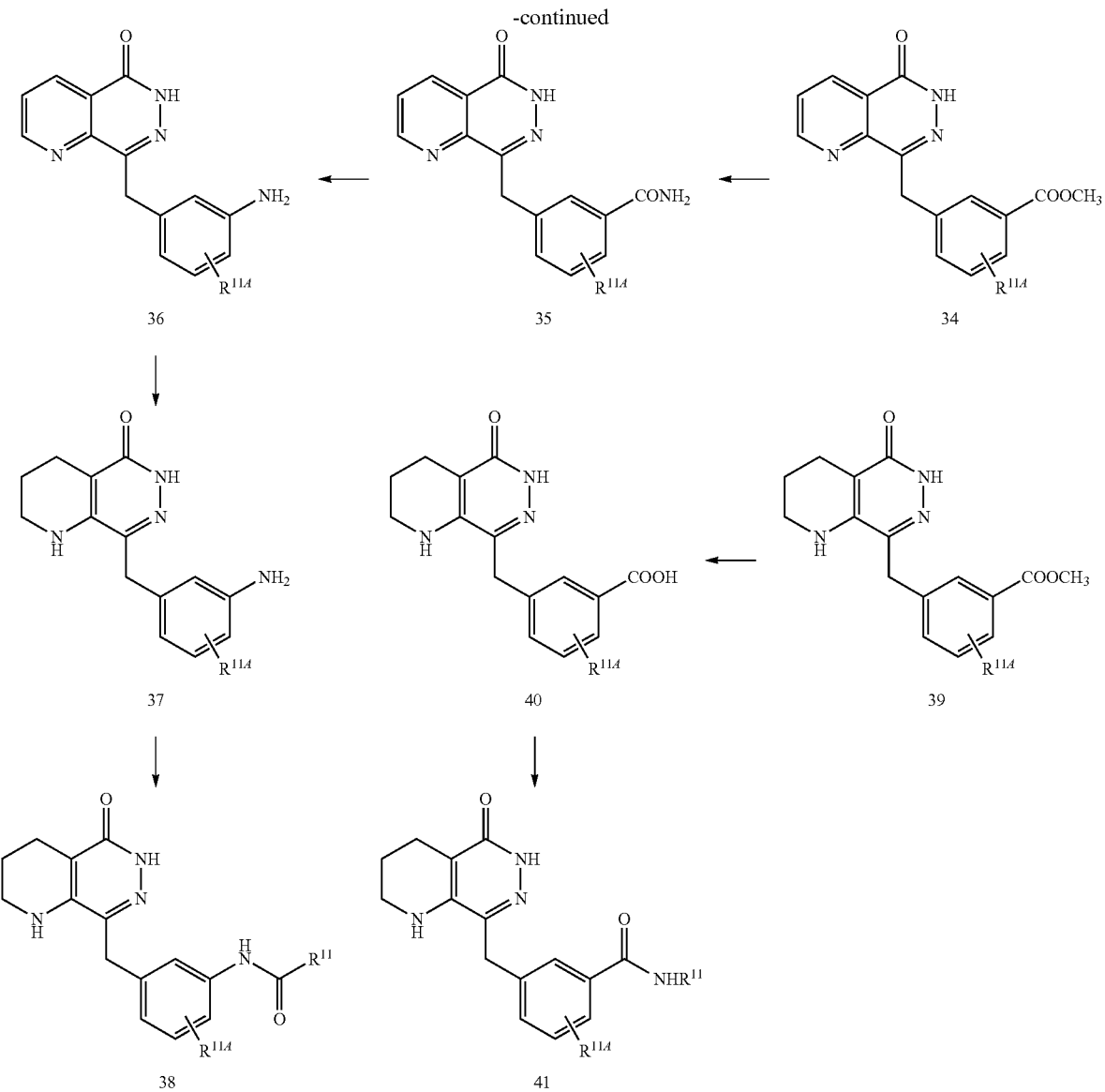

A benzylic bromide of Formula (30) wherein $R^{11}$ is as described herein, can be converted to a Grignard reagent and then added to a diester (31) to give a keto-ester of Formula (32) as shown in Scheme 5. The addition of the Grignard reagent is typically performed at cold temperatures, before warming up the reaction to room temperature. The reaction is typically performed in a solvent such as but not limited to tetrahydrofuran, ether and the like, or mixtures thereof. The Grignard reagent may be purchased commercially or prepared from Mg using standard conditions available in the literature. The addition of hydrazine to a compound of Formula (32) under conditions described in Scheme I at room temperature will provide a phthalazinone of Formula (33). The bromide can be converted to an ester of Formula (34) under palladium catalyzed carboxylation conditions. The transformation typically requires the use of a palladium catalyst and a base, such as but not limited to triethylamine, in addition to carbon monoxide and methanol. Typical palladium catalysts include [1,1'-bis(diphenylphosphino)ferrocene]dichloropalladium(II) dichloromethane and the like.

The reaction is typically conducted at elevated temperatures and may require the use of a solvent such as but not limited to N,N-dimethylformamide. The ester of Formula (34) can be converted to a primary amide of Formula (35) using ammonia, followed by a Hoffman rearrangement with bromine and aqueous potassium hydroxide to provide an aniline of Formula (36). The first step typically requires an elevated temperature, and the second step typically requires a decreased temperature for the additions, followed by heating. The pyridine ring can be reduced under catalytic conditions, such as but not limited to the use of hydrogen gas and platinum on carbon to provide a compound of Formula (37). Amide formation using either an acid chloride of Formula $R^{11}C(O)Cl$ or an acid of Formula $R^{11}C(O)OH$ under standard peptide coupling conditions known to those skilled in the art and widely available in the literature will provide compounds of Formula (38). Alternatively, an ester of Formula (34) can be reduced to a compound of Formula (39) using the conditions described above, followed by hydrolysis to provide an acid of Formula (40). Typical hydrolysis conditions include but are not limited to using an aqueous base such as lithium hydroxide at elevated temperatures. Amide formation using a primary or secondary amine of Formula $NH_2R^{11}$ or $NH(R^{11})_2$ employing standard peptide coupling conditions known to those skilled in the art and widely available in the literature, will provide an amide of Formula (41).

The following examples are presented to provide what is believed to be the most useful and readily understood description of procedures and conceptual aspects of this invention. The exemplified compounds were named using ACD/ChemSketch Version 5.06 (5 Jun. 2001, Advanced Chemistry Development Inc., Toronto, Ontario), except for Examples 160, 320 and 487, which were named using ChemDraw Ver. 9.0.5 (CambridgeSoft, Cambridge, Mass.). Intermediates were named using IUPAC standards.

Example 1

2-fluoro-5-((4-oxo-3,4,5,6,7,8-hexahydrophthalazin-1-yl)methyl)benzoic acid

Example 1A 3-hydroxy-4,5,6,7-tetrahydro-2-benzofuran-1(3H)-one

To a solution of 1-cyclohexene-1,2-dicarboxylic anhydride (25.2 g) in tetrahydrofuran (125 mL) at 0° C. was added sodium borohydride (1.51 g). The mixture was warmed to ambient temperature for 30 minutes, heated at reflux for 5 hours, cooled, treated with 1N hydrochloric acid and concentrated. The concentrate was partitioned between ethyl acetate and brine, and the organic layer was washed with brine and water and concentrated. The concentrate was purified by flash chromatography with 50% ethyl acetate in hexane.

Example 1B tributyl(3-oxo-1,3,4,5,6,7-hexahydro-2-benzofuran-1-yl)phosphonium bromide A solution of EXAMPLE 1A (3 g) in acetic acid (10 mL) at ambient temperature was treated with tri-n-butyl phosphine (4.81 mL) and 33% hydrobromic acid in acetic acid (3.34 mL), heated at reflux for 21 hours, cooled and concentrated. The concentrate was purified by flash chromatography on silica gel with 10% methanol in dichloromethane.

Example 1C 2-fluoro-5-((3-oxo-4,5,6,7-tetrahydroisobenzofuran-1(3H)-ylidene)methyl)benzonitrile To a solution of EXAMPLE 1B (3.05 g) in dichloromethane (30 mL) was added 2-fluoro-5-formylbenzonitrile (1.08 g) and triethylamine (1.02 mL). The mixture was stirred at ambient temperature for 16 hours and concentrated. The concentrate was partitioned between ethyl acetate and brine. The organic layer was washed with brine and concentrated. The concentrate was purified by flash chromatography on silica gel with 50% ethyl acetate in hexane.

Example 1D 2-fluoro-5-((4-oxo-3,4,5,6,7,8-hexahydrophthalazin-1-yl)methyl)benzoic acid To a suspension of EXAMPLE 1C (1.46 g) in water (15 mL) was added 50% sodium hydroxide. The mixture was heated at 90° C. for 1 hour. After cooling to 70° C., hydrazine monohydrate (0.54 mL) was added, and the solution was stirred at 70° C. for 17 hours. The solution was cooled to ambient temperature and brought to pH 4 with 6N hydrochloric acid. The precipitate was filtered, washed with water and dried. $^1$H NMR (DMSO-$d_6$) δ 1.55-1.69 (m, 4H), 2.31-2.42 (m, 4H), 3.93 (s, 2H), 7.24 (dd, J=10.8, 8.5 Hz, 1H), 7.40-7.48 (m, 1H), 7.68 (dd, J=6.9, 2.2 Hz, 1H), 12.61 (s, 1H), 13.22 (brs, 1H).

Example 2

4-(3-amino-4-fluorobenzyl)-5,6,7,8-tetrahydrophthalazin-1(2H)-one

Example 2A 3-(4-fluoro-3-nitrobenzylidene)-4,5,6,7-tetrahydroisobenzofuran-1(3H)-one This example was prepared as described in EXAMPLE 1C by substituting 4-fluoro-3-nitrobenzaldehyde for 2-fluoro-5-formylbenzonitrile.

Example 2B 3-(3-amino-4-fluorobenzylidene)-4,5,6,7-tetrahydroisobenzofuran-1(3H)-one A solution of EXAMPLE 2A (2.25 g) and ammonium chloride (0.83 g) in ethanol (35 mL) and water (25 mL) at 70° C. was treated with iron powder (4.35 g), stirred for 3 hours and filtered through diatomaceous earth (CELITE®, World Minerals, Santa Barbara, Calif.) with hot ethanol. The filtrate was concentrated, and the concentrate was stirred with water for 30 minutes and filtered. The solid was washed with water and dried.

Example 2C 4-(3-amino-4-fluorobenzyl)-5,6,7,8-tetrahydrophthalazin-1(2H)-one

To a solution of EXAMPLE 2B (1.42 g) in ethanol (10 mL) was added hydrazine monohydrate (0.27 mL). The mixture stirred at reflux for 1 hour, cooled to 0° C., and filtered. The solid was washed with water and dried. $^1$H NMR (CD$_3$OD) δ 1.63-1.75 (m, 4H), 2.36-2.45 (m, 2H), 2.46-2.53 (m, 2H), 3.84 (s, 2H), 6.42-6.49 (m, 1H), 6.64 (dd, J=8.6, 2.2 Hz, 1H), 6.86 (dd, J=11.2, 8.1 Hz, 1H).

Example 3

4-((2-fluoro-5-((4-oxo-3,4,5,6,7,8-hexahydrophthalazin-1-yl)methyl)phenyl)amino)-4-oxobutanoic acid To a solution of EXAMPLE 2 (872 mg) in acetonitrile was added succinic anhydride (370 mg). The mixture was heated at reflux for 17 hours, cooled and concentrated. The concentrate was purified by HPLC (Zorbax® C-18 ODS packing material [Agilent Technologies, Santa Clara, Calif.], 0-100% acetonitrile/water with 0.1% trifluoroacetic acid). $^1$H NMR (DMSO-$d_6$) δ 1.53-1.66 (m, 4H), 2.30-2.43 (m, 4H), 2.55-2.67 (m, 2H), 3.26-3.31 (m, 2H), 3.85 (s, 2H), 6.85-6.99 (m, 1H), 7.15 (dd, J=10.8, 8.5 Hz, 1H), 7.74 (d, J=6.4 Hz, 1H), 9.70 (brs, 1H), 12.09 (brs, 1H), 12.61 (s, 1H).

Example 4

1-(2-fluoro-5-((4-oxo-3,4,5,6,7,8-hexahydrophthalazin-1-yl)methyl)phenyl)pyrrolidine-2,5-dione To EXAMPLE 3 (905 mg) in dichloromethane (30 mL) and N,N-dimethylformamide (6 mL) was added 1,1'-carbonyldiimidazole (785 mg). The mixture was stirred at ambient temperature for 3 hours and concentrated. The concentrate was purified by HPLC (Zorbax® C-18 ODS packing material [Agilent Technologies, Santa Clara, Calif.], 0-100% acetonitrile/water with 0.1% trifluoroacetic acid). $^1$H NMR (DMSO-$d_6$): δ 1.57-1.69 (m, 4H), 2.32-2.42 (m, 4H), 2.78-2.89 (m, 4H), 3.93 (s, 2H), 7.09-7.13 (m, 1H), 7.32-7.33 (m, 1H), 7.34 (d, J=1.2 Hz, 1H), 12.62 (s, 1H).

Example 5

4-(3-(1,4-diazepan-1-ylcarbonyl)-4-fluorobenzyl)-5,6,7,8-tetrahydrophthalazin-1(2H)-one

Example 5A tert-butyl 4-(2-fluoro-5-((4-oxo-3,4,5,6,7,8-hexahydrophthalazin-1-yl)methyl)benzoyl)-1,4-diazepane-1-carboxylate To EXAMPLE 1 (294 mg) in 1:1 N,N-dimethylformamide/pyridine (6 mL) was added 1,1'-carbonyldiimidazole (166 mg). The mixture was stirred at ambient temperature for 30 minutes, and tert-butyl 1-homopiperazine carboxylate (189 μL) was added. The mixture was stirred for 18 hours and concentrated. The concentrate was purified by flash chromatography on silica gel with 5% methanol in ethyl acetate.

Example 5B 4-(3-(1,4-diazepan-1-ylcarbonyl)-4-fluorobenzyl)-5,6,7,8-tetrahydrophthalazin-1(2H)-one To a solution of EXAMPLE 5A (330 mg) in dichloromethane (8 mL) at 0° C. was added trifluoroacetic acid (8 mL). The solution was warmed to ambient temperature, and acetonitrile was added. The mixture was concentrated. The concentrate was purified by HPLC (Zorbax® C-18 ODS packing material [Agilent Technologies, Santa Clara, Calif.], 0-100% acetonitrile/water with 0.1% trifluoroacetic acid). The product was dissolved in methanol/dichloromethane and treated with 1M hydrochloric acid in diethyl ether and filtered to give the title compound as the hydrochloride salt. $^1$H NMR (CD$_3$OD) δ 1.70-1.76 (m, 4H), 2.02-2.11 (m, 2H), 2.52 (d, J=27.5 Hz, 4H), 3.32-3.36 (m, 2H), 3.40-3.46 (m, 2H), 3.51 (t, J=6.1 Hz, 2H), 3.95-4.01 (m, 2H), 4.06 (s, 2H), 7.19 (t, J=9.0 Hz, 1H), 7.29-7.34 (m, 1H), 7.36-7.41 (m, 1H).

Example 6

4-(3-(aminomethyl)-4-fluorobenzyl)-5,6,7,8-tetrahydrophthalazin-1(2H)-one

Example 6A

This example was prepared as described in EXAMPLE 2C by substituting EXAMPLE 1C for EXAMPLE 2B.

Example 6B 4-(3-(aminomethyl)-4-fluorobenzyl)-5,6,7,8-tetrahydrophthalazin-1(2H)-one To a solution of EXAMPLE 6A (1.5 g) in 20% ammonia in methanol (150 mL) was added Raney nickel (15 g). The mixture was shaken under hydrogen (60 psi) at ambient temperature for 2 hours, filtered, and concentrated. The concentrate was purified by HPLC (Zorbax® C-18 ODS packing material [Agilent Technologies, Santa Clara, Calif.], 0-100% acetonitrile/water with 0.1% trifluoroacetic acid) to give the title compound as the trifluoroacetate salt. $^1$H NMR (CD$_3$OD) δ1.55-1.65 (m, 4H), 2.33-2.41 (m, 4H), 3.90 (s, 2H), 4.04 (s, 2H), 7.21-7.25 (m, 1H), 7.27-7.29 (m, 1H), 7.31 (d, J=7.0 Hz, 1H), 8.20-8.27 (brs, 2H).

Example 7

4-(3-((dimethylamino)methyl)-4-fluorobenzyl)-5,6,7,8-tetrahydrophthalazin-1(2H)-one To a solution of EXAMPLE 6 (75 mg) in methanol (8 mL) was added 37 wt % formaldehyde in water (39 μL) and triethylamine (36 μL). The solution was stirred at ambient temperature for 1 hour. Sodium cyanoborohydride (49 mg) and zinc chloride (35 mg) were added, and the mixture was stirred for 60 hours and was concentrated. The concentrate was dissolved in trifluoroacetic acid/methanol and purified by HPLC (Zorbax® C-18 ODS packing material [Agilent Technologies, Santa Clara, Calif.], 0-100% acetonitrile/water with 0.1% trifluoroacetic acid). The product was dissolved in methanol/dichloromethane and treated with 1M hydrochloric acid in diethyl ether to give the title compound as the hydrochloride salt. $^1$H NMR (CD$_3$OD) δ1.68-1.80 (m, 4H), 2.50-2.60 (m, 4H), 2.88 (s, 6H), 4.10 (s, 2H), 4.39 (s, 2H), 7.22-7.27 (m, 1H), 7.40-7.44 (m, 1H), 7.46 (dd, J=6.9, 2.0 Hz, 1H).

Example 8

4-(4-fluoro-3-((isopropylamino)methyl)benzyl)-5,6,7,8-tetrahydrophthalazin-1(2H)-one This example was prepared as the hydrochloride salt as described in EXAMPLE 7 by substituting acetone for formaldehyde. $^1$H NMR (CD$_3$OD) δ1.39 (d, J=6.7 Hz, 6H), 1.68-1.77 (m, 4H), 2.43-2.59 (m, 4H), 3.41-3.50 (m, 1H), 4.05 (s, 2H), 4.24 (s, 2H), 7.18-7.24 (m, 1H), 7.35-7.38 (m, 1H), 7.38-7.42 (m, 1H).

Example 9

4-(3-((cyclohexylamino)methyl)-4-fluorobenzyl)-5,6,7,8-tetrahydrophthalazin-1(2H)-one This example was prepared as the hydrochloride salt as described in EXAMPLE 7 by substituting cyclohexanone for formaldehyde. $^1$H NMR (CD$_3$OD) δ 1.32-1.46 (m, 4H), 1.68-1.81 (m, 6H), 1.84-1.94 (m, 2H), 2.13-2.22 (m, 2H), 2.43-2.61 (m, 4H), 3.08-3.18 (m, 1H), 4.07 (s, 2H), 4.26 (s, 2H), 7.18-7.23 (m, 1H), 7.35-7.39 (m, 1H), 7.40-7.43 (m, 1H).

Example 10

4-(4-fluoro-3-((tetrahydro-2H-pyran-4-ylamino)methyl)benzyl)-5,6,7,8-tetrahydrophthalazin-1(2H)-one This example was prepared as the hydrochloride salt as described in EXAMPLE 7 by substituting tetrahydro-4H- pyran-4-one for formaldehyde. ¹H NMR (CD₃OD) δ 1.66-1.76 (m, 6H), 2.04-2.14 (m, 2H), 2.40-2.57 (m, 4H), 3.40-3.51 (m, 3H), 4.03 (s, 2H), 4.05 (d, J=4.6 Hz, 2H), 4.29 (s, 2H), 7.18-7.25 (m, 1H), 7.36-7.39 (m, 1H), 7.40 (d, J=1.8 Hz, 1H).

Example 11

4-(4-fluoro-3-((methyl((1-methylpyrrolidin-3-yl)methyl)amino)methyl)benzyl)-5,6,7,8-tetrahydrophthalazin-1(2H)-one To a solution of EXAMPLE 6 (75 mg) in methanol (8 mL) was added 3-formyl-pyrrolidine-1-carboxylic acid tert-butyl ester (104 mg) and triethylamine (36 µL). The mixture was stirred at ambient temperature for 1 hour. Sodium cyanoborohydride (49 mg) and zinc chloride (35 mg) were added. The mixture was stirred for 60 hours and trifluoroacetic acid was added and the mixture stirred for one hour and was concentrated. The concentrate was dissolved in water/acetonitrile and was purified by HPLC (Zorbax® C-18 ODS packing material [Agilent Technologies, Santa Clara, Calif.], 0-100% acetonitrile/water with 0.1% trifluoroacetic acid). The residue was treated as described above with 37 wt % formaldehyde in water (39 µL), followed by treatment with 1M hydrochloric acid in diethyl ether to obtain the title compound as the HCl salt. ¹H NMR (CD₃OD) δ1.69-1.74 (m, 6H), 1.80-1.88 (m, 3H), 2.10-2.20 (m, 2H), 2.44-2.58 (m, 6H), 3.10 (dd, J=11.4, 7.5 Hz, 2H), 3.22-3.26 (m, 1H), 3.34-3.38 (m, 2H), 3.52-3.56 (m, 1H), 4.03 (s, 2H), 4.31 (s, 2H), 7.18-7.23 (m, 1H), 7.35-7.39 (m, 1H), 7.49 (dd, J=6.9, 2.0 Hz, 1H).

Example 12

4-(4-fluoro-3-((methyl(((2R)-1-methylpyrrolidin-2-yl)methyl)amino)methyl)benzyl)-5,6,7,8-tetrahydrophthalazin-1(2H)-one This example was prepared as the hydrochloride salt as described in EXAMPLE 11 by substituting N-(tert-butoxycarbonyl)-D-prolinal for 3-formyl-pyrrolidine-1-carboxylic acid tert-butyl ester. ¹H NMR (CD₃OD) δ 1.74-1.83 (m, 4H), 1.95-2.07 (m, 1H), 2.10-2.28 (m, 2H), 2.52-2.70 (m, 5H), 2.91 (s, 3H), 3.04 (s, 3H), 3.21-3.29 (m, 1H), 3.63-3.69 (m, 1H), 3.73-3.81 (m, 1H), 3.90-4.00 (m, 1H), 4.05-4.13 (m, 1H), 4.20 (s, 2H), 4.50-4.62 (m, 2H), 7.27 (t, J=9.1 Hz, 1H), 7.44-7.49 (m, 1H), 7.64 (d, J=5.2 Hz, 1H).

Example 13

4-(3-((cyclopropylamino)methyl)benzyl)-5,6,7,8-tetrahydrophthalazin-1(2H)-one

Example 13A

3-(3-(diethoxymethyl)benzylidene)-4,5,6,7-tetrahydroisobenzofuran-1(3H)-one

This example was prepared as described in EXAMPLE 1C by substituting 3-(diethoxymethyl)benzaldehyde for 2-fluoro-5-formylbenzonitrile.

Example 13B

4-(3-(diethoxymethyl)benzyl)-5,6,7,8-tetrahydrophthalazin-1(2H)-one

This example was prepared as described in EXAMPLE 2C by substituting EXAMPLE 13A for EXAMPLE 2B.

Example 13C

3-((4-oxo-3,4,5,6,7,8-hexahydrophthalazin-1-yl)methyl)benzaldehyde

To a solution of EXAMPLE 13B (681 mg) in a 1:1 mixture of ethanol/water (20 mL) was added concentrated sulfuric acid (0.4 mL). The mixture was refluxed for 16 hours. The mixture was cooled and concentrated, and the concentrate was triturated with saturated sodium bicarbonate. The solid was filtered, washed with water and dried.

Example 13D

4-(3-((cyclopropylamino)methyl)benzyl)-5,6,7,8-tetrahydrophthalazin-1(2H)-one A solution of EXAMPLE 13C (80 mg) and cyclopropylamine (51 mg) in methanol (8 mL) was stirred at ambient temperature for 1 hour. Sodium cyanoborohydride (57 mg) was added, and the solution was stirred for 18 hours and was concentrated. The concentrate was dissolved in methanol/trifluoroacetic acid and was purified by HPLC (Zorbax® C-18 ODS packing material [Agilent Technologies, Santa Clara, Calif.], 0-100% acetonitrile/water with 0.1% trifluoroacetic acid). The product was dissolved in methanol/dichloromethane and was treated with 1M hydrochloric acid in diethyl ether and concentrated to give the title compound as the hydrochloride salt. ¹H NMR (CD₃OD) δ 0.82-0.92 (m, 4H), 1.65-1.77 (m, 4H), 2.41-2.60 (m, 4H), 2.69-2.79 (m, 1H), 4.11 (s, 2H), 4.28 (s, 2H), 7.31 (d, J=6.7 Hz, 1H), 7.34-7.40 (m, 2H), 7.41-7.45 (m, 1H).

Example 14

4-(3-((isopropylamino)methyl)benzyl)-5,6,7,8-tetrahydrophthalazin-1(2H)-one

This example was prepared as the hydrochloride salt as described in EXAMPLE 13 by substituting isopropylamine for cyclopropylamine. ¹H NMR (CD₃OD) δ1.38 (d, J=6.7 Hz, 6H), 1.68-1.79 (m, 4H), 2.41-2.65 (m, 4H), 3.38-3.48 (m, 1H), 4.12 (s, 2H), 4.17 (s, 2H), 7.31 (d, J=7.1 Hz, 1H), 7.35-7.38 (m, 1H), 7.38-7.41 (m, 1H), 7.41-7.46 (m, 1H).

Example 15

4-(3-(morpholin-4-ylmethyl)benzyl)-5,6,7,8-tetrahydrophthalazin-1(2H)-one

This example was prepared as the hydrochloride salt as described in EXAMPLE 13 by substituting morpholine for cyclopropylamine. ¹H NMR (CD₃OD) δ1.67-1.78 (m, 4H), 2.39-2.57 (m, 4H), 3.13-3.24 (m, 2H), 3.32-3.39 (m, 2H), 3.71-3.80 (m, 2H), 4.03 (dd, J=13.3, 3.2 Hz, 2H), 4.08 (s, 2H), 4.34 (s, 2H), 7.37 (d, J=6.7 Hz, 1H), 7.39-7.42 (m, 1H), 7.41-7.44 (m, 1H), 7.44-7.48 (m, 1H).

Example 16

4-(3-(pyrrolidin-1-ylmethyl)benzyl)-5,6,7,8-tetrahydrophthalazin-1(2H)-one

This example was prepared as the hydrochloride salt as described in EXAMPLE 13 by substituting pyrrolidine for cyclopropylamine. ¹H NMR (CD₃OD) δ1.67-1.79 (m, 4H), 1.95-2.07 (m, 2H), 2.11-2.24 (m, 2H), 2.44-2.65 (m, 4H), 3.09-3.26 (m, 2H), 3.41-3.54 (m, 2H), 4.15 (s, 2H), 4.35 (s, 2H), 7.32-7.37 (m, 1H), 7.39-7.47 (m, 3H).

Example 17

4-(3-((cyclohexylamino)methyl)benzyl)-5,6,7,8-tetrahydrophthalazin-1(2H)-one

This example was prepared as the hydrochloride salt as described in EXAMPLE 13 by substituting cyclohexylamine for cyclopropylamine. $^1$H NMR (CD$_3$OD) δ1.20-1.27 (m, 1H), 1.31-1.45 (m, 4H), 1.66-1.78 (m, 5H), 1.85-1.93 (m, 2H), 2.12-2.20 (m, 2H), 2.45-2.60 (m, 4H), 3.08 (dd, J=14.6, 7.6 Hz, 1H), 4.11 (s, 2H), 4.19 (s, 2H), 7.32 (d, J=7.0 Hz, 1H), 7.34-7.38 (m, 1H), 7.38-7.42 (m, 1H), 7.41-7.45 (m, 1H).

Example 18

4-(3-((methylamino)methyl)benzyl)-5,6,7,8-tetrahydrophthalazin-1(2H)-one

This example was prepared as the hydrochloride salt as described in EXAMPLE 13 by substituting 2M methylamine in methanol for cyclopropylamine. $^1$H NMR (CD$_3$OD) δ1.69-1.78 (m, 4H), 2.45-2.59 (m, 4H), 2.70 (s, 3H), 4.13 (s, 2H), 4.16 (s, 2H), 7.30-7.33 (m, 1H), 7.33-7.37 (m, 1H), 7.37-7.40 (m, 1H), 7.43 (t, J=7.4 Hz, 1H).

Example 19

4-(3-((ethylamino)methyl)benzyl)-5,6,7,8-tetrahydrophthalazin-1(2H)-one

This example was prepared as the hydrochloride salt as described in EXAMPLE 13 by substituting 2-Methylamine in methanol for cyclopropylamine. $^1$H NMR (CD$_3$OD) δ1.33 (t, J=7.2 Hz, 3H), 1.66-1.80 (m, 4H), 2.42-2.62 (m, 4H), 3.10 (q, J=7.4 Hz, 2H), 4.13 (s, 2H), 4.16 (s, 2H), 7.31 (d, J=7.1 Hz, 1H), 7.34-7.37 (m, 1H), 7.38-7.40 (m, 1H), 7.41-7.45 (m, 1H).

Example 20

4-(3-((4-methylpiperidin-1-yl)methyl)benzyl)-5,6,7,8-tetrahydrophthalazin-1(2H)-one This example was prepared as the hydrochloride salt as described in EXAMPLE 13 by substituting 4-methylpiperidine for cyclopropylamine. $^1$H NMR (CD$_3$OD) δ0.99 (d, J=6.4 Hz, 3H), 1.39-1.54 (m, 2H), 1.67-1.76 (m, 5H), 1.83-1.95 (m, 2H), 2.44-2.63 (m, 4H), 2.92-3.04 (m, 2H), 3.35-3.46 (m, 2H), 4.15 (s, 2H), 4.26 (s, 2H), 7.34-7.37 (m, 1H), 7.40-7.44 (m, 2H), 7.44-7.47 (m, 1H).

Example 21

4-(3-(((2-(4-(trifluoromethyl)phenyl)ethyl)amino)methyl)benzyl)-5,6,7,8-tetrahydrophthalazin-1(2H)-one This example was prepared as the hydrochloride salt as described in EXAMPLE 13 by substituting 3-(trifluoromethyl)phenethylamine for cyclopropylamine. $^1$H NMR (CD$_3$OD) δ1.64-1.72 (m, 4H), 2.40-2.57 (m, 4H), 3.06-3.14 (m, 2H), 3.27-3.29 (m, 2H), 4.07 (s, 2H), 4.22 (s, 2H), 7.33 (d, J=7.3 Hz, 1H), 7.35-7.38 (m, 1H), 7.38-7.42 (m, 1H), 7.44 (t, J=7.5 Hz, 1H), 7.55 (d, J=0.9 Hz, 1H), 7.55-7.58 (m, 1H), 7.59 (d, J=5.2 Hz, 1H), 7.60-7.62 (m, 1H).

Example 22

4-(3-((cyclohexyl(methyl)amino)methyl)benzyl)-5,6,7,8-tetrahydrophthalazin-1(2H)-one This example was prepared as the hydrochloride salt as described in EXAMPLE 13 by substituting N-methyl cyclohexylamine for cyclopropylamine. $^1$H NMR (CD$_3$OD) δ1.23-1.40 (m, 3H), 1.53-1.65 (m, 2H), 1.67-1.79 (m, 5H), 1.90-2.00 (m, 2H), 2.02-2.18 (m, 2H), 2.40-2.49 (m, 2H), 2.49-2.58 (m, 2H), 2.71 (s, 3H), 3.16-3.28 (m, 1H), 4.07 (s, 2H), 4.17 (d, J=12.9 Hz, 1H), 4.45 (d, J=13.2 Hz, 1H), 7.34-7.36 (m, 1H), 7.37-7.39 (m, 1H), 7.41 (s, 1H), 7.43-7.49 (m, 1H).

Example 23

4-(3-((2-ethylpyrrolidin-1-yl)methyl)benzyl)-5,6,7,8-tetrahydrophthalazin-1(2H)-one This example was prepared as the hydrochloride salt as described in EXAMPLE 13 by substituting 2-ethylpyrrolidine for cyclopropylamine. $^1$H NMR (CD$_3$OD) δ0.94 (t, J=7.5 Hz, 3H), 1.52-1.63 (m, 1H), 1.69-1.77 (m, 4H), 1.78-1.87 (m, 2H), 1.91-2.04 (m, 1H), 2.05-2.17 (m, 1H), 2.31-2.44 (m, 1H), 2.45-2.64 (m, 4H), 3.19-3.28 (m, 1H), 3.34-3.47 (m, 2H), 4.15 (s, 2H), 4.21 (d, J=12.9 Hz, 1H), 4.50 (d, J=13.2 Hz, 1H), 7.33-7.38 (m, 1H), 7.40-7.44 (m, 2H), 7.44-7.48 (m, 1H).

Example 24

4-(4-((cyclopropylamino)methyl)benzyl)-5,6,7,8-tetrahydrophthalazin-1(2H)-one

Example 24A 3-(4-(diethoxymethyl)benzylidene)-4,5,67-tetrahydroisobenzofuran-1(3H)-one This example was prepared as described in EXAMPLE 1C by substituting 4-(diethoxymethyl)benzaldehyde for 2-fluoro-5-formylbenzonitrile.

Example 24B 4-(4-(diethoxymethyl)benzyl)-5,6,7,8-tetrahydrophthalazin-1(2H)-one

This example was prepared as described in EXAMPLE 2C by substituting EXAMPLE 24A for EXAMPLE 2B.

Example 24C 4-((4-oxo-3,4,5,6,7,8-hexahydrophthalazin-1-yl)methyl)benzaldehyde

This example was prepared as described in EXAMPLE 13C by substituting EXAMPLE 24B for EXAMPLE 13B.

Example 24D 4-(4-((cyclopropylamino)methyl)benzyl)-5,6,7,8-tetrahydrophthalazin-1(2H)-one This example was prepared as the hydrochloride salt as described in EXAMPLE 13D by substituting EXAMPLE

Example 25

4-(4-((isopropylamino)methyl)benzyl)-5,6,7,8-tetrahydrophthalazin-1(2H)-one

This example was prepared as the hydrochloride salt as described in EXAMPLE 13D by substituting EXAMPLE 24C for EXAMPLE 13C and 2-propylamine for cyclopropylamine. $^1$H NMR (CD$_3$OD) δ1.38 (d, J=6.4 Hz, 6H), 1.65-1.72 (m, 4H), 2.37-2.45 (m, 2H), 2.46-2.52 (m, 2H), 3.39-3.50 (m, 1H), 4.01 (s, 2H), 4.17 (s, 2H), 7.31 (d, J=8.3 Hz, 2H), 7.44 (d, J=8.0 Hz, 2H).

Example 26

4-(4-(morpholin-4-ylmethyl)benzyl)-5,6,7,8-tetrahydrophthalazin-1(2H)-one

This example was prepared as the hydrochloride salt as described in EXAMPLE 13D by substituting EXAMPLE 24C for EXAMPLE 13C and morpholine for cyclopropylamine. $^1$H NMR (CD$_3$OD) δ1.65-1.76 (m, 4H), 2.43-2.48 (m, 2H), 2.49-2.58 (m, 2H), 3.13-3.24 (m, 2H), 3.33-3.37 (m, 2H), 3.36-3.41 (m, 1H), 3.70-3.80 (m, 2H), 3.99-4.03 (m, 1H), 4.06 (s, 2H), 4.34 (s, 2H), 7.35 (d, J=8.0 Hz, 2H), 7.49 (d, J=8.0 Hz, 2H).

Example 27

4-(4-(pyrrolidin-1-ylmethyl)benzyl)-5,6,7,8-tetrahydrophthalazin-1(2H)-one

This example was prepared as the hydrochloride salt as described in EXAMPLE 13D by substituting EXAMPLE 24C for EXAMPLE 13C and pyrrolidine for cyclopropylamine. $^1$H NMR (CD$_3$OD) δ1.63-1.76 (m, 4H), 1.94-2.06 (m, 2H), 2.10-2.24 (m, 2H), 2.37-2.46 (m, 2H), 2.46-2.55 (m, 2H), 3.11-3.23 (m, 2H), 3.38-3.58 (m, 2H), 4.02 (s, 2H), 4.34 (s, 2H), 7.33 (d, J=7.7 Hz, 2H), 7.46 (d, J=8.0 Hz, 2H).

Example 28

4-(4-((cyclohexylamino)methyl)benzyl)-5,6,7,8-tetrahydrophthalazin-1(2H)-one

This example was prepared as the hydrochloride salt as described in EXAMPLE 13D by substituting EXAMPLE 24C for EXAMPLE 13C and cyclohexylamine for cyclopropylamine. $^1$H NMR (CD$_3$OD) δ1.21-1.29 (m, 1H), 1.33-1.43 (m, 4H), 1.64-1.75 (m, 5H), 1.86-1.93 (m, 2H), 2.13-2.21 (m, 2H), 2.37-2.44 (m, 2H), 2.49 (t, J=4.9 Hz, 2H), 3.05-3.16 (m, 1H), 4.01 (s, 2H), 4.18 (s, 2H), 7.30 (d, J=8.0 Hz, 2H), 7.43 (d, J=8.0 Hz, 2H).

Example 29

4-(4-((4-phenylpiperidin-1-yl)methyl)benzyl)-5,6,7,8-tetrahydrophthalazin-1(2H)-one This example was prepared as the hydrochloride salt as described in EXAMPLE 13D by substituting EXAMPLE 24C for EXAMPLE 13C and 4-phenylpiperidine for cyclopropylamine. $^1$H NMR (CD$_3$OD) δ1.64-1.76 (m, 4H), 1.93-2.03 (m, 2H), 2.05-2.15 (m, 2H), 2.40-2.49 (m, 2H), 2.48-2.55 (m, 2H), 2.81-2.94 (m, 1H), 3.10-3.23 (m, 2H), 3.54-3.64 (m, 2H), 4.04 (s, 2H), 4.33 (s, 2H), 7.19-7.22 (m, 1H), 7.24 (d, J=7.1 Hz, 2H), 7.28-7.33 (m, 2H), 7.36 (d, J=8.0 Hz, 2H), 7.51 (d, J=7.7 Hz, 2H).

Example 30

4-(4-((methylamino)methyl)benzyl)-5,6,7,8-tetrahydrophthalazin-1(2H)-one

This example was prepared as the hydrochloride salt as described in EXAMPLE 13D by substituting EXAMPLE 24C for EXAMPLE 13C and 2M methylamine in methanol for cyclopropylamine. $^1$H NMR (CD$_3$OD) δ1.64-1.73 (m, 4H), 2.38-2.44 (m, 2H), 2.47-2.54 (m, 2H), 2.71 (s, 3H), 4.02 (s, 2H), 4.15 (s, 2H), 7.31 (d, J=8.3 Hz, 2H), 7.43 (d, J=8.0 Hz, 2H).

Example 31

4-(4-((ethylamino)methyl)benzyl)-5,6,7,8-tetrahydrophthalazin-1(2H)-one

This example was prepared as the hydrochloride salt as described in EXAMPLE 13D by substituting EXAMPLE 24C for EXAMPLE 13C and 2-Methylamine in methanol for cyclopropylamine. $^1$H NMR (CD$_3$OD) δ61.32 (t, J=7.4 Hz, 3H), 1.64-1.72 (m, 4H), 2.37-2.44 (m, 2H), 2.45-2.52 (m, 2H), 3.10 (q, J=7.4 Hz, 2H), 4.01 (s, 2H), 4.15 (s, 2H), 7.30 (d, J=8.3 Hz, 2H), 7.43 (d, J=8.0 Hz, 2H).

Example 32

4-(4-((4-methylpiperidin-1-yl)methyl)benzyl)-5,6,7,8-tetrahydrophthalazin-1(2H)-one This example was prepared as the hydrochloride salt as described in EXAMPLE 13D by substituting EXAMPLE 24C for EXAMPLE 13C and 4-methylpiperidine for cyclopropylamine. $^1$H NMR (CD$_3$OD) δ0.99 (d, J=6.4 Hz, 3H), 1.33-1.48 (m, 2H), 1.66-1.75 (m, 5H), 1.85-1.95 (m, 2H), 2.40-2.48 (m, 2H), 2.48-2.57 (m, 2H), 2.90-3.05 (m, 2H), 3.44 (d, J=12.3 Hz, 2H), 4.04 (s, 2H), 4.25 (s, 2H), 7.33 (d, J=8.0 Hz, 2H), 7.46 (d, J=8.0 Hz, 2H).

Example 33

4-(4-(((2-(3-(trifluoromethyl)phenyl)ethyl)amino)methyl)benzyl)-5,6,7,8-tetrahydrophthalazin-1(2H)-one This example was prepared as the hydrochloride salt as described in EXAMPLE 13D by substituting EXAMPLE 24C for EXAMPLE 13C and 3-(trifluoromethyl)phenethylamine for cyclopropylamine. $^1$H NMR (CD$_3$OD) δ1.62-1.72 (m, 4H), 2.38-2.44 (m, 2H), 2.46-2.52 (m, 2H), 3.06-3.14 (m, 2H), 3.27-3.35 (m, 2H), 4.02 (s, 2H), 4.22 (s, 2H), 7.31 (d, J=8.3 Hz, 2H), 7.45 (d, J=8.3 Hz, 2H), 7.53-7.57 (m, 2H), 7.57-7.62 (m, 2H).

Example 34

4-(4-((cyclohexyl(methyl)amino)methyl)benzyl)-5,6,7,8-tetrahydrophthalazin-1(2H)-one This example was prepared as the hydrochloride salt as described in EXAMPLE 13D by substituting EXAMPLE 24C for EXAMPLE 13C and N-methylcyclohexylamine for cyclopropylamine. $^1$H NMR (CD$_3$OD) δ1.20-1.31 (m, 1H), 1.32-1.44 (m, 2H), 1.54-1.63 (m, 2H), 1.65-1.75 (m, 5H), 1.91-2.01 (m, 2H), 2.05-2.18 (m, 2H), 2.39-2.46 (m, 2H), 2.47-2.53 (m, 2H), 2.71 (s, 3H), 3.23-3.29 (m, 1H), 4.03 (s, 2H), 4.13 (d, J=13.2 Hz, 1H), 4.47 (d, J=13.2 Hz, 1H), 7.34 (d, J=8.3 Hz, 2H), 7.43-7.46 (m, 2H).

Example 35

4-(4-((2-methylpyrrolidin-1-yl)methyl)benzyl)-5,6,7,8-tetrahydrophthalazin-1(2H)-one This example was prepared as the hydrochloride salt as described in EXAMPLE 13D by substituting EXAMPLE 24C for EXAMPLE 13C and 2-methylpyrrolidine for cyclopropylamine. $^1$H NMR (CD$_3$OD) δ1.39 (d, J=6.7 Hz, 3H), 1.66-1.78 (m, 5H), 1.93-2.02 (m, 1H), 2.03-2.13 (m, 1H), 2.29-2.38 (m, 1H), 2.39-2.45 (m, 2H), 2.47-2.53 (m, 2H), 3.15-3.27 (m, 1H), 3.34-3.40 (m, 1H), 3.51-3.62 (m, 1H), 4.02 (s, 2H), 4.09-4.17 (m, 1H), 4.43-4.55 (m, 1H), 7.33 (d, J=8.0 Hz, 2H), 7.46 (d, J=8.3 Hz, 2H).

Example 36

4-(4-((4-methyl-1,4-diazepan-1-yl)methyl)benzyl)-5,6,7,8-tetrahydrophthalazin-1(2H)-one This example was prepared as the hydrochloride salt as described in EXAMPLE 13D by substituting EXAMPLE 24C for EXAMPLE 13C and 1-methylhomopiperazine for cyclopropylamine. $^1$H NMR (CD$_3$OD) δ1.68-1.79 (m, 4H), 2.29-2.42 (m, 2H), 2.46-2.53 (m, 2H), 2.53-2.62 (m, 2H), 2.97 (s, 3H), 3.35-3.44 (m, 1H), 3.47-3.65 (m, 2H), 3.67-3.96 (m, 5H), 4.11 (s, 2H), 4.46 (s, 2H), 7.35 (d, J=8.0 Hz, 2H), 7.59 (d, J=8.0 Hz, 2H).

Example 37

4-(3-((4-methyl-1,4-diazepan-1-yl)methyl)benzyl)-5,6,7,8-tetrahydrophthalazin-1(2H)-one This example was prepared as the hydrochloride salt as described in EXAMPLE 13D by substituting 1-methylhomopiperazine for cyclopropylamine. $^1$H NMR (CD$_3$OD) δ1.68-1.81 (m, 4H), 2.29-2.41 (m, 2H), 2.44-2.53 (m, 2H), 2.55-2.64 (m, 2H), 2.98 (s, 3H), 3.33-3.40 (m, 1H), 3.40-3.56 (m, 2H), 3.58-3.72 (m, 1H), 3.73-3.97 (m, 4H), 4.15 (s, 2H), 4.46 (s, 2H), 7.37 (d, J=7.7 Hz, 1H), 7.46 (t, J=7.8 Hz, 1H), 7.51 (d, J=6.1 Hz, 2H).

Example 38

4-(4-fluoro-3-pyrimidin-2-ylbenzyl)-5,6,7,8-tetrahydrophthalazin-1(2H)-one

Example 38A 3-(3-bromo-4-fluorobenzylidene)-4,5,6,7-tetrahydroisobenzofuran-1(3H)-one This example was prepared as described in EXAMPLE 1C by substituting 3-bromo-4-fluorobenzaldehyde for 2-fluoro-5-formylbenzonitrile.

Example 38B 4-(3-bromo-4-fluorobenzyl)-5,6,7,8-tetrahydrophthalazin-1(2H)-one

This example was prepared as described in EXAMPLE 2D by substituting EXAMPLE 38A for EXAMPLE 2B.

Example 38C 4-(4-fluoro-3-pyrimidin-2-ylbenzyl)-5,6,7,8-tetrahydrophthalazin-1(2H)-one To EXAMPLE 38B (75 mg) in N,N-dimethylformamide (8 mL) was added 2-tributylstannylpyrimidine (81 mg), tris(dibenzylidineacetone)dipalladium(0) (20 mg), tri-o-tolylphosphine (20 mg) and triethylamine (92 μL). The mixture was stirred at 70° C. for 17 hours. After cooling, the mixture was filtered, and the filtrate was concentrated. The concentrate was purified by HPLC (Zorbax® C-18 ODS packing material [Agilent Technologies, Santa Clara, Calif.], 0-100% acetonitrile/water with 0.1% trifluoroacetic acid). The product was dissolved in methanol/dichloromethane and treated with 1M hydrochloric acid in diethyl ether and concentrated to provide the title compound as the hydrochloride salt. $^1$H NMR (CD$_3$OD) δ1.69-1.78 (m, 4H), 2.48-2.60 (m, 4H), 4.11 (s, 2H), 7.27 (dd, J=10.8, 8.5 Hz, 1H), 7.43-7.50 (m, 1H), 7.61 (t, J=5.1 Hz, 1H), 7.87 (dd, J=7.1, 2.4 Hz, 1H), 9.01 (d, J=5.1 Hz, 2H).

Example 39

4-(4-fluoro-3-pyridin-3-ylbenzyl)-5,6,7,8-tetrahydrophthalazin-1(2H)-one

To EXAMPLE 38B (75 mg), 3-pyridineboronic acid (54 mg) and dichlorobis(triphenylphosphine)palladium (II) (28 mg) in 7:3:2 1,2-dimethoxyethane/water/ethanol (3 mL) was added 2M sodium carbonate (0.22 mL). The mixture was stirred in a CEM Explorer® microwave reactor (Matthews, N.C.) for 10 minutes at 150° C. After cooling, the mixture was filtered, and the filtrate was concentrated. The concentrate was purified by HPLC (Zorbax® C-18 ODS packing material [Agilent Technologies, Santa Clara, Calif.], 0-100% acetonitrile/water with 0.1% trifluoroacetic acid). The product was dissolved in methanol/dichloromethane and was treated with 1M hydrochloric acid in diethyl ether and concentrated to provide the title compound as the hydrochloride salt. $^1$H NMR (CD$_3$OD) δ1.70-1.80 (m, 4H), 2.50-2.62 (m, 4H), 4.17 (s, 2H), 7.33 (dd, J=10.7, 8.5 Hz, 1H), 7.40-7.48 (m, 1H), 7.60 (dd, J=7.3, 1.8 Hz, 1H), 8.22 (dd, J=8.2, 5.8 Hz, 1H), 8.87 (d, J=8.2 Hz, 1H), 8.90 (d, J=5.5 Hz, 1H), 9.12 (s, 1H).

Example 40

4-(4-fluoro-3-pyridin-4-ylbenzyl)-5,6,7,8-tetrahydrophthalazin-1(2H)-one

This example was prepared as the hydrochloride salt as described in EXAMPLE 39 by substituting 4-pyridine boronic acid for 3-pyridine boronic acid. $^1$H NMR (CD$_3$OD) δ1.68-1.84 (m, 4H), 2.46-2.64 (m, 4H), 4.15 (s, 2H), 7.35 (dd, J=11.0, 8.5 Hz, 1H), 7.48-7.53 (m, 1H), 7.69 (dd, J=7.2, 2.0 Hz, 1H), 8.32 (d, J=5.8 Hz, 2H), 8.91 (d, J=6.7 Hz, 2H).

Example 41

N,N-diethyl-2'-fluoro-5'-((4-oxo-3,4,5,6,7,8-hexahydrophthalazin-1-yl)methyl)-1,1'-biphenyl-2-carboxamide This example was prepared as the hydrochloride salt as described in EXAMPLE 39 by substituting (2-(N,N-diethylaminocarbonyl)phenyl)boronic acid for 3-pyridineboronic acid. $^1$H NMR (CD$_3$OD) δ0.83 (t, J=7.2 Hz, 3H), 0.93 (t, J=7.2 Hz, 3H), 1.72-1.83 (m, 4H), 2.51-2.66 (m, 4H), 2.73-3.01 (m, 2H), 3.02-3.25 (m, 2H), 4.11 (s, 2H), 7.13-7.17 (m, 1H), 7.17-7.19 (m, 1H), 7.26-7.31 (m, 1H), 7.38-7.41 (m, 2H), 7.47-7.50 (m, 1H), 7.51-7.54 (m, 1H).

Example 42

N-(2-fluoro-5-((4-oxo-3,4,5,6,7,8-hexahydrophthalazin-1-yl)methyl)phenyl)-3-piperidin-1-ylpropanamide To 3-(1-piperidinyl)propionic acid (28 mg) in dichloromethane (3 mL) was added oxalyl chloride (24 μL) and a drop of N,N-dimethylformamide. The mixture was stirred at ambient temperature for 1 hour and concentrated. The concentrate was dissolved in dichloromethane (3 mL) and added to a solution of EXAMPLE 2C (50 mg) in tetrahydrofuran (3 mL). Triethylamine (31 μL) was also added. The mixture was stirred at ambient temperature for 16 hours and was concentrated. The concentrate was purified by HPLC (Zorbax® C-18 ODS packing material [Agilent Technologies, Santa Clara, Calif.], 0-100% acetonitrile/water with 0.1% trifluoroacetic acid). The product was dissolved in methanol/dichloromethane and treated with 1M hydrochloric acid in diethyl ether and was concentrated to provide the title compound as the hydrochloride salt. $^1$H NMR (CD$_3$OD) δ1.50-1.59 (m, 1H), 1.68-1.75 (m, 4H), 1.76-1.87 (m, 3H), 1.92-2.01 (m, 2H), 2.41-2.57 (m, 4H), 2.94-2.98 (m, 2H), 2.98-3.03 (m, 2H), 3.45 (t, J=6.9 Hz, 2H), 3.57 (d, J=12.2 Hz, 2H), 3.99 (s, 2H), 6.99-7.05 (m, 1H), 7.11 (dd, J=10.4, 8.5 Hz, 1H), 7.81 (dd, J=7.3, 1.8 Hz, 1H).

Example 43

N-(2-fluoro-5-((4-oxo-3,4,5,6,7,8-hexahydrophthalazin-1-yl)methyl)phenyl)-3-(4-methylpiperazin-1-yl)propanamide This example was prepared as the hydrochloride salt as described in EXAMPLE 42 by substituting 3-(4-methylpiperazin-1-yl)propionic acid for 3-(1-piperidinyl)propionic acid. $^1$H NMR (CD$_3$OD) δ 1.65-1.79 (m, 4H), 2.38-2.58 (m, 4H), 3.03 (s, 3H), 3.07 (t, J=6.7 Hz, 2H), 3.60-3.65 (m, 2H), 3.65-3.68 (m, 3H), 3.70-3.89 (m, 4H), 3.97-4.06 (m, 1H), 4.00 (s, 2H), 6.99-7.04 (m, 1H), 7.12 (dd, J=10.7, 8.5 Hz, 1H), 7.83 (dd, J=7.3, 1.8 Hz, 1H).

Example 44

2-amino-N-(2-fluoro-5-((4-oxo-3,4,5,6,7,8-hexahydrophthalazin-1-yl)methyl)phenyl)acetamide A solution of EXAMPLE 2 (50 mg) and Boc-L-glycine N-hydroxysuccinimide ester (54 mg) in tetrahydrofuran (4 mL) was stirred at ambient temperature for 16 hours and was concentrated. To this solid in dichloromethane (2 mL) was added trifluoroacetic acid (1 mL) and the mixture stirred at ambient temperature for 1 hour and concentrated. The concentrate was purified by HPLC (Zorbax® C-18 ODS packing material [Agilent Technologies, Santa Clara, Calif.], 0-100% acetonitrile/water with 0.1% trifluoroacetic acid) to provide the title compound as the trifluoroacetate salt. $^1$H NMR (CD$_3$OD) δ 1.65-1.74 (m, 4H), 2.38-2.55 (m, 4H), 3.89 (s, 2H), 3.96 (s, 2H), 7.00-7.06 (m, 1H), 7.09-7.16 (m, 1H), 7.87 (dd, J=7.4, 2.1 Hz, 1H).

Example 45

3-cyclohexyl-N-(2-fluoro-5-((4-oxo-3,4,5,6,7,8-hexahydrophthalazin-1-yl)methyl)phenyl)propanamide This example was prepared as described in EXAMPLE 42 by substituting cyclohexanepropionic acid for 3-(1-piperidinyl)propionic acid. $^1$H NMR (CD$_3$OD) δ 0.90-1.00 (m, 2H) 1.16-1.33 (m, 4H) 1.53-1.61 (m, 2H) 1.63-1.68 (m, 1H) 1.70-1.74 (m, 5H) 1.74-1.82 (m, 3H) 2.39-2.46 (m, 4H) 2.48-2.51 (m, 2H) 3.94 (s, 2H) 6.96-7.01 (m, 1H) 7.07 (dd, J=10.7, 8.5 Hz, 1H) 7.69 (dd, J=7.2, 1.7 Hz, 1H).

Example 46

N-(2-fluoro-5-((4-oxo-3,4,5,6,7,8-hexahydrophthalazin-1-yl)methyl)phenyl)piperidine-3-carboxamide This example was prepared as the trifluoroacetate salt as described in EXAMPLE 42 by substituting 1-(tert-butoxycarbonyl)-3-piperidine carboxylic acid for 3-(1-piperidinyl) propionic acid. $^1$H NMR (CD$_3$OD) δ 1.66-1.76 (m, 4H), 1.79-1.87 (m, 1H), 1.89-2.03 (m, 2H), 2.12 (dd, J=9.3, 4.9 Hz, 1H), 2.38-2.56 (m, 4H), 2.96-3.04 (m, 1H), 3.08-3.15 (m, 1H), 3.17-3.25 (m, 2H), 3.33-3.35 (m, 1H), 3.95 (s, 2H), 6.99-7.06 (m, 1H), 7.07-7.15 (m, 1H), 7.71 (dd, J=7.5, 2.0 Hz, 1H).

Example 47

4-(4-fluoro-3-(2-oxopyrrolidin-1-yl)benzyl)-5,6,7,8-tetrahydrophthalazin-1(2H)-one To a solution of EXAMPLE 2 (200 mg) in dichloromethane (5 mL) was added 4-chlorobutanoylchloride (103 mg) and triethylamine (0.12 mL). The solution was stirred at ambient temperature for 16 hours and was concentrated. The concentrate was dissolved in ethanol (2 mL) and added to a solution of 21 wt % sodium ethoxide in ethanol (0.47 mL). The mixture was stirred at ambient temperature for 16 hours, treated with 2M hydrochloric acid (1 mL) and concentrated. The concentrate was purified by HPLC (Zorbax® C-18 ODS packing material [Agilent Technologies, Santa Clara, Calif.], 0-100% acetonitrile/water with 0.1% trifluoroacetic acid). $^1$H NMR (CD$_3$OD) δ 1.66-1.77 (m, 4H), 2.15-2.27 (m, 2H), 2.40-2.51 (m, 4H), 2.51-2.58 (m, 2H), 3.78-3.86 (m, 2H), 3.97 (s, 2H), 7.11-7.15 (m, 1H), 7.16-7.19 (m, 1H), 7.22-7.27 (m, 1H).

Example 48

N-(2-fluoro-5-((4-oxo-3,4,5,6,7,8-hexahydrophthalazin-1-yl)methyl)phenyl)azetidine-3-carboxamide This example was prepared as the trifluoroacetate salt as described in EXAMPLE 42 by substituting 1-(tert-butoxycarbonyl)-3-azetidine carboxylic acid for 3-(1-piperidinyl) propionic acid. $^1$H NMR (CD$_3$OD) δ 1.64-1.78 (m, 4H), 2.40-2.49 (m, 2H), 2.47-2.55 (m, 2H), 3.81-3.93 (m, 1H), 3.96 (s, 2H), 4.20-4.33 (m, 4H), 6.99-7.06 (m, 1H), 7.07-7.15 (m, 1H), 7.87 (dd, J=7.3, 2.2 Hz, 1H).

Example 49

N-(2-(isopropylamino)ethyl)-3-((4-oxo-3,4,5,6,7,8-hexahydrophthalazin-1-yl)methyl)benzamide Example 49A methyl 3-((3-oxo-4,5,6,7-tetrahydroisobenzofuran-1 (3H)-ylidene)methyl)benzoate This example was prepared as described in EXAMPLE 1C by substituting methyl-3-formylbenzoate for 2-fluoro-5-formylbenzonitrile.

Example 49B 3-((3-oxo-4,5,6,7-tetrahydroisobenzofuran-1(3H)-ylidene)methyl)benzoic acid EXAMPLE 49A (6.09 g) in 1:1 tetrahydrofuran/water (60 mL) at ambient temperature was treated with lithium hydroxide monohydrate (1.8 g) and stirred for 16 hours. The mixture was acidified with 2N hydrochloric acid and partitioned between ethyl acetate and brine. The organic layer was washed with water and concentrated, and the concentrate was purified by flash chromatography on silica gel with ethyl acetate.

Example 49C 3-((4-oxo-3,4,5,6,7,8-hexahydrophthalazin-1-yl) methyl)benzoic acid

This example was prepared as described in EXAMPLE 2C by substituting EXAMPLE 49B for EXAMPLE 2B.

Example 49D

N-(2-(isopropylamino)ethyl)-3-((4-oxo-3,4,5,6,7,8-hexahydrophthalazin-1-yl)methyl)benzamide To a solution of EXAMPLE 49C (75 mg) in N,N-dimethylformamide (3 mL) was added N-isopropylethylenediamine (27 mg), 1-(3-dimethylaminopropyl)-3-ethylcarbodiimide hydrochloride (50 mg), 1-hydroxybenzotriazole hydrate (35 mg) and triethylamine (0.11 mL). The mixture was stirred at ambient temperature for 16 hours and was partitioned between brine and water. The organics were washed with brine and concentrated. The concentrate was purified by HPLC (Zorbax® C-18 ODS packing material [Agilent Technologies. Santa Clara, Calif.], 0-100% acetonitrile/water with 0.10% trifluoroacetic acid) to provide the title compound as the trifluoroacetate salt. $^1$H NMR (CD$_3$OD) δ 1.34 (d, J=6.7 Hz, 6H), 1.65-1.74 (m, 4H), 2.37-2.44 (m, 2H), 2.47-2.54 (m, 2H), 3.23 (t, J=5.9 Hz, 2H), 3.39-3.47 (m, 1H), 3.67 (t, J=5.9 Hz, 2H), 4.05 (s, 2H), 7.41-7.44 (m, 2H), 7.71-7.74 (m, 2H).

Example 50

N-(2-fluoro-5-((4-oxo-3,4,5,6,7,8-hexahydrophthalazin-1-yl)methyl)phenyl)-2-morpholin-4-ylacetamide This example was prepared as the trifluoroacetate salt as described in EXAMPLE 41 by substituting morpholin-4-yl-acetic acid for 3-(1-piperidinyl)propionic acid. $^1$H NMR (CD$_3$OD) δ 1.65-1.73 (m, 4H), 2.38-2.46 (m, 2H), 2.46-2.52 (m, 2H), 3.34-3.52 (m, 4H), 3.90-4.03 (m, 6H), 4.19 (s, 2H), 7.03-7.09 (m, 1H), 7.10-7.17 (m, 1H), 7.85 (dd, J=7.3, 2.1 Hz, 1H).

Example 51

N-(2-morpholin-4-ylethyl)-3-((4-oxo-3,4,5,6,7,8-hexahydrophthalazin-1-yl)methyl)benzamide Example 51A 3-((4-oxo-3,4,5,6,7,8-hexahydrophthalazin-1-yl) methyl)benzoic acid The title compound was prepared according to procedure for EXAMPLE 1 substituting 3-formylbenzonitrile for 2-fluoro-5-formylbenzonitrile in EXAMPLE 1C. MS (DCI/NH$_4$) m z 285 (M+H)$^+$.

Example 51B

N-(2-morpholin-4-ylethyl)-3-((4-oxo-3,4,5,6,7,8-hexahydrophthalazin-1-yl)methyl)benzamide To a solution of EXAMPLE 51A (75 mg, 0.26 mmol) in anhydrous dichloromethane (5 mL) was added 4-(2-aminoethyl)morpholine (68 mg, 0.52 mmol), benzotriazol-1-yl-oxytripyrrolidinophosphonium hexafluorophosphate (271 mg, 0.52 mmol), and N,N'-diisopropylethylamine (0.18 mmol, 1.04 mmol) under nitrogen. The reaction mixture was stirred at room temperature for 16 hours, and concentrated. The residue was separated by HPLC (Zorbax® C-18 ODS packing material [Agilent Technologies, Santa Clara, Calif.], 0.1% trifluoroacetic acid/CH$_3$CN/H$_2$O) to provide the title compound as a trifluoroacetic acid salt. MS (DCI/NH$_3$) m/z 397 (M+H)$^+$; $^1$H NMR (500 MHz, CD$_3$OD): δ 1.64-1.75 (m, 4H), 2.37-2.45 (m, 2H), 2.45-2.55 (m, 2H), 3.15-3.27 (m, 2H), 3.40 (t, J=5.80 Hz, 2H), 3.63-3.71 (m, 2H), 3.74-3.81 (m, 4H), 4.02-4.13 (m, 4H), 7.42-7.46 (m, 2H), 7.71-7.75 (m, 2H).

Example 52

3-((4-oxo-3,4,5,6,7,8-hexahydrophthalazin-1-yl) methyl)-N-(2-pyrrolidin-1-ylethyl)benzamide The title compound was prepared as a trifluoroacetic acid salt according to procedure for EXAMPLE 51 substituting 1-(2-aminoethyl)pyrrolidine for 4-(2-aminoethyl)morpholine. MS (DCI/NH$_3$) m/z 381 (M+H)$^+$; $^1$H NMR (500 MHz, CD$_3$OD): δ 1.65-1.74 (m, 4H), 1.97-2.08 (m, 2H), 2.13-2.22 (m, 2H), 2.39-2.45 (m, 2H), 2.46-2.54 (m, 2H), 3.10-3.20 (m, 2H), 3.42 (t, J=5.80 Hz, 2H), 3.73 (t, J=5.95 Hz, 2H), 3.75-3.82 (m, 2H), 4.05 (s, 2H), 7.42-7.46 (m, 2H), 7.70-7.74 (m, 2H).

Example 53

4-(3-((2-methylpyrrolidin-1-yl)carbonyl)benzyl)-5,6,7,8-tetrahydrophthalazin-1(2H)-one The title compound was prepared as a trifluoroacetic acid salt according to procedure for EXAMPLE 51 substituting 2-methylpyrrolidine for 4-(2-aminoethyl)morpholine. MS (DCI/NH$_3$) m/z 352 (M+H)$^+$; $^1$H NMR (500 MHz, CD$_3$OD): δ 0.86 (d, J=6.41 Hz, 1H), 1.33 (d, J=6.41 Hz, 2H), 1.60-1.67 (m, 2H), 1.70 (d, J=2.75 Hz, 3H), 1.73-1.80 (m, 1H), 1.90-1.99 (m, 1H), 2.11-2.22 (m, 1H), 2.39-2.47 (m, 2H), 2.46-2.56 (m, 2H), 3.43-3.51 (m, 1H), 3.57-3.67 (m, 1H), 4.02 (s, 2H), 4.21-4.28 (m, 1H), 7.24-7.33 (m, 2H), 7.33-7.36 (m, 1H), 7.37-7.42 (m, 1H).

Example 54

N-azepan-1-yl-3-((4-oxo-3,4,5,6,7,8-hexahydrophthalazin-1-yl)methyl)benzamide

The title compound was prepared as a trifluoroacetic acid salt according to procedure for EXAMPLE 51 substituting 1-aminohomopiperidine for 4-(2-aminoethyl)morpholine. MS (DCI/NH$_3$) m/z 381 (M+H)$^+$; $^1$H NMR (500 MHz, CD$_3$OD): δ 1.68-1.74 (m, 4H), 1.73-1.81 (m, 4H), 1.92-2.01 (m, 4H), 2.41-2.46 (m, 2H), 2.48-2.54 (m, 2H), 3.53-3.60 (m, 4H), 4.06 (s, 2H), 7.45-7.50 (m, 2H), 7.70-7.73 (m, 2H).

Example 55

4-(3-(piperazin-1-ylcarbonyl)benzyl)-5,6,7,8-tetrahydrophthalazin-1(2H)-one

Example 55A tert-butyl 4-(3-((4-oxo-3,4,5,6,7,8-hexahydrophthalazin-1-yl)methyl)benzoyl)piperazine-1-carboxylate The title compound was prepared according to procedure for EXAMPLE 51 substituting tert-butyl 1-piperazine carboxylate for 4-(2-aminoethyl)morpholine. MS (DCI/NH$_3$) m/z 453 (M+H)$^+$.

Example 55B 4-(3-(piperazin-1-ylcarbonyl)benzyl)-5,6,7,8-tetrahydrophthalazin-1(2H)-one To a solution of EXAMPLE 55A (480 mg, 1.76 mmol) in methylene chloride (10 mL) was added trifluoroacetic acid (5 mL). The solution was stirred at room temperature for 1 hour, and was concentrated. The residue was purified by HPLC (Zorbax® C-18 ODS packing material [Agilent Technologies, Santa Clara, Calif.], 0.1% trifluoroacetic acid/CH$_3$CN/H$_2$O) to provide the title compound as a trifluoroacetic acid salt. MS (DCI/NH$_3$) m/z 353 (M+H)$^+$; $^1$H NMR (500 MHz, CD$_3$OD): δ 1.68-1.74 (m, 4H), 2.43-2.48 (m, 2H), 2.48-2.54 (m, 2H), 3.19-3.29 (m, 3H), 3.67-3.97 (m, 5H), 4.04 (s, 2H), 7.30-7.33 (m, 1H), 7.33-7.36 (m, 1H), 7.36-7.39 (m, 1H), 7.44 (t, J=7.48 Hz, 1H).

Example 56

N-azetidin-3-yl-3-((4-oxo-3,4,5,6,7,8-hexahydrophthalazin-1-yl)methyl)benzamide

The title compound was prepared as a trifluoroacetic acid salt according to procedure for EXAMPLE 55 substituting 3-amino-1-N-Boc-azetidine for tert-butyl 1-piperazine carboxylate. MS (DCI/NH$_3$) m/z 339 (M+H)$^+$; $^1$H NMR (500 MHz, CD$_3$OD): δ 1.63-1.76 (m, 4H), 2.37-2.45 (m, 2H), 2.46-2.55 (m, 2H), 4.05 (s, 2H), 4.28-4.37 (m, 4H), 4.76-4.82 (m, 1H), 7.41-7.45 (m, 2H), 7.69-7.74 (m, 2H).

Example 57

3-((4-oxo-3,4,5,6,7,8-hexahydrophthalazin-1-yl)methyl)-N-piperidin-3-ylbenzamide The title compound was prepared as a trifluoroacetic acid salt according to procedure for EXAMPLE 55 substituting (+/−)-3-amino-1-N-Boc-piperidine for tert-butyl 1-piperazine carboxylate. MS (DCI/NH$_3$) m/z 367 (M+H)$^+$; $^1$H NMR (500 MHz, CD$_3$OD): δ 1.68-1.72 (m, 4H), 1.72-1.77 (m, 1H), 1.80-1.89 (m, 1H), 2.02-2.15 (m, 2H), 2.37-2.46 (m, 2H), 2.47-2.54 (m, 2H), 2.85-3.00 (m, 2H), 3.33-3.39 (m, 1H), 3.52 (dd, J=12.21, 4.27 Hz, 1H), 4.04 (s, 2H), 4.18-4.26 (m, 1H), 7.40-7.43 (m, 2H), 7.66-7.71 (m, 2H).

Example 58

N-(4-(dimethylamino)phenyl)-3-((4-oxo-3,4,5,6,7,8-hexahydrophthalazin-1-yl)methyl)benzamide The title compound was prepared as a trifluoroacetic acid salt according to procedure for EXAMPLE 51 substituting N,N-dimethyl-1,4-phenylenediamine for 4-(2-aminoethyl)morpholine. MS (DCI/NH$_3$) m/z 403 (M+H)$^+$; $^1$H NMR (500 MHz, CD$_3$OD): δ 1.67-1.73 (m, 4H), 2.42-2.48 (m, 2H), 2.47-2.55 (m, 2H), 3.28 (s, 6H), 4.08 (s, 2H), 7.43-7.45 (m, 1H), 7.45-7.49 (m, 1H), 7.55 (d, J=8.85 Hz, 2H), 7.77-7.80 (m, 1H), 7.79-7.82 (m, 1H), 7.89-7.93 (m, 2H).

Example 59

N-(2-(4-methylpiperazin-1-yl)ethyl)-3-((4-oxo-3,4,5,6,7,8-hexahydrophthalazin-1-yl)methyl)benzamide The title compound was prepared as a trifluoroacetic acid salt according to procedure for EXAMPLE 51 substituting 2-(4-methyl-piperazin-1-yl)-ethylamine for 4-(2-aminoethyl)morpholine. MS (DCI/NH$_3$) m/z 410 (M+H)$^+$; $^1$H NMR (500 MHz, CD$_3$OD): δ 1.67-1.73 (m, 4H), 2.41-2.46 (m, 2H), 2.48-2.54 (m, 2H), 2.82 (t, J=6.41 Hz, 2H), 2.87 (s, 3H), 2.89-3.09 (m, 3H), 3.17-3.26 (m, 2H), 3.33-3.41 (m, 1H), 3.57 (t, J=6.26 Hz, 2H), 4.04 (s, 2H), 4.72-4.83 (m, 2H), 7.39-7.44 (m, 2H), 7.63-7.66 (m, 1H), 7.66-7.69 (m, 1H).

Example 60

4-(3-((4-(isoxazol-5-ylcarbonyl)piperazin-1-yl)carbonyl)benzyl)-5,6,7,8-tetrahydrophthalazin-1(2H)-one A solution of isoxazole-5-carboxylic acid (32 mg, 0.28 mmol) in a mixture of anhydrous N,N-dimethylformamide (2 mL) and pyridine (2 mL) was treated with 1,1'-carbonyldiimidazole (48 mg, 0.30 mmol) at 40° C. for 2 hours. EXAMPLE 55 (50 mg, 0.14 mmol) was added and the reaction mixture was heated at 60° C. for 3 hours. After cooling, the reaction mixture was concentrated on a rotary evaporator and the residue was purified by HPLC (Zorbax® C-18 ODS packing material [Agilent Technologies, Santa Clara, Calif.], 0.1% trifluoroacetic acid/CH$_3$CN/H$_2$O) to provide the title compound as a trifluoroacetic acid salt. MS (DCI/NH$_3$) m/z 448 (M+H)+; 1H NMR (500 MHz, CD3OD): δ 1.65-1.76 (m, 4H), 2.41-2.47 (m, 2H), 2.48-2.56 (m, 2H), 3.51-3.66 (m, 3H), 3.66-3.79 (m, 3H), 3.79-3.94 (m, 2H), 4.04 (s, 2H), 7.27-7.30 (m, 1H), 7.32-7.35 (m, 1H), 7.36-7.39 (m, 1H), 7.43 (t, J=7.48 Hz, 1H), 7.61-7.66 (m, 1H), 7.86-7.91 (m, 1H).

Example 61

4-(3-((4-phenylpiperidin-1-yl)carbonyl)benzyl)-5,6,7,8-tetrahydrophthalazin-1(2H)-one The title compound was prepared as a trifluoroacetic acid salt according to procedure for EXAMPLE 51 substituting 4-phenylpiperidine for 4-(2-aminoethyl)morpholine. MS (DCI/NH3) m/z 428 (M+H)+; 1H NMR (500 MHz, CD3OD): δ 1.54-1.65 (m, 1H), 1.64-1.71 (m, 4H), 1.72-1.82 (m, 2H), 1.91-1.99 (m, 1H), 2.40-2.45 (m, 2H), 2.49-2.51 (m, 2H), 2.80-2.89 (m, 1H), 2.89-2.98 (m, 1H), 3.15-3.26 (m, 1H), 3.71-3.82 (m, 1H), 4.04 (s, 2H), 4.72-4.81 (m, 1H), 7.16-7.20 (m, 1H), 7.22-7.26 (m, 3H), 7.27-7.30 (m, 2H), 7.30-7.32 (m, 1H), 7.34 (d, J=7.93 Hz, 1H), 7.42 (t, J=7.63 Hz, 1H).

Example 62

3-((4-oxo-3,4,5,6,7,8-hexahydrophthalazin-1-yl)methyl)-N-(piperidin-2-ylmethyl)benzamide The title compound was prepared as a trifluoroacetic acid salt according to procedure for EXAMPLE 55 substituting tert-butyl 2-(aminomethyl)piperidine-1-carboxylate for tert-butyl 1-piperazine carboxylate. MS (DCI/NH3) m/z 381 (M+H)+; 1H NMR (500 MHz, CD3OD): δ1.46-1.56 (m, 2H), 1.60-1.78 (m, 6H), 1.79-1.93 (m, 2H), 2.38-2.47 (m, 2H), 2.47-2.55 (m, 2H), 3.14 (dd, J=13.27, 4.42 Hz, 2H), 3.46-3.52 (m, 1H), 3.55-3.64 (m, 1H), 4.04 (s, 2H), 4.91-5.05 (m, 1H), 7.27-7.32 (m, 1H), 7.35-7.40 (m, 2H), 7.43 (t, J=7.48 Hz, 1H).

Example 63

3-((4-oxo-3,4,5,6,7,8-hexahydrophthalazin-1-yl)methyl)-N-(piperidin-4-ylmethyl)benzamide The title compound was prepared as a trifluoroacetic acid salt according to procedure for EXAMPLE 55 substituting 4-aminomethyl-piperidine-1-carboxylic acid tert-butyl ester for tert-butyl 1-piperazine carboxylate. MS (DCI/NH3) m/z 381 (M+H)+; 1H NMR (500 MHz, CD3OD): δ 1.40-1.52 (m, 2H), 1.64-1.74 (m, 4H), 1.91-2.03 (m, 3H), 2.37-2.47 (m, 2H), 2.47-2.55 (m, 2H), 2.93-3.02 (m, 2H), 3.32-3.36 (m, 2H), 3.37-3.44 (m, 2H), 4.04 (s, 2H), 7.38-7.43 (m, 2H), 7.65-7.69 (m, 2H).

Example 64

3-((4-oxo-3,4,5,6,7,8-hexahydrophthalazin-1-yl)methyl)-N-(2-piperidin-1-ylethyl)benzamide The title compound was prepared as a trifluoroacetic acid salt according to procedure for EXAMPLE 51 substituting 2-(piperidin-1-yl)ethanamine for 4-(2-aminoethyl)morpholine. MS (DCI/NH3) m/z 395 (M+H)+; 1H NMR (500 MHz, CD3OD): δ 1.50-1.58 (m, 1H), 1.67-1.73 (m, 4H), 1.76-1.88 (m, 3H), 1.97 (d, J=14.34 Hz, 2H), 2.38-2.47 (m, 2H), 2.46-2.54 (m, 2H), 2.93-3.04 (m, 2H), 3.32-3.37 (m, 2H), 3.68 (d, J=12.21 Hz, 2H), 3.74 (t, J=6.10 Hz, 2H), 4.05 (s, 2H), 7.42-7.45 (m, 2H), 7.70-7.74 (m, 2H).

Example 65

N-(1-methylazetidin-3-yl)-3-((4-oxo-3,4,5,6,7,8-hexahydrophthalazin-1-yl)methyl)benzamide To a solution of EXAMPLE 56 (25 mg, 0.07 mmol) in methanol (2 mL) was added formaldehyde (37% in water, 16 μL, 0.21 mmol) and triethylamine (10 μL, 0.07 mmol). The mixture was stirred at room temperature for 2 hours before sodium cyanoborohydride (13 mg, 0.21 mmol) and zinc chloride (10 mg) were added. The reaction mixture was stirred at room temperature for 16 hours, and concentrated. The residue was dissolved in 1:1 mixture of acetonitrile and water, and purified by HPLC (Zorbax® C-18 ODS packing material [Agilent Technologies, Santa Clara, Calif.], 0.1% trifluoroacetic acid/CH3CN/H2O) to provide the title compound as a trifluoroacetic acid salt. MS (DCI/NH3) m/z 353 (M+H)+; 1H NMR (500 MHz, CD3OD): δ 1.63-1.74 (m, 4H), 2.36-2.45 (m, 2H), 2.46-2.53 (m, 2H), 3.01 (d, J=17.70 Hz, 3H), 4.06 (d, J=10.68 Hz, 2H), 4.21-4.28 (m, 1H), 4.31 (dd, J=11.44, 8.70 Hz, 1H), 4.56-4.66 (m, 2H), 5.51 (s, 1H), 7.41-7.44 (m, 1H), 7.44-7.48 (m, 1H), 7.70-7.78 (m, 2H).

Example 66 methyl 4-((4-oxo-3,4,5,6,7,8-hexahydrophthalazin-1-yl)methyl)pyridine-2-carboxylate

Example 66A

3-((2-bromopyridin-4-yl)methylene)-4,5,6,7-tetrahydroisobenzofuran-1(3H)-one The title compound was prepared according to the procedure for EXAMPLE 1C, substituting 2-bromo-pyridine-4-carbaldehyde for 2-fluoro-5-formylbenzonitrile. MS (DCI/NH3) m/z 307 (M+H)+.

Example 66B

4-((2-bromopyridin-4-yl)methyl)-5,6,7,8-tetrahydrophthalazin-1(2H)-one

The title compound was prepared according to the procedure for EXAMPLE 2C substituting EXAMPLE 66A for EXAMPLE 2B. MS (DCI/NH3) m/z 321 (M+H)+.

Example 66C methyl 4-((4-oxo-3,4,5,6,7,8-hexahydrophthalazin-1-yl)methyl)pyridine-2-carboxylate A mixture of EXAMPLE 66B (800 mg, 2.5 mmol), dichloro(1,1'-ferrocenylbis(diphenyl-phosphine))palladium (II) dichloromethane (125 mg, 0.15 mmol) and triethylamine (1 ml) in a mixture of methanol (40 ml) and N,N-dimethylformamide (16 ml) was heated at 110° C. in a pressure vessel under 30 psi of carbon monoxide for 16 hours. After cooling, the solid material was filtered off, and the filtrate was concentrated. The residual solid was washed with methanol, and dried to provide the title compound. MS (DCI/NH3) m/z 300 (M+H)+.

Example 67

N-methyl-4-((4-oxo-3,4,5,6,7,8-hexahydrophthalazin-1-yl)methyl)pyridine-2-carboxamide A solution of EXAMPLE 66 (100 mg, 0.33 mmol) in methanol (5 ml) was treated with methylamine (2.0 N in methanol, 2 ml) at 50° C. for 24 hours, and concentrated. The residue was washed with methanol, and dried to provide the title compound. MS (DCI/NH$_3$) m/z 299 (M+H)$^+$.

Example 68

4-((2-(methylthio)pyrimidin-4-yl)methyl)-5,6,7,8-tetrahydrophthalazin-1(2H)-one

Example 68A 3-((2-(methylthio)pyrimidin-4-yl)methylene)-4,5,6,7-tetrahydroisobenzofuran-1(3H)-one The title compound was prepared according to the procedure for EXAMPLE 1C, substituting 2-methylthio-4-pyrimidine-carboxaldehyde for 2-fluoro-5-formylbenzonitrile. MS (DCI/NH$_3$) m/z 275 (M+H)$^+$.

Example 68B 4-((2-(methylthio)pyrimidin-4-yl)methyl)-5,6,7,8-tetrahydrophthalazin-1(2H)-one The title compound was prepared according to the procedure for EXAMPLE 2C, substituting EXAMPLE 68A for EXAMPLE 2B. MS (DCI/NH$_3$) m/z 289 (M+H)$^+$.

Example 69

4-((2-(methylsulfonyl)pyrimidin-4-yl)methyl)-5,6,7,8-tetrahydrophthalazin-1(2H)-one To a suspension of EXAMPLE 68 (280 mg, 1 mmol) in methylene chloride (5 mL) was added m-chloroperoxybenzoic acid (256 mg, 1.5 mmol). The reaction mixture was stirred at room temperature for 4 hours, and concentrated. The residual solid was separated by flash chromatography on silica gel (80% ethyl acetate in hexane) to provide the title compound. MS (DCI/NH$_3$) m/z 321 (M+H)$^+$; $^1$H NMR (300 MHz, CD$_3$OD): δ 1.61-1.89 (m, 4H), 2.37-2.71 (m, 4H), 3.32 (s, 3H), 4.29 (s, 2H), 7.65 (d, J=5.09 Hz, 1H), 8.88 (d, J=5.43 Hz, 1H).

Example 70

4-((2-(methylsulfinyl)pyrimidin-4-yl)methyl)-5,6,7,8-tetrahydrophthalazin-1(2H)-one The title compound was isolated as a side product in EXAMPLE 69. MS (ESI) m/z 305 (M+H)$^+$.

Example 71

4-((3-bromopyridin-4-yl)methyl)-5,6,7,8-tetrahydrophthalazin-1(2H)-one

Example 71A 3-((3-bromopyridin-1-yl)methylene)-4,5,6,7-tetrahydroisobenzofuran-1(3H)-one The title compound was prepared according to the procedure for EXAMPLE 1C, substituting 3-bromoisonicotinaldehyde for 2-fluoro-5-formylbenzonitrile. MS (DCI/NH$_3$) m/z 306 (M+H)$^+$.

Example 71B 4-((3-bromopyridin-4-yl)methyl)-5,6,7,8-tetrahydrophthalazin-1(2H)-one The title compound was prepared according to the procedure for EXAMPLE 2C, substituting EXAMPLE 71A for EXAMPLE 2B. MS (DCI/NH$_3$) m/z 321 (M+H)$^+$.

Example 72

4-((6-bromopyridin-3-yl)methyl)-5,6,7,8-tetrahydrophthalazin-1(2H)-one

Example 72A 3-((6-bromopyridin-3-yl)methylene)-4,5,6,7-tetrahydroisobenzofuran-1(3H)-one The title compound was prepared according to the procedure for EXAMPLE 1C, substituting 6-bromonicotinaldehyde for 2-fluoro-5-formylbenzonitrile. MS (DCI/NH$_3$) m/z 306 (M+H)$^+$.

Example 72B 4-((6-bromopyridin-3-yl)methyl)-5,6,7,8-tetrahydrophthalazin-1(2H)-one The title compound was prepared according to the procedure for EXAMPLE 2C, substituting EXAMPLE 72A for EXAMPLE 2B. MS (DCI/NH$_3$) m/z 321 (M+H)$^+$.

Example 73

4-((2-bromopyridin-3-yl)methyl)-5,6,7,8-tetrahydrophthalazin-1(2H)-one

Example 73A 3-((2-bromopyridin-3-yl)methylene)-4,5,6,7-tetrahydroisobenzofuran-1(3H)-one The title compound was prepared according to the procedure for EXAMPLE 1C, substituting 2-bromonicotinaldehyde for 2-fluoro-5-formylbenzonitrile. MS (DCI/NH$_3$) m/z 306 (M+H)$^+$.

Example 73B 4-((2-bromopyridin-3-yl)methyl)-5,6,7,8-tetrahydrophthalazin-1(2H)-one The title compound was prepared according to the procedure for EXAMPLE 2C, substituting EXAMPLE 72A for EXAMPLE 2B. MS (DCI/NH$_3$) m/z 321 (M+H)$^+$.

Example 74 methyl 6-((4-oxo-3,4,5,6,7,8-hexahydrophthalazin-1-yl)methyl)pyridine-2-carboxylate

Example 74A 3-((6-bromopyridin-2-yl)methylene)-4,5,6,7-tetrahydroisobenzofuran-1(3H)-one The title compound was prepared according to the procedure for EXAMPLE 1C, substituting 6-bromo-pyridine-2-carbaldehyde for 2-fluoro-5-formylbenzonitrile. MS (DCI/NH$_3$) m/z 300 (M+H)$^+$.

Example 74B 4-((6-bromopyridin-2-yl)methyl)-5,6,7,8-tetrahydrophthalazin-1(2H)-one The title compound was prepared according to the procedure for EXAMPLE 2C, substituting EXAMPLE 74A for EXAMPLE 2B. MS (DCI/NH$_3$) m/z 321 (M+H)$^+$.

Example 74C methyl 6-((4-oxo-3,4,5,6,7,8-hexahydrophthalazin-1-yl)methyl)picolinate The title compound was prepared according to the procedure for EXAMPLE 66C, substituting EXAMPLE 74B for EXAMPLE 66B. MS (DCI/NH$_3$) m/z 300 (M+H)$^+$.

Example 75

N-ethyl-4-((4-oxo-3,4,5,6,7,8-hexahydrophthalazin-1-yl)methyl)pyridine-2-carboxamide The title compound was prepared according to procedure for EXAMPLE 67, substituting ethylamine for methylamine. MS (ESI) m/z 313 (M+H)$^+$.

Example 76

N-isopropyl-4-((4-oxo-3,4,5,6,7,8-hexahydrophthalazin-1-yl)methyl)pyridine-2-carboxamide The title compound was prepared according to procedure for EXAMPLE 67, substituting isopropyl amine for methyl amine. MS (ESI) m/z 327 (M+H)$^+$.

Example 77

N-cyclohexyl-4-((4-oxo-3,4,5,6,7,8-hexahydrophthalazin-1-yl)methyl)pyridine-2-carboxamide The title compound was prepared according to procedure for EXAMPLE 67, substituting cyclohexanamine for methyl amine. MS (ESI) m/z 367 (M+H)$^+$; $^1$H NMR (300 MHz, dimethylsulfoxide-d$_6$): δ 1.23-1.45 (m, 6H), 1.60-1.64 (m, 4H), 1.65-1.86 (m, 5H), 2.30-2.40 (m, 4H), 4.03 (s, 2H), 7.41 (dd, J=4.92, 1.86 Hz, 1H), 7.86 (s, 1H), 8.41 (d, J=8.82 Hz, 1H), 8.53 (d, J=5.09 Hz, 1H), 12.64 (s, 1H).

Example 78

N-methyl-N-((1-methylpiperidin-2-yl)methyl)-3-((4-oxo-3,4,5,6,7,8-hexahydrophthalazin-1-yl)methyl)benzamide The title compound was prepared as a trifluoroacetic acid salt according to procedure for EXAMPLE 65, substituting EXAMPLE 62 for EXAMPLE 56. MS (DCI/NH$_3$) m/z 409 (M+H)$^+$; $^1$H NMR (500 MHz, CD$_3$OD): δ 1.47-1.57 (m, 1H), 1.58-1.67 (m, 1H), 1.67-1.77 (m, 6H), 1.77-1.87 (m, 1H), 1.85-1.95 (m, 1H), 2.43-2.51 (m, 2H), 2.53-2.63 (m, 2H), 2.99 (s, 3H), 3.08 (s, 3H), 3.26 (dd, J=13.73, 3.36 Hz, 2H), 3.51-3.61 (m, 1H), 3.95 (dd, J=13.27, 11.44 Hz, 1H), 4.13 (s, 2H), 5.11-5.24 (m, 1H), 7.35-7.40 (m, 2H), 7.41-7.47 (m, 2H).

Example 79

N-((1-methylpiperidin-4-yl)methyl)-3-((4-oxo-3,4,5,6,7,8-hexahydrophthalazin-1-yl)methyl)benzamide The title compound was prepared as a trifluoroacetic acid salt according to procedure for EXAMPLE 65, substituting EXAMPLE 63 for EXAMPLE 56. MS (DCI/NH$_3$) m/z 395 (M+H)$^+$; $^1$H NMR (500 MHz, CD$_3$OD): δ 1.49-1.61 (m, 2H), 1.69-1.78 (m, 4H), 1.90-1.98 (m, 1H), 1.97-2.08 (m, 2H), 2.43-2.53 (m, 2H), 2.54-2.65 (m, 2H), 2.85 (s, 3H), 2.95-3.04 (m, 2H), 3.32-3.38 (m, 2H), 3.53 (dd, J=10.53, 1.98 Hz, 2H), 4.15 (s, 2H), 7.39-7.41 (m, 1H), 7.43 (t, J=7.63 Hz, 1H), 7.68 (s, 1H), 7.70-7.73 (m, 1H).

Example 80

N-methyl-6-((4-oxo-3,4,5,6,7,8-hexahydrophthalazin-1-yl)methyl)pyridine-2-carboxamide The title compound was prepared according to procedure for EXAMPLE 67, substituting EXAMPLE 74 for EXAMPLE 66. MS (ESI) m/z 299 (M+H)$^+$; $^1$H NMR (300 MHz, CD$_3$OD): δ 1.61-1.81 (m, 4H), 2.38-2.61 (m, 4H), 2.95 (s, 3H), 4.22 (s, 2H), 7.41 (dd, J=7.46, 1.36 Hz, 1H), 7.88 (t, J=7.63 Hz, 1H), 7.91-7.98 (m, 1H).

Example 81

N-ethyl-6-((4-oxo-3,4,5,6,7,8-hexahydrophthalazin-1-yl)methyl)pyridine-2-carboxamide The title compound was prepared according to procedure for EXAMPLE 67, substituting EXAMPLE 74 for EXAMPLE 66, and ethylamine for methylamine. MS (ESI) m/z 313 (M+H)$^+$.

Example 82

N-isopropyl-6-((4-oxo-3,4,5,6,7,8-hexahydrophthalazin-1-yl)methyl)pyridine-2-carboxamide The title compound was prepared according to procedure for EXAMPLE 67, substituting EXAMPLE 74 for EXAMPLE 66, and isopropylamine for methylamine. MS (ESI) m/z 327 (M+H)$^+$.

Example 83

N-cyclopropyl-6-((4-oxo-3,4,5,6,7,8-hexahydro-phthalazin-1-yl)methyl)pyridine-2-carboxamide The title compound was prepared according to procedure for EXAMPLE 67, substituting EXAMPLE 74 for EXAMPLE 66, and cyclopropylamine for methylamine. MS (ESI) m/z 325 (M+H)$^+$.

Example 84

N-cyclohexyl-6-((4-oxo-3,4,5,6,7,8-hexahydro-phthalazin-1-yl)methyl)pyridine-2-carboxamide The title compound was prepared according to procedure for EXAMPLE 67, substituting EXAMPLE 74 for EXAMPLE 66, and cyclohexylamine for methylamine. MS (ESI) m/z 367 (M+H)$^+$.

Example 85 methyl 3-((4-oxo-3,4,5,6,7,8-hexahydrophthalazin-1-yl)methyl)pyridine-2-carboxylate The title compound was prepared according to procedure for EXAMPLE 66C, substituting EXAMPLE 73B for EXAMPLE 66B. MS (DCI/NH$_3$) m/z 300 (M+H)$^+$.

Example 86 methyl 5-((4-oxo-3,4,5,6,7,8-hexahydrophthalazin-1-yl)methyl)pyridine-2-carboxylate The title compound was prepared according to the procedure for EXAMPLE 66C, substituting EXAMPLE 72B for EXAMPLE 66B. MS (DCI/NH$_3$) m/z 300 (M+H)$^+$.

Example 87

4-((5-bromothiophen-2-yl)methyl)-5,6,7,8-tetrahy-drophthalazin-1(2H)-one

Example 87A 3-((5-bromothiophen-2-yl)methylene)-4,5,6,7-tet-rahydroisobenzofuran-1(3H)-one The title compound was prepared according to procedure for EXAMPLE 1C, substituting 5-bromothiophene-2-carbal-dehyde for 2-fluoro-5-formylbenzonitrile. MS (DCI/NH$_3$) m/z 312 (M+H)$^+$.

Example 87B 4-((5-bromothiophen-2-yl)methyl)-5,6,7,8-tetrahy-drophthalazin-1(2H)-one The title compound was prepared according to the procedure for EXAMPLE 2C, substituting EXAMPLE 87A for EXAMPLE 2B. MS (DCI/NH$_3$) m/z 326 (M+H)$^+$.

Example 88

4-((3-bromothiophen-2-yl)methyl)-5,6,7,8-tetrahy-drophthalazin-1(2H)-one

Example 88A 3-((3-bromothiophen-2-yl)methylene)-4,5,6,7-tet-rahydroisobenzofuran-1(3H)-one The title compound was prepared according to procedure for EXAMPLE 1C, substituting 3-bromothiophene-2-carbal-dehyde for 2-fluoro-5-formylbenzonitrile. MS (DCI/NH$_3$) m/z 312 (M+H)$^+$.

Example 88B 4-((3-bromothiophen-2-yl)methyl)-5,6,7,8-tetrahy-drophthalazin-1(2H)-one The title compound was prepared according to the procedure for EXAMPLE 2C substituting EXAMPLE 88A for EXAMPLE 2B. MS (DCI/NH$_3$) m/z 326 (M+H)$^+$.

Example 89

4-(3-aminobenzyl)-5,6,7,8-tetrahydrophthalazin-1 (2H)-one

The title compound was prepared according to the procedure for EXAMPLE 2, substituting 3-nitrobenzaldehyde for 4-fluoro-3-nitrobenzaldehyde in EXAMPLE 2A. MS (DCI/NH$_3$) m/z 256 (M+H)$^+$; $^1$H NMR (300 MHz, CD$_3$OD): δ 1.62-1.75 (m, 4H), 2.37-2.44 (m, 2H), 2.46-2.54 (m, 2H), 3.86 (s, 2H), 6.46-6.54 (m, 2H), 6.57 (dd, J=7.93, 1.98 Hz, 1H), 7.01 (t, J=7.73 Hz, 1H).

Example 90

4-(3-bromobenzyl)-5,6,7,8-tetrahydrophthalazin-1 (2H)-one

The title compound was prepared according to the procedure for EXAMPLE 2C. substituting 3-bromobenzaldehyde for 4-fluoro-3-nitrobenzaldehyde. MS (DCI/NH$_3$) m/z 256 (M+H)$^+$; $^1$H NMR (300 MHz, CD$_3$OD): δ 1.64-1.77 (m, 4H), 2.37-2.46 (m, 2H), 2.47-2.55 (m, 2H), 3.96 (s, 2H), 7.13-7.18 (m, 1H), 7.18-7.24 (m, 1H), 7.35-7.40 (m, 2H).

Example 91

4-(thien-2-ylmethyl)-5,6,7,8-tetrahydrophthalazin-1 (2H)-one

A mixture of EXAMPLE 87 (100 mg, 0.31 mmol) and acetamide (1 g) was stirred at 180° C. overnight. After cooling, the mixture was dissolved in methanol, and separated by HPLC (Zorbax® C-8 packing material [Agilent Technologies, Santa Clara, Calif.]0.1% trifluoroacetic acid/CH$_3$CN/H$_2$O) to provide the title compound. MS (DCI/NH$_3$) m/z 247 (M+H)$^+$.

Example 92 methyl 5-((4-oxo-3,4,5,6,7,8-hexahydrophthalazin-1-yl)methyl)thiophene-2-carboxylate The title compound was prepared according to the procedure for EXAMPLE 66C, substituting EXAMPLE 87 for EXAMPLE 66B. MS (DCI/NH$_3$) m/z 305 (M+H)$^+$.

Example 93

N-methyl-5-((4-oxo-3,4,5,6,7,8-hexahydrophthalazin-1-yl)methyl)pyridine-2-carboxamide The title compound was prepared according to procedure for EXAMPLE 67, substituting EXAMPLE 86 for 66. MS (ESI) m/z 299 (M+H)$^+$, $^1$H NMR (300 MHz, dimethylsulfoxide-d$_6$): δ 1.51-1.73 (m, 4H), 2.40 (d, J=14.92 Hz, 4H), 2.81 (d, J=5.09 Hz, 3H), 4.02 (s, 2H), 7.75 (dd, J=7.97, 2.20 Hz, 1H), 7.96 (d, J=8.14 Hz, 1H), 8.49 (d, 11.70 Hz, 1H), 8.70 (d, J=4.75 Hz, 1H), 12.60 (s, 1H).

Example 94

N-ethyl-5-((4-oxo-3,4,5,6,7,8-hexahydrophthalazin-1-yl)methyl)pyridine-2-carboxamide The title compound was prepared according to procedure for EXAMPLE 67, substituting EXAMPLE 86 for EXAMPLE 66, and ethylamine for methylamine. MS (ESI) m/z 313 (M+H)$^+$.

Example 95

N-methyl-3-((4-oxo-3,4,5,6,7,8-hexahydrophthalazin-1-yl)methyl)pyridine-2-carboxamide The title compound was prepared according to procedure for EXAMPLE 67, substituting EXAMPLE 85 for 66. MS (ESI) m/z 299 (M+H)$^+$, $^1$H NMR (300 MHz, dimethylsulfoxide-d$_6$) δ 1.53-1.79 (m, 4H), 2.29-2.44 (m, 4H), 2.73 (d, J=5.16 Hz, 3H), 4.35 (s, 2H), 7.50 (dd, J=7.73, 4.56 Hz, 1H), 7.66 (dd, J=7.93, 1.59 Hz, 1H), 8.49 (dd, J=4.36, 1.59 Hz, 1H), 8.65 (d, J=5.16 Hz, 1H), 12.35 (s, 1H).

Example 96

N-ethyl-3-((4-oxo-3,4,5,6,7,8-hexahydrophthalazin-1-yl)methyl)pyridine-2-carboxamide The title compound was prepared according to procedure for EXAMPLE 67, substituting EXAMPLE 85 for EXAMPLE 66, and ethylamine for methylamine. MS (ESI) m/z 313 (M+H)$^+$.

Example 97

N,N-dimethyl-N'-(3-((4-oxo-3,4,5,6,7,8-hexahydrophthalazin-1-yl)methyl)phenyl)sulfamide To a solution of EXAMPLE 89 (50 mg, 02 mmol) in dichloromethane (4 mL) was added dimethylsulfamoyl chloride (31 mg, 0.22 mmol) and pyridine (17 mL, 0.22 mol). The solution was stirred at room temperature for 16 hours, and was concentrated. The residue was separated by HPLC (Zorbax® C-18 ODS packing material [Agilent Technologies, Santa Clara, Calif.], 0.1% trifluoroacetic acid/CH$_3$CN/H$_2$O) to provide the title compound as a trifluoroacetic acid salt. MS (DCI/NH$_3$) m/z 363 (M+H)$^+$; $^1$H NMR (400 MHz, CD$_3$OD): δ 1.64-1.76 (m, 4H), 2.37-2.46 (m, 2H), 2.47-2.54 (m, 2H), 2.72 (s, 6H), 3.95 (s, 2H), 6.91-6.96 (m, 1H), 7.02-7.06 (m, 2H), 7.19-7.24 (m, 1H).

Example 98

N-(3-((4-oxo-3,4,5,6,7,8-hexahydrophthalazin-1-yl)methyl)phenyl)-3-piperidin-1-ylpropanamide To a solution of 3-(piperidin-1-yl)propanoic acid (31 mg) in anhydrous dichloromethane (2 mL) was added oxalyl chloride (25.7 µL) and a drop of N,N-dimethylformamide. The solution was stirred for 1 hour, and was concentrated. The residue was re-dissolved in anhydrous dichloromethane (2 mL), and was quickly added to a solution of EXAMPLE 89 (50 mg) in anhydrous tetrahydrofuran (2 mL). Triethylamine (32.8 µL) was added, and the reaction mixture was stirred at room temperature overnight. The mixture was concentrated. The residue was partitioned between ethyl acetate and brine. The organic phase was washed with brine and concentrated. The residual solid was separated on HPLC (Zorbax® C-18 ODS packing material [Agilent Technologies, Santa Clara, Calif.], 0.1% trifluoroacetic acid/CH$_3$CN/H$_2$O) to provide the title compound as a trifluoroacetic acid salt. MS (DCI/NH$_3$) m/z 395 (M+H)$^+$; $^1$H NMR (400 MHz, CD$_3$OD): δ 1.48-1.60 (m, 1H), 1.65-1.71 (m, 4H), 1.73-1.87 (m, 3H), 1.92-2.01 (m, 2H), 2.38-2.45 (m, 2H), 2.46-2.53 (m, 2H), 2.87 (t, J=6.60 Hz, 2H), 2.93-3.03 (m, 2H), 3.44 (t, J=6.75 Hz, 2H), 3.57 (d, J=12.58 Hz, 2H), 3.97 (s, 2H), 6.95-7.00 (m, 1H), 7.26 (t, J=7.83 Hz, 1H), 7.36-7.39 (m, 1H), 7.41-7.48 (m, 1H).

Example 99

4-chloro-N-(3-((4-oxo-3,4,5,6,7,8-hexahydrophthalazin-1-yl)methyl)phenyl butanamide A solution of EXAMPLE 89 (150 mg, 0.59 mmol) and 4-chlorobutanoyl chloride (83 mg, 0.59 mmol) in dichloromethane (5 mL) was stirred at room temperature for 16 hours, and was concentrated. The residue was partitioned between ethyl acetate and brine. The organic phase was washed with brine, and concentrated to provide the title compound. MS (DCI/NH$_3$) m/z 360 (M+H)$^+$; $^1$H NMR (400 MHz, CD$_3$OD): δ 1.66-1.73 (m, 4H), 2.07-2.15 (m, 2H), 2.40-2.46 (m, 2H), 2.48-2.51 (m, 2H), 2.50-2.56 (m, 2H), 3.63 (t, J=6.44 Hz, 2H), 3.96 (s, 2H), 6.93 (d, J=7.67 Hz, 1H), 7.21-7.26 (m, 1H), 7.36 (s, 1H), 7.38-7.46 (m, 1H).

Example 100

4-(3-(2-oxopyrrolidin-1-yl)benzyl)-5,6,7,8-tetrahydrophthalazin-1(2H)-one

A suspension of EXAMPLE 90 (150 mg, 0.47 mmol), pyrrolidine-2-one (80 mg, 0.94 mmol), tris(dibenzylideneacetone)dipalladium(0) (43 mg, 0.05 mmol), Xantphos (4,5-bis(diphenylphosphino)-9,9-dimethylxanthene) (4,5-bis(diphenylphosphino)-9,9-dimethylxanthene) (41 mg, 0.07 mmol) and cesium carbonate (214 mg, 0.66 mmol) in anhydrous dioxane (2 mL) was heated in a CEM Explorer® microwave reactor (Matthews, N.C.) at 200° C. for 30 minutes. After cooling, the reaction mixture was concentrated. The residue was separated by HPLC (Zorbax® C-18 ODS packing material [Agilent Technologies. Santa Clara, Calif.], 0.1% trifluoroacetic acid/CH₃CN/H₂O) to provide the title compound as a trifluoroacetic acid salt. MS (DCI/NH₃) m/z 324 (M+H)⁺; ¹H NMR (400 MHz, CD₃OD): δ 1.65-1.75 (m, 4H), 2.11-2.23 (m, 2H), 2.41-2.47 (m, 2H), 2.48-2.53 (m, 2H), 2.57 (t, J=7.98 Hz, 2H), 3.83-3.92 (m, 2H), 3.99 (s, 2H), 7.01 (d, J=7.67 Hz, 1H), 7.31 (t, J=7.98 Hz, 1H), 7.38-7.42 (m, 1H), 7.51 (t, J=1.69 Hz, 1H).

Example 101

4-((2-(2-oxoazetidin-1-yl)pyridin-4-yl)methyl)-5,6,7,8-tetrahydrophthalazin-1(2H)-one A microwave tube was charged with tris(dibenzylideneacetone)dipalladium(0) (5.4 mg, 0.006 mmol), Xantphos (4,5-bis(diphenylphosphino)-9,9-dimethylxanthene) (5.4 mg, 0.01 mmol), EXAMPLE 103 (50 mg, 0.16 mmol), azetidin-2-one (53 mg, 0.62 mmol) and Cs₂CO₃ (70 mg, 0.21 mmol). Anhydrous dioxane was added, and the suspension was heated in a CEM Explorer® microwave reactor (Matthews, N.C.) at 200° C. for 30 minutes. After concentration, the residue was partitioned between ethyl acetate and brine. The organic phase was concentrated. The residual solid was separated by flash chromatography on silica gel (100% ethyl acetate) to provide the title compound. MS (DCI/NH₃) m/z 311 (M+H)⁺.

Example 102

4-((2-(2-oxopyrrolidin-1-yl)pyridin-4-yl)methyl)-5,6,7,8-tetrahydrophthalazin-1(2H)-one The title compound was prepared according to procedure for EXAMPLE 101, substituting pyrroline-2-one for azetidin-2-one. MS (ESI) m/z 339 (M+H)⁺.

Example 103

4-((2-bromopyridin-4-yl)methyl)-5,6,7,8-tetrahydrophthalazin-1(2H)-one

The title compound was prepared as described in EXAMPLE 66B. MS (DCI/NH₃) m/z 321 (M+H)⁺.

Example 104

4-((6-(2-oxopyrrolidin-1-yl)pyridin-3-yl)methyl)-5,6,7,8-tetrahydrophthalazin-1(2H)-one The title compound was prepared according to procedure for EXAMPLE 101, substituting EXAMPLE 72 for EXAMPLE 103, and pyrroline-2-one for azetidin-2-one. MS (ESI) m/z 325 (M+H)⁺.

Example 105

4-((6-(2-oxoazetidin-1-yl)pyridin-3-yl)methyl)-5,6,7,8-tetrahydrophthalazin-1(2H)-one The title compound was prepared according to procedure for EXAMPLE 101, substituting EXAMPLE 72 for EXAMPLE 103. MS (ESI) m/z 311 (M+H)⁺.

Example 106

N-(5-((4-oxo-3,4,5,6,7,8-hexahydrophthalazin-1-yl)methyl)pyridin-2-yl)benzamide

The title compound was prepared according to procedure for EXAMPLE 101, substituting EXAMPLE 72 for EXAMPLE 103, and benzamide for azetidin-2-one. MS (ESI) m/z 361 (M+H)⁺; ¹H NMR (300 MHz, dimethylsulfoxide-d₆): δ 1.48-1.70 (m, 4H), 2.41 (d, J=17.29 Hz, 4H), 3.92 (s, 2H), 7.86 (t, J=1.86 Hz, 3H), 7.86-7.90 (m, 2H), 7.99-8.06 (m, 1H), 8.12 (d, J=8.48 Hz, 1H), 8.24 (d, J=2.37 Hz, 1H), 10.72 (s, 1H) 12.60 (s, 1H).

Example 107

N-(5-((4-oxo-3,4,5,6,7,8-hexahydrophthalazin-1-yl)methyl)pyridin-2-yl)isonicotinamide The title compound was prepared according to procedure for EXAMPLE 101, substituting EXAMPLE 72 for EXAMPLE 103, and isonicotinamide for azetidin-2-one. MS (ESI) m/z 362 (M+H)⁺; ¹H NMR (300 MHz, dimethylsulfoxide-d₆): δ 1.65 (d, J=5.09 Hz, 4H), 2.41 (d, J=16.28 Hz, 4H), 3.93 (s, 2H), 7.68 (dd, J=8.48, 2.37 Hz, 1H), 7.90-8.00 (m, 2H), 8.11 (d, J=8.48 Hz, 1H), 8.27 (d, J=2.03 Hz, 1H), 8.76-8.82 (m, 2H), 11.12 (s, 1H), 12.60 (s, 1H).

Example 108

N-(5-((4-oxo-3,4,5,6,7,8-hexahydrophthalazin-1-yl)methyl)pyridin-2-yl)nicotinamide The title compound was prepared according to procedure for EXAMPLE 101, substituting EXAMPLE 72 for EXAMPLE 103, and nicotinamide for azetidin-2-one. MS (ESI) m/z 362 (M+H)⁺.

Example 109

4-((5'-((4-oxo-3,4,5,6,7,8-hexahydrophthalazin-1-yl)methyl)-2,2'-bipyridin-5-yl)methyl)-5,6,7,8-tetrahydrophthalazin-1(2H)-one The title compound was a side-product of EXAMPLE 108. MS (ESI) m/z 481 (M+H)⁺.

Example 110

N-methyl-5-((4-oxo-3,4,5,6,7,8-hexahydrophthalazin-1-yl)methyl)thiophene-2-carboxamide The title compound was prepared according to procedure for EXAMPLE 67, substituting EXAMPLE 92 for 66. MS (ESI) m/z 304 (M+H)⁺; ¹H NMR (300 MHz, dimethylsulfoxide-d₆): δ 1.63 (d, J=3.05 Hz, 4H), 2.29-2.46 (m, 4H), 2.72 (d, J=4.41 Hz, 3H), 4.09 (s, 2H), 6.88 (d, J=3.73 Hz, 1H), 7.51 (d, J=3.73 Hz, 1H), 8.31 (d, J=4.41 Hz, 1H), 12.66 (s, 1H).

Example 111

N¹-(3-((4-oxo-3,4,5,6,7,8-hexahydrophthalazin-1-yl)methyl)phenyl)glycinamide

A solution of EXAMPLE 89 (50 mg, 0.2 mmol) and 2,5-dioxopyrrolidin-1-yl 2-(tert-butoxycarbonylamino)acetate 59 mg, 0.22 mmol) in anhydrous tetrahydrofuran (4 mL) was stirred at room temperature for 16 hours, and concentrated. The residual solid was dissolved in dichloromethane (4 mL) and treated with trifluoroacetic acid (2 mL) at room temperature for 1 hour. The reaction mixture was concentrated and the residue was separated by HPLC (Zorbax® C-18 ODS packing material [Agilent Technologies, Santa Clara, Calif.], 0.1% trifluoroacetic acid/CH₃CN/H₂O) to provide the title compound as a trifluoroacetic acid salt. MS (DCI/NH$_3$) m/z 313 (M+H)$^+$; $^1$H NMR (300 MHz, CD$_3$OD): δ 1.64-1.75 (m, 4H), 2.36-2.45 (m, 2H), 2.46-2.54 (m, 2H), 3.80 (s, 2H), 3.98 (s, 2H), 7.00 (d, J=7.80 Hz, 1H), 7.28 (t, J=7.97 Hz, 1H), 7.37-7.40 (m, 1H), 7.42-7.47 (m, 1H).

Example 112

N-(3-((4-oxo-3,4,5,6,7,8-hexahydrophthalazin-1-yl)methyl)phenyl)azetidine-2-carboxamide Example 112A tert-butyl 2-(3-((4-oxo-3,4,5,6,7,8-hexahydrophthalazin-1-yl)methyl)phenylcarbamoyl)azetidine-1-carboxylate The title compound was prepared according to procedure for EXAMPLE 98, substituting 1-(tert-butoxycarbonyl)azetidine-2-carboxylic acid for 3-(piperidin-1-yl)propanoic acid. MS (DCI/NH$_3$) m/z 439 (M+H)$^+$.

Example 112B

N-(3-((4-oxo-3,4,5,6,7,8-hexahydrophthalazin-1-yl)methyl)phenyl)azetidine-2-carboxamide A solution of EXAMPLE 112A (64 mg) in dichloromethane (4 mL) was treated with trifluoroacetic acid (2 mL) at room temperature for 1 hour. The reaction mixture was concentrated and the residue was purified by HPLC (Zorbax® C-18 ODS packing material [Agilent Technologies, Santa Clara, Calif.], 0.1% trifluoroacetic acid/CH$_3$CN/H$_2$O) to provide the title compound as a trifluoroacetic acid salt. MS (DCI/NH$_3$) m/z 339 (M+H)$^+$; $^1$H NMR (300 MHz, CD$_3$OD): δ 1.64-1.73 (m, 4H), 2.36-2.44 (m, 2H), 2.46-2.53 (m, 2H), 2.57-2.69 (m, 1H), 2.81-2.93 (m, 1H), 3.94-4.04 (m, 1H), 3.98 (s, 2H), 4.08-4.20 (m, 1H), 5.07 (dd, J=9.49, 7.80 Hz, 1H), 7.03 (d, J=8.14 Hz, 1H), 7.30 (t, J=7.80 Hz, 1H), 7.41 (t, —1.70 Hz, 1H), 7.49 (dd, J=7.97, 1.53 Hz, 1H).

Example 113

N-(3-((4-oxo-3,4,5,6,7,8-hexahydrophthalazin-1-yl)methyl)phenyl)azetidine-3-carboxamide The title compound was prepared according to procedure for EXAMPLE 112, substituting 1-(tert-butoxycarbonyl)azetidine-3-carboxylic acid for 1-(tert-butoxycarbonyl)azetidine-2-carboxylic acid. MS (DCI/NH$_3$) m/z 339 (M+H)$^+$; $^1$H NMR (300 MHz, CD$_3$OD): δ1.62-1.75 (m, 4H), 2.36-2.44 (m, 2H), 2.46-2.54 (m, 2H), 3.69-3.83 (m, 1H), 3.97 (s, 2H), 4.17-4.33 (m, 4H), 7.00 (dd, J=7.14, 1.19 Hz, 1H), 7.27 (t, J=7.93 Hz, 1H), 7.40 (t, J=1.59 Hz, 1H), 7.45-7.51 (m, 1H).

Example 114

N-(3-((4-oxo-3,4,5,6,7,8-hexahydrophthalazin-1-yl)methyl)phenyl)methanesulfonamide The title compound was prepared according to the procedure for EXAMPLE 97, substituting methanesulfonyl chloride for dimethylsulfamoyl chloride. MS (DCI/NH$_3$) m/z 334 (M+H)$^+$; $^1$H NMR (500 MHz, dimethylsulfoxide-d$_6$): δ 1.53-1.67 (m, 4H), 2.29-2.42 (m, 4H), 2.95 (s, 3H), 3.88 (s, 2H), 6.92 (d, J=7.63 Hz, 1H), 7.00 (s, 1H), 7.06 (dd, J=7.93, 1.22 Hz, 1H), 7.26 (t, J=7.78 Hz, 1H), 9.68 (br s, 1H), 12.63 (br s, 1H).

Example 115

N-(3-((4-oxo-3,4,5,6,7,8-hexahydrophthalazin-1-yl)methyl)phenyl)propane-2-sulfonamide The title compound was prepared according to the procedure for EXAMPLE 97, substituting propane-2-sulfonyl chloride for dimethylsulfamoyl chloride. MS (DCI/NH$_3$) m/z 362 (M+H)$^+$; $^1$H NMR (500 MHz, dimethylsulfoxide-d$_6$): δ 1.19 (d, J=7.02 Hz, 6H), 1.53-1.66 (m, 4H), 2.25-2.33 (m, 2H), 2.34-2.41 (m, 2H), 3.08-3.22 (m, 1H), 3.87 (s, 2H), 6.88-6.91 (m, 1H), 7.01 (s, 1H), 7.08 (dd, J=8.24, 1.22 Hz, 1H), 7.23 (t, J=7.78 Hz, 1H), 9.68 (br s, 1H), 12.64 (br s, 1H).

Example 116

N-(3-((4-oxo-3,4,5,6,7,8-hexahydrophthalazin-1-yl)methyl)phenyl)benzenesulfonamide The title compound was prepared according to the procedure for EXAMPLE 97, substituting benzenesulfonyl chloride for dimethylsulfamoyl chloride. MS (DCI/NH$_3$) m/z 396 (M+H)$^+$; $^1$H NMR (500 MHz, dimethylsulfoxide-d$_6$): δ 1.48-1.60 (m, 4H), 2.10-2.21 (m, 2H), 2.29-2.39 (m, 2H), 3.78 (s, 2H), 6.83-6.87 (m, 2H), 6.92 (dd, J=8.09, 1.37 Hz, 1H), 7.15 (t, J=7.78 Hz, 1H), 7.48 (t, J=7.78 Hz, 2H), 7.58 (t, J=7.48 Hz, 1H), 7.64-7.69 (m, 2H), 10.24 (br s, 1H), 12.64 (br s, 1H).

Example 117

N-(3-((4-oxo-3,4,5,6,7,8-hexahydrophthalazin-1-yl)methyl)phenyl)pyridine-3-sulfonamide The title compound was prepared according to the procedure for EXAMPLE 97, substituting pyridine-3-sulfonyl chloride hydrochloride for dimethylsulfamoyl chloride. MS (DCI/NH$_3$) m/z 397 (M+H)$^+$; $^1$H NMR (500 MHz, dimethylsulfoxide-d$_6$): δ 1.50-1.61 (m, 4H), 2.12-2.21 (m, 2H), 2.33-2.40 (m, 2H), 3.80 (s, 2H), 6.85 (s, 1H), 6.92 (d, J=7.63 Hz, 1H), 6.96 (dd, J=7.93, 1.22 Hz, 1H), 7.19 (t, J=7.78 Hz, 1H), 7.55 (dd, J=8.09, 4.73 Hz, 1H), 8.02-8.06 (m, 1H), 8.75 (dd, J=4.88, 1.53 Hz, 1H), 8.77 (d, J=1.83 Hz, 1H), 10.43 (br s, 1H), 12.63 (br s, 1H).

Example 118

N-(3-((4-oxo-3,4,5,6,7,8-hexahydrophthalazin-1-yl)methyl)phenyl)furan-2-sulfonamide The title compound was prepared according to the procedure for EXAMPLE 97, substituting furan-2-sulfonyl chloride for dimethylsulfamoyl chloride. MS (DCI/NH$_3$) m/z 386 (M+H)$^+$; $^1$H NMR (500 MHz, dimethylsulfoxide-d$_6$): δ 1.52-1.63 (m, 4H), 2.19-2.28 (m, 2H), 2.32-2.40 (m, 2H), 3.82 (s, 2H), 6.57 (dd, J=3.66, 1.83 Hz, 1H), 6.89 (d, J=1.53 Hz, 1H), 6.91 (d, J=7.63 Hz, 1H), 6.95-6.99 (m, 1H), 7.04 (d, J=3.36 Hz, 1H), 7.20 (t, J=7.78 Hz, 1H), 7.90 (dd, J=1.83, 0.92 Hz, 1H), 10.60 (br s, 1H), 12.65 (br s, 1H).

Example 119

1-methyl-N-(3-((4-oxo-3,4,5,6,7,8-hexahydrophthalazin-1-yl)methyl)phenyl)-1H-imidazole-4-sulfonamide The title compound was prepared according to the procedure for EXAMPLE 97, substituting 1-methyl-1H-imidazole-4-sulfonyl chloride for dimethylsulfamoyl chloride. MS (DCI/CH$_3$) m/z 400 (M+H)$^+$. $^1$H NMR (500 MHz, dimethylsulfoxide-d$_6$): δ 1.55-1.61 (m, 4H), 2.24-2.32 (m, 2H), 2.32-2.40 (m, 2H), 3.63 (s, 3H), 3.80 (s, 2H), 6.80 (d, J=7.93 Hz, 1H), 6.92 (s, 1H), 6.99 (dd, J=8.09, 1.37 Hz, 1H), 7.13 (t, J=7.78 Hz, 1H), 7.70 (d, J=1.22 Hz, 1H), 7.73 (d, J=1.22 Hz, 1H), 10.15 (br s, 1H), 12.64 (br s, 1H).

Example 120

N-(3-((4-oxo-3,4,5,6,7,8-hexahydrophthalazin-1-yl)methyl)phenyl)thiophene-2-sulfonamide The title compound was prepared according to the procedure for EXAMPLE 97, substituting thiophene-2-sulfonyl chloride for dimethylsulfamoyl chloride. MS (DCI/NH$_3$) m/z 402 (M+H)$^+$; $^1$H NMR (500 MHz, dimethylsulfoxide-d$_6$): δ 1.41-1.64 (m, 4H), 2.18-2.24 (m, 2H), 2.34-2.40 (m, 2H), 3.82 (s, 2H), 6.90-6.94 (m, 2H), 6.97 (d, J=7.93 Hz, 1H), 7.06 (dd, J=5.03, 3.81 Hz, 1H), 7.17-7.24 (m, 1H), 7.45 (dd, J=3.81, 1.37 Hz, 1H), 7.85 (dd, J=5.03, 1.37 Hz, 1H), 10.36 (br s, 1H), 12.65 (br s, 1H).

Example 121

4-cyano-N-(3-((4-oxo-3,4,5,6,7,8-hexahydrophthalazin-1-yl)methyl)phenyl)benzenesulfonamide The title compound was prepared according to the procedure for EXAMPLE 97, substituting 4-cyanobenzene-1-sulfonyl chloride for dimethylsulfamoyl chloride. MS (DCI/NH$_3$) m/z 421 (M+H)$^+$; $^1$H NMR (500 MHz, dimethylsulfoxide-d$_6$): δ 1.49-1.62 (m, 4H), 2.14-2.20 (m, 2H), 2.31-2.39 (m, 2H), 3.80 (s, 2H), 6.84 (s, 1H), 6.90 (d, J=7.63 Hz, 1H), 6.94 (dd, J=7.93, 1.22 Hz, 1H), 7.19 (t, J=7.93 Hz, 1H), 7.83 (d, J=8.85 Hz, 2H), 8.00 (d, J=8.54 Hz, 2H), 10.52 (br s, 1H), 12.65 (br s, 1H).

Example 122

N-(3-((4-oxo-3,4,5,6,7,8-hexahydrophthalazin-1-yl)methyl)phenyl)naphthalene-1-sulfonamide The title compound was prepared according to the procedure for EXAMPLE 97, substituting naphthalene-1-sulfonyl chloride for dimethylsulfamoyl chloride. MS (DCI/NH$_3$) m/z 421 (M+H)$^+$; $^1$H NMR (500 MHz, dimethylsulfoxide-d$_6$): δ 1.41-1.47 (m, 2H), 1.47-1.56 (m, 2H), 2.00-2.10 (m, 2H), 2.30-2.39 (m, 2H), 3.71 (s, 2H), 6.75-6.80 (m, 2H), 6.83-6.89 (m, 1H), 7.07 (t, J=7.78 Hz, 1H), 7.50-7.56 (m, 1H), 7.64 (t, J=7.02 Hz, 1H), 7.67-7.72 (m, 1H), 8.04 (d, J=7.63 Hz, 1H), 8.06-8.10 (m, 1H), 8.18 (d, J=8.24 Hz, 1H), 8.67 (d, J=8.54 Hz, 1H), 10.65 (br s, 1H), 12.64 (br s, 1H).

Example 123

4-((6-bromopyridin-2-yl)methyl)-5,6,7,8-tetrahydrophthalazin-1(2H)-one

The title compound was prepared as described in EXAMPLE 74B. MS (DCI/NH$_3$) m/z 321 (M+H)$^+$.

Example 125

4-((6-(2-oxopyrrolidin-1-yl)pyridin-2-yl)methyl)-5,6,7,8-tetrahydrophthalazin-1(2H)-one The title compound was prepared according to procedure for EXAMPLE 101, substituting EXAMPLE 123 for EXAMPLE 103, and pyrroline-2-one for azetidin-2-one. MS (ESI) m/z 325 (M+H)$^+$.

Example 126

N-(6-((4-oxo-3,4,5,6,7,8-hexahydrophthalazin-1-yl)methyl)pyridin-2-yl)benzamide

The title compound was prepared according to procedure for EXAMPLE 101, substituting EXAMPLE 123 for EXAMPLE 103, and benzylamide for azetidin-2-one. MS (ESI) m/z 361 (M+H)$^+$; $^1$H NMR (300 MHz, dimethylsulfoxide-d): δ 1.63 (m, 4H), 2.40 (m, 4H), 4.02 (s, 2H), 6.95 (d, J=7.46 Hz, 1H), 7.38-7.54 (m, 2H), 7.50-7.62 (m, 1H), 7.67-7.84 (m, 1H), 7.90-8.12 (m, 3H), 10.69 (s, 1H), 12.61 (s, 1H).

Example 127

4-((3'-((isopropylamino)methyl)-1,1'-biphenyl-3-yl)methyl)-5,6,7,8-tetrahydrophthalazin-1(2H)-one

Example 127A

3'-((4-oxo-3,4,5,6,7,8-hexahydrophthalazin-1-yl)methyl)biphenyl-3-carbaldehyde

A suspension of EXAMPLE 90 (500 mg, 1.57 mmol), 3-formylphenylboronic acid (352 mg, 2.35 mmol), dichlorobis(triphenylphosphine)palladium(II) (112 mg, 0.16 mmol) and sodium carbonate (2M solution, 3.13 mmol, 1.6 mL) in a 7/3/3 mixture of 1,2-dimethoxyethane/water/ethanol (23 mL) was purged with nitrogen, and heated at 70° C. for 16 hours. After cooling to room temperature, the reaction mixture was concentrated on a rotary evaporator. The crude solid was separated by HPLC (Zorbax® C-18 ODS packing material [Agilent Technologies, Santa Clara, Calif.], 0.1% trifluoroacetic acid/CH$_3$CN/H$_2$O) to provide the title compound. MS (DCI/NH$_3$) m/z 345 (M+H)$^+$.

Example 127B 4-((3'-((isopropylamino)methyl)-1,1'-biphenyl-3-yl)methyl)-5,6,7,8-tetrahydrophthalazin-1(2H)-one The title compound was prepared as a trifluoroacetic acid salt according to procedure for EXAMPLE 65, substituting EXAMPLE 127A for formaldehyde, and propan-2-amine for EXAMPLE 56. MS (DCI/NH$_3$) m/z 388 (M+H)$^+$; $^1$H NMR (500 MHz, CD$_3$OD): δ 1.41 (d, J=6.71 Hz, 6H), 1.64-1.76 (m, 4H), 2.43-2.48 (m, 2H), 2.48-2.53 (m, 2H), 3.42-3.52 (m, 1H), 4.06 (s, 2H), 4.27 (s, 2H), 7.22 (d, J=7.93 Hz, 1H), 7.41 (t, J=7.63 Hz, 1H), 7.45-7.50 (m, 2H), 7.51-7.56 (m, 2H), 7.64-7.69 (m, 1H), 7.71-7.74 (m, 1H).

Example 128

4-((3'-((cyclopentylamino)methyl)-1,1'-biphenyl-3-yl)methyl)-5,6,7,8-tetrahydrophthalazin-1(2H)-one The title compound was prepared as a trifluoroacetic acid salt according to procedure for EXAMPLE 65, substituting EXAMPLE 127A for formaldehyde, and cyclopentanamine for EXAMPLE 56. MS (DCI/NH$_3$) m/z 414 (M+H)$^+$.

Example 129

4-((3'-((2-methylpyrrolidin-1-yl)methyl)-1,1'-biphenyl-3-yl)methyl)-5,6,7,8-tetrahydrophthalazin-1(2H)-one The title compound was prepared as a trifluoroacetic acid salt according to procedure for EXAMPLE 65, substituting EXAMPLE 127A for formaldehyde and 2-methylpyrrolidine for EXAMPLE 56. MS (DCI/NH$_3$) m/z 414 (M+H)$^+$.

Example 130

4-((3'-((cyclopropylamino)methyl)-1,1'-biphenyl-3-yl)methyl)-5,6,7,8-tetrahydrophthalazin-1(2H)-one The title compound was prepared as a trifluoroacetic acid salt according to procedure for EXAMPLE 65, substituting EXAMPLE 127A for formaldehyde, and cyclopropanamine for EXAMPLE 56. MS (DCI/NH$_3$) m/z 386 (M+H)$^+$.

Example 131

4-((3'-((cyclobutylamino)methyl)-1,1'-biphenyl-3-yl)methyl)-5,6,7,8-tetrahydrophthalazin-1(2H)-one The title compound was prepared as a trifluoroacetic acid salt according to procedure for EXAMPLE 65, substituting EXAMPLE 127A for formaldehyde, and cyclobutanamine for EXAMPLE 56. MS (DCI/NH$_3$) m/z 400 (M+H)$^+$.

Example 132

4-((2-bromo-1-oxidopyridin-4-yl)methyl)-5,6,7,8-tetrahydrophthalazin-1(2H)-one

A solution of EXAMPLE 103 (100 mg, 0.31 mmol) in dichloromethane (15 ml) was treated with meta-chloroperoxybenzoic acid (100 mg, 0.58 mmol) at room temperature overnight, and concentrated. The residue was dissolved in methanol, and separated by HPLC (Zorbax® C-18 ODS packing material [Agilent Technologies, Santa Clara, Calif.], 0.1% trifluoroacetic acid, CH$_3$CN/H$_2$O) to provide the title compound as a trifluoroacetic acid salt. MS (DCI/NH$_3$) m/z 336 (M+H)$^+$.

Example 133

4-((1-oxido-2-(2-oxopyrrolidin-1-yl)pyridin-4-yl)methyl)-5,6,7,8-tetrahydrophthalazin-1(2H)-one The title compound was prepared according to procedure for EXAMPLE 132, substituting EXAMPLE 102 for EXAMPLE 103. MS (ESI) m/z 341 (M+H)$^+$.

Example 134 methyl 5-((4-oxo-3,4,5,6,7,8-hexahydrophthalazin-1-yl)methyl)thiophene-3-carboxylate Example 134A 3-((4-bromothiophen-2-yl)methylene)-4,5,6,7-tetrahydroisobenzofuran-1(3H)-one The title compound was prepared according to the procedure for EXAMPLE 1C, substituting 5-bromothiophene-2-carbaldehyde for 2-fluoro-5-formylbenzonitrile. MS (DCI/NH$_4$) m/z 312 (M+H)$^+$.

Example 134B 4-((4-bromothiophen-2-yl)methyl)-5,6,7,8-tetrahydrophthalazin-1(2H)-one The title compound was prepared according to the procedure for EXAMPLE 2C substituting EXAMPLE 134A for EXAMPLE 2B. MS (DCI/NH$_3$) m/z 326 (M+H)$^+$.

Example 134C methyl 5-((4-oxo-3,4,5,6,7,8-hexahydrophthalazin-1-yl)methyl)thiophene-3-carboxylate The title compound was prepared according to the procedure for EXAMPLE 66, substituting EXAMPLE 134B for EXAMPLE 66B. MS (DCI/NH$_3$) m/z 305 (M+H)$^+$.

Example 135

4-(3-((4-(2-(2-(2-aminoethoxy)ethoxy)ethyl)-1,4-diazepan-1-yl)carbonyl)-4-fluorobenzyl)phthalazin-1(2H)-one Example 135A tert-butyl 2-(2-(2-(4-(2-fluoro-5-((4-oxo-3,4,5,6,7,8-hexahydrophthalazin-1-yl)methyl)benzoyl)-1,4-diazepan-1-yl)ethoxy)ethoxy)ethylcarbamate To a solution of 2-(2-(-t-Boc-aminoethoxy)ethoxy)ethyl bromide (Toronto, 137 mg, 0.44 mmol) in N,N-dimethylformamide (4 mL) was added EXAMPLE 5 (84 mg, 0.22 mmol) and potassium carbonate (91 mg, 0.66 mmol). The reaction mixture was heated at 35° C. overnight, and partitioned between ethyl acetate and brine. The organic phase was washed with brine, and concentrated. The residue was separated by HPLC (Zorbax® C-18 ODS packing material [Agilent Technologies, Santa Clara, Calif.], 250×2.54 column, mobile phase A: 0.1% trifluoroacetic acid in H$_2$O: B: 0.1% trifluoroacetic acid in CH$_3$CN; 0-100% gradient) to provide the title compound as a trifluoroacetic acid salt. MS (DCI/NH$_3$) m/z 612 (M+H)$^+$.

Example 135B 4-(3-((4-(2-(2-(2-aminoethoxy)ethoxy)ethyl)-1,4-diazepan-1-yl)carbonyl)-4-fluorobenzyl)phthalazin-1(2H)-one To a suspension of EXAMPLE 135A (43 mg, 0.06 mmol) in dichloromethane (5 mL) was added trifluoroacetic acid (1 mL) at room temperature. The solution remained at room temperature for 1 hour, and was concentrated. The residue was purified by HPLC (Zorbax® C-18 ODS packing material [Agilent Technologies, Santa Clara, Calif.], 250×2.54 column, mobile phase A: 0.1% trifluoroacetic acid in H$_2$O; B: 0.1% trifluoroacetic acid in CH$_3$CN; 0-100% gradient) to provide the title compound as a trifluoroacetic acid salt. The trifluoroacetic acid salt was dissolved in a mixture of methylene chloride and methanol, and was treated with 1M solution of HCl in ether. Removal of the volatiles afforded the title compound as a HCl salt. MS (DCI/NH$_3$) m/z 338 (M+H)$^+$.

Example 136

1-methyl-N-(3-((4-oxo-3,4,5,6,7,8-hexahydrophthalazin-1-yl)methyl)phenyl)cyclopropanecarboxamide A solution of EXAMPLE 89 (20 mg, 0.08 mmol), 1-methylcyclopropanecarboxylic acid (10 mg, 0.096 mmol), HATU (2-(1H-7-azabenzotriazol-1-yl)-1,1,3,3-tetramethyl uronium hexafluorophosphate methanaminium) (38 mg, 0.1 mmol) and triethylamine (20 mg, 0.2 mmol) in dimethylacetamide (2.5 mL) was stirred at room temperature for 18 hours, and concentrated. The residue was dissolved in a 1:1 mixture of dimethylsulfoxide/methanol, and separated by HPLC (Waters Sunfire® C-8 analytical column [Milford, Mass.], 0.1% trifluoroacetic acid/water/CH$_3$CN) to provide the title compound. MS (DCI/NH$_3$) m/z 338 (M+H)$^+$; $^1$H NMR (500 MHz, D$_2$O/dimethylsulfoxide-d$_6$): δ 0.57-0.69 (m, 2H), 1.02-1.10 (m, 2H), 1.38 (s, 3H), 1.57-1.65 (m, 4H), 2.29-2.44 (m, 4H), 3.87 (s, 2H), 6.89 (d, J=7.63 Hz, 1H), 7.23 (t, J=7.93 Hz, 1H), 7.42 (s, 1H), 7.46 (d, J=8.24 Hz, 1H).

Example 137

2-methyl-N-(3-((4-oxo-3,4,5,6,7,8-hexahydrophthalazin-1-yl)methyl)phenyl)cyclopropanecarboxamide The title compound was prepared according to the procedure for EXAMPLE 136, substituting 2-methylcyclopropanecarboxylic acid for 1-methylcyclopropanecarboxylic acid. MS (DCI/NH$_3$) m/z 338 (M+H)$^+$.

Example 138

3-ethoxy-N-(3-((4-oxo-3,4,5,6,7,8-hexahydrophthalazin-1-yl)methyl)phenyl)propanamide The title compound was prepared according to the procedure for EXAMPLE 136, substituting 3-ethoxypropanoic acid for 1-methylcyclopropanecarboxylic acid. MS (DCI/NH$_3$) m/z 356 (M+H)$^+$; $^1$H NMR (500 MHz, D$_2$O/dimethylsulfoxide-d$_6$): δ $^1$H NMR (500 MHz, Solvent) δ 1.08 (t, J=7.02 Hz, 3H), 1.54-1.64 (m, 4H), 2.32-2.42 (m, 4H), 2.51 (t, J=6.26 Hz, 2H), 3.43 (q, J=7.02 Hz, 2H), 3.64 (t, J=6.26 Hz, 2H), 3.88 (s, 2H), 6.90 (d, J=7.63 Hz, 1H), 7.24 (t, 7.78 Hz, 1H), 7.36 (s, 1H), 7.48 (d, J=7.93 Hz, 1H).

Example 139

5-oxo-N-(3-((4-oxo-3,4,5,6,7,8-hexahydrophthalazin-1-yl)methyl)phenyl)-L-prolinamide The title compound was prepared according to the procedure for EXAMPLE 136, substituting (S)-5-oxopyrrolidine-2-carboxylic acid for 1-methylcyclopropanecarboxylic acid. MS (DCI/NH$_3$) m/z 367 (M+H)$^+$; $^1$H NMR (500 MHz, D$_2$O/dimethylsulfoxide-d$_6$): δ $^1$H NMR (500 MHz, Solvent) δ 1.56-1.66 (m, 4H), 1.93-2.03 (m, 1H), 2.14-2.27 (m, 2H), 2.32-2.43 (m, 5H), 3.96 (s, 2H), 4.19 (dd, J=8.70, 4.42 Hz, 1H), 6.94 (d, J=7.63 Hz, 1H), 7.27 (t, J=7.93 Hz, 1H), 7.40 (s, 1H), 7.49 (d, J=7.93 Hz, 1H).

Example 140

5-oxo-N-(3-((4-oxo-3,4,5,6,7,8-hexahydrophthalazin-1-yl)methyl)phenyl)-D-prolinamide The title compound was prepared according to the procedure for EXAMPLE 136, substituting (R)-5-oxopyrrolidine-2-carboxylic acid for 1-methylcyclopropanecarboxylic acid. MS (DCI/NH$_3$) m/z 367 (M+H)$^+$; $^1$H NMR (500 MHz, D$_2$O/dimethylsulfoxide-d$_6$): δ 1.56-1.66 (m, 4H), 1.93-2.02 (m, 1H), 2.13-2.25 (m, 2H), 2.32-2.42 (m, 5H), 3.89 (s, 2H), 4.18 (dd, J=8.70, 4.42 Hz, 1H), 6.94 (d, J=7.63 Hz, 1H), 7.27 (t, J=7.93 Hz, 1H), 7.39 (s, 1H), 7.49 (d, J=8.24 Hz, 1H).

Example 141

N$^1$-(3-((4-oxo-3,4,5,6,7,8-hexahydrophthalazin-1-yl)methyl)phenyl)cyclopropane-1,1-dicarboxamide The title compound was prepared according to the procedure for EXAMPLE 136, substituting 1-carbamoylcyclopropanecarboxylic acid for 1-methylcyclopropanecarboxylic acid. MS (DCI/NH$_3$) m/z 367 (M+H)$^+$; $^1$H NMR (500 MHz, D$_2$O/dimethylsulfoxide-d$_6$): δ 1.35-1.44 (m, 4H), 1.55-1.67 (m, 4H), 2.31-2.44 (m, 4H), 3.88 (s, 2H), 6.91 (d, J=7.63 Hz, 1H), 7.26 (t, J=7.78 Hz, 1H), 7.40 (s, 1H), 7.43 (d, J=7.93 Hz, 1H).

Example 142

2-(benzyloxy)-N-(3-((4-oxo-3,4,5,6,7,8-hexahydrophthalazin-1-yl)methyl)phenyl)acetamide The title compound was prepared according to the procedure for EXAMPLE 136, substituting 2-(benzyloxy)acetic acid for 1-methylcyclopropanecarboxylic acid. MS (DCI/NH$_3$) m/z 404 (M+H)$^+$. $^1$H NMR (500 MHz, D$_2$O/dimethylsulfoxide-d$_6$): δ 1.56-1.64 (m, 4H), 2.32-2.42 (m, 4H), 3.89 (s, 2H), 4.06 (s, 2H), 4.60 (s, 2H), 6.93 (d, J=7.63 Hz, 1H), 7.26 (t, J=7.78 Hz, 1H), 7.31-7.34 (m, 1H), 7.36-7.42 (m, 5H), 7.50 (d, J=7.93 Hz, 1H).

Example 143

N-(3-((4-oxo-3,4,5,6,7,8-hexahydrophthalazin-1-yl)methyl)phenyl)-3-phenylpropanamide The title compound was prepared according to the procedure for EXAMPLE 136, substituting 3-phenylpropanoic acid for 1-methylcyclopropanecarboxylic acid. MS (DCI/NH$_3$) m/z 388 (M+H)$^+$; $^1$H NMR (500 MHz, D$_2$O/dimethylsulfoxide-d$_6$): δ 1.55-1.65 (m, 4H), 2.32-2.42 (m, 4H), 2.60 (t, J=7.63 Hz, 2H), 2.89 (t, J=7.63 Hz, 2H), 3.87 (s, 2H), 6.89 (d, J=7.63 Hz, 1H), 7.18 (t, J=7.17 Hz, 1H), 7.21-7.26 (m, 3H), 7.28 (t, J=7.48 Hz, 2H), 7.32 (s, 1H), 7.45 (d, J=8.24 Hz, 1H).

Example 144

3-(2,5-dimethoxyphenyl)-N-(3-((4-oxo-3,4,5,6,7,8-hexahydrophthalazin-1-yl)methyl)phenyl)propanamide The title compound was prepared according to procedure for EXAMPLE 136, substituting 3-(2,5-dimethoxyphenyl)propanoic acid for 1-methylcyclopropanecarboxylic acid. MS (DCI/NH$_3$) m/z 448 (M+H)$^+$.

Example 145

N-(3-((4-oxo-3,4,5,6,7,8-hexahydrophthalazin-1-yl)methyl)phenyl)-1-phenylcyclopropanecarboxamide The title compound was prepared according to the procedure for EXAMPLE 136, substituting 1-phenylcyclopropanecarboxylic acid for 1-methylcyclopropanecarboxylic acid. MS (DCI/NH$_3$) m/z 400 (M+H)$^+$.

Example 146

(2S)—N-(3-((4-oxo-3,4,5,6,7,8-hexahydrophthalazin-1-yl)methyl)phenyl)-2-phenylbutanamide The title compound was prepared according to the procedure for EXAMPLE 136, substituting (S)-2-phenylbutanoic acid for 1-methylcyclopropanecarboxylic acid. MS (DCI/NH$_3$) m/z 402 (M+H)$^+$.

Example 147

N-(3-((4-oxo-3,4,5,6,7,8-hexahydrophthalazin-1-yl)methyl)phenyl)-4-phenylbutanamide The title compound was prepared according to procedure for EXAMPLE 136, substituting 4-phenylbutanoic acid for 1-methylcyclopropanecarboxylic acid. MS (DCI/NH$_3$) m/z 402 (M+H)$^+$.

Example 148

2-(3-methylphenoxy)-N-(3-((4-oxo-3,4,5,6,7,8-hexahydrophthalazin-1-yl)methyl)phenyl)acetamide The title compound was prepared according to the procedure for EXAMPLE 136, substituting 2-(m-tolyloxy)acetic acid for 1-methylcyclopropanecarboxylic acid. MS (DCI/NH$_3$) m/z 404 (M+H)$^+$.

Example 149

2-(2-methylphenoxy)-N-(3-((4-oxo-3,4,5,6,7,8-hexahydrophthalazin-1-yl)methyl)phenyl)acetamide The title compound was prepared according to the procedure for EXAMPLE 136, substituting 2-(o-tolyloxy)acetic acid for 1-methylcyclopropanecarboxylic acid. MS (DCI/NH$_3$) m/z 404 (M+H)$^+$.

Example 150

2-(4-methylphenoxy)-N-(3-((4-oxo-3,4,5,6,7,8-hexahydrophthalazin-1-yl)methyl)phenyl)acetamide The title compound was prepared according to procedure for EXAMPLE 136, substituting 2-(p-tolyloxy)acetic acid for 1-methylcyclopropanecarboxylic acid. MS (DCI/NH$_3$) m/z 404 (M+H)$^+$; $^1$H NMR (500 MHz, D$_2$O/dimethylsulfoxide-d$_6$): δ 1.56-1.65 (m, 4H), 2.23 (s, 3H), 2.33-2.44 (m, 4H), 3.89 (s, 2H), 4.61 (s, 2H), 6.88 (d, J=8.54 Hz, 2H), 6.94 (d, J=7.63 Hz, 1H), 7.11 (d, J=8.24 Hz, 2H), 7.27 (t, J=7.78 Hz, 1H), 7.41 (s, 1H), 7.50 (d, J=8.24 Hz, 1H).

Example 151

(2R)-2-methoxy-N-(3-((4-oxo-3,4,5,6,7,8-hexahydrophthalazin-1-yl)methyl)phenyl)-2-phenylacetamide The title compound was prepared according to procedure for EXAMPLE 136, substituting (R)-2-methoxy-2-phenylacetic acid for 1-methylcyclopropanecarboxylic acid. MS (DCI/NH$_3$) m/z 404 (M+H)$^+$; $^1$H NMR (500 MHz, D$_2$O/dimethylsulfoxide-d$_6$): δ 1.53-1.66 (m, 4H), 2.29-2.44 (m, 4H), 3.35 (s, 3H), 3.87 (s, 2H), 4.81 (s, 1H), 6.91 (d, J=7.63 Hz, 1H), 7.25 (t, J=7.93 Hz, 1H), 7.33-7.36 (m, 1H), 7.39 (t, J=7.17 Hz, 2H), 7.45-7.49 (m, 3H), 7.52 (d, J=8.24 Hz, 1H).

Example 152

(2S)-2-methoxy-N-(3-((4-oxo-3,4,5,6,7,8-hexahydrophthalazin-1-yl)methyl)phenyl)-2-phenylacetamide The title compound was prepared according to the procedure for EXAMPLE 136, substituting (S)-2-methoxy-2-phenylacetic acid for 1-methylcyclopropanecarboxylic acid. MS (DCI/NH$_3$) m/z 404 (M+H)$^+$; $^1$H NMR (500 MHz, D$_2$O/dimethylsulfoxide-d$_6$): δ 1.53-1.66 (m, 4H), 2.30-2.42 (m, 4H), 3.34 (s, 3H), 3.87 (s, 2H), 4.81 (s, 1H), 6.91 (d, J=7.63 Hz, 1H), 7.25 (t, J=7.93 Hz, 1H), 7.32-7.36 (m, 1H), 7.39 (t, J=7.17 Hz, 2H), 7.44-7.49 (m, 3H), 7.51 (d, J=8.24 Hz, 1H).

Example 153

N-(3-((4-oxo-3,4,5,6,7,8-hexahydrophthalazin-1-yl)methyl)phenyl)-3-phenoxypropanamide The title compound was prepared according to procedure for EXAMPLE 136, substituting 3-phenoxypropanoic acid for 1-methylcyclopropanecarboxylic acid. MS (DCI/NH$_3$) m/z 404 (M+H)$^+$.

Example 154

N-(3-((4-oxo-3,4,5,6,7,8-hexahydrophthalazin-1-yl)methyl)phenyl)-4-thien-2-ylbutanamide The title compound was prepared according to procedure for EXAMPLE 136, substituting 4-(thiophen-2-yl)butanoic acid for 1-methylcyclopropanecarboxylic acid. MS (DCI/NH$_3$) m z 408 (M+H)$^+$.

Example 155

1-acetyl-N-(3-((4-oxo-3,4,5,6,7,8-hexahydrophthalazin-1-yl)methyl)phenyl)piperidine-4-carboxamide The title compound was prepared according to the procedure for EXAMPLE 136, substituting 1-acetylpiperidine-4-carboxylic acid for 1-methylcyclopropanecarboxylic acid. MS (DCI/NH$_3$) m/z 409 (M+H)$^+$; $^1$H NMR (500 MHz, D$_2$O/ dimethylsulfoxide-$d_6$): δ 1.36-1.46 (m, 1H), 1.52-1.67 (m, 5H), 1.79 (t, J=14.19 Hz, 2H), 2.02 (s, 3H), 2.30-2.43 (m, 4H), 2.56-2.63 (m, 1H), 3.06 (t, J=12.97 Hz, 1H), 3.85-3.90 (m, 2H), 3.97 (s, 2H), 4.39 (d, J=13.43 Hz, 1H), 6.89 (d, J=7.63 Hz, 1H), 7.24 (t, J=7.78 Hz, 1H), 7.38 (s, 1H), 7.48 (d, J=8.24 Hz, 1H).

Example 156

2-(3,5-difluorophenyl)-N-(3-((4-oxo-3,4,5,6,7,8-hexahydrophthalazin-1-yl)methyl)phenyl)acetamide The title compound was prepared according to procedure for EXAMPLE 136, substituting 2-(3,5-difluorophenyl)acetic acid for 1-methylcyclopropanecarboxylic acid. MS (DCI/NH$_3$) m/z 410 (M+H)$^+$; $^1$H NMR (500 MHz, D$_2$O/dimethylsulfoxide-$d_6$): δ 1.53-1.67 (m, 4H), 2.31-2.42 (m, 4H), 3.67 (s, 2H), 3.88 (s, 2H), 6.91 (d, J=7.63 Hz, 1H), 7.04 (d, J=6.41 Hz, 1H), 7.07-7.13 (m, 1H), 7.25 (t, J=7.93 Hz, 1H), 7.36 (s, 1H), 7.46 (d, J=8.24 Hz, 1H).

Example 157

N$^2$-acetyl-N$^1$-(3-((4-oxo-3,4,5,6,7,8-hexahydrophthalazin-1-yl)methyl)phenyl)-L-leucinamide The title compound was prepared according to procedure for EXAMPLE 136, substituting (S)-2-acetamido-4-methylpentanoic acid for 1-methylcyclopropanecarboxylic acid. MS (DCI/NH$_3$) m/z 411 (M+H)$^+$; $^1$H NMR (500 MHz, D$_2$O/dimethylsulfoxide-$d_6$): δ 0.88 (d, J=6.71 Hz, 3H), 0.90 (d, J=6.71 Hz, 3H), 1.43-1.53 (m, 2H), 1.56-1.66 (m, 5H), 1.87 (s, 3H), 2.29-2.43 (m, 4H), 3.88 (s, 2H), 4.39 (dd, J=9.61, 5.34 Hz, 1H), 6.91 (d, J=7.63 Hz, 1H), 7.25 (t, J=7.78 Hz, 1H), 7.38 (s, 1H), 7.49 (d, J=8.24 Hz, 1H).

Example 158

N$^1$-(3-((4-oxo-3,4,5,6,7,8-hexahydrophthalazin-1-yl)methyl)phenyl)-N$^2$,N$^2$-dipropyl-L-alaninamide The title compound was prepared according to procedure for EXAMPLE 136, substituting (S)-2-(dipropylamino)propanoic acid for 1-methylcyclopropanecarboxylic acid. MS (DCI/NH$_3$) m/z 411 (M+H)$^+$.

Example 159

4-oxo-N-(3-((4-oxo-3,4,5,6,7,8-hexahydrophthalazin-1-yl)methyl)phenyl)-4-phenylbutanamide The title compound was prepared according to procedure for EXAMPLE 136, substituting 4-oxo-4-phenylbutanoic acid for 1-methylcyclopropanecarboxylic acid. MS (DCI/NH$_3$) m/z 411 (M+H)$^+$; $^1$H NMR (500 MHz, D$_2$O/dimethylsulfoxide-$d_6$): δ 1.55-1.66 (m, 4H), 2.31-2.42 (m, 4H), 2.70 (t, J=6.26 Hz, 2H), 3.32 (t, J=6.26 Hz, 2H), 3.87 (s, 2H), 6.88 (d, J=7.63 Hz, 1H), 7.23 (t, J=7.93 Hz, 1H), 7.37 (s, 1H), 7.45 (d, J=8.24 Hz, 1H), 7.55 (t, J=7.63 Hz, 2H), 7.66 (t, J=7.32 Hz, 1H), 7.99 (t, J=6.41 Hz, 2H).

Example 160

N-(2-oxo-2-(3-((4-oxo-3,4,5,6,7,8-hexahydrophthalazin-1-yl)methyl)phenylamino)ethyl)benzamide The title compound was prepared according to procedure for EXAMPLE 136, substituting 2-benzamidoacetic acid for 1-methylcyclopropanecarboxylic acid. MS (DCI/NH$_3$) m/z 417 (M+H)$^+$. $^1$H NMR (500 MHz, D$_2$O/dimethylsulfoxide-$d_6$): δ 1.55-1.66 (m, 4H), 2.31-2.40 (m, 4H), 3.89 (s, 2H), 4.04 (s, 2H), 6.92 (d, J=7.93 Hz, 1H), 7.26 (t, J=7.93 Hz, 1H), 7.38 (s, 1H), 7.47 (d, J=8.24 Hz, 1H), 7.49-7.54 (m, 2H), 7.58 (t, J=7.32 Hz, 1H), 7.85-7.90 (m, 2H).

Example 161

3-(3-methoxyphenyl)-N-(3-((4-oxo-3,4,5,6,7,8-hexahydrophthalazin-1-yl)methyl)phenyl)propanamide The title compound was prepared according to procedure for EXAMPLE 136, substituting 3-(3-methoxyphenyl)propanoic acid for 1-methylcyclopropanecarboxylic acid. MS (DCI/NH$_3$) m/z 418 (M+H)$^+$.

Example 162

3-(4-methoxyphenyl)-N-(3-((4-oxo-3,4,5,6,7,8-hexahydrophthalazin-1-yl)methyl)phenyl)propanamide The title compound was prepared according to procedure for EXAMPLE 136, substituting 3-(4-methoxyphenyl)propanoic acid for 1-methylcyclopropanecarboxylic acid. MS (DCI/NH$_4$) m/z 418 (M+H)$^+$.

Example 163

2-(3,4-dimethylphenoxy)-N-(3-((4-oxo-3,4,5,6,7,8-hexahydrophthalazin-1-yl)methyl)phenyl)acetamide The title compound was prepared according to procedure for EXAMPLE 136, substituting 2-(3,4-dimethylphenoxy)acetic acid for 1-methylcyclopropanecarboxylic acid. MS (DCI/NH$_3$) m/z 418 (M+H)$^+$.

Example 164

(2R)-2-hydroxy-N-(3-((4-oxo-3,4,5,6,7,8-hexahydrophthalazin-1-yl)methyl)phenyl)-4-phenylbutanamide The title compound was prepared according to procedure for EXAMPLE 136, substituting (R)-2-hydroxy-4-phenylbutanoic acid for 1-methylcyclopropanecarboxylic acid. MS (DCI/NH$_3$) m/z 418 (M+H)$^+$; $^1$H NMR (500 MHz, D$_2$O/dimethylsulfoxide-$d_6$): δ 1.55-1.65 (m, 4H), 1.80-1.90 (m, 1H), 1.95-2.03 (m, 1H), 2.31-2.44 (m, 4H), 2.69 (t, J=7.93 Hz, 2H), 3.88 (s, 2H), 3.96 (s, 1H), 4.01 (dd, J=8.09, 4.12 Hz, 1H), 6.91 (d, J=7.63 Hz, 1H), 7.17-7.23 (m, 3H), 7.25 (t, J=7.78 Hz, 1H), 7.29 (t, J=7.48 Hz, 2H), 7.49 (s, 1H), 7.53 (d, J=7.93 Hz, 1H).

Example 165

N-(3-((4-oxo-3,4,5,6,7,8-hexahydrophthalazin-1-yl)methyl)phenyl)-4-phenoxybutanamide The title compound was prepared according to procedure for EXAMPLE 136, substituting 4-phenoxybutanoic acid for 1-methylcyclopropanecarboxylic acid. MS (DCI/NH$_3$) m/z 418 (M+H)$^+$; $^1$H NMR (500 MHz, D$_2$O/dimethylsulfoxide-$d_6$): δ 1.55-1.67 (m, 4H), 1.96-2.06 (m, 2H), 2.31-2.42 (m, 4H), 2.47 (t, J=7.48 Hz, 2H), 3.88 (s, 2H), 3.99 (t, J=6.26 Hz, 2H), 6.87-6.91 (m, 2H), 6.91-6.96 (m, 2H), 7.24 (t, J=7.78 Hz, 1H), 7.26-7.30 (m, 2H), 7.36 (s, 1H), 7.48 (d, J=8.24 Hz, 1H).

Example 166

4-oxo-N-(3-((4-oxo-3,4,5,6,7,8-hexahydrophthalazin-1-yl)methyl)phenyl)-4-thien-2-ylbutanamide The title compound was prepared according to the procedure for EXAMPLE 136, substituting 4-oxo-4-(thiophen-2-yl)butanoic acid for 1-methylcyclopropanecarboxylic acid. MS (DCI/NH$_3$) m/z 422 (M+H)$^+$; $^1$H NMR (500 MHz, D$_2$O/dimethylsulfoxide-d$_6$): δ 1.55-1.65 (m, 4H), 2.32-2.42 (m, 4H), 2.69 (t, J=6.41 Hz, 2H), 3.26 (t, J=6.41 Hz, 2H), 3.87 (s, 2H), 6.88 (d, J=7.63 Hz, 1H), 7.23 (t, J=7.93 Hz, 1H), 7.25-7.29 (m, 1H), 7.37 (s, 1H), 7.44 (d, J=8.24 Hz, 1H), 7.97 (d, J=4.88 Hz, 1H), 7.99 (d, J=2.75 Hz, 1H).

Example 167

2-((4-methylpyrimidin-2-yl)thio)-N-(3-((4-oxo-3,4,5,6,7,8-hexahydrophthalazin-1-yl)methyl)phenyl)acetamide The title compound was prepared according to procedure for EXAMPLE 136, substituting 2-(4-methylpyrimidin-2-ylthio)acetic acid for 1-methylcyclopropanecarboxylic acid. MS (DCI/NH$_3$) m/z 422 (M+H)$^+$.

Example 168

3-(2-chlorophenyl)-N-(3-((4-oxo-3,4,5,6,7,8-hexahydrophthalazin-1-yl)methyl)phenyl)propanamide The title compound was prepared according to procedure for EXAMPLE 136, substituting 3-(2-chlorophenyl)propanoic acid for 1-methylcyclopropanecarboxylic acid. MS (DCI/NH$_3$) m/z 422 (M+H)$^+$.

Example 169

3-(4-chlorophenyl)-N-(3-((4-oxo-3,4,5,6,7,8-hexahydrophthalazin-1-yl)methyl)phenyl)propanamide The title compound was prepared according to procedure for EXAMPLE 136, substituting 3-(4-chlorophenyl)propanoic acid for 1-methylcyclopropanecarboxylic acid. MS (DCI/NH$_3$) m/z 422 (M+H)$^+$.

Example 170

3-methyl-N-(3-((4-oxo-3,4,5,6,7,8-hexahydrophthalazin-1-yl)methyl)phenyl)-2-phenylpentanamide The title compound was prepared according to procedure for EXAMPLE 136, substituting 3-methyl-2-phenylpentanoic acid for 1-methylcyclopropanecarboxylic acid. MS (DCI/NH$_3$) m/z 430 (M+H)$^+$.

Example 171

2-(4-chloro-2-methylphenoxy)-N-(3-((4-oxo-3,4,5,6,7,8-hexahydrophthalazin-1-yl)methyl)phenyl)acetamide The title compound was prepared according to procedure for EXAMPLE 136, substituting 2-(4-chloro-2-methylphenoxy)acetic acid for 1-methylcyclopropanecarboxylic acid. MS (DCI/NH$_3$) m/z 438 (M+H)$^+$.

Example 172

N-(3-((4-oxo-3,4,5,6,7,8-hexahydrophthalazin-1-yl)methyl)phenyl)-N'-phenylpentanediamide The title compound was prepared according to procedure for EXAMPLE 136, substituting 5-oxo-5-(phenylamino)pentanoic acid for 1-methylcyclopropanecarboxylic acid. MS (DCI/NH$_3$) m/z 445 (M+H)$^+$; $^1$H NMR (500 MHz, D$_2$O/dimethylsulfoxide-d$_6$): δ 1.55-1.65 (m, 4H), 1.84-1.94 (m, 2H), 2.31-2.42 (m, 8H), 3.87 (s, 2H), 6.89 (d, J=7.63 Hz, 1H), 7.05 (t, J=7.32 Hz, 1H), 7.24 (t, J=7.93 Hz, 1H), 7.30 (t, J=8.09 Hz, 2H), 7.36 (s, 1H), 7.48 (d, J=8.24 Hz, 1H), 7.57 (d, J=7.63 Hz, 2H).

Example 173

4-(4-methoxyphenyl)-4-oxo-N-(3-((4-oxo-3,4,5,6,7,8-hexahydrophthalazin-1-yl)methyl)phenyl)butanamide The title compound was prepared according to procedure for EXAMPLE 136, substituting 4-(4-methoxyphenyl)-4-oxobutanoic acid for 1-methylcyclopropanecarboxylic acid. MS (DCI/NH$_3$) m/z 446 (M+H)$^+$.

Example 174

N-(3-((4-oxo-3,4,5,6,7,8-hexahydrophthalazin-1-yl)methyl)phenyl)-2,2-diphenylacetamide The title compound was prepared according to procedure for EXAMPLE 136, substituting 2,2-diphenylacetic acid for 1-methylcyclopropanecarboxylic acid. MS (DCI/NH$_3$) m/z 450 (M+H)$^+$.

Example 175

N-(3-((4-oxo-3,4,5,6,7,8-hexahydrophthalazin-1-yl)methyl)phenyl)-3-(phenylsulfonyl)propanamide The title compound was prepared according to procedure for EXAMPLE 136, substituting 3-(phenylsulfonyl)propanoic acid for 1-methylcyclopropanecarboxylic acid. MS (DCI/NH$_3$) m/z 452 (M+H)$^+$; $^1$H NMR (500 MHz, D$_2$O/dimethylsulfoxide-d$_6$): δ 1.52-1.70 (m, 4H), 2.29-2.42 (m, 4H), 2.66 (t, J=7.32 Hz, 2H), 3.59 (t, J=7.32 Hz, 2H), 3.87 (s, 2H), 6.90 (d, J=7.32 Hz, 1H), 7.20-7.26 (m, 2H), 7.37 (d, J=8.54 Hz, 1H), 7.66 (t, J=7.63 Hz, 2H), 7.74 (t, J=7.48 Hz, 1H), 7.91 (d, J=7.32 Hz, 2H).

Example 176

N-(3-((4-oxo-3,4,5,6,7,8-hexahydrophthalazin-1-yl)methyl)phenyl)-2-(3-phenoxyphenyl)acetamide The title compound was prepared according to the procedure for EXAMPLE 136, substituting 2-(3-phenoxyphenyl)acetic acid for 1-methylcyclopropanecarboxylic acid. MS (DCI/NH$_3$) m/z 466 (M+H)$^+$; $^1$H NMR (500 MHz, D$_2$O/dimethylsulfoxide-d$_6$): δ 1.54-1.65 (m, 4H), 2.29-2.42 (m, 4H), 3.60 (s, 2H), 3.87 (s, 2H), 6.86-6.92 (m, 2H), 6.98-7.03

(m, 3H), 7.10 (d, J=7.93 Hz, 1H), 7.16 (t, J=7.48 Hz, 1H), 7.24 (t, J=7.78 Hz, 1H), 7.32-7.37 (m, 2H), 7.38-7.42 (m, 2H), 7.46 (d, J=8.24 Hz, 1H).

Example 177

4-ethyl-N-(3-((4-oxo-3,4,5,6,7,8-hexahydro-phthalazin-1-yl)methyl)phenyl)benzamide The title compound was prepared according to the procedure for EXAMPLE 136, substituting 4-ethylbenzoic acid for 1-methylcyclopropanecarboxylic acid. MS (DCI/NH$_3$) m/z 388 (M+H)$^+$.

Example 178

3-fluoro-2-methyl-N-(3-((4-oxo-3,4,5,6,7,8-hexahydrophthalazin-1-yl)methyl)phenyl)benzamide The title compound was prepared according to the procedure for EXAMPLE 136, substituting 3-fluoro-2-methylbenzoic acid for 1-methylcyclopropanecarboxylic acid. MS (DCI/NH$_3$) m/z 392 (M+H)$^+$.

Example 179

5-fluoro-2-methyl-N-(3-((4-oxo-3,4,5,6,7,8-hexahydrophthalazin-1-yl)methyl)phenyl)benzamide The title compound was prepared according to the procedure for EXAMPLE 136, substituting 5-fluoro-2-methylbenzoic acid for 1-methylcyclopropanecarboxylic acid. MS (DCI/NH$_3$) m/z 392 (M+H)$^+$.

Example 180

3-fluoro-4-methyl-N-(3-((4-oxo-3,4,5,6,7,8-hexahydrophthalazin-1-yl)methyl)phenyl)benzamide The title compound was prepared according to the procedure for EXAMPLE 136, substituting 3-fluoro-4-methylbenzoic acid for 1-methylcyclopropanecarboxylic acid. MS (DCI/NH$_3$) m/z 392 (M+H)$^+$.

Example 181

2,3-difluoro-N-(3-((4-oxo-3,4,5,6,7,8-hexahydro-phthalazin-1-yl)methyl)phenyl)benzamide The title compound was prepared according to the procedure for EXAMPLE 136, substituting 2,3-difluorobenzoic acid for 1-methylcyclopropanecarboxylic acid. MS (DCI/NH$_4$) m/z 396 (M+H)$^+$.

Example 182

2,4-difluoro-N-(3-((4-oxo-3,4,5,6,7,8-hexahydro-phthalazin-1-yl)methyl)phenyl)benzamide The title compound was prepared according to the procedure for EXAMPLE 136, substituting 2,4-difluorobenzoic acid for 1-methylcyclopropanecarboxylic acid. MS (DCI/NH$_3$) m/z 396 (M+H)$^+$.

Example 183

2,5-difluoro-N-(3-((4-oxo-3,4,5,6,7,8-hexahydro-phthalazin-1-yl)methyl)phenyl)benzamide The title compound was prepared according to the procedure for EXAMPLE 136, substituting 2,5-difluorobenzoic acid for 1-methylcyclopropanecarboxylic acid. MS (DCI/NH$_3$) m/z 396 (M+H)$^+$.

Example 184

3,5-difluoro-N-(3-((4-oxo-3,4,5,6,7,8-hexahydro-phthalazin-1-yl)methyl)phenyl)benzamide The title compound was prepared according to the procedure for EXAMPLE 136, substituting 3,5-difluorobenzoic acid for 1-methylcyclopropanecarboxylic acid. MS (DCI/NH$_3$) m z 396 (M+H)$^+$.

Example 185

N-(3-((4-oxo-3,4,5,6,7,8-hexahydrophthalazin-1-yl)methyl)phenyl)-4-propylbenzamide The title compound was prepared according to the procedure for EXAMPLE 136, substituting 4-propylbenzoic acid for 1-methylcyclopropanecarboxylic acid. MS (DCI/NH$_3$) m/z 402 (M+H)$^+$.

Example 186

4-isopropyl-N-(3-((4-oxo-3,4,5,6,7,8-hexahydro-phthalazin-1-yl)methyl)phenyl)benzamide The title compound was prepared according to the procedure for EXAMPLE 136, substituting 4-isopropylbenzoic acid for 1-methylcyclopropanecarboxylic acid. MS (DCI/NH$_3$) m/z 402 (M+H)$^+$.

Example 187

2-ethoxy-N-(3-((4-oxo-3,4,5,6,7,8-hexahydro-phthalazin-1-yl)methyl)phenyl)benzamide The title compound was prepared according to the procedure for EXAMPLE 136, substituting 4-ethoxybenzoic acid for 1-methylcyclopropanecarboxylic acid. MS (DCI/NH$_3$) m/z 404 (M+H)$^+$.

Example 188

4-isopropoxy-N-(3-((4-oxo-3,4,5,6,7,8-hexahydro-phthalazin-1-yl)methyl)phenyl)benzamide The title compound was prepared according to the procedure for EXAMPLE 136, substituting 4-isopropoxybenzoic acid for 1-methylcyclopropanecarboxylic acid. MS (DCI/NH$_3$) m/z 418 (M+H)$^+$; $^1$H NMR (500 MHz, D$_2$O/dimethyl-sulfoxide-d$_6$): δ 1.30 (d, J=6.10 Hz, 6H), 1.53-1.67 (m, 4H), 2.33-2.46 (m, 4H), 3.91 (s, 2H), 4.67-4.80 (m, 1H), 6.94 (d, J=7.63 Hz, 1H), 7.02 (d, J=8.85 Hz, 2H), 7.29 (t, J=7.78 Hz, 1H), 7.55 (s, 1H), 7.62 (d, J=8.24 Hz, 1H), 7.89 (d, J=8.85 Hz, 2H).

Example 189

4-(diethylamino)-N-(3-((4-oxo-3,4,5,6,7,8-hexahydrophthalazin-1-yl)methyl)phenyl)benzamide The title compound was prepared according to the procedure for EXAMPLE 136, substituting 4-(diethylamino)benzoic acid for 1-methylcyclopropanecarboxylic acid. MS (DCI/NH$_3$) m/z 431 (M+H)$^+$; $^1$H NMR (500 MHz, D$_2$O/dimethylsulfoxide-d$_6$): δ 1.1 (t, J=7.02 Hz, 6H), 1.57-1.66 (m, 4H), 2.34-2.44 (m, 4H), 3.45 (q, J=7.02 Hz, 4H), 3.91 (s, 2H), 6.87 (d, J=8.85 Hz, 2H), 6.91 (d, J=7.63 Hz, 1H), 7.27 (t, J=7.93 Hz, 1H), 7.55 (s, 1H), 7.62 (d, J=8.24 Hz, 1H), 7.85 (d, J=8.85 Hz, 2H).

Example 190

4-butoxy-N-(3-((4-oxo-3,4,5,6,7,8-hexahydrophthalazin-1-yl)methyl)phenyl)benzamide The title compound was prepared according to the procedure for EXAMPLE 136, substituting 4-butoxybenzoic acid for 1-methylcyclopropanecarboxylic acid. MS (DCI/NH$_3$) m/z 432 (M+H)$^+$.

Example 191

2-fluoro-N-(3-((4-oxo-3,4,5,6,7,8-hexahydrophthalazin-1-yl)methyl)phenyl)-5-(trifluoromethyl)benzamide The title compound was prepared according to the procedure for EXAMPLE 136, substituting 2-fluoro-5-(trifluoromethyl)benzoic acid for 1-methylcyclopropanecarboxylic acid. MS (DCI/NH$_3$) m/z 446 (M+H)$^+$.

Example 192

2-chloro-N-(3-((4-oxo-3,4,5,6,7,8-hexahydrophthalazin-1-yl)methyl)phenyl)-5-(trifluoromethyl)benzamide The title compound was prepared according to the procedure for EXAMPLE 136, substituting 2-chloro-5-(trifluoromethyl)benzoic acid for 1-methylcyclopropanecarboxylic acid. MS (DCI/NH$_3$) m/z 461 (M+H)$^+$.

Example 193

N-(3-((4-oxo-3,4,5,6,7,8-hexahydrophthalazin-1-yl)methyl)phenyl)-2-furamide

The title compound was prepared according to the procedure for EXAMPLE 136, substituting furan-2-carboxylic acid for 1-methylcyclopropanecarboxylic acid. MS (DCI/NH$_3$) m/z 350 (M+H)$^+$.

Example 194

N-(3-((4-oxo-3,4,5,6,7,8-hexahydrophthalazin-1-yl)methyl)phenyl)-3-furamide

The title compound was prepared according to the procedure for EXAMPLE 136, substituting furan-3-carboxylic acid for 1-methylcyclopropanecarboxylic acid. MS (DCI/NH$_3$) m/z 350 (M+H)$^+$.

Example 195

2,5-dimethyl-N-(3-((4-oxo-3,4,5,6,7,8-hexahydrophthalazin-1-yl)methyl)phenyl)-3-furamide The title compound was prepared according to the procedure for EXAMPLE 136, substituting 2,5-dimethylfuran-3-carboxylic acid for 1-methylcyclopropanecarboxylic acid. MS (DCI/NH$_3$) m/z 378 (M+H)$^+$.

Example 196

N-(3-((4-oxo-3,4,5,6,7,8-hexahydrophthalazin-1-yl)methyl)phenyl)thiophene-2-carboxamide The title compound was prepared according to the procedure for EXAMPLE 136, substituting thiophene-2-carboxylic acid for 1-methylcyclopropanecarboxylic acid. MS (DCI/NH$_3$) m/z 366 (M+H)$^+$.

Example 197

N-(3-((4-oxo-3,4,5,6,7,8-hexahydrophthalazin-1-yl)methyl)phenyl)thiophene-3-carboxamide The title compound was prepared according to the procedure for EXAMPLE 136, substituting thiophene-3-carboxylic acid for 1-methylcyclopropanecarboxylic acid. MS (DCI/NH$_3$) m/z 366 (M+H)$^+$; $^1$H NMR (500 MHz, D$_2$O/dimethylsulfoxide-d$_6$): δ 1.54-1.66 (m, 4H), 2.32-2.44 (m, 4H), 3.92 (s, 2H), 6.96 (d, J=7.63 Hz, 1H), 7.30 (t, J=7.93 Hz, 1H), 7.53 (s, 1H), 7.59-7.65 (m, 3H), 8.31 (dd, J=2.75, 1.53 Hz, 1H).

Example 198

3-methyl-N-(3-((4-oxo-3,4,5,6,7,8-hexahydrophthalazin-1-yl)methyl)phenyl)thiophene-2-carboxamide The title compound was prepared according to the procedure for EXAMPLE 136, substituting 3-methylthiophene-2-carboxylic acid for 1-methylcyclopropanecarboxylic acid. MS (DCI/NH$_3$) m/z 380 (M+H)$^+$.

Example 199

5-methyl-N-(3-((4-oxo-3,4,5,6,7,8-hexahydrophthalazin-1-yl)methyl)phenyl)thiophene-2-carboxamide The title compound was prepared according to the procedure for EXAMPLE 136, substituting 5-methylthiophene-2-carboxylic acid for 1-methylcyclopropanecarboxylic acid. MS (DCI/NH$_3$) m/z 380 (M+H)$^+$.

Example 200

N²-(3-((4-oxo-3,4,5,6,7,8-hexahydrophthalazin-1-yl)methyl)phenyl)-1H-pyrrole-2-carboxamide The title compound was prepared according to the procedure for EXAMPLE 136, substituting pyrrole-3-carboxylic acid for 1-methylcyclopropanecarboxylic acid. MS (DCI/NH$_3$) m/z 349 (M+H)$^+$; $^1$H NMR (500 MHz, D$_2$O/dimethylsulfoxide-d$_6$): δ 1.56-1.66 (m, 4H), 2.33-2.44 (m, 4H), 3.91 (s, 2H), 6.18 (dd, J=3.51, 2.29 Hz, 1H), 6.92 (d, J=7.63 Hz, 1H), 6.98 (d, J=1.53 Hz, 1H), 7.03-7.07 (m, 1H), 7.27 (t, J=7.93 Hz, 1H), 7.53 (s, 1H), 7.60 (d, J=7.93 Hz, 1H).

Example 201

1-methyl-N-(3-((4-oxo-3,4,5,6,7,8-hexahydrophthalazin-1-yl)methyl)phenyl)-1H-pyrrole-2-carboxamide The title compound was prepared according to the procedure for EXAMPLE 136, substituting 1-methyl-1H-pyrrole-2-carboxylic acid for 1-methylcyclopropanecarboxylic acid. MS (DCI/NH$_3$) m/z 363 (M+H)$^+$.

Example 202

2,5-dimethyl-N-(3-((4-oxo-3,4,5,6,7,8-hexahydrophthalazin-1-yl)methyl)phenyl)-1H-pyrrole-3-carboxamide The title compound was prepared according to the procedure for EXAMPLE 136, substituting 2,5-dimethyl-1H-pyrrole-3-carboxylic acid for 1-methylcyclopropanecarboxylic acid. MS (DCI/NH$_3$) m/z 377 (M+H)$^+$.

Example 203

1,2,5-trimethyl-N-(3-((4-oxo-3,4,5,6,7,8-hexahydrophthalazin-1-yl)methyl)phenyl)-1H-pyrrole-3-carboxamide The title compound was prepared according to the procedure for EXAMPLE 136, substituting 1-methyl-1H-pyrrole-3-carboxylic acid for 1-methylcyclopropanecarboxylic acid. MS (DCI/NH$_3$) m/z 363 (M+H)$^+$.

Example 204

N-(3-((4-oxo-3,4,5,6,7,8-hexahydrophthalazin-1-yl)methyl)phenyl)-1,3-thiazole-2-carboxamide The title compound was prepared according to the procedure for EXAMPLE 136, substituting thiazole-2-carboxylic acid for 1-methylcyclopropanecarboxylic acid. MS (DCI/NH$_3$) m/z 367 (M+H)$^+$.

Example 205

N-(3-((4-oxo-3,4,5,6,7,8-hexahydrophthalazin-1-yl)methyl)phenyl)-1,3-thiazole-4-carboxamide The title compound was prepared according to the procedure for EXAMPLE 136, substituting thiazole-4-carboxylic acid for 1-methylcyclopropanecarboxylic acid. MS (DCI/NH$_3$) m/z 367 (M+H)$^+$.

Example 206

N-(3-((4-oxo-3,4,5,6,7,8-hexahydrophthalazin-1-yl)methyl)phenyl)-1,3-thiazole-5-carboxamide The title compound was prepared according to the procedure for EXAMPLE 136, substituting thiazole-5-carboxylic acid for 1-methylcyclopropanecarboxylic acid. MS (DCI/NH$_3$) m/z 367 (M+H)$^+$; $^1$H NMR (500 MHz, D$_2$O/dimethylsulfoxide-d$_6$): δ 1.54-1.67 (m, 2H), 2.32-2.44 (m, 2H), 3.92 (s, 2H), 7.00 (d, J=7.63 Hz, 1H), 7.32 (t, J=7.93 Hz, 1H), 7.49 (s, 1H), 7.59 (d, J=8.24 Hz, 1H), 8.66 (s, 1H), 9.27 (s, 1H).

Example 208

N-(3-((4-oxo-3,4,5,6,7,8-hexahydrophthalazin-1-yl)methyl)phenyl)isoxazole-5-carboxamide The title compound was prepared according to the procedure for EXAMPLE 136, substituting isoxazole-5-carboxylic acid for 1-methylcyclopropanecarboxylic acid. MS (DCI/NH$_3$) m/z 351 (M+H)$^+$; $^1$H NMR (500 MHz, D$_2$O/dimethylsulfoxide-d$_6$): δ 1.54-1.68 (m, 4H), 2.33-2.45 (m, 4H), 3.93 (s, 2H), 7.03 (d, J=7.63 Hz, 1H), 7.22 (d, J=2.14 Hz, 1H), 7.34 (t, J=7.93 Hz, 1H), 7.54 (s, 1H), 7.63 (d, J=7.93 Hz, 1H), 8.77 (d, J=1.83 Hz, 1H).

Example 209

3,5-dimethyl-N-(3-((4-oxo-3,4,5,6,7,8-hexahydrophthalazin-1-yl)methyl)phenyl)isoxazole-4-carboxamide The title compound was prepared according to the procedure for EXAMPLE 136, substituting 3,5-dimethylisoxazole-4-carboxylic acid for 1-methylcyclopropanecarboxylic acid. MS (DCI/NH$_3$) m/z 379 (M+H)$^+$.

Example 210

N-(3-((4-oxo-3,4,5,6,7,8-hexahydrophthalazin-1-yl)methyl)phenyl)nicotinamide

The title compound was prepared according to the procedure for EXAMPLE 136, substituting nicotinic acid for 1-methylcyclopropanecarboxylic acid. MS (DCI/NH$_3$) m/z 361 (M+H)$^+$.

Example 211

N-(3-((4-oxo-3,4,5,6,7,8-hexahydrophthalazin-1-yl)methyl)phenyl)isonicotinamide

The title compound was prepared according to the procedure for EXAMPLE 136, substituting isonicotinic acid for 1-methylcyclopropanecarboxylic acid. MS (DCI/NH$_3$) m/z 361 (M+H)$^1$H NMR (500 MHz, D$_2$O/dimethylsulfoxide-d$_6$): δ 1.57-1.68 (m, 4H), 2.33-2.45 (m, 4H), 3.94 (s, 2H), 7.04 (d, J=7.63 Hz, 1H), 7.36 (t, J=7.78 Hz, 1H), 7.56 (s, 1H), 7.66 (d, J=8.24 Hz, 1H), 8.10 (d, J=6.41 Hz, 2H), 8.90 (d, J=6.10 Hz, 2H).

Example 212

3-hydroxy-N-(3-((4-oxo-3,4,5,6,7,8-hexahydrophthalazin-1-yl)methyl)phenyl)pyridine-2-carboxamide The title compound was prepared according to the procedure for EXAMPLE 136, substituting 3-hydroxypicolinic acid for 1-methylcyclopropanecarboxylic acid. MS (DCI/NH$_3$) m/z 377 (M+H)$^+$.

Example 213

2-hydroxy-N-(3-((4-oxo-3,4,5,6,7,8-hexahydrophthalazin-1-yl)methyl)phenyl)nicotinamide The title compound was prepared according to the procedure for EXAMPLE 136, substituting 2-hydroxynicotinic acid for 1-methylcyclopropanecarboxylic acid. MS (DCI/NH$_3$) m/z 377 (M+H)$^+$.

Example 214

6-hydroxy-N-(3-((4-oxo-3,4,5,6,7,8-hexahydrophthalazin-1-yl)methyl)phenyl)nicotinamide The title compound was prepared according to the procedure for EXAMPLE 136, substituting 6-hydroxynicotinic acid for 1-methylcyclopropanecarboxylic acid. MS (DCI/NH$_3$) m/z 377 (M+H)$^+$; $^1$H NMR (500 MHz, D$_2$O/dimethylsulfoxide-d$_6$): δ 1.53-1.65 (m, 4H), 2.32-2.43 (m, 4H), 3.91 (s, 2H), 6.45 (d, J=10.07 Hz, 1H), 6.95 (d, J=7.63 Hz, 1H), 7.29 (t, J=7.93 Hz, 1H), 7.46 (s, 1H), 7.57 (d, —=8.24 Hz, 1H), 7.98 (dd, J=9.76, 2.75 Hz, 1H), 8.16 (d, J=2.14 Hz, 1H).

Example 215

N-(3-((4-oxo-3,4,5,6,7,8-hexahydrophthalazin-1-yl)methyl)phenyl)-2-pyridin-2-ylacetamide The title compound was prepared according to the procedure for EXAMPLE 136, substituting 2-(pyridin-2-yl)acetic acid for 1-methylcyclopropanecarboxylic acid. MS (DCI/NH$_3$) m/z 375 (M+H)$^+$.

Example 216

N-(3-((4-oxo-3,4,5,6,7,8-hexahydrophthalazin-1-yl)methyl)phenyl)-2-pyridin-3-ylacetamide The title compound was prepared according to the procedure for EXAMPLE 136, substituting 2-(pyridin-3-yl)acetic acid for 1-methylcyclopropanecarboxylic acid. MS (DCI/NH$_3$) m/z 375 (M+H)$^+$; $^1$H NMR (500 MHz, D$_2$O/dimethylsulfoxide-d$_6$): δ 1.54-1.66 (m, 4H), 2.30-2.42 (m, 4H), 3.88 (s, 2H), 3.98 (s, 2H), 6.94 (d, J=7.32 Hz, 1H), 7.27 (t, J=7.93 Hz, 1H), 7.38 (s, 1H), 7.46 (d, J=8.85 Hz, 1H), 8.04 (dd, J=7.93, 5.80 Hz, 1H), 8.52 (d, J=8.24 Hz, 1H), 8.81 (d, J=5.49 Hz, 1H), 8.85 (s, 1H).

Example 217

5-methyl-N-(3-((4-oxo-3,4,5,6,7,8-hexahydrophthalazin-1-yl)methyl)phenyl)pyrazine-2-carboxamide The title compound was prepared according to the procedure for EXAMPLE 136, substituting 5-methylpyrazine-2-carboxylic acid for 1-methylcyclopropanecarboxylic acid. MS (DCI/NH$_3$) m/z 376 (M+H)$^+$; $^1$H NMR (500 MHz, D$_2$O/dimethylsulfoxide-d$_6$): δ 1.54-1.69 (m, 4H), 2.34-2.46 (m, 4H), 2.63 (s, 3H), 3.93 (s, 2H), 7.00 (d, J=7.63 Hz, 1H), 7.33 (t, J=8.09 Hz, 1H), 7.68-7.74 (m, 2H), 8.68 (s, 1H), 9.13 (d, J=1.22 Hz, 1H).

Example 218

N-(3-((4-oxo-3,4,5,6,7,8-hexahydrophthalazin-1-yl)methyl)phenyl)-1H-indole-3-carboxamide The title compound was prepared according to the procedure for EXAMPLE 136, substituting 1H-indole-3-carboxylic acid for 1-methylcyclopropanecarboxylic acid. MS (DCI/NH$_4$) m/z 399 (M+H)$^+$.

Example 219

5-methyl-N-(3-((4-oxo-3,4,5,6,7,8-hexahydrophthalazin-1-yl)methyl)phenyl)-1-yl)methyl)phenyl)-1-phenyl-1H-pyrazole-4-carboxamide The title compound was prepared according to the procedure for EXAMPLE 136, substituting 5-methyl-1-phenyl-1H-pyrazole-4-carboxylic acid for 1-methylcyclopropanecarboxylic acid. MS (DCI/NH$_3$) m/z 440 (M+H)$^+$.

Example 220

6-chloro-N-(3-((4-oxo-3,4,5,6,7,8-hexahydrophthalazin-1-yl)methyl)phenyl)-2H-chromene-3-carboxamide The title compound was prepared according to the procedure for EXAMPLE 136, substituting 6-chloro-2H-chromene-3-carboxylic acid for 1-methylcyclopropanecarboxylic acid. MS (DCI/NH$_3$) m/z 448 (M+H)$^+$.

Example 221

N$^3$,N$^3$-dimethyl-N$^1$-(3-((4-oxo-3,4,5,6,7,8-hexahydrophthalazin-1-yl)methyl)phenyl)-beta-alaninamide The title compound was prepared according to the procedure for EXAMPLE 136, substituting 3-(dimethylamino)propanoic acid for 1-methylcyclopropanecarboxylic acid. MS (DCI/NH$_4$) m/z 355 (M+H)$^+$; $^1$H NMR (500 MHz, D$_2$O/dimethylsulfoxide-d$_6$): δ 1.55-1.66 (m, 4H), 2.30-2.43 (m, 4H), 2.77-2.93 (m, 100H), 3.93 (s, 2H), 6.74 (s, 1H), 6.90 (dd, J=8.09, 1.37 Hz, 1H), 7.06 (d, J=—7.63 Hz, 1H), 7.37 (t, J=7.78 Hz, 1H).

Example 222

4-(2-(3-bromophenyl)ethyl)-5,6,7,8-tetrahydrophthalazin-1(2H)-one

Example 222A 2-(3-bromophenyl)-N-methoxy-N-methylacetamide

To a solution of 2-(3-bromophenyl)acetic acid (4.4 g, 20.56 mmol) in N,N-dimethylformamide (125 ml) was successively added N,O-dimethylhydroxyamine (4.5 g, 46.26 mmol), triethylamine (10 ml), 1-ethyl-3-(3-dimethylaminopropyl) carbodiimide hydrochloride (8.9 g, 46.26 mmol) and 1-hydroxybenzotriazole (6.24 g, 46.26 mmol). The reaction mixture was stirred at room temperature overnight, and partitioned between ethyl acetate and brine. The organic phase was washed with brine, and concentrated. The residue was purified by flash chromatography on silica gel (50% ethyl acetate in hexane) to provide the title compound. MS (DCI/NH$_3$) m/z 258 (M+H)$^+$.

Example 222B 2-(3-bromophenyl)acetaldehyde

A solution of EXAMPLE 222A (2.5 g, 9.7 mmol) in anhydrous tetrahydrofuran (50 ml) was treated with LiAlH$_4$ (0.37 g, 9.7 mmol) at 0° C. for 10 minutes, and quenched with water. The mixture was partitioned between ethyl acetate and saturated ammonium chloride. The organic phase was washed with water and concentrated. The residue was purified by flash chromatography on silica gel (20% ethyl acetate in hexane) to provide the title compound. MS (DCI/NH$_3$) m/z 199 (M+H)$^+$.

Example 222C 3-(2-(3-bromophenyl)ethylidene)-4,5,6,7-tetrahydroisobenzofuran-1(3H)-one The title compound was prepared according to the procedure for EXAMPLE 1C, substituting EXAMPLE 222B for 2-fluoro-5-formylbenzonitrile. MS (DCI/NH$_3$) m/z 319 (M+H)$^+$.

Example 222D 4-(2-(3-bromophenyl)ethyl)-5,6,7,8-tetrahydrophthalazin-1(2H)-one

The title compound was prepared according to the procedure for EXAMPLE 2C, substituting EXAMPLE 222C for EXAMPLE 2B. MS (DCI/NH$_3$) m/z 333 (M+H)$^+$.

Example 223

4-(2-(3-bromo-4-fluorophenyl)ethyl)-5,6,7,8-tetrahydrophthalazin-1(2H)-one

Example 223A 2-(3-bromo-4-fluorophenyl)acetaldehyde

The title compound was prepared according to the procedure for EXAMPLE 222, substituting 2-(3-bromo-4-fluorophenyl)acetic acid for 2-(3-bromophenyl)acetic acid in EXAMPLE 223B. MS (DCI/NH$_3$) m/z 216 (M+H)$^+$.

Example 223B 4-(2-(3-bromo-4-fluorophenyl)ethyl)-5,6,7,8-tetrahydrophthalazin-1(2H)-one The title compound was prepared according to the procedure for EXAMPLE 1C, substituting EXAMPLE 223A for 2-fluoro-5-formylbenzonitrile. MS (DCI/NH$_3$) m/z 351 (M+H)$^+$.

Example 224

4-(2,2,2-trifluoro-1-phenylethyl)-5,6,7,8-tetrahydrophthalazin-1(2H)-one

Example 224A 3-(2,2,2-trifluoro-1-phenylethylidene)-4,5,6,7-tetrahydroisobenzofuran-1(3H)-one The title compound was prepared according to the procedure for EXAMPLE 1C, substituting 2,2,2-trifluoro-1-phenylethanone for 2-fluoro-5-formylbenzonitrile. MS (DCI/NH$_3$) m/z 295 (M+H)$^+$.

Example 224B 4-(2,2,2-trifluoro-1-phenylethyl)-5,6,7,8-tetrahydrophthalazin-1(2H)-one The title compound was prepared according to the procedure for EXAMPLE 2C, substituting EXAMPLE 224A for EXAMPLE 2B. MS (DCI/NH$_3$) m/z 309 (M+H)$^+$.

Example 225

2-hydroxy-4-methyl-N-(3-((4-oxo-3,4,5,6,7,8-hexahydrophthalazin-1-yl)methyl)phenyl)benzamide The title compound was prepared according to the procedure for EXAMPLE 136, substituting 2-hydroxy-4-methylbenzoic acid for 1-methylcyclopropanecarboxylic acid. MS (DCI/NH$_3$) m/z 390 (M+H)$^+$.

Example 226

4-acetyl-N-(3-((4-oxo-3,4,5,6,7,8-hexahydrophthalazin-1-yl)methyl)phenyl)benzamide The title compound was prepared according to the procedure for EXAMPLE 136, substituting 4-acetylbenzoic acid for 1-methylcyclopropanecarboxylic acid. MS (DCI/NH$_3$) m/z 402 (M+H)$^+$; $^1$H NMR (500 MHz, D$_2$O/dimethylsulfoxide-(d$_6$): δ 1.54-1.69 (m, 4H), 2.34-2.46 (m, 4H), 2.64 (s, 3H), 3.93 (s, 2H), 6.99 (d, J=7.63 Hz, 1H), 7.32 (t, J=7.93 Hz, 1H), 7.57 (s, 1H), 7.65 (d, J=7.93 Hz, 1H), 8.01-8.05 (m, 2H), 8.05-8.10 (m, 2H).

Example 227

3-methoxy-4-methyl-N-(3-((4-oxo-3,4,5,6,7,8-hexahydrophthalazin-1-yl)methyl)phenyl)benzamide The title compound was prepared according to the procedure for EXAMPLE 136, substituting 3-methoxy-4-methylbenzoic acid for 1-methylcyclopropanecarboxylic acid. MS (DCI/NH$_3$) m/z 404 (M+H)$^+$.

Example 228

4-ethoxy-N-(3-((4-oxo-3,4,5,6,7,8-hexahydrophthalazin-1-yl)methyl)phenyl)benzamide The title compound was prepared according to the procedure for EXAMPLE 136, substituting 4-ethoxybenzoic acid for 1-methylcyclopropanecarboxylic acid. MS (DCI/NH$_3$) m/z 404 (M+H)$^+$.

Example 229

3-fluoro-4-methoxy-N-(3-((4-oxo-3,4,5,6,7,8-hexahydrophthalazin-1-yl)methyl)phenyl)benzamide The title compound was prepared according to the procedure for EXAMPLE 136, substituting 3-fluoro-4-methoxybenzoic acid for 1-methylcyclopropanecarboxylic acid. MS (DCI/NH$_4$) m/z 408 (M+H)$^+$.

Example 230

N-(3-((4-oxo-3,4,5,6,7,8-hexahydrophthalazin-1-yl)methyl)phenyl)-1-naphthamide

The title compound was prepared according to the procedure for EXAMPLE 136, substituting 1-naphthoic acid for 1-methylcyclopropanecarboxylic acid. MS (DCI/NH$_3$) m/z 410 (M+H)$^+$.

Example 231

N-(3-((4-oxo-3,4,5,6,7,8-hexahydrophthalazin-1-yl)methyl)phenyl)-2-naphthamide

The title compound was prepared according to the procedure for EXAMPLE 136, substituting 2-naphthoic acid for 1-methylcyclopropanecarboxylic acid. MS (DCI/NH$_3$) m/z 410 (M+H)$^+$.

Example 232

5-chloro-2-hydroxy-N-(3-((4-oxo-3,4,5,6,7,8-hexahydrophthalazin-1-yl)methyl)phenyl)benzamide The title compound was prepared according to the procedure for EXAMPLE 136, substituting 2-hydroxy-5-methylbenzoic acid for 1-methylcyclopropanecarboxylic acid. MS (DCI/NH$_3$) m/z 390 (M+H)$^+$.

Example 233

4-tert-butyl-N-(3-((4-oxo-3,4,5,6,7,8-hexahydrophthalazin-1-yl)methyl)phenyl)benzamide The title compound was prepared according to the procedure for EXAMPLE 136, substituting 4-tert-butylbenzoic acid for 1-methylcyclopropanecarboxylic acid. MS (DCI/NH$_3$) m/z 416 (M+H)$^+$.

Example 234

4-(acetylamino)-N-(3-((4-oxo-3,4,5,6,7,8-hexahydrophthalazin-1-yl)methyl)phenyl)benzamide The title compound was prepared according to the procedure for EXAMPLE 136, substituting 4-acetamidobenzoic acid for 1-methylcyclopropanecarboxylic acid. MS (DCI/NH$_3$) m/z 417 (M+H)$^+$; $^1$H NMR (500 MHz, D$_2$O/dimethylsulfoxide-d$_6$): δ 1.53-1.68 (m, 4H), 2.10 (s, 3H), 2.33-2.44 (m, 4H), 3.92 (s, 2H), 6.95 (d, J=7.93 Hz, 1H), 7.30 (t, J=7.93 Hz, 1H), 7.56 (s, 1H), 7.63 (d, J=7.63 Hz, 1H), 7.70 (d, J=8.85 Hz, 2H), 7.90 (d, J=8.85 Hz, 2H).

Example 235

N-(3-((4-oxo-3,4,5,6,7,8-hexahydrophthalazin-1-yl)methyl)phenyl)-4-propoxybenzamide The title compound was prepared according to the procedure for EXAMPLE 136, substituting 4-propoxybenzoic acid for 1-methylcyclopropanecarboxylic acid. MS (DCI/NH$_4$) m/z 418 (M+H)$^+$.

Example 236

1-hydroxy-N-(3-((4-oxo-3,4,5,6,7,8-hexahydrophthalazin-1-yl)methyl)phenyl)-2-naphthamide The title compound was prepared according to the procedure for EXAMPLE 136, substituting 1-hydroxy-2-naphthoic acid for 1-methylcyclopropanecarboxylic acid. MS (DCI/NH$_3$) m/z 426 (M+H)$^+$.

Example 237

2-chloro-5-(methylthio)-N-(3-((4-oxo-3,4,5,6,7,8-hexahydrophthalazin-1-yl)methyl)phenyl)benzamide The title compound was prepared according to the procedure for EXAMPLE 136, substituting 2-chloro-5-(methylthio)benzoic acid for 1-methylcyclopropanecarboxylic acid. MS (DCI/NH$_3$) m/z 440 (M+H)$^+$.

Example 238

3,4-diethoxy-N-(3-((4-oxo-3,4,5,6,7,8-hexahydrophthalazin-1-yl)methyl)phenyl)benzamide The title compound was prepared according to the procedure for EXAMPLE 136, substituting 3,4-diethoxybenzoic acid for 1-methylcyclopropanecarboxylic acid. MS (DCI/NH$_3$) m/z 448 (M+H)$^+$.

Example 239

2-benzyl-N-(3-((4-oxo-3,4,5,6,7,8-hexahydrophthalazin-1-yl)methyl)phenyl)benzamide The title compound was prepared according to the procedure for EXAMPLE 136, substituting 2-benzoylbenzoic acid for 1-methylcyclopropanecarboxylic acid. MS (DCI/NH$_3$) m/z 450 (M+H)$^+$.

Example 240

2-anilino-N-(3-((4-oxo-3,4,5,6,7,8-hexahydrophthalazin-1-yl)methyl)phenyl)benzamide The title compound was prepared as a trifluoroacetic acid salt according to the procedure for EXAMPLE 136, substituting 2-(phenylamino)benzoic acid for 1-methylcyclopropanecarboxylic acid. MS (DCI/NH$_3$) m/z 451 (M+H)$^+$; $^1$H NMR (500 MHz, D$_2$O/dimethylsulfoxide-d$_6$): δ 1.55-1.68 (m, 4H), 2.31-2.45 (m, 4H), 3.91 (s, 2H), 6.91-6.99 (m, 3H), 7.13 (d, J=7.63 Hz, 2H), 7.27-7.34 (m, 4H), 7.38-7.42 (m, 1H), 7.49 (s, 1H), 7.58 (d, J=8.85 Hz, 1H), 7.71-7.75 (m, 1H).

Example 241

2-benzoyl-N-(3-((4-oxo-3,4,5,6,7,8-hexahydrophthalazin-1-yl)methyl)phenyl)benzamide The title compound was prepared as according to the procedure for EXAMPLE 136, substituting 2-benzoylbenzoic acid for 1-methylcyclopropanecarboxylic acid. MS (DCI/NH$_3$) m/z 464 (M+H)$^+$.

Example 242

N-(3-((4-oxo-3,4,5,6,7,8-hexahydrophthalazin-1-yl)methyl)phenyl)-2-(2-phenylethyl)benzamide The title compound was prepared according to the procedure for EXAMPLE 136, substituting 2-phenethylbenzoic acid for 1-methylcyclopropanecarboxylic acid. MS (DCI/NH$_3$) m/z 464 (M+H)$^+$.

Example 243

5-bromo-2-chloro-N-(3-((4-oxo-3,4,5,6,7,8-hexahydrophthalazin-1-yl)methyl)phenyl)benzamide The title compound was prepared according to the procedure for EXAMPLE 136, substituting 5-bromo-2-chlorobenzoic acid for 1-methylcyclopropanecarboxylic acid. MS (DCI/NH$_3$) m z 472 (M+H)$^+$.

Example 244

2-(4-methylbenzoyl)-N-(3-((4-oxo-3,4,5,6,7,8-hexahydrophthalazin-1-yl)methyl)phenyl)benzamide The title compound was prepared according to the procedure for EXAMPLE 136, substituting 2-(4-methylbenzoyl)benzoic acid for 1-methylcyclopropanecarboxylic acid. MS (DCI/NH$_3$) m/z 478 (M+H)$^+$.

Example 245

2-iodo-N-(3-((4-oxo-3,4,5,6,7,8-hexahydrophthalazin-1-yl)methyl)phenyl)benzamide The title compound was prepared according to the procedure for EXAMPLE 136, substituting 2-iodobenzoic acid for 1-methylcyclopropaneccarboxylic acid. MS (DCI/NH$_3$) m/z 486 (M+H)$^+$.

Example 246

3-iodo-N-(3-((4-oxo-3,4,5,6,7,8-hexahydrophthalazin-1-yl)methyl)phenyl)benzamide The title compound was prepared according to the procedure for EXAMPLE 136, substituting 3-iodobenzoic acid for 1-methylcyclopropanecarboxylic acid. MS (DCI/NH$_3$) m/z 486 (M+H)$^+$.

Example 247

4-iodo-N-(3-((4-oxo-3,4,5,6,7,8-hexahydrophthalazin-1-yl)methyl)phenyl)benzamide The title compound was prepared according to the procedure for EXAMPLE 136, substituting 4-iodobenzoic acid for 1-methylcyclopropanecarboxylic acid. MS (DCI/NH$_3$) m/z 486 (M+H)$^+$.

Example 248

N-(2'-fluoro-5'-((4-oxo-3,4,5,6,7,8-hexahydrophthalazin-1-yl)methyl)-1-biphenyl-3-yl)acetamide The title compound was prepared as a free base according to the procedure for EXAMPLE 39, substituting 3-acetamidophenylboronic acid for 3-pyridineboronic acid, but eliminating the last HCl salt formation step. MS (DCI/NH$_3$) m/z 392 (M+H)$^+$; $^1$H NMR (500 MHz, dimethylsulfoxide-d$_6$): δ 1.58-1.67 (m, 4H), 2.05 (s, 3H), 2.33-2.39 (m, 2H), 2.40-2.46 (m, 2H), 3.95 (s, 2H), 7.16 (d, J=7.02 Hz, 1H), 7.18-7.21 (m, 1H), 7.22-7.27 (m, 1H), 7.30 (dd, J=7.63, 2.14 Hz, 1H), 7.38 (t, J=7.93 Hz, 1H), 7.59 (d, J=7.32 Hz, 1H), 7.76 (s, 1H), 10.04 (br s, 1H), 12.61 (br s, 1H).

Example 249

4-((6-fluoro-3'-(methylsulfonyl)-1,1'-biphenyl-3-yl)methyl)-5,6,7,8-tetrahydrophthalazin-1(2H)-one The title compound was prepared as free base according to the procedure for EXAMPLE 39, substituting 3-(methylsulfonyl)phenylboronic acid for 3-pyridineboronic acid, but eliminating the last HCl salt formation step. MS (DCI/NH$_3$) m/z 413 (M+H)$^+$; $^1$H NMR (500 MHz, dimethylsulfoxide-d$_6$): δ 1.57-1.73 (m, 4H), 2.34-2.41 (m, 2H), 2.41-2.48 (m, 2H), 3.28 (s, 3H), 3.98 (s, 2H), 7.24-7.28 (m, 1H), 7.28-7.33 (m, 1H), 7.47 (dd, J=7.63, 2.14 Hz, 1H), 7.77 (t, J=7.78 Hz, 1H), 7.90 (d, J=7.93 Hz, 1H), 7.96-8.00 (m, 1H), 8.04 (s, 1H), 12.61 (br s, 1H).

Example 250

4-((6-fluoro-3'-(pyrrolidin-1-ylcarbonyl)-1,1'-biphenyl-3-yl)methyl)-5,6,7,8-tetrahydrophthalazin-1(2H)-one The title compound was prepared as free base according to the procedure for EXAMPLE 39, substituting 3-(pyrrolidine-1-carbonyl)phenylboronic acid for 3-pyridineboronic acid, but eliminating the last HCl salt formation step. MS (DCI/NH$_3$) m/z 432 (M+H)$^+$.

Example 251

4-((6-fluoro-4'-(pyrrolidin-1-ylcarbonyl)-1,1'-biphenyl-3-yl)methyl)-5,6,7,8-tetrahydrophthalazin-1(2H)-one The title compound was prepared as free base according to the procedure for EXAMPLE 39, substituting 4-(pyrrolidine-1-carbonyl)phenylboronic acid for 3-pyridineboronic acid, but eliminating the last HCl salt formation step. MS (DCI/NH$_3$) m/z 432 (M+H)$^+$; $^1$H NMR (500 MHz, dimethylsulfoxide-d$_6$): δ 1.57-1.68 (m, 4H), 1.78-1.93 (m, 4H), 2.32-2.39 (m, 2H), 2.40-2.47 (m, 2H), 3.39-3.53 (m, 4H), 3.95 (s, 2H), 7.21-7.24 (m, 1H), 7.24-7.31 (m, 1H), 7.39 (dd, J=7.63, 1.86 Hz, 1H), 7.55-7.59 (m, 2H), 7.60-7.64 (m, 2H), 12.60 (br s, 1H).

Example 252

2'-fluoro-5'-((4-oxo-3,4,5,6,7,8-hexahydrophthalazin-1-yl)methyl)-1,1'-biphenyl-3-carboxamide The title compound was prepared as free base according to the procedure for EXAMPLE 39, substituting 3-carbamoylphenylboronic acid for 3-pyridineboronic acid, but eliminating the last HCl salt formation step. MS (DCI/NH$_3$) m/z 378 (M+H)$^+$; $^1$H NMR (500 MHz, dimethylsulfoxide-d$_6$): δ 1.55-1.72 (m, 4H), 2.33-2.41 (m, 2H), 2.41-2.47 (m, 2H), 3.97 (s, 2H), 7.19-7.24 (m, 1H), 7.24-7.30 (m, 1H), 7.42 (dd, J=7.63, 2.14 Hz, 1H), 7.44 (s, 1H), 7.56 (t, J=7.78 Hz, 1H), 7.68 (d, J=7.63 Hz, 1H), 7.88-7.92 (m, 1H), 8.02 (s, 1H), 8.07 (s, 1H), 12.61 (s, 1H).

Example 253

2'-fluoro-N,N-dimethyl-5'-((4-oxo-3,4,5,6,7,8-hexahydrophthalazin-1-yl)methyl)-1,1'-biphenyl-4-carboxamide The title compound was prepared as free base according to the procedure for EXAMPLE 39, substituting 4-(dimethylcarbamoyl)phenylboronic acid for 3-pyridineboronic acid, but eliminating the last HCl salt formation step. MS (DCI/NH$_3$) m/z 406 (M+H)$^+$. $^1$H NMR (500 MHz, dimethylsulfoxide-d$_6$): δ 1.56-1.69 (m, 4H), 2.31-2.40 (m, 2H), 2.40-2.47 (m, 2H), 2.95 (s, 3H), 3.00 (s, 3H), 3.96 (s, 2H), 7.20-7.24 (m, 1H), 7.24-7.30 (m, 1H), 7.40 (dd, J=7.48, 1.98 Hz, 1H), 7.49-7.52 (m, 1H), 7.56-7.59 (m, 2H), 7.60-7.65 (m, 1H), 12.61 (br s, 1H).

Example 254

4-(3,3,3-trifluoro-2-phenylpropyl)-5,6,7,8-tetrahydrophthalazin-1(2H)-one

Example 254A 3-(1,1,1-trifluoro-3-phenylpropan-2-ylidene)-4,5,6,7-tetrahydroisobenzofuran-1(3H)-one The title compound was prepared according to the procedure for EXAMPLE 1C, substituting 1,1,1-trifluoro-3-phenylpropan-2-one for 2-fluoro-5-formylbenzonitrile. MS (DCI/NH$_3$) m/z 309 (M+H)$^+$.

Example 254B 4-(3,3,3-trifluoro-2-phenylpropyl)-5,6,7,8-tetrahydrophthalazin-1(2H)-one The title compound was prepared according to the procedure for EXAMPLE 2C, substituting EXAMPLE 254A for EXAMPLE 2B. MS (DCI/NH$_3$) m/z 323 (M+H)$^+$.

Example 255

4-(2-phenylethyl)-5,6,7,8-tetrahydrophthalazin-1(2H)-one

The title compound was prepared as a side product according to the procedure for EXAMPLE 101, substituting EXAMPLE 222 for EXAMPLE 103. MS (DCI/NH$_3$) m/z 255 (M+H)$^+$.

Example 256

4-(2-(3-bromophenyl)propyl)-5,6,7,8-tetrahydrophthalazin-1(2H)-one

Example 256A 2-(3-bromophenyl)-N-methoxy-N-methylpropanamide

A solution of EXAMPLE 222A (3.5 g, 13.56 mmol) in anhydrous tetrahydrofuran (50 ml) was treated with 1N sodium dicyanamide v solution in tetrahydrofuran (16 ml, 16.27 mmol) at −78° C. for 1 hour. Iodomethane (3.85 g, 27.1 mmol) was added through a syringe, and the mixture was allowed to warm up to room temperature for 2 hours. The mixture was concentrated, and the residue was partitioned between ethyl acetate and brine. The organic phase was concentrated, the residue was purified by flash column chromatography (30% ethyl acetate in hexane) to provide the title compound. MS (DCI/NH$_3$) m/z 273 (M+H)$^+$.

Example 256B 2-(3-bromophenyl)propanal

The title compound was prepared according to the procedure for EXAMPLE 222B, substituting EXAMPLE 256A for EXAMPLE 222A. MS (DCI/NH$_3$) m/z 214 (M+H)$^+$.

Example 256C 3-(2-(3-bromophenyl)propylidene)-4,5,6,7-tetrahydroisobenzofuran-1(3H)-one The title compound was prepared according to the procedure for EXAMPLE 1C, substituting 256B for 2-fluoro-5-formylbenzonitrile. MS (DCI/NH$_3$) m/z 334 (M+H)$^+$.

Example 256D 4-(2-(3-bromophenyl)propyl)-5,6,7,8-tetrahydrophthalazin-1(2H)-one The title compound was prepared according to the procedure for EXAMPLE 2C, substituting EXAMPLE 256C for EXAMPLE 2B. MS (DCI/NH$_3$) m/z 348 (M+H)$^+$.

Example 257 tert-butyl 2-((4-oxo-3,4,5,6,7,8-hexahydrophthalazin-1-yl)methyl)piperazine-1-carboxylate

Example 257A 4-benzyl 1-tert-butyl 2-(methoxy(methyl)carbamoyl)piperazine-1,4-dicarboxylate The title compound was prepared according to the procedure for EXAMPLE 222A, substituting 4-(benzyloxycarbonyl)-1-(tert-butoxycarbonyl)piperazine-2-carboxylic acid for 2-(3-bromophenyl)acetic acid. MS (DCI/NH$_3$) m/z 408 (M+H)$^+$.

Example 257B 4-benzyl 1-tert-butyl 2-formylpiperazine-1,4-dicarboxylate

The title compound was prepared according to the procedure for EXAMPLE 222B, substituting EXAMPLE 257A for EXAMPLE 222A. MS (DCI/NH$_3$) m/z 349 (M+H)$^+$.

Example 257C 4-benzyl 1-tert-butyl 2-((3-oxo-4,5,6,7-tetrahydroisobenzofuran-1(3H)-ylidene)methyl)piperazine-1,4-dicarboxylate The title compound was prepared according to the procedure for EXAMPLE 1C, substituting EXAMPLE 257B for 2-fluoro-5-formylbenzonitrile. MS (DCI/NH$_3$) m/z 469 (M+H)$^+$.

Example 257D 4-benzyl 1-tert-butyl 2-((4-oxo-3,4,5,6,7,8-hexahydrophthalazin-1-yl)methyl)piperazine-1,4-dicarboxylate The title compound was prepared according to the procedure for EXAMPLE 2C, substituting EXAMPLE 257C for EXAMPLE 2B. MS (DCI/NH$_3$) m/z 483 (M+H)$^+$.

Example 257E tert-butyl 2-((4-oxo-3,4,5,6,7,8-hexahydrophthalazin-1-yl)methyl)piperazine-1-carboxylate A solution of EXAMPLE 257D (0.77 g, 1.6 mmol) in tetrahydrofuran (100 ml) was treated with 10% palladium on carbon (85 mg, 0.8 mmol) at room temperature under hydrogen (balloon) overnight. The catalyst was removed by filtration, and the filtrate was concentrated. The residue was purified by flash chromatography (0-15% gradient of methanol in CH$_2$Cl$_2$) to provide the title compound. MS (DCI/NH$_3$) m/z 349 (M+H)$^+$.

Example 258

4-benzyl 1-tert-butyl 2-((4-oxo-3,4,5,6,7,8-hexahydrophthalazin-1-yl)methyl)piperazine-1,4-dicarboxylate The title compound was prepared as described in EXAMPLE 257D. MS (DCI/NH$_3$) m/z 483 (M+H)$^+$.

Example 259

4-(2-(3-nitrophenyl)ethyl)-5,6,7,8-tetrahydrophthalazin-1(2H)-one

Example 259A

N-methoxy-N-methyl-2-(3-nitrophenyl)acetamide

The title compound was prepared according to the procedure for EXAMPLE 222A, substituting 3-nitrobenzoic acid for 2-(3-bromophenyl)acetic acid. MS (DCI/NH$_3$) m/z 225 (M+H)$^+$.

Example 259B 2-(3-nitrophenyl)acetaldehyde

The title compound was prepared according to the procedure for EXAMPLE 222B, substituting EXAMPLE 259A for EXAMPLE 222A.

Example 259C 3-(2-(3-nitrophenyl)ethylidene)-4,5,6,7-tetrahydroisobenzofuran-1(3H)-one The title compound was prepared according to the procedure for EXAMPLE 1C, substituting EXAMPLE 259B for 2-fluoro-5-formylbenzonitrile. MS (DCI/NH$_3$) m/z 286 (M+H)$^+$.

Example 259D 4-(2-(3-nitrophenyl ethyl)-5,6,7,8-tetrahydrophthalazin-1(2H)-one The title compound was prepared according to the procedure for EXAMPLE 2C, substituting EXAMPLE 259C for EXAMPLE 2B. MS (DCI/NH$_3$) m/z 300 (M+H)$^+$.

Example 260

4-(2-(3-aminophenyl)ethyl)-5,6,7,8-tetrahydrophthalazin-1(2H)-one

A suspension of EXAMPLE 259 (110 mg, 0.17 mmol) in methanol (20 ml) was treated with Raney Nickel (20 mg) at room temperature under hydrogen (balloon) overnight. The solid material was filtered off, and the filtrate was concentrated to give the title compound. MS (DCI/NH$_3$) m/z 270 (M+H)$^+$.

Example 261

4-(piperazin-2-ylmethyl)-5,6,7,8-tetrahydrophthalazin-1(2H)-one

A solution of EXAMPLE 258 (35 mg, 0.1 mmol) in trifluoroacetic acid (5 ml) was stirred at room temperature for 1 hour, and was concentrated. The residue was purified by HPLC (Zorbax® C-18 ODS packing material [Agilent Technologies, Santa Clara, Calif.], 0.1% trifluoroacetic acid/CH$_3$CN/H$_2$O) to provide the title compound as a trifluoroacetic acid salt. MS (DCI/NH$_3$) m/z 249 (M+H)$^+$.

Example 262

4-(2-(3-(2-oxopyrrolidin-1-yl)phenyl)ethyl)-5,6,7,8-tetrahydrophthalazin-1(2H)-one To a solution of EXAMPLE 260 (100 mg, 0.37 mmol) in methylene chloride (5 mL) was added 4-chlorobutyrlchloride (52.3 mg, 0.37 mmol) and triethylamine (0.12 mL, 0.45 mmol). The mixture was stirred at room temperature overnight, and was concentrated. The residue was dissolved in absolute ethanol (5 mL), and was treated with sodium ethoxide (0.2 mL, 21 wt % in ethanol) at room temperature for 16 hours. 1 mL of 2N HCl was added, and the mixture was concentrated. The residue was separated by HPLC (Zorbax® C-18 ODS packing material [Agilent Technologies, Santa Clara, Calif.], 0.1% trifluoroacetic acid/CH$_3$CN/H$_2$O) to provide the title compound as a trifluoroacetic acid salt. MS (DCI/NH$_3$) m/z 338 (M+H)$^+$.

Example 263

N-(3-(2-(4-oxo-3,4,5,6,7,8-hexahydrophthalazin-1-yl)ethyl)phenyl)-2-phenoxyacetamide A solution of 2-phenoxyacetic acid (28 mg, 0.186 mmol) in anhydrous dichloromethane (3 ml) was treated with oxalyl chloride (35.3 mg, 0.186 mmol) and a drop of N,N-dimethylformamide at room temperature for 1 hour, and was concentrated. The residue was re-dissolved in anhydrous dichloromethane (5 ml). A suspension of EXAMPLE 260 (50 mg, 0.186 mmol) in anhydrous tetrahydrofuran (2 ml) was then added. The reaction mixture was stirred at room temperature overnight, and was concentrated. The residue was purified by HPLC (Zorbax® C-18 ODS packing material [Agilent Technologies, Santa Clara, Calif.], 0.1% trifluoroacetic acid, $CH_3CN/H_2O$) to provide the title compound as a trifluoroacetic acid salt. MS ($DCI/NH_3$) m/z 404 (M+H)$^+$; $^1$H NMR (300 MHz, dimethylsulfoxide-d$_6$): δ 1.60-1.70 (m, 4H), 2.35-2.39 (m, 2H), 2.42-2.50 (m, 2H), 2.66-2.93 (m, 4H), 4.68 (s, 2H), 6.82-7.09 (m, 4H), 7.23 (t, J=7.80 Hz, 1H), 7.24-7.38 (m, 2H), 7.40-7.60 (m, 2H), 10.01 (s, 1H) 12.54 (s, 1H).

Example 264

4-(2-(6-fluoro-3'-(morpholin-4-ylcarbonyl)-1,1'-biphenyl-3-yl)ethyl)-5,6,7,8-tetrahydrophthalazin-1(2H)-one A microwave vial charged with EXAMPLE 223 (50 mg, 0.14 mmol), dichlorobis(triphenylphosphine)palladium (II) (10 mg, 0.014 mmol), 3-(morpholine-4-carbonyl)phenylboronic acid (40 mg, 0.17 mmol), a mixture of DME(7)/water (3)/ethanol(2) (3 ml), and sodium carbonate solution (2M, 0.1 ml) was heated in a CEM Explorer® microwave reactor (Matthews, N.C.) at 150° C. for 15 minutes. After cooling, the reaction mixture was diluted with methanol (20 ml), and filtered. The filtrate was concentrated, and the residue was separated by HPLC (Zorbax® C-18 ODS packing material [Agilent Technologies, Santa Clara, Calif.], 0.1% trifluoroacetic acid/$CH_3CN/H_2O$) to provide the title compound. MS ($DCI/NH_3$) m/z 462 (M+H)$^+$; $^1$H NMR (300 MHz, dimethylsulfoxide-d$_6$): δ 1.60-1.67 (m, 4H), 2.35-2.39 (m, 2H), 2.44-2.50 (m, 2H), 2.75-3.01 (m, 4H), 3.44-3.73 (m, 8H), 7.17-7.28 (m, 1H), 7.27-7.34 (m, 1H), 7.38-7.47 (m, 1H), 7.50-7.67 (m, 4H), 12.55 (s, 1H).

Example 265 methyl 3-(2-(4-oxo-3,4,5,6,7,8-hexahydrophthalazin-1-yl)ethyl)benzoate

The title compound was prepared according to the procedure for EXAMPLE 66, substituting EXAMPLE 222 for EXAMPLE 66B. MS ($DCI/NH_3$) m/z 313 (M+H)$^+$.

Example 266 methyl 3-(1-methyl-2-(4-oxo-3,4,5,6,7,8-hexahydrophthalazin-1-yl)ethyl)benzoate

The title compound was prepared according to the procedure for EXAMPLE 66, substituting EXAMPLE 256 for EXAMPLE 66B. MS ($DCI/NH_3$) m/z 237 (M+H)$^+$.

Example 267

4-(2-(6-fluoro-4'-(morpholin-4-ylcarbonyl)-1,1'-biphenyl-3-yl)ethyl)-5,6,7,8-tetrahydrophthalazin-1(2H)-one The title compound was prepared according to the procedure for EXAMPLE 264, substituting 4-(morpholine-4-carbonyl)phenylboronic acid for 3-(morpholine-4-carbonyl)phenylboronic acid. MS ($DCI/NH_3$) m/z 462 (M+H)$^+$.

Example 268

4-(2-(6-fluoro-2'-(pyrrolidin-1-ylcarbonyl)-1,1'-biphenyl-3-yl)ethyl)-5,6,7,8-tetrahydrophthalazin-1(2H)-one The title compound was prepared according to the procedure for EXAMPLE 264 substituting 2-(pyrrolidine-1-carbonyl)phenylboronic acid for 3-(morpholine-4-carbonyl)phenylboronic acid. MS ($DCI/NH_3$) m/z 446 (M+H)$^+$.

Example 269

4-(2-(6-fluoro-3'-(pyrrolidin-1-ylcarbonyl)-1,1'-biphenyl-3-yl)ethyl)-5,6,7,8-tetrahydrophthalazin-1(2H)-one The title compound was prepared according to the procedure for EXAMPLE 264, substituting 3-(pyrrolidine-1-carbonyl)phenylboronic acid for 3-(morpholine-4-carbonyl)phenylboronic acid. MS ($DCI/NH_3$) m/z 446 (M+H)$^+$; $^1$H NMR (300 MHz, CDCl$_3$): δ 1.64-1.81 (m, 4H), 1.83-2.03 (m, 4H), 2.43-2.47 (m, 2H), 2.56-2.59 (m, 2H), 2.76-2.88 (m, 2H), 2.93-3.06 (m, 2H), 3.48 (t, J=6.54 Hz, 2H), 3.67 (t, J=6.74 Hz, 2H), 7.01-7.11 (m, 1H), 7.11-7.21 (m, 1H), 7.29 (dd, J=7.54, 2.38 Hz, 1H), 7.39-7.54 (m, 2H), 7.55-7.62 (m, 1H), 7.69 (s, 1H), 10.10 (s, 1H).

Example 270

N-cyclopropyl-2'-fluoro-5'-(2-(4-oxo-3,4,5,6,7,8-hexahydrophthalazin-1-yl)ethyl)-1,1'-biphenyl-3-carboxamide The title compound was prepared according to the procedure for EXAMPLE 264, substituting 3-(cyclopropylcarbamoyl)phenylboronic acid for 3-(morpholine-4-carbonyl)phenylboronic acid. MS ($DCI/NH_3$) m/z 432 (M+H)$^+$.

Example 271

N-(2-(dimethylamino)ethyl)-2'-fluoro-5'-(2-(4-oxo-3,4,5,6,7,8-hexahydrophthalazin-1-yl)ethyl)-1,1'-biphenyl-3-carboxamide The title compound was prepared according to the procedure for EXAMPLE 264, substituting 3-(2-(dimethylamino)ethylcarbamoyl)phenylboronic acid for 3-(morpholine-4-carbonyl)-phenylboronic acid. MS ($DCI/NH_3$) m/z 463 (M+H)$^+$; $^1$H NMR (300 MHz, CDCl$_3$): δ 2.28-2.39 (m, 2H), 2.35 (m, 3H), 2.45 (s, 6H), 2.60-2.69 (m, 2H), 2.73-2.82 (m, 2H), 2.87 (t, J=7.14 Hz, 2H), 3.01 (t, J=7.14 Hz, 2H), 3.54-3.64 (m, 1H), 3.69 (q, J=5.29 Hz, 2H), 6.95-7.10 (m, 1H), 7.10-7.20 (m, 1H), 7.35-7.53 (m, 2H), 7.65-7.80 (m, 2H), 7.79-7.88 (m, 1H).

Example 272

2'-fluoro-5'-(2-(4-oxo-3,4,5,6,7,8-hexahydrophthalazin-1-yl)ethyl)-1,1'-biphenyl-3-carboxamide The title compound was prepared according to the procedure for EXAMPLE 264, substituting 3-carbamoylphenylboronic acid for 3-(morpholine-4-carbonyl)phenylboronic acid.

MS (DCI/NH$_3$) m/z 392 (M+H)$^+$; $^1$H NMR (500 MHz, pyridine-d$_5$): δ 1.54 (s, 4H), 2.27 (s, 2H), 2.70 (s, 2H), 2.76-2.95 (m, 2H), 2.98-3.21 (m, 2H), 7.19-7.27 (m, 2H), 7.31 (s, 1H), 7.49 (d, J=7.02 Hz, 1H), 7.82 (d, J=7.32 Hz, 1H), 8.42 (d, J=7.63 Hz, 1H), 8.47 (s, 1H), 8.68 (s, 1H), 9.02 (s, 1H), 14.05 (s, 1H).

Example 273

N-(2'-fluoro-5'-(2-(4-oxo-3,4,5,6,7,8-hexahydrophthalazin-1-yl)ethyl)-1,1'-biphenyl-3-yl)methanesulfonamide The title compound was prepared according to the procedure for EXAMPLE 264, substituting 3-(methylsulfonamido)phenylboronic acid for 3-(morpholine-4-carbonyl)phenylboronic acid. MS (DCI/NH$_3$) m/z 442 (M+H)$^+$; $^1$H NMR (300 MHz, CDCl$_3$): δ 2.31-2.48 (m, 4H), 2.59 (m, 4H), 2.77-2.96 (m, 4H), 3.02 (t, J=7.80 Hz, 3H), 6.92-7.03 (m, 1H), 7.02-7.12 (m, 1H), 7.10-7.22 (m, 2H), 7.27-7.33 (m, 1H), 7.32-7.47 (m, 2H), 10.96 (s, 1H).

Example 274

N-(2'-fluoro-5'-(2-(4-oxo-3,4,5,6,7,8-hexahydrophthalazin-1-yl)ethyl)-1,1'-biphenyl-3-yl)acetamide The title compound was prepared according to the procedure for EXAMPLE 264, substituting 3-acetamidophenylboronic acid for 3-(morpholine-4-carbonyl)phenylboronic acid. MS (DCI/NH$_3$) m/z 406 (M+H)$^+$; $^1$H NMR (300 MHz, CDCl$_3$): δ 2.06-2.21 (m, 4H), 2.25 (s, 3H), 2.34 (m, 2H), 2.58 (m, 2H), 2.80-2.94 (m, 2H), 2.92-3.06 (m, 2H), 6.93-7.10 (m, 2H), 7.10-7.19 (m, 1H), 7.23 (d, J=4.36 Hz, 1H), 7.27-7.33 (m, 1H), 7.38 (t, J=7.73 Hz, 1H), 7.67-7.76 (m, 1H), 11.25 (s, 1H).

Example 275

4-(2-(6-fluoro-3'-(morpholin-4-ylcarbonyl)-1,1'-biphenyl-3-yl)propyl)-5,6,7,8-tetrahydrophthalazin-1(2H)-one The title compound was prepared according to the procedure for EXAMPLE 264 substituting EXAMPLE 293 for EXAMPLE 223. MS (DCI/NH$_3$) m/z 476 (M+H)$^+$.

Example 276

4-(2-(6-fluoro-3'-(pyrrolidin-1-ylcarbonyl)-1,1'-biphenyl-3-yl)propyl)-5,6,7,8-tetrahydrophthalazin-1(2H)-one The title compound was prepared according to the procedure for EXAMPLE 264 substituting EXAMPLE 293 for EXAMPLE 223, and 3-(pyrrolidine-1-carbonyl)phenylboronic acid for 3-(morpholine-4-carbonyl)phenylboronic acid. MS (DCI/NH$_3$) m/z 460 (M+H)$^+$; $^1$H NMR (300 MHz, CDCl$_3$): δ 1.36 (d, J=6.74 Hz, 3H), 1.61-1.78 (m, 4H), 1.76-2.06 (m, 4H), 2.26-2.45 (m, 2H), 2.49-2.67 (m, 2H), 2.84 (m, 2H), 3.21-3.36 (m, 1H), 3.40-3.57 (m, 2H), 3.59-3.83 (m, 2H), 7.13-7.23 (m, 2H), 7.36 (t, J=7.93 Hz, 1H), 7.40-7.51 (m, 3H), 7.55-7.64 (m, 1H), 7.73 (s, 1H) 9.98 (s, 1H).

Example 277

N-cyclopropyl-2'-fluoro-5'-(1-methyl-2-(4-oxo-3,4,5,6,7,8-hexahydrophthalazin-1-yl)ethyl)-1,1'-biphenyl-3-carboxamide The title compound was prepared according to the procedure for EXAMPLE 264, substituting EXAMPLE 293 for EXAMPLE 223, and 3-(cyclopropylcarbamoyl)phenylboronic acid for 3-(morpholine-4-carbonyl)phenylboronic acid. MS (DCI/NH$_3$) m/z 446 (M+H)$^+$.

Example 278

4-(3-amino-4-chlorobenzyl)-5,6,7,8-tetrahydrophthalazin-1(2H)-one

The title compound was prepared according to the procedure for EXAMPLE 2, substituting 4-chloro-3-nitrobenzaldehyde for 4-fluoro-3-nitrobenzaldehyde. MS (DCI/NH$_3$) m/z 290 (M+H)$^+$.

Example 279

4-(3-amino-4-methoxybenzyl)-5,6,7,8-tetrahydrophthalazin-1(2H)-one

The title compound was prepared according to the procedure for EXAMPLE 2, substituting 4-methoxy-3-nitrobenzaldehyde for 4-fluoro-3-nitrobenzaldehyde. MS (DCI/NH$_3$) m/z 286 (M+H)$^+$.

Example 280

4-(3-amino-4-hydroxybenzyl)-5,6,7,8-tetrahydrophthalazin-1(2H)-one

The title compound was prepared according to the procedure for EXAMPLE 2, substituting 4-hydroxy-3-nitrobenzaldehyde for 4-fluoro-3-nitrobenzaldehyde. MS (DCI/NH$_3$) m/z 272 (M+H)$^+$.

Example 281

4-(3-amino-4-methylbenzyl)-5,6,7,8-tetrahydrophthalazin-1(2H)-one

The title compound was prepared according to the procedure for EXAMPLE 2, substituting 4-methyl-3-nitrobenzaldehyde for 4-fluoro-3-nitrobenzaldehyde. MS (DCI/NH$_3$) m/z 270 (M+H)$^+$.

Example 282

N-(2-(dimethylamino)ethyl)-3'-(1-methyl-2-(4-oxo-3,4,5,6,7,8-hexahydrophthalazin-1-yl)ethyl)-1,1'-biphenyl-3-carboxamide The title compound was prepared according to the procedure for EXAMPLE 264, substituting EXAMPLE 256 for EXAMPLE 223, and 3-(2-(dimethylamino)ethylcarbamoyl)

181 phenylboronic acid for 3-(morpholine-4-carbonyl)phenylboronic acid. MS (DCI/NH$_3$) m/z 459 (M+H)$^+$.

Example 283

3'-(1-methyl-2-(4-oxo-3,4,5,6,7,8-hexahydrophthalazin-1-yl)ethyl)-1,1'-biphenyl-3-carboxamide The title compound was prepared according to the procedure for EXAMPLE 264, substituting EXAMPLE 256 for EXAMPLE 223, and 3-carbamoylphenylboronic acid for 3-(morpholine-4-carbonyl)phenylboronic acid. MS (DCI/NH$_3$) m/z 388 (M+H)$^+$; $^1$H NMR (300 MHz, CD$_3$OD): δ 1.40 (d, J=7.14 Hz, 3H), 1.53-1.81 (m, 4H), 2.25-2.59 (m, 4H), 2.91 (d, J=7.14 Hz, 2H), 3.31-3.41 (m, 1H), 7.23 (d, J=7.54 Hz, 1H), 7.36 (t, J=7.93 Hz, 1H), 7.42-7.51 (m, 2H), 7.50-7.59 (m, 1H), 7.73 (d, J=7.93 Hz, 1H), 7.79-7.91 (m, 1H), 8.09 (s, 1H).

Example 284

N-(3'-(1-methyl-2-(4-oxo-3,4,5,6,7,8-hexahydrophthalazin-1-yl)ethyl)-1,1'-biphenyl-3-yl)acetamide The title compound was prepared according to the procedure for EXAMPLE 264, substituting EXAMPLE 256 for EXAMPLE 223, and 3-acetamidophenylboronic acid for 3-(morpholine-4-carbonyl)phenylboronic acid. MS (DCI/NH$_3$) m/z 402 (M+H)$^+$; $^1$H NMR (300 MHz, CD$_3$OD): δ 1.40 (d, J=7.12 Hz, 3H), 1.50-1.78 (m, 4H), 2.16 (s, 3H), 2.36-2.53 (m, 4H), 2.83 (m, 1H), 2.88 (d, J=7.46 Hz, 2H), 7.16-7.23 (m, 1H), 7.22-7.29 (m, 1H), 7.29-7.36 (m, 2H), 7.36-7.45 (m, 2H), 7.47-7.67 (m, 1H), 7.72 (t, J=1.86 Hz, 1H).

Example 285

3'-(1-(4-oxo-3,4,5,6,7,8-hexahydrophthalazin-1-yl)ethyl)-1,1'-biphenyl-3-carboxamide Example 285A 1-bromo-3-(1-bromoethyl)benzene A solution of 3-bromoethyl benzene (2 g, 11 mmol). N-bromosuccinimide (91.9 g, 11 mmol) and azobisisobutyronitrile (10 mg, 0.06 mmol) in chloroform (30 ml) was stirred at 65° C. under nitrogen for 18 hours. After cooling, the reaction mixture was concentrated, and the residue was partitioned between ethyl acetate and brine. The organic layer was washed with brine, and was concentrated. The residue was separated by flash chromatography on silica gel (10% ethyl acetate in hexane) to provide the title compound. MS (DCI/NH$_3$) m/z 262 (M+H)$^+$.

Example 285B (1-(3-bromophenyl)ethyl)triphenylphosphonium bromide

A solution of EXAMPLE 285A (1.0 g, 3.8 mmol) and triphenylphosphine (1.1 g, 4.2 mmol) in toluene (15 ml) was heated at 120° C. under nitrogen for three days. After cooling to room temperature, the solid material was collected by filtration, washed with toluene, and dried to provide the title compound.

182

Example 285C 3-(1-(3-bromophenyl)ethylidene)-4,5,6,7-tetrahydroisobenzofuran-1(3H)-one A suspension of EXAMPLE 285B (1.88 g, 3.4 mmol) in tetrahydrofuran (100 ml) was treated with potassium t-butoxide (1N solution in tetrahydrofuran, 3.4 ml, 3.4 mmol) at −78° C. for 1 hour, and was allowed to warm up to 0° C. over 30 minutes. A solution of 4,5,6,7-tetrahydroisobenzofuran-1,3-dione (0.54 g, 3.4 mmol) in tetrahydrofuran (10 ml) was then added. The reaction mixture was warmed up to room temperature, and stirred at room temperature for additional 4 hours. After quenching with water, the reaction mixture was partitioned between ethyl acetate and brine. The organic phase was washed with brine, and concentrated. The residue was separated by flash chromatography (20% ethyl acetate in hexane) to provide the title compound. MS (DCI/NH$_3$) m/z 320 (M+H)$^+$.

Example 285D 4-(1-(3-bromophenyl)ethyl)-5,6,7,8-tetrahydrophthalazin-1(2H)-one

The title compound was prepared according to the procedure for EXAMPLE 2C, substituting EXAMPLE 285C for EXAMPLE 2B. MS (DCI/NH$_3$) m/z 334 (M+H)$^+$.

Example 285E

3'-(1-(4-oxo-3,4,5,6,7,8-hexahydrophthalazin-1-yl)ethyl)-1,1'-biphenyl-3-carboxamide The title compound was prepared according to the procedure for EXAMPLE 264, substituting EXAMPLE 285D for EXAMPLE 223, and 3-carbamoylphenylboronic acid for 3-(morpholine-4-carbonyl)phenylboronic acid. MS (DCI/NH$_3$) m/z 374 (M+H)$^+$; $^1$H NMR (300 MHz, CD$_3$OD): δ 1.59 (d, J=7.12 Hz, 3H), 1.61-1.81 (m, 4H), 2.10-2.22 (m, 1H), 2.39-2.55 (m, 2H), 2.61-2.73 (m, 1H), 4.32 (q, J=6.78 Hz, 1H), 7.08-7.21 (m, 1H), 7.35-7.43 (m, 1H), 7.48-7.59 (m, 3H), 7.75 (d, J=7.80 Hz, 1H), 7.80-7.87 (m, 1H), 8.06-8.11 (m, 1H).

Example 286

N-(3'-(1-(4-oxo-3,4,5,6,7,8-hexahydrophthalazin-1-yl)ethyl)-1,1'-biphenyl-3-yl)acetamide The title compound was prepared according to the procedure for EXAMPLE 264, substituting EXAMPLE 285D for EXAMPLE 223, and 3-acetamidophenylboronic acid for 3-(morpholine-4-carbonyl)phenylboronic acid. MS (DCI/NH$_3$) m/z 388 (M+H)$^+$; $^1$H NMR (300 MHz, CD OD): δ 1.58 (d, J=7.12 Hz, 3H), 1.60-1.82 (m, 4H), 2.14 (s, 3H), 2.10-2.23 (m, 1H), 2.47-2.55 (m, 2H), 2.60-2.73 (m, 1H), 4.30 (q, J=6.78 Hz, 1H), 7.15 (d, J=7.46 Hz, 1H), 7.23-7.30 (m, 1H), 7.31-7.40 (m, 2H), 7.41-7.47 (m, 1H), 7.47-7.56 (m, 1H), 7.56-7.69 (m, 1H), 7.77 (t, J=1.86 Hz, 1H).

Example 287

N-(2-(dimethylamino)ethyl)-3'-(1-(4-oxo-3,4,5,6,7,8-hexahydrophthalazin-1-yl)ethyl)-1,1'-biphenyl-3-carboxamide The title compound was prepared according to the procedure for EXAMPLE 264, substituting EXAMPLE 285D for EXAMPLE 223, and 3-(2-(dimethylamino)ethylcarbamoyl)phenylboronic acid for 3-(morpholine-4-carbonyl)phenylboronic acid. MS (DCI/NH$_3$) m/z 445 (M+H)$^+$.

Example 288

3-(1-methyl-2-(4-oxo-3,4,5,6,7,8-hexahydrophthalazin-1-yl)ethyl)benzoic acid A solution of EXAMPLE 266 (50 mg, 0.16 mmol) in tetrahydrofuran (10 ml) was treated with a solution of LiOH.H$_2$O (100 mg, 4 mmol) in water (4 ml) at 50° C. overnight. The mixture was concentrated, and the residue was purified by HPLC (Zorbax® C-18 ODS packing material [Agilent Technologies, Santa Clara, Calif.], 0.1% trifluoroacetic acid/CH$_3$CN/H$_2$O) to provide the title compound. MS (DCI/NH$_3$) m/z 313 (M+H)$^+$.

Example 289

N-(2-fluoro-5-((4-oxo-3,4,5,6,7,8-hexahydrophthalazin-1-yl)methyl)phenyl)-4-(4-methoxyphenyl)-4-oxobutanamide To a solution of 4-(4-methoxyphenyl)-4-oxobutanoic acid (29 mg, 0.14 mmol) in dioxane (1.5 mL) was added 2-(1H-7-azabenzotriazol-1-yl)-1,1,3,3-tetramethyl uronium hexafluorophosphate methanaminium (HATU) (42 mg) and N,N'-diisopropylethylamine (32 µL). The mixture was stirred at room temperature for 15 minutes, and EXAMPLE 2 (25 mg, 0.091 mmol) was added. The reaction mixture was stirred at room temperature for 16 hours, and was concentrated. The crude was separated by HPLC (Zorbax® C-18 ODS packing material [Agilent Technologies, Santa Clara, Calif.], 0.1% trifluoroacetic acid/CH$_3$CN/H$_2$O) to provide the title compound as a trifluoroacetic acid salt. MS (DCI/NH$_3$) m/z 464 (M+H)$^+$; $^1$H NMR (500 MHz, dimethylsulfoxide-d$_6$): δ 1.53-1.66 (m, 4H), 2.29-2.40 (m, 4H), 2.74 (t, J=6.41 Hz, 2H), 3.25 (t, J=6.56 Hz, 2H), 3.84 (s, 2H), 3.85 (s, 3H), 6.88-6.96 (m, 1H), 7.05 (d, J=8.85 Hz, 2H), 7.12-7.20 (m, 1H), 7.74 (d, J=6.41 Hz, 1H), 7.97 (d, J=9.15 Hz, 2H), 9.75 (br s, 1H), 12.60 (br s, 1H).

Example 290

1-(2-fluoro-5-((4-oxo-3,4,5,6,7,8-hexahydrophthalazin-1-yl)methyl)phenyl)-3,4-dimethyl-1H-pyrrole-2,5-dione To a solution of EXAMPLE 2 (100 mg, 0.37 mmol) in acetic acid (8 mL) was added 3,4-dimethylfuran-2,5-dione (46 mg, 0.37 mmol). The reaction mixture was heated at 80° C. for 16 hours, and concentrated. The residue was separated by HPLC (Zorbax® C-18 ODS packing material [Agilent Technologies, Santa Clara, Calif.], 0.1% trifluoroacetic acid/CH$_3$CNH$_2$O) to provide the title compound as a trifluoroacetic acid salt. MS (DCI/NH$_3$) m/z 382 (M+H)$^+$; $^1$H NMR (500 MHz, dimethylsulfoxide-d$_6$): δ 1.56-1.68 (m, 4H), 1.98 (s, 6H), 2.30-2.43 (m, 4H), 3.93 (s, 2H), 7.18 (dd, J=7.02, 1.53 Hz, 1H), 7.31-7.35 (m, 2H), 12.63 (br s, 1H).

Example 291

3-(2-fluoro-5-((4-oxo-3,4,5,6,7,8-hexahydrophthalazin-1-yl)methyl)phenyl)-3-azabicyclo(3.1.0)hexane-2,4-dione To a suspension of EXAMPLE 2 (210 mg, 0.77 mmol) in acetonitrile (8 mL) was added 3-oxabicyclo(3.1.0)hexane-2,4-dione (95 mg, 0.85 mmol) and stirred at 80° C. for 16 hours. The reaction mixture was cooled and concentrated on a rotary evaporator. The residual solid was dissolved in dioxane (4 mL), and treated with O-(benzotriazol-1-yl, N,N,N',N'-tetramethyluronium hexafluorophosphate (380 mg, 0.99 mmol) and N,N'-diisopropylethylamine (0.3 mL, 1.69 mmol) at room temperature for an additional 16 hours. The reaction mixture was concentrated, and separated by HPLC (Zorbax® C-18 ODS packing material [Agilent Technologies, Santa Clara, Calif.], 0.1% trifluoroacetic acid/CH$_3$CN/H$_2$O) to provide the title compound as a trifluoroacetic acid salt. MS (DCI/NH$_3$) m/z 368 (M+H)$^+$; $^1$H NMR (400 MHz, dimethylsulfoxide-d$_6$): δ 1.57-1.64 (m, 4H), 1.66-1.72 (m, 2H), 2.32-2.41 (m, 4H), 2.75 (dd, J=7.82, 3.22 Hz, 2H), 3.91 (s, 1H), 7.16 (d, J=7.36 Hz, 1H), 7.27-7.29 (m, 1H), 7.29-7.32 (m, 1H), 12.61 (br s, 1H).

Example 292

4-((4-(phenoxyacetyl)piperazin-2-yl)methyl)-5,6,7,8-tetrahydrophthalazin-1(2H)-one A solution of EXAMPLE 258 (138 mg, 0.29 mmol) in methylene chloride (10 ml) was treated with trifluoroacetic acid (2 ml) at 40° C. for 2 hours, and concentrated. The residue was purified by HPLC (Zorbax® C-18 ODS packing material [Agilent Technologies, Santa Clara, Calif.], 0.1% trifluoroacetic acid/CH$_3$CN/H$_2$O) to provide the title compound as TFA salt. MS (DCI/NH$_3$) m/z 383 (M+H)$^+$.

Example 293

4-(2-(3-bromo-4-fluorophenyl)propyl)-5,6,7,8-tetrahydrophthalazin-1(2H)-one

Example 293A

2-(3-bromo-4-fluorophenyl)-N-methoxy-N-methylacetamide

The title compound was prepared according to the procedure for EXAMPLE 222A, substituting 2-(3-bromo-4-fluorophenyl)acetic acid for 2-(3-bromophenyl)acetic acid. MS (DCI/NH$_3$) m/z 276 (M+H)$^+$.

Example 293B

2-(3-bromo-4-fluorophenyl)-N-methoxy-N-methylpropanamide

The title compound was prepared according to the procedure for EXAMPLE 256A, substituting EXAMPLE 293A for EXAMPLE 222A. MS (DCI NH$_3$) m/z 291 (M+H)$^+$.

Example 293C

2-(3-bromo-4-fluorophenyl)propanal

The title compound was prepared according to the procedure for EXAMPLE 256B, substituting EXAMPLE 293B for EXAMPLE 256A. MS (DCI/NH$_3$) m/z 232 (M+H)$^+$.

Example 293D 3-(2-(3-bromo-4-fluorophenyl)propylidene)-4,5,6,7-tetrahydroisobenzofuran-1(3H)-one The title compound was prepared according to the procedure for EXAMPLE 1C, substituting 293C for 2-fluoro-5-formylbenzonitrile. MS (DCI/NH$_3$) m/z 352 (M+H)$^+$.

Example 293E 4-(2-(3-bromo-4-fluorophenyl)propyl)-5,6,7,8-tetrahydrophthalazin-1(2H)-one The title compound was prepared according to the procedure for EXAMPLE 2C, substituting EXAMPLE 293D for EXAMPLE 2B. MS (DCI/NH$_3$) m/z 366 (M+H)$^+$.

Example 294

4-oxo-N-(3-(2-(4-oxo-3,4,5,6,7,8-hexahydrophthalazin-1-yl)ethyl)phenyl)-4-phenylbutanamide A mixture of 4-oxo-4-phenylbutanoic acid (50 mg, 0.28 mmol), 2-(3H-(1,2,3)triazolo(4,5-b)pyridin-3-yl)-1,1,3,3-tetramethylisouroniumhexafluorophosphate (V) (106 mg, 0.28 mmol) and Hunig's base (120 mg, 0.9 mmol) in anhydrous N,N-dimethylformamide (0.5 ml) was stirred at room temperature for 10 minutes, and EXAMPLE 260 (50 mg, 0.18 mmol) was added in one portion. The reaction mixture was stirred at room temperature for another 1 hour, and was diluted with 5 mL of methanol. The solid material was collected by filtration, washed with methanol, and dried to provide the title compound. MS (DCI/NH$_3$) m/z 430 (M+H)$^+$. $^1$H NMR (300 MHz, dimethylsulfoxide-d$_6$): δ 1.54-1.77 (m, 4H), 2.30-2.42 (m, 2H), 2.42-2.49 (m, 2H), 2.65-2.79 (m, 4H), 2.79-2.89 (m, 2H), 3.30-3.38 (m, 2H), 6.90 (d, J=7.80 Hz, 1H), 7.19 (t, J=7.80 Hz, 1H), 7.38-7.49 (m, 2H), 7.54 (t, J=7.46 Hz, 2H), 7.61-7.69 (m, 1H), 7.99 (t, J=6.61 Hz, 2H), 9.96 (s, 1H), 12.52 (s, 1H).

Example 295

2'-fluoro-5'-(1-methyl-2-(4-oxo-3,4,5,6,7,8-hexahydrophthalazin-1-yl)ethyl)-1,1'-biphenyl-3-carboxamide The title compound was prepared according to the procedure for EXAMPLE 264, substituting EXAMPLE 293 for EXAMPLE 223, and 3-carbamoylphenylboronic acid for 3-(morpholine-4-carbonyl)phenylboronic acid. MS (DCI/NH$_3$) m/z 406 (M+H)$^+$.

Example 296

N-(2'-fluoro-5'-(1-methyl-2-(4-oxo-3,4,5,6,7,8-hexahydrophthalazin-1-yl)ethyl)-1,1'-biphenyl-3-yl)acetamide The title compound was prepared according to the procedure for EXAMPLE 264, substituting EXAMPLE 293 for EXAMPLE 223, and 3-acetamidophenylboronic acid for 3-(morpholine-4-carbonyl)phenylboronic acid. MS (DCI/NH$_3$) m/z 420 (M+H)$^+$.

Example 297

N-((2'-fluoro-5'-(1-methyl-2-(4-oxo-3,4,5,6,7,8-hexahydrophthalazin-1-yl)ethyl)-1,1'-yl)ethyl)-biphenyl-3-yl)methyl)methanesulfonamide The title compound was prepared according to the procedure for EXAMPLE 264, substituting EXAMPLE 293 for EXAMPLE 223, and 3-(methylsulfonamidomethyl)phenylboronic acid for 3-(morpholine-4-carbonyl)phenylboronic acid. MS (DCI/NH$_3$) m/z 470 (M+H)$^+$.

Example 298

2-(2-fluoro-5-((4-oxo-3,4,5,6,7,8-hexahydrophthalazin-1-yl)methyl)phenyl)hexahydro-1H-isoindole-1,3(2H)-dione The title compound was prepared according to the procedure for EXAMPLE 291, substituting hexahydroisobenzofuran-1,3-dione for oxabicyclo(3.1.0)hexane-2,4-dione. MS (DCI/NH$_3$) m/z 410 (M+H)$^+$; $^1$H NMR (300 MHz, dimethylsulfoxide-d$_6$): δ 1.31-1.53 (m, 5H), 1.57-1.68 (m, 4H), 1.66-1.78 (m, 3H), 1.76-1.92 (m, 2H), 2.29-2.43 (m, 4H), 3.93 (s, 2H), 7.12-7.17 (m, 1H), 7.28-7.33 (m, 1H), 7.33-7.37 (m, 1H), 12.63 (br s, 1H).

Example 299

1-(2-fluoro-5-((4-oxo-3,4,5,6,7,8-hexahydrophthalazin-1-yl)methyl)phenyl)-3,3-dimethylpyrrolidine-2,5-dione The title compound was prepared according to the procedure for EXAMPLE 291, substituting 3,3-dimethyldihydrofuran-2,5-dione for oxabicyclo(3.1.0)hexane-2,4-dione. MS (DCI/NH$_3$) m/z 384 (M+H)$^+$; $^1$H NMR (300 MHz, dimethylsulfoxide-d$_6$): δ 1.31 (s, 6H), 1.54-1.70 (m, 4H), 2.30-2.44 (m, 4H), 2.78 (s, 2H), 3.94 (s, 2H), 7.19 (d, J=7.46 Hz, 1H), 7.30-7.33 (m, 1H), 7.35 (s, 1H), 12.62 (br s, 1H).

Example 300

4-(4-fluoro-3-(2-methyl-5-oxopyrrolidin-1-yl)benzyl)-5,6,7,8-tetrahydrophthalazin-1(2H)-one

Example 300A 4-fluoro-3-(2-methyl-5-oxopyrrolidin-1-yl)benzaldehyde

A 100 mL round bottom flask was charged with 3-bromo-4-fluorobenzaldehyde (1.0 g, 4.93 mmol), tris(dibenzylideneacetone)dipalladium(0) (450 mg, 0.493 mmol), Xantphos (4,5-bis(diphenylphosphino)-9,9-dimethylxanthene) (428 mg, 0.739 mmol), and cesium carbonate (2.4 g, 7.39 mmol). The mixture was purged with nitrogen, and anhydrous dioxane (15 mL), and 5-methylpyrrolidinone (0.586 g, 5.91 mmol) were added. The reaction mixture was purged with nitrogen again, and heated at 100° C. for 20 hours. After cooling to room temperature, the reaction mixture was partitioned between ethyl acetate and brine. The organic phase was dried over MgSO$_4$, filtered and concentrated. The residue was separated by flash chromatography (50% ethyl acetate in hexane) to provide the title compound. MS (DCI/NH$_3$) m/z 222 (M+H)$^+$.

Example 300B 4-(4-fluoro-3-(2-methyl-5-oxopyrrolidin-1-yl)benzyl)-5,6,7,8-tetrahydrophthalazin-1(2H)-one A solution of EXAMPLE 1B (486 mg, 1.16 mmol), EXAMPLE 300A (265 mg) and triethylamine (0.16 mL) in dichloromethane (8 mL) was stirred at room temperature for 16 hours, and concentrated. The residue was dissolved in ethanol (5 mL) and treated with hydrazine monohydrate (0.11 mL) at 80° C. for 2 hours. The mixture was allowed to cool and the precipitated solid was filtered and dried to provide the title compound. MS (DCI/NH$_3$) m/z 356 (M+H)$^+$; $^1$H NMR (400 MHz, dimethylsulfoxide-d$_6$): δ 1.02 (d, J=6.14 Hz, 3H), 1.57-1.63 (m, 4H), 1.64-1.72 (m, 1H), 2.27-2.34 (m, 1H), 2.34-2.40 (m, 4H), 2.41-2.46 (m, 2H), 3.90 (s, 2H), 4.08 (q, J=6.44 Hz, 1H), 7.10-7.14 (m, 1H), 7.14-7.18 (m, 1H), 7.20-7.27 (m, 1H), 12.61 (s, 1H).

Example 301

4-(4-fluoro-3-(2-oxo-1,3-oxazolidin-3-yl)benzyl)-5,6,7,8-tetrahydrophthalazin-1(2H)-one

Example 301A 4-fluoro-3-(2-oxooxazolidin-3-yl)benzaldehyde

The title compound was prepared according to the procedure for EXAMPLE 300A, substituting oxazolidin-2-one for 5-methylpyrrolidinone. MS (DCI/NH$_3$) m/z 210 (M+H)$^+$.

Example 301B 4-(4-fluoro-3-(2-oxo-1,3-oxazolidin-3-yl)benzyl)-5,6,7,8-tetrahydrophthalazin-1(2H)-one The title compound was prepared according to the procedure for EXAMPLE 300B, substituting EXAMPLE 301A for EXAMPLE 300A. MS (DCI/NH$_3$) m/z 344 (M+H)$^+$; $^1$H NMR (300 MHz, dimethylsulfoxide-d$_6$): δ 1.55-1.75 (m, 4H), 2.30-2.45 (m, 4H), 3.90 (s, 2H), 3.98 (t, J=7.93 Hz, 2H), 4.45 (dd, J=8.72, 7.14 Hz, 2H), 7.11-7.17 (m, 1H), 7.25 (dd, J=10.91, 8.53 Hz, 1H), 7.36 (dd, J=7.54, 2.38 Hz, 1H), 12.61 (br s, 1H).

Example 302

4-(4-fluoro-3-(2-oxoazepan-1-yl)benzyl)-5,6,7,8-tetrahydrophthalazin-1(2H)-one

Example 302A 4-fluoro-3-(2-oxoazepan-1-yl)benzaldehyde

The title compound was prepared according to the procedure for EXAMPLE 300A, substituting azepan-2-one for 5-methylpyrrolidinone. MS (DCI/NH$_3$) m/z 236 (M+H)$^+$.

Example 302B 4-(4-fluoro-3-(2-oxoazepan-yl)benzyl)-5,6,7,8-tetrahydrophthalazin-1(2H)-one The title compound was prepared according to the procedure for EXAMPLE 300B, substituting EXAMPLE 302A for EXAMPLE 300A. MS (DCI/NH$_3$) m/z 370 (M+H)$^+$; $^1$H NMR (300 MHz, dimethylsulfoxide-d$_6$): δ 1.54-1.65 (m, 4H), 1.65-1.80 (m, 6H), 2.32-2.45 (m, 4H), 2.54-2.63 (m, 2H), 3.57-3.72 (m, 2H), 3.88 (s, 2H), 7.04-7.12 (m, 2H), 7.13-7.22 (m, 1H), 12.61 (br s, 1H).

Example 303

1-(2-fluoro-5-((4-oxo-3,4,5,6,7,8-hexahydrophthalazin-1-yl)methyl)phenyl)piperidine-2,6-dione The title compound was prepared according to the procedure for EXAMPLE 291, substituting dihydro-2H-pyran-2,6 (3H)-dione for oxabicyclo(3.1.0)hexane-2,4-dione. MS (DCI/NH$_3$) m/z 370 (M+H)$^+$; $^1$H NMR (300 MHz, dimethylsulfoxide-d$_6$): δ 1.53-1.69 (m, 4H), 1.84-1.97 (m, 1H), 1.98-2.11 (m, 1H), 2.29-2.42 (m, 4H), 2.75 (t, J=6.44 Hz, 4H), 3.90 (s, 2H), 7.04 (d, J=7.80 Hz, 1H), 7.24 (s, 1H), 7.26 (d, J=1.36 Hz, 1H), 12.63 (s, 1H).

Example 304

4-(4-fluoro-3-(2-oxoimidazolidin-1-yl)benzyl)-5,6,7,8-tetrahydrophthalazin-1(2H)-one

Example 304A 4-fluoro-3-(2-oxoimidazolidin-1-yl)benzaldehyde

The title compound was prepared according to the procedure for EXAMPLE 300A, substituting imidazolidin-2-one for 5-methylpyrrolidinone. MS (DCI/NH$_3$) m/z 209 (M+H)$^+$.

Example 304B 4-(4-fluoro-3-(2-oxoimidazolidin-1-yl)benzyl)-5,6,7,8-tetrahydrophthalazin-1(2H)-one The title compound was prepared according to the procedure for EXAMPLE 300B, substituting EXAMPLE 304A for EXAMPLE 300A. MS (DCI/NH$_3$) m/z 343 (M+H)$^+$; $^1$H NMR (300 MHz, dimethylsulfoxide-d): δ 1.55-1.69 (m, 4H), 2.31-2.44 (m, 4H), 3.39 (t, J=7.97 Hz, 2H), 3.75-3.83 (m, 2H), 3.86 (s, 2H), 6.86 (br s, 1H), 6.94-7.03 (m, 1H), 7.16 (dd, J=1.19, 8.48 Hz, 1H), 7.31 (dd, J=7.63, 2.20 Hz, 1H), 12.61 (br s, 1H).

Example 305

4-(3-(1,1-dioxidoisothiazolidin-2-yl)-4-fluorobenzyl)-5,6,7,8-tetrahydrophthalazin-1(2H)-one To a solution of EXAMPLE 2 (150 mg, 0.55 mmol) in dichloromethane (5 mL) was added 3-chloropropane-1-sulfonyl chloride (97 mg, 0.55 mmol), and the mixture stirred for 16 hours. The reaction mixture was concentrated, and the residual solid was dissolved in dioxane (3 mL). Sodium ethoxide (0.14 mL, 21 wt % in ethyl alcohol) was then added, and the solution was heated at 80° C. for 16 hours. After cooling, the reaction mixture was concentrated. The residue was separated by HPLC (Zorbax® C-18 ODS packing material [Agilent Technologies, Santa Clara, Calif.], 0.1% trifluoroacetic acid/CH$_3$CN/H$_2$O) to provide the title compound as free base. MS (DCI/NH$_3$) m/z 378 (M+H)$^+$; $^1$H NMR (300 MHz, dimethylsulfoxide-d$_6$): δ 1.56-1.70 (m, 4H), 2.33-2.47

(m, 6H), 3.40 (t, J=7.29 Hz, 2H), 3.72 (t, J=6.44 Hz, 2H), 3.90 (s, 2H), 7.09-7.16 (m, 1H), 7.23 (d, J=8.48 Hz, 1H), 7.25-7.28 (m, 1H), 12.61 (br s, 1H).

Example 306

4-(4-fluoro-3-(2-oxoazetidin-1-yl)benzyl)-5,6,7,8-tetrahydrophthalazin-1(2H)-one

Example 306A 4-fluoro-3-(2-oxoazetidin-1-yl)benzaldehyde

The title compound was prepared according to the procedure for EXAMPLE 300A, substituting azetidin-2-one for 5-methylpyrrolidinone. MS (DCI/NH$_3$) m/z 194 (M+H)$^+$.

Example 306B 4-(4-fluoro-3-(2-oxoazetidin-1-yl)benzyl)-5,6,7,8-tetrahydrophthalazin-1(2H)-one The title compound was prepared according to the procedure for EXAMPLE 300B, substituting EXAMPLE 306A for EXAMPLE 300A. MS (DCI/NH$_3$) m/z 328 (M+H)$^+$. $^1$H NMR (300 MHz, dimethylsulfoxide-d$_6$): δ 1.55-1.68 (m, 4H), 2.31-2.43 (m, 4H), 3.11 (t, J=4.58 Hz, 2H), 3.82 (q, J=4.41 Hz, 2H), 3.86 (s, 2H), 6.86-6.94 (m, 1H), 7.18 (dd, J=11.87, 8.48 Hz, 1H), 7.74 (dd, J=7.63, 2.20 Hz, 1H), 12.60 (br s, 1H).

Example 307

4-(4-fluoro-3-(2-oxopiperidin-1-yl)benzyl)-5,6,7,8-tetrahydrophthalazin-1(2H)-one

Example 307A 4-fluoro-3-(2-oxopiperidin-1-yl)benzaldehyde

The title compound was prepared according to the procedure for EXAMPLE 300A, substituting piperidin-2-one for 5-methylpyrrolidinone. MS (DCI/NH$_3$) m/z 222 (M+H)$^+$.

Example 307B 4-(4-fluoro-3-(2-oxopiperidin-1-yl)benzyl)-5,6,7,8-tetrahydrophthalazin-1(2H)-one The title compound was prepared according to the procedure for EXAMPLE 300B, substituting EXAMPLE 307A for EXAMPLE 300A. MS (DCI/NH$_3$) m/z 356 (M+H)$^+$; $^1$H NMR (300 MHz, dimethylsulfoxide-d$_6$): δ 1.54-1.67 (m, 4H), 1.77-1.93 (m, 4H), 2.31-2.44 (m, 6H), 3.44-3.53 (m, 2H), 3.88 (s, 2H), 7.10-7.14 (m, 1H), 7.15 (d, J=6.35 Hz, 1H), 7.17-7.23 (m, 1H), 12.62 (s, 1H).

Example 308

N-(3-furylmethyl)-3-((4-oxo-3,4,5,6,7,8-hexahydrophthalazin-1-yl)methyl)benzamide

Example 308A methyl 3-((3-oxo-4,5,6,7-tetrahydroisobenzofuran-1(3H)-ylidene)methyl)benzoate A solution of EXAMPLE 1B (25.8 g, 61.5 mmol), methyl-3-formylbenzoate (10.01 g, 61.0 mmol), and triethylamine (8.7 mL, 62.4 mmol) in dichloromethane (125 mL) was stirred at room temperature for 16 hours, and concentrated. The residue was stirred with a mixture of ethyl acetate and water. The precipitated solid was filtered, washed with water, and dried to provide the title compound. MS (DCI/NH$_3$) m/z 285 (M+H)$^+$.

Example 308B 3-((3-oxo-4,5,6,7-tetrahydroisobenzofuran-1(3H)-ylidene)methyl)benzoic acid A solution of EXAMPLE 308A (9.9 g, 35 mmol) in 1:1 mixture of tetrahydrofuran/water (100 mL) was treated with lithium hydroxide monohydrate (2.93 g, 70 mmol) at room temperature for 16 hours. Ethyl acetate was added (100 mL) and the mixture washed with 2M HCl (100 mL). The combined organics were concentrated and dried under vacuum to provide the title compound. MS (DCI/NH$_3$) m/z 271 (M+H)$^+$.

Example 308C 3-((4-oxo-3,4,5,6,7,8-hexahydrophthalazin-1-yl)methyl)benzoic acid A solution of EXAMPLE 308B (9.0 g, 33.33 mmol) in absolute ethanol (120 mL) was heated with hydrazine monohydrate (3.3 mL, 66.66 mmol) at 80° C. for 16 hours. After cooling to room temperature, the precipitated solid was filtered, and dried to provide the title compound. MS (DCI/NH$_3$) m/z 285 (M+H)$^+$.

Example 308D 3-((4-oxo-3,4,5,6,7,8-hexahydrophthalazin-1-yl)methyl)benzoyl chloride A solution of EXAMPLE 308C (2.73 g, 9.6 mmol) in anhydrous tetrahydrofuran (30 mL) was treated with oxalyl chloride (1.3 mL, 14.4 mmol) and a couple of drops of N,N-dimethylformamide at room temperature for 10 minutes and at 50° C. for 1 hour. The reaction mixture was concentrated and dried to provide the title compound. MS (DCI/NH$_3$) m/z 303 (M+H)$^+$.

Example 308E

N-(3-furylmethyl)-3-((4-oxo-3,4,5,6,7,8-hexahydrophthalazin-1-yl)methyl)benzamide A solution of EXAMPLE 308D (19 mg, 0.06 mmol), furan-3-ylmethanamine (0.07 mmol) and triethylamine (14.6 mg, 0.14 mmol) in tetrahydrofuran (1.0 mL) was stirred at room temperature for 16 hours. The reaction mixture was concentrated. The residue was dissolved in 1:1 mixture of dimethylsulfoxide/methanol and purified by HPLC (Waters Sunfire® C-8 analytical column [Milford, Mass.]/0.1% trifluoroacetic acid/water/100% CH$_3$CN) to provide the title compound. MS (DCI/NH$_3$) m/z 363 (M+H)$^+$; $^1$H NMR (500 MHz, D$_2$O/dimethylsulfoxide-d$_6$): δ 1.54-1.69 (m, 4H), 2.32-2.45 (m, 4H), 3.96 (s, 2H), 4.29 (s, 2H), 6.41-6.49 (m, 1H), 7.32-7.37 (m, 1H), 7.41 (t, J=7.63 Hz, 1H), 7.52-7.60 (m, 2H), 7.64-7.72 (m, 2H).

Example 309

3-((4-oxo-3,4,5,6,7,8-hexahydrophthalazin-1-yl)methyl)-N-(thien-2-ylmethyl)benzamide The title compound was prepared according to the procedure for EXAMPLE 308, substituting thiophen-2-ylmethanamine for furan-3-ylmethanamine. MS (DCI/NH$_3$) m/z 380 (M+H)$^+$; $^1$H NMR (500 MHz, D$_2$O/dimethylsulfoxide-d$_6$): δ 1.56-1.70 (m, 4H), 2.32-2.43 (m, 4H), 3.97 (s, 2H), 4.61 (s, 2H), 6.97 (dd, J=5.03, 3.51 Hz, 1H), 7.02 (d, J=2.44 Hz, 1H), 7.34-7.39 (m, 2H), 7.42 (t, J=7.63 Hz, 1H), 7.67 (s, 1H), 7.70 (d, J=7.93 Hz, 1H).

Example 310

3-((4-oxo-3,4,5,6,7,8-hexahydrophthalazin-1-yl)methyl)-N-(thien-3-ylmethyl)benzamide The title compound was prepared according to the procedure for EXAMPLE 308, substituting thiophen-3-ylmethanamine for furan-3-ylmethanamine. MS (DCI/NH$_3$) m/z 380 (M+H)$^+$.

Example 311

3-((4-oxo-3,4,5,6,7,8-hexahydrophthalazin-1-yl)methyl)-N-(pyridin-3-ylmethyl)benzamide The title compound was prepared according to the procedure for EXAMPLE 308, substituting pyridin-3-ylmethanamine for furan-3-ylmethanamine. MS (DCI/NH$_3$) m/z 375 (M+H)$^+$; $^1$H NMR (500 MHz, D$_2$O/dimethylsulfoxide-d$_6$): δ 1.53-1.70 (m, 4H), 2.31-2.45 (m, 4H), 3.98 (s, 2H), 4.61 (s, 2H), 7.37-7.41 (m, 1H), 7.45 (t, J=7.63 Hz, 1H), 7.69 (s, 1H), 7.74 (d, J=7.63 Hz, 1H), 7.91 (dd, J=7.93, 5.49 Hz, 1H), 8.37 (d, J=7.93 Hz, 1H), 8.72 (d, J=5.19 Hz, 1H), 8.78 (s, 1H).

Example 312

3-((4-oxo-3,4,5,6,7,8-hexahydrophthalazin-1-yl)methyl)-N-(pyridin-4-ylmethyl)benzamide The title compound was prepared according to the procedure for EXAMPLE 308, substituting pyridin-4-ylmethanamine for furan-3-ylmethanamine. MS (DCI/NH$_3$) m/z 375 (M+H)$^+$.

Example 313

N-(2-(dimethylamino)ethyl)-3-((4-oxo-3,4,5,6,7,8-hexahydrophthalazin-1-yl)methyl)benzamide The title compound was prepared according to the procedure for EXAMPLE 308, substituting N$^1$,N$^1$-dimethylethane-1,2-diamine for furan-3-ylmethanamine. MS (DCI/NH$_3$) m/z 355 (M+H)$^+$; $^1$H NMR (500 MHz, D$_2$O/dimethylsulfoxide-d$_6$): δ 1.56-1.66 (m, 4H), 2.33-2.44 (m, 4H), 2.84 (s, 6H), 3.26 (t, J=5.95 Hz, 2H), 3.60 (t, J=5.95 Hz, 2H), 3.98 (s, 2H), 7.38-7.41 (m, 1H), 7.45 (t, J=7.63 Hz, 1H), 7.67 (s, 1H), 7.71 (d, J=7.93 Hz, 1H).

Example 314

N-(3-(dimethylamino)propyl)-3-((4-oxo-3,4,5,6,7,8-hexahydrophthalazin-1-yl)methyl)benzamide The title compound was prepared according to the procedure for EXAMPLE 308, substituting N$^1$,N$^1$-dimethylpropane-1,3-diamine for furan-3-ylmethanamine. MS (DCI/NH$_3$) m/z 369 (M+H)$^+$.

Example 315

3-((4-oxo-3,4,5,6,7,8-hexahydrophthalazin-1-yl)methyl)-N-(3-pyrrolidin-1-ylpropyl)benzamide The title compound was prepared according to the procedure for EXAMPLE 308, substituting 3-(pyrrolidin-1-yl)propan-1-amine for furan-3-ylmethanamine. MS (DCI/NH$_3$) m/z 395 (M+H)$^+$.

Example 316

3-((4-oxo-3,4,5,6,7,8-hexahydrophthalazin-1-yl)methyl)-N-(3-piperidin-1-ylpropyl)benzamide The title compound was prepared according to the procedure for EXAMPLE 308, substituting 3-(piperidin-1-yl)propan-1-amine for furan-3-ylmethanamine. MS (DCI/NH$_3$) m/z 409 (M+H)$^+$.

Example 317

N-(3-morpholin-4-ylpropyl)-3-((4-oxo-3,4,5,6,7,8-hexahydrophthalazin-1-yl)methyl)benzamide The title compound was prepared according to the procedure for EXAMPLE 308, substituting 3-morpholinopropan-1-amine for furan-3-ylmethanamine. MS (DCI/NH$_3$) m/z 411 (M+H)$^+$; $^1$H NMR (500 MHz, D$_2$O/dimethylsulfoxide-d$_6$): δ 1.56-1.68 (m, 4H), 1.87-1.97 (m, 2H), 2.31-2.45 (m, 4H), 3.08 (t, J=12.05 Hz, 2H), 3.11-3.17 (m, 2H), 3.33 (t, J=6.71 Hz, 2H), 3.42 (d, J=12.51 Hz, 2H), 3.65 (t, J=12.05 Hz, 2H), 3.96-4.02 (m, 2H), 3.97 (s, 2H), 7.35-7.39 (m, 1H), 7.43 (t, J=7.63 Hz, 1H), 7.65 (s, 1H), 7.69 (d, J=7.93 Hz, 1H).

Example 318

N-(2-(1H-indol-3-yl)ethyl)-3-((4-oxo-3,4,5,6,7,8-hexahydrophthalazin-1-yl)methyl)benzamide The title compound was prepared according to the procedure for EXAMPLE 308, substituting 2-(1H-indol-3-yl)ethanamine for furan-3-ylmethanamine. MS (DCI/NH$_3$) m/z 427 (M+H)$^+$.

Example 319

3-((4-oxo-3,4,5,6,7,8-hexahydrophthalazin-1-yl)methyl)-N-1,3-thiazol-2-ylbenzamide The title compound was prepared according to the procedure for EXAMPLE 308, substituting thiazol-2-amine for furan-3-ylmethanamine. MS (DCI/NH$_3$) m/z 367 (M+H)$^+$; $^1$H NMR (500 MHz, D$_2$O/dimethylsulfoxide-d$_6$): δ 1.59-1.68 (m, 4H), 2.35-2.46 (m, 4H), 4.01 (s, 2H), 7.28 (d, J=3.66 Hz, 1H), 7.45-7.48 (m, 1H), 7.50 (t, J=7.48 Hz, 1H), 7.56 (d, J=3.66 Hz, 1H), 7.87 (s, 1H), 7.93 (d, J=7.63 Hz, 1H).

Example 320 benzyl 2-oxo-2-(3-(2-(4-oxo-3,4,5,6,7,8-hexahydrophthalazin-1-yl)ethyl)phenylamino)ethylcarbamate The title compound was prepared according to the procedure for EXAMPLE 294, substituting 2-(benzyloxycarbonylamino)acetic acid for 4-oxo-4-phenylbutanoic acid. MS (DCI/NH$_3$) m/z 461 (M+H)$^+$.

Example 321

4-oxo-N-(3-(2-(4-oxo-3,4,5,6,7,8-hexahydrophthalazin-1-yl)ethyl)phenyl)-4-(4-phenoxyphenyl) butanamide The title compound was prepared according to the procedure for EXAMPLE 294, substituting 4-oxo-4-(4-phenoxyphenyl)butanoic acid for 4-oxo-4-phenylbutanoic acid. MS (DCI/NH$_3$) m/z 522 (M+H)$^+$.

Example 322 benzyl 3-(((3-(2-(4-oxo-3,4,5,6,7,8-hexahydrophthalazin-1-yl)ethyl)phenyl)amino)carbonyl)piperidine-1-carboxylate The title compound was prepared according to the procedure for EXAMPLE 294, substituting 1-(benzyloxycarbonyl)piperidine-3-carboxylic acid for 4-oxo-4-phenylbutanoic acid. MS (DCI/NH$_3$) m/z 515 (M+H)$^+$.

Example 323

2-(4-methylphenoxy)-N-(3-(2-(4-oxo-3,4,5,6,7,8-hexahydrophthalazin-1-yl)ethyl)phenyl)acetamide The title compound was prepared according to the procedure for EXAMPLE 294, substituting 2-(p-tolyloxy)acetic acid for 4-oxo-4-phenylbutanoic acid. MS (DCI/NH$_3$) m/z 418 (M+H)$^+$.

Example 324

2-(4-methoxyphenoxy)-N-(3-(2-(4-oxo-3,4,5,6,7,8-hexahydrophthalazin-1-yl)ethyl)phenyl)acetamide The title compound was prepared according to the procedure for EXAMPLE 294, substituting 2-(4-methoxyphenoxy)acetic acid for 4-oxo-4-phenylbutanoic acid. MS (DCI/NH$_3$) m/z 434 (M+H)$^+$.

Example 325

4-(4-fluoro-3-(3-methyl-2-oxoimidazolidin-1-yl)benzyl)-5,6,7,8-tetrahydrophthalazin-1(2H)-one

Example 325A 4-fluoro-3-(3-methyl-2-oxoimidazolidin-1-yl)benzaldehyde

The title compound was prepared according to the procedure for EXAMPLE 300A, substituting 1-methylimidazolidin-2-one for 5-methylpyrrolidinone. MS (DCI/NH$_3$) m/z 223 (M+H)$^+$.

Example 325B 4-(4-fluoro-3-(3-methyl-2-oxoimidazolidin-1-yl)benzyl)-5,6,7,8-tetrahydrophthalazin-1(2H)-one The title compound was prepared according to the procedure for EXAMPLE 300B, substituting EXAMPLE 325A for EXAMPLE 300A. MS (DCI/H$_3$) m/z 357 (M+H)$^+$; $^1$H NMR (300 MHz, DMSO-d$_6$): δ 1.54-1.69 (m, 4H), 2.32-2.43 (m, 4H), 2.74 (s, 3H), 3.39-3.44 (m, 2H), 3.67-3.76 (m, 2H), 3.86 (s, 2H), 6.97-7.05 (m, 1H), 7.17 (dd, J=1.19, 8.48 Hz, 1H), 7.31 (dd, J=7.63, 2.20 Hz, 1H), 12.60 (s, 1H).

Example 326

4-(4-fluoro-3-(2-oxotetrahydropyrimidin-1(2H)-yl)benzyl)-5,6,7,8-tetrahydrophthalazin-1(2H)-one

Example 326A 4-fluoro-3-(2-oxotetrahydropyrimidin-1(2H)-yl)benzaldehyde

The title compound was prepared according to the procedure for EXAMPLE 300A, substituting tetrahydropyrimidin-2(1H)-one for 5-methylpyrrolidinone. MS (DCI/NH$_3$) m/z 223 (M+H)$^+$.

Example 326B 4-(4-fluoro-3-(2-oxotetrahydropyrimidin-1(2H)-yl)benzyl)-5,6,7,8-tetrahydrophthalazin-1(2H)-one The title compound was prepared according to the procedure for EXAMPLE 300B, substituting EXAMPLE 326A for EXAMPLE 300A. MS (DCI/NH$_3$) m/z 357 (M+H)$^+$; $^1$H NMR (300 MHz, DMSO-d$_6$): δ 1.57-1.68 (m, 4H), 1.87-2.00 (m, 2H), 2.33-2.43 (m, 4H), 3.23 (t, J=5.76 Hz, 2H), 3.44-3.52 (m, 2H), 3.86 (s, 2H), 6.60 (s, 1H), 7.00-7.07 (m, 1H), 7.09-7.18 (m, 2H), 12.61 (s, 1H).

Example 327

4-(3-(3-tert-butyl-2-oxoimidazolidin-1-yl)-4-fluorobenzyl)-5,6,7,8-tetrahydrophthalazin-1(2H)-one

Example 327A 3-(3-tert-butyl-2-oxoimidazolidin-1-yl)-4-fluorobenzaldehyde

The title compound was prepared according to the procedure for EXAMPLE 300A, substituting 1-tert-butylimidazolidin-2-one for 5-methylpyrrolidinone. MS (DCI/NH$_3$) m/z 265 (M+H)$^+$.

Example 327B 4-(3-(3-tert-butyl-2-oxoimidazolidin-1-yl)-4-fluorobenzyl)-5,6,7,8-tetrahydrophthalazin-1(2H)-one The title compound was prepared according to the procedure for EXAMPLE 300B, substituting EXAMPLE 327A for EXAMPLE 300A. MS (DCI/NH$_3$) m/z 399 (M+H)$^+$; $^1$H NMR (300 MHz, DMSO-d$_6$): δ 1.3 (s, 9H), 1.53-1.68 (m, 4H), 2.31-2.45 (m, 4H), 3.43-3.48 (m, 2H), 3.58-3.69 (m, 2H), 3.86 (s, 2H), 6.95-7.02 (m, 1H), 7.15 (dd, J=11.36, 8.31 Hz, 1H), 7.28 (dd, J=7.46, 2.03 Hz, 1H), 12.59 (s, 1H).

Example 328

4-(4-fluoro-3-((1S,4R)-3-oxo-2-azabicyclo(2.2.1)hept-2-yl)benzyl)-5,6,7,8-tetrahydrophthalazin-1(2H)-one

Example 328A 4-fluoro-3-((1S,4R)-3-oxo-2-azabicyclo(2.2.1)heptan-2-yl)benzaldehyde The title compound was prepared according to the procedure for EXAMPLE 300A, substituting (1S,4R)-2-azabicyclo(2.2.1)heptan-3-one for 5-methylpyrrolidinone. MS (DCI/NH$_3$) m/z 234 (M+H)$^+$.

Example 328B 4-(4-fluoro-3-((1S,4R)-3-oxo-2-azabicyclo(2.2.1)hept-2-yl)benzyl)-5,6,7,8-tetrahydrophthalazin-1(2H)-one The title compound was prepared according to the procedure for EXAMPLE 300B, substituting EXAMPLE 328A for EXAMPLE 300A. MS (DCI/NH$_3$) m/z 368 (M+H)$^+$; $^1$H NMR (300 MHz, DMSO-d$_6$): δ 1.49-1.56 (m, 2H), 1.57-1.65 (m, 4H), 1.69-1.76 (m, 1H), 1.79-1.86 (m, 1H), 1.89-1.96 (m, 1H), 1.97-2.03 (m, 1H), 2.32-2.45 (m, 4H), 2.74-2.82 (m, 1H), 3.87 (s, 2H), 4.25 (s, 1H), 7.01-7.08 (m, 1H), 7.16-7.23 (m, 1H), 7.23-7.28 (m, 1H), 12.59 (br s, 1H).

Example 329

N-(2-ethylphenyl)-3-((4-oxo-3,4,5,6,7,8-hexahydrophthalazin-1-yl)methyl)benzamide The title compound was prepared according to the procedure for EXAMPLE 308, substituting 2-ethylaniline for furan-3-ylmethanamine. MS (DCI/NH$_3$) m/z 388 (M+H)$^+$.

Example 330

N-(3-ethylphenyl)-3-((4-oxo-3,4,5,6,7,8-hexahydrophthalazin-1-yl)methyl)benzamide The title compound was prepared according to the procedure for EXAMPLE 308, substituting 3-ethylaniline for furan-3-ylmethanamine. MS (DCI/NH$_3$) m/z 388 (M+H)$^+$.

Example 331

N-(4-ethylphenyl)-3-((4-oxo-3,4,5,67,8-hexahydrophthalazin-1-yl)methyl)benzamide The title compound was prepared according to the procedure for EXAMPLE 308, substituting 4-ethylaniline for furan-3-ylmethanamine. MS (DCI/NH$_3$) m/z 388 (M+H)$^+$.

Example 332

3-((4-oxo-3,4,5,6,7,8-hexahydrophthalazin-1-yl)methyl)-N-(2-propylphenyl)benzamide The title compound was prepared according to the procedure for EXAMPLE 308, substituting 2-propylaniline for furan-3-ylmethanamine. MS (DCI/NH$_3$) m/z 402 (M+H)$^+$.

Example 333

N-(2-isopropylphenyl)-3-((4-oxo-3,4,5,6,7,8-hexahydrophthalazin-1-yl)methyl)benzamide The title compound was prepared according to the procedure for EXAMPLE 308, substituting 2-isopropylaniline for furan-3-ylmethanamine. MS (DCI/NH$_3$) m/z 402 (M+H)$^+$.

Example 334

N-(4-isopropylphenyl)-3-((4-oxo-3,4,5,6,7,8-hexahydrophthalazin-1-yl)methyl)benzamide The title compound was prepared according to the procedure for EXAMPLE 308, substituting 4-isopropylaniline for furan-3-ylmethanamine. MS (DCI/NH$_3$) m/z 402 (M+H)$^+$; $^1$H NMR (500 MHz, D$_2$O/DMSO-d$_6$): δ 1.20 (d, J=7.02 Hz, 6H), 1.55-1.72 (m, 4H), 2.34-2.47 (m, 4H), 2.82-2.96 (m, 1H), 4.01 (s, 2H), 7.23 (d, J=8.24 Hz, 2H), 7.39 (d, J=7.63 Hz, 1H), 7.47 (t, J=7.63 Hz, 1H), 7.63 (d, J=8.54 Hz, 2H), 7.74 (s, 1H), 7.80 (d, J=7.93 Hz, 1H).

Example 335

N-(3-tert-butylphenyl)-3-((4-oxo-3,4,5,6,7,8-hexahydrophthalazin-1-yl)methyl)benzamide The title compound was prepared according to the procedure for EXAMPLE 308, substituting 3-tert-butylaniline for furan-3-ylmethanamine. MS (DCI/NH$_3$) m/z 416 (M+H)$^+$.

Example 336

N-(4-tert-butylphenyl)-3-((4-oxo-3,4,5,6,7,8-hexahydrophthalazin-1-yl)methyl)benzamide The title compound was prepared according to the procedure for EXAMPLE 308, substituting 4-tert-butylaniline for furan-3-ylmethanamine. MS (DCI/NH$_3$) m/z 416 (M+H)$^+$.

Example 337

N-1,1'-biphenyl-4-yl-3-((4-oxo-3,4,5,6,7,8-hexahydrophthalazin-1-yl)methyl)benzamide The title compound was prepared according to the procedure for EXAMPLE 308, substituting biphenyl-4-amine for furan-3-ylmethanamine. MS (DCI/NH$_3$) m/z 436 (M+H)$^+$; $^1$H NMR (500 MHz, D$_2$O/DMSO-d$_6$): δ 1.57-1.70 (m, 4H), 2.34-2.48 (m, 4H), 4.02 (s, 2H), 7.36 (t, J=7.32 Hz, 1H), 7.42

(d, J=7.93 Hz, 1H), 7.45-7.48 (m, 2H), 7.49-7.52 (m, 1H), 7.66-7.71 (m, 4H), 7.78 (s, 1H), 7.81-7.87 (m, 3H).

Example 338

N-(2-fluoro-4-methylphenyl)-3-((4-oxo-3,4,5,6,7,8-hexahydrophthalazin-1-yl)methyl)benzamide The title compound was prepared according to the procedure for EXAMPLE 308, substituting 2-fluoro-4-methylaniline for furan-3-ylmethanamine. MS (DCI/NH$_3$) m/z 392 (M+H)$^+$.

Example 339

N-(3-fluoro-4-methylphenyl)-3-((4-oxo-3,4,5,6,7,8-hexahydrophthalazin-1-yl)methyl)benzamide The title compound was prepared according to the procedure for EXAMPLE 308, substituting 3-fluoro-4-methylaniline for furan-3-ylmethanamine. MS (DCI/NH$_3$) m/z 392 (M+H)$^+$.

Example 340

N-(4-fluoro-2-methylphenyl)-3-((4-oxo-3,4,5,6,7,8-hexahydrophthalazin-1-yl)methyl)benzamide The title compound was prepared according to the procedure for EXAMPLE 308, substituting 4-fluoro-2-methylaniline for furan-3-ylmethanamine. MS (DCI/NH$_3$) m z 392 (M+H)$^+$.

Example 341

N-(4-fluoro-3-methylphenyl)-3-((4-oxo-3,4,5,6,7,8-hexahydrophthalazin-1-yl)methyl)benzamide The title compound was prepared according to the procedure for EXAMPLE 308, substituting 4-fluoro-3-methylaniline for furan-3-ylmethanamine. MS (DCI/NH$_3$) m/z 392 (M+H)$^+$.

Example 342

N-(3-chloro-4-methylphenyl)-3-((4-oxo-3,4,5,6,7,8-hexahydrophthalazin-1-yl)methyl)benzamide The title compound was prepared according to the procedure for EXAMPLE 308, substituting 3-chloro-4-methylaniline for furan-3-ylmethanamine. MS (DCI/NH$_3$) m/z 408 (M+H)$^+$.

Example 343

N-(4-chloro-3-methylphenyl)-3-((4-oxo-3,4,5,6,7,8-hexahydrophthalazin-1-yl)methyl)benzamide The title compound was prepared according to the procedure for EXAMPLE 308, substituting 4-chloro-3-methylaniline for furan-3-ylmethanamine. MS (DCI/NH$_3$) m/z 408 (M+H)$^+$.

Example 344

N-(3-bromo-4-methylphenyl)-3-((4-oxo-3,4,5,6,7,8-hexahydrophthalazin-1-yl)methyl)benzamide The title compound was prepared according to the procedure for EXAMPLE 308, substituting 3-bromo-4-methylaniline for furan-3-ylmethanamine. MS (DCI/NH$_3$) m/z 452 (M+H)$^+$.

Example 345

N-(4-bromo-3-methylphenyl)-3-((4-oxo-3,4,5,6,7,8-hexahydrophthalazin-1-yl)methyl)benzamide The title compound was prepared according to the procedure for EXAMPLE 308, substituting 4-bromo-3-methylaniline for furan-3-ylmethanamine. MS (DCI/NH$_3$) m/z 452 (M+H)$^+$.

Example 346

N-(3-fluoro-4-methoxyphenyl)-3-((4-oxo-3,4,5,6,7,8-hexahydrophthalazin-1-yl)methyl)benzamide The title compound was prepared according to the procedure for EXAMPLE 308, substituting 3-fluoro-4-methoxyaniline for furan-3-ylmethanamine. MS (DCI/NH$_3$) m/z 408 (M+H)$^+$; $^1$H NMR (500 MHz, D$_2$O/DMSO-d$_6$): δ 1.55-1.69 (m, 4H), 2.33-2.49 (m, 4H), 3.83 (s, 3H), 4.01 (s, 2H), 7.16 (t, J=9.31 Hz, 1H), 7.40 (d, J=7.93 Hz, 1H), 7.44-7.50 (m, 2H), 7.69 (dd, J=13.58, 2.59 Hz, 1H), 7.73 (s, 1H), 7.79 (d, J=7.93 Hz, 1H).

Example 347

N-(3-methoxy-5-(trifluoromethyl)phenyl)-3-((4-oxo-3,4,5,6,7,8-hexahydrophthalazin-1-yl)methyl)benzamide The title compound was prepared according to the procedure for EXAMPLE 308, substituting 3-methoxy-5-(trifluoromethyl)aniline for furan-3-ylmethanamine. MS (DCI/NH$_3$) m/z 458 (M+H)$^+$.

Example 348

N-(2-hydroxy-6-methylphenyl)-3-((4-oxo-3,4,5,6,7,8-hexahydrophthalazin-1-yl)methyl)benzamide The title compound was prepared according to the procedure for EXAMPLE 308, substituting 2-amino-3-methylphenol for furan-3-ylmethanamine. MS (DCI/NH$_3$) m/z 390 (M+H)$^+$.

Example 349

N-(3-hydroxy-2-methylphenyl)-3-((4-oxo-3,4,5,6,7,8-hexahydrophthalazin-1-yl)methyl)benzamide The title compound was prepared according to the procedure for EXAMPLE 308, substituting 3-amino-2-methylphenol for furan-3-ylmethanamine. MS (DCI/NH$_3$) m/z 390 (M+H)$^+$.

Example 350

N-(3-hydroxy-4-methylphenyl)-3-((4-oxo-3,4,5,6,7,8-hexahydrophthalazin-1-yl)methyl)benzamide The title compound was prepared according to the procedure for EXAMPLE 308, substituting 2-amino-5-methylphenol for furan-3-ylmethanamine. MS (DCI/NH$_3$) m/z 390 (M+H)$^+$.

Example 351

N-(2-methoxy-5-methylphenyl)-3-((4-oxo-3,4,5,6,7,8-hexahydrophthalazin-1-yl)methyl)benzamide The title compound was prepared according to the procedure for EXAMPLE 308, substituting 2-methoxy-5-methylaniline for furan-3-ylmethanamine. MS (DCI/NH$_3$) m/z 404 (M+H)$^+$.

Example 352

N-(3-methoxy-4-methylphenyl)-3-((4-oxo-3,4,5,6,7,8-hexahydrophthalazin-1-yl)methyl)benzamide The title compound was prepared according to the procedure for EXAMPLE 308, substituting 5-methoxy-2-methylaniline for furan-3-ylmethanamine. MS (DCI/NH$_3$) m/z 404 (M+H)$^+$.

Example 353

N-(3-hydroxy-4-methoxyphenyl)-3-((4-oxo-3,4,5,6,7,8-hexahydrophthalazin-1-yl)methyl)benzamide The title compound was prepared according to the procedure for EXAMPLE 308, substituting 5-amino-2-methoxyphenol for furan-3-ylmethanamine. MS (DCI/NH$_3$) m/z 406 (M+H)$^+$.

Example 354

N-(2-ethoxyphenyl)-3-((4-oxo-3,4,5,6,7,8-hexahydrophthalazin-1-yl)methyl)benzamide The title compound was prepared according to the procedure for EXAMPLE 308, substituting 2-ethoxyaniline for furan-3-ylmethanamine. MS (DCI/NH$_3$) m/z 404 (M+H)$^+$.

Example 355

3-((4-oxo-3,4,5,6,7,8-hexahydrophthalazin-1-yl)methyl)-N-(4-propoxyphenyl)benzamide The title compound was prepared according to the procedure for EXAMPLE 308, substituting 4-propoxyaniline for furan-3-ylmethanamine. MS (DCI/NH$_3$) m/z 418 (M+H)$^+$.

Example 356

N-(5-tert-butyl-2-methoxyphenyl)-3-((4-oxo-3,4,5,6,7,8-hexahydrophthalazin-1-yl)methyl)benzamide The title compound was prepared according to the procedure for EXAMPLE 308, substituting 5-tert-butyl-2-methoxyaniline for furan-3-ylmethanamine. MS (DCI/NH$_3$) m/z 446 (M+H)$^+$.

Example 357

N-(5-(acetylamino)-2-methoxyphenyl)-3-((4-oxo-3,4,5,6,7,8-hexahydrophthalazin-1-yl)methyl)benzamide The title compound was prepared according to the procedure for EXAMPLE 308, substituting N-(3-amino-4-methoxyphenyl)acetamide for furan-3-ylmethanamine. MS (DCI/NH$_3$) m/z 447 (M+H)$^+$.

Example 358

N-2,3-dihydro-1,4-benzodioxin-6-yl-3-((4-oxo-3,4,5,6,7,8-hexahydrophthalazin-1-yl)methyl)benzamide The title compound was prepared according to the procedure for EXAMPLE 308, substituting 2,3-dihydrobenzo(b)(1,4)dioxin-6-amine for furan-3-ylmethanamine. MS (DCI/NH$_3$) m/z 418 (M+H)$^+$; $^1$H NMR (500 MHz, D$_2$O/DMSO-d$_6$): δ 1.56-1.68 (m, 4H), 2.34-2.48 (m, 4H), 4.00 (s, 2H), 4.15-4.32 (m, 4H), 6.84 (d, J=8.85 Hz, 1H), 7.16 (dd, J=8.85, 2.44 Hz, 1H), 7.34 (d, J=2.44 Hz, 1H), 7.38 (d, J=7.93 Hz, 1H), 7.46 (t, J=7.63 Hz, 1H), 7.72 (s, 1H), 7.77 (d, J=7.63 Hz, 1H).

Example 359

N-(5-chloro-2,4-dimethoxyphenyl)-3-((4-oxo-3,4,5,6,7,8-hexahydrophthalazin-1-yl)methyl)benzamide The title compound was prepared according to the procedure for EXAMPLE 308, substituting 5-chloro-2,4-dimethoxyaniline for furan-3-ylmethanamine. MS (DCI/NH$_3$) m/z 454 (M+H)$^+$.

Example 360

N-(3-(methylthio)phenyl)-3-((4-oxo-3,4,5,6,7,8-hexahydrophthalazin-1-yl)methyl)benzamide The title compound was prepared according to the procedure for EXAMPLE 308, substituting 3-(methylthio)aniline for furan-3-ylmethanamine. MS (DCI/NH$_3$) m/z 406 (M+H)$^+$.

Example 361

N-(4-(methylthio)phenyl)-3-((4-oxo-3,4,5,6,7,8-hexahydrophthalazin-1-yl)methyl)benzamide The title compound was prepared according to the procedure for EXAMPLE 308, substituting 4-(methylthio)aniline for furan-3-ylmethanamine. MS (DCI/NH$_3$) m/z 406 (M+H)$^+$.

Example 362

3-((4-oxo-3,4,5,6,7,8-hexahydrophthalazin-1-yl)methyl)-N-(4-piperidin-1-ylphenyl)benzamide The title compound was prepared according to the procedure for EXAMPLE 308, substituting 4-(piperidin-1-yl)aniline for furan-3-ylmethanamine. MS (DCI/NH$_3$) m/z 443 (M+H)$^+$.

Example 363

N-(4-morpholin-4-ylphenyl)-3-((4-oxo-3,4,5,6,7,8-hexahydrophthalazin-1-yl)methyl)benzamide The title compound was prepared according to the procedure for EXAMPLE 308, substituting 4-morpholinoaniline for furan-3-ylmethanamine. MS (DCI/NH$_3$) m/z 445 (M+H)$^+$; $^1$H NMR (500 MHz, D$_2$O/DMSO-d$_6$): δ 1.57-1.68 (m, 4H), 2.34-2.46 (m, 4H), 3.15-3.23 (m, 4H), 3.79-3.82 (m, 4H), 4.01 (s, 2H), 7.10 (d, J=9.15 Hz, 2H), 7.39 (d, J=7.63 Hz, 1H), 7.45-7.50 (m, 1H), 7.66 (d, J=9.15 Hz, 2H), 7.72-7.77 (m, 1H), 7.80 (d, J=7.93 Hz, 1H).

Example 364

N-(2-anilinophenyl)-3-((4-oxo-3,4,5,6,7,8-hexahydrophthalazin-1-yl)methyl)benzamide The title compound was prepared according to the procedure for EXAMPLE 308, substituting N$^1$-phenylbenzene-1,2-diamine for furan-3-ylmethanamine. MS (DCI/NH$_3$) m/z 451 (M+H)$^+$; $^1$H NMR (500 MHz, D$_2$O/DMSO-d$_6$): δ 1.54-1.69 (m, 4H), 2.31-2.44 (m, 4H), 3.95 (s, 2H), 6.78 (t, J=7.32 Hz, 1H), 6.86 (d, J=7.63 Hz, 2H), 7.02-7.09 (m, 1H), 7.15-7.23 (m, 3H), 7.28-7.32 (m, 1H), 7.35-7.39 (m, 1H), 7.42 (t, J=7.63 Hz, 1H), 7.59 (d, J=7.32 Hz, 1H), 7.63 (s, 1H), 7.69 (d, J=7.63 Hz, 1H).

Example 365

N-(4-((4-methoxyphenyl)amino)phenyl)-3-((4-oxo-3,4,5,6,7,8-hexahydrophthalazin-1-yl)methyl)benzamide The title compound was prepared according to the procedure for EXAMPLE 308, substituting N$^1$-(4-methoxyphenyl)benzene-1,2-diamine for furan-3-ylmethanamine. MS (DCI/NH$_4$) m/z 481 (M+H)$^+$.

Example 366

3-((4-oxo-3,4,5,6,7,8-hexahydrophthalazin-1-yl)methyl)-N-quinolin-6-ylbenzamide

The title compound was prepared according to the procedure for EXAMPLE 308, substituting quinolin-7-amine for furan-3-ylmethanamine. MS (DCI/NH$_3$) m/z 411 (M+H)$^+$; $^1$H NMR (500 MHz, D$_2$O/DMSO-d$_6$): δ 1.57-1.72 (m, 4H), 2.36-2.49 (m, 4H), 4.04 (s, 2H), 7.44-7.50 (m, 1H), 7.54 (t, J=7.63 Hz, 1H), 7.82 (s, 1H), 7.88 (dd, J=8.24, 5.19 Hz, 2H), 8.19 (d, J=9.15 Hz, 1H), 8.27 (dd, J=9.15, 2.14 Hz, 1H), 8.74 (d, J=2.44 Hz, 1H), 8.88 (d, J=7.93 Hz, 1H), 9.04 (d, J=4.88 Hz, 1H).

Example 367

N-(5-hydroxy-1-naphthyl)-3-((4-oxo-3,4,5,6,7,8-hexahydrophthalazin-1-yl)methyl)benzamide The title compound was prepared according to the procedure for EXAMPLE 308, substituting 5-aminonaphthalen-1-ol for furan-3-ylmethanamine. MS (DCI/NH$_3$) m/z 426 (M+H)$^+$.

Example 368

N-1H-indazol-6-yl-3-((4-oxo-3,4,5,6,7,8-hexahydrophthalazin-1-yl)methyl)benzamide The title compound was prepared according to the procedure for EXAMPLE 308, substituting 1H-indazol-6-amine for furan-3-ylmethanamine. MS (DCI/NH$_3$) m/z 400 (M+H)$^+$.

Example 369

8-(4-fluorobenzyl)pyrido(3,2-d)pyridazin-5(6H)-one

Example 369A methyl 2-(2-(4-fluorophenyl)acetyl)nicotinate

To a solution of dimethylpyridine-2,3-dicarboxylate (1.0 g, 5.1 mmol) in tetrahydrofuran (50 ml) was added (4-fluorobenzyl)magnesium chloride (0.25 M in tetrahydrofuran, 20 ml, 5.1 mmol) through a syringe at −78° C. The reaction mixture was stirred at the same temperature for 30 minutes and was quenched with addition of water. After warming up to room temperature, the reaction mixture was partitioned between ethyl acetate and brine. The organic phase was washed with brine and concentrated. The residue was purified by flash chromatography (15% ethyl acetate in hexane) to give the title compound. MS (DCI/NH$_3$) m/z 274 (M+H)$^+$.

Example 369B 8-(4-fluorobenzyl)pyrido(3,2-d)pyridazin-5(6H)-one

A solution of EXAMPLE 369A (0.46 g, 1.68 mmol) in ethanol (20 ml) was treated with hydrazine (108 mg, 3.37 mmol) at room temperature for 5 hours. The reaction mixture was concentrated to about 5 mL. The solid was collected by filtration, washed with ethanol and dried to provide the title compound. MS (DCI/NH$_3$) m/z 256 (M+H)$^+$.

Example 370

8-(3-chloro-4-fluorobenzyl)pyrido(3,2-d)pyridazin-5(6H)-one

Example 370A methyl 2-(2-(3-chloro-4-fluorophenyl)acetyl)nicotinate

The title compound was prepared according to the procedure for EXAMPLE 369A, substituting (2-chloro-4-fluorobenzyl)magnesium chloride for (4-fluorobenzyl)magnesium chloride. MS (DCI/NH$_3$) m/z 308 (M+H)$^+$.

Example 370B 8-(3-chloro-4-fluorobenzyl)pyrido(3,2-d)pyridazin-5(6H)-one

The title compound was prepared according to the procedure for EXAMPLE 369B, substituting EXAMPLE 370A for EXAMPLE 369A. MS (DCI/NH$_3$) m/z 290 (M+H)$^+$.

Example 371

(3aR)-8-((4-oxo-3,4,5,6,7,8-hexahydrophthalazin-1-yl)methyl)-2,3,3a,4-tetrahydro-1H-pyrrolo(2,1-d)(1,4)benzoxazin-1-one

Example 371A (R)-1-oxo-2,3,3a,4-tetrahydro-1H-benzo(b)pyrrolo(1,2-d)(1,4)oxazine-8-carbaldehyde The title compound was prepared according to the procedure for EXAMPLE 300A, substituting (R)-5-(hydroxymethyl)pyrrolidin-2-one for 5-methylpyrrolidinone. MS (DCI/NH$_3$) m/z 232 (M+H)$^+$.

Example 371B (3aR)-8-((4-oxo-3,4,5,6,7,8-hexahydrophthalazin-1-yl)methyl)-2,3,3a,4-tetrahydro-1H-pyrrolo(2,1-c)(1,4)benzoxazin-1-one The title compound was prepared according to the procedure for EXAMPLE 300B, substituting EXAMPLE 371A for EXAMPLE 300A. MS (DCI/NH$_3$) m/z 352 (M+H)$^+$; $^1$H NMR (300 MHz, DMSO-d$_6$): δ 1.54-1.63 (m, 4H), 1.64-1.72 (m, 1H), 2.13-2.22 (m, 1H), 2.23-2.31 (m, 1H), 2.33-2.44 (m, 4H), 2.54-2.64 (m, 1H), 3.72 (t, J=10.17 Hz, 1H), 3.78-3.84 (m, 2H), 3.91-4.05 (m, 1H), 4.48 (dd, J=10.51, 3.05 Hz, 1H), 6.77-6.82 (m, 1H), 6.84-6.89 (m, 1H), 8.26 (d, J=2.03 Hz, 1H), 12.58 (br s, 1H).

Example 372

N-(2-fluoro-5-((4-oxo-3,4,5,6,7,8-hexahydrophthalazin-1-yl)methyl)phenyl)-N-methylmethanesulfonamide

Example 372A

N-(2-fluoro-5-formylphenyl)-N-methylmethanesulfonamide

The title compound was prepared according to the procedure for EXAMPLE 300A, substituting N-methylmethanesulfonamide for 5-methylpyrrolidinone. MS (DCI/NH$_3$) m/z 232 (M+H)$^+$.

Example 372B

N-(2-fluoro-5-((4-oxo-3,4,5,6,7,8-hexahydrophthalazin-1-yl)methyl)phenyl)-N-methylmethanesulfonamide The title compound was prepared according to the procedure for EXAMPLE 300B, substituting EXAMPLE 372A for EXAMPLE 300A. MS (DCI/NH$_3$) m/z 366 (M+H)$^+$; $^1$H NMR (300 MHz, DMSO-d$_6$): δ 1.57-1.71 (m, 4H), 2.34-2.47 (m, 4H), 3.13 (s, 6H), 3.93 (s, 2H), 7.25 (dd, J=8.33, 1.98 Hz, 1H), 7.51 (d, J=7.93 Hz, 1H), 7.58 (d, J=1.98 Hz, 1H), 12.62 (br s, 1H).

Example 373

N-(2-fluoro-5-((4-oxo-3,4,5,6,7,8-hexahydrophthalazin-1-yl)methyl)phenyl)-2-hydroxy-2-methylpropanamide

Example 373A

N-(2-fluoro-5-formylphenyl)-2-hydroxy-2-methylpropanamide

The title compound was prepared according to the procedure for EXAMPLE 300A, substituting 5,5-dimethyloxazolidine-2,4-dione for 5-methylpyrrolidinone. MS (DCI/NH$_3$) m/z 226 (M+H)$^+$.

Example 373B

N-(2-fluoro-5-((4-oxo-3,4,5,6,7,8-hexahydrophthalazin-1-yl)methyl)phenyl)-2-hydroxy-2-methylpropanamide The title compound was prepared according to the procedure for EXAMPLE 300B, substituting EXAMPLE 373A for EXAMPLE 300A. MS (DCI/NH$_3$) m/z 360 (M+H)$^+$; $^1$H NMR (300 MHz, DMSO-d$_6$): δ 1.34 (s, 6H), 1.53-1.70 (m, 4H), 2.29-2.45 (m, 4H), 3.87 (s, 2H), 6.85-7.02 (m, 1H), 7.20 (dd, J=10.91, 8.53 Hz, 1H), 7.91 (dd, J=7.54, 1.98 Hz, 1H), 9.24 (s, 1H), 12.62 (s, 1H).

Example 374

(3aS)-8-((4-oxo-3,4,5,6,7,8-hexahydrophthalazin-1-yl)methyl)-2,3,3a,4-tetrahydro-1H-pyrrolo(2,1-c)(1,4)benzoxazin-1-one

Example 374A (S)-1-oxo-2,3,3a,4-tetrahydro-1H-benzo(b)pyrrolo(1,2-d)(1,4)oxazine-8-carbaldehyde The title compound was prepared according to the procedure for EXAMPLE 300A, substituting (S)-5-(hydroxymethyl)pyrrolidin-2-one for 5-methylpyrrolidinone. MS (DCI/NH$_3$) m/z 232 (M+H)$^+$.

Example 374B (3aS)-8-((4-oxo-3,4,5,6,7,8-hexahydrophthalazin-1-yl)methyl)-2,3,3a,4-tetrahydro-1H-pyrrolo(2,1-c)(1,4)benzoxazin-1-one The title compound was prepared according to the procedure for EXAMPLE 300A, substituting EXAMPLE 374A for EXAMPLE 300B. MS (DCI/NH$_3$) m/z 352 (M+H)$^+$; $^1$H NMR (300 MHz, DMSO-d$_6$): δ 1.54-1.62 (m, 4H), 1.63-1.76 (m, 1H), 2.13-2.22 (m, 1H), 2.23-2.31 (m, 2H), 2.32-2.40 (m, 4H), 3.72 (t, J=10.31 Hz, 1H), 3.81 (s, 2H), 3.90-4.04 (m, 1H), 4.48 (dd, J=10.71, 3.17 Hz, 1H), 6.77-6.83 (m, 1H), 6.84-6.91 (m, 1H), 8.26 (d, J=1.98 Hz, 1H), 12.58 (br s, 1H).

Example 375

3-((4-oxo-3,4,5,6,7,8-hexahydrophthalazin-1-yl)methyl)-N-(2-phenylethyl)benzamide The title compound was prepared according to the procedure for EXAMPLE 308, substituting 2-phenylethanamine for furan-3-ylmethanamine. MS (DCI/NH$_3$) m/z 388 (M+H)$^+$; $^1$H NMR (500 MHz, D$_2$O/DMSO-d$_6$): δ 1.56-1.69 (m, 4H), 2.33-2.45 (m, 4H), 2.84 (t, J=7.48 Hz, 2H), 3.43-3.51 (m, 2H), 3.96 (s, 2H), 7.21 (t, J=7.17 Hz, 1H), 7.23-7.26 (m, 2H), 7.27-7.32 (m, 2H), 7.32-7.36 (m, 1H), 7.40 (t, J=7.63 Hz, 1H), 7.60 (s, 1H), 7.64 (d, J=7.93 Hz, 1H).

Example 376

N-(2-(2-methylphenyl)ethyl)-3-((4-oxo-3,4,5,6,7,8-hexahydrophthalazin-1-yl)methyl)benzamide The title compound was prepared according to the procedure for EXAMPLE 308, substituting 2-o-tolylethanamine for furan-3-ylmethanamine. MS (DCI/NH$_3$) m/z 402 (M+H)$^+$.

Example 377

N-(2-(3-methylphenyl)ethyl)-3-((4-oxo-3,4,5,6,7,8-hexahydrophthalazin-1-yl)methyl)benzamide The title compound was prepared according to the procedure for EXAMPLE 308, substituting 2-o-tolylethanamine for furan-3-ylmethanamine. MS (DCI/NH$_3$) m/z 402 (M+H)$^+$.

Example 378

N-(2-(4-methylphenyl)ethyl)-3-((4-oxo-3,4,5,6,7,8-hexahydrophthalazin-1-yl)methyl)benzamide The title compound was prepared according to the procedure for EXAMPLE 308, substituting 2-p-tolylethanamine for furan-3-ylmethanamine. MS (DCI/NH$_3$) m/z 402 (M+H)$^+$.

Example 379

3-((4-oxo-3,4,5,6,7,8-hexahydrophthalazin-1-yl)methyl)-N-(2-pyridin-2-ylethyl)benzamide The title compound was prepared according to the procedure for EXAMPLE 308, substituting 2-(pyridin-2-yl)ethanamine for furan-3-ylmethanamine. MS (DCI/NH$_3$) m/z 389 (M+H)$^+$; $^1$H NMR (500 MHz, D$_2$O/DMSO-d$_6$): δ 1.57-1.68 (m, 4H), 2.31-2.43 (m, 4H), 3.24 (t, J=6.56 Hz, 2H), 3.69 (t, J=6.41 Hz, 2H), 3.95 (s, 2H), 7.33-7.37 (m, 1H), 7.40 (t, J=7.63 Hz, 1H), 7.53 (s, 1H), 7.57 (d, J=7.63 Hz, 1H), 7.86-7.89 (m, 1H), 7.90-7.94 (m, 1H), 8.40-8.49 (m, 1H), 8.75 (d, J=4.88 Hz, 1H).

Example 380

3-((4-oxo-3,4,5,6,7,8-hexahydrophthalazin-1-yl)methyl)-N-(2-pyridin-3-ylethyl)benzamide The title compound was prepared according to the procedure for EXAMPLE 308, substituting 3-(pyridin-2-yl)ethanamine for furan-3-ylmethanamine. MS (DCI/NH$_3$) m/z 389 (M+H)$^+$.

Example 381

3-((4-oxo-3,4,5,6,7,8-hexahydrophthalazin-1-yl)methyl)-N-(2-pyridin-4-ylethyl)benzamide The title compound was prepared according to the procedure for EXAMPLE 308, substituting 4-(pyridin-2-yl)ethanamine for furan-3-ylmethanamine. MS (DCI/NH$_3$) m/z 389 (M+H)$^+$.

Example 382

N-(2-(2-methoxyphenyl)ethyl)-3-((4-oxo-3,4,5,6,7,8-hexahydrophthalazin-1-yl)methyl)benzamide The title compound was prepared according to the procedure for EXAMPLE 308, substituting 2-(2-methoxyphenyl)ethanamine for furan-3-ylmethanamine. MS (DCI/NH$_3$) m/z 418 (M+H)$^+$.

Example 383

N-(2-(3-methoxyphenyl)ethyl)-3-((4-oxo-3,4,5,6,7,8-hexahydrophthalazin-1-yl)methyl)benzamide The title compound was prepared according to the procedure for EXAMPLE 308, substituting 3-(2-methoxyphenyl)ethanamine for furan-3-ylmethanamine. MS (DCI/NH$_3$) m/z 418 (M+H)$^+$.

Example 384

N-(2-(4-methoxyphenyl)ethyl)-3-((4-oxo-3,4,5,6,7,8-hexahydrophthalazin-1-yl)methyl)benzamide The title compound was prepared according to the procedure for EXAMPLE 308, substituting 4-(2-methoxyphenyl)ethanamine for furan-3-ylmethanamine. MS (DCI/NH$_3$) m/z 418 (M+H)$^+$; $^1$H NMR (500 MHz, D$_2$O/DMSO-d$_6$): δ 1.55-1.68 (m, 4H), 2.32-2.45 (m, 4H), 2.77 (t, J=7.48 Hz, 2H), 3.37-3.47 (m, 2H), 3.71 (s, 3H), 3.96 (s, 2H), 6.83-6.88 (m, 2H), 7.14-7.20 (m, 2H), 7.32-7.36 (m, 1H), 7.40 (t, J=7.63 Hz, 1H), 7.61 (s, 1H), 7.64 (d, J=7.63 Hz, 1H).

Example 385

N-(2-(2-fluorophenyl)ethyl)-3-((4-oxo-3,4,5,6,7,8-hexahydrophthalazin-1-yl)methyl)benzamide The title compound was prepared according to the procedure for EXAMPLE 308, substituting 2-(2-fluorophenyl)ethanamine for furan-3-ylmethanamine. MS (DCI/NH$_3$) m/z 406 (M+H)$^+$.

Example 386

N-(2-(3-fluorophenyl)ethyl)-3-((4-oxo-3,4,5,6,7,8-hexahydrophthalazin-1-yl)methyl)benzamide The title compound was prepared according to the procedure for EXAMPLE 308, substituting 2-(3-fluorophenyl)ethanamine for furan-3-ylmethanamine. MS (DCI/NH$_3$) m/z 406 (M+H)$^+$.

Example 387

N-(2-(4-fluorophenyl)ethyl)-3-((4-oxo-3,4,5,6,7,8-hexahydrophthalazin-1-yl)methyl)benzamide The title compound was prepared according to the procedure for EXAMPLE 308, substituting 2-(4-fluorophenyl)ethanamine for furan-3-ylmethanamine. MS (DCI/NH$_3$) m/z 406 (M+H)$^+$.

Example 388

N-(2-(2-chlorophenyl)ethyl)-3-((4-oxo-3,4,5,6,7,8-hexahydrophthalazin-1-yl)methyl)benzamide The title compound was prepared according to the procedure for EXAMPLE 308, substituting 2-(2-chlorophenyl)ethanamine for furan-3-ylmethanamine. MS (DCI/NH$_3$) m/z 422 (M+H)$^+$.

Example 389

N-(2-(3-chlorophenyl)ethyl)-3-((4-oxo-3,4,5,6,7,8-hexahydrophthalazin-1-yl)methyl)benzamide The title compound was prepared according to the procedure for EXAMPLE 308, substituting 2-(3-chlorophenyl)ethanamine for furan-3-ylmethanamine. MS (DCI/NH$_3$) m/z 422 (M+H)$^+$.

Example 390

N-(2-(4-chlorophenyl)ethyl)-3-((4-oxo-3,4,5,6,7,8-hexahydrophthalazin-1-yl)methyl)benzamide The title compound was prepared according to the procedure for EXAMPLE 308, substituting 2-(4-chlorophenyl)ethanamine for furan-3-ylmethanamine. MS (DCI/NH$_3$) m/z 422 (M+H)$^+$.

Example 391

N-(2-(3-bromophenyl)ethyl)-3-((4-oxo-3,4,5,6,7,8-hexahydrophthalazin-1-yl)methyl)benzamide The title compound was prepared according to the procedure for EXAMPLE 308, substituting 2-(3-bromophenyl)ethanamine for furan-3-ylmethanamine. MS (DCI/NH$_3$) m/z 467 (M+H)$^+$.

Example 392

N-(2-(4-bromophenyl)ethyl)-3-((4-oxo-3,4,5,6,7,8-hexahydrophthalazin-1-yl)methyl)benzamide The title compound was prepared according to the procedure for EXAMPLE 308, substituting 2-(4-bromophenyl)ethanamine for furan-3-ylmethanamine. MS (DCI/NH$_3$) m/z 467 (M+H)$^+$.

Example 393

N-(2-(1,1'-biphenyl-4-yl)ethyl)-3-((4-oxo-3,4,5,6,7,8-hexahydrophthalazin-1-yl)methyl)benzamide The title compound was prepared according to the procedure for EXAMPLE 308, substituting 2-(biphenyl-4-yl)ethanamine for furan-3-ylmethanamine. MS (DCI/NH$_3$) m/z 464 (M+H)$^+$; $^1$H NMR (500 MHz, D$_2$O/DMSO-d$_6$): δ 1.54-1.67 (m, 4H), 2.30-2.44 (m, 4H), 2.89 (t, J=7.48 Hz, 2H), 3.52 (t, J=7.32 Hz, 2H), 3.96 (s, 2H), 7.33-7.37 (m, 4H), 7.41 (t, J=7.63 Hz, 1H), 7.44-7.50 (m, 2H), 7.59 (d, J=8.24 Hz, 2H), 7.64 (d, J=8.24 Hz, 2H), 7.64-7.68 (m, 2H).

Example 394

3-((4-oxo-3,4,5,6,7,8-hexahydrophthalazin-1-yl)methyl)-N-(2-(3-(trifluoromethyl)phenyl)ethyl)benzamide The title compound was prepared according to the procedure for EXAMPLE 308, substituting 2-(3-(trifluoromethyl)phenyl)ethanamine for furan-3-ylmethanamine. MS (DCI/NH$_3$) m/z 456 (M+H)$^+$.

Example 395

3-((4-oxo-3,4,5,6,7,8-hexahydrophthalazin-1-yl)methyl)-N-(2-(4-(trifluoromethyl)phenyl)ethyl)benzamide The title compound was prepared according to the procedure for EXAMPLE 308, substituting 2-(4-(trifluoromethyl)phenyl)ethanamine for furan-3-ylmethanamine. MS (DCI/NH$_3$) m/z 456 (M+H)$^+$.

Example 396

3-((4-oxo-3,4,5,6,7,8-hexahydrophthalazin-1-yl)methyl)-N-(2-(4-phenoxyphenyl)ethyl)benzamide The title compound was prepared according to the procedure for EXAMPLE 308, substituting 2-(4-phenoxyphenyl)ethanamine for furan-3-ylmethanamine. MS (DCI/NH$_3$) m/z 480 (M+H)$^+$; $^1$H NMR (500 MHz, D$_2$O/DMSO-d$_6$): δ 1.55-1.66 (m, 4H), 2.32-2.43 (m, 4H), 2.83 (t, J=7.32 Hz, 2H), 3.48 (t, J=7.32 Hz, 2H), 3.96 (s, 2H), 6.91-6.94 (m, 2H), 6.96 (d, J=7.63 Hz, 2H), 7.12 (t, J=7.48 Hz, 1H), 7.26 (d, J=8.54 Hz, 2H), 7.32-7.35 (m, 1H), 7.35-7.38 (m, 2H), 7.38-7.43 (m, 1H), 7.62 (s, 1H), 7.64 (d, J=7.63 Hz, 1H).

Example 397

N-(2-(3,4-dimethylphenyl)ethylphenyl)ethyl)-3-((4-oxo-3,4,5,6,78-hexahydrophthalazin-1-yl)methyl)benzamide The title compound was prepared according to the procedure for EXAMPLE 308, substituting 2-(3,4-dimethylphenyl)ethanamine for furan-3-ylmethanamine. MS (DCI/NH$_3$) m/z 416 (M+H)$^+$.

Example 398

N-(2-(2,4-dimethylphenyl)ethyl)-3-((4-oxo-3,4,5,6,7,8-hexahydrophthalazin-1-yl)methyl)benzamide The title compound was prepared according to the procedure for EXAMPLE 308, substituting 2-(2,4-dimethylphenyl)ethanamine for furan-3-ylmethanamine. MS (DCI/NH$_3$) m/z 416 (M+H)$^+$.

Example 399

N-(2-(2,5-dimethylphenyl)ethyl)-3-((4-oxo-3,4,5,6,7,8-hexahydrophthalazin-1-yl)methyl)benzamide The title compound was prepared according to the procedure for EXAMPLE 308, substituting 2-(2,5-dimethylphenyl)ethanamine for furan-3-ylmethanamine. MS (DCI/NH$_3$) m/z 416 (M+H)$^+$.

Example 400

N-(2-(3-ethoxy-4-methoxyphenyl)ethyl)-3-((4-oxo-3,4,5,6,7,8-hexahydrophthalazin-1-yl)methyl)benzamide The title compound was prepared according to the procedure for EXAMPLE 308, substituting 2-(3-ethoxy-4-methoxyphenyl)ethanamine for furan-3-ylmethanamine. MS (DCI/NH$_3$) m/z 462 (M+H)$^+$.

Example 401

N-(2-(4-ethoxy-3-methoxyphenyl)ethyl)-3-((4-oxo-3,4,5,6,7,8-hexahydrophthalazin-1-yl)methyl)benzamide The title compound was prepared according to the procedure for EXAMPLE 308, substituting 2-(4-ethoxy-3-methoxyphenyl)ethanamine for furan-3-ylmethanamine. MS (DCI/NH$_3$) m/z 462 (M+H)$^+$.

Example 402

N-(2-(2,3-dimethoxyphenyl)ethyl)-3-((4-oxo-3,4,5,6,7,8-hexahydrophthalazin-1-yl)methyl)benzamide The title compound was prepared according to the procedure for EXAMPLE 308, substituting 2-(2,3-dimethoxyphenyl)ethanamine for furan-3-ylmethanamine. MS (DCI/NH$_3$) m/z 448 (M+H)$^+$.

Example 403

N-(2-(2,4-dimethoxyphenyl)ethyl)-3-((4-oxo-3,4,5,6,7,8-hexahydrophthalazin-1-yl)methyl)benzamide The title compound was prepared according to the procedure for EXAMPLE 308, substituting 2-(2,4-dimethoxyphenyl)ethanamine for furan-3-ylmethanamine. MS (DCI/NH$_3$) m/z 448 (M+H)$^+$.

Example 404

N-(2-(2,5-dimethoxyphenyl)ethyl)-3-((4-oxo-3,4,5,6,7,8-hexahydrophthalazin-1-yl)methyl)benzamide The title compound was prepared according to the procedure for EXAMPLE 308, substituting 2-(2,5-dimethoxyphenyl)ethanamine for furan-3-ylmethanamine. MS (DCI/NH$_3$) m/z 448 (M+H)$^+$.

Example 405

N-(2-(3,4-dimethoxyphenyl)ethyl)-3-((4-oxo-3,4,5,6,7,8-hexahydrophthalazin-1-yl)methyl)benzamide The title compound was prepared according to the procedure for EXAMPLE 308, substituting 2-(3,4-dimethoxyphenyl)ethanamine for furan-3-ylmethanamine. MS (DCI/NH$_3$) m/z 448 (M+H)$^+$.

Example 406

N-(2-(3,5-dimethoxyphenyl)ethyl)-3-((4-oxo-3,4,5,6,7,8-hexahydrophthalazin-1-yl)methyl)benzamide The title compound was prepared according to the procedure for EXAMPLE 308, substituting 2-(3,5-dimethoxyphenyl)ethanamine for furan-3-ylmethanamine. MS (DCI/NH$_3$) m/z 448 (M+H)$^+$.

Example 407

N-(2-(1,3-benzodioxol-5-yl)ethyl)-3-((4-oxo-3,4,5,6,7,8-hexahydrophthalazin-1-yl)methyl)benzamide The title compound was prepared according to the procedure for EXAMPLE 308, substituting 2-(benzo(d)(1,3)dioxol-5-yl)ethanamine for furan-3-ylmethanamine. MS (DCI/NH$_3$) m/z 432 (M+H)$^+$; $^1$H NMR (500 MHz, D$_2$O/DMSO-d$_6$): δ 1.54-1.72 (m, 4H), 2.32-2.44 (m, 4H), 2.75 (t, J=7.32 Hz, 2H), 3.43 (t, J=7.32 Hz, 2H), 3.96 (s, 2H), 5.94 (s, 2H), 6.70 (dd, J=7.93, 1.53 Hz, 1H), 6.80 (s, 1H), 6.81-6.83 (m, 1H), 7.32-7.36 (m, 1H), 7.40 (t, J=7.63 Hz, 1H), 7.61 (s, 1H), 7.64 (d, J=17.93 Hz, 1H).

Example 408

N-(2-(2,3-dichlorophenyl)ethyl)-3-((4-oxo-3,4,5,6,7,8-hexahydrophthalazin-1-yl)methyl)benzamide The title compound was prepared according to the procedure for EXAMPLE 308, substituting 2-(2,3-dichlorophenyl)ethanamine for furan-3-ylmethanamine. MS (DCI/NH$_3$) m/z 457 (M+H)$^+$.

Example 409

N-(2-(3,4-dichlorophenyl)ethyl)-3-((4-oxo-3,4,5,6,7,8-hexahydrophthalazin-1-yl)methyl)benzamide The title compound was prepared according to the procedure for EXAMPLE 308, substituting 2-(3,4-dichlorophenyl)ethanamine for furan-3-ylmethanamine. MS (DCI/NH$_3$) m/z 457 (M+H)$^+$.

Example 410

N-(2-(2,6-dichlorophenyl)ethyl)-3-((4-oxo-3,4,5,6,7,8-hexahydrophthalazin-1-yl)methyl)benzamide The title compound was prepared according to the procedure for EXAMPLE 308, substituting 2-(2,6-dichlorophenyl)ethanamine for furan-3-ylmethanamine. MS (DCI/NH$_3$) m/z 457 (M+H)$^+$.

Example 411

(3aS,4R,7S,7aR)-5-(2-fluoro-5-((4-oxo-3,4,5,6,7,8-hexahydrophthalazin-1-yl)methyl)phenyl)-2,2-dimethyltetrahydro-4,7-methano(1,3)dioxolo(4,5-c)pyridin-6(3aH)-one

Example 411A 3-((3aS,4R,7S,7aR)-2,2-dimethyl-6-oxotetrahydro-4,7-methano(1,3)dioxolo(4,5-c)pyridin-5(4H)-yl)-4-fluorobenzaldehyde The title compound was prepared according to the procedure for EXAMPLE 300A, substituting (1S,2R,6S,7R)-4,4-dimethyl-3,5-dioxa-8-azatricyclo(5.2.1.0(2,6))decan-9-one for 5-methylpyrrolidinone. MS (DCI/NH$_3$) m/z 306 (M+H)$^+$.

Example 411B (3aS,4R,7S,7aR)-5-(2-fluoro-5-((4-oxo-3,4,5,6,7,8-hexahydrophthalazin-1-yl)methyl)phenyl)-2,2-dimethyltetrahydro-4,7-methano(1,3)dioxolo(4,5-c)pyridin-6(3aH)-one The title compound was prepared according to the procedure for EXAMPLE 300B, substituting EXAMPLE 411A for EXAMPLE 300B. MS (DCI/NH$_3$) m/z 440 (M+H)$^+$; $^1$H NMR (300 MHz, DMSO-d$_6$): δ 1.29-1.34 (m, 3H), 1.42 (s, 3H), 1.55-1.67 (m, 4H), 2.01-2.11 (m, 1H), 2.12-2.21 (m, 1H), 2.32-2.45 (m, 4H), 2.77-2.84 (m, 1H), 3.88 (s, 2H), 4.16-4.24 (m, 1H), 4.58-4.64 (m, 1H), 4.64-4.69 (m, 1H), 7.02-7.09 (m, 1H), 7.22 (dd, J=11.19, 8.48 Hz, 1H), 7.31 (dd, J=7.46, 2.03 Hz, 1H), 12.59 (s, 1H).

Example 412

4-(1-(3-bromo-4-fluorophenyl)ethyl)-5,6,7,8-tetrahydrophthalazin-1(2H)-one

Example 412A 1-(3-bromo-4-fluorophenyl)ethanol

A solution of 1-(3-bromo-4-fluorophenyl)ethanone (15.0 g, 69 mmol) in tetrahydrofuran (200 mL) was treated with sodium borohydride (5.3 g, 138 mmol) at 0° C.

After the addition, the ice bath was removed, and the mixture was stirred at room temperature for 30 minutes and at reflux overnight. After cooling, 1N HCl (10 mL) was slowly added and the reaction mixture was concentrated. The residue was partitioned between ethyl acetate and brine. The organic phase was washed with water, and concentrated. The residue was purified by flash chromatography (30% ethyl acetate in hexane) to provide the title compound. MS (DCI/NH$_3$) m/z 220 (M+H)$^+$.

Example 412B 2-bromo-4-(1-bromoethyl)-1-fluorobenzene

To a solution of EXAMPLE 412A (1.5 g, 6.8 mmol) and triphenyl phosphine (1.9 g, 7.2 mmol) in dimethylformamide (20 ml) was added bromine (1.1 g, 6.8 mmol) through a syringe. After the addition, the reaction mixture was stirred at room temperature for additional 15 minutes, and partitioned between water (100 ml) and ethyl acetate (200 ml). The organic phase was washed with brine and concentrated. The residue was purified by flash chromatography (2.6% ethyl acetate in hexane) to provide the title compound. MS (DCI/NH$_4$) m/z 282 (M+H)$^+$.

Example 412C (1-(3-bromo-4-fluorophenyl)ethyl)triphenylphosphonium bromide

The title compound was prepared according to the procedure for EXAMPLE 285B, substituting EXAMPLE 412B for EXAMPLE 285A.

Example 412D 3-(1-(3-bromo-4-fluorophenyl)ethylidene)-4,5,6,7-tetrahydroisobenzofuran-1(3H)-one The title compound was prepared according to the procedure for EXAMPLE 285C, substituting EXAMPLE 412C for EXAMPLE 285B. MS (DCI/NH$_3$) m/z 338 (M+H)$^+$.

Example 412E 4-(1-(3-bromophenyl ethyl)-5,6,7,8-tetrahydrophthalazin-1(2H)-one The title compound was prepared according to the procedure for EXAMPLE 2C, substituting EXAMPLE 412D for EXAMPLE 2B. MS (DCI/NH$_3$) m/z 352 (M+H)$^+$.

Example 413

4-(1-(4-fluoro-3-(2-oxopyrrolidin-1-yl)phenyl)ethyl)-5,6,7,8-tetrahydrophthalazin-1(2H)-one The title compound was prepared according to procedure for EXAMPLE 101, substituting EXAMPLE 412 for EXAMPLE 103, and pyrroline-2-one for azetidin-2-one. MS (ESI) m/z 356 (M+H)$^+$; $^1$H NMR (300 MHz, DMSO-d$_6$): δ 1.42 (d, J=6.74 Hz, 3H), 1.46-1.70 (m, 4H), 1.93-2.16 (m, 4H), 2.29-2.67 (m, 6H), 4.25 (q, J=6.74 Hz, 1H), 7.07-7.15 (m, 1H), 7.18 (s, 1H), 7.19-7.29 (m, 1H), 12.70 (s, 1H).

Example 414

8-(4-fluorobenzyl)-1,2,3,4-tetrahydropyrido(3,2-d)pyridazin-5(6H)-one

A mixture of EXAMPLE 369 (150 mg, 0.6 mmol), 5% platinum on carbon (30 mg), concentrated aqueous HCl (50 μL) and dimethylformamide (5 ml) in a pressure vessel was stirred at room temperature under 50 psi of hydrogen for 16 hours. The mixture was filtered, and the filtrate was concentrated. The residual solid was purified by HPLC (Zorbax® C-18 ODS packing material [Agilent Technologies. Santa Clara, Calif.], 0.1% TFA/CH$_3$CNH$_2$O) to provide the title product as TFA salt. MS (EST) m/z 260 (M+H)$^+$.

Example 415

8-(3-bromo-4-fluorobenzyl)pyrido(3,2-d pyridazin-5(6H)-one

Example 415A methyl 2-(2-(3-bromo-4-fluorophenyl)acetyl)nicotinate

A mixture of magnesium turnings (880 mg, 37 mmol) and 2-bromo-4-(bromomethyl)-1-fluorobenzene (1.0 g, 3.7 mmol) in anhydrous diethyl ether (15 ml) was treated with a piece of iodine. The mixture was then heated to gentle reflux until the color of the mixture disappeared, after which the heating continued for additional hour. The suspension was cooled to room temperature, and cannulated into a solution of dimethylpyridine-2,3-dicarboxylate (1.0 g, 5.1 mmol) in tetrahydrofuran (50 ml) at −78° C. The reaction mixture was maintained at the same temperature for 30 minutes, and was quenched with addition of water. After warming up to room temperature, the reaction mixture was partitioned between ethyl acetate and brine. The organic phase was washed with brine and concentrated. The residue was purified by flash chromatography (15% ethyl acetate in hexane) to provide the title compound. MS (DCI/NH$_3$) m/z 353 (M+H)$^+$.

Example 415B 8-(3-bromo-4-fluorobenzyl)pyrido(3,2-d)pyridazin-5(6H)-one

The title compound was prepared according to the procedure for EXAMPLE 369B substituting EXAMPLE 415A for EXAMPLE 369A. MS (DCI/NH$_3$) m/z 335 (M+H)$^+$.

Example 418

N-(2-(dimethylamino)ethyl)-N-ethyl-3-((4-oxo-3,4,5,6,7,8-hexahydrophthalazin-1-yl)methyl)benzamide The title compound was prepared according to the procedure for EXAMPLE 308, substituting N$^1$-ethyl-N$^2$,N$^2$-dimethylethane-1,2-diamine for furan-3-ylmethanamine. MS (DCI/NH$_3$) m/z 383 (M+H)$^+$.

Example 419

N-(2-(diethylamino)ethyl)-N-methyl-3-((4-oxo-3,4,5,6,7,8-hexahydrophthalazin-1-yl)methyl)benzamide The title compound was prepared according to the procedure for EXAMPLE 308, substituting N$^1$,N$^1$-diethyl-N$^2$-methylethane-1,2-diamine for furan-3-ylmethanamine. MS (DCI/NH$_3$) m/z 397 (M+H)$^+$.

Example 420

N-benzyl-N-ethyl-3-((4-oxo-3,4,5,6,7,8-hexahydrophthalazin-1-yl)methyl)benzamide The title compound was prepared according to the procedure for EXAMPLE 308, substituting N-benzylethanamine for furan-3-ylmethanamine. MS (DCI/NH$_3$) m/z 402 (M+H)$^+$; $^1$H NMR (500 MHz, D$_2$O/pyridine-d$_5$): δ 0.97-1.11 (m, 3H), 1.36-1.57 (m, 4H), 2.22-2.30 (m, 2H), 2.50-2.66 (m, 2H), 3.27-3.45 (m, 2H), 3.98 (s, 2H), 4.61-4.74 (m, 2H), 7.26-7.31 (m, 1H), 7.32-7.40 (m, 6H), 7.42-7.47 (m, 1H), 7.52 (s, 1H).

Example 421

N-benzyl-N-isopropyl-3-((4-oxo-3,4,5,6,7,8-hexahydrophthalazin-1-yl)methyl)benzamide The title compound was prepared according to the procedure for EXAMPLE 308, substituting N-benzylpropan-2-amine for furan-3-ylmethanamine. MS (DCI/NH$_3$) m/z 416 (M+H)$^+$.

Example 422

N-benzyl-N-butyl-3-((4-oxo-3,4,5,6,7,8-hexahydrophthalazin-1-yl)methyl)benzamide The title compound was prepared according to the procedure for EXAMPLE 308, substituting N-benzylbutan-1-amine for furan-3-ylmethanamine. MS (DCI/NH$_3$) m/z 430 (M+H)$^+$.

Example 423

N,N-dibenzyl-3-((4-oxo-3,4,5,6,7,8-hexahydrophthalazin-1-yl)methyl)benzamide

The title compound was prepared according to the procedure for EXAMPLE 308, substituting dibenzylamine for furan-3-ylmethanamine. MS (DCI/NH$_3$) m/z 464 (M+H)$^+$.

Example 424

N-benzyl-N-(2-hydroxyethyl)-3-((4-oxo-3,4,5,6,7,8-hexahydrophthalazin-1-yl)methyl)benzamide The title compound was prepared according to the procedure for EXAMPLE 308, substituting 2-(benzylamino)ethanol for furan-3-ylmethanamine. MS (DCI/NH$_3$) m/z 418 (M+H)$^+$; $^1$H NMR (500 MHz, D$_2$O/pyridine-d$_5$): δ 1.40-1.54 (m, 4H), 2.21-2.33 (m, 2H), 2.50-2.61 (m, 2H), 3.62-3.78 (m, 2H), 3.89-4.02 (m, 2H), 3.96 (s, 2H), 4.82-4.97 (m, 2H), 7.25-7.29 (m, 1H), 7.30-7.36 (m, 5H), 7.36-7.43 (m, 1H), 7.43-7.47 (m, 1H), 7.50 (d, J=7.32 Hz, 1H).

Example 426

N-methyl-3-((4-oxo-3,4,5,6,7,8-hexahydrophthalazin-1-yl)methyl)-N-(2-pyridin-2-ylethyl)benzamide The title compound was prepared according to the procedure for EXAMPLE 308, substituting N-methyl-2-(pyridin-2-yl)ethanamine for furan-3-ylmethanamine. MS (DCI/NH$_3$) m/z 403 (M+H)$^+$; $^1$H NMR (500 MHz, D$_2$O/pyridine-d$_5$): δ 1.42-1.52 (m, 4H), 2.24-2.34 (m, 2H), 2.51-2.62 (m, 2H), 2.97 (s, 3H), 3.07-3.21 (m, 2H), 3.83-3.94 (m, 2H), 3.99 (s, 2H), 7.12 (dd, J=7.32, 5.49 Hz, 1H), 7.14-7.20 (m, 1H), 7.28-7.32 (m, 2H), 7.32-7.37 (m, 1H), 7.37-7.45 (m, 1H), 7.57 (t, J=7.63 Hz, 1H), 8.55 (d, J=3.66 Hz, 1H).

Example 427

N-(2-(3,4-dimethoxyphenyl)ethyl)-N-methyl-3-((4-oxo-3,4,5,6,7,8-hexahydrophthalazin-1-yl)methyl)benzamide The title compound was prepared according to the procedure for EXAMPLE 308, substituting 2-(3,4-dimethoxyphenyl)-N-methylethanamine for furan-3-ylmethanamine. MS (DCI/NH$_3$) m/z 462 (M+H)$^+$.

Example 428

4-(3-((4-hydroxypiperidin-1-yl)carbonyl)benzyl)-5,6,7,8-tetrahydrophthalazin-1(2H)-one The title compound was prepared according to the procedure for EXAMPLE 308, substituting piperidin-4-ol for

Example 429

1-(3-((4-oxo-3,4,5,6,7,8-hexahydrophthalazin-1-yl)methyl)benzoyl)piperidine-3-carboxamide The title compound was prepared according to the procedure for EXAMPLE 308, substituting piperidine-3-carboxamide for furan-3-ylmethanamine. MS (DCI/NH$_3$) m/z 395 (M+H)$^+$.

Example 430

1-(3-((4-oxo-3,4,5,6,7,8-hexahydrophthalazin-1-yl)methyl)benzoyl)piperidine-4-carboxamide The title compound was prepared according to the procedure for EXAMPLE 308, substituting piperidine-4-carboxamide for furan-3-ylmethanamine. MS (DCI/NH$_3$) m/z 395 (M+H)$^+$; $^1$H NMR (500 MHz, D$_2$O/pyridine-d$_5$): δ 1.41-1.55 (m, 4H), 1.82-1.97 (m, 4H), 2.27-2.37 (m, 2H), 2.54-2.61 (m, 2H), 2.63-2.73 (m, 1H), 2.94-3.06 (m, 2H), 4.00 (s, 2H), 4.16-4.32 (m, 2H), 7.32-7.36 (m, 1H), 7.36-7.40 (m, 2H), 7.48-7.51 (m, 1H).

Example 434

4-(3-((4-(2-oxo-2,3-dihydro-1H-benzimidazol-1-yl)piperidin-1-yl)carbonyl)benzyl)-5,6,7,8-tetrahydrophthalazin-1(2H)-one The title compound was prepared according to the procedure for EXAMPLE 308, substituting 1-(piperidin-4-yl)-1H-benzo(d)imidazol-2(3H)-one for furan-3-ylmethanamine. MS (DCI/NH$_3$) m/z 484 (M+H)$^+$.

Example 435

4-(3-((4-methylpiperazin-1-yl)carbonyl)benzyl)-5,6,7,8-tetrahydrophthalazin-1(2H)-one The title compound was prepared according to the procedure for EXAMPLE 308, substituting 1-methylpiperazine for furan-3-ylmethanamine. MS (DCI/NH$_3$) m/z 367 (M+H)$^+$; $^1$H NMR (500 MHz, D$_2$O/pyridine-d$_5$): δ 1.46-1.52 (m, 4H), 2.24 (s, 3H), 2.29-2.34 (m, 2H), 2.37-2.42 (m, 4H), 2.54-2.62 (m, 2H), 3.61-3.73 (m, 4H), 4.02 (s, 2H), 7.35-7.39 (m, 1H), 7.39-7.43 (m, 2H), 7.51 (s, 1H).

Example 436

4-(3-((4-ethylpiperazin-1-yl)carbonyl)benzyl)-5,6,7,8-tetrahydrophthalazin-1(2H)-one The title compound was prepared according to the procedure for EXAMPLE 308, substituting 1-ethylpiperazine for furan-3-ylmethanamine. MS (DCI/NH$_3$) m/z 381 (M+H)$^+$.

furan-3-ylmethanamine. MS (DCI/NH$_3$) m/z 368 (M+H)$^+$; $^1$H NMR (500 MHz, D$_2$O/pyridine-d$_5$): δ 1.42-1.52 (m, 4H), 1.63-1.75 (m, 2H), 1.87-1.98 (m, 2H), 2.27-2.35 (m, 2H), 2.54-2.62 (m, 2H), 3.25-3.40 (m, 2H), 4.01 (s, 2H), 4.01-4.04 (m, 2H), 4.05-4.07 (m, 1H), 7.35 (t, J=7.17 Hz, 1H), 7.37-7.40 (m, 1H), 7.40-7.44 (m, 1H), 7.51 (s, 1H).

Example 437

4-(3-((4-oxo-3,4,5,6,7,8-hexahydrophthalazin-1-yl)methyl)benzoyl)piperazine-1-carbaldehyde The title compound was prepared according to the procedure for EXAMPLE 308, substituting piperazine-1-carbaldehyde for furan-3-ylmethanamine. MS (DCI/NH$_3$) m/z 381 (M+H)$^+$.

Example 438

4-(3-((4-acetylpiperazin-1-yl)carbonyl)benzyl)-5,6,7,8-tetrahydrophthalazin-1(2H)-one The title compound was prepared according to the procedure for EXAMPLE 308, substituting 1-(piperazin-1-yl)ethanone for furan-3-ylmethanamine. MS (DCI/NH$_3$) m/z 395 (M+H)$^+$; $^1$H NMR (500 MHz, D$_2$O/pyridine-d$_5$): δ 1.44-1.57 (m, 4H), 2.09 (s, 3H), 2.28-2.39 (m, 2H), 2.51-2.66 (m, 2H), 3.39-3.73 (m, 8H), 4.03 (s, 2H), 7.36-7.39 (m, 1H), 7.43 (t, J=7.02 Hz, 2H), 7.54 (s, 1H).

Example 439

4-(3-((4-(2-hydroxyethyl)piperazin-1-yl)carbonyl)benzyl)-5,6,7,8-tetrahydrophthalazin-1(2H)-one The title compound was prepared according to the procedure for EXAMPLE 308, substituting 2-(piperazin-1-yl)ethanol for furan-3-ylmethanamine. MS (DCI/NH$_3$) m/z 397 (M+H)$^+$; $^1$H NMR (500 MHz, D$_2$O/pyridine-d$_5$): δ 1.42-1.55 (m, 4H), 2.27-2.37 (m, 2H), 2.50-2.62 (m, 6H), 2.69 (t, J=5.80 Hz, 2H), 3.54-3.75 (m, 4H), 3.89 (t, J=5.80 Hz, 2H), 4.02 (s, 2H), 7.35-7.38 (m, 1H), 7.39-7.43 (m, 2H), 7.50 (s, 1H).

Example 440

4-(3-((4-phenylpiperazin-1-yl)carbonyl)benzyl)-5,6,7,8-tetrahydrophthalazin-1(2H)-one The title compound was prepared according to the procedure for EXAMPLE 308, substituting 1-phenylpiperazine for furan-3-ylmethanamine. MS (DCI/NH$_3$) m/z 429 (M+H)$^+$; $^1$H NMR (500 MHz, D$_2$O/pyridine-d$_5$): δ 1.44-1.57 (m, 4H), 2.27-2.42 (m, 2H), 2.52-2.66 (m, 2H), 3.08-3.20 (m, 4H), 3.68-3.83 (m, 4H), 4.04 (s, 2H), 6.91 (t, J=7.32 Hz, 1H), 6.98 (d, J=7.93 Hz, 2H), 7.28-7.34 (m, 2H), 7.37-7.41 (m, 1H), 7.44 (t, J=7.48 Hz, 1H), 7.46-7.49 (m, 1H), 7.57 (s, 1H).

Example 441

4-(3-((4-pyridin-2-ylpiperazin-1-yl)carbonyl)benzyl)-5,6,7,8-tetrahydrophthalazin-1(2H)-one The title compound was prepared according to the procedure for EXAMPLE 308, substituting 1-(pyridin-2-yl)piperazine for furan-3-ylmethanamine. MS (DCI/NH$_3$) m/z 430 (M+H)$^+$; $^1$H NMR (500 MHz, D$_2$O/pyridine-d$_5$): δ 1.46-1.55 (m, 4H), 2.29-2.40 (m, 2H), 2.52-2.65 (m, 2H), 3.53-3.63 (m, 4H), 3.64-3.78 (m, 4H), 4.03 (s, 2H), 6.66 (dd, J=6.71, 4.58 Hz, 1H), 6.73 (d, J=8.54 Hz, 1H), 7.37-7.41 (m, 1H), 7.43 (d, J=7.63 Hz, 1H), 7.45-7.48 (m, 1H), 7.49-7.54 (m, 1H), 7.57 (s, 1H), 8.29 (dd, J=4.88, 1.22 Hz, 1H).

Example 442

4-(3-((4-pyrimidin-2-ylpiperazin-1-yl)carbonyl)benzyl)-5,6,7,8-tetrahydrophthalazin-1(2H)-one The title compound was prepared according to the procedure for EXAMPLE 308, substituting 2-(piperazin-1-yl)pyrimidine for furan-3-ylmethanamine. MS (DCI/NH$_3$) m/z 431 (M+H)$^+$; $^1$H NMR (500 MHz, D$_2$O/pyridine-d$_5$): δ 1.42-1.59 (m, 4H), 2.26-2.40 (m, 2H), 2.50-2.66 (m, 2H), 3.62-3.74 (m, 4H), 3.82-3.91 (m, 4H), 4.03 (s, 2H), 6.55 (t, J=4.73 Hz, 1H), 7.38 (d, J=5.80 Hz, 1H), 7.40-7.45 (m, 1H), 7.45-7.49 (m, 1H), 7.57 (s, 1H), 8.38 (d, J=4.88 Hz, 2H).

Example 443

4-(3-((4-(2-(2-hydroxyethoxy)ethyl)piperazin-1-yl)carbonyl)benzyl)-5,6,7,8-tetrahydrophthalazin-1(2H)-one The title compound was prepared according to the procedure for EXAMPLE 308, substituting 2-(2-(piperazin-1-yl)ethoxy)ethanol for furan-3-ylmethanamine. MS (DCI/NH$_3$) m/z 441 (M+H)$^+$.

Example 444

4-(3-((4-(2-fluorophenyl)piperazin-1-yl)carbonyl)benzyl)-5,6,7,8-tetrahydrophthalazin-1(2H)-one The title compound was prepared according to the procedure for EXAMPLE 308, substituting 1-(2-fluorophenyl)piperazine for furan-3-ylmethanamine. MS (DCI/NH$_3$) m/z 447 (M+H)$^+$.

Example 445

4-(3-((4-(4-fluorophenyl)piperazin-1-yl)carbonyl)benzyl)-5,6,7,8-tetrahydrophthalazin-1(2H)-one The title compound was prepared according to the procedure for EXAMPLE 308, substituting 1-(4-fluorophenyl)piperazine for furan-3-ylmethanamine. MS (DCI/NH$_3$) m/z 447 (M+H)$^+$; $^1$H NMR (500 MHz, D$_2$O/pyridine-d$_5$): δ 1.44-1.56 (m, 4H), 2.30-2.39 (m, 2H), 2.53-2.63 (m, 2H), 3.02-3.12 (m, 4H), 3.68-3.81 (m, 4H), 4.05 (s, 2H), 6.93-6.97 (m, 2H), 7.04-7.09 (m, 2H), 7.37-7.41 (m, 1H), 7.44 (t, J=7.32 Hz, 1H), 7.46-7.51 (m, 1H), 7.57 (s, 1H).

Example 446

4-(3-((4-(2-chlorophenyl)piperazin-1-yl)carbonyl)benzyl)-5,6,7,8-tetrahydrophthalazin-1(2H)-one The title compound was prepared according to the procedure for EXAMPLE 308, substituting 1-(2-chlorophenyl)piperazine for furan-3-ylmethanamine. MS (DCI/NH$_3$) m/z 463 (M+H)$^+$.

Example 447

4-(3-((4-methyl-1,4-diazepan-1-yl)carbonyl)benzyl)-5,6,7,8-tetrahydrophthalazin-1(2H)-one The title compound was prepared according to the procedure for EXAMPLE 308, substituting 1-methyl-4-(piperazin-1-yl)azepane for furan-3-ylmethanamine. MS (DCI/NH$_3$) m/z 381 (M+H)$^+$; $^1$H NMR (500 MHz, D$_2$O/pyridine-d$_5$): δ 1.44-1.48 (m, 1H), 1.48-1.51 (m, 4H), 1.92-2.01 (m, 2H), 2.28-2.36 (m, 2H), 2.51-2.55 (m, 2H), 2.58 (s, 3H), 2.64 (t, J=5.65 Hz, 1H), 2.84-2.94 (m, 2H), 3.64-3.71 (m, 3H), 3.88-3.92 (m, 1H), 4.01 (s, 2H), 7.33-7.39 (m, 1H), 7.39-7.41 (m, 1H), 7.41-7.45 (m, 1H), 7.51 (s, 1H).

Example 448

4-(3-(1-dioxido-1,2-thiazinan-2-yl)-4-fluorobenzyl)-5,6,7,8-tetrahydrophthalazin-1(2H)-one

Example 448A 3-(1,1-dioxido-1,2-thiazinan-2-yl)-4-fluorobenzaldehyde

The title compound was prepared according to the procedure for EXAMPLE 300A, substituting 1,4-butanesultam for 5-methylpyrrolidinone. MS (DCI/NH$_3$) m/z 258 (M+H)$^+$.

Example 448B 4-(3-(1,1-dioxido-1,2-thiazinan-2-yl)-4-fluorobenzyl)-5,6,7,8-tetrahydrophthalazin-1(2H)-one The title compound was prepared according to the procedure for EXAMPLE 300B, substituting EXAMPLE 448A for EXAMPLE 300A. MS (DCI/NH$_3$) m/z 392 (M+H)$^+$; $^1$H NMR (300 MHz, DMSO-d$_6$): δ 1.57-1.71 (m, 4H), 1.75-1.87 (m, 2H), 2.13-2.24 (m, 2H), 2.34-2.46 (m, 4H), 3.16-3.28 (m, 2H), 3.46-3.58 (m, 2H), 3.92 (s, 2H), 7.23 (dd, J=8.13, 2.18 Hz, 1H), 7.48 (d, J=7.93 Hz, 1H), 7.57 (d, J=1.59 Hz, 1H), 12.61 (br s, 1H).

Example 449

8-(4-fluoro-3-(2-oxoazetidin-1-yl)benzyl)pyrido(2,3-d)pyridazin-5(6H)-one

The title compound was prepared according to procedure for EXAMPLE 101, substituting EXAMPLE 415 for EXAMPLE 103. MS (ESI) m/z 325 (M+H)$^+$.

Example 450

8-(3-chloro-4-fluorobenzyl)-2,3,4,6-tetrahydropyrido(2,3-d)pyridazin-5(1H)-one

The title compound was prepared as TFA salt according to procedure for EXAMPLE 414, substituting EXAMPLE 370 for EXAMPLE 369. MS (ESI) m/z 294 (M+H)$^+$.

Example 451

4-(1-(4-fluoro-3-(2-oxoazetidin-1-yl)phenyl)ethyl)-5,6,7,8-tetrahydrophthalazin-1(2H)-one The title compound was prepared according to procedure for EXAMPLE 101, substituting EXAMPLE 412 for EXAMPLE 103. MS (ESI) m/z 342 (M+H)$^+$; $^1$H NMR (300 MHz, DMSO-d$_6$): 1.41 (d, J=7.12 Hz, 3H), 1.44-1.67 (m, 4H), 1.84-2.08 (m, 1H), 2.34 (m, 2H), 2.53-2.74 (m, 1H), 3.11 (t, J=4.58 Hz, 2H), 3.72-3.88 (m, 2H), 4.22 (q, J=6.78 Hz, 1H), 6.81-6.95 (m, 1H), 7.18 (dd, J=11.87, 8.48 Hz, 1H), 7.76 (dd, J=7.46, 2.37 Hz, 1H), 12.70 (s, 1H).

Example 452

1-(3-((4-oxo-3,4,5,6,7,8-hexahydrophthalazin-1-yl) methyl)phenyl)pyrrolidine-2,5-dione The title compound was prepared according to the procedure for EXAMPLEs 2, 3 and 4, substituting 3-nitrobenzaldehyde for 4-fluoro-3-nitrobenzaldehyde. MS (DCI/NH$_3$) m/z 256 (M+H)$^+$.

Example 453

N-(2-fluoro-5-((4-oxo-3,4,5,6,7,8-hexahydrophthalazin-1-yl)methyl)phenyl)-2-(2-oxopyrrolidin-1-yl)acetamide The title compound was prepared as TFA salt according to the procedure for EXAMPLE 136, substituting EXAMPLE 2 for EXAMPLE 89, and 2-(2-oxopyrrolidin-1-yl)acetic acid for 1-methylcyclopropanecarboxylic acid. MS (DCI/NH$_3$) m/z 356 (M+H)$^+$. MS (DCI/NH$_3$) m/z 399 (M+H)$^+$; $^1$H NMR (300 MHz, DMSO-d$_6$): δ 1.53-1.67 (m, 4H), 1.89-2.06 (m, 2H), 2.26 (t, J=7.97 Hz, 2H), 2.31-2.43 (m, 4H), 3.39-3.47 (m, 2H), 3.86 (s, 2H), 4.07 (s, 2H), 6.93-6.99 (m, 1H), 7.18 (dd, J=10.85, 8.48 Hz, 1H), 7.71 (dd, J=7.46, 2.03 Hz, 1H), 9.82 (br s, 1H), 12.61 (br s, 1H).

Example 454

N-(2-fluoro-5-((4-oxo-3,4,5,6,7,8-hexahydrophthalazin-1-yl)methyl)phenyl)-5-methyl-1-phenyl-1H-pyrazole-4-carboxamide The title compound was prepared as TFA salt according to the procedure for EXAMPLE 136, substituting EXAMPLE 2 for EXAMPLE 89, and 5-methyl-1-phenyl-1H-pyrazole-4-carboxylic acid for 1-methylcyclopropanecarboxylic acid. MS (DCI/NH$_3$) m/z 356 (M+H)$^+$. MS (DCI/NH$_3$) m/z 458 (M+H)$^+$.

Example 455

N-(2-fluoro-5-((4-oxo-3,4,5,6,7,8-hexahydrophthalazin-1-yl)methyl)phenyl)-5-oxohexanamide The title compound was prepared as TFA salt according to the procedure for EXAMPLE 136, substituting EXAMPLE 2 for EXAMPLE 89, and 5-oxohexanoic acid for 1-methylcyclopropanecarboxylic acid. MS (DCI/NH$_3$) m/z 386 (M+H)$^+$; $^1$H NMR (300 MHz, DMSO-d$_6$): δ 1.53-1.65 (m, 4H), 1.67-1.80 (m, 2H), 2.08 (s, 3H), 2.28-2.34 (m, 2H), 2.34-2.41 (m, 4H), 2.42-2.49 (m, 2H), 3.85 (s, 2H), 6.82-6.96 (m, 1H), 7.15 (dd, J=10.85, 8.48 Hz, 1H), 7.67 (dd, J=7.46, 1.70 Hz, 1H), 9.60 (br s, 1H), 12.61 (br s, 1H).

Example 456

N-(2-fluoro-5-((4-oxo-3,4,5,6,7,8-hexahydrophthalazin-1-yl)methyl)phenyl)-3-methoxypropanamide The title compound was prepared as TFA salt according to the procedure for EXAMPLE 136, substituting EXAMPLE 2 for EXAMPLE 89, and 3-methoxypropanoic acid for 1-methylcyclopropanecarboxylic acid. MS (DCI/NH$_3$) m/z 360 (M+H)$^+$; $^1$H NMR (300 MHz, DMSO-d$_6$): δ 1.55-1.66 (m, 4H), 2.30-2.43 (m, 4H), 2.60 (t, J=6.10 Hz, 2H), 3.23 (s, 3H), 3.59 (t, J=6.27 Hz, 2H), 3.86 (s, 2H), 6.85-6.99 (m, 1H), 7.16 (dd, J=10.85, 8.48 Hz, 1H), 7.74 (dd, J=7.46, 1.70 Hz, 1H), 9.64 (br s, 1H), 12.61 (br s, 1H).

Example 457

N-(2-fluoro-5-((4-oxo-3,4,5,6,7,8-hexahydrophthalazin-1-yl)methyl)phenyl)-N'-phenylpentanediamide The title compound was prepared as TFA salt according to the procedure for EXAMPLE 136, substituting EXAMPLE 2 for EXAMPLE 89, and 5-oxo-5-(phenylamino)pentanoic acid for 1-methylcyclopropanecarboxylic acid. MS (DCI/NH$_3$) m/z 463 (M+H)$^+$; $^1$H NMR (300 MHz, DMSO-d$_6$): δ 1.55-1.67 (m, 4H), 1.83-1.94 (m, 2H), 2.31-2.40 (m, 6H), 2.40-2.45 (m, 2H), 3.85 (s, 2H), 6.89-6.96 (m, 1H), 6.98-7.06 (m, 1H), 7.15 (dd, J=10.85, 8.48 Hz, 1H), 7.24-7.32 (m, 2H), 7.59 (d, J=7.46 Hz, 2H), 7.71 (dd, J=7.97, 1.53 Hz, 1H), 9.67 (br s, 1H), 9.88 (br s, 1H), 12.62 (br s, 1H).

Example 458 benzyl 2-(dimethylamino)-5-((4-oxo-3,4,5,6,7,8-hexahydrophthalazin-1-yl)methyl)phenylcarbamate Example 458A 4-(dimethylamino)-N-methoxy-N-methyl-3-nitrobenzamide To a solution of 4-fluoro-3-nitrobenzoic acid (5 g, 27.0 mmol) in dimethylformamide (100 mL) was added N,O-dimethylhydroxylamine hydrochloride (5.93 g, 60.8 mmol) and triethylamine (17.0 mL, 122 mmol). 1-Ethyl-3-(3-dimethylaminopropyl) carbodiimide hydrochloride (11.65 g, 60.8 mmol) and hydroxybenzotriazole (9.31 g, 60.8 mmol) were added and the reaction mixture was stirred at room temperature for 3 days. The reaction mixture was concentrated and partitioned between ethyl acetate (150 mL) and brine (150 mL). The organics were concentrated on rotary evaporator and the crude was purified by flash chromatography eluting with 40% ethyl acetate in hexanes to provide the title product. MS (DCI/NH$_3$) m/z 254 (M+H)$^+$.

Example 458B 3-amino-4-(dimethylamino)-N-methoxy-N-methylbenzamide

A solution of EXAMPLE 458A (2.34 g, 9.24 mmol) in tetrahydrofuran (40 mL) was treated with Raney Ni (2.0 g, Raney 2800, slurry in water) at room temperature under a hydrogen (balloon) for 16 hours. The catalyst was filtered off, and the filtrate was concentrated. The residue was used the subsequent step without further purification.

Example 458C benzyl 2-(dimethylamino)-5-(methoxy(methyl)carbamoyl)phenylcarbamate To a solution of EXAMPLE 458B in a mixture of tetrahydrofuran (20 mL) and water (20 mL) was added cesium carbonate (6.02 g, 18.58 mmol) and benzyl chloroformate (1.5 mL, 10.16 mmol). The reaction mixture was stirred at room temperature for 16 hours, and concentrated. The residue was partitioned between ethyl acetate (100 mL) and brine (75 mL). The organic layer was washed with brine, and concentrated. The residual oil was purified by flash chromatography eluting with 40% ethyl acetate in hexanes to provide the title product. MS (DCI/NH$_3$) m/z 358 (M+H)$^+$.

Example 458D benzyl 2-(dimethylamino)-5-formylphenylcarbamate

A solution of EXAMPLE 458C (2.89 g, 8.1 mmol) in anhydrous tetrahydrofuran (20 mL) was treated with lithium aluminum hydride (1.0 M solution in tetrahydrofuran, 8.1 mL, 8.1 mmol) at 0° C. for 10 minutes. The reaction was quenched with water, and the mixture was partitioned between ethyl acetate and diluted HCl solution. The organic layer was washed with brine, and concentrated on a rotary evaporator. The residual oil was purified by flash chromatography eluting with 20% ethyl acetate in hexanes to provide the title product. MS (DCI/NH$_3$) m/z 299 (M+H)$^+$.

Example 458E benzyl 2-(dimethylamino)-5-((4-oxo-3,4,5,6,7,8-hexahydrophthalazin-1-yl)methyl)phenylcarbamate The title compound was prepared according to the procedure for EXAMPLE 300B, substituting EXAMPLE 458D for EXAMPLE 300A. MS (DCI/NH$_3$) m/z 433 (M+H)$^1$.

Example 459

8-(4-fluoro-3-(2-oxoazetidin-1-yl)benzyl)-1,2,3,4-tetrahydropyrido(3,2-d)pyridazin-5(6H)-one The title compound was prepared according to procedure for EXAMPLE 414, substituting EXAMPLE 449 for EXAMPLE 369. MS (EST) m/z 329 (M+H)$^+$; $^1$H NMR (300 MHz, DMSO-d$_6$): δ 1.61-1.76 (m, 2H), 2.33 (t, J=6.35 Hz, 2H), 3.12 (t, J=4.56 Hz, 2H), 3.17 (m, 2H), 3.77 (s, 2H), 3.81 (q, J=4.36 Hz, 2H), 6.32 (s, 1H), 6.87-7.01 (m, 1H), 7.17 (dd, J=11.90, 8.33 Hz, 1H), 7.78 (dd, J=7.54, 2.38 Hz, 1H), 11.80 (s, 1H).

Example 460

4-(3-bromo-4-fluorophenyl)-5,6,7,8-tetrahydrophthalazin-1(2H)-one

Example 460A 3-(3-bromo-4-fluorophenyl)-3-methoxy-4,5,6,7-tetrahydroisobenzofuran-1(3H)-one To a solution of 2-bromo-1-fluoro-4-iodobenzene (13.23 g, 44 mmol) in anhydrous tetrahydrofuran (30 mL) was added isopropylmagnesium chloride (2.0 M solution in tetrahydrofuran, 24.18 mL, 48.4 mmol) at −20° C. After the addition, the reaction mixture was stirred at 0° C. for 3 hours, and was added to a solution of 3,4,5,6-tetrahydrophthalic anhydride (6.08 g, 40 mmol) in anhydrous tetrahydrofuran (60 mL) at −78° C. The mixture was stirred for 2 hours, and a saturated aqueous ammonium chloride solution was added to the reaction mixture, which then was stirred at room temperature for 30 minutes. Anhydrous magnesium sulfate was added to the reaction mixture, and the mixture was filtered. The filtrate was concentrated. Thionyl chloride (10.4 mL, 142 mol) was added dropwise to methanol (40 mL) at −10° C., and the solution was stirred at 0° C. for 30 minutes. To the thionyl chloride solution was then added the residue from the filtrate in anhydrous methanol (15 mL). The reaction mixture was stirred at room temperature overnight, and was concentrated. The residue was dissolved in methylene chloride (40 mL), and was treated with triethylamine (5.58 mL) at 0° C. for 1 hour. Water was added, and the mixture was washed with sodium bicarbonate, brine and water. The organic phase was dried over magnesium sulfate, filtered and concentrated. The residue was separated by flash chromatography (10-35% gradient ethyl acetate in hexane) to provide the title compound. MS (DCI/NH$_3$) m/z 341, 343 (M+H)$^+$.

Example 460B 4-(3-bromo-4-fluorophenyl)-5,6,7,8-tetrahydrophthalazin-1(2H)-one

A solution of EXAMPLE 460A (9.5 g, 27.8 mmol) and hydrazine monohydrate (1.76 mL, 36.2 mmol) in ethanol (70 mL) was heated under reflux for 4 hours. After cooling to room temperature, the solids were collected by filtration, washed with ethanol and dried to provide the title compound. MS (DCI/NH$_3$) m/z 323, 325 (M+H)$^+$; $^1$H NMR (300 MHz, DMSO-D$_6$): δ 1.57-1.65 (m, 2H), 1.66-1.74 (m, 2H), 2.34 (t, J=5.75 Hz, 2H), 2.45 (t, J=6.15 Hz, 2H), 7.45 (t, J=8.72 Hz, 1H), 7.49-7.55 (m, 1H), 7.80 (dd, J=6.74, 2.38 Hz, 1H), 12.85 (br s, 1H).

Example 461

4-(4-fluoro-3-(2-oxoazetidin-1-yl)phenyl)-5,6,7,8-tetrahydrophthalazin-1(2H)-one Example 461A 2-(benzyloxymethyl)-4-(3-bromo-4-fluorophenyl)-5,6,7,8-tetrahydrophthalazin-1(2H)-one To a solution of EXAMPLE 460 (2.0 g, 6.19 mmol) in anhydrous dimethylformamide (30 mL) was added potassium t-butoxide (1 M solution in tetrahydrofuran, 6.50 mL, 6.5 mmol). The solution was stirred at room temperature for 30 minutes, and benzyl chloromethylether (1.163 g, 7.43 mmol) was added. The reaction mixture was stirred at room temperature overnight. After quenching with water, the reaction mixture was partitioned between water and ethyl acetate. The organic phase was washed with water, and concentrated. The residue was separated by flash chromatography (20-60% gradient ethyl acetate in hexane) to provide the title compound. MS (DCI/NH$_3$) m/z 443 (M+H)$^+$.

Example 461B 2-(benzyloxymethyl)-4-(4-fluoro-3-(2-oxoazetidin-1-yl)phenyl)-5,6,7,8-tetrahydrophthalazin-1(2H)-one A microwave reactor tube was charged with EXAMPLE 461A (137 mg, 0.309 mmol), tris(dibenzylideneacetone)dipalladium(0) (28.3 mg, 0.031 mmol), 4,5-bis(diphenylphosphino)-9,9-dimethylxanthene (Xantphos) (26.9 mg, 0.046 mmol), 2-azetidinone (44 mg, 0.619 mmol), and potassium phosphate tribasic (98 mg, 0.464 mmol). Anhydrous dioxane (3 mL) was added. The suspension was purged with nitrogen, and was capped with a microwave septum. The reaction mixture was heated in a CEM Explorer® microwave reactor (Matthews, N.C.) at 200° C. for 50 minutes. After cooling, the reaction mixture was partitioned between ethyl acetate and brine. The organic phase was washed with water, and concentrated. The residue was separated by flash chromatography (20-70% gradient ethyl acetate in hexane) to provide the title compound. MS (DCI/NH$_3$) m/z 434 (M+H)$^+$.

Example 461C 4-(4-fluoro-3-(2-oxoazetidin-1-yl)phenyl)-5,6,7,8-tetrahydrophthalazin-1(2H)-one To a solution of EXAMPLE 461B (140 mg, 0.323 mmol) in methanol (10 mL) was added 20% palladium hydroxide on carbon (80 mg) under nitrogen. This suspension was purged with hydrogen, and stirred under hydrogen (balloon) at 50° C. for 4 hours. The mixture was filtered, and the filtrate was concentrated. The residue was recrystallized from methanol (4 mL) to provide the title compound. The mother liquor was separated by HPLC (Zorbax® C-18 ODS packing material [Agilent Technologies. Santa Clara, Calif.), 250×2.54 column. Mobile phase A: 0.1% TFA in H$_2$O; B: 0.1% TFA in CH$_3$CN; 0-100% gradient) to provide additional title compound. MS (DCI/NH$_3$) m/z 314 (M+H)$^+$; $^1$H NMR (400 MHz, DMSO-d$_6$), δ 1.57-1.63 (m, 2H), 1.67-1.74 (m, 2H), 2.33 (t, J=5.83 Hz, 2H), 2.45 (t, J=6.14 Hz, 2H), 3.14-3.18 (m, 2H), 3.86-3.90 (m, 2H), 7.16-7.21 (m, 1H), 7.34 (dd, J=11.66, 8.59 Hz, 1H), 7.93 (dd, J=7.52, 2.30 Hz, 1H), 12.89 (s, 1H).

Example 462

2-fluoro-5-((5-oxo-5,6-dihydropyrido(2,3-d)pyridazin-8-yl)methyl)benzamide

Example 462A methyl 2-fluoro-5-((5-oxo-5,6-dihydropyrido(3,2-d)pyridazin-8-yl)methyl)benzoate The title compound was prepared according to the procedure for EXAMPLE 66C, substituting EXAMPLE 415 for EXAMPLE 66B. MS (DCI/NH$_3$) m/z 314 (M+H)$^+$.

Example 462B 2-fluoro-5-((5-oxo-5,6-dihydropyrido(2,3-d)pyridazin-8-yl)methyl)benzamide A solution of EXAMPLE 462A (1 g, 3.2 mmol) in 7N ammonia in methanol (5 ml) was heated at 70° C. overnight, and cooled to room temperature. The solid was collected by filtration, washed with methanol and dried to provide the title compound. MS (DCI/NH$_3$) m/z 299 (M+H)$^+$.

Example 463

8-(3-amino-4-fluorobenzyl)pyrido(2,3-d)pyridazin-5(6H)-one

A mixture of 1.5 N aqueous KOH solution (2 ml) and 3 g of ice was treated with bromine (80 mg, 0.5 mmol) at −10° C. for 10 minutes. EXAMPLE 462 (100 mg, 0.3 mmol) was added. The reaction mixture was stirred at −10° C. for an additional 10 minutes, and was then allowed to warm up to 65° C. for 1 hour. After cooling, the mixture was partitioned between ethyl acetate and brine. The organic phase was washed with brine, and concentrated to about 10 mL. The solid was collected by filtration, washed with methanol, and dried to provide the title compound. MS (DCI/NH$_3$) m/z 271 (M+H)$^+$.

Example 464

8-(4-fluoro-3-(2-oxopyrrolidin-1-yl)benzyl)-2,3,4,6-tetrahydropyrido(2,3-d)pyridazin-5(1H)-one Example 464A 6-(benzyloxymethyl)-8-(3-bromo-4-fluorobenzyl)pyrido(3,2-d)pyridazin-5(6H)-one A solution of EXAMPLE 415 (1 g, 3 mmol) in anhydrous dimethylformamide (100 ml) was treated with potassium t-butoxide (1N solution in tetrahydrofuran, 3 mL, 3 mmol) at room temperature for 30 minutes. Benzyloxychloromethane (0.6 g, 3.6 mmol) was then added, and the mixture was stirred at room temperature overnight. After quenching with water, the reaction mixture was partitioned between ethyl acetate and brine. The organic layer was washed with brine, and concentrated. The residue was purified by flash chromatography (85% ethyl acetate in hexane) to provide the title compound. MS (DCI/NH$_3$) m/z 454 (M+H)$^+$.

Example 464B 6-(benzyloxymethyl)-8-(4-fluoro-3-(2-oxopyrrolidin-1-yl)benzyl)pyrido(3,2-d)pyridazin-5(6H)-one The title compound was prepared according to procedure for EXAMPLE 101, substituting EXAMPLE 464A for EXAMPLE 103. MS (ESI) m/z 459 (M+H)$^+$.

Example 464C 8-(4-fluoro-3-(2-oxopyrrolidin-1-yl)benzyl)-2,3,4,6-tetrahydropyrido(2,3-d)pyridazin-5(1H)-one A mixture of EXAMPLE 464B (130 mg, 0.28 mmol), 5% platinum on carbon (25 mg), 5% Pd(OH)$_2$ on carbon (25 mg), concentrated aqueous HCl (66 μL) and dimethylformamide (10 ml) was stirred in a pressure vessel at room temperature under 40 psi of hydrogen for 48 hours. The volatiles were removed, the residue was separated by HPLC (Zorbax® C-18 ODS packing material [Agilent Technologies, Santa Clara, Calif.], 0.1% TFA/CH$_3$CN/H$_2$O) to provide the title product as TFA salt. MS (ESI) m/z 343 (M+H)$^+$; $^1$H NMR (300 MHz, DMSO-d$_6$): δ 1.57-1.81 (m, 2H), 2.01-2.18 (m, 2H), 2.26-2.46 (m, 4H), 3.17 (m, 2H), 3.72 (t, J=6.94 Hz, 2H), 3.84 (s, 2H), 6.39 (s, 1H), 7.16-7.19 (m, 1H), 7.18-7.25 (m, 1H), 7.29 (dd, J=7.54, 1.98 Hz, 1H), 11.89 (s, 1H).

Example 465 methyl 2-fluoro-5-((5-oxo-1,2,3,4,5,6-hexahydropyrido(2,3-d)pyridazin-8-yl)methyl)benzoate The title compound was prepared as TFA salt according to procedure for EXAMPLE 414, substituting EXAMPLE 462A for EXAMPLE 369. MS (EST) m/z 318 (M+H)$^+$; $^1$H NMR (300 MHz, DMSO-d$_6$): δ 1.61-1.75 (m, 2H), 2.34 (t, J=6.15 Hz, 2H), 3.17 (m, 2H), 3.44 (s, 3H), 3.84 (s, 2H), 6.39 (s, 1H), 7.27 (dd, J=10.91, 8.53 Hz, 1H), 7.46-7.56 (m, 1H), 7.76 (dd, J=7.14, 2.38 Hz, 1H), 11.84 (s, 1H).

Example 467

8-(3-amino-4-fluorobenzyl)-2,3,4,6-tetrahydropyrido(2,3-d)pyridazin-5(1H)-one

The title compound was prepared as TFA salt according to procedure for EXAMPLE 414, substituting EXAMPLE 463 for EXAMPLE 369. MS (ESI) m/z 275 (M+H)$^+$; $^1$H NMR (300 MHz, DMSO-d$_6$): 1.62-1.74 (m, 2H), 2.35 (t, J=6.27 Hz, 2H), 3.10-3.23 (m, 2H), 3.69 (s, 2H), 4.91 (s, 2H), 6.25 (s, 1H), 6.45-6.54 (m, 1H), 6.64 (dd, J=8.82, 2.03 Hz, 1H), 6.92 (dd, J=11.53, 8.48 Hz, 1H), 11.93 (s, 1H).

Example 468

2-fluoro-5-((5-oxo-1,2,3,4,5,6-hexahydropyrido(2,3-d)pyridazin-8-yl)methyl)benzoic acid The title compound was prepared according to procedure for EXAMPLE 288, substituting EXAMPLE 465 for EXAMPLE 266. MS (EST) m/z 304 (M+H)$^+$; $^1$H NMR (300 MHz, DMSO-d$_6$): δ 1.61-1.77 (m, 2H), 2.34 (t, J=6.10 Hz, 2H), 3.06-3.25 (m, 2H), 3.84 (s, 2H), 6.36 (s, 1H), 7.22 (dd, J=10.85, 8.48 Hz, 1H), 7.39-7.52 (m, 1H), 7.73 (dd, J=7.12, 2.37 Hz, 1H), 11.82 (s, 1H) 13.19 (s, 1H).

Example 470

N-ethyl-2-fluoro-5-((5-oxo-1,2,3,4,5,6-hexahydropyrido(2,3-d)pyridazin-8-yl)methyl)benzamide The title compound was prepared as TFA salt according to procedure for EXAMPLE 48, substituting EXAMPLE 468 for EXAMPLE 48C, and ethylamine for 1-(3-dimethylaminopropyl)-3-ethylcarbodiimide. MS (ESI) m/z 331 (M+H)$^+$; $^1$H NMR (300 MHz, DMSO-d$_6$): 1.09 (t, J=7.14 Hz, 3H), 1.58-1.74 (m, 2H), 2.34 (t, J=6.15 Hz, 2H), 3.12-3.20 (m, 2H), 3.20-3.29 (m, 2H), 3.82 (s, 2H), 6.39 (s, 1H), 7.19 (dd, J=10.31, 8.33 Hz, 1H), 7.30-7.38 (m, 1H), 7.47 (dd, J=6.74, 2.38 Hz, 1H), 8.17-8.29 (m, 1H), 11.88 (s, 1H).

Example 471

N-cyclobutyl-2-fluoro-5-((5-oxo-1,2,3,4,5,6-hexahydropyrido(2,3-d)pyridazin-8-yl)methyl)benzamide The title compound was prepared as TFA salt according to procedure for EXAMPLE 48, substituting EXAMPLE 468 for EXAMPLE 48C, and cyclobutanamine for 1-(3-dimethylaminopropyl)-3-ethylcarbodiimide. MS (ESI) m/z 357 (M+H)$^+$; $^1$H NMR (300 MHz, DMSO-d$_6$): δ 1.56-1.77 (m, 4H), 1.90-2.10 (m, 2H), 2.12-2.28 (m, 2H), 2.33 (t, J=6.35 Hz, 2H), 3.05-3.25 (m, 2H), 3.81 (s, 2H), 4.27-4.45 (m, 1H), 6.35 (s, 1H), 7.18 (dd, J=10.31, 8.33 Hz, 1H), 7.26-7.37 (m, 1H), 7.42 (dd, J=6.74, 2.38 Hz, 1H), 8.49 (d, J=7.54 Hz, 1H), 11.84 (s, 1H).

Example 472

2-fluoro-5-((5-oxo-1,2,3,4,5,6-hexahydropyrido(2,3-d)pyridazin-8-yl)methyl)-N-(2-pyrrolidin-1-ylethyl)benzamide The title compound was prepared as TFA salt according to procedure for EXAMPLE 48, substituting EXAMPLE 468 for EXAMPLE 48C, and 2-(pyrrolidin-1-yl)ethanamine for 1-(3-dimethylaminopropyl)-3-ethylcarbodiimide. MS (ESI) m/z 400 (M+H)$^+$; $^1$H NMR (300 MHz, DMSO-d$_6$): δ 1.63-1.76 (m, 2H), 1.76-1.93 (m, 2H), 1.93-2.10 (m, 2H), 2.34 (t, J=6.10 Hz, 2H), 2.61-2.76 (m, 2H), 2.96-3.12 (m, 2H), 3.12-3.22 (m, 2H), 3.25-3.40 (m, 2H), 3.52-3.68 (m, 2H), 3.84 (s, 2H), 6.35 (s, 1H), 7.25 (dd, J=10.85, 8.48 Hz, 1H), 7.33-7.49 (m, 1H), 7.57 (dd, J=7.12, 2.37 Hz, 1H), 8.31-8.50 (m, 1H), 11.84 (s, 1H).

Example 473

8-(4-fluoro-3-((4-(morpholin-4-ylcarbonyl)piperazin-1-yl)carbonyl)benzyl)-2,3,4,6-tetrahydropyrido(2,3-d)pyridazin-5(1H)-one The title compound was prepared as TFA salt according to procedure for EXAMPLE 48, substituting EXAMPLE 468 for EXAMPLE 48C, and morpholino(piperazin-1-yl)methanone for 1-(3-dimethylaminopropyl)-3-ethylcarbodiimide. MS (EST) m/z 485 (M+H)$^+$; $^1$H NMR (300 MHz, DMSO-d): δ 1.60-1.78 (m, 2H), 2.35 (t, J=6.15 Hz, 2H), 3.05-3.28 (m, 12H), 3.51-3.58 (m, 4H), 3.60-3.70 (m, 2H), 3.82 (s, 2H), 6.41 (s, 1H), 7.16-7.29 (m, 2H), 7.29-7.37 (m, 1H), 11.92 (s, 1H).

Example 474

N-(2-fluoro-5-((5-oxo-1,2,3,4,5,6-hexahydropyrido(2,3-d)pyridazin-8-yl)methyl)phenyl)-N'-phenylpentanediamide The title compound was prepared as TFA salt according to the procedure for EXAMPLE 136, substituting EXAMPLE 467 for EXAMPLE 89, and 5-oxo-5-(phenylamino)pentanoic acid for 1-methylcyclopropanecarboxylic acid. MS (ESI) m/z 464 (M+H)$^+$; $^1$H NMR (300 MHz, DMSO-d): δ 1.62-1.75 (m, 2H), 1.81-1.96 (m, 2H), 2.34 (t, J=7.12 Hz, 4H), 2.42 (t, J=8.14 Hz, 2H), 3.09-3.22 (m, 2H), 3.77 (s, 2H), 6.30 (s, 1H), 6.93-7.07 (m, 1H), 7.14 (dd, J=10.85, 8.48 Hz, 1H), 7.22-7.34 (m, 3H), 7.59 (d, J=7.80 Hz, 2H), 7.68-7.77 (m, 1H), 9.62 (s, 1H), 9.87 (s, 1H), 11.82 (s, 1H).

Example 475

1-(2-fluoro-5-((5-oxo-1,2,3,4,5,6-hexahydropyrido(2,3-d)pyridazin-8-yl)methyl)phenyl)pyrrolidine-2,5-dione

Example 475A 4-(2-fluoro-5-((5-oxo-5,6-dihydropyrido(3,2-d)pyridazin-8-yl)methyl)phenylamino)-4-oxobutanoic acid The title compound was prepared according to procedure for EXAMPLE 3, substituting EXAMPLE 463 for EXAMPLE 2. MS (ESI) m/z 371 (M+H)$^+$.

Example 475B 1-(2-fluoro-5-((5-oxo-5,6-dihydropyrido(3,2-d)pyridazin-8-yl)methyl)phenyl)pyrrolidine-2,5-dione The title compound was prepared according to procedure for EXAMPLE 4, substituting EXAMPLE 475A for EXAMPLE 3. MS (ESI) m/z 353 (M+H)$^+$.

Example 475C 1-(2-fluoro-5-((5-oxo-1,2,3,4,5,6-hexahydropyrido (2,3-d)pyridazin-8-yl)methyl)phenyl)pyrrolidine-2,5-dione The title compound was prepared according to procedure for EXAMPLE 414, substituting EXAMPLE 475B for EXAMPLE 369. MS (ESI) m/z 357 (M+H)$^+$; $^1$H NMR (300 MHz, DMSO-d$_6$): δ 1.58-1.78 (m, 2H), 2.33 (t, J=6.27 Hz, 2H), 2.72-2.90 (m, 4H), 3.07-3.23 (m, 2H), 3.84 (s, 2H), 6.34 (s, 1H), 7.13 (dd, J=6.95, 2.20 Hz, 1H), 7.27-7.37 (m, 1H), 7.37-7.43 (m, 1H), 11.83 (s, 1H).

Example 476

N-(2-fluoro-5-((5-oxo-1,2,3,4,5,6-hexahydropyrido (2,3-d)pyridazin-8-yl)methyl)phenyl)-3-methoxypropanamide The title compound was prepared as TFA salt according to the procedure for EXAMPLE 136, substituting EXAMPLE 467 for EXAMPLE 89, and 3-methoxypropanoic acid for 1-methylcyclopropanecarboxylic acid. MS (ESI) m/z 361 (M+H)$^+$; $^1$H NMR (300 MHz, DMSO-d$_6$): δ 1.63-1.74 (m, 2H), 2.33 (t, J=6.15 Hz, 2H), 2.60 (t, J=6.15 Hz, 2H), 3.09-3.21 (m, 2H), 3.24 (s, 3H), 3.59 (t, J=6.15 Hz, 2H), 3.77 (s, 2H), 6.33 (s, 1H), 6.93-7.05 (m, 1H), 7.14 (dd, J=10.91, 8.53 Hz, 1H), 7.69-7.80 (m, 1H), 9.63 (s, 1H), 11.85 (s, 1H).

Example 477

N-(2-fluoro-5-((5-oxo-1,2,3,4,5,6-hexahydropyrido (2,3-d)pyridazin-8-yl)methyl)phenyl)-5-oxohexanamide The title compound was prepared as TFA salt according to the procedure for EXAMPLE 136, substituting EXAMPLE 467 for EXAMPLE 89, and 5-oxohexanoic acid for 1-methylcyclopropanecarboxylic acid. MS (ESI) m/z 387 (M+H)$^+$; $^1$H NMR (300 MHz, DMSO-d$_6$): 1.64-1.80 (m, 4H), 2.08 (s, 3H), 2.27-2.39 (m, 4H), 2.42-2.50 (m, 2H), 3.10-3.23 (m, 2H), 3.77 (s, 2H), 6.34 (s, 1H), 6.94-7.04 (m, 1H), 7.13 (dd, J=10.85, 8.48 Hz, 1H), 7.66-7.71 (m, 1H), 9.58 (s, 1H), 11.86 (s, 1H).

Example 478

N-(2-fluoro-5-((5-oxo-1,2,3,4,5,6-hexahydropyrido (2,3-d)pyridazin-8-yl)methyl)phenyl)-3-phenoxypropanamide The title compound was prepared as TFA salt according to the procedure for EXAMPLE 136, substituting EXAMPLE 467 for EXAMPLE 89, and 3-phenoxypropanoic acid for 1-methylcyclopropanecarboxylic acid. MS (ESI) m/z 423 (M+H)$^+$; $^1$H NMR (300 MHz, DMSO-d$_6$): δ 1.55-1.74 (m, 2H), 2.33 (t, J=6.15 Hz, 2H), 2.84 (t, J=6.15 Hz, 2H), 3.08-3.21 (m, 2H), 3.78 (s, 2H), 4.24 (t, J=6.15 Hz, 2H), 6.36 (s, 1H), 6.88-6.96 (m, 3H), 6.97-7.05 (m, 1H), 7.16 (dd, J=10.91, 8.53 Hz, 1H), 7.25-7.31 (m, 2H), 7.77 (dd, J=7.54, 1.98 Hz, 1H), 9.79 (s, 1H), 11.89 (s, 1H).

Example 479

N-(2-fluoro-5-((5-oxo-1,2,3,4,5,6-hexahydropyrido (2,3-d)pyridazin-8-yl)methyl)phenyl)-4-oxo-4-phenylbutanamide The title compound was prepared according to the procedure for EXAMPLE 136, substituting EXAMPLE 467 for EXAMPLE 89, and 4-oxo-4-phenylbutanoic acid for 1-methylcyclopropanecarboxylic acid. MS (ESI) m/z 435 (M+H)$^+$; $^1$H NMR (300 MHz, DMSO-d$_6$): δ 1.63-1.73 (m, 2H), 2.32 (t, J=5.95 Hz, 2H), 2.75-2.79 (m, 2H), 3.08-3.19 (m, 2H), 3.27-3.36 (m, 2H), 3.75 (s, 2H), 6.27 (s, 1H), 6.91-7.04 (m, 1H), 7.14 (dd, J=10.91, 8.53 Hz, 1H), 7.54 (t, J=7.54 Hz, 2H), 7.59-7.69 (m, 1H), 7.70-7.77 (m, 1H), 7.94-8.03 (m, 2H), 9.74 (s, 1H), 11.78 (s, 1H).

Example 481

2-(4-(benzyloxy)phenoxy)-N-(2-fluoro-5-((5-oxo-1, 2,3,4,5,6-hexahydropyrido(2,3-d)pyridazin-8-yl) methyl)phenyl)acetamide The title compound was prepared as TFA salt according to the procedure for EXAMPLE 136, substituting EXAMPLE 467 for EXAMPLE 89, and 2-(4-(benzyloxy)phenoxy)acetic acid for 1-methylcyclopropanecarboxylic acid. MS (ESI) m/z 515 (M+H)$^+$; $^1$H NMR (300 MHz, DMSO-d$_6$): δ 1.53-1.81 (m, 2H), 2.22-2.39 (m, 2H), 3.07-3.21 (m, 2H), 3.78 (s, 2H), 4.66 (s, 2H), 5.04 (s, 2H), 6.34 (s, 1H), 6.83-6.99 (m, 4H), 7.02-7.10 (m, 1H), 7.14-7.23 (m, 1H), 7.30-7.37 (m, 2H), 7.37-7.46 (m, 3H), 7.65 (dd, J=7.54, 1.98 Hz, 1H), 9.77 (s, 1H), 11.84 (s, 1H).

Example 483

N-(2-fluoro-5-((5-oxo-1,2,3,4,5,6-hexahydropyrido (2,3-d)pyridazin-8-yl)methyl)phenyl)-2-(4-methoxyphenoxy)acetamide The title compound was prepared as TFA salt according to the procedure for EXAMPLE 136, substituting EXAMPLE 467 for EXAMPLE 89, and 2-(4-methoxyphenoxy)acetic acid for 1-methylcyclopropanecarboxylic acid. MS (ESI) m/z 438 (M+H)$^+$; $^1$H NMR (300 MHz, DMSO-d$_6$): 1.63-1.75 (m, 2H), 2.33 (t, J=6.27 Hz, 2H), 3.08-3.24 (m, 2H), 3.70 (s, 3H), 3.79 (s, 2H), 4.66 (s, 2H), 6.35 (s, 1H), 6.84-6.96 (m, 4H), 7.01-7.11 (m, 1H), 7.18 (dd, J=10.85, 8.48 Hz, 1H), 7.66 (dd, J=7.63, 2.20 Hz, 1H), 9.73 (s, 1H), 11.85 (s, 1H).

Example 484

N-cyclopropyl-2-fluoro-5-((5-oxo-1,2,3,4,5,6-hexahydropyrido(2,3-d)pyridazin-8-yl)methyl)benzamide The title compound was prepared as TFA salt according to procedure for EXAMPLE 48, substituting EXAMPLE 468 for EXAMPLE 48C, and cyclopropanamine for 1-(3-dimethylaminopropyl)-3-ethylcarbodiimide. MS (ESI) m/z 343 (M+H)$^+$; $^1$H NMR (300 MHz, DMSO-d$_6$): 0.44-0.59 (m, 2H), 0.63-0.76 (m, 2H), 1.60-1.78 (m, 2H), 2.34 (t, J=6.35 Hz, 2H), 2.74-2.90 (m, 1H), 3.09-3.22 (m, 2H), 3.81 (s, 2H), 6.39 (s, 1H), 7.03-7.25 (m, 1H), 7.25-7.37 (m, 1H), 7.42 (dd, J=6.74, 2.38 Hz, 1H), 8.33 (d, J=3.97 Hz, 1H), 11.89 (s, 1H).

Example 485

8-(3-((4-(2-ethoxyethyl)piperazin-1-yl)carbonyl)-4-fluorobenzyl)-2,3,4,6-tetrahydropyrido(2,3-d)pyridazin-5(1H)-one The title compound was prepared as TFA salt according to procedure for EXAMPLE 48, substituting EXAMPLE 468 for EXAMPLE 48C, and 1-(2-ethoxyethyl)piperazine for 1-(3-dimethylaminopropyl)-3-ethylcarbodiimide. MS (ESI) m/z 444 (M+H)$^+$; $^1$H NMR (300 MHz, DMSO-d$_6$): 1.09 (t, J=9.0 Hz, 3H), 1.61-1.76 (m, 2H), 2.56-2.69 (m, 2H), 3.01-3.11 (m, 2H), 3.11-3.24 (m, 4H), 3.35-3.43 (m, 4H), 3.43-3.61 (m, 4H), 3.82 (s, 2H), 6.35 (s, 1H), 7.18-7.26 (m, 1H), 7.28-7.34 (m, 1H), 7.34-7.41 (m, 1H), 11.84 (s, 1H).

Example 486

2-fluoro-5-((5-oxo-1,2,3,4,5,6-hexahydropyrido(2,3-d)pyridazin-8-yl)methyl)-N-(2-piperidin-1-ylethyl)benzamide The title compound was prepared according to procedure for EXAMPLE 48, substituting EXAMPLE 468 for EXAMPLE 48C, and 2-(piperidin-1-yl)ethanamine for 1-(3-dimethylaminopropyl)-3-ethylcarbodiimide. MS (ESI) m/z 414 (M+H)$^+$; $^1$H NMR (300 MHz, DMSO-d$_6$): 1.33-1.49 (m, 2H), 1.50-1.64 (m, 4H), 1.62-1.75 (m, 2H), 2.33 (t, J=6.35 Hz, 2H), 2.54-2.82 (m, 4H), 3.10-3.20 (m, 2H), 3.20-3.35 (m, 2H), 3.37-3.55 (m, 2H), 3.82 (s, 2H), 6.35 (s, 1H), 7.20 (dd, J=10.51, 8.53 Hz, 1H), 7.33-7.44 (m, 1H), 7.53 (dd, J=7.14, 2.38 Hz, 1H), 8.51 (dd, J=4.36, 1.59 Hz, 1H) 11.83 (s, 1H).

Example 487

2-fluoro-5-((5-oxo-1,2,3,4,5,6-hexahydropyrido(3,2-d)pyridazin-8-yl)methyl)-N-(2-oxo-2-(piperidin-1-yl)ethyl)benzamide The title compound was prepared according to procedure for EXAMPLE 48, substituting EXAMPLE 468 for EXAMPLE 48C, and 2-amino-1-(piperidin-1-yl)ethanone for 1-(3-dimethylaminopropyl)-3-ethylcarbodiimide. MS (ESI) m/z 428 (M+H)$^+$; $^1$H NMR (300 MHz, DMSO-d$_6$): 1.44 (m, 2H), 1.48-1.65 (m, 4H), 1.65-1.79 (m, 2H), 2.33 (t, J=6.27 Hz, 2H), 3.10-3.24 (m, 2H), 3.34-3.42 (m, 2H), 3.41-3.50 (m, 2H), 3.84 (s, 2H), 4.13 (d, J=5.09 Hz, 2H), 6.00-6.50 (m, 1H), 7.05-7.28 (m, 1H), 7.32-7.53 (m, 1H), 7.63 (dd, J=7.12, 2.37 Hz, 1H), 8.17 (q, J=5.09 Hz, 1H), 11.82 (s, 1H).

Example 490

4-(4-fluoro-3-((4-pyrimidin-2-ylpiperazin-1-yl)carbonyl)benzyl)-5,6,7,8-tetrahydrophthalazin-1(2H)-one To a solution of EXAMPLE 1 (100 mg, 0.33 mmol) in dimethlyacetamide (5 mL) was added 2-(1H-7-azabenzotriazol-1-yl)-1,1,3,3-tetramethyl uronium hexafluorophosphate methanaminium (HATU) (126 mg, 0.33 mmol) and triethylamine (92 µL, 0.66 mmol) and stirred for 20 minutes at room temperature. (Piperazin-1-yl)pyrimidine dihydrochloride (78 mg, 0.33 mmol) was then added and the reaction mixture was stirred at room temperature for 16 hours. After concentration, the residual oil was purified by HPLC (Zorbax®J C-18 ODS packing material [Agilent Technologies, Santa Clara, Calif.], 0.1% TFA/CH$_3$CN/H$_2$O) to provide the title product. MS (DCI/NH$_3$) m/z 449 (M+H)$^+$; $^1$H NMR (300 MHz, DMSO-d$_6$): δ 1.53-1.71 (m, 4H), 2.32-2.44 (m, 4H), 3.24-3.39 (m, 2H), 3.67-3.78 (m, 4H), 3.79-3.88 (m, 2H), 3.93 (s, 2H), 6.67 (t, J=4.75 Hz, 1H), 7.21-7.23 (m, 1H), 7.24-7.28 (m, 1H), 7.30-7.35 (m, 1H), 8.39 (d, J=4.75 Hz, 2H), 12.62 (br s, 1H).

Example 491

4-(4-fluoro-3-(2-oxopyrrolidin-1-yl)phenyl)-5,6,7,8-tetrahydrophthalazin-1(2H)-one The title compound was prepared according to the procedure for EXAMPLE 461, substituting 2-pyrrolidinone for 2-azetidinone in EXAMPLE 461B. MS (DCI/NH$_3$) m/z 328 (M+H)$^+$; $^1$H NMR (400 MHz, CD$_2$OD): δ 1.73-1.79 (m, 2H), 1.83-1.90 (m, 2H), 2.22-2.29 (m, 2H), 2.55-2.60 (m, 4H), 2.69 (t, J=5.83 Hz, 2H), 3.91 (t, J=7.06 Hz, 2H), 7.35-7.41 (m, 1H), 7.48-7.52 (m, 1H), 7.60-7.64 (m, 1H).

Example 492

4-(3-{[4-(cyclopropylcarbonyl)piperazin-1-yl]carbonyl}-4-fluorobenzyl)-5,6,7,8-tetrahydrophthalazin-1(2H)-one

Example 492A 3-hydroxy-4,5,6,7-tetrahydroisobenzofuran-1(3H)-one

To a solution of 1-cyclohexene-1,2-dicarboxylic anhydride (25.2 g, 165.6 mmol) in tetrahydrofuran (125 mL) placed in an ice bath was added sodium borohydride (1.51 g, 39.97 mmol). The ice bath was removed and the mixture was stirred at room temperature for 30 minutes, and under reflux for 5 hours. After cooling to room temperature, 1N HCl was added, and the reaction mixture concentrated. The residue was partitioned between ethyl acetate and brine. The organic layer was washed with brine, water and concentrated. The residue was purified by flash chromatography on silica gel eluting with 50% ethyl acetate in hexanes to provide the title compound. MS (ESI) m/z 155 (M+H)$^+$.

Example 492B tributyl(3-oxo-1,3,4,5,6,7-hexahydroisobenzofuran-1-yl)phosphonium bromide To a flask charged with EXAMPLE 1A (3.0 g, 19.5 mmol) in acetic acid (10 mL) was added tri-n-butyl phosphine (4.81 mL, 19.5 mmol) and a 33% solution of HBr in acetic acid (3.34 mL, 13.65 mmol). The reaction mixture was refluxed for 21 hours, and concentrated. The residue was purified by flash chromatography on silica gel eluting with 10% methanol in dichloromethane to provide the title compound. MS (DCI/NH$_3$) m/z 420 (M+H)$^+$.

Example 492C (E)-3-(3-bromo-4-fluorobenzylidene)-2,3,4,5,6,7-hexahydro-1H-inden-1-one To a solution of EXAMPLE 492B (27.3 g, 65 mmol) in anhydrous dichloromethane (200 mL) was added 3-bromo-4-fluorobenzaldehyde (13.2 g, 65 mmol) and triethylamine (9.0 mL, 65 mmol). The reaction mixture was stirred at ambient temperature for 18 hours, and concentrated. The residue was partitioned between ethyl acetate and brine. The organics were concentrated, and purified by flash chromatography on silica gel eluting with 50% ethyl acetate in hexanes to provide the title compound. MS (DCI/NH$_3$) m/z 325 (M+H)$^+$.

Example 492D 4-(3-bromo-4-fluorobenzyl)-5,6,7,8-tetrahydrophthalazin-1(2H)-one

A solution of EXAMPLE 492C (16 g, 49.5 mmol) in ethanol (200 mL) was treated with hydrazine monohydrate (4.8 mL, 99 mmol) at 80° C. for 2 hours, and cooled to room temperature. The mixture was filtered and the solid was dried to provide the title compound. MS (DCI/NH$_3$) m/z 339 (M+H)$^+$.

Example 492E methyl 2-fluoro-5-((4-oxo-3,4,5,6,7,8-hexahydrophthalazin-1-yl)methyl)benzoate A 250 mL pressure bottle was charged with EXAMPLE 492D (7.3 g, 21.65 mmol), a mixture of methanol (60 mL) and N,N-dimethylformamide (5 mL), [1,1'-bis(diphenylphosphino)ferrocene]dichloropalladium(II) (0.317 g, 0.433 mmol), and triethylamine (6.04 ml, 43.3 mmol). The mixture was purged, and pressurized with carbon monoxide (60 psi), and stirred at 110° C. for 16 hours. Solid material was filtered off, and the filtrate was concentrated. The residue was purified by flash chromatography on silica gel eluting with 50% ethyl acetate in hexanes to provide the title compound. MS (DCI/NH$_3$) m/z 317 (M+H)$^+$.

Example 492F 2-fluoro-5-((4-oxo-3,4,5,6,7,8-hexahydrophthalazin-1-yl)methyl)benzoic acid A solution of EXAMPLE 492E (5.7 g, 18 mmol) in 1:1 tetrahydrofuran/water (100 mL) was treated with lithium hydroxide monohydrate (1.5 g, 36 mmol) at ambient temperature for 16 hours. The reaction mixture was acidified with 2 N HCl to a pH 3, and concentrated. The residue was partitioned between ethyl acetate and brine. The organics were concentrated and dried to provide the title compound. MS (DCI/NH$_3$) m/z 303 (M+H)$^+$.

Example 492G 4-(3-{[4-(cyclopropylcarbonyl)piperazin-1-yl]carbonyl}-4-fluorobenzyl)-5,6,7,8-tetrahydrophthalazin-1(2H)-one To a solution of EXAMPLE 492F (390 mg, 1.3 mmol) in dimethylacetamide (10 mL) was added 2-(1H-7-azabenzotriazol-1-yl)-1,1,3,3-tetramethyl uronium hexafluorophosphate methanaminium (HATU) and triethylamine (0.36 mL, 2.6 mmol). The reaction mixture was stirred at ambient temperature for 16 hours and concentrated. The residue was partitioned between ethyl acetate and brine. The organics were concentrated, and the residue was purified by HPLC (Zorbax C-18, 0.1% TFA/CH$_3$CN/H$_2$O) to provide the title compound as the TFA salt. The TFA salt was dissolved in a mixture of methylene chloride and methanol, and treated with 1M HCl in ether. Concentration of the mixture yielded the title compound as the HCl salt. MS (DCI/NH$_3$) m/z 439 (M+H)$^+$; $^1$H NMR (CD$_3$OD) δ 0.79-0.93 (m, 4H), 1.70-1.76 (m, 4H), 1.86-2.05 (m, 1H), 2.46-2.57 (m, 4H), 3.33-3.45 (m, 2H), 3.52-3.64 (m, 2H), 3.65-3.78 (m, 2H), 3.80-3.93 (m, 2H), 4.03 (s, 2H), 7.17 (t, J=8.92 Hz, 1H), 7.24-7.29 (m, 1H), 7.33-7.40 (m, 1H).

Example 493 methyl 4-({2-fluoro-5-[(4-oxo-3,4,5,6,7,8-hexahydrophthalazin-1-yl)methyl]phenyl}amino)-4-oxobutanoate Example 493A 3-(benzyloxycarbonylamino)-4-fluorobenzoic acid To a solution of 3-amino-4-fluorobenzoic acid (30 g, 193 mmol) in a mixture of tetrahydrofuran (300 mL) and water (300 mL) was added cesium carbonate (157 g, 483 mmol) and benzyl chloroformate (30.4 mL, 213 mmol). This mixture was stirred at ambient temperature for 16 hours, and was concentrated to about 200 mL. The residue was acidified with 2N HCl to a pH 3, and was partitioned between ethyl acetate and brine. The precipitated solid was collected by filtration, washed with ethyl acetate and water, and dried to provide the title compound. MS (DCI/NH$_3$) m/z 290 (M+H)$^+$.

Example 493B benzyl 2-fluoro-5-(methoxy(methyl)carbamoyl)phenylcarbamate

To a solution of EXAMPLE 493A (38.4 g, 133 mmol) in a mixture of dioxane (500 mL) and dichloromethane (200 mL) was added N,O-dimethylhydroxylamine hydrochloride (29.2 g, 299 mmol) and triethylamine. 1-Ethyl-3-(3-dimethylaminopropyl) carbodiimide hydrochloride (EDC) (57.3 g, 299 mmol) and N-hydroxybenzotriazole (HOBt) (40.4 g, 299 mmol) were added. The reaction mixture stirred at room temperature for 16 hours and concentrated. The crude mixture was partitioned between ethyl acetate and water. The organic layer was washed with brine, and concentrated. The residue was purified by flash chromatography eluting with 40% ethyl acetate in hexanes to provide the title compound. MS (DCI/NH$_3$) m/z 333 (M+H)$^+$.

Example 493C

To a solution of EXAMPLE 493B (27 g, 81 mmol) in anhydrous tetrahydrofuran (100 mL) was added lithium aluminum hydride solution (1M) in tetrahydrofuran (41 mL) at 0° C. After stirring at 0° C. for 15 minutes, the reaction was quenched with water. The mixture was partitioned between ethyl acetate and dilute aqueous HCl solution. The organics were washed with water and concentrated. The residue was purified by flash chromatography eluting with 25% ethyl acetate in hexanes to provide the title compound. MS (DCI/NH$_3$) m/z 274 (M+H)$^+$.

Example 493D (Z)-benzyl 2-fluoro-5-((3-oxo-4,5,6,7-tetrahydroisobenzofuran-1(3H)-ylidene)methyl)phenylcarbamate To a solution of EXAMPLE 492B (25.2 g, 60.2 mmol) in dichloromethane (200 mL) was added EXAMPLE 493C (16.5 g, 60.2 mmol) and triethylamine (8.3 mL, 60.2 mmol). The reaction mixture was stirred at ambient temperature for 16 hours and concentrated. Ethyl acetate was added and the mixture washed with water and brine. The organics were concentrated and dried to provide the title compound. MS (DCI/NH$_3$) m/z 394 (M+H)$^+$.

Example 493E benzyl 2-fluoro-5-((4-oxo-3,4,5,6,7,8-hexahydrophthalazin-1-yl)methyl)phenylcarbamate To a solution of EXAMPLE 493D (14.6 g, 37.1 mmol) in ethanol (150 mL) was added hydrazine monohydrate (3.6 mL, 74.2 mmol) and the mixture was heated at 80° C. for 16 hours. The mixture was cooled and the precipitated solid was filtered and dried to provide the title compound. MS (DCI/NH$_3$) m/z 408 (M+H)$^+$.

Example 493F 4-(3-amino-4-fluorobenzyl)-5,6,7,8-tetrahydrophthalazin-1(2H)-one

To a solution of EXAMPLE 493E (1.65 g, 4.05 mmol) in tetrahydrofuran (100 mL) was added 20% Pd(OH)$_2$/C (0.32 g) under nitrogen. The suspension was purged, and pressurized with hydrogen at 30 psi with stirring for 1 hour. The solid material was filtered off and the filtrate concentrated to provide the title compound. MS (DCI/NH$_3$) m/z 274 (M+H)$^+$.

Example 493G 4-(2-fluoro-5-((4-oxo-3,4,5,6,7,8-hexahydrophthalazin-1-yl)methyl)phenylamino)-4-oxobutanoic acid To a solution of EXAMPLE 493F (1.1 g, 4 mmol) in a mixture of acetonitrile (20 mL) and dioxane (20 mL) was added succinic anhydride (800 mg, 8 mmol). The mixture was stirred at 80° C. for 18 hours, and concentrated. The crude solid was triturated from methanol to provide the title compound. MS (DCI/NH$_3$) m/z 374 (M+H)$^+$.

Example 493H methyl 4-({2-fluoro-5-[(4-oxo-3,4,5,6,7,8-hexahydrophthalazin-1-yl)methyl]phenyl}amino)-4-oxobutanoate To a solution of EXAMPLE 493G (230 mg, 0.6 mmol) in N,N-dimethylformamide (8 mL) was added potassium bicarbonate (123 mg, 1.23 mmol) and iodomethane (0.08 mL, 1.23 mmol). The mixture was stirred at room temperature for 16 hours and was concentrated. The residue was purified by flash chromatography on silica gel eluting with 8% methanol in dichloromethane to provide the title compound. MS (DCI/NH$_3$) m/z 388 (M+H)$^+$; $^1$H NMR (DMSO-d$_6$) δ 1.52-1.69 (m, 4H), 2.27-2.43 (m, 4H), 2.53-2.61 (m, 2H), 2.61-2.68 (m, 2H), 3.59 (s, 3H), 3.85 (s, 2H), 6.89-6.96 (m, 1H), 7.15 (dd, J=11.10, 8.33 Hz, 1H), 7.72 (d, J=7.54 Hz, 1H), 9.72 (s, 1H), 12.61 (s, 1H).

Example 494

4-{2-fluoro-5-[(4-oxo-3,4,5,6,7,8-hexahydrophthalazin-1-yl)methyl]benzoyl}-N,N-dimethylpiperazine-1-carboxamide The title compound was prepared, using the appropriate reagents, as the TFA salt according to the procedure for EXAMPLE 492. MS (DCI/NH$_3$) m/z 442 (M+H)$^+$; $^1$H NMR (CD$_3$OD) δ 1.67-1.76 (m, 4H), 2.41-2.48 (m, 2H), 2.48-2.55 (m, 2H), 2.86 (s, 6H), 3.17-3.23 (m, 2H), 3.32-3.40 (m, 4H), 3.75-3.82 (m, 2H), 3.99 (s, 2H), 7.12-7.18 (m, 1H), 7.23 (dd, J=6.29, 2.30 Hz, 1H), 7.32-7.37 (m, 1H).

Example 495

4-(4-fluoro-3-{[4-(piperidin-1-ylcarbonyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 492. MS (DCI/NH$_3$) m/z 482 (M+H)$^+$; $^1$H NMR (CD$_3$OD) δ 1.52-1.59 (m, 4H), 1.60-1.67 (m, 2H), 1.69-1.77 (m, 4H), 2.41-2.47 (m, 2H), 2.48-2.54 (m, 2H), 3.18-3.22 (m, 2H), 3.23-3.28 (m, 4H), 3.33-3.40 (m, 4H), 3.75-3.80 (m, 2H), 3.99 (s, 2H), 7.15 (t, J=8.90 Hz, 1H), 7.23 (dd, J=6.44, 2.15 Hz, 1H), 7.32-7.37 (m, 1H).

Example 496

4-{4-fluoro-3-[(4-pyrazin-2-ylpiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 492. MS (DCI/NH$_3$) m/z 449 (M+H)$^+$; $^1$H NMR (CD$_3$OD) δ 1.69-1.78 (m, 4H), 2.42-2.48 (m, 2H), 2.49-2.57 (m, 2H), 3.44-3.51 (m, 2H), 3.61-3.69 (m, 2H), 3.74-3.80 (m, 2H), 3.87-3.92 (m, 2H), 4.00 (s, 2H), 7.13-7.21 (m, 1H), 7.26 (dd, J=6.29, 2.30 Hz, 1H), 7.34-7.39 (m, 1H), 7.83 (d, J=2.46 Hz, 1H), 8.16 (dd, J=2.61, 1.38 Hz, 1H), 8.25 (s, 1H).

Example 497

4-{4-fluoro-3-[(4-pyridin-4-ylpiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 492. MS (DCI/NH$_3$) m/z 448 (M+H)$^+$; $^1$H NMR (CD$_3$OD) δ 1.67-1.77 (m, 4H), 2.42-2.49 (m, 2H), 2.49-2.55 (m, 2H), 3.55-3.64 (m, 2H), 3.71-3.77 (m, 2H), 3.86-3.92 (m, 2H), 3.92-3.97 (m, 2H), 4.01 (s, 2H), 7.14-7.18 (m, 2H), 7.18-7.22 (m, 1H), 7.29 (dd, J=6.44, 2.46 Hz, 1H), 7.36-7.43 (m, 1H), 8.17 (d, J=7.67 Hz, 2H).

Example 498

1-{2-fluoro-5-[(4-oxo-3,4,5,6,7,8-hexahydrophthalazin-1-yl)methyl]benzoyl}piperidine-4-carboxamide The title compound was prepared, using the appropriate reagents, as the TFA salt according to the procedure for EXAMPLE 492. MS (DCI/NH$_3$) m/z 413 (M+H)$^+$.

Example 499

4-(4-fluoro-3-{[4-(6-methylpyrazin-2-yl)piperazin-1-yl]carbonyl}benzyl)-5,6,7,8-tetrahydrophthalazin-1(2H)-one The title compound was prepared, using the appropriate reagents, as the free base? according to the procedure for EXAMPLE 492. MS (DCI/NH$_3$) m/z 463 (M+H)$^+$; $^1$H NMR (CD$_3$OD) δ 1.68-1.77 (m, 4H), 2.38 (s, 3H), 2.43-2.49 (m, 2H), 2.49-2.56 (m, 2H), 3.43-3.51 (m, 2H), 3.58-3.66 (m, 2H), 3.73-3.78 (m, 2H), 3.88 (dd, J=6.44, 3.99 Hz, 2H), 4.00 (s, 2H), 7.14-7.21 (m, 1H), 7.26 (dd, J=6.44, 2.15 Hz, 1H), 7.34-7.40 (m, 1H), 7.73 (s, 1H), 8.02 (s, 1H).

Example 500

1-{2-fluoro-5-[(4-oxo-3,4,5,6,7,8-hexahydrophthalazin-1-yl)methyl]benzoyl}piperidine-3-carboxamide The title compound was prepared, using the appropriate reagents, as the free base according to the procedure for EXAMPLE 492. MS (DCI/NH$_3$) m/z 413 (M+H)$^+$.

Example 501

4-[3-({4-[2-(dimethylamino)ethyl]piperazin-1-yl}carbonyl)-4-fluorobenzyl]-5,6,7,8-tetrahydrophthalazin-1(2H)-one The title compound was prepared, using the appropriate reagents, as the TFA salt according to the procedure for EXAMPLE 492. MS (DCI/NH$_3$) m/z 442 (M+H)$^+$; $^1$H NMR (CD$_3$OD) δ 1.69-1.76 (m, 4H), 2.42-2.47 (m, 2H), 2.48-2.53 (m, 2H), 2.56-2.62 (m, 2H), 2.68-2.75 (m, 2H), 2.84 (t, J=6.14 Hz, 2H), 2.93 (s, 6H), 3.31-3.36 (m, 2H), 3.38-3.45 (m, 2H), 3.79-3.88 (m, 2H), 3.99 (s, 2H), 7.13-7.19 (m, 1H), 7.21 (dd, J=6.29, 2.30 Hz, 1H), 7.33-7.39 (m, 1H).

Example 502

4-{4-fluoro-3-[(4-methyl-1,4-diazepan-1-yl)carbonyl]benzyl}-5,6,7,8-tetrahydrophthalazin-1(2H)-one The title compound was prepared, using the appropriate reagents, as the TFA salt according to the procedure for EXAMPLE 492. MS (DCI/NH$_3$) m/z 399 (M+H)$^+$; $^1$H NMR (CD$_3$OD) δ 1.67-1.77 (m, 4H), 2.11-2.33 (m, 2H), 2.41-2.48 (m, 2H), 2.49-2.56 (m, 2H), 2.90-2.95 (m, 1H), 2.98 (s, 3H), 3.34-3.43 (m, 1H), 3.44-3.58 (m, 3H), 3.61-3.70 (m, 1H), 3.71-3.78 (m, 1H), 3.82-3.91 (m, 1H), 4.00 (s, 2H), 7.15-7.20 (m, 1H), 7.26-7.30 (m, 1H), 7.36-7.41 (m, 1H).

Example 503

4-{4-fluoro-3-[(4-hydroxypiperidin-1-yl)carbonyl]benzyl}-5,6,7,8-tetrahydrophthalazin-1(2H)-one The title compound was prepared, using the appropriate reagents, as the free base according to the procedure for EXAMPLE 492. MS (DCI/NH$_3$) m/z 386 (M+H)$^+$; $^1$H NMR (CD$_3$OD) δ 1.39-1.49 (m, 1H), 1.50-1.59 (m, 1H), 1.69-1.74 (m, 4H), 1.77-1.85 (m, 1H), 1.90-1.98 (m, 1H), 2.41-2.47 (m, 2H), 2.48-2.55 (m, 2H), 3.12-3.23 (m, 1H), 3.33-3.41 (m, 1H), 3.45-3.55 (m, 1H), 3.83-3.93 (m, 1H), 3.99 (s, 2H), 4.13-4.22 (m, 1H), 7.11-7.17 (m, 1H), 7.18-7.22 (m, 1H), 7.30-7.36 (m, 1H).

Example 504

N-[2-(dimethylamino)ethyl]-2-fluoro-N-methyl-5-[(4-oxo-3,4,5,6,7,8-hexahydrophthalazin-1-yl)methyl]benzamide The title compound was prepared, using the appropriate reagents, as the TFA salt according to the procedure for EXAMPLE 492. MS (DCI/NH$_3$) m/z 387 (M+H)$^+$; $^1$H NMR (CD$_3$OD) δ 1.69-1.76 (m, 4H), 2.42-2.47 (m, 2H), 2.48-2.54 (m, 2H), 2.99 (s, 3H), 3.01 (s, 6H), 3.45 (t, J=6.26 Hz, 2H), 3.91 (t, J=6.26 Hz, 2H), 4.00 (s, 2H), 7.15-7.20 (m, 1H), 7.28 (dd, J=6.41, 2.44 Hz, 1H), 7.37-7.41 (m, 1H).

Example 505

N,N-diethyl-1-{2-fluoro-5-[(4-oxo-3,4,5,6,7,8-hexahydrophthalazin-1-yl)methyl]benzoyl}piperidine-3-carboxamide The title compound was prepared, using the appropriate reagents, as the TFA salt according to the procedure for EXAMPLE 492. MS (DCI/NH$_3$) m/z 469 (M+H)$^+$.

Example 506

8-(3-{[4-(cyclopropylcarbonyl)piperazin-1-yl]carbonyl}-4-fluorobenzyl)-2,3,4,6-tetrahydropyrido[2,3-d]pyridazin-5(1H)-one Example 506A (3-bromo-4-fluorobenzyl)magnesium bromide To a mixture of magnesium turnings (1.36 g, 56 mmol) and 2-bromo-4-(bromomethyl)-1-fluorobenzene (5.0 g, 18.6 mmol) in diethyl ether (100 mL) was added a granule of iodine. The slightly purple suspension was stirred at ambient temperature for 5-10 minutes, and the color of the mixture disappeared. The exothermic mixture was refluxed with stirring for an additional 1 hour, and cooled to room temperature. The formed Grignard reagent was directly used in the next step without further purification.

Example 506B methyl 2-(2-(3-bromo-4-fluorophenyl)acetyl)nicotinate

To a solution of dimethylpyridine-2,3-dicarboxylate (5.45 g, 19 mmol) in tetrahydrofuran (200 mL) was added a suspension of 506A (19 mmol) at −78° C. The mixture was stirred at −78° C. for 30 minutes, and warmed to room temperature and quenched with water. This mixture was partitioned between ethyl acetate and brine. The organic phase was washed with brine and concentrated. The residue was purified by flash chromatography (15% ethyl acetate in hexane) to give the title compound. MS (DCI/NH$_3$) m/z 353 (M+H)$^+$.

Example 506C 8-(3-bromo-4-fluorobenzyl)pyrido[3,2-d]pyridazin-5(6H)-one

A solution of EXAMPLE 506B (3.2 g, 9.1 mmol) in ethanol (50 mL) was treated with hydrazine (455 mg, 9.1 mmol) at 90° C. for 5 hours. Solid precipitated, and after cooling to room temperature, was collected by filtration, washed with ethanol, and dried to give the title compound. MS (DCI/NH$_3$) m/z 335 (M+H)$^+$.

Example 506D methyl 2-fluoro-5-((5-oxo-5,6-dihydropyrido[3,2-d] pyridazin-8-yl)methyl)benzoate A 250 mL high pressure vessel was charged with EXAMPLE 506C (4.5 g, 13.47 mmol), methanol (50 mL), N,N-dimethylformamide (50 mL), [1,1'-bis(diphenylphosphino)ferrocene]dichloropalladium(II) (0.099 g, 0.135 mmol) and triethylamine (3.75 ml, 26.9 mmol). The mixture was purged and pressurized with carbon monoxide (60 psi), and stirred at 100° C. for 5 hours. Solid material was filtered off and the filtrate was concentrated. The solid was collected by filtration, washed with methanol, and dried to give the title compound. MS (DCI/NH$_3$) m/z 314 (M+H)$^+$.

Example 506E methyl 2-fluoro-5-((5-oxo-1,2,3,4,5,6-hexahydropyrido[3,2-d]pyridazin-8-yl)methyl)benzoate In a 250 mL high pressure vessel, EXAMPLE 506D (3.3 g, 10.53 mmol) and 5% Pt/C (0.330 g, 1.692 mmol) were suspended in 30 mL of acetic acid. This suspension was purged and pressurized with 30 psi of hydrogen, and stirred at ambient temperature for 32 hours.

Solid material was filtered off and the filtrate concentrated. The formed solid was collected by filtration, washed with methanol and dried to give the title compound. MS (DCI/NH$_3$) m/z 318 (M+H)$^+$.

Example 506F 2-fluoro-5-((5-oxo-1,2,3,4,5,6-hexahydropyrido[3,2-d]pyridazin-8-yl)methyl)benzoic acid A solution of EXAMPLE 506E (2.8 g, 8.8 mmol) in tetrahydrofuran (150 mL) was treated with LiOH (253 mg, 10.6 mmol) in water (20 mL) at 50° C. overnight. After cooling to room temperature, the mixture was acidified with dilute HCl to pH 4, and concentrated to about 10 mL. The solid material was collected by filtration, washed with water and dried to provide the title compound. MS (DCI/NH$_3$) m/z 305 (M+H)$^+$.

Example 506G 8-(3-{[4-(cyclopropylcarbonyl)piperazin-1-yl]carbonyl}-4-fluorobenzyl)-2,3,4,6-tetrahydropyrido[2,3-d]pyridazin-5(1H)-one To a solution of EXAMPLE 506F (100 mg, 0.33 mmol) in anhydrous N,N-dimethylformamide (2 mL) was added cyclopropyl(piperazin-1-yl)methanone (66 mg, 0.43 mmol), 1-ethyl-3-(3-dimethylaminopropyl) carbodiimide hydrochloride (EDC) (82 mg, 0.43 mmol), N-hydroxybenzotriazole (HOBT) (66 mg, 0.43 mmol) and triethyl amine (44 mg, 0.43 mmol). The reaction mixture was warmed until homogeneous. The solution was stirred at ambient temperature for 16 hours and concentrated. The residue was purified by HPLC (Zorbax C-18, 0.1% TFA/CH$_3$CN/H$_2$O) to provide the title compound as the TFA salt. MS (DCI/NH$_3$) m/z 440 (M+H); $^1$H NMR (DMSO-d$_6$) δ 0.60-0.82 (m, 4H), 1.59-1.79 (m, 2H), 1.94 (m, 1H), 2.34 (t, J=6.27 Hz, 2H), 3.00-3.35 (m, 4H), 3.38-3.79 (m, 2H), 3.82 (s, 2H), 3.83-4.11 (m, 4H), 6.37 (s, 1H), 7.15-7.27 (m, 1H), 7.24-7.30 (m, 1H), 7.30-7.40 (m, 1H), 11.87 (s, 1H).

Example 507

1-{2-fluoro-5-[(5-oxo-1,2,3,4,5,6-hexahydropyrido[2,3-d]pyridazin-8-yl)methyl]phenyl}piperidine-2,6-dione

Example 507A 2-fluoro-5-((5-oxo-5,6-dihydropyrido[3,2-d]pyridazin-8-yl)methyl)benzamide EXAMPLE 506D (1.5 g, 4.8 mmol) was suspended in a solution of NH$_3$ in methanol (7N, 50 mL) in a pressure tube. The tube was sealed and heated at 110° C. for 48 hours. After cooling to room temperature the precipitate was collected by filtration, washed with methanol, and dried to give the title compound. MS (DCI/NH$_3$) m/z 299 (M+H)$^+$.

Example 507B 8-(3-amino-4-fluorobenzyl)pyrido[3,2-d]pyridazin-5(6H)-one

To a mixture of ice (30 g) and solution of KOH (1.7 g, 30.2 mmol) in water (2 mL) was added bromine (0.17 ml, 3.35 mmol) at −10° C. After stirring at −10° C. for 10 minutes, EXAMPLE 507A (1.0 g, 3.35 mmol) was added. The mixture was stirred at −10° C. for an additional 10 minutes and at 65° C. for 1 hour. After cooling, the mixture was acidified with HCl to pH 7, and partitioned between brine and ethyl acetate. The organic phase was washed with brine, and concentrated. The residue was purified by flash chromatography (70% ethyl acetate in hexane) to give the title compound. MS (DCI/NH$_3$) m/z 299 (M+H)$^+$.

Example 507C 1-(2-fluoro-5-((5-oxo-5,6-dihydropyrido[3,2-d]pyridazin-8-yl)methyl)phenyl)piperidine-2,6-dione To a solution of EXAMPLE 507B (200 mg, 0.74 mmol) in acetonitrile (20 mL) was added dihydro-2H-pyran-2,6(3H)-dione (84 mg, 0.74 mmol). The mixture was stirred at 80° C. for 6 days and concentrated. The residue was dissolved in dichloromethane (20 mL) and treated with 1,1'-carbonyldiimidazole (CDI) (104 mg, 0.74 mmol) at ambient temperature for 5 days. The mixture was concentrated and the residue partitioned between ethyl acetate and brine. The organic phase was washed with brine, and was concentrated. The residue was purified by flash chromatography (2%-15% gradient methanol in ethyl acetate) to provide the title compound. MS (DCI/NH$_3$) m/z 367 (M+H)$^+$.

Example 507D

1-{2-fluoro-5-[(5-oxo-1,2,3,4,5,6-hexahydropyrido[2,3-d]pyridazin-8-yl)methyl]phenyl}piperidine-2,6-dione To a solution of EXAMPLE 507C (200 mg, 0.546 mmol) in N,N-dimethylformamide (20 mL) in a 100 mL pressure bottle was added 5% Pt/C (60.0 mg, 0.308 mmol) and concentrated HCl (55 μl, 1.2 eq). The reaction mixture was purged and pressurized with hydrogen (30 psi), and stirred at ambient temperature for 3 days. An additional 60 mg of 5% Pt/C and 40 μL of concentrated HCl were added and the mixture stirred at ambient temperature for 3 days. Solid material was filtered off and the filtrate was concentrated. The residue was purified by HPLC (Zorbax C-18, 0.1% TFA/CH$_3$CN/H$_2$O) to provide the title compound as the TFA salt. MS (DCI/NH$_3$) m/z 371 (M+H)$^+$; $^1$H NMR (DMSO-d$_6$) δ 1.58-1.78 (m, 2H), 1.82-2.10 (m, 2H), 2.34 (t, J=6.15 Hz, 2H), 2.76 (t, J=6.35 Hz, 4H), 3.81 (s, 2H), 3.79-4.01 (m, 2H), 6.37 (s, 1H), 7.07 (dd, J=7.14, 2.38 Hz, 1H), 7.18-7.28 (m, 1H), 7.28-7.38 (m, 1H), 11.88 (s, 1H).

Example 508

8-[3-({4-[2-(dimethylamino)ethyl]piperazin-1-yl}carbonyl)-4-fluorobenzyl]-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 371 (M+H)$^+$.

Example 509

8-{4-fluoro-3-[(4-methyl-1,4-diazepan-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 400 (M+H)$^+$

Example 510

8-{4-fluoro-3-[(4-pyridin-4-ylpiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 449 (M+H)$^+$; $^1$H NMR (DMSO-d$_6$) δ 1.60-1.82 (m, 2H), 2.35 (t, J=6.10 Hz, 2H), 3.09-3.25 (m, 2H), 3.43 (m, 2H), 3.68 (m, 2H), 3.74-3.88 (m, 4H), 3.84 (s, 2H), 6.38 (s, 1H), 7.17 (d, J=7.12 Hz, 2H), 7.21-7.29 (m, 1H), 7.28-7.33 (m, 1H), 7.34-7.42 (m, 1H), 8.30 (d, J=7.46 Hz, 2H), 11.86 (s, 1H).

Example 511

8-{4-fluoro-3-[(4-pyrazin-2-ylpiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 450 (M+H)$^+$; $^1$H NMR (DMSO-d$_6$) δ 1.61-1.76 (m, 2H), 2.34 (t, J=6.15 Hz, 2H), 3.10-3.24 (m, 2H), 3.34 (m, 2H), 3.54 (m, 2H), 3.67 (m, 2H), 3.74 (m, 2H), 3.83 (s, 2H), 6.43 (s, 1H), 7.20-7.27 (m, 1H), 7.28 (dd, J=6.54, 2.18 Hz, 1H), 7.31-7.38 (m, 1H), 7.87 (d, J=2.78 Hz, 1H), 8.10 (d, J=2.78 Hz, 1H), 8.32 (s, 1H), 11.95 (s, 1H).

Example 512

4-{2-fluoro-5-[(5-oxo-1,2,3,4,5,6-hexahydropyrido[2,3-d]pyridazin-8-yl)methyl]benzoyl}-N,N-dimethylpiperazine-1-carboxamide The title compound was prepared, using the appropriate reagents, as the TFA salt according to the procedure for EXAMPLE 506. MS (DCI/NH$_3$) m/z 443 (M+H)$^+$; $^1$H NMR (DMSO-d$_6$) δ 1.37-1.52 (m, 2H), 2.09 (t, J=6.15 Hz, 2H), 2.17-2.29 (m, 2H), 2.75-2.85 (m, 2H), 2.91 (m, 6H), 2.91-3.01 (m, 4H), 3.38 (m, 2H), 3.56 (s, 2H), 6.17 (s, 1H), 6.91-6.99 (m, 1H), 6.97-7.03 (m, 1H), 7.04-7.10 (m, 1H), 11.68 (s, 1H).

Example 513

N-[2-(dimethylamino)ethyl]-2-fluoro-N-methyl-5-[(5-oxo-1,2,3,4,5,6-hexahydropyrido[2,3-d]pyridazin-8-yl)methyl]benzamide The title compound was prepared, using the appropriate reagents, as the TFA salt according to the procedure for EXAMPLE 506. MS (DCI/NH$_3$) m/z 388 (M+H)$^+$; $^1$H NMR (DMSO-d$_6$) δ 1.57-1.77 (m, 2H), 2.33 (t, J=6.15 Hz, 2H), 2.74-2.97 (m, 1H), 2.85 (s, 3H), 2.86 (s, 3H), 2.87 (s, 3H), 3.16 (m, 2H), 3.24-3.40 (m, 1H), 3.74-3.82 (m, 2H), 3.82 (s, 2H), 6.36 (s, 1H), 7.17-7.30 (m, 2H), 7.32-7.44 (m, 1H), 11.85 (s, 1H).

Example 514

4-(3-{[4-(3-chlorobenzyl)piperazin-1-yl]carbonyl}-4-fluorobenzyl)-5,6,7,8-tetrahydrophthalazin-1(2H)-one The title compound was prepared, using the appropriate reagents, as the TFA salt according to the procedure for EXAMPLE 492. MS (DCI/NH$_3$) m/z 495 (M+H)$^+$; $^1$H NMR (DMSO-d$_6$) δ 1.55-1.73 (m, 4H), 2.33-2.44 (m, 4H), 3.03-3.24 (m, 2H), 3.35-3.55 (m, 2H), 3.64-3.90 (m, 6H), 4.29 (s, 2H), 7.21-7.24 (m, 1H), 7.24-7.29 (m, 1H), 7.31-7.37 (m, 1H), 7.41-7.46 (m, 1H), 7.47-7.52 (m, 1H), 7.52-7.55 (m, 1H), 7.59 (s, 1H), 12.61 (br s, 1H).

Example 515

4-{4-fluoro-3-[(4-phenylpiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 492. MS (DCI/NH$_3$) m/z 447 (M+H)$^+$; $^1$H NMR (DMSO-d$_6$) δ 1.55-1.69 (m, 4H), 2.31-2.43 (m, 4H), 3.03-3.13 (m, 2H), 3.18-3.27 (m, 2H), 3.31-3.40 (m, 2H), 3.73-3.82 (m, 2H), 3.92 (s, 2H), 6.82 (t, J=7.21 Hz, 1H), 6.92-6.95 (m, 1H), 6.95-6.98 (m, 1H), 7.20-7.25 (m, 3H), 7.26 (d, J=6.14 Hz, 1H), 7.28-7.33 (m, 1H), 12.60 (br s, 1H).

Example 516

8-{4-fluoro-3-[(4-methylpiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 386 (M+H)$^+$; $^1$H NMR (DMSO-d$_6$) δ 1.52-1.78 (m, 2H), 2.35 (t, J=6.10 Hz, 2H), 2.84 (s, 3H), 2.92-3.25 (m, 6H), 3.39 (m, 2H), 3.57 (m, 2H), 3.83 (s, 2H), 6.37 (s, 1H), 7.06-7.36 (m, 2H), 7.33-7.51 (m, 1H), 11.86 (s, 1H).

Example 517

4-(3-{[4-(2-chlorophenyl)piperazin-1-yl]carbonyl}-4-fluorobenzyl)-5,6,7,8-tetrahydrophthalazin-1(2H)-one The title compound was prepared, using the appropriate reagents, as the TFA salt according to the procedure for EXAMPLE 492. MS (DCI/NH$_3$) m/z 481 (M+H)$^+$; $^1$H NMR (DMSO-d$_6$) δ 1.55-1.70 (m, 4H), 2.33-2.43 (m, 4H), 2.87-2.96 (m, 2H), 2.99-3.06 (m, 2H), 3.33-3.42 (m, 2H), 3.76-3.85 (m, 2H), 3.93 (s, 2H), 7.04-7.10 (m, 1H), 7.16 (dd, J=7.98, 1.53 Hz, 1H), 7.23 (d, J=2.76 Hz, 1H), 7.24-7.27 (m, 1H), 7.28-7.30 (m, 1H), 7.30-7.34 (m, 1H), 7.43 (dd, J=7.98, 1.53 Hz, 1H), 12.61 (br s, 1H).

Example 518

4-(3-{[4-(2-chlorobenzyl)piperazin-1-yl]carbonyl}-4-fluorobenzyl)-5,6,7,8-tetrahydrophthalazin-1(2H)-one The title compound was prepared, using the appropriate reagents, as the TFA salt according to the procedure for EXAMPLE 492. MS (DCI/NH$_3$) m/z 495 (M+H)$^+$; $^1$H NMR (DMSO-d$_6$) δ 1.54-1.70 (m, 4H), 2.32-2.43 (m, 4H), 3.08-3.29 (m, 2H), 3.36-3.52 (m, 2H), 3.96-4.20 (m, 6H), 4.32 (s, 2H), 7.23-7.29 (m, 2H), 7.31-7.37 (m, 1H), 7.43-7.50 (m, 2H), 7.55-7.60 (m, 1H), 7.63-7.68 (m, 1H), 12.61 (br s, 1H).

Example 519

1-{2-fluoro-5-[(5-oxo-1,2,3,4,5,6-hexahydropyrido[2,3-d]pyridazin-8-yl)methyl]benzoyl}piperidine-3-carboxamide The title compound was prepared, using the appropriate reagents, as the TFA salt according to the procedure for EXAMPLE 506. MS (DCI/NH$_3$) m/z 414 (M+H)$^+$.

Example 520

4-{3-[(4-acetylpiperazin-1-yl)carbonyl]-4-fluorobenzyl}-5,6,7,8-tetrahydrophthalazin-1(2H)-one The title compound was prepared, using the appropriate reagents, as the free base according to the procedure for EXAMPLE 492. MS (DCI/NH$_3$) m/z 413 (M+H)$^+$; $^1$H NMR (DMSO-d$_6$) δ 1.56-1.68 (m, 4H), 2.00 (s, 1.5H), 2.02 (s, 1.5H), 2.32-2.41 (m, 4H), 3.14-3.21 (m, 1H), 3.21-3.27 (m, 1H), 3.35-3.43 (m, 2H), 3.48-3.55 (m, 2H), 3.55-3.62 (m, 1H), 3.63-3.70 (m, 1H), 3.92 (s, 2H), 7.20-7.27 (m, 2H), 7.28-7.32 (m, 1H), 12.63 (br s, 1H).

Example 522

4-(4-fluoro-3-{[4-(2-furoyl)piperazin-1-yl]carbonyl}benzyl)-5,6,7,8-tetrahydrophthalazin-1(2H)-one The title compound was prepared, using the appropriate reagents, as the free base according to the procedure for EXAMPLE 492. MS (DCI/NH$_3$) m/z 465 (M+H)$^+$; $^1$H NMR (DMSO-d$_6$) δ 1.55-1.70 (m, 4H), 2.31-2.43 (m, 4H), 3.28-3.37 (m, 2H), 3.56-3.66 (m, 2H), 3.69-3.80 (m, 4H), 3.92 (s, 2H), 6.63 (dd, J=3.38, 1.84 Hz, 1H), 7.02 (d, J=3.38 Hz, 1H), 7.21-7.27 (m, 2H), 7.28-7.35 (m, 1H), 7.84 (s, 1H), 12.61 (br s, 1H)

Example 523

4-(4-fluoro-3-{[4-(2-fluorophenyl)piperazin-1-yl]carbonyl}benzyl)-5,6,7,8-tetrahydrophthalazin-1(2H)-one The title compound was prepared, using the appropriate reagents, as the free base according to the procedure for EXAMPLE 492. MS (DCI/NH$_3$) m/z 465 (M+H)$^+$; $^1$H NMR (DMSO-d$_6$) δ 1.56-1.69 (m, 4H), 2.31-2.44 (m, 4H), 2.90-2.98 (m, 2H), 3.02-3.10 (m, 2H), 3.32-3.38 (m, 2H), 3.75-3.83 (m, 2H), 3.93 (s, 2H), 6.97-7.02 (m, 1H), 7.02-7.08 (m, 1H), 7.08-7.13 (m, 1H), 7.14-7.18 (m, 1H), 7.20-7.23 (m, 1H), 7.23-7.27 (m, 1H), 7.28-7.33 (m, 1H), 12.61 (br s, 1H).

Example 524

4-(3-{[4-(2,4-difluorophenyl)piperazin-1-yl]carbonyl}-4-fluorobenzyl)-5,6,7,8-tetrahydrophthalazin-1(2H)-one The title compound was prepared, using the appropriate reagents, as the TFA salt according to the procedure for EXAMPLE 492. MS (DCI/NH$_3$) m/z 483 (M+H)$^+$; $^1$H NMR (DMSO-d$_6$) δ 1.56-1.71 (m, 4H), 2.32-2.43 (m, 4H), 2.86-2.94 (m, 2H), 2.97-3.06 (m, 2H), 3.31-3.42 (m, 2H), 3.74-3.83 (m, 2H), 3.92 (s, 2H), 6.96-7.03 (m, 1H), 7.05-7.13 (m, 1H), 7.17-7.21 (m, 1H), 7.22-7.23 (m, 1H), 7.24-7.27 (m, 1H), 7.28-7.33 (m, 1H), 12.61 (br s, 1H).

Example 525

4-{3-[(4-benzoylpiperazin-1-yl)carbonyl]-4-fluorobenzyl}-5,6,7,8-tetrahydrophthalazin-1(2H)-one The title compound was prepared, using the appropriate reagents, as the free base according to the procedure for EXAMPLE 492. MS (DCI/NH$_3$) m/z 475 (M+H)$^+$; $^1$H NMR (DMSO-d$_6$) δ 1.54-1.69 (m, 4H), 2.31-2.44 (m, 4H), 3.21-3.35 (m, 2H), 3.39-3.52 (m, 2H), 3.52-3.63 (m, 2H), 3.66-3.78 (m, 2H), 3.91 (s, 2H), 7.19-7.26 (m, 2H), 7.27-7.33 (m, 1H), 7.39-7.49 (m, 5H), 12.60 (br s, 1H).

Example 526

8-(4-fluoro-3-{[4-(piperidin-1-ylcarbonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 483 (M+H)$^+$; $^1$H NMR (DMSO-d$_6$) δ 1.36-1.58 (m, 6H), 1.62-1.79 (m, 2H), 2.34 (t, J=0.10 Hz, 2H), 2.98-3.10 (m, 2H), 3.10-3.27 (m, 10H), 3.64 (m, 2H), 3.82 (s, 2H), 6.37 (s, 1H), 7.17-7.24 (m, 1H), 7.23-7.28 (m, 1H), 7.28-7.37 (m, 1H), 11.88 (s, 1H).

Example 527

4-(4-fluoro-3-{[4-(3-fluorophenyl)piperazin-1-yl]carbonyl}benzyl)-5,6,7,8-tetrahydrophthalazin-1(2H)-one The title compound was prepared, using the appropriate reagents, as the free base according to the procedure for EXAMPLE 492. MS (DCI/NH$_3$) m/z 465 (M+H)$^+$; $^1$H NMR (DMSO-d$_6$) δ 1.57-1.70 (m, 4H), 2.32-2.45 (m, 4H), 3.09-3.16 (m, 2H), 3.23-3.29 (m, 2H), 3.30-3.37 (m, 2H), 3.71-3.79 (m, 2H), 3.92 (s, 2H), 6.55-6.61 (m, 1H), 6.72-6.76 (m, 1H), 6.76-6.79 (m, 1H), 7.19-7.25 (m, 2H), 7.25-7.28 (m, 1H), 7.28-7.34 (m, 1H), 12.60 (br s, 1H).

Example 528

4-(4-fluoro-3-{[4-(4-fluorophenyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 492. MS (DCI/NH$_3$) m/z 465 (M+H)$^+$; $^1$H NMR (DMSO-d$_6$) δ 1.55-1.70 (m, 4H), 2.31-2.44 (m, 4H), 2.97-3.06 (m, 2H), 3.10-3.20 (m, 2H), 3.29-3.38 (m, 2H), 3.72-3.83 (m, 2H), 3.92 (s, 2H), 6.95-7.00 (m, 2H), 7.04-7.10 (m, 2H), 7.20-7.24 (m, 1H), 7.23-7.28 (m, 1H), 7.28-7.34 (m, 1H), 12.61 (br s, 1H).

Example 529

4-{4-fluoro-3-[(4-pyridin-2-ylpiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 492. MS (DCI/NH$_3$) m/z 448 (M+H)$^+$; $^1$H NMR (DMSO-d$_6$) δ 1.55-1.70 (m, 4H), 2.31-2.44 (m, 4H), 3.33-3.43 (m, 2H), 3.52-3.59 (m, 2H), 3.64-3.73 (m, 2H), 3.74-3.82 (m, 2H), 3.93 (s, 2H), 6.80-6.86 (m, 1H), 7.09 (d, J=8.59 Hz, 1H), 7.22-7.29 (m, 2H), 7.30-7.37 (m, 1H), 7.76-7.84 (m, 1H), 8.10 (dd, J=5.52, 1.84 Hz, 1H), 12.61 (br s, 1H).

Example 530

N,N-diethyl-4-{2-fluoro-5-[(4-oxo-3,4,5,6,7,8-hexahydrophthalazin-1-yl)methyl]benzoyl}piperazine-1-carboxamide The title compound was prepared, using the appropriate reagents, as the TFA salt according to the procedure for EXAMPLE 492. MS (DCI/NH$_3$) m/z 470 (M+H)$^+$; $^1$H NMR (DMSO-d$_6$) δ 1.04 (t, J=7.06 Hz, 6H), 1.57-1.67 (m, 4H), 2.32-2.42 (m, 4H), 2.99-3.06 (m, 2H), 3.10-3.17 (m, 6H), 3.19-3.26 (m, 2H), 3.57-3.66 (m, 2H), 3.91 (s, 2H), 7.19-7.22 (m, 1H), 7.22-7.25 (m, 1H), 7.26-7.32 (m, 1H), 12.60 (br s, 1H).

Example 531

4-{4-fluoro-3-[(4-isopropylpiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 492. MS (DCI/NH$_3$) m/z 413 (M+H)$^+$; $^1$H NMR (DMSO-d$_6$) δ 1.26 (d, J=6.75 Hz, 6H), 1.54-1.69 (m, 4H), 2.32-2.43 (m, 4H), 2.87-3.01 (m, 1H), 3.05-3.23 (m, 2H), 3.29-3.45 (m, 2H), 3.48-3.63 (m, 3H), 3.93 (s, 2H), 4.64 (d, J=6.44 Hz, 1H), 7.23-7.30 (m, 2H), 7.32-7.38 (m, 1H), 12.62 (br s, 1H).

Example 532

8-(4-fluoro-3-{[4-(2-oxo-2-pyrrolidin-1-ylethyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 483 (M+H)$^+$; $^1$H NMR (DMSO-d$_6$) δ 1.60-1.75 (m, 2H), 1.77-1.86 (m, 2H), 1.89-1.94 (m, 2H), 2.34 (t, J=6.10 Hz, 2H), 3.08-3.25 (m, 4H), 3.26-3.45 (m, 6H), 3.56 (m, 4H), 3.83 (s, 2H), 4.21 (s, 2H), 6.36 (s, 1H), 7.13-7.33 (m, 2H), 7.32-7.51 (m, 1H), 11.85 (s, 1H).

Example 533

4-(4-fluoro-3-{[4-(morpholin-4-ylcarbonyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 492. MS (DCI/NH$_3$) m/z 484 (M+H)$^+$; $^1$H NMR (DMSO-d$_6$) δ 1.56-1.67 (m, 4H), 2.30-2.41 (m, 4H), 3.11 (dd, J=6.14, 3.38 Hz, 2H), 3.13-3.17 (m, 4H), 3.19-3.25 (m, 4H), 3.53-3.57 (m, 4H), 3.59-3.66 (m, 2H), 3.91 (s, 2H), 7.19-7.22 (m, 1H), 7.22-7.25 (m, 1H), 7.27-7.32 (m, 1H), 12.60 (br s, 1H).

Example 534

1-{2-fluoro-5-[(5-oxo-1,2,3,4,5,6-hexahydropyrido[2,3-d]pyridazin-8-yl)methyl]benzoyl}piperidine-4-carboxamide The title compound was prepared, using the appropriate reagents, as the TFA salt according to the procedure for EXAMPLE 506. MS (DCI/NH$_3$) m/z 414 (M+H)$^+$.

Example 535

8-(4-fluoro-3-{[4-(2-hydroxyethyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 416 (M+H)$^+$.

Example 536

8-{4-fluoro-3-[(4-pyrimidin-2-ylpiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 450 (M+H)$^+$; $^1$H NMR (DMSO-d$_6$) δ 1.39-1.85 (m, 2H), 2.33 (t, J=6.10 Hz, 2H), 3.06-3.21 (m, 2H), 3.24-3.35 (m, 2H), 3.55-3.96 (m, 8H), 6.40 (s, 1H), 6.67 (t, J=4.75 Hz, 1H), 7.16-7.26 (m, 1H), 7.24-7.30 (m, 1H), 7.30-7.39 (m, 1H), 8.38 (d, J=4.75 Hz, 2H), 11.91 (s, 1H).

Example 537

4-(4-fluoro-3-{[4-(2-oxo-2-pyrrolidin-1-ylethyl) piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 492. MS (DCI/NH$_3$) m/z 482 (M+H)$^+$; $^1$H NMR (CD$_3$OD) δ 1.69-1.76 (m, 4H), 1.93 (q, J=6.55 Hz, 2H), 2.01 (q, J=6.55 Hz, 2H), 2.42-2.48 (m, 2H), 2.49-2.56 (m, 2H), 3.34-3.41 (m, 2H), 3.43 (t, J=6.75 Hz, 4H), 3.49 (t, J=6.90 Hz, 4H), 3.67-3.77 (m, 2H), 4.00 (s, 2H), 4.19 (s, 2H), 7.19 (dd, J=9.51, 8.59 Hz, 1H), 7.29 (dd, J=6.29, 2.30 Hz, 1H), 7.38-7.43 (m, 1H).

Example 538

N-{2-fluoro-5-[(4-oxo-3,4,5,6,7,8-hexahydrophthalazin-1-yl)methyl]phenyl}-N'-isopropylurea To a solution of EXAMPLE 493F (75 mg, 0.27 mmol) in N,N-dimethylformamide (8 mL) was added isopropyl isocyanate (23 mg, 0.27 mmol) and triethylamine (0.12 mL, 0.81 mmol). The reaction mixture was stirred at 70° C. for 16 hours and was concentrated. The residue was purified by HPLC (Zorbax C-18, 0.1% TFA/CH$_3$CN/H$_2$O) to provide the title compound. MS (DCI/NH$_3$) m/z 359 (M+H)$^+$.

Example 539

N-{2-fluoro-5-[(4-oxo-3,4,5,6,7,8-hexahydrophthalazin-1-yl)methyl]phenyl}-N'-propylurea The title compound was prepared, using the appropriate reagents, according to the procedure for EXAMPLE 538. MS (DCI/NH$_3$) m/z 359 (M+H)$^+$.

Example 540

N-cyclopentyl-N'-{2-fluoro-5-[(4-oxo-3,4,5,6,7,8-hexahydrophthalazin-1-yl)methyl]phenyl}urea The title compound was prepared, using the appropriate reagents, according to the procedure for EXAMPLE 538. MS (DCI/NH$_3$) m/z 385 (M+H)$^+$.

Example 541

N-(2,4-difluorophenyl)-N'-{2-fluoro-5-[(4-oxo-3,4,5,6,7,8-hexahydrophthalazin-1-yl)methyl]phenyl}urea The title compound was prepared, using the appropriate reagents, according to the procedure for EXAMPLE 538. MS (DCI/NH$_3$) m/z 429 (M+H)$^+$.

Example 542

N-(tert-butyl)-N'-{2-fluoro-5-[(4-oxo-3,4,5,6,7,8-hexahydrophthalazin-1-yl)methyl]phenyl}urea The title compound was prepared, using the appropriate reagents, according to the procedure for EXAMPLE 538. MS (DCI/NH$_3$) m/z 373 (M+H)$^+$.

Example 543 benzyl 4-{2-fluoro-5-[(4-oxo-3,4,5,6,7,8-hexahydrophthalazin-1-yl)methyl]benzoyl}piperazine-1-carboxylate To a solution of EXAMPLE 492F (1.5 g, 5 mmol) in N,N-dimethylformamide (20 mL) was added benzylpiperazine-1-carboxylate (1.09 g, 5 mmol), 1-ethyl-3-(3-dimethylaminopropyl) carbodiimide hydrochloride (EDC) (1.9 g, 10 mmol), N-hydroxybenzotriazole (HOBt) (1.34 g, 10 mmol), and triethylamine (1.4 mL, 10 mmol). The reaction mixture was stirred at ambient temperature for 16 hours and was concentrated. The residue was diluted with ethyl acetate and washed with brine. The organic layer was concentrated and the residue purified by flash chromatography on silica gel eluting with 60% ethyl acetate in hexanes to provide the title compound. MS (DCI/NH$_3$) m/z 505 (M+H)$^+$; $^1$H NMR (CD$_3$OD) δ 1.67-1.77 (m, 4H), 2.39-2.56 (m, 4H), 3.33-3.37 (m, 2H), 3.42-3.54 (m, 2H), 3.54-3.65 (m, 2H), 3.71-3.80 (m, 2H), 3.98 (s, 2H), 5.14 (s, 2H), 7.11-7.19 (m, 1H), 7.23 (dd, J=6.35, 2.38 Hz, 1H), 7.29-7.32 (m, 1H), 7.33-7.38 (m, 5H).

Example 544 benzyl 4-{2-fluoro-5-[(4-oxo-3,4,5,6,7,8-hexahydrophthalazin-1-yl)methyl]benzoyl}-1,4-diazepane-1-carboxylate The title compound was prepared, using the appropriate reagents, as a free base according to the procedure for EXAMPLE 543, but was purified by HPLC (Zorbax C-18, 0.1% TFA/CH$_3$CN/H$_2$O) instead of flash chromatography. MS (DCI/NH$_3$) m/z 519 (M+H)$^+$.

Example 545

8-{4-fluoro-3-[(4-pyridin-2-ylpiperazin-1-yl)carbonyl]benzyl}-2,3,4,6-tetrahydropyrido[2,3-d]pyridazin-5(1H)-one The title compound was prepared, using the appropriate reagents, as TFA salt according to the procedure for EXAMPLE 506. MS (DCI/NH$_3$) m/z 449 (M+H)$^+$; $^1$H NMR (DMSO-d$_6$) δ 1.60-1.80 (m, 2H), 2.35 (t, J=6.10 Hz, 2H), 3.10-3.24 (m, 2H), 3.39 (m, 2H), 3.55 (m, 2H), 3.68 (m, 2H), 3.73-3.81 (m, 2H), 3.84 (s, 2H), 6.41 (s, 1H), 6.78-6.88 (m, 1H), 7.09 (d, J=8.81 Hz, 1H), 7.20-7.28 (m, 1H), 7.26-7.32 (m, 1H), 7.32-7.42 (m, 1H), 7.79 (t, J=7.29 Hz, 1H), 8.00-8.14 (m, 1H), 11.90 (s, 1H).

Example 546

8-{4-fluoro-3-[(4-phenylpiperazin-1-yl)carbonyl] benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 448 (M+H)$^+$; $^1$H NMR (DMSO-d$_6$) δ 1.52-1.78 (m, 2H), 2.34 (t, J=6.10 Hz, 2H), 3.09 (m, 2H), 3.13-3.26 (m, 4H), 3.35 (m, 2H), 3.68-3.85 (m, 2H), 3.83 (s, 2H), 6.36 (s, 1H), 6.82 (t, J=7.29 Hz, 1H), 6.96 (d, J=7.80 Hz, 2H), 7.22 (d, J=8.48 Hz, 2H), 7.24-7.30 (m, 2H), 7.30-7.39 (m, 1H), 11.85 (s, 1H).

Example 547

8-(4-fluoro-3-{[4-(3-fluorophenyl)piperazin-1-yl]
carbonyl}benzyl)-2,3,4,6-tetrahydropyrido[2,3-d]
pyridazin-5(1H)-one The title compound was prepared, using the appropriate reagents, as the TFA salt according to the procedure for EXAMPLE 506. MS (DCI/NH$_3$) m/z 466 (M+H)$^+$; $^1$H NMR (DMSO-d$_6$) δ 1.55-1.87 (m, 2H), 2.35 (t, J=6.10 Hz, 2H), 3.07-3.22 (m, 4H), 3.21-3.30 (m, 2H), 3.34 (m, 2H), 3.76 (m, 2H), 3.83 (s, 2H), 6.41 (s, 1H), 6.49-6.70 (m, 1H), 6.69-6.86 (m, 2H), 7.12-7.25 (m, 1H), 7.22-7.31 (m, 2H), 7.31-7.45 (m, 1H), 11.91 (s, 1H).

Example 548

8-(4-fluoro-3-{[4-(4-fluorophenyl)piperazin-1-yl]
carbonyl}benzyl)-2,3,4,6-tetrahydropyrido[2,3-d]
pyridazin-5(1H)-one The title compound was prepared, using the appropriate reagents, as the TFA salt according to the procedure for EXAMPLE 506. MS (DCI/NH$_3$) m/z 466 (M+H)$^+$; $^1$H NMR (DMSO-d$_6$) δ 1.53-1.86 (m, 2H), 2.35 (t, J=6.15 Hz, 2H), 3.03 (m, 2H), 3.09-3.24 (m, 4H), 3.36 (m, 2H), 3.78 (m, 2H), 3.83 (s, 2H), 6.43 (s, 1H), 6.94-7.02 (m, 2H), 7.02-7.12 (m, 2H), 7.19-7.31 (m, 2H), 7.30-7.40 (m, 1H), 11.94 (s, 1H).

Example 549

8-(4-fluoro-3-{[4-(2-fluorophenyl)piperazin-1-yl]
carbonyl}benzyl)-2,3,4,6-tetrahydropyrido[2,3-d]
pyridazin-5(1H)-one The title compound was prepared, using the appropriate reagents, as the TFA salt according to the procedure for EXAMPLE 506. MS (DCI/NH$_3$) m/z 466 (M+H)$^+$; $^1$H NMR (DMSO-d$_6$) δ 1.61-1.81 (m, 2H), 2.34 (t, J=6.15 Hz, 2H), 2.96 (m, 2H), 3.00-3.12 (m, 2H), 3.13-3.22 (m, 2H), 3.38 (m, 2H), 3.80 (m, 2H), 3.83 (s, 2H), 6.38 (s, 1H), 6.96-7.05 (m, 1H), 7.06-7.13 (m, 2H), 7.13-7.19 (m, 1H), 7.19-7.30 (m, 2H), 7.30-7.38 (m, 1H), 11.87 (s, 1H).

Example 550

8-(3-{[4-(2,4-difluorophenyl)piperazin-1-yl]carbonyl}-4-fluorobenzyl)-2,3,4,6-tetrahydropyrido[2,3-d]
pyridazin-5(1H)-one The title compound was prepared, using the appropriate reagents, according to the procedure for EXAMPLE 506. MS (DCI/NH$_3$) m/z 466 (M+H)$^+$; $^1$H NMR (DMSO-d$_6$) δ 1.62-1.77 (m, 2H), 2.34 (t, J=6.35 Hz, 2H), 2.90 (m, 2H), 2.96-3.06 (m, 2H), 3.17 (m, 2H), 3.29-3.48 (m, 2H), 3.79 (m, 2H), 3.82 (s, 2H), 6.35 (s, 1H), 7.02 (dd, J=7.93, 2.78 Hz, 1H), 7.08 (dd, J=9.12, 5.95 Hz, 1H), 7.16-7.22 (m, 1H), 7.22-7.30 (m, 2H), 7.30-7.38 (m, 1H), 11.85 (s, 1H).

Example 551

8-{3-[(4-benzoylpiperazin-1-yl) carbonyl]-4-fluorobenzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 476 (M+H)$^+$; $^1$H NMR (DMSO-d$_6$) δ 1.57-1.78 (m, 2H), 2.34 (t, J=6.10 Hz, 2H), 3.17 (m, 4H), 3.21-3.37 (m, 2H), 3.45 (m, 2H), 3.69 (m, 2H), 3.82 (s, 2H), 6.40 (s, 1H), 7.18-7.30 (m, 2H), 7.29-7.38 (m, 1H), 7.39-7.50 (m, 5H), 11.92 (s, 1H).

Example 553

8-(4-fluoro-3-{[4-(2-furoyl)piperazin-1-yl]
carbonyl}benzyl)-2,3,4,6-tetrahydropyrido[2,3-d]
pyridazin-5(1H)-one The title compound was prepared, using the appropriate reagents, as the TFA salt according to the procedure for EXAMPLE 506. MS (DCI/NH$_3$) m/z 466 (M+H)$^+$; $^1$H NMR (DMSO-d$_6$) δ 1.59-1.79 (m, 2H), 2.35 (t, J=6.10 Hz, 2H), 3.06-3.25 (m, 2H), 3.33 (m, 2H), 3.65 (m, 2H), 3.68-3.81 (m, 4H), 3.83 (s, 2H), 6.43 (s, 1H), 6.63 (dd, J=3.56, 1.86 Hz, 1H), 7.03 (dd, J=3.39, 0.68 Hz, 1H), 7.18-7.31 (m, 2H), 7.31-7.39 (m, 1H), 7.83-7.86 (m, 1H), 11.93 (s, 1H).

Example 554

8-(3-{[4-(2-chlorophenyl)piperazin-1-yl]carbonyl}-4-fluorobenzyl)-2,3,4,6-tetrahydropyrido[2,3-d]pyridazin-5(1H)-one The title compound was prepared, using the appropriate reagents, (as a TFA salt?) according to the procedure for EXAMPLE 506. MS (DCI/NH$_3$) m/z 482 (M+H)$^+$; $^1$H NMR (DMSO-d$_6$) δ 1.56-1.80 (m, 2H), 2.34 (t, J=6.27 Hz, 2H), 2.75-2.98 (m, 2H), 2.96-3.09 (m, 2H), 3.17 (m, 2H), 3.35 (m, 2H), 3.74-3.83 (m, 2H), 3.83 (s, 2H), 6.36 (s, 1H), 7.02-7.10 (m, 1H), 7.17 (dd, J=8.14, 1.36 Hz, 1H), 7.20-7.31 (m, 2H), 7.30-7.38 (m, 2H), 7.43 (dd, J=7.97, 1.53 Hz, 1H), 11.85 (s, 1H).

Example 555

4-{2-fluoro-5-[(5-oxo-1,2,3,4,5,6-hexahydropyrido
[2,3-d]pyridazin-8-yl)methyl]benzoyl}-2-morpholin-4-ylpiperazine-1-carbaldehyde The title compound was prepared, using the appropriate reagents, as the TFA salt according to the procedure for EXAMPLE 506. MS (DCI/NH$_3$) m/z 482 (M+H)$^1$.

Example 556

8-(4-fluoro-3-{[4-(methylsulfonyl)piperazin-1-yl]
carbonyl}benzyl)-2,3,4,6-tetrahydropyrido[2,3-d]
pyridazin-5(1H)-one The title compound was prepared, using the appropriate reagents, as the TFA salt according to the procedure for EXAMPLE 506. MS (DCI/NH$_3$) m/z 450 (M+H); $^1$H NMR (DMSO-d$_6$) δ 1.63-1.81 (m, 2H), 2.35 (t, J=6.27 Hz, 2H), 2.91 (m, 3H), 3.09 (m, 2H), 3.12-3.24 (m, 4H), 3.32 (m, 2H), 3.74 (m, 2H), 3.82 (s, 2H), 6.38 (s, 1H), 7.17-7.29 (m, 2H), 7.31-7.39 (m, 1H), 11.89 (s, 1H).

Example 557

N,N-diethyl-4-{2-fluoro-5-[(5-oxo-1,2,3,4,5,6-hexahydropyrido[2,3-d]pyridazin-8-yl)methyl]
benzoyl}piperazine-1-carboxamide The title compound was prepared, using the appropriate reagents, as the TFA salt according to the procedure for EXAMPLE 506. MS (DCI/NH$_3$) m/z 471 (M+H)$^+$; $^1$H NMR (DMSO-d$_6$) δ 1.04 (t, J=6.95 Hz, 6H), 1.51-1.85 (m, 2H), 2.35 (t, J=6.27 Hz, 2H), 3.04 (m, 2H), 3.07-3.38 (m, 10H), 3.64 (m, 2H), 3.82 (s, 2H), 6.39 (s, 1H), 7.02-7.28 (m, 2H), 7.26-7.45 (m, 1H), 11.90 (s, 1H).

Example 559

8-{3-[(4-acetylpiperazin-1-yl)carbonyl]-4-fluorobenzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 412 (M+H)$^+$.

Example 560

2-(4-{2-fluoro-5-[(5-oxo-1,2,3,4,5,6-hexahydropyrido[2,3-d]pyridazin-8-yl)methyl]benzoyl}piperazin-1-yl)-N,N-dimethylacetamide The title compound was prepared, using the appropriate reagents, as the TFA salt according to the procedure for EXAMPLE 506. MS (DCI/NH$_3$) m/z 457 (M+H)$^+$.

Example 561

8-(4-fluoro-3-{[4-(2-phenoxyethyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 492 (M+H)$^+$; $^1$H NMR (DMSO-d$_6$) δ 1.61-1.84 (m, 2H), 2.35 (t, J=6.10 Hz, 2H), 3.17 (m, 6H), 3.58 (s, 4H), 3.83 (s, 2H), 4.19-4.53 (m, 4H), 6.37 (s, 1H), 6.94-7.06 (m, 3H), 7.21-7.45 (m, 5H), 11.86 (s, 1H).

Example 562

8-(4-fluoro-3-{[4-(phenylsulfonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 512 (M+H)$^+$; $^1$H NMR (DMSO-d$_6$) 1.54-1.73 (m, 2H), 2.34 (t, J=6.10 Hz, 2H), 2.88 (m, 2H), 2.92-3.03 (m, 2H), 3.07-3.18 (m, 2H), 3.30 (m, 2H), 3.66-3.77 (m, 2H), 3.83 (s, 2H), 6.32 (s, 1H), 6.94-7.23 (m, 2H), 7.22-7.44 (m, 1H), 7.44-7.87 (m, 5H), 11.84 (s, 1H).

Example 563

2-fluoro-N-[2-(4-methylpiperazin-1-yl)ethyl]-5-[(5-oxo-1,2,3,4,5,6-hexahydropyrido[2,3-d]pyridazin-8-yl)methyl]benzamide The title compound was prepared, using the appropriate reagents, as the TFA salt according to the procedure for EXAMPLE 506. MS (DCI/NH$_3$) m/z 429 (M+H)$^+$.

Example 564

8-{3-[(4-cyclopentylpiperazin-1-yl)carbonyl]-4-fluorobenzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 440 (M+H)$^+$; $^1$H NMR (DMSO-d$_6$) δ 1.29-1.86 (m, 8H), 2.01 (m, 2H), 2.35 (t, J=6.10 Hz, 2H), 2.98 (m, 1H), 3.03-3.29 (m, 4H), 3.43 (m, 2H), 3.56 (m, 4H), 3.83 (s, 2H), 6.38 (s, 1H), 7.04-7.34 (m, 2H), 7.34-7.54 (m, 1H), 11.86 (s, 1H).

Example 565

8-{4-fluoro-3-[(4-isobutyrylpiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 442 (M+H)$^+$; $^1$H NMR (DMSO-d$_6$) δ 0.99 (d, J=4.41 Hz, 6H), 1.61-1.78 (m, 2H), 2.35 (t, J=6.10 Hz, 2H), 2.88 (m, 1H), 3.07-3.32 (m, 4H), 3.45 (m, 2H), 3.58 (m, 4H), 3.82 (s, 2H), 6.40 (s, 1H), 7.04-7.31 (m, 2H), 7.29-7.50 (m, 1H), 11.90 (s, 1H).

Example 566

8-(4-fluoro-3-{[4-(2-morpholin-4-ylethyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 485 (M+H)$^+$; $^1$H NMR (DMSO-d$_6$) δ 1.61-1.78 (m, 2H), 2.35 (t, J=6.10 Hz, 2H), 2.73 (m, 2H), 2.81-2.92 (m, 2H), 2.99 (m, 2H), 3.17 (m, 6H), 3.25 (t, J=5.93 Hz, 2H), 3.35 (m, 2H), 3.73-3.82 (m, 6H), 3.83 (s, 2H), 6.39 (s, 1H), 7.09-7.32 (m, 2H), 7.29-7.54 (m, 1H), 11.88 (s, 1H).

Example 567

8-(4-fluoro-3-{[4-(pyrrolidine-1-ylcarbonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 468 (M+H)$^+$.

Example 568

8-(3-{[4-(cyclohexylcarbonyl)piperazin-1-yl]carbonyl}-4-fluorobenzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 482 (M+H)$^+$; $^1$H NMR (DMSO-d$_6$) δ 1.04-1.42 (m, 5H), 1.47-1.81 (m, 6H), 2.35 (t, J=6.10 Hz, 2H), 3.08-3.29 (m, 6H), 3.43 (s, 2H), 3.57 (s, 4H), 3.82 (s, 2H), 6.39 (s, 1H), 7.09-7.31 (m, 2H), 7.28-7.46 (m, 1H), 11.90 (s, 1H).

Example 569

8-(4-fluoro-3-{[4-(tetrahydrofuran-2-ylcarbonyl) piperazin-1-yl]carbonyl}benzyl)-2,3,4,6-tetrahydro-pyrido[2,3-d]pyridazin-5(1H)-one The title compound was prepared, using the appropriate reagents, as the TFA salt according to the procedure for EXAMPLE 506. MS (DCI/NH$_3$) m/z 470 (M+H)$^+$.

Example 570

8-(4-fluoro-3-{[4-(2-piperidin-1-ylethyl)piperazin-1-yl]carbonyl}benzyl)-2,3,4,6-tetrahydropyrido[2,3-d] pyridazin-5(1H)-one The title compound was prepared, using the appropriate reagents, as the TFA salt according to the procedure for EXAMPLE 506. MS (DCI/NH$_3$) m/z 483 (M+H)$^+$; $^1$H NMR (DMSO-d$_6$) 1.53 (m, 2H), 1.72 (m, 6H), 2.34 (t, J=6.27 Hz, 2H), 2.64 (m, 2H), 2.69-2.85 (m, 2H), 2.92 (m, 2H), 3.11-3.23 (m, 4H), 3.23-3.41 (m, 4H), 3.59-3.78 (m, 2H), 3.83 (s, 2H), 6.38 (s, 1H), 6.99-7.31 (m, 2H), 7.28-7.52 (m, 1H), 11.86 (s, 1H).

Example 571

4-(4-fluoro-3-{[4-(2-morpholin-4-ylethyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 484 (M+H)$^+$; $^1$H NMR (CD$_3$OD) δ 1.68-1.77 (m, 4H), 2.41-2.47 (m, 2H), 2.49-2.55 (m, 2H), 2.60-2.70 (m, 2H), 2.74-2.82 (m, 2H), 2.92 (t, J=5.95 Hz, 2H), 3.32-3.36 (m, 6H), 3.40-3.48 (m, 2H), 3.82-3.87 (m, 2H), 3.89-3.95 (m, 4H), 3.99 (s, 2H), 7.14-7.19 (m, 1H), 7.21 (dd, J=6.41, 2.14 Hz, 1H), 7.35-7.39 (m, 1H).

Example 572

8-{4-fluoro-3-[(4-hydroxypiperidin-1-yl)carbonyl] benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 387 (M+H)$^+$; $^1$H NMR (DMSO-d$_6$) δ 1.15-1.44 (m, 2H), 1.56-1.86 (m, 4H), 2.34 (t, J=6.10 Hz, 2H), 2.94-3.11 (m, 1H), 3.11-3.24 (m, 3H), 3.25-3.41 (m, 1H), 3.61-3.79 (m, 1H), 3.82 (s, 2H), 3.92-4.14 (m, 1H), 6.40 (s, 1H), 6.89-7.25 (m, 2H), 7.24-7.45 (m, 1H), 11.90 (s, 1H).

Example 573

8-(4-fluoro-3-{[4-(6-methylpyrazin-2-yl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 464 (M+H)$^+$; $^1$H NMR (DMSO-d$_6$) δ 1.64-1.78 (m, 2H), 2.31 (s, 3H), 2.35 (t, J=6.27 Hz, 2H), 3.11-3.26 (m, 2H), 3.35 (m, 2H), 3.52 (m, 2H), 3.67 (m, 2H), 3.74 (m, 2H), 3.84 (s, 2H), 6.44 (s, 1H), 7.20-7.31 (m, 2H), 7.31-7.39 (m, 1H), 7.78 (s, 1H), 8.12 (s, 1H), 11.95 (s, 1H).

Example 574

4-(4-fluoro-3-{[4-(phenylsulfonyl)piperazin-1-yl] carbonyl}benzyl)-5,6,7,8-tetrahydrophthalazin-1 (2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 511 (M+H)$^+$; $^1$H NMR (CD$_3$OD) δ 1.64-1.75 (m, 4H), 2.37-2.44 (m, 2H), 2.45-2.54 (m, 2H), 2.94-3.01 (m, 2H), 3.04-3.16 (m, 2H), 3.39-3.46 (m, 2H), 3.83 (t, J=5.03 Hz, 2H), 3.95 (s, 2H), 7.08-7.13 (m, 1H), 7.15 (dd, J=6.41, 2.14 Hz, 1H), 7.30-7.35 (m, 1H), 7.63 (t, J=7.63 Hz, 2H), 7.71 (t, J=7.32 Hz, 1H), 7.77 (d, J=1.53 Hz, 1H), 7.79 (s, 1H).

Example 575

4-{3-[(4-cyclopentylpiperazin-1-yl)carbonyl]-4-fluorobenzyl}-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 439 (M+H)$^+$; $^1$H NMR (CD$_3$OD) δ 1.65-1.80 (m, 8H), 1.80-1.90 (m, 2H), 2.10-2.25 (m, 2H), 2.41-2.47 (m, 2H), 2.49-2.56 (m, 2H), 3.03-3.24 (m, 3H), 3.48-3.64 (m, 4H), 3.70-3.86 (m, 2H), 4.00 (s, 2H), 7.17-7.21 (m, 1H), 7.30 (dd, J=6.41, 2.14 Hz, 1H), 7.39-7.42 (m, 1H).

Example 576

4-(4-fluoro-3-{[4-(pyrrolidine-1-ylcarbonyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 468 (M+H)$^+$; $^1$H NMR (CD$_3$OD) δ 1.69-1.77 (m, 4H), 1.82-1.89 (m, 4H), 2.42-2.47 (m, 2H), 2.48-2.55 (m, 2H), 3.23-3.27 (m, 2H), 3.34-3.39 (m, 8H), 3.39-3.44 (m, 1H), 3.76-3.81 (m, 2H), 3.99 (s, 2H), 7.13-7.19 (m, 1H), 7.24 (dd, J=6.26, 2.29 Hz, 1H), 7.32-7.37 (m, 1H).

Example 577

4-(4-fluoro-3-{[4-(2-phenoxyethyl)piperazin-1-yl] carbonyl}benzyl)-5,6,7,8-tetrahydrophthalazin-1 (2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 491 (M+H)$^+$; $^1$H NMR (CD$_3$OD) δ 1.66-1.79 (m, 4H), 2.39-2.47 (m, 2H), 2.48-2.55 (m, 2H), 3.35-3.48 (m, 2H), 3.48-3.61 (m, 4H), 3.64-3.69 (m, 2H), 3.69-

3.78 (m, 2H), 4.00 (s, 2H), 4.34-4.44 (m, 2H), 6.99-7.00 (m, 1H), 7.01-7.03 (m, 2H), 7.17-7.23 (m, 1H), 7.28-7.31 (m, 1H), 7.30-7.35 (m, 2H), 7.38-7.44 (m, 1H).

Example 578

2-fluoro-N-[2-(4-methylpiperazin-1-yl)ethyl]-5-[(4-oxo-3,4,5,6,7,8-hexahydrophthalazin-1-yl)methyl]benzamide The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 428 (M+H)$^+$; $^1$H NMR (CD$_3$OD) δ 1.66-1.78 (m, 4H), 2.38-2.46 (m, 2H), 2.46-2.56 (m, 2H), 2.81-2.87 (m, 3H), 2.89 (s, 3H), 2.94-3.07 (m, 3H), 3.33-3.44 (m, 4H), 3.58 (t, J=6.26 Hz, 2H), 4.00 (s, 2H), 7.16 (dd, J=10.83, 8.39 Hz, 1H), 7.38-7.42 (m, 1H), 7.59 (dd, J=6.87, 2.29 Hz, 1H).

Example 579

4-{4-fluoro-3-[(4-isobutyrylpiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 441 (M+H)$^+$; $^1$H NMR (CD$_3$OD) δ 1.04-1.17 (m, 6H), 1.67-1.79 (m, 4H), 2.41-2.48 (m, 2H), 2.49-2.57 (m, 2H), 2.85-3.03 (m, 1H), 3.32-3.45 (m, 2H), 3.54-3.63 (m, 2H), 3.66-3.73 (m, 2H), 3.73-3.86 (m, 2H), 3.99 (s, 2H), 7.14-7.20 (m, 1H), 7.22-7.29 (m, 1H), 7.34-7.38 (m, 1H).

Example 580

4-{3-[(4-ethylpiperazin-1-yl)carbonyl]-4-fluorobenzyl}-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/H$_3$) m/z 399 (M+H); $^1$H NMR (CD$_3$OD) δ 1.37 (t, J=7.32 Hz, 3H), 1.67-1.81 (m, 4H), 2.41-2.48 (m, 2H), 2.48-2.57 (m, 2H), 2.98-3.22 (m, 2H), 3.26 (q, J=7.32 Hz, 2H), 3.40-3.87 (m, 6H), 4.00 (s, 2H), 7.17-7.22 (m, 1H), 7.29 (dd, J=6.41, 2.14 Hz, 1H), 7.38-7.44 (m, 1H).

Example 581 benzyl (3S)-1-{2-fluoro-5-[(4-oxo-3,4,5,6,7,8-hexahydrophthalazin-1-yl)methyl]phenyl}-2,5-dioxopyrrolidin-3-ylcarbamate To a solution of EXAMPLE 493F (200 mg, 0.732 mmol) in a mixture of dioxane (6 mL) and acetonitrile (2 mL) was added N-(carbobenzyloxy-L-aspartic anhydride (365 mg, 1.464 mmol). The mixture was heated at 80° C. for 24 hours, cooled to ambient temperature and concentrated. The residue was dissolved in anhydrous methylene chloride (10 mL) and was treated with 1,1'-carbonyldiimidazole (CDI) (356 mg, 2.195 mmol) at ambient temperature overnight. The mixture was directly purified by flash chromatography [0-15% methanol in 2:1 ethyl acetate/hexane] to give a mixture of two major products. The slower diluting fraction was further purified by HPLC (Zorbax, C-18, 250×2.54 column, Mobile phase A: 0.1% TFA in H$_2$O; B: 0.1% TFA in CH$_3$CN; 0-100% gradient) to provide the title compound as the TFA salt. MS (DCI/NH$_3$) m/z 399 (M+H)$^+$.

Example 582

3-{2-fluoro-5-[(5-oxo-1,2,3,4,5,6-hexahydropyrido[2,3-d]pyridazin-8-yl)methyl]phenyl}-5-isopropylimidazolidine-2,4-dione

Example 582A 2-fluoro-5-((5-oxo-5,6-dihydropyrido[3,2-d]pyridazin-8-yl)methyl)benzamide A solution of EXAMPLE 506D (1 g, 3.2 mmol) in methanol (20 mL) was treated with 7N ammonia in methanol (15 mL) in a pressure tube at 90° C. overnight. After cooling to room temperature, the white solid material was collected by filtration, washed with methanol, and dried to give the title compound. MS (DCI/NH$_3$) m/z 299 (M+H)$^+$.

Example 582B 8-(3-amino-4-fluorobenzyl)pyrido[3,2-d]pyridazin-5(6H)-one

To a mixture of ice (50 g) and a solution of KOH (2 g, 36 mmol) in 8 mL of water was added bromine (0.2 mL, 4 mmol) at –10° C. The mixture was stirred at –10° C. for 10 minutes, and EXAMPLE 582A (1.2 g, 0.4 mmol) was added. This mixture was stirred at –10° C. for an additional 10 minutes and at 65° C. for 1 hour. After cooling to room temperature, the mixture was partitioned between water (100 mL) and ethyl acetate (200 mL). The organic phase was washed with brine, water and concentrated to about 10 mL. The formed solid material was washed with methanol and dried to give the title compound. MS (DCI/NH$_3$) m/z 271 (M+H)$^+$.

Example 582C 8-(3-amino-4-fluorobenzyl)-1,2,3,4-tetrahydropyrido[3,2-d]pyridazin-5(6H)-one A mixture of EXAMPLE 582B (1.3 g, 4.8 mmol), 5% Pt/C (650 mg), concentrated HCl (0.8 mL) and N,N-dimethylformamide (150 mL) in a pressure vessel was purged and pressurized with hydrogen at ambient temperature for 16 hours. Solid material was filtered off and the filtrate concentrated. The residue was purified by HPLC (Zorbax C-18, 0.1% TFA/CH$_3$CN/H$_2$O) to provide the title compound as the TFA salt. MS (ESI) m/z 275 (M+H)$^+$.

Example 582D

3-{2-fluoro-5-[(5-oxo-1,2,3,4,5,6-hexahydropyrido[2,3-d]pyridazin-8-yl)methyl]phenyl}-5-isopropylimidazolidine-2,4-dione A suspension of EXAMPLE 582C (50 mg, 0.18 mmol) in CH$_3$CN (15 mL) was heated until homogeneous. After cooling, methyl 2-isocyanato-3-methylbutanoate (32 mg, 0.18 mmol) was added, and the mixture stirred at 65° C. overnight. The mixture was concentrated and the residue dissolved in N,N-dimethylformamide (10 mL), 2N NaOH (1 mL) was added, and the mixture stirred at room temperature overnight. Solvent was removed and the residue purified by HPLC (Zorbax C-8, 0.1% TFA/CH$_3$CN/H$_2$O) to provide the title compound as the TFA salt. MS (DCI/NH$_3$) m/z 416 (M+H)$^+$; $^1$H NMR (DMSO-d$_6$) δ 0.88 (d, J=6.74 Hz, 3H), 0.92 (d, J=6.74 Hz, 3H), 1.56-1.75 (m, 2H), 1.98-2.19 (m, 1H), 2.34 (t, J=6.15 Hz, 2H), 3.01-3.27 (m, 2H), 3.74 (s, 2H), 4.10 (dd, J=8.53, 4.56 Hz, 1H), 6.34 (s, 1H), 6.67-6.86 (m, 1H), 6.93 (d, J=8.72 Hz, 1H), 7.08 (dd, J=11.50, 8.33 Hz, 1H), 8.48 (d, J=2.78 Hz, 1H), 11.90 (s, 1H).

Example 583

(3S)-3-amino-1-{2-fluoro-5-[(4-oxo-3,4,5,6,7,8-hexahydrophthalazin-1-yl)methyl]phenyl}pyrrolidine-2,5-dione To a solution of EXAMPLE 581 (150 mg, 0.297 mmol) in methanol (10 mL) was added 10% palladium on carbon (30 mg) under nitrogen. This suspension was purged with hydrogen, and stirred under hydrogen (balloon) for 1.5 hours. Solid material was filtered off and the filtrate concentrated. The residue was purified by HPLC (Zorbax, C-18, 250×2.54 column, Mobile phase A: 0.1% TFA in H$_2$O; B: 0.1% TFA in CH$_3$CN; 0-100% gradient) to provide the title compound as the TFA salt. MS (DCI/NH$_3$) m/z 371 (M+H)$^+$; $^1$H NMR (CD$_3$OD) δ 1.62 (m, 4H), 2.33-2.40 (m, 4H), 2.84-2.93 (m, 1H), 3.18-3.30 (m, 1H), 3.96 (s, 2H), 4.56-4.65 (m, 1H), 7.09 (d, J=5.83 Hz, 1H), 7.36-7.44 (m, 2H), 8.71 (s, 2H) 12.64 (s, 1H).

Example 584

N-{2-fluoro-5-[(4-oxo-3,4,5,6,7,8-hexahydrophthalazin-1-yl)methyl]phenyl}-4-methylpiperazine-1-carboxamide To a solution of EXAMPLE 493F (75 mg, 0.27 mmol) in 1:1 tetrahydrofuran/acetonitrile (6 mL) was added 4-methylpiperazine-1-carbonylchloride (179 mg, 1.1 mmol) and triethylamine (56 mg, 0.55 mmol). The mixture was heated at 70° C. for 18 hours and was concentrated. The residue was purified by HPLC (Zorbax C-18, 0.1% TFA/CH$_3$CN/H$_2$O) to provide the title compound as a free base. MS (DCI/NH$_3$) m/z 400 (M+H)$^+$.

Example 585

4-{4-fluoro-3-[(4-propionylpiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 427 (M+H)$^+$; $^1$H NMR (CD$_3$OD) δ 1.06-1.15 (m, 3H), 1.67-1.75 (m, 4H), 2.40 (q, J=7.63 Hz, 2H), 2.43-2.48 (m, 2H), 2.48-2.55 (m, 2H), 3.32-3.43 (m, 2H), 3.51-3.59 (m, 2H), 3.62-3.71 (m, 2H), 3.73-3.83 (m, 2H), 3.99 (s, 2H), 7.14-7.19 (m, 1H), 7.23-7.28 (m, 1H), 7.33-7.38 (m, 1H).

Example 586

4-(3-{[4-(ethylsulfonyl)piperazin-1-yl]carbonyl}-4-fluorobenzyl)-5,6,7,8-tetrahydrophthalazin-1(2H)-one The title compound was prepared, using the appropriate reagents, as the TFA salt according to the procedure for EXAMPLE 543, but was purified by HPLC (Zorbax C-18. 0.1% TFA/CH$_3$CN/H$_2$O) instead of flash chromatography. MS (DCI/NH$_3$) m/z 463 (M+H)$^+$; $^1$H NMR (DMSO-d$_6$) δ 1.21 (t, J=7.48 Hz, 3H), 1.55-1.72 (m, 4H), 2.32-2.43 (m, 4H), 3.08 (q, J=7.53 Hz, 2H), 3.11-3.18 (m, 2H), 3.23-3.32 (m, 4H), 3.64-3.79 (m, 2H), 3.92 (s, 2H), 7.20-7.23 (m, 1H), 7.23-7.27 (m, 1H), 7.29-7.33 (m, 1H), 12.63 (br s, 1H).

Example 587

4-(3-[4-(2,2-dimethylpropanoyl)piperazin-1-yl]carbonyl-4-fluorobenzyl)-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 455 (M+H)$^+$; $^1$H NMR (CD$_3$OD) δ 1.28 (s, 9H), 1.68-1.77 (m, 4H), 2.42-2.48 (m, 2H), 2.48-2.55 (m, 2H), 3.34-3.39 (m, 2H), 3.60-3.67 (m, 2H), 3.73-3.81 (m, 4H), 4.00 (s, 2H), 7.14-7.19 (m, 1H), 7.25 (dd, J=6.26, 2.29 Hz, 1H), 7.33-7.38 (m, 1H).

Example 590

4-(4-fluoro-3-{[4-(phenoxyacetyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 505 (M+H)$^+$; $^1$H NMR (CD$_3$OD) δ 1.67-1.76 (m, 4H), 2.42-2.48 (m, 2H), 2.47-2.53 (m, 2H), 3.33-3.45 (m, 2H), 3.54-3.62 (m, 2H), 3.66-3.73 (m, 2H), 3.74-3.86 (m, 2H), 3.99 (s, 2H), 4.79 (s, 2H), 6.92-7.00 (m, 3H), 7.16 (t, J=9.00 Hz, 1H), 7.23-7.30 (m, 3H), 7.33-7.39 (m, 1H).

Example 591

8-(4-fluoro-3-{[4-(phenoxyacetyl)piperazin-1-yl]carbonyl}benzyl)-2,3,4,6-tetrahydropyrido[2,3-d]pyridazin-5(1H)-one The title compound was prepared, using the appropriate reagents, as TFA salt according to the procedure for EXAMPLE 506. MS (DCI/NH$_3$) m/z 506 (M+H)$^+$; $^1$H NMR (DMSO-d$_6$) δ 1.58-1.78 (m, 2H), 2.34 (t, J=6.27 Hz, 2H), 3.06-3.34 (m, 4H), 3.44 (m, 2H), 3.56 (m, 2H), 3.66 (m, 2H), 3.83 (s, 2H), 4.84 (d, J=16.95 Hz, 2H), 6.39 (s, 1H), 6.84-6.99 (m, 3H), 7.16-7.31 (m, 4H), 7.31-7.39 (m, 1H), 11.90 (s, 1H).

Example 593

8-(3-{[4-(2,2-dimethylpropanoyl)piperazin-1-yl]carbonyl}-4-fluorobenzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 456 (M+H)$^+$; $^1$H NMR (DMSO-d$_6$) δ 1.19 (s, 9H), 1.50-1.80 (m, 2H), 2.35 (t, J=6.10

Hz, 2H), 2.97-3.32 (m, 4H), 3.47-3.58 (m, 2H), 3.62 (s, 4H), 3.83 (s, 2H), 6.42 (s, 1H) 7.10-7.28 (m, 2H), 7.29-7.46 (m, 1H) 11.93 (s, 1H).

Example 594

8-(3-{[4-(ethylsulfonyl)piperazin-1-yl]carbonyl}-4-fluorobenzyl)-2,3,4,6-tetrahydropyrido[2,3-d]pyridazin-5(H)-one The title compound was prepared, using the appropriate reagents, as the TFA salt according to the procedure for EXAMPLE 506. MS (DCI/NH$_3$) m/z 464 (M+H)$^+$; $^1$H NMR (DMSO-d$_6$) δ 1.21 (t, J=7.46 Hz, 3H), 1.63-1.77 (m, 2H), 2.35 (t, J=6.10 Hz, 2H), 3.08 (q, J=7.23 Hz, 2H), 3.13-3.22 (m, 4H), 3.21-3.35 (m, 4H), 3.71 (s, 2H), 3.82 (s, 2H), 6.40 (s, 1H), 7.08-7.28 (m, 2H), 7.29-7.47 (m, 1H), 11.91 (s, 1H).

Example 595

N-(1-{2-fluoro-5-[(5-oxo-1,2,3,4,5,6-hexahydropyrido[2,3-d]pyridazin-8-yl)methyl]benzoyl}pyrrolidine-3-yl)-N-methylacetamide The title compound was prepared, using the appropriate reagents, as the TFA salt according to the procedure for EXAMPLE 506. MS (DCI/NH$_3$) m/z 428 (M+H)$^+$.

Example 596

N-ethyl-N-(1-{2-fluoro-5-[(5-oxo-1,2,3,4,5,6-hexahydropyrido[2,3-d]pyridazin-8-yl)methyl]benzoyl}pyrrolidine-3-yl)acetamide The title compound was prepared, using the appropriate reagents, as the TFA salt according to the procedure for EXAMPLE 506. MS (DCI/NH$_3$) m/z 442 (M+H)$^+$.

Example 597

8-{4-fluoro-3-[(4-propionylpiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 428 (M+H)$^+$; $^1$H NMR (DMSO-d$_6$) δ 0.99 (t, J=6.95 Hz, 3H), 1.58-1.82 (m, 2H), 2.22-2.44 (m, 4H), 3.04-3.31 (m, 4H), 3.41 (m, 2H), 3.52 (m, 2H), 3.56-3.72 (m, 2H), 3.83 (s, 2H), 6.45 (s, 1H), 7.05-7.28 (m, 2H), 7.28-7.50 (m, 1H), 11.96 (s, 1H).

Example 598

3-{2-fluoro-5-[(5-oxo-1,2,3,4,5,6-hexahydropyrido[2,3-d]pyridazin-8-yl)methyl]phenyl}-5-methylimidazolidine-2,4-dione The title compound was prepared, using the appropriate reagents, as the TFA salt according to the procedure for EXAMPLE 582. MS (DCI/NH$_3$) m/z 372 (M+H)$^+$.

Example 599

8-(4-fluoro-3-{[4-(4-methoxyphenyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 478 (M+H)$^+$; $^1$H NMR (DMSO-d$_6$) δ 1.62-1.79 (m, 2H), 2.35 (t, J=6.10 Hz, 2H), 3.02 (m, 2H), 3.07-3.24 (m, 4H), 3.39 (m, 2H), 3.70 (s, 3H), 3.81 (m, 2H), 3.84 (s, 2H), 6.46 (s, 1H), 6.89 (d, J=8.48 Hz, 2H), 7.00 (d, J=8.81 Hz, 2H), 7.18-7.31 (m, 2H), 7.31-7.40 (m, 1H), 11.99 (s, 1H).

Example 600

8-[4-fluoro-3-({4-[(4-methoxyphenyl)sulfonyl]piperazin-1-yl}carbonyl)benzyl]-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 542 (M+H)$^+$; $^1$H NMR (DMSO-d$_6$) δ 1.55-1.77 (m, 2H), 2.34 (t, J=6.10 Hz, 2H), 2.74-2.89 (m, 2H), 2.94 (m, 2H), 3.09-3.19 (m, 2H), 3.24-3.36 (m, 2H), 3.71 (m, 2H), 3.78 (s, 2H), 3.87 (s, 3H), 6.34 (s, 1H), 7.17 (d, J=8.81 Hz, 2H), 7.16-7.23 (m, 2H), 7.23-7.37 (m, 1H), 7.67 (d, J=9.15 Hz, 2H), 11.87 (s, 1H).

Example 601

8-(4-fluoro-3-{[4-(4-methoxybenzoyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 506 (M+H)$^+$; $^1$H NMR (DMSO-d$_6$) δ 1.57-1.80 (m, 2H), 2.35 (t, J=6.10 Hz, 2H), 3.09-3.22 (m, 2H), 3.29 (m, 2H), 3.48 (m, 2H), 3.55 (m, 2H), 3.69 (m, 2H), 3.79 (s, 3H), 3.83 (s, 2H), 6.43 (s, 1H), 6.98 (d, J=8.48 Hz, 2H), 7.16-7.30 (m, 2H), 7.28-7.36 (m, 1H), 7.40 (d, J=8.81 Hz, 2H), 11.94 (s, 1H).

Example 602

8-[4-fluoro-3-({4-[3-(trifluoromethyl)phenyl]piperazin-1-yl}carbonyl)benzyl]-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 516 (M+H)$^+$; $^1$H NMR (DMSO-d$_6$) δ 1.55-1.83 (m, 2H), 2.35 (t, J=6.10 Hz, 2H), 3.09-3.26 (m, 4H), 3.27-3.43 (m, 4H), 3.79 (m, 2H), 3.83 (s, 2H), 6.41 (s, 1H), 7.11 (d, J=7.80 Hz, 1H), 7.17-7.32 (m, 4H), 7.31-7.39 (m, 1H), 7.44 (t, J=7.80 Hz, 1H), 11.91 (s, 1H).

Example 603 tert-butyl 3-{2-fluoro-5-[(5-oxo-1,2,3,4,5,6-hexahydropyrido[2,3-d]pyridazin-8-yl)methyl]benzoyl}tetrahydropyrimidine-1(2H)-carboxylate The title compound was prepared, using the appropriate reagents, as the TFA salt according to the procedure for EXAMPLE 506. MS (DCI/NH$_3$) m z 542 (M+H)$^+$; $^1$H NMR (DMSO-d$_6$) 1.41 (s, 9H), 1.59 (m, 2H), 1.63-1.78 (m, 2H), 2.33 (t, J=5.43 Hz, 2H), 3.14-3.22 (m, 2H), 3.21-3.38 (m, 1H), 3.43-3.54 (m, 2H), 3.62-3.78 (m, 1H), 3.71-3.83 (m, 2H), 5.11 (s, 2H), 6.38 (d, J=2.03 Hz, 1H), 7.00-7.29 (m, 2H), 7.29-7.59 (m, 1H), 11.89 (s, 1H).

Example 604

8-(3-{[3-[3-(dimethylamino)propyl]tetrahydropyrimidin-1(2H)-yl]carbonyl}-4-fluorobenzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 457 (M+H)$^+$.

Example 605

5-benzyl-3-{2-fluoro-5-[(5-oxo-1,2,3,4,5,6-hexahydropyrido[2,3-d]pyridazin-8-yl)methyl]phenyl}imidazolidine-2,4-dione The title compound was prepared, using the appropriate reagents, as the TFA salt according to the procedure for EXAMPLE 582. MS (DCI/NH$_3$) m/z 448 (M+H)$^+$.

Example 606

3-{2-fluoro-5-[(5-oxo-1,2,3,4,5,6-hexahydropyrido[2,3-d]pyridazin-8-yl)methyl]phenyl}dihydropyrimidine-2,4(1H,3H)-dione The title compound was prepared, using the appropriate reagents, as the TFA salt according to the procedure for EXAMPLE 582. MS (DCI/NH$_3$) m/z 372 (M+H)$^+$; $^1$H NMR (DMSO-d$_6$) δ 1.68 (m, 2H), 2.27-2.37 (m, 2H), 2.40 (t, J=6.27 Hz, 2H), 3.17 (m, 2H), 3.33 (m, 2H), 3.73 (s, 2H), 6.24 (s, 1H), 6.66-6.82 (m, 2H), 7.05 (dd, J=11.36, 8.31 Hz, 1H), 8.31 (s, 1H), 11.79 (s, 1H).

Example 607

8-{4-fluoro-3-[(3-oxopiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 386 (M+H)$^+$; $^1$H NMR (DMSO-d$_6$) 1.47-1.78 (m, 2H), 2.34 (t, J=6.10 Hz, 2H), 3.07-3.24 (m, 2H), 3.39 (m, 2H), 3.69-3.81 (m, 2H), 3.83 (s, 2H), 4.11 (s, 2H), 6.38 (s, 1H), 7.04-7.30 (m, 2H), 7.31-7.41 (m, 1H), 8.13 (s, 1H), 11.89 (s, 1H).

Example 609

8-{3-[(4-benzoylpiperidin-1-yl)carbonyl]-4-fluorobenzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 475 (M+H)$^+$; $^1$H NMR (DMSO-d$_6$) δ 1.38-1.58 (m, 2H), 1.59-1.74 (m, 2H), 1.70-1.81 (m, 1H), 1.91 (m, 1H), 2.33 (t, 0.1=6.10 Hz, 2H), 2.90-3.08 (m, 1H), 3.13-3.21 (m, 2H), 3.21-3.29 (m, 1H), 3.45 (m, 1H), 3.65-3.83 (m, 1H), 3.82 (s, 2H), 4.52 (m, 1H), 6.39 (s, 1H), 7.14-7.28 (m, 2H), 7.28-7.35 (m, 1H), 7.55 (t, J=7.29 Hz, 2H), 7.60-7.70 (m, 1H), 7.95-8.04 (m, 2H), 11.88 (s, 1H).

Example 610

8-(4-fluoro-3-{[4-(4-methoxybenzoyl)piperidin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 505 (M+H)$^+$; $^1$H NMR (DMSO-d$_6$) 1.38-1.58 (m, 2H), 1.60-1.74 (m, 3H), 1.81-1.88 (m, 1H), 2.33 (t, J=6.10 Hz, 2H), 2.91-3.06 (m, 1H), 3.17 (m, 2H), 3.19-3.30 (m, 1H), 3.45 (m, 1H), 3.72 (m, 1H), 3.82 (s, 2H), 3.85 (s, 3H), 4.52 (m, 1H), 6.41 (s, 1H), 7.06 (d, J=9.15 Hz, 2H), 7.13-7.26 (m, 2H), 7.27-7.36 (m, 1H), 7.99 (d, J=9.15 Hz, 2H), 11.89 (s, 1H).

Example 611

8-(4-fluoro-3-{[4-(1H-indol-6-ylcarbonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 515 (M+H)$^+$; $^1$H NMR (DMSO-d$_6$) δ 1.60-1.74 (m, 2H), 2.34 (t, J=6.10 Hz, 2H), 3.17 (m, 2H), 3.30 (m, 2H), 3.52 (m, 2H), 3.57-3.66 (m, 2H), 3.69 (m, 2H), 3.82 (s, 2H), 6.48 (s, 1H), 7.06 (m, 2H), 7.16-7.30 (m, 2H), 7.30-7.38 (m, 1H), 7.47 (dd, J=4.92, 2.20 Hz, 2H), 7.58 (d, J=8.14 Hz, 1H), 11.30 (s, 1H), 11.91 (s, 1H).

Example 612

8-(3-{[4-(3-chlorobenzoyl)piperidin-1-yl]carbonyl}-4-fluorobenzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 510 (M+H)$^+$; $^1$H NMR (DMSO-d$_6$) δ 1.36-1.55 (m, 2H), 1.61-1.74 (m, 3H), 1.81-1.88 (m, 1H), 2.33 (t, J=6.10 Hz, 2H), 2.91-3.09 (m, 1H), 3.12-3.20 (m, 2H), 3.20-3.32 (m, 1H), 3.44 (m, 1H), 3.69-3.81 (m, 1H), 3.82 (s, 2H), 4.51 (m, 1H), 6.41 (s, 1H), 7.13-7.27 (m, 2H), 7.26-7.36 (m, 1H), 7.58 (t, J=7.80 Hz, 1H), 7.73 (dd, J=7.46, 1.70 Hz, 1H), 7.90-8.04 (m, 2H), 11.90 (s, 1H).

Example 613 benzyl 4-{2-fluoro-5-[(5-oxo-1,2,3,4,5,6-hexahydropyrido[2,3-d]pyridazin-8-yl)methyl]benzoyl}piperazine-1-carboxylate The title compound was prepared, using the appropriate reagents, according to the procedure for EXAMPLE 506. MS (DCI/NH$_3$) m/z 506 (M+H)$^+$; $^1$H NMR (DMSO-d$_6$) δ 1.51-1.76 (m, 2H), 2.33 (t, J=6.10 Hz, 2H), 3.17 (m, 2H), 3.24 (m, 2H), 3.35-3.44 (m, 2H), 3.48 (m, 2H), 3.64 (m, 2H), 3.81 (s, 2H), 5.10 (s, 2H), 6.34 (s, 1H), 7.17-7.28 (m, 2H), 7.29-7.36 (m, 1H), 7.34-7.40 (m, 5H), 11.83 (s, 1H).

Example 614 tert-butyl (3R)-4-{2-fluoro-5-[(5-oxo-1,2,3,4,5,6-hexahydropyrido[2,3-d]pyridazin-8-yl)methyl]benzoyl}-3-phenylpiperazine-1-carboxylate The title compound was prepared, using the appropriate reagents, as the TFA salt according to the procedure for EXAMPLE 506. MS (DCI/NH$_3$) m/z 548 (M+H)$^+$.

Example 616

8-(3-{[(2R)-4-benzoyl-2-methylpiperazin-1-yl]carbonyl}-4-fluorobenzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 490 (M+H)$^+$.

Example 617

8-[4-fluoro-3-(piperazin-1-ylcarbonyl)benzyl]-2,3,4,6-tetrahydropyrido[2,3-d]pyridazin-5(1H)-one The title compound was prepared, using the appropriate reagents, as TFA salt according to the procedure for EXAMPLE 506. MS (DCI/NH$_3$) m/z 372 (M+H)$^+$.

Example 618

N'-{2-fluoro-5-[(4-oxo-3,4,5,6,7,8-hexahydrophthalazin-1-yl)methyl]phenyl}-N-methyl-N-phenylurea The title compound was prepared, using the appropriate reagents, as the TFA salt according to the procedure for EXAMPLE 584. MS (DCI/NH$_3$) m/z 407 (M+H)$^+$.

Example 619

N-ethyl-N-(1-{2-fluoro-5-[(4-oxo-3,4,5,6,7,8-hexahydrophthalazin-1-yl)methyl]benzoyl}pyrrolidine-3-yl)acetamide The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 441 (M+H)$^+$; $^1$H NMR (DMSO-d$_6$) δ 0.89-1.15 (m, 3H), 1.52-1.65 (m, 4H), 1.90-2.00 (m, 2H), 2.01-2.16 (m, 3H), 2.27-2.40 (m, 4H), 3.18-3.32 (m, 4H), 3.35-3.43 (m, 2H), 3.60-3.74 (m, 1H), 3.90 (s, 2H), 7.17-7.25 (m, 2H), 7.25-7.32 (m, 1H), 12.60 (br s, 1H).

Example 620

4-[4-fluoro-3-({4-[(4-methoxyphenyl)sulfonyl]piperazin-1-yl}carbonyl)benzyl]-5,6,7,8-tetrahydrophthalazin-1(2H)-one The title compound was prepared, using the appropriate reagents, as the free base according to the procedure for EXAMPLE 543, but was purified by HPLC (Zorbax C-18, 0.1% TFA/CH$_3$CN/H$_2$O) instead of flash chromatography. MS (DCI/NH$_3$) m/z 541 (M+H)$^+$.

Example 621

4-[4-fluoro-3-({4-[3-(trifluoromethyl)phenyl]piperazin-1-yl}carbonyl)benzyl]-5,6,7,8-tetrahydrophthalazin-1(2H)-one The title compound was prepared, using the appropriate reagents, as the free base according to the procedure for EXAMPLE 543, but was purified by HPLC (Zorbax C-18, 0.1% TFA/CH$_3$CN/H$_2$O) instead of flash chromatography. MS (DCI/NH$_3$) m/z 515 (M+H)$^+$; $^1$H NMR (CD$_3$OD) δ 1.68-1.77 (m, 4H), 2.43-2.48 (m, 2H), 2.49-2.55 (m, 2H), 3.16-3.24 (m, 2H), 3.32-3.36 (m, 2H), 3.46-3.55 (m, 2H), 3.90-3.95 (m, 2H), 4.00 (s, 2H), 7.11 (d, J=7.63 Hz, 1H), 7.17 (t, J=8.85 Hz, 1H), 7.19-7.24 (m, 2H), 7.26 (dd, J=6.41, 2.14 Hz, 1H), 7.34-7.38 (m, 1H), 7.41 (t, J=7.78 Hz, 1H).

Example 622

4-(4-fluoro-3-{[4-(4-methoxybenzoyl)piperazin-1-yl]carbonyl}benzyl)-5,6,7,8-tetrahydrophthalazin-1(2H)-one The title compound was prepared, using the appropriate reagents, as the free base according to the procedure for EXAMPLE 543, but was purified by HPLC (Zorbax C-18, 0.1% TFA/CH$_3$CN/H$_2$O) instead of flash chromatography. MS (DCI/NH$_3$) m/z 505 (M+H)$^+$; $^1$H NMR (CD$_3$OD) δ 1.66-1.77 (m, 4H), 2.41-2.47 (m, 2H), 2.47-2.53 (m, 2H), 3.37-3.48 (m, 2H), 3.55-3.67 (m, 2H), 3.67-3.77 (m, 2H), 3.77-3.82 (m, 2H), 3.83 (s, 3H), 3.99 (s, 2H), 7.00 (d, J=8.85 Hz, 2H), 7.14-7.19 (m, 1H), 7.25 (dd, J=6.10, 2.14 Hz, 1H), 7.33-7.38 (m, 1H), 7.42 (d, J=8.54 Hz, 2H).

Example 623

4-(4-fluoro-3-{[4-(4-methoxyphenyl)piperazin-1-yl]carbonyl}benzyl)-5,6,7,8-tetrahydrophthalazin-1(2H)-one The title compound was prepared, using the appropriate reagents, as the free base according to the procedure for EXAMPLE 543, but was purified by HPLC (Zorbax C-18, 0.1% TFA/CH$_3$CN/H$_2$O) instead of flash chromatography. MS (DCI/NH$_3$) m/z 477 (M+H)$^+$; $^1$H NMR (CD$_3$OD) δ 1.67-1.77 (m, 4H), 2.42-2.48 (m, 2H), 2.49-2.56 (m, 2H), 3.19-3.27 (m, 2H), 3.33-3.41 (m, 2H), 3.56-3.65 (m, 2H), 3.78 (s, 3H), 3.96-4.07 (m, 4H), 6.93-6.94 (m, 1H), 6.95-6.97 (m, 1H), 7.16-7.18 (m, 2H), 7.19-7.21 (m, 1H), 7.28 (dd, J=6.41, 2.14 Hz, 1H), 7.35-7.41 (m, 1H).

Example 624

4-(3-{[4-(cyclohexylcarbonyl)piperazin-1-yl]carbonyl}-4-fluorobenzyl)-5,6,7,8-tetrahydrophthalazin-1(2H)-one The title compound was prepared, using the appropriate reagents, as the free base according to the procedure for EXAMPLE 543, but was purified by HPLC (Zorbax C-18, 0.1% TFA/CH$_3$CN/H$_2$O) instead of flash chromatography. MS (DCI/NH$_3$) m/z 481 (M+H)$^+$; $^1$H NMR (CD$_3$OD) δ 1.19-1.29 (m, 1H), 1.30-1.40 (m, 2H), 1.41-1.49 (m, 2H), 1.65-1.74 (m, 7H), 1.76-1.84 (m, 2H), 2.41-2.48 (m, 2H), 2.48-

2.56 (m, 2H), 2.58-2.73 (m, 1H), 3.33-3.43 (m, 2H), 3.52-3.62 (m, 2H), 3.64-3.72 (m, 2H), 3.72-3.85 (m, 2H), 3.99 (s, 2H), 7.14-7.20 (m, 1H), 7.22-7.28 (m, 1H), 7.33-7.39 (m, 1H).

Example 625

N-[({2-fluoro-5-[(4-oxo-3,4,5,6,7,8-hexahydro-phthalazin-1-yl)methyl]phenyl}amino)carbonyl] glycine To a solution of EXAMPLE 493F (100 mg, 0.37 mmol) in tetrahydrofuran (5 mL) was added ethyl-2-isocyanoacetate (47 mg, 0.37 mmol). The solution was stirred at room temperature for 16 hours and sodium hydroxide (15 mg, 0.37 mmol) was added. The mixture was heated at 70° C. for 2 hours and was concentrated. The residue was purified by HPLC (Zorbax C-18, 0.1% TFA/$CH_3CN/H_2O$) to provide the title compound. MS (DCI/$NH_3$) m/z 375 (M+H)$^+$.

Example 626

N-[({2-fluoro-5-[(4-oxo-3,4,5,6,7,8-hexahydro-phthalazin-1-yl)methyl]phenyl}amino)carbonyl] leucine The title compound was prepared, using the appropriate reagents, as the free base according to the procedure for EXAMPLE 625. MS (DCI/$NH_3$) m/z 431 (M+H)$^+$.

Example 627

N-[({2-fluoro-5-[(4-oxo-3,4,5,6,7,8-hexahydro-phthalazin-1-yl)methyl]phenyl}amino)carbonyl] alanine The title compound was prepared, using the appropriate reagents, as the free base according to the procedure for EXAMPLE 625. MS (DCI/$NH_3$) m/z 389 (M+H)$^+$.

Example 628

N-[({2-fluoro-5-[(4-oxo-3,4,5,6,7,8-hexahydro-phthalazin-1-yl)methyl]phenyl}amino)carbonyl] phenylalanine The title compound was prepared, using the appropriate reagents, as the free base according to the procedure for EXAMPLE 625. MS (DCI/$NH_3$) m/z 465 (M+H)$^+$.

Example 629 ethyl N-[({2-fluoro-5-[(4-oxo-3,4,5,6,7,8-hexahydro-phthalazin-1-yl)methyl]phenyl}amino)carbonyl] glycinate To a solution of EXAMPLE 493F (2.0 g, 7.3 mmol) in a mixture of tetrahydrofuran (25 mL) and N,N-dimethylformamide (2 mL) was added ethyl-2-isocyanoacetate (0.95 g, 7.3 mmol). The mixture was stirred at room temperature for 16 hours and was concentrated. The residue was partitioned between ethyl acetate and brine and the organic layer was washed with brine and concentrated. The residue was purified by flash chromatography on silica gel eluting with 70% ethyl acetate in hexanes to provide the title compound. MS (DCI/$NH_3$) m/z 403 (M+H)$^+$; $^1$H NMR (DMSO-$d_6$) δ 1.19 (t, J=7.17 Hz, 3H), 1.52-1.63 (m, 4H), 2.29-2.40 (m, 4H), 3.81 (s, 2H), 3.86 (d, J=5.80 Hz, 2H), 4.10 (q, J=7.12 Hz, 2H), 6.69-6.77 (m, 1H), 6.88-6.97 (m, 1H), 7.09 (dd, J=11.29, 8.54 Hz, 1H), 7.94 (dd, J=7.93, 1.83 Hz, 1H), 8.56 (br s, 1H), 12.60 (br s, 1H).

Example 630

3-{2-fluoro-5-[(4-oxo-3,4,5,6,7,8-hexahydro-phthalazin-1-yl)methyl]phenyl}imidazolidine-2,4-dione To a solution of EXAMPLE 629 (650 mg, 1.6 mmol) in 1:1 chloroform/ethanol (40 mL) was added 10N HCl (20 mL). The mixture was heated at 80° C. for 2 days and was concentrated. The residue was purified by HPLC (Zorbax C-18, 0.1% TFA/$CH_3CN/H_2O$) to yield the title compound as a free base. MS (DCI/$NH_3$) m/z 357 (M+H)$^+$; $^1$H NMR (CD$_3$OD) δ 1.69-1.75 (m, 4H), 2.43-2.48 (m, 2H), 2.48-2.54 (m, 2H), 4.01 (s, 2H), 4.15 (s, 2H), 7.18-7.20 (m, 1H), 7.21-7.25 (m, 1H), 7.31-7.35 (m, 1H).

Example 631

8-(4-fluoro-3-{[4-(2-methoxyphenyl)piperazin-1-yl] carbonyl}benzyl)-2,3,4,6-tetrahydropyrido[2,3-d] pyridazin-5(1H)-one The title compound was prepared, using the appropriate reagents, as the TFA salt according to the procedure for EXAMPLE 506. MS (DCI/$NH_3$) m/z 478 (M+H)$^+$; $^1$H NMR (DMSO-$d_6$) δ 1.48-1.83 (m, 2H), 2.35 (t, J=6.10 Hz, 2H), 2.93 (m, 2H), 2.99-3.09 (m, 2H), 3.09-3.26 (m, 2H), 3.37 (m, 2H), 3.76 (m, 2H), 3.79 (s, 3H), 3.84 (s, 2H), 6.46 (s, 1H), 6.84-6.96 (m, 2H), 6.94-7.05 (m, 2H), 7.18-7.30 (m, 2H), 7.30-7.38 (m, 1H), 11.97 (s, 1H).

Example 632

8-(4-fluoro-3-{[4-(1,3,5-triazin-2-yl)piperazin-1-yl] carbonyl}benzyl)-2,3,4,6-tetrahydropyrido[2,3-d] pyridazin-5(1H)-one The title compound was prepared, using the appropriate reagents, as the TFA salt according to the procedure for EXAMPLE 506. MS (DCI/$NH_3$) m/z 451 (M+H)$^+$; $^1$H NMR (DMSO-$d_6$) δ 1.62-1.82 (m, 2H), 2.35 (t, J=6.10 Hz, 2H), 3.10-3.23 (m, 2H), 3.30-3.39 (m, 2H), 3.75 (m, 2H), 3.76-3.82 (m, 2H), 3.84 (s, 2H), 3.86-3.94 (m, 2H), 6.45 (s, 1H), 7.16-7.31 (m, 2H), 7.32-7.40 (m, 1H), 8.64 (s, 2H), 11.96 (s, 1H).

Example 633

8-(3-{[4-(2,3-dihydro-1,4-benzodioxin-2-ylcarbonyl) piperazin-1-yl]carbonyl}-4-fluorobenzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/$NH_3$) m/z 451 (M+H)$^+$; $^1$H NMR (DMSO-$d_6$) δ 1.61-1.79 (m, 2H), 2.34 (t, J=6.27 Hz, 2H), 3.11-3.22 (m, 2H), 3.28 (m, 2H), 3.65 (m, 6H), 3.83 (s, 2H), 4.06-4.39 (m, 2H), 5.23 (m, 1H), 6.39 (s, 1H), 6.85 (s, 4H), 7.17-7.32 (m, 2H), 7.30-7.41 (m, 1H), 11.89 (s, 1H).

Example 634

4-(3-{[4-(cyclopropylcarbonyl)-1,4-diazepan-1-yl]carbonyl}-4-fluorobenzyl)-5,6,7,8-tetrahydrophthalazin-1(2H)-one Example 634A 4-(3-(1,4-diazepane-1-carbonyl)-4-fluorobenzyl)-5,6,7,8-tetrahydrophthalazin-1(2H)-one To a solution of EXAMPLE 544 (584 mg, 1.13 mmol) in 1:1 dichloromethane/methanol (20 mL) was added 10% Pd/C (150 mg) under nitrogen. The suspension was purged with hydrogen, and stirred under hydrogen at room temperature for 18 hours. Solid material was filtered off, and the filtrate was concentrated to provide the title compound. MS (DCI/NH$_3$) m/z 385 (M+H)$^+$.

Example 634B 4-(3-{[4-(cyclopropylcarbonyl)-1,4-diazepan-1-yl]carbonyl}-4-fluorobenzyl)-5,6,7,8-tetrahydrophthalazin-1(2H)-one To a solution of EXAMPLE 634A (30 mg, 0.08 mmol) in N,N-dimethylformamide (2 mL) was added cyclopropanecarboxylic acid (6.7 mg, 0.08 mmol), 1-ethyl-3-(3-dimethylaminopropyl) carbodiimide hydrochloride (EDC) (30 mg, 0.16 mmol), N-hydroxybenzotriazole (HOBt) (24 mg, 0.16 mmol) and triethylamine (0.02 mL, 0.16 mmol). The mixture was stirred at room temperature for 16 hours, filtered, and concentrated. The residue was purified by HPLC (Zorbax C-18, 0.1% TFA/CH$_3$CN/H$_2$O) to yield the title compound as a TFA salt. MS (DCI/NH$_3$) m/z 453 (M+H)$^+$; $^1$H NMR (CD$_3$OD) δ 0.77-0.85 (m, 4H), 0.85-0.96 (m, 1H), 1.67-1.78 (m, 4H), 1.86-2.10 (m, 2H), 2.39-2.47 (m, 2H), 2.47-2.56 (m, 2H), 3.34-3.50 (m, 2H), 3.54-3.68 (m, 2H), 3.74-3.79 (m, 1H), 3.79-3.88 (m, 2H), 3.99 (s, 2H), 3.99-4.04 (m, 1H), 7.09-7.14 (m, 1H), 7.14-7.19 (m, 1H), 7.30-7.37 (m, 1H).

Example 635

4-[4-fluoro-3-({4-[(1-methylcyclopropyl)carbonyl]-1,4-diazepan-1-yl}carbonyl)benzyl]-5,6,7,8-tetrahydrophthalazin-1(2H)-one The title compound was prepared, using the appropriate reagents, as the TFA salt according to the procedure for EXAMPLE 634. MS (DCI/NH$_3$) m/z 467 (M+H)$^+$; $^1$H NMR (CD$_3$OD) δ 0.56-0.66 (m, 2H), 0.83-0.96 (m, 2H), 1.26-1.32 (m, 3H), 1.53-1.66 (m, 1H), 1.67-1.78 (m, 4H), 1.95-2.06 (m, 1H), 2.38-2.47 (m, 2H), 2.48-2.56 (m, 2H), 3.33-3.41 (m, 1H), 3.43-3.50 (m, 1H), 3.57-3.69 (m, 2H), 3.75-3.86 (m, 2H), 3.89-3.97 (m, 2H), 3.98 (s, 2H), 7.01-7.10 (m, 1H), 7.11-7.19 (m, 1H), 7.31-7.37 (m, 1H).

Example 636

4-[4-fluoro-3-({4-[(1-methyl-1H-imidazol-4-yl)carbonyl]-1,4-diazepan-1-yl}carbonyl)benzyl]-5,6,7,8-tetrahydrophthalazin-1(2H)-one The title compound was prepared, using the appropriate reagents, according to the procedure for EXAMPLE 634. After HPLC purification, the compound was treated with 1M HCl in ether to give the HCl salt. MS (DCI/NH$_3$) m/z 493 (M+H)$^+$.

Example 637

4-[4-fluoro-3-({4-[(1-methyl-1H-imidazol-5-yl)carbonyl]-1,4-diazepan-1-yl}carbonyl)benzyl]-5,6,7,8-tetrahydrophthalazin-1(2H)-one The title compound was prepared, using the appropriate reagents, according to the procedure for EXAMPLE 634. After HPLC purification, the compound was treated with 1M HCl in ether to give the HCl salt. MS (DCI/NH$_3$) m/z 493 (M+H)$^+$.

Example 638

8-(4-fluoro-3-{[(2R),-2-phenylpiperazin-1-yl]carbonyl}benzyl),-2,3,4,6-tetrahydropyrido[2,3-d]pyridazin-5(1H),-one A solution of EXAMPLE 614 (60 mg, 0.1 mmol) in tetrahydrofuran (10 mL) was treated with trifluoroacetic acid (5 mL) at room temperature for 3 days and was concentrated. The residue was purified by HPLC (Zorbax C-18, 0.1% TFA/CH$_3$CN/H$_2$O) to provide the title compound as the TFA salt. MS (DCI/NH$_3$) m/z 448 (M+H)$^+$; $^1$H NMR (DMSO-d$_6$) δ 1.48-1.86 (m, 2H), 2.14-2.42 (m, 2H), 3.02-3.37 (m, 2H), 3.40-3.73 (m, 2H), 3.87 (m, 4H), 3.84 (s, 2H), 4.63 (m, 1H), 6.37 (s, 1H), 7.20-7.37 (m, 3H), 7.37-7.47 (m, 2H), 7.48-7.63 (m, 3H), 9.56 (s, 1H), 11.86 (s, 1H).

Example 639

8-[4-fluoro-3-({4-[(4R),-1,3-thiazolidin-4-ylcarbonyl]piperazin-1-yl}carbonyl),benzyl]-2,3,4,6-tetrahydropyrido[2,3-d]pyridazin-5(1H),-one The title compound was prepared, using the appropriate reagents, as the TFA salt according to the procedure for EXAMPLE 506. MS (DCI/NH$_3$) m/z 484 (M+H)$^+$.

Example 640

8-(3-{[4-(cyclopentylcarbonyl),piperazin-1-yl]carbonyl}-4-fluorobenzyl),-2,3,4,6-tetrahydropyrido[2,3-d]pyridazin-5(1H),-one The title compound was prepared, using the appropriate reagents, as the TFA salt according to the procedure for EXAMPLE 506. MS (DCI/NH$_3$) m/z 468 (M+H)$^+$; $^1$H NMR (DMSO-d$_6$) δ 1.42-1.63 (m, 4H), 1.64-1.85 (m, 6H), 2.35 (t, J=0.10 Hz, 2H), 2.82-3.08 (m, 1H), 3.12-3.30 (m, 4H), 3.35-3.52 (m, 2H), 3.50-3.71 (m, 4H), 3.83 (s, 2H), 6.41 (s, 1H), 7.10-7.28 (m, 2H), 7.28-7.51 (m, 1H), 11.92 (s, 1H).

Example 641

8-[3-({4-[(5-chloropyridin-2-yl),carbonyl]piperazin-1-yl}carbonyl),-4-fluorobenzyl]-2,3,4,6-tetrahydropyrido[2,3-d]pyridazin-5(1H),-one The title compound was prepared, using the appropriate reagents, as the TFA salt according to the procedure for EXAMPLE 506. MS (DCI/NH$_3$) m/z 511 (M+H)$^+$.

Example 643

8-[4-fluoro-3-({4-[(1-isopropyl-1H-1,2,3-benzotriazol-5-yl),carbonyl]piperazin-1-yl)}carbonyl),benzyl]-2,3,4,6-tetrahydropyrido[2,3-d]pyridazin-5(1H),-one The title compound was prepared, using the appropriate reagents, as the TFA salt according to the procedure for EXAMPLE 506. MS (DCI/NH$_3$) m/z 559 (M+H)$^+$.

Example 644

8-(4-fluoro-3-{[4-(4-methylpiperazin-1-yl),piperidin-1-yl]carbonyl}benzyl),-2,3,4,6-tetrahydropyrido[2,3-d]pyridazin-5(1H),-one The title compound was prepared, using the appropriate reagents, as the TFA salt according to the procedure for EXAMPLE 506. MS (DCI/NH$_3$) m/z 469 (M+H)$^+$.

Example 645

8-(4-fluoro-3-{[4-(quinolin-2-ylcarbonyl),piperazin-1-yl]carbonyl}benzyl),-2,3,4,6-tetrahydropyrido[2,3-d]pyridazin-5(1H),-one The title compound was prepared, using the appropriate reagents, as the TFA salt according to the procedure for EXAMPLE 506. MS (DCI/NH$_3$) m/z 527 (M+H)$^+$.

Example 646

8-[3-({4-[(6-chloropyridin-3-yl),carbonyl]piperazin-1-yl}carbonyl)-4-fluorobenzyl]-2,3,4,6-tetrahydropyrido[2,3-d]pyridazin-5(H)-one The title compound was prepared, using the appropriate reagents, as the TFA salt according to the procedure for EXAMPLE 506. MS (DCI/NH$_3$) m/z 511 (M+H)$^+$.

Example 647

8-{4-fluoro-3-[(4-{[1-isopropyl-2-(trifluoromethyl)-1H-benzimidazol-5-yl]carbonyl}piperazin-1-yl),carbonyl]benzyl}-2,3,4,6-tetrahydropyrido[2,3-d]pyridazin-5(1H),-one The title compound was prepared, using the appropriate reagents, as the TFA salt according to the procedure for EXAMPLE 506. MS (DCI/NH$_3$) m/z 626 (M+H)$^+$.

Example 649

8-[4-fluoro-3-({4-[(6-hydroxypyridin-3-yl),carbonyl]piperazin-1-yl}carbonyl),benzyl]-2,3,4,6-tetrahydropyrido[2,3-d]pyridazin-5(1H),-one The title compound was prepared, using the appropriate reagents, as the TFA salt according to the procedure for EXAMPLE 506. MS (DCI/NH$_3$) m/z 493 (M+H)$^+$.

Example 651

8-[3-({4-[(6-chloro-5-hydroxypyridin-3-yl),carbonyl]piperazin-1-yl}carbonyl),-4-fluorobenzyl]-2,3,4,6-tetrahydropyrido[2,3-d]pyridazin-5(1H),-one The title compound was prepared, using the appropriate reagents, as the TFA salt according to the procedure for EXAMPLE 506. MS (DCI/NH$_3$) m/z 527 (M+H)$^+$; $^1$H NMR (DMSO-d$_6$) δ 1.60-1.79 (m, 2H), 2.34 (t, J=6.10 Hz, 2H), 3.11-3.23 (m, 2H), 3.27 (m, 2H), 3.48 (m, 2H), 3.58 (m, 2H), 3.63-3.73 (m, 2H), 3.82 (s, 2H), 6.43 (s, 1H), 7.18-7.29 (m, 2H), 7.30-7.39 (m, 1H), 7.64 (d, J=2.03 Hz, 1H), 7.80 (d, J=2.37 Hz, 1H), 11.92 (s, 1H).

Example 654

8-[4-fluoro-3-({4-[(2-methyl-1H-benzimidazol-5-yl),carbonyl]piperazin-1-yl}carbonyl),benzyl]-2,3,4,6-tetrahydropyrido[2,3-d]pyridazin-5(1H),-one The title compound was prepared, using the appropriate reagents, as the TFA salt according to the procedure for EXAMPLE 506. MS (DCI/NH$_3$) m/z 530 (M+H)$^+$.

Example 655

8-(3-{[4-(1H-benzimidazol-6-ylcarbonyl),piperazin-1-yl]carbonyl}-4-fluorobenzyl),-2,3,4,6-tetrahydropyrido[2,3-d]pyridazin-5(H),-one The title compound was prepared, using the appropriate reagents, as the TFA salt according to the procedure for EXAMPLE 506. MS (DCI/NH$_3$) m/z 516 (M+H)$^+$.

Example 657

8-(4-fluoro-3-{[4-(quinolin-3-ylcarbonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 527 (M+H)$^+$.

Example 658

8-[3-({4-[(2-chloropyridin-3-yl)carbonyl]piperazin-1-yl}carbonyl)-4-fluorobenzyl]-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 511 (M+H)$^+$.

Example 659 benzyl 4-{2-fluoro-5-[(5-oxo-1,2,3,4,5,6-hexahydropyrido[2,3-d]pyridazin-8-yl)methyl]benzoyl}-1,4-diazepane-1-carboxylate The title compound was prepared, using the appropriate reagents, as the TFA salt according to the procedure for EXAMPLE 506. MS (DCI/NH$_3$) m/z 520 (M+H)$^+$; $^1$H NMR (DMSO-d$_6$) δ 1.51 (m, 1H), 1.69 (m, 2H), 1.74-1.86 (m, 1H), 2.22-2.40 (m, 2H), 3.17 (m, 2H), 3.22-3.42 (m, 2H), 3.46 (m, 4H), 3.51-3.68 (m, 1H), 3.67-3.79 (m, 1H), 3.81 (s, 2H), 5.09 (s, 2H), 6.43 (s, 1H), 7.07-7.43 (m, 8H), 11.68-12.04 (s, 1H).

Example 660

8-{4-fluoro-3-[(4-isonicotinoylpiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 477 (M+H)$^+$.

Example 661

8-(4-fluoro-3-{[4-(pyridin-3-ylcarbonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 477 (M+H)$^+$.

Example 662

8-(4-fluoro-3-{[4-(pyrazin-2-ylcarbonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 478 (M+H)$^+$.

Example 663

8-(3-{[4-(1H-benzimidazol-5-ylcarbonyl)piperazin-1-yl]carbonyl}-4-fluorobenzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 516 (M+H)$^+$.

Example 664

8-(4-fluoro-3-{[4-(pyrimidin-5-ylcarbonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 478 (M+H)$^+$.

Example 665

8-(4-fluoro-3-{[4-(pyridin-2-ylcarbonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 477 (M+H)$^+$.

Example 666 ethyl 4-{2-fluoro-5-[(5-oxo-1,2,3,4,5,6-hexahydropyrido[2,3-d]pyridazin-8-yl)methyl]benzoyl}piperazine-1-carboxylate The title compound was prepared, using the appropriate reagents, as the TFA salt according to the procedure for EXAMPLE 506. MS (DCI/NH$_3$) m/z 444 (M+H)$^+$; $^1$H NMR (DMSO-d$_6$) δ 1.19 (t, J=7.14 Hz, 3H), 1.52-1.78 (m, 2H), 2.35 (t, J=6.15 Hz, 2H), 3.08-3.29 (m, 4H), 3.33 (m, 2H), 3.45 (m, 2H), 3.62 (m, 2H), 3.82 (s, 2H), 4.06 (q, J=7.14 Hz, 2H), 6.41 (s, 1H), 6.99-7.46 (m, 3H), 11.93 (s, 1H).

Example 667

8-{3-[(2,2-dimethyl-3-oxopiperazin-1-yl)carbonyl]-4-fluorobenzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 414 (M+H)$^+$; $^1$H NMR (DMSO-d$_6$) δ 1.68 (s, 6H), 1.71 (m, 2H), 2.34 (t, J=6.10 Hz, 2H), 3.17 (m, 4H), 3.30 (m, 2H), 3.81 (s, 2H), 6.42 (s, 1H), 7.16-7.34 (m, 3H), 8.15 (s, 1H), 11.90 (s, 1H).

Example 668

4-(3-{[(2R)-4-benzoyl-2-methylpiperazin-1-yl]carbonyl}-4-fluorobenzyl)-5,6,7,8-tetrahydrophthalazin-1(2H)-one The title compound was prepared, using the appropriate reagents, as the TFA salt according to the procedure for EXAMPLE 543, but was purified by HPLC (Zorbax C-18. 0.1% TFA/CH$_3$CN/H$_2$O) instead of flash chromatography. MS (DCI/NH$_3$) m/z 489 (M+H)$^+$; $^1$H NMR (CD$_3$OD) δ 1.17-1.33 (m, 2H), 1.64-1.80 (m, 4H), 2.38-2.56 (m, 4H), 2.98-3.13 (m, 1H), 3.16-3.27 (m, 1H), 3.34 (s, 3H), 3.39-3.59 (m, 1H), 3.63-3.86 (m, 1H), 3.99 (s, 2H), 4.41-4.60 (m, 1H), 7.10-7.18 (m, 1H), 7.19-7.27 (m, 1H), 7.29-7.39 (m, 1H), 7.41-7.55 (m, 5H).

Example 669

4-(4-fluoro-3-{[4-(1,3,5-triazin-2-yl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 450 (M+H)$^+$; $^1$H NMR (CD$_3$OD) δ 1.68-1.77 (m, 4H), 2.43-2.48 (m, 2H), 2.49-2.56 (m, 2H), 3.44-3.52 (m, 2H), 3.86-3.90 (m, 2H), 3.92-3.97 (m, 2H), 4.01 (s, 2H), 4.05-4.10 (m, 2H), 7.15-7.22 (m, 1H), 7.27 (dd, J=6.41, 2.14 Hz, 1H), 7.33-7.42 (m, 1H), 8.61 (s, 1H), 8.63 (s, 1H).

Example 672

5-benzyl-3-{2-fluoro-5-[(4-oxo-3,4,5,6,7,8-hexahydrophthalazin-1-yl)methyl]phenyl}imidazolidine-2,4-dione The title compound was prepared, using the appropriate reagents, as the free base according to the procedure for EXAMPLE 630. MS (DCI/NH$_3$) m/z 441 (M+H)$^+$; $^1$H NMR (CD$_3$OD) δ 1.61-1.77 (m, 4H), 2.38-2.46 (m, 2H), 2.47-2.55 (m, 2H), 3.03 (dd, J=13.73, 7.32 Hz, 1H), 3.19 (dd, J=13.73, 5.19 Hz, 1H), 3.90 (s, 2H), 4.57-4.66 (m, 1H), 6.74-6.80 (m, 1H), 6.99 (dd, J=10.98, 8.54 Hz, 1H), 7.19-7.25 (m, 3H), 7.25-7.32 (m, 2H), 7.85 (dd, J=7.63, 2.14 Hz, 1H).

Example 673

4-[3-({4-[(6-chloropyridin-3-yl)carbonyl]piperazin-1-yl}carbonyl)-4-fluorobenzyl]-5,6,7,8-tetrahydrophthalazin-1(2H)-one

Example 673A 4-(4-fluoro-3-(piperazine-1-carbonyl)benzyl)-5,6,7,8-tetrahydrophthalazin-1(2H)-one The title compound was prepared, using the appropriate reagents, according to the procedure for EXAMPLE 634A substituting EXAMPLE 543 for EXAMPLE 544. MS (DCI/NH$_3$) m/z 371 (M+H)$^+$.

Example 673B

4-[3-({4-[(6-chloropyridin-3-yl)carbonyl]piperazin-1-yl}carbonyl)-4-fluorobenzyl]-5,6,7,8-tetrahydrophthalazin-1(2H)-one The title compound was prepared, using the appropriate reagents, as the TFA salt according to the procedure for EXAMPLE 634B substituting EXAMPLE 673A for EXAMPLE 634A. MS (DCI/NH$_3$) m/z 510 (M+H)$^+$; $^1$H NMR (CD$_3$OD) δ 1.65-1.78 (m, 4H), 2.39-2.55 (m, 4H), 3.37-3.44 (m, 1H), 3.46-3.52 (m, 1H), 3.53-3.59 (m, 1H), 3.63-3.70 (m, 1H), 3.73-3.78 (m, 1H), 3.79-3.84 (m, 1H), 3.88 (s, 2H), 3.95-4.03 (m, 2H), 7.11-7.21 (m, 1H), 7.22-7.30 (m, 1H), 7.31-7.43 (m, 1H), 7.64-7.70 (m, 1H), 7.95-8.04 (m, 1H), 8.55-8.66 (m, 1H).

Example 674

4-(4-fluoro-3-{[4-(1,3-thiazol-4-ylcarbonyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 482 (M+H)$^+$; $^1$H NMR (CD$_3$OD) δ 1.66-1.80 (m, 4H), 2.41-2.55 (m, 4H), 3.37-3.54 (m, 2H), 3.71-3.81 (m, 2H), 3.83-3.95 (m, 4H), 4.00 (s, 2H), 7.13-7.22 (m, 1H), 7.23-7.30 (m, 1H), 7.31-7.43 (m, 1H), 8.13 (s, 1H), 9.00-9.10 (m, 1H).

Example 675

4-[4-fluoro-3-({4-[(5-oxopyrrolidin-2-yl)carbonyl]piperazin-1-yl}carbonyl)benzyl]-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 482 (M+H)$^+$.

Example 677

4-{3-[(4-{[(4R)-5,5-dimethyl-1,3-thiazolidin-4-yl]carbonyl}piperazin-1-yl)carbonyl]-4-fluorobenzyl}-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 514 (M+H)$^+$; $^1$H NMR (CD$_3$OD) δ 1.38-1.46 (m, 3H), 1.61-1.76 (m, 7H), 2.41-2.47 (m, 2H), 2.49-2.57 (m, 2H), 3.36-3.49 (m, 2H), 3.53-3.64 (m, 2H), 3.66-3.77 (m, 1H), 3.84-3.93 (m, 1H), 4.00 (s, 2H), 4.05-4.15 (m, 1H), 4.43-4.55 (m, 2H), 4.80-4.95 (m, 2H), 7.15-7.21 (m, 1H), 7.23-7.29 (m, 1H), 7.36-7.40 (m, 1H).

Example 678

4-(4-fluoro-3-{[4-(1H-pyrazol-3-ylcarbonyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 465 (M+H)$^+$; $^1$H NMR (CD$_2$OD) δ 1.66-1.77 (m, 4H), 2.39-2.48 (m, 2H), 2.48-2.58 (m, 2H), 3.37-3.52 (m, 2H), 3.68-3.79 (m, 1H), 3.79-3.93 (m, 3H), 3.92-3.99 (m, 1H), 4.00 (s, 2H), 4.04-4.16 (m, 1H), 6.63-6.71 (m, 1H), 7.13-7.21 (m, 1H), 7.23-7.29 (m, 1H), 7.32-7.39 (m, 1H), 7.67-7.74 (m, 1H).

Example 679

4-(4-fluoro-3-{[4-(pyrazin-2-ylcarbonyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 477 (M+H)$^+$; $^1$H NMR (CD$_3$OD) δ 1.67-1.77 (m, 4H), 2.42-2.55 (m, 4H), 3.39-3.46 (m, 1H), 3.47-3.55 (m, 1H), 3.57-3.63 (m, 1H), 3.69-3.75 (m, 1H), 3.76-3.81 (m, 1H), 3.81-3.87 (m, 1H), 3.90 (s, 2H), 3.96-4.04 (m, 2H), 7.12-7.21 (m, 1H), 7.22-7.32 (m, 1H), 7.31-7.40 (m, 1H), 8.58-8.76 (m, 2H), 8.89 (d, J=6.10 Hz, 1H).

Example 680

4-(3-{[4-(1H-benzimidazol-5-ylcarbonyl)piperazin-1-yl]carbonyl}-4-fluorobenzyl)-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 515 (M+H)$^+$.

Example 681

4-[4-fluoro-3-(methylamino)benzyl]-5,6,7,8-tetrahydrophthalazin-1(2H)-one

Example 681A

N-(2-fluoro-5-((4-oxo-3,4,5,6,7,8-hexahydrophthalazin-1-yl)methyl)phenyl)-2,4-dinitrobenzenesulfonamide To a solution of EXAMPLE 493F (2.0 g, 7.3 mmol) in dichloromethane (15 mL) was added 2,4-dinitrobenzene-1-sulfonyl chloride (1.95 g, 7.3 mmol) and pyridine (0.7 mL, 8.8 mmol). The mixture was stirred at room temperature for 16 hours and was concentrated. The residue was partitioned between ethyl acetate and water and the organic layer collected and concentrated. The residue was purified by flash chromatography eluting with 60% ethyl acetate in hexanes to provide the title compound. MS (DCI/NH$_3$) m/z 504 (M+H)$^+$.

Example 681B

N-(2-fluoro-5-((4-oxo-3,4,5,6,7,8-hexahydrophthalazin-1-yl)methyl)phenyl)-N-methyl-2,4-dinitrobenzenesulfonamide To a solution of EXAMPLE 681A (1.4 g, 2.8 mmol) in N,N-dimethylformamide (8 mL) was added methyl iodide (0.21 mL, 3.3 mmol) and potassium carbonate (1.92 g, 13.9 mmol). The mixture was stirred at room temperature for 16 hours and was concentrated. The residue was partitioned between ethyl acetate and water and the organic layer concentrated. The residue was purified by flash chromatography eluting with 60% ethyl acetate in hexanes to provide the title compound. MS (DCI/NH$_3$) m/z 518 (M+H)$^+$.

Example 681C

4-[4-fluoro-3-(methylamino)benzyl]-5,6,7,8-tetrahydrophthalazin-1(2H)-one

To a solution of EXAMPLE 681B (940 mg, 1.8 mmol) in dichloromethane (15 mL) was added thioglycolic acid (0.16 mL, 2.4 mmol) and triethylamine (0.5 mL, 3.6 mmol). The mixture was stirred at ambient temperature for 5 minutes and washed with brine. The organic layer was concentrated and the residue purified by flash chromatography on silica gel eluting with 5% methanol in dichloromethane to provide the title compound. MS (DCI/NH$_3$) m/z 288 (M+H)$^+$.

Example 682

8-{4-fluoro-3-[(4-isonicotinoyl-1,4-diazepan-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 491 (M+H)$^+$.

Example 683

8-(4-fluoro-3-{[4-(pyridin-3-ylcarbonyl)-1,4-diazepan-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 491 (M+H)$^+$.

Example 684

8-(4-fluoro-3-{[4-(pyridin-2-ylcarbonyl)-1,4-diazepan-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 491 (M+H)$^+$.

Example 685

8-(4-fluoro-3-{[4-(pyrimidin-5-ylcarbonyl)-1,4-diazepan-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 492 (M+H)$^+$.

Example 686

8-(3-{[4-(1H-benzimidazol-6-ylcarbonyl)-1,4-diazepan-1-yl]carbonyl}-4-fluorobenzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 530 (M+H)$^+$.

Example 687

8-(4-fluoro-3-{[4-(quinolin-2-ylcarbonyl)-1,4-diazepan-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 541 (M+H)$^+$; $^1$H NMR (DMSO-d$_6$) δ 1.56-2.00 (m, 4H), 2.27-2.42 (m, 2H), 3.10-3.25 (m, 2H), 3.30-3.45 (m, 1H), 3.44-3.67 (m, 3H), 3.67-3.93 (m, 6H), 6.47 (m, 1H), 6.97-7.43 (m, 3H), 7.49-7.72 (m, 3H), 7.71-8.00 (m, 1H), 7.96-8.12 (m, 1H), 8.29-8.73 (m, 1H), 11.93 (s, 0.5H), 11.99 (s, 0.5H).

Example 688

8-(4-fluoro-3-{[4-(quinolin-3-ylcarbonyl)-1,4-diazepan-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 541 (M+H)$^+$; $^1$H NMR (DMSO-d$_6$) δ 1.51-1.81 (m, 4H), 2.21-2.42 (m, 2H), 3.04-3.26 (m, 3H), 3.39 (m, 2H), 3.49 (m, 2H), 3.60-3.70 (m, 1H), 3.75 (m, 2H), 3.84 (s, 1H), 3.87 (s, 1H), 6.49 (s, 1H), 7.07-7.41 (m, 3H), 7.60-7.77 (m, 1H), 7.78-7.97 (m, 1H), 7.97-8.16 (m, 2H), 8.48 (s, 0.5H), 8.50 (s, 0.5H), 8.92 (s, 0.5H), 8.94 (s, 0.5H), 11.97 (s, 0.5H), 11.99 (s, 0.5H).

Example 689

8-[4-fluoro-3-({4-[(2-methyl-1H-benzimidazol-5-yl)carbonyl]-1,4-diazepan-1-yl}carbonyl)benzyl]-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 544 (M+H)$^+$.

Example 690

8-[4-fluoro-3-({4-[(1-isopropyl-1H-1,2,3-benzotriazol-5-yl)carbonyl]-1,4-diazepan-1-yl}carbonyl)benzyl]-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 573 (M+H)$^+$.

Example 691

8-(4-fluoro-3-{[4-(4-fluorobenzoyl)piperidin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 493 (M+H)$^+$; $^1$H NMR (DMSO-d$_6$) δ 1.35-1.59 (m, 2H), 1.60-1.81 (m, 3H), 1.91 (m, 1H), 2.33 (m, 2H), 2.90-3.07 (m, 1H), 3.07-3.31 (m, 3H), 3.45 (m, 1H), 3.65-3.82 (m, 1H), 3.82 (s, 2H), 4.52 (m, 1H), 6.41 (s, 1H), 6.89-7.32 (m, 3H), 7.37 (t, J=8.92 Hz, 2H), 8.10 (dd, J=8.72, 5.55 Hz, 2H), 11.89 (s, 1H).

Example 692

8-[3-({4-[(5,5-dimethyl-1,3-thiazolidin-4-yl)carbonyl]piperazin-1-yl}carbonyl)-4-fluorobenzyl]-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 515 (M+H)$^+$.

Example 693

8-(4-fluoro-3-{[4-(pyrazin-2-ylcarbonyl)-1,4-diazepan-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 492 (M+H)$^+$.

Example 694

8-(4-fluoro-3-{[4-(2-furoyl)-1,4-diazepan-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 480 (M+H)$^+$.

Example 695

8-{4-fluoro-3-[(4-pyridin-3-ylpiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 449 (M+H)$^+$; $^1$H NMR (DMSO-d$_6$) δ 1.52-1.80 (m, 2H), 2.35 (t, J=6.10 Hz, 2H), 3.18 (m, 2H), 3.39 (m, 4H), 3.47-3.61 (m, 2H), 3.76-3.84 (m, 2H), 3.84 (s, 2H), 6.44 (s, 1H), 7.05-7.33 (m, 2H), 7.30-7.48 (m, 1H), 7.82 (dd, J=8.98, 5.26 Hz, 1H), 8.02 (dd, J=8.81, 2.37 Hz, 1H), 8.24 (d, J=5.42 Hz, 1H), 8.46 (d, J=2.71 Hz, 1H), 11.92 (s, 1H).

Example 696

8-{4-fluoro-3-[(4-pyrimidin-5-ylpiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 450 (M+H)$^+$.

Example 697

8-{4-fluoro-3-[(4-methyl-3-oxopiperazin-1-yl)carbonyl]benzyl}-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 400 (M+H)$^+$.

Example 698 tert-butyl 4-[{2-fluoro-5-[(5-oxo-1,2,3,4,5,6-hexahydropyrido[2,3-d]pyridazin-8-yl)methyl]benzoyl}(methyl)amino]piperidine-1-carboxylate The title compound was prepared, using the appropriate reagents, as the TFA salt according to the procedure for EXAMPLE 506. MS (DCI/NH$_3$) m/z 500 (M+H)$^+$.

Example 699 tert-butyl 4-({2-fluoro-5-[(5-oxo-1,2,3,4,5,6-hexahydropyrido[2,3-d]pyridazin-8-yl)methyl]benzoyl}amino)piperidine-1-carboxylate The title compound was prepared, using the appropriate reagents, as the TFA salt according to the procedure for EXAMPLE 506. MS (DCI/NH$_3$) m/z 486 (M+H)$^+$.

Example 700 tert-butyl 1-{2-fluoro-5-[(5-oxo-1,2,3,4,5,6-hexahydropyrido[2,3-d]pyridazin-8-yl)methyl]benzoyl}piperidin-4-ylcarbamate The title compound was prepared, using the appropriate reagents, as the TFA salt according to the procedure for EXAMPLE 506. MS (DCI/NH$_3$) m/z 486 (M+H)$^+$)$^+$; $^1$H NMR (DMSO-d$_6$) 1.20-1.30 (m, 1H), 1.38 (s, 9H), 1.59-1.74 (m, 3H), 1.78 (m, 1H), 2.34 (t, J=6.10 Hz, 2H), 2.85-2.99 (m, 2H), 3.03-3.12 (m, 1H), 3.17 (m, 2H), 3.35 (m, 1H), 3.50 (m, 1H), 3.81 (s, 2H), 4.33 (m, 1H), 6.42 (s, 1H), 7.13-7.26 (m, 2H), 7.26-7.38 (m, 1H), 7.95 (s, 1H), 11.90 (s, 1H).

Example 701

8-[4-fluoro-3-({4-[(4R)-1,3-thiazolidin-4-ylcarbonyl]-1,4-diazepan-1-yl}carbonyl)benzyl]-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m z 501 (M+H)$^+$.

Example 702

8-(4-fluoro-3-{[4-(1H-pyrazol-3-ylcarbonyl)-1,4-diazepan-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 480 (M+H)$^+$.

Example 703

8-(4-fluoro-3-{[4-(1,3-thiazol-4-ylcarbonyl)-1,4-diazepan-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 497 (M+H)$^+$.

Example 704

8-(4-fluoro-3-{[4-(1H-pyrazol-3-ylcarbonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 466 (M+H)$^+$.

Example 705

8-(4-fluoro-3-{[4-(1,3-thiazol-4-ylcarbonyl)piperazin-1-yl]carbonyl}benzyl)-2,3,4,6-tetrahydropyrido[2,3-d]pyridazin-5(1H)-one The title compound was prepared, using the appropriate reagents, as the TFA salt according to the procedure for EXAMPLE 506. MS (DCI/NH$_3$) m/z 483 (M+H)$^+$)$^+$; $^1$H NMR (DMSO-d$_6$) δ 1.71-1.92 (m, 2H), 2.53 (t, J=6.10 Hz, 2H), 3.46 (m, 2H), 3.70-3.83 (m, 4H), 3.88 (m, 4H), 3.93 (s, 2H), 7.16 (t, J=8.98 Hz, 1H), 7.29 (dd, J=6.27, 1.86 Hz, 1H), 7.32-7.46 (m, 1H), 8.13 (d, J=1.70 Hz, 1H), 9.05 (s, 1H).

Example 706

2-fluoro-N-methyl-5-[(5-oxo-1,2,3,4,5,6-hexahydropyrido[2,3-d]pyridazin-8-yl)methyl]-N-piperidin-4-ylbenzamide The title compound was prepared, using the appropriate reagents, as the TFA salt according to the procedure for EXAMPLE 638. MS (DCI/NH$_3$) m/z 400 (M+H)$^+$.

Example 707

2-fluoro-5-[(5-oxo-1,2,3,4,5,6-hexahydropyrido[2,3-d]pyridazin-8-yl)methyl]-N-piperidin-4-ylbenzamide The title compound was prepared, using the appropriate reagents, as the TFA salt according to the procedure for EXAMPLE 638. MS (DCI/NH$_3$) m/z 466 (M+H)$^+$; $^1$H NMR (CD$_3$OD) δ 1.71-1.91 (m, 4H), 2.20 (dd, J=14.07, 3.22 Hz, 2H), 2.51 (t, —6.27 Hz, 2H), 3.07-3.22 (m, 2H), 3.22-3.30 (m, 2H), 3.37-3.49 (m, 4H), 4.03-4.29 (m, 1H), 7.14 (dd, J=10.51, 8.48 Hz, 1H), 7.33-7.48 (m, 1H), 7.51 (dd, J=6.78, 2.37 Hz, 1H).

Example 708

8-{3-[(4-aminopiperidin-1-yl)carbonyl]-4-fluorobenzyl}-2,3,4,6-tetrahydropyrido[2,3-d]pyridazin-5(1H)-one The title compound was prepared, using the appropriate reagents, as the TFA salt according to the procedure for EXAMPLE 638. MS (DCI/NH$_3$) m/z 386 (M+H)$^+$.

Example 709

2-fluoro-N-(4-hydroxycyclohexyl)-5-[(5-oxo-1,2,3,4,5,6-hexahydropyrido[2,3-d]pyridazin-8-yl)methyl]benzamide The title compound was prepared, using the appropriate reagents, as the TFA salt according to the procedure for EXAMPLE 506. MS (DCI/NH$_3$) m/z 401 (M+H)$^+$.

Example 710

2-fluoro-N-methyl-5-[(5-oxo-1,2,3,4,5,6-hexahydropyrido[2,3-d]pyridazin-8-yl)methyl]-N-[1-(pyridin-3-ylcarbonyl)piperidin-4-yl]benzamide The title compound was prepared, using the appropriate reagents, as the TFA salt according to the procedure for EXAMPLE 506. MS (DCI/NH$_3$) m/z 505 (M+H)$^+$.

Example 711 tert-butyl 2-(ethyl{2-fluoro-5-[(4-oxo-3,4,5,6,7,8-hexahydrophthalazin-1-yl)methyl]benzoyl}amino)ethylcarbamate To a solution of EXAMPLE 492F (500 mg, 1.654 mmol) in anhydrous N,N-dimethylformamide (15 mL) was added N-Boc-N'-ethyl-1,2-ethylene diamine hydrochloride (446 mg, 1.985 mmol), 1-ethyl-3-[3-(dimethylamino)propyl]-carbodiimide hydrochloride (EDC) (476 mg, 2.481 mmol), 1-hydroxybenzotriazole monohydrate (380 mg, 2.481 mmol), and triethylamine (0.807 mL, 5.79 mmol). The mixture was stirred at ambient temperature overnight and was partitioned between ethyl acetate and brine. The organic phase was washed with brine and water and concentrated. The residue was purified by flash chromatography (ethyl acetate) to give the title compound. MS (DCI/NH$_3$) m/z 473 (M+H)$^+$; $^1$H NMR (CDCl$_3$) δ 1.07 (t, J=7.21 Hz, 3H), 1.45 (s, 9H), 1.71 (m, 4H), 2.33-2.42 (m, 2H), 2.55-2.62 (m, 2H), 3.17-3.29 (m, 2H), 3.38-3.45 (m, 2H), 3.58-3.64 (m, 2H), 3.87-3.91 (m, 2H), 5.06 (s, 1H), 6.98-7.05 (m, 1H), 7.13-7.19 (m, 2H), 11.34 (s, 1H).

Example 712

2-fluoro-N-(1-isonicotinoylpiperidin-4-yl)-N-methyl-5-[(5-oxo-1,2,3,4,5,6-hexahydropyrido[2,3-d]pyridazin-8-yl)methyl]benzamide The title compound was prepared, using the appropriate reagents, as the TFA salt according to the procedure for EXAMPLE 506. MS (DCI/NH$_3$) m/z 505 (M+H)$^+$.

Example 713

N-[1-(1H-benzimidazol-5-ylcarbonyl)piperidin-4-yl]-2-fluoro-5-[(5-oxo-1,2,3,4,5,6-hexahydropyrido[2,3-d]pyridazin-8-yl)methyl]benzamide The title compound was prepared, using the appropriate reagents, as the TFA salt according to the procedure for EXAMPLE 506. MS (DCI/NH$_3$) m/z 530 (M+H)$^+$.

Example 714

2-fluoro-5-[(4-oxo-3,4,5,6,7,8-hexahydrophthalazin-1-yl)methyl]-N-[2-(2-oxopyrrolidin-1-yl)ethyl]benzamide To a solution of EXAMPLE 492F (102 mg, 0.337 mmol) in anhydrous N,N-dimethylformamide (8 mL) was added 1-(2-aminoethyl)pyrrolidin-2-one hydrochloride (83 mg, 0.506 mmol), 1-ethyl-3-[3-(dimethylamino)propyl]-carbodiimide hydrochloride (EDC) (97 mg, 0.506 mmol), 1-hydroxybenzotriazole monohydrate (78 mg, 0.506 mmol), and triethylamine (0.165 mL, 3.5 mmol). The mixture was stirred at ambient temperature overnight, and was partitioned between ethyl acetate and brine. The organic phase was washed with brine and water and concentrated. The residue was purified by flash chromatography (15% methanol in 2:1 ethyl acetate/hexane) to provide the title compound. MS (DCI/NH$_3$) m/z 413 (M+H)$^+$; $^1$H NMR (CD$_3$OD) δ 1.71 (t, J=2.90 Hz, 4H), 1.99-2.05 (m, 2H), 2.33 (t, J=8.09 Hz, 2H), 2.44 (m, 2H), 2.50 (m, 2H), 3.49 (t, J=5.49 Hz, 2H), 3.52-3.57 (m, 4H), 3.99 (s, 2H), 7.13 (dd, J=10.37, 8.54 Hz, 1H), 7.33-7.38 (m, 1H), 7.51 (dd, J=6.71, 2.14 Hz, 1H).

Example 715

2-fluoro-N-[1-(2-furoyl)piperidin-4-yl]-N-methyl-5-[(5-oxo-1,2,3,4,5,6-hexahydropyrido[2,3-d]pyridazin-8-yl)methyl]benzamide The title compound was prepared, using the appropriate reagents, as the TFA salt according to the procedure for EXAMPLE 506. MS (DCI/NH$_3$) m/z 494 (M+H)$^+$.

Example 716

2-fluoro-N-methyl-5-[(5-oxo-1,2,3,4,5,6-hexahydropyrido[2,3-d]pyridazin-8-yl)methyl]-N-{1-[(4R)-1,3-thiazolidin-4-ylcarbonyl]piperidin-4-yl}benzamide The title compound was prepared, using the appropriate reagents, as the TFA salt according to the procedure for EXAMPLE 506. MS (DCI/NH$_3$) m/z 515 (M+H)$^+$.

Example 717

2-fluoro-N-methyl-5-[(5-oxo-1,2,3,4,5,6-hexahydropyrido[2,3-d]pyridazin-8-yl)methyl]-N-[1-(1,3-thiazol-4-ylcarbonyl)piperidin-4-yl]benzamide The title compound was prepared, using the appropriate reagents, as the TFA salt according to the procedure for EXAMPLE 506. MS (DCI/NH$_3$) m/z 511 (M+H)$^+$.

Example 718

2-fluoro-N-methyl-5-[(5-oxo-1,2,3,4,5,6-hexahydropyrido[2,3-d]pyridazin-8-yl)methyl]-N-[1-(1H-pyrazol-4-ylcarbonyl)piperidin-4-yl]benzamide The title compound was prepared, using the appropriate reagents, as the TFA salt according to the procedure for EXAMPLE 506. MS (DCI/NH$_3$) m/z 494 (M+H)$^+$.

Example 719

N-(2-aminoethyl)-N-ethyl-2-fluoro-5-[(4-oxo-3,4,5,6,7,8-hexahydrophthalazin-1-yl)methyl]benzamide A solution of EXAMPLE 711 (662 mg, 1.40 mmol) in 20 mL of methylene chloride was treated with trifluoroacetic acid (5 mL) at ambient temperature for 1 hour. Toluene (10 mL) was added and the solution concentrated. The residue was dissolved in methylene chloride and methanol, and treated with an access of 2M HCl in ether. Concentration provided the title compound as the HCl salt. MS (DCI/NH$_3$) m/z 373 (M+H)$^+$; $^1$H NMR (CD$_3$OD) δ 1.10 (t, J=7.02 Hz, 3H), 1.71-1.78 (m, 4H), 2.47-2.50 (m, 2H), 2.55 (m, 2H), 3.24 (t, J=6.41 Hz, 2H), 3.29-3.33 (m, 2H), 3.80 (t, J=6.41 Hz, 2H), 4.08 (s, 2H), 7.19 (t, J=9.00 Hz, 1H), 7.29-7.32 (m, 1H), 7.36-7.40 (m, 1H).

Example 720

4-{4-fluoro-3-[(4-isonicotinoylpiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 476 (M+H)$^+$; $^1$H NMR (CD$_3$OD) δ 1.66-1.79 (m, 4H), 2.41-2.55 (m, 4H), 3.34-3.41 (m, 2H), 3.46-3.56 (m, 2H), 3.74-3.83 (m, 2H), 3.85-3.93 (m, 2H), 3.95-4.05 (m, 2H), 7.11-7.21 (m, 1H), 7.22-7.30 (m, 1H), 7.32-7.44 (m, 1H), 7.75-7.81 (m, 1H), 7.82-7.91 (m, 1H), 8.76-8.89 (m, 2H).

Example 721

2-fluoro-N-methyl-5-[(5-oxo-1,2,3,4,5,6-hexahydropyrido[2,3-d]pyridazin-8-yl)methyl]-N-[1-(pyridin-2-ylcarbonyl)piperidin-4-yl]benzamide The title compound was prepared, using the appropriate reagents, as the TFA salt according to the procedure for EXAMPLE 506. MS (DCI/NH$_3$) m z 505 (M+H)$^+$.

Example 722

4-(4-fluoro-3-{[4-(pyridin-3-ylcarbonyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 476 (M+H)$^+$; $^1$H NMR (CD$_3$OD) δ 1.66-1.79 (m, 4H), 2.40-2.47 (m, 2H), 2.48-2.57 (m, 2H), 3.38-3.51 (m, 2H), 3.51-3.63 (m, 2H), 3.75-3.84 (m, 2H), 3.85-3.95 (m, 2H), 4.00 (s, 2H), 7.11-7.22

(m, 1H), 7.22-7.29 (m, 1H), 7.30-7.42 (m, 1H), 7.71-7.85 (m, 1H), 8.17-8.30 (m, 1H), 8.72-8.87 (m, 2H).

Example 723

4-[3-({4-[(5-chloro-6-hydroxypyridin-3-yl)carbonyl]piperazin-1-yl}carbonyl)-4-fluorobenzyl]-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 526 (M+H)$^+$.

Example 724

2-fluoro-5-[(5-oxo-1,2,3,4,5,6-hexahydropyrido[2,3-d]pyridazin-8-yl)methyl]-N-[1-(pyridin-3-ylcarbonyl)piperidin-4-yl]benzamide The title compound was prepared, using the appropriate reagents, as the TFA salt according to the procedure for EXAMPLE 506. MS (DCI/NH$_3$) m/z 491 (M+H)$^+$.

Example 725

4-{4-fluoro-3-[(4-{[1-isopropyl-2-(trifluoromethyl)-1H-benzimidazol-5-yl]carbonyl}piperazin-1-yl)carbonyl]benzyl}-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 625 (M+H)$^+$; $^1$H NMR (CD$_3$OD) δ 1.65-1.73 (m, 4H), 1.74 (d, J=7.02 Hz, 6H), 2.39-2.47 (m, 2H), 2.47-2.57 (m, 2H), 3.40-3.70 (m, 4H), 3.73-3.95 (m, 4H), 3.99 (s, 2H), 4.93-5.17 (m, 1H), 7.13-7.21 (m, 1H), 7.22-7.29 (m, 1H), 7.31-7.39 (m, 1H), 7.55 (d, J=8.54 Hz, 1H), 7.92 (s, 1H), 8.00 (d, J=8.54 Hz, 1H).

Example 726

2-fluoro-N-[1-(2-furoyl)piperidin-4-yl]-5-[(5-oxo-1,2,3,4,5,6-hexahydropyrido[2,3-d]pyridazin-8-yl)methyl]benzamide The title compound was prepared, using the appropriate reagents, as the TFA salt according to the procedure for EXAMPLE 506. MS (DCI/NH$_3$) m/z 480 (M+H)$^+$.

Example 727

4-[4-fluoro-3-({4-[(4R)-1,3-thiazolidin-4-ylcarbonyl]piperazin-1-yl}carbonyl)benzyl]-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 486 (M+H)$^+$; $^1$H NMR (CD$_3$OD) δ 1.68-1.77 (m, 4H), 2.42-2.48 (m, 2H), 2.48-2.54 (m, 2H), 3.12-3.23 (m, 1H), 3.37-3.50 (m, 2H), 3.54-3.64 (m, 2H), 3.65-3.73 (m, 3H), 3.77-3.95 (m, 3H), 4.36-4.43 (m, 1H), 4.44-4.51 (m, 1H), 4.89-5.01 (m, 2H), 7.15-7.20 (m, 1H), 7.23-7.28 (m, 1H), 7.36-7.40 (m, 1H).

Example 728

4-[4-fluoro-3-({4-[(1-isopropyl-1H-1,2,3-benzotriazol-5-yl)carbonyl]piperazin-1-yl}carbonyl)benzyl]-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 558 (M+H)$^+$; $^1$H NMR (CD$_3$OD) δ 1.65-1.75 (m, 4H), 1.73 (d, J=6.71 Hz, 6H), 2.41-2.47 (m, 2H), 2.48-2.54 (m, 2H), 3.43-3.67 (m, 4H), 3.69-3.94 (m, 4H), 3.99 (s, 2H), 5.21-5.30 (m, 1H), 7.12-7.20 (m, 1H), 7.23-7.29 (m, 1H), 7.31-7.40 (m, 1H), 7.63 (d, J=8.85 Hz, 1H), 7.93 (d, J=8.54 Hz, 1H), 8.12 (s, 1H).

Example 729

2-fluoro-5-[(5-oxo-1,2,3,4,5,6-hexahydropyrido[2,3-d]pyridazin-8-yl)methyl]-N-{1-[(4R)-1,3-thiazolidin-4-ylcarbonyl]piperidin-4-yl}benzamide The title compound was prepared, using the appropriate reagents, as the TFA salt according to the procedure for EXAMPLE 506. MS (DCI/NH$_3$) m/z 501 (M+H)$^+$.

Example 730

4-(4-fluoro-3-{[4-(pyridin-2-ylcarbonyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 476 (M+H)$^+$; $^1$H NMR (CD$_3$OD) δ 1.64-1.78 (m, 4H), 2.39-2.56 (m, 4H), 3.36-3.43 (m, 1H), 3.46-3.55 (m, 2H), 3.57-3.67 (m, 1H), 3.72-3.85 (m, 2H), 3.90 (s, 2H), 3.96-4.05 (m, 2H), 7.09-7.20 (m, 1H), 7.22-7.30 (m, 1H), 7.31-7.41 (m, 1H), 7.49-7.59 (m, 1H), 7.68 (t, J=8.70 Hz, 1H), 7.94-8.07 (m, 1H), 8.61 (dd, J=27.46, 3.97 Hz, 1H).

Example 731

2-fluoro-5-[(5-oxo-1,2,3,4,5,6-hexahydropyrido[2,3-d]pyridazin-8-yl)methyl]-N-[1-(1,3-thiazol-4-ylcarbonyl)piperidin-4-yl]benzamide The title compound was prepared, using the appropriate reagents, as the TFA salt according to the procedure for EXAMPLE 506. MS (DCI/NH$_3$) m/z 497 (M+H)$^+$; $^1$H NMR (DMSO-d$_6$) δ 1.34-1.59 (m, 2H), 1.62-1.75 (m, 2H), 1.89 (m, 2H), 2.33 (t, J=6.10 Hz, 2H), 2.92-3.10 (m, 1H), 3.10-3.22 (m, 2H), 3.20-3.31 (m, 1H), 3.81 (s, 2H), 3.93-4.21 (m, 2H), 4.35 (d, J=1.70 Hz, 1H), 6.38 (s, 1H), 7.19 (dd, J=10.17, 8.48 Hz, 1H), 7.24-7.38 (m, 1H), 7.36-7.54 (m, 1H), 8.14 (d, J=1.70 Hz, 1H), 8.32 (d, J=7.46 Hz, 1H), 9.17 (d, J=2.03 Hz, 1H), 11.85 (s, 1H).

Example 733

4-(4-fluoro-3-{[4-(pyrimidin-5-ylcarbonyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 477 (M+H)$^+$; $^1$H NMR (CD$_3$OD) δ 1.66-1.78 (m, 4H), 2.40-2.48 (m, 2H), 2.48-2.55 (m, 2H), 3.41-3.53 (m, 3H), 3.58-3.66 (m, 1H), 3.77-3.91 (m, 4H), 4.00 (s, 2H), 7.10-7.20 (m, 1H), 7.23-7.31 (m, 1H), 7.31-7.42 (m, 1H), 8.85-8.95 (m, 2H), 9.24 (s, 1H).

Example 734

2-fluoro-5-[(5-oxo-1,2,3,4,5,6-hexahydropyrido[2,3-d]pyridazin-8-yl)methyl]-N-[1-(1H-pyrazol-4-ylcarbonyl)piperidin-4-yl]benzamide The title compound was prepared, using the appropriate reagents, as the TFA salt according to the procedure for EXAMPLE 506. MS (DCI/NH$_3$) m/z 480 (M+H)$^+$; $^1$H NMR (DMSO-d$_6$) δ 1.31-1.56 (m, 2H), 1.60-1.75 (m, 2H), 1.77-1.96 (m, 2H), 2.24-2.39 (m, 2H), 3.00-3.23 (m, 6H), 3.82 (s, 2H), 4.17-4.62 (m, 1H), 6.40 (s, 1H), 6.54 (d, J=2.37 Hz, 1H), 6.97 (d, J=3.39 Hz, 1H), 7.14-7.25 (m, 1H), 7.28-7.39 (m, 1H), 7.44 (dd, J=6.95, 2.20 Hz, 1H), 7.78 (d, J=2.03 Hz, 1H), 8.30 (d, J=7.46 Hz, 1H), 11.87 (s, 1H).

Example 735

4-[4-fluoro-3-({4-[(6-hydroxypyridin-3-yl)carbonyl]piperazin-1-yl}carbonyl)benzyl]-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 492 (M+H)$^+$.

Example 736

2-fluoro-5-[(5-oxo-1,2,3,4,5,6-hexahydropyrido[2,3-d]pyridazin-8-yl)methyl]-N-[1-(pyridin-2-ylcarbonyl)piperidin-4-yl]benzamide The title compound was prepared, using the appropriate reagents, as the TFA salt according to the procedure for EXAMPLE 506. MS (DCI/NH$_3$) m/z 491 (M+H)$^+$.

Example 738

2-fluoro-N-(1-isonicotinoylpiperidin-4-yl)-5-[(5-oxo-1,2,3,4,5,6-hexahydropyrido[2,3-d]pyridazin-8-yl)methyl]benzamide The title compound was prepared, using the appropriate reagents, as the TFA salt according to the procedure for EXAMPLE 506. MS (DCI/NH$_3$) m/z 491 (M+H)$^+$; $^1$H NMR (DMSO-d$_6$) δ 1.44-1.74 (m, 2H), 1.75-1.89 (m, 2H), 1.97 (m, 1H), 2.02-2.21 (m, 1H), 2.51 (t, J=6.27 Hz, 2H), 3.01-3.21 (m, 1H), 3.22-3.32 (m, 3H), 3.58 (m, 1H), 3.92 (s, 2H), 4.03-4.28 (m, 1H), 4.57 (m, 1H), 7.14 (dd, J=10.34, 8.65 Hz, 1H), 7.26-7.45 (m, 1H), 7.53 (dd, J=6.78, 2.03 Hz, 1H), 7.82 (d, J=6.44 Hz, 2H), 8.84 (d, J=5.76 Hz, 2H).

Example 739

4-(4-fluoro-3-{[4-(quinolin-2-ylcarbonyl)piperazin-1-yl]carbonyl}benzyl)-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 526 (M+H)$^+$; $^1$H NMR (CD$_3$OD) δ 1.61-1.78 (m, 4H), 2.38-2.56 (m, 4H), 3.41-3.48 (m, 1H), 3.50-3.57 (m, 1H), 3.57-3.62 (m, 1H), 3.66-3.74 (m, 1H), 3.82-3.90 (m, 2H), 3.95 (s, 2H), 3.96-3.99 (m, 1H), 4.00-4.05 (m, 1H), 7.09-7.22 (m, 1H), 7.23-7.30 (m, 1H), 7.31-7.43 (m, 1H), 7.64-7.76 (m, 2H), 7.79-7.90 (m, 1H), 7.96-8.03 (m, 1H), 8.04-8.13 (m, 1H), 8.46-8.55 (m, 1H).

Example 740

N-[(1S,2S)-2-aminocyclohexyl]-2-fluoro-5-[(5-oxo-1,2,3,4,5,6-hexahydropyrido[2,3-d]pyridazin-8-yl)methyl]benzamide The title compound was prepared, using the appropriate reagents, as the TFA salt according to the procedure for EXAMPLE 506. MS (DCI/NH$_3$) m/z 400 (M+H)$^+$.

Example 742

N-[2-(benzoylamino)ethyl]-N-ethyl-2-fluoro-5-[(4-oxo-3,4,5,6,7,8-hexahydrophthalazin-1-yl)methyl]benzamide To a suspension of EXAMPLE 719 as the HCl salt (65 mg, 0.134 mmol) in a mixture of tetrahydrofuran (2 mL) and acetonitrile (2 mL) was added 2,5-dioxopyrrolidin-1-yl benzoate (44 mg, 0.201 mmol) and triethylamine (0.056 mL, 0.403 mmol). The solution was heated at 60° C. overnight. After concentration, the residue was purified by HPLC (Zorbax, C-18, 250×2.54 column, Mobile phase A: 0.1% TFA in H$_2$O; B: 0.1% TFA in CH$_3$CN; 0-100% gradient) to provide the title compound as the TFA salt. MS (DCI/NH$_3$) m/z 477 (M+H)$^+$; $^1$H NMR (CD$_3$OD) δ 1.08 (t, J=7.20 Hz, 3H), 1.66-1.72 (m, 4H), 2.32-2.40 (m, 2H), 2.43-2.51 (m, 2H), 3.27-3.32 (m, 2H), 3.38-3.45 (m, 2H), 3.68-3.72 (m, 2H), 3.94 (s, 2H), 7.01-7.30 (m, 5H), 7.11-7.15 (m, 1H), 7.43-7.47 (m, 1H), 7.80-7.83 (m, 1H).

Example 743

N-[2-(ethyl{2-fluoro-5-[(4-oxo-3,4,5,6,7,8-hexahydrophthalazin-1-yl)methyl]benzoyl}amino)ethyl]pyrrolidine-1-carboxamide To a suspension of EXAMPLE 719 as the HCl salt (65 mg, 0.134 mmol) in a mixture of tetrahydrofuran (2 mL) and acetonitrile (2 mL) was added triethylamine (0.056 mL, 0.403 mmol) and 1-pyrrolidinecarbonyl chloride (0.030 mL, 0.269 mmol). The solution was heated at 60° C. overnight. After concentration, the residue was purified by HPLC (Zorbax, C-18, 250×2.54 column, Mobile phase A: 0.1% TFA in H$_2$O; B: 0.1% TFA in CH$_3$CN; 0-100% gradient) to provide the title compound. MS (DCI/NH$_3$) m/z 470 (M+H)$^+$; $^1$H NMR (CD$_3$OD) δ 1.05 (t, J=7.02 Hz, 2H), 1.24 (t, J=7.17 Hz, 1H), 1.69-1.74 (m, 4H), 1.88-1.92 (m, 4H), 2.42-2.46 (m, 2H), 2.49-2.52 (m, 2H), 3.17-3.26 (m, 4H), 3.28-3.35 (m, 2H), 3.45 (t, J=6.26 Hz, 2H), 3.65 (t, J=6.26 Hz, 2H), 3.98 (s, 1H), 3.99 (s, 1H), 7.11 (t, J=9.00 Hz, 1H), 7.15-7.20 (m, 1H), 7.27-7.35 (m, 1H).

Example 745

2-fluoro-5-[(5-oxo-1,2,3,4,5,6-hexahydropyrido[2,3-d]pyridazin-8-yl)methyl]-N-(1-pyridin-2-ylpiperidin-4-yl)benzamide The title compound was prepared, using the appropriate reagents, as the TFA salt according to the procedure for EXAMPLE 506. MS (DCI/NH$_3$) m/z 463 (M+H)$^+$; $^1$H NMR (DMSO-d$_6$) δ 1.56 (q, J=10.5 Hz, 2H), 1.65-1.74 (m, 2H), 1.95 (dd, J=13.09, 3.17 Hz, 2H), 2.34 (t, J=6.15 Hz, 2H), 2.75 (d, J=4.36 Hz, 1H), 3.26 (t, J=11.70 Hz, 2H), 3.82 (s, 2H), 4.07-4.21 (m, 3H), 6.38 (s, 1H), 6.83 (t, J=6.35 Hz, 1H), 7.15-7.29 (m, 2H), 7.32-7.39 (m, 1H), 7.44 (dd, J=6.94, 2.18 Hz, 1H), 7.85 (t, J=7.73 Hz, 1H), 8.04 (dd, J=5.75, 1.78 Hz, 1H), 8.28 (d, J=7.54 Hz, 1H), 11.86 (s, 1H).

Example 746

N-(1-{2-fluoro-5-[(5-oxo-1,2,3,4,5,6-hexahydropyrido[2,3-d]pyridazin-8-yl)methyl]benzoyl}piperidin-4-yl)pyridine-2-carboxamide Example 746A tert-butyl 1-(2-fluoro-5-((5-oxo-1,2,3,4,5,6-hexahydropyrido[3,2-d]pyridazin-8-yl)methyl)benzoyl)piperidin-4-ylcarbamate To a solution of EXAMPLE 506F (400 mg, 1.32 mmol) in anhydrous N,N-dimethylformamide (20 mL) was added tert-butyl piperidin-4-ylcarbamate (264 mg, 1.32 mmol), 1-ethyl-3-[3-(dimethylamino)propyl]-carbodiimide hydrochloride (EDC) (327 mg, 1.72 mmol), 1-hydroxybenzotriazole monohydrate (264 mg, 1.72 mmol), and triethylamine (173 mg, 1.72 mmol). The reaction mixture was stirred at ambient temperature overnight, and partitioned between methylene chloride and brine. The organic phase was washed with brine, water, and concentrated. The residue was purified by HPLC (Zorbax, C-18, 250×2.54 column, Mobile phase A: 0.1% TFA in H$_2$O: B: 0.1% TFA in CH$_3$CN; 0-100% gradient) to provide the title compound as TFA salt. MS (DCI/NH$_3$) m/z 486 (M+H)$^+$.

Example 746B 8-(3-(4-aminopiperidine-1 carbonyl)-4-fluorobenzyl)-1,2,3,4-tetrahydropyrido[3,2-d]pyridazin-5(6H)-one A solution of EXAMPLE 746A (1.5 g) in tetrahydrofuran (15 mL) was treated with trifluoroacetic acid (2 mL) at 60° C. overnight and concentrated. The residue was purified by HPLC (Zorbax, C-18, 250×2.54 column. Mobile phase A: 0.1% TFA in H$_2$O; B: 0.1% TFA in CH$_3$CN; 0-100% gradient) to provide the title compound as TFA salt. MS (DCI/NH$_3$) m/z 386 (M+H)$^+$.

Example 746C

N-(1-{2-fluoro-5-[(5-oxo-1,2,3,4,5,6-hexahydropyrido[2,3-d]pyridazin-8-yl)methyl]benzoyl}piperidin-4-yl)pyridine-2-carboxamide To a solution of EXAMPLE 746B (50 mg, 0.13 mmol) in anhydrous N,N-dimethylformamide (4 mL) was added picolinic acid (20 mg, 0.17 mmol), 1-ethyl-3-[3-(dimethylamino)propyl]-carbodiimide hydrochloride (EDC) (32 mg, 0.17 mmol), 1-hydroxybenzotriazole monohydrate (26 mg, 0.17 mmol), and triethylamine (17 mg, 0.17 mmol). The mixture was heated until homogeneous and stirred at ambient temperature overnight. The mixture was partitioned between methylene chloride and brine. The organic phase was washed with brine, water, and concentrated. The residue was purified by HPLC (Zorbax, C-18, 250×2.54 column, Mobile phase A: 0.1% TFA in H$_2$O; B: 0.1% TFA in CH$_3$CN; 0-100% gradient) to provide the title compound. MS (DCI/NH$_3$) m/z 491 (M+H)$^+$; $^1$H NMR (DMSO-d$_6$) δ 1.53-1.78 (m, 5H), 1.84-1.92 (m, 1H), 2.35 (t, J=6.27 Hz, 2H), 2.88-2.99 (m, 1H), 3.11-3.24 (m, 4H), 3.42 (d, J=13.90 Hz, 1H), 3.83 (s, 2H), 4.05-4.14 (m, 1H), 4.49 (d, J=13.22 Hz, 1H), 6.42 (s, 1H), 7.18-7.35 (m, 2H), 7.56-7.63 (m, 1H), 7.95-8.06 (m, 2H), 8.64 (d, J=4.07 Hz, 2H), 11.91 (s, 1H).

Example 747

N-(1-{2-fluoro-5-[(5-oxo-1,2,3,4,5,6-hexahydropyrido[2,3-d]pyridazin-8-yl)methyl]benzoyl}piperidin-4-yl)nicotinamide The title compound was prepared, using the appropriate reagents, as the TFA salt according to the procedure for EXAMPLE 746C. MS (DCI/NH$_3$) m/z 491 (M+H)$^+$; $^1$H NMR (DMSO-d$_6$) δ 1.41-1.60 (m, 2H), 1.65-1.75 (m, 2H), 1.83 (d, J=10.31 Hz, 1H), 1.94 (d, J=11.90 Hz, 1H), 2.35 (t, J=6.15 Hz, 2H), 2.99 (t, J=11.30 Hz, 1H), 3.13-3.23 (m, 3H), 3.44 (d, J=13.48 Hz, 1H), 3.84 (s, 2H), 4.05-4.15 (m, 1H), 4.46 (d, J=13.48 Hz, 1H), 6.42 (s, 1H), 7.18-7.27 (m, 2H), 7.30-7.36 (m, 1H), 7.59 (dd, J=7.93, 5.16 Hz, 1H), 8.28 (d, J=8.33 Hz, 1H), 8.58 (d, J=7.54 Hz, 1H), 8.75 (dd, J=5.16, 1.59 Hz, 1H), 9.03 (d, J=11.98 Hz, 1H), 11.92 (s, 1H).

Example 748

N-(1-{2-fluoro-5-[(5-oxo-1,2,3,4,5,6-hexahydropyrido[2,3-d]pyridazin-8-yl)methyl]benzoyl}piperidin-4-yl)isonicotinamide The title compound was prepared, using the appropriate reagents, as the TFA salt according to the procedure for EXAMPLE 746C. MS (DCI/NH$_3$) m/z 491 (M+H)$^+$; $^1$H NMR (DMSO-d$_6$) δ 1.40-1.60 (m, 2H), 1.66-1.73 (m, 2H), 1.78-1.85 (m, 1H), 1.93 (d, J=10.51 Hz, 1H), 2.35 (t, J=6.27 Hz, 2H), 2.93-3.03 (m, 1H), 3.12-3.23 (m, 3H), 3.43 (d, J=13.56 Hz, 1H), 3.83 (s, 2H), 4.04-4.15 (m, 1H), 4.46 (d, J=12.89 Hz, 1H), 6.40 (s, 1H), 7.19-7.25 (m, 2H), 7.31-7.35 (m, 1H), 7.82-7.88 (m, 2H), 8.68 (d, J=7.46 Hz, 1H), 8.74-8.80 (m, 2H), 11.91 (s, 1H).

Example 749

N-(1-{2-fluoro-5-[(5-oxo-1,2,3,4,5,6-hexahydropyrido[2,3-d]pyridazin-8-yl)methyl]benzoyl}piperidin-4-yl)-1H-indazole-6-carboxamide The title compound was prepared, using the appropriate reagents, as the TFA salt according to the procedure for EXAMPLE 746C. MS (DCI/NH$_3$) m/z 530 (M+H)$^+$; $^1$H NMR (DMSO-d$_6$) δ 1.45-1.59 (m, 2H), 1.65-1.73 (m, 2H), 1.78-1.87 (m, 1H), 1.94 (d, J=10.17 Hz, 1H), 2.34 (t, J=6.10 Hz, 2H), 2.91-3.03 (m, 1H), 3.15-3.22 (m, 3H), 3.45 (d, J=13.22 Hz, 1H), 3.83 (s, 2H), 4.07-4.18 (m, 1H), 4.50 (d, J=12.88 Hz, 1H), 6.41 (s, 1H), 7.18-7.27 (m, 2H), 7.33 (dd, J=5.26, 1.86 Hz, 1H), 7.82 (d, J=8.81 Hz, 1H), 7.96 (dd, J=8.48, 1.36 Hz, 1H), 8.26 (s, 1H), 8.50-8.57 (m, 1H), 9.23 (s, 1H), 11.89 (s, 1H).

Example 750

N-(1-{2-fluoro-5-[(5-oxo-1,2,3,4,5,6-hexahydropyrido[2,3-d]pyridazin-8-yl)methyl]benzoyl}piperidin-4-yl)-2-furamide The title compound was prepared, using the appropriate reagents, as the TFA salt according to the procedure for EXAMPLE 746C. MS (DCI/NH$_3$) m/z 480 (M+H)$^+$; $^1$H NMR (DMSO-d$_6$) δ 1.40-1.58 (m, 2H), 1.66-1.77 (m, 3H), 1.86 (d, J=10.51 Hz, 1H), 2.34 (t, J=6.10 Hz, 2H), 2.86-2.96 (m, 1H), 3.09-3.22 (m, 3H), 3.41 (d, J=12.54 Hz, 1H), 3.83 (s, 2H), 3.99-4.08 (m, 1H), 4.48 (d, J=13.22 Hz, 1H), 6.43 (s, 1H) 6.61 (dd, J=3.39, 1.70 Hz, 1H), 7.10 (d, J=3.73 Hz, 1H), 7.18-7.27 (m, 2H), 7.29-7.36 (m, 1H), 7.83 (s, 1H), 8.28 (s, 1H), 11.92 (s, 1H).

Example 751

N-(1-{2-fluoro-5-[(5-oxo-1,2,3,4,5,6-hexahydropyrido[2,3-d]pyridazin-8-yl)methyl]benzoyl}piperidin-4-yl)-1,3-thiazole-4-carboxamide The title compound was prepared, using the appropriate reagents, as the TFA salt according to the procedure for EXAMPLE 746C. MS (DCI/NH$_3$) m/z 497 (M+H)$^+$; $^1$H NMR (DMSO-d$_6$) δ 1.50-1.62 (m, 1H), 1.63-1.78 (m, 3H), 1.86 (d, J=10.31 Hz, 1H), 2.35 (t, J=6.15 Hz, 2H), 2.87-2.97 (m, 1H), 3.11-3.22 (m, 2H), 3.41 (d, J=13.09 Hz, 1H), 3.83 (s, 2H), 4.04-4.13 (m, 1H), 4.49 (d, J=13.09 Hz, 2H), 6.40 (s, 1H), 7.17-7.25 (m, 2H), 7.28-7.36 (m, 1H), 8.32 (d, J=1.98 Hz, 1H), 8.37 (s, 1H), 9.17 (d, J=1.98 Hz, 1H), 11.90 (s, 1H).

Example 753

N-{2-fluoro-5-[(4-oxo-3,4,5,6,7,8-hexahydrophthalazin-1-yl)methyl]phenyl}-N-methylcyclobutanecarboxamide To a solution of EXAMPLE 681C (40 mg, 0.14 mmol) in N,N-dimethylformamide (3 mL) was added (cyclobutanecarboxylic acid (14 mg, 0.14 mmol), 1-ethyl-3-(3-dimethylaminopropyl) carbodiimide hydrochloride (EDC) (53 mg, 0.28 mmol). N-hydroxybenzotriazole (HOBt) (38 mg, 0.28 mmol), and triethylamine (28 mg, 0.28 mmol). The reaction mixture was stirred at ambient temperature for 16 hours and was concentrated. The residue was purified by HPLC (Zorbax C-18, 0.1% TFA/CH$_3$CN/H$_2$O) to provide the title compound (13 mg, 25%). MS (DCI/NH$_3$) m/z 370 (M+H)$^+$.

Example 754

4-[4-fluoro-3-({4-[(2-methyl-1H-benzimidazol-5-yl)carbonyl]piperazin-1-yl}carbonyl)benzyl]-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 529 (M+H)$^+$; $^1$H NMR (CD$_3$OD) δ 1.64-1.80 (m, 4H), 2.40-2.47 (m, 2H), 2.47-2.56 (m, 2H), 2.88 (s, 3H), 3.39-3.68 (m, 4H), 3.71-3.94 (m, 4H), 3.99 (s, 2H), 7.12-7.21 (m, 1H), 7.22-7.27 (m, 1H), 7.34-7.41 (m, 1H), 7.64 (d, J=8.24 Hz, 1H), 7.82 (d, J=8.54 Hz, 1H), 7.84 (s, 1H).

Example 755

4-[3-({4-[(2-chloropyridin-3-yl)carbonyl]piperazin-1-yl}carbonyl)-4-fluorobenzyl]-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 510 (M+H)$^+$; $^1$H NMR (CD$_3$OD) δ 1.65-1.81 (m, 4H), 2.39-2.56 (m, 4H), 3.22-3.28 (m, 1H), 3.35-3.46 (m, 2H), 3.46-3.54 (m, 1H), 3.73-3.86 (m, 2H), 3.90 (s, 2H), 3.95-4.04 (m, 2H), 7.10-7.22 (m, 1H), 7.26 (d, J=9.76 Hz, 1H), 7.30-7.40 (m, 1H), 7.44-7.54 (m, 1H), 7.82-7.92 (m, 1H), 8.42-8.52 (m, 1H).

Example 756

4-{4-fluoro-3-[(4-pyridin-3-ylpiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 448 (M+H)$^+$; $^1$H NMR (CD$_3$OD) δ 1.67-1.79 (m, 4H), 2.41-2.49 (m, 2H), 2.49-2.57 (m, 2H), 3.41-3.50 (m, 2H), 3.52-3.63 (m, 4H), 3.91-3.98 (m, 2H), 4.01 (s, 2H), 7.19 (t, J=9.00 Hz, 1H), 7.27 (dd, J=6.26, 2.29 Hz, 1H), 7.36-7.42 (m, 1H), 7.85 (dd, J=9.00, 5.34 Hz, 1H), 8.08-8.13 (m, 1H), 8.16 (d, J=5.49 Hz, 1H), 8.39 (d, J=2.75 Hz, 1H).

Example 757

4-{4-fluoro-3-[(4-pyrimidin-5-ylpiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 543, but was purified by HPLC (Zorbax C-18, 0.1% TFA/CH$_3$CN/H$_2$O) instead of flash chromatography. MS (DCI/NH$_3$) m/z 449 (M+H)$^+$; $^1$H NMR (CD$_3$OD) δ 1.66-1.80 (m, 4H), 2.41-2.48 (m, 2H), 2.48-2.56 (m, 2H), 3.33-3.39 (m, 2H), 3.41-3.50 (m, 2H), 3.50-3.67 (m, 2H), 3.90-3.98 (m, 2H), 4.00 (s, 2H), 7.13-7.23 (m, 1H), 7.24-7.31 (m, 1H), 7.34-7.43 (m, 1H), 8.52 (s, 2H), 8.61 (s, 1H).

Example 758

N-(1-{2-fluoro-5-[(5-oxo-1,2,3,4,5,6-hexahydropyrido[2,3-d]pyridazin-8-yl)methyl]benzoyl}piperidin-4-yl)-1H-pyrazole-4-carboxamide The title compound was prepared, using the appropriate reagents, as the TFA salt according to the procedure for EXAMPLE 746C. MS (DCI/NH$_3$) m/z 480 (M+H)$^+$; $^1$H NMR (DMSO-d$_6$) δ 1.43-1.59 (m, 2H), 1.65-1.77 (m, 3H), 1.83-1.90 (m, 1H), 2.34 (t, J=6.27 Hz, 2H), 2.87-2.97 (m, 1H), 3.10-3.22 (m, 2H), 3.40 (d, J=13.22 Hz, 1H), 3.83 (s, 2H), 4.00-4.10 (m, 1H), 4.47 (d, J=13.22 Hz, 1H), 6.39 (s, 1H), 6.67 (d, J=2.03 Hz, 1H), 7.17-7.26 (m, 3H), 7.29-7.34 (m, 1H), 7.74 (d, J=2.03 Hz, 1H), 8.04 (s, 1H), 11.89 (s, 1H).

Example 759

4-{4-fluoro-3-[(4-methyl-3-oxopiperazin-1-yl)carbonyl]benzyl}-5,6,7,8-tetrahydrophthalazin-1(2H)-one The title compound was prepared, using the appropriate reagents, as the TFA salt according to the procedure for EXAMPLE 634 substituting EXAMPLE 673A for EXAMPLE 634A. MS (DCI/NH$_3$) m/z 399 (M+H)$^+$; $^1$H NMR (CD$_2$OD) δ 1.66-1.78 (m, 4H), 2.39-2.48 (m, 2H), 2.48-2.56 (m, 2H), 2.99 (d, J=5.49 Hz, 3H), 3.39 (t, J=5.19 Hz, 1H), 3.49 (t, J=5.49 Hz, 1H), 3.60 (t, J=5.19 Hz, 1H), 3.91-4.00 (m, 2H), 4.00 (s, 2H), 4.27-4.36 (m, 1H), 7.14-7.21 (m, 1H), 7.25-7.29 (m, 1H), 7.36-7.40 (m, 1H).

Example 761

N-{2-[(cyclopropylcarbonyl)amino]ethyl}-N-ethyl-2-fluoro-5-[(4-oxo-3,4,5,6,7,8-hexahydrophthalazin-1-yl)methyl]benzamide To a suspension of EXAMPLE 719 as the HCl salt (59 mg, 0.134 mmol) in anhydrous pyridine (2 mL) was added cyclopropanecarbonyl chloride (0.018 mL, 0.20 mmol). This solution was stirred at ambient temperature overnight and concentrated. The residue was purified by HPLC (Zorbax, C-18, 250×2.54 column, Mobile phase A: 0.1% TFA in H$_2$O; B: 0.1% TFA in CH$_3$CN; 0-100% gradient) to provide the title compound as the TFA salt. MS (DCI/NH$_3$) m/z 441 (M+H)$^+$; $^1$H NMR (CD$_3$OD) δ 0.72-0.77 (m, 3H), 0.81-0.85 (m, 1H), 1.05 (t, J=7.02 Hz, 2H), 1.24 (t, J=7.17 Hz, 1H), 1.52-1.57 (m, 1H), 1.71 (t, J=2.75 Hz, 4H), 2.43-2.47 (m, J=1.83 Hz, 2H), 2.48-2.52 (m, J=1.53 Hz, 2H), 3.24 (t, J=7.17 Hz, 2H), 3.29-3.34 (m, 2H), 3.49 (t, J=6.56 Hz, 1H), 3.63 (t, J=6.41 Hz, 2H), 3.99 (s, 2H), 7.10-7.20 (m, 2H), 7.28-7.33 (m, 1H).

Example 762

N-{2-[(2,6-difluorobenzoyl)amino]ethyl}-N-ethyl-2-fluoro-5-[(4-oxo-3,4,5,6,7,8-hexahydrophthalazin-1-yl)methyl]benzamide The title compound was prepared, using the appropriate reagents, as the TFA salt according to the procedure for EXAMPLE 761. MS (DCI/NH$_3$) m/z 513 (M+H)$^+$; $^1$H NMR (CD$_3$OD) δ 1.03-1.10 (m, 2H), 1.22-1.29 (m, 1H), 1.66-1.73 (m, 4H), 2.44 (d, J=2.44 Hz, 2H), 2.47-2.51 (m, 2H), 3.26 (q, J=7.32 Hz, 1H), 3.30-3.35 (m, 2H), 3.38-3.47 (m, 1H), 3.58-3.62 (m, 1H), 3.69-3.73 (m, 2H), 3.99 (s, 2H), 7.00-7.07 (m, 1H), 7.12-7.18 (m, 2H), 7.24 (dd, J=6.10, 2.14 Hz, 1H), 7.28-7.35 (m, 1H), 7.44-7.51 (m, 1H).

Example 763

N-[2-(ethyl{2-fluoro-5-[(4-oxo-3,4,5,6,7,8-hexahydrophthalazin-1-yl)methyl]benzoyl}amino)ethyl]nicotinamide To a suspension of EXAMPLE 719 as the HCl salt (59 mg, 0.134 mmol) in a mixture of anhydrous tetrahydrofuran (2 mL) and acetonitrile (2 mL) was added triethylamine (0.056 mL, 0.403 mmol) and 2,5-dioxopyrrolidin-1-yl nicotinate (44 mg, 0.201 mmol). This suspension was heated at 60° C. overnight and concentrated. The residue was purified by HPLC (Zorbax, C-18, 250×2.54 column, Mobile phase A: 0.1% TFA in H$_2$O: B: 0.1% TFA in CH$_3$CN; 0-100% gradient) to provide the title compound as the TFA salt. MS (DCI/NH$_3$) m/z 478 (M+H)$^+$; $^1$H NMR (CD$_3$OD) δ 1.08 (t, J=7.17 Hz, 3H), 1.67-1.72 (m, 4H), 2.39-2.43 (m, 2H), 2.46-2.51 (m, 2H), 3.27-3.32 (m, 2H), 3.44-3.53 (m, 1H), 3.73 (t, J=5.95 Hz, 1H), 3.79-3.84 (m, 2H), 3.97 (s, 2H), 7.09-7.16 (m, 2H), 7.29-7.35 (m, 1H), 7.84 (dd, J=7.93, 5.49 Hz, 1H), 8.51-8.57 (m, 1H), 8.81 (dd, J=10.99, 4.88 Hz, 1H), 9.08 (s, 1H).

The foregoing is meant to be illustrative of the invention and not meant to limit it to disclosed embodiments. Variations and changes obvious to one skilled in the art are intended to be within the scope and nature of the invention as defined in the appended claims.

We claim:

1. A method of treating leukemia, colon cancer, carcinomas of the breast, or cervical carcinomas in a mammal comprising administering thereto a therapeutically acceptable amount of a compound of selected from the group consisting of 4-(3-(1,4-diazepan-1-ylcarbonyl)-4-fluorobenzyl)-5,6,7,8-tetrahydrophthalazin-1(2h)-one;

4-((2-fluoro-5-((4-oxo-3,4,5,6,7,8-hexahydrophthalazin-1-yl)methyl)phenyl)amino)-4-oxobutanoic acid; and 1-(2-fluoro-5-((4-oxo-3,4,5,6,7,8-hexahydrophthalazin-1-yl)methyl)phenyl)pyrrolidine-2,5-dione;

or a pharmaceutically acceptable salt thereof.

2. A method according to claim 1 additionally comprising radiotherapy.

3. A method according to claim 1 additionally comprising administering a chemotherapeutic agent selected from temozolomide, dacarbazine, cyclophosphamide, carmustine, melphalan, lomustine, carboplatin, cisplatin, 5-FU+/−leucovorin, gemcitabine, methotrexate, bleomycin, irinotecan, camptothecin, or topotecan.

* * * * *